United States Patent
Tatlock et al.

(10) Patent No.: US 10,220,037 B2
(45) Date of Patent: Mar. 5, 2019

(54) SUBSTITUTED CARBONUCLEOSIDE DERIVATIVES USEFUL AS ANTICANCER AGENTS

(71) Applicant: Pfizer Inc., New York, NY (US)

(72) Inventors: John Howard Tatlock, San Diego, CA (US); Indrawan James McAlpine, San Diego, CA (US); Michelle Bich Tran-Dube, San Diego, CA (US); Eugene Yuanjin Rui, San Diego, CA (US); Martin James Wythes, Solana Beach, CA (US); Robert Arnold Kumpf, Carlsbad, CA (US); Michele Ann McTigue, Encinitas, CA (US); Ryan Patman, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/612,030

(22) Filed: Jun. 2, 2017

(65) Prior Publication Data
US 2017/0348313 A1   Dec. 7, 2017

Related U.S. Application Data

(60) Provisional application No. 62/506,076, filed on May 15, 2017, provisional application No. 62/431,714, filed on Dec. 8, 2016, provisional application No. 62/376,856, filed on Aug. 18, 2016, provisional application No. 62/346,226, filed on Jun. 6, 2016.

(51) Int. Cl.
| | | |
|---|---|---|
| *C07D 487/04* | (2006.01) | |
| *A61K 31/519* | (2006.01) | |
| *C07D 519/00* | (2006.01) | |
| *A61K 31/137* | (2006.01) | |
| *A61K 31/53* | (2006.01) | |
| *C07D 237/22* | (2006.01) | |
| *C07D 251/16* | (2006.01) | |
| *C07D 471/06* | (2006.01) | |
| *C07D 239/42* | (2006.01) | |
| *C07D 239/84* | (2006.01) | |
| *C07D 251/18* | (2006.01) | |
| *C07D 491/048* | (2006.01) | |
| *A61P 35/00* | (2006.01) | |
| *A61P 35/02* | (2006.01) | |
| *A61P 35/04* | (2006.01) | |
| *A61K 31/02* | (2006.01) | |
| *C07C 255/34* | (2006.01) | |

(52) U.S. Cl.
CPC ......... *A61K 31/519* (2013.01); *A61K 31/137* (2013.01); *A61K 31/53* (2013.01); *C07D 237/22* (2013.01); *C07D 239/42* (2013.01); *C07D 239/84* (2013.01); *C07D 251/16* (2013.01); *C07D 251/18* (2013.01); *C07D 471/06* (2013.01); *C07D 487/04* (2013.01); *C07D 491/048* (2013.01); *C07D 519/00* (2013.01); *A61K 31/02* (2013.01); *C07C 255/34* (2013.01)

(58) Field of Classification Search
CPC ........................... C07D 487/04; A61K 31/519
USPC ........................................ 544/280; 514/265.1
See application file for complete search history.

(56) References Cited

U.S. PATENT DOCUMENTS

| | | | |
|---|---|---|---|
| 6,106,864 | A | 8/2000 | Dolan et al. |
| 2008/0269059 | A1 | 10/2008 | Ziemer et al. |
| 2015/0064196 | A1 | 3/2015 | Thakkar et al. |

FOREIGN PATENT DOCUMENTS

| | | |
|---|---|---|
| WO | 9111172 | 8/1991 |
| WO | 9402518 | 2/1994 |
| WO | 9855148 | 12/1998 |
| WO | 0035298 | 6/2000 |
| WO | 02068393 A1 | 9/2002 |
| WO | 2014100719 A2 | 6/2014 |
| WO | 2015013256 A1 | 1/2015 |
| WO | 2015200680 A2 | 12/2015 |

(Continued)

OTHER PUBLICATIONS

Das, Subha R., et al., "The 5'-Nor Aristeromycin Analogues of 5'-Deoxy-5'-Methylthioadenosine and 5'-Deoxy-5'-Thiophenyladenosine", Nucleosides, Nucleotides and Nucleic Acids, 33: 668-677, 2014.

(Continued)

*Primary Examiner* — Susanna Moore
(74) *Attorney, Agent, or Firm* — David Rubin

(57) ABSTRACT

Compounds of the general formula):

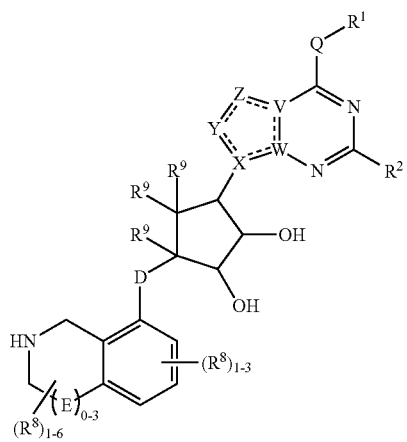

processes for the preparation of these compounds, compositions containing these compounds, and the uses of these compounds.

17 Claims, No Drawings

Specification includes a Sequence Listing.

(56) References Cited

FOREIGN PATENT DOCUMENTS

| WO | 2017032840 A1 | | 3/2017 |
|---|---|---|---|
| WO | WO 2017032840 | * | 3/2017 |

OTHER PUBLICATIONS

International Search Report and the Written Opinion of the International Searching Authority, PCT/IB2017/053295, dated Oct. 5, 2017.
Aggarwal, P., et al., "Nuclear Cyclin D1/CDK4 Kinase Regulates CUL4 Expression and Triggers Neoplastic Growth via Activation of the PRMT5 Methyltransferase", Cancer Cell, 2010, 329-340, 18.
Bandyopadhyay, S., et al., "HOXA9 Methylation by PRMT5 Is Essential for Endothelial Cell Expression of Leukocyte Adhesion Molecules", Molecular and Cellular Biology, 2012, 1202-1213, 32(7).
Bao, X, et al., "Overexpression of PRMT5 Promotes Tumor Cell Growth and Is Associated with Poor Disease Prognosis in Epithelial Ovarian Cancer", Journal of Histochemistry and Cytochemistry, 2013, 206-217, 6(3).
Bligh, Cavan M., et al., "Preparation of Both C5' Epimers of 5'-C-Methyladenosine: Reagent Control Trumps Substrate Control", The Journal of Organic Chemistry, 2014, 3238-3243, 79.
Cho, E., et al., "Arginine methylation controls growth regulation by E2F-1", The EMBO Journal, 2012, 1785-1797, 31.
Gu, Z., et al., "Protein arginine methyltransferase 5 is essential for growth of lung cancer cells", Biochem J., 2012, 235-241, 446.
Jansson, M., et al., "Arginine methylation regulates the p53 response", Nature Cell Biology, 2008, 431-1439, 10(12).
Karkhanis, V., et al., "Versatility of PRMT5-induced methylation in growth control and development", Trends in Biochemical Sciences, 2011, 633-641, 36(12).
Kim, Y.C., et al., "Microneedles for drug and vaccine delivery", Advanced Drug Delivery Reviews, 2012, 1547-1568, 64.
Kim, JM, et al., "Identification of Gastric Cancer-Related Genes Using a cDNA Microarray Containing Novel Expressed Sequence Tags Expressed in Gastric Cancer Cells", Clinical Cancer Research, 2005, 473-482, 11.
Kirby, G., et al., "Formation and Reactions of C-Nitrosoformate Esters, a New Class of Transient Dienophiles", Journal Chemical Society Perkin Trans., 1985, 1437-1442.
Liang, A., et al., "Fast-dissolving intraoral drug delivery systems", Expert Opinion on Therapeutic Patents, 2001, 981-986, 11(6).
Ueda, T., et al., "Palladium-Catalyzed Fluorocarbonylation Using N-Formylsaccharin as CO Source: General Access to Carboxylic Acid Derivatives", Organic Letters, 2013, 5370-5373, 15(20).
Montgomery, J., et al., "Analogs of Tubercidin", Journal of Medicinal Chemistry, 1967, 665-667, 10.
Nicholas, C., et al., "PRMT5 is Upregulated in Malignant and Metastatic Melanoma and Regulates Expression of MITF and p27Kip1", PLOS One, 2013, e74710, 8(9).
Powers, M et al., "Protein Arginine Methyltransferase 5 Accelerates Tumor Growth by Arginine Methylation of the Tumor Suppressor Programmed Cell Death 4", Cancer Research, 2011, 5579-5587, 71(16).
Shireman, B. et al., "Rapid syntheses of either enantiomer of important carbocyclic nucleoside precursors", Tetrahedron Letters, 2000, 9537-9540, 41.
Singh, R., et al., "2-Azabicyclo[2.2.1]hept-5-en-3-one: Chemical Profile of a Versatile Synthetic Building Block and its Impact on the Development of Therapeutics", Chemical Review, 2012, 4642-4686, 112.
Trost, B., et al., "Catalytic asymmetric allylic alkylation employing heteroatom nucleophiles: a powerful method for C—X bond formation", Chemical Science, 2010, 427-440, 1.
Trost, B., et al., "New Class of Nucleophiles for Palladium-Catalyzed Asymmetric Allylic Alkylation. Total Synthesis of Agelastatin A", Journal of American Chemical Society, 2006, 6054-6055, 128.
Trost, B., et al., "Palladium-Catalyzed Enantioselective Synthesis of Carbanucleosides", Journal of American Chemical Society, 2000, 5947-5956, 122.
Trost, B., et al., "Palladium-Catalyzed Asymmetric Allylic Alkylation of Electron-Deficient Pyrroles with Meso Electrophiles", Organic Letters, 2012, 2254-2257, 14(9).
Verma, R., et al., "Current Status of Drug Delivery Technologies and Future Directions", Pharmaceutical Technology On-Line, 2001, 1-14, 25(2).
Wang, L., et al., "Protein Arginine Methyltransferase 5 Suppresses the Transcription of the RB Family of Tumor Suppressors in Leukemia and Lymphoma Cells", Molecular and Cellular Biology, 2008, 6262-6277, 28(20).
Wei, H., et al., "PRMT5 dimethylates R30 of the p65 subunit to activate NF-kB", PNAS, 2013, 13516-13521, 10(33).
Zheng, S., et al., "Arginine Methylation-Dependent Reader-Writer Interplay Governs Growth Control by E2F-1", Molecular Cell, 2013, 37-51, 52.

* cited by examiner

SUBSTITUTED CARBONUCLEOSIDE DERIVATIVES USEFUL AS ANTICANCER AGENTS

FIELD OF THE INVENTION

This invention relates to novel carbonucleoside derivatives useful in the treatment of abnormal cell growth, such cancer, in mammals. This invention also relates to a method of using such compounds in the treatment of abnormal cell growth in mammals, especially humans, and to pharmaceutical compositions as anticancer agents.

BACKGROUND OF THE INVENTION

Post-translational modification of arginine residues by methylation is important for many critical cellular processes including chromatin remodeling, gene transcription, protein translation, signal transduction, RNA splicing and cell proliferation. Arginine methylation is catalyzed by protein arginine methyltransferase (PRMT) enzymes. There are nine PRMT members in all, and eight have reported enzymatic activity on target substrates.

The protein arginine methyltransferase (PRMT) family of enzymes utilize S-adenosyl methionine (SAM) to transfer methyl groups to arginine residues on target proteins. Type I PRMTs catalyze formation of mono-methyl arginine and asymmetric di-methyl arginines while Type II PRMTs catalyze mono-methyl arginine and symmetric di-methyl arginines. PRMT5 is a Type II enzyme, twice transferring a methyl group from SAM to the two ω-guanidino nitrogen atoms of arginine, leading to ω-NG, N'G di-symmetric methylation of protein substrates.

PRMT5 protein is found in both the nucleus and cytoplasm, and has multiple protein substrates such as histones, transcription factors and spliceosome proteins. PRMT5 has a binding partner, Mep50 (methylosome protein 50) and functions in multiple protein complexes. PRMT5 is associated with chromatin remodeling complexes (SWI/SNF, NuRD) and epigenetically controls genes involved in development, cell proliferation, and differentiation, including tumor suppressors, through methylation of histones (Karkhanis, V. et al., Versatility of PRMT5 Induced Methylation in Growth Control and Development, *Trends Biochem Sci* 36(12) 633-641 (2011)). PRMT5 also controls gene expression through association with protein complexes that recruit PRMT5 to methylate several transcription factors p53 (Jansson, M. et al., Arginine Methylation Regulates the p53 Response, *Nat. Cell Biol.* 10, 1431-1439 (2008)); E2F1 (Zheng, S. et al., Arginine Methylation-Dependent Reader-Writer Interplay Governs Growth Control by E2F-1, *Mol Cell* 52(1), 37-51 (2013)); HOXA9 (Bandyopadhyay, S. et al., HOXA9 Methylation by PRMT5 is Essential for Endothelial Cell Expression of Leukocyte Adhesion Molecules, *Mol. Cell. Biol.* 32(7):1202-1213 (2012)); and NFκB (Wei, H. et al., PRMT5 dimethylates R30 of the p65 Subunit to Activate NFκB, *PNAS* 110(33), 13516-13521 (2013)). In the cytoplasm, PRMT5 has a diverse set of substrates involved in other cellular functions including RNA splicing (Sm proteins), golgi assembly (gm130), ribosome biogenesis (RPS10), piRNA mediated gene silencing (Piwi proteins) and EGFR signaling (Karkhanis, 2011).

Additional papers relating to PRMT5 include: Aggarwal, P. et al., (2010) Nuclear Cyclin D1/CDK4 Kinase Regulates CUL4B Expression and Triggers Neoplastic Growth via Activation of the PRMT5 Methyltransferase, *Cancer Cell* 18: 329-340; Bao, X. et al., Overexpression of PRMT5 Promotes Tumor Cell Growth and is Associated with Poor Disease Prognosis in Epithelial Ovarian Cancer, *J Histochem Cytochem* 61: 206-217 (2013); Cho E. et al., Arginine Methylation Controls Growth Regulation by E2F1, *EMBO J.* 31(7) 1785-1797 (2012); Gu, Z. et al., Protein Arginine Methyltransferase 5 Functions in Opposite Ways in the Cytoplasm and Nucleus of Prostate Cancer Cells, *PLoS One* 7(8) e44033 (2012); Gu, Z. et al., Protein Arginine Methyltransferase 5 is Essential for Growth of Lung Cancer Cells, *Biochem J.* 446: 235-241 (2012); Kim, J. et al., Identification of Gastric Cancer Related Genes Using a cDNA Microarray Containing Novel Expressed Sequence Tags Expressed in Gastric Cancer Cells, *Clin Cancer Res.* 11(2) 473-482 (2005); Nicholas, C. et al., PRMT5 is Upregulated in Malignant and Metastatic Melanoma and Regulates Expression of MITF and p27(Kip1), *PLoS One* 8(9) e74710 (2012); Powers, M. et al., Protein Arginine Methyltransferase 5 Accelerates Tumor Growth by Arginine Methylation of the Tumor Suppressor Programmed Cell Death 4, *Cancer Res.* 71(16) 5579-5587 (2011); Wang, L. et al., Protein Arginine Methyltransferase 5 Suppresses the Transcription of the RB Family of Tumor Suppressors in Leukemia and Lymphoma Cells, *Mol. Cell Biol.* 28(20), 6262-6277 (2008).

PRMT5 is overexpressed in many cancers and has been observed in patient samples and cell lines including B-cell lymphoma and leukemia (Wang, 2008) and the following solid tumors: gastric (Kim 2005) esophageal (Aggarwal, 2010), breast (Powers, 2011), lung (Gu, 2012), prostate (Gu, 2012), melanoma (Nicholas 2012), colon (Cho, 2012) and ovarian (Bao, 2013). In many of these cancers, overexpression of PRMT5 correlated with poor prognosis. Aberrant arginine methylation of PRMT5 substrates has been linked to other indications in addition to cancer, such as metabolic disorders, inflammatory and autoimmune disease and hemaglobinopathies.

SUMMARY OF THE INVENTION

Given its role in regulating various biological processes, PRMT5 is an attractive target for modulation with small molecule inhibitors. To date, few effective PRMT5 inhibitors have been developed, and no PRMT5 inhibitors have entered the clinic.

Each of the embodiments of the compounds of the present invention described below can be combined with any other embodiment of the compounds of the present invention described herein not inconsistent with the embodiment with which it is combined. Furthermore, each of the embodiments below describing the invention envisions within its scope pharmaceutically acceptable salts of the compounds of the invention. Accordingly, the phrase "or a pharmaceutically acceptable salt thereof" is implicit in the description of all compounds described herein.

The invention includes embodiments wherein there is provided a compound of formula (I):

Embodiments of the present invention include compounds of formula (I):

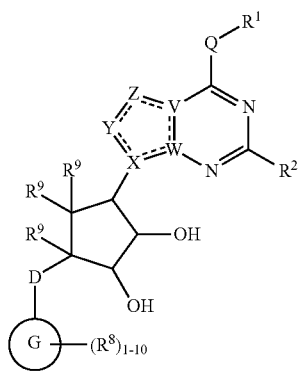

(I)

or a pharmaceutically acceptable salt thereof, wherein:
$R^1$ is selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$, where each $R^4$ is independently $A-R^{14}$, where A is absent, $(C_1-C_3)$alkyl, —C(O)— or —SO$_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;
$R^2$ is hydrogen, halogen, $(C_1-C_8)$alkyl, hydroxy, $(C_1-C_8)$alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;
each $R^3$ is independently selected from hydrogen, hydroxy, $NH_2$; $(C_1-C_8)$alkyl or heteroalkyl having 1-8 atoms, or when D is $C(R^3)_2$, $R^3$ is additionally selected from fluorine, $(C_1-C_8)$alkylene or heteroalkylene bound to an atom on G to form a ring fused to G, where $R^3$ is optionally substituted with 1-6 $R^8$;
each $R^9$ is independently hydrogen or fluorine;
D is $C(R^3)_2$, $NR^3$, O, S or $S(O)_{1-2}$;
G is a $(C_5-C_{12})$aryl or a 5-12 membered heteroaryl ring system fused to $(C_3-C_{10})$cycloalkyl or heterocyclyl ring system;
each $R^8$ is absent or is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$, $N(R^4)_2$, CN, halogen and $CON(R^4)_2$, where two $R^8$ optionally join to form a 4-6 membered spiro-cycloalkyl ring, a cycloalkyl fused ring, or a alkylene bridge spanning G, and where two $R^8$ optionally join to form carbonyl;
where each $R^4$ is independently $A-R^{14}$, where A is absent, $(C_1-C_3)$alkyl, —C(O)— or —SO$_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;
Q is absent or is a divalent moiety selected from O, S, NH and $(C_1-C_8)$alkylene;
V is N or C if Z is present, where if V forms a double bond V is carbon, or V is N or CH and forms a double bond with W if Z is absent;
W is N or C, where if W forms a double bond if W is carbon;
X is N or C if Y is present, where if X forms a double bond X is carbon, or X is O, $NR^{16}$ or $C(R^{16})_2$ if Y is absent, where $R^{16}$ is H or methyl;
Y is absent, $CR^{10}$, N, $NR^{10}$, O or S, or Y is absent, hydrogen or $(C_1-C_8)$alkyl if Z is absent, where each $R^{19}$ is independently selected from hydrogen, $(C_1-C_8)$alkyl, hydroxy, $(C_1-C_8)$alkoxy, halogen, SH, S—$(C_1-C_8)$alkyl and $N(R^{11})_2$ if Y is $CR^{10}$, where Y forms a double bond with an adjacent ring member when Y is $CR^{10}$ or N, and where each $R^{11}$ is independently hydrogen, $(C_1-C_8)$alkyl, $(C_5-C_{12})$aryl or 5-12 membered heteroaryl or two $R^{11}$ join to form a 4-6 membered heterocyclic ring containing 1-3 heteroatoms selected from N, O and S, or Y is $C(R^{10})_2$ and the two $R^{10}$ and the carbon to which they are associated form a carbonyl or a thiocarbonyl;
Z is absent, $CR^{12}$, N, $NR^{12}$, O or S, or Z is absent, hydrogen or $(C_1-C_8)$alkyl if Y is absent, where each $R^{12}$ is independently selected from hydrogen, $(C_1-C_8)$alkyl, hydroxy, $(C_1-C_8)$alkoxy, fluoro, chloro, bromo, SH, S—$(C_1-C_8)$alkyl and $N(R^{13})_2$, where Z forms a double bond with an adjacent ring member if it is $CR^{12}$ or N, where each $R^{13}$ is independently hydrogen, $(C_1-C_8)$alkyl, $(C_5-C_{12})$aryl or 5-12 membered heteroaryl, or two $R^{13}$ join to form a 4-6 membered heterocyclic ring containing 1-3 heteroatoms selected from N, O and S, and where Z is not $NR^{12}$ if X is N, V is C, W is C and Y is $CR^{10}$, or Z is $C(R^{12})_2$ and the two $R^{12}$ and the carbon to which they are associated form a carbonyl or a thiocarbonyl; and
each ----- is absent or an optional bond, where no more than two, non-adjacent ----- may be present.

Embodiments of the present invention also include compounds of formula (II):

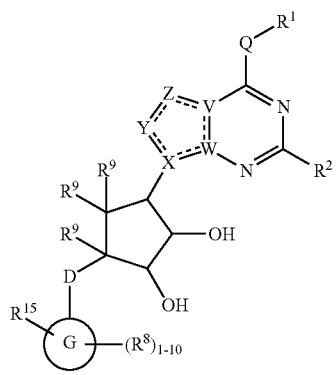

(II)

or a pharmaceutically acceptable salt thereof, wherein:
$R^1$ is selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$, where each $R^4$ is independently $A-R^{14}$, where A is absent, $(C_1-C_3)$alkyl, —C(O)— or —SO$_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;
$R^2$ is hydrogen, halogen, $(C_1-C_8)$alkyl, hydroxy, $(C_1-C_8)$alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

each $R^3$ is independently selected from hydrogen, hydroxy, $NH_2$; $(C_1-C_8)$alkyl or heteroalkyl having 1-8 atoms, or when D is $C(R^3)_2$, $R^3$ is additionally selected from fluorine, $(C_1-C_8)$alkylene or heteroalkylene bound to an atom on G to form a ring fused to G, where $R^3$ is optionally substituted with 1-6 $R^8$;

each $R^9$ is independently hydrogen or fluorine;

D is $C(R^3)_2$, O, or $S(O)_{1-2}$;

G is a $(C_5-C_{12})$aryl, 5-12 membered heteroaryl ring system;

$R^{15}$ is heteroalkyl having 1-8 atoms bound to an atom on G and optionally substituted with 1-6 $R^8$, or $R^{15}$ is heteroalkylene bound to an atom on G, optionally substituted with 1-6 $R^8$, and bound to an adjacent atom on G (i.e., the two ends of $R^{15}$ when $R^{15}$ is heteroalkylene are bound to adjacent carbons on the G ring);

each $R^8$ is absent or is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$, $N(R^4)_2$, CN, halogen and $CON(R^4)_2$, where two $R^8$ optionally join to form a 4-6 membered spiro-cycloalkyl ring, a cycloalkyl fused ring, or a alkylene bridge spanning G, and where two $R^8$ optionally join to form carbonyl;

where each $R^4$ is independently $A-R^{14}$, where A is absent, $(C_1-C_3)$alkyl, —C(O)— or —$SO_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

Q is absent or is a divalent moiety selected from O, S, NH and $(C_1-C_8)$alkylene;

V is N or C, where if V forms a double bond V is carbon;

W is N or C, where if W forms a double bond W is carbon;

X is N or C, where if X forms a double bond X is carbon;

Y is $CR^{10}$, N, $NR^{10}$, O or S, where each $R^{10}$ is independently selected from hydrogen, $(C_1-C_8)$alkyl, hydroxy, $(C_1-C_8)$alkoxy, or $R^{10}$ is optionally selected from halogen, SH, S—$(C_1-C_8)$alkyl and $N(R^{11})_2$ if Y is $CR^{10}$, where Y forms a double with an adjacent ring member when Y is $CR^{10}$ or N, and where each $R^{11}$ is independently hydrogen, $(C_1-C_8)$alkyl, $(C_5-C_{12})$aryl or 5-12 membered heteroaryl or two $R^{11}$ join to form a 4-6 membered heterocyclic ring containing 1-3 heteroatoms selected from N, O and S, or Y is $C(R^{10})_2$ and the two $R^{10}$ and the carbon to which they are associated form a carbonyl or a thiocarbonyl;

Z is $CR^{12}$, N, $NR^{12}$, O or S, where each $R^{12}$ is independently selected from hydrogen, $(C_1-C_8)$alkyl, hydroxy, $(C_1-C_8)$alkoxy, or $R^{12}$ is optionally selected from fluoro, chloro, bromo, iodo, SH, S—$(C_1-C_8)$alkyl and $N(R^{13})_2$ if Z is $CR^{12}$, where Z forms a double bond with an adjacent ring member if it is $CR^{12}$ or N, where each $R^{13}$ is independently hydrogen, $(C_1-C_8)$alkyl, $(C_5-C_{12})$aryl or 5-12 membered heteroaryl, or two $R^{13}$ join to form a 4-6 membered heterocyclic ring containing 1-3 heteroatoms selected from N, O and S, and where Z is not $NR^{12}$ if X is N, V is C, W is C and Y is $CR^{10}$, or Z is $C(R^{12})_2$ and the two $R^{12}$ and the carbon to which they are associated form a carbonyl or a thiocarbonyl; and each ----- is an optional bond, where no more than two, non-adjacent ----- may be present, provided that D is $S(O)1-2$ when G is $C_{10}$aryl or a 10-membered heteroaryl.

Additional embodiments of the present invention include compounds of formula (III):

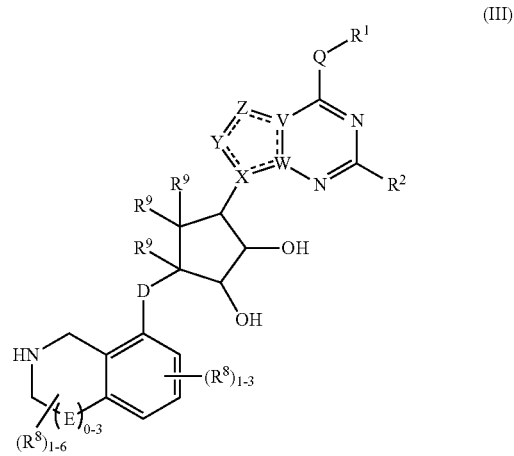

(III)

or a pharmaceutically acceptable salt thereof, wherein:

each $R^1$ is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$, where each $R^4$ is independently $A-R^{14}$, where A is absent, $(C_1-C_3)$alkyl, —C(O)— or —$SO_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

$R^2$ is hydrogen, halogen, $(C_1-C_8)$alkyl, hydroxy, $(C_1-C_8)$alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

each $R^3$ is independently hydrogen, hydroxy or $NH_2$; or when D is $C(R^3)_2$, $R^3$ is additionally selected from fluorine;

each $R^9$ is independently hydrogen or fluorine;

D is $C(R^3)_2$, O, or $S(O)_{1-2}$;

E is $NR^1$, $CH_2$, $C(R^1)_2$, O or —$S(O)_2$;

each $R^8$ is absent or is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$, $N(R^4)_2$, CN, halogen and $CON(R^4)^2$, where two $R^8$ optionally join to form a 4-6 membered spiro-cycloalkyl ring, a cycloalkyl fused ring, or a alkylene bridge spanning G, and where two $R^8$ optionally join to form carbonyl;

where each $R^4$ is independently $A-R^{14}$, where A is absent, $(C_1-C_3)$alkyl, —C(O)— or —$SO_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

Q is absent or is a divalent moiety selected from O, S, NH and $(C_1-C_8)$alkylene;

V is N or C, where if V forms a double bond V is carbon;

W is N or C, where if W forms a double bond W is carbon;

X is N or C, where if X forms a double bond X is carbon;

Y is $CR^{10}$, N, $NR^{10}$, O or S, where each $R^{10}$ is independently selected from hydrogen, $(C_1-C_8)$alkyl, hydroxy, $(C_1-C_8)$alkoxy, halogen, SH, S—$(C_1-C_8)$alkyl and $N(R^{11})_2$ if Y is $CR^{10}$, where Y forms a double with an adjacent ring member when Y is $CR^{10}$ or N, and where each $R^{11}$ is independently hydrogen, $(C_1-C_8)$alkyl, $(C_5-C_{12})$aryl or 5-12 membered heteroaryl or two $R^{11}$ join to form a 4-6 membered heterocyclic ring containing 1-3 heteroatoms selected from N, O and S, or Y is $C(R^{10})_2$ and the two $R^{10}$ and the carbon to which they are associated form a carbonyl or a thiocarbonyl;

Z is $CR^{12}$, N, $NR^{12}$, O or S, where each $R^{12}$ is independently selected from hydrogen, $(C_1-C_8)$alkyl, hydroxy, $(C_1-C_8)$alkoxy, fluoro, chloro, bromo, SH, S—$(C_1-C_8)$alkyl and $N(R^{13})_2$, where Z forms a double bond with an adjacent ring member if it is $CR^{12}$ or N, where each $R^{13}$ is independently hydrogen, $(C_1-C_8)$alkyl, $(C_5-C_{12})$aryl or 5-12 membered heteroaryl, or two $R^{13}$ join to form a 4-6 membered heterocyclic ring containing 1-3 heteroatoms selected from N, O and S, and where Z is not $NR^{12}$ if X is N, V is C, W is C and Y is $CR^{10}$, or Z is $C(R^{12})_2$ and the two $R^{12}$ and the carbon to which they are associated form a carbonyl or a thiocarbonyl; and each ----- is an optional bond, where no more than two, non-adjacent ----- may be present.

Additional embodiments of the present invention include compounds of formula (IV):

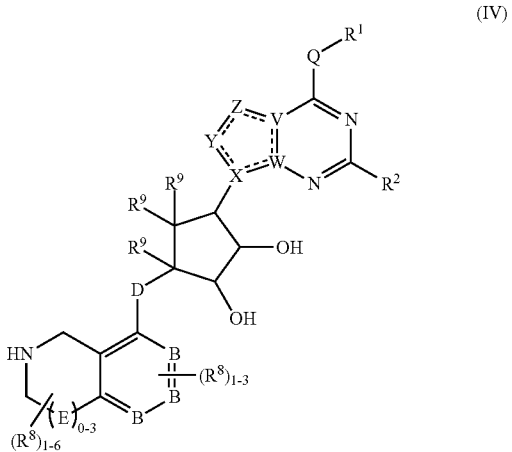

(IV)

or a pharmaceutically acceptable salt thereof, wherein:

each $R^1$ is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$, where each $R^4$ is independently A-$R^{14}$, where A is absent, $(C_1-C_3)$alkyl, —C(O)— or —$SO_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

$R^2$ is hydrogen, halogen, $(C_1-C_8)$alkyl, hydroxy, $(C_1-C_8)$alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

each $R^3$ is independently hydrogen, hydroxy or $NH_2$; or when D is $C(R^3)_2$, $R^3$ is additionally selected from fluorine;

each $R^9$ is independently hydrogen or fluorine;

B is N or C;

E is $NR^1$, $CH_2$, $C(R^1)_2$, O or —$S(O)_2$;

each $R^8$ is absent or is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$, $N(R^4)_2$, CN, halogen and $CON(R^4)_2$, where two R8 optionally join to form a 4-6 membered spiro-cycloalkyl ring, a cycloalkyl fused ring, or a alkylene bridge spanning G, and where two $R^8$ optionally join to form carbonyl;

where each $R^4$ is independently A-$R^{14}$, where A is absent, $(C_1-C_3)$alkyl, —C(O)— or —$SO_2$—, and $R^{14}$ is hydrogen, $(C_1-C_8)$alkyl, $(C_8-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

Q is absent or is a divalent moiety selected from O, S, NH and $(C_1-C_8)$alkylene;

V is N or C, where if V forms a double bond V is carbon;

W is N or C, where if W forms a double bond W is carbon;

X is N or C, where if X forms a double bond X is carbon;

Y is $CR^{10}$, N, $NR^{10}$, O or S, where each $R^{10}$ is independently selected from hydrogen, $(C_1-C_8)$alkyl, hydroxy, $(C_1-C_8)$alkoxy, halogen, SH, S—$(C_1-C_8)$alkyl and $N(R^{11})_2$ if Y is $CR^{10}$, where Y forms a double with an adjacent ring member when Y is $CR^{10}$ or N, and where each $R^{11}$ is independently hydrogen, $(C_1-C_8)$alkyl, $(C_5-C_{12})$aryl or 5-12 membered heteroaryl or two $R^{11}$ join to form a 4-6 membered heterocyclic ring containing 1-3 heteroatoms selected from N, O and S, or Y is $C(R^{10})_2$ and the two $R^{10}$ and the carbon to which they are associated form a carbonyl or a thiocarbonyl;

Z is $CR^{12}$, N, $NR^{12}$, O or S, where each $R^{12}$ is independently selected from hydrogen, $(C_1-C_8)$alkyl, hydroxy, $(C_1-C_8)$alkoxy, fluoro, chloro, bromo, SH, S—$(C_1-C_8)$alkyl and $N(R^{13})_2$, where Z forms a double bond with an adjacent ring member if it is $CR^{12}$ or N, where each $R^{13}$ is independently hydrogen, $(C_1-C_8)$alkyl, $(C_8-C_{12})$aryl or 5-12 membered heteroaryl, or two $R^{13}$ join to form a 4-6 membered heterocyclic ring containing 1-3 heteroatoms selected from N, O and S, and where Z is not $NR^{12}$ if X is N, V is C, W is C and Y is $CR^{10}$, or Z is $C(R^{12})_2$ and the two $R^{12}$ and the carbon to which they are associated form a carbonyl or a thiocarbonyl; and each ----- is an optional bond, where no more than two, non-adjacent ----- may be present.

Further embodiments of the present invention include compounds as described herein where

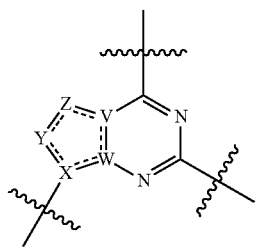

is selected from:
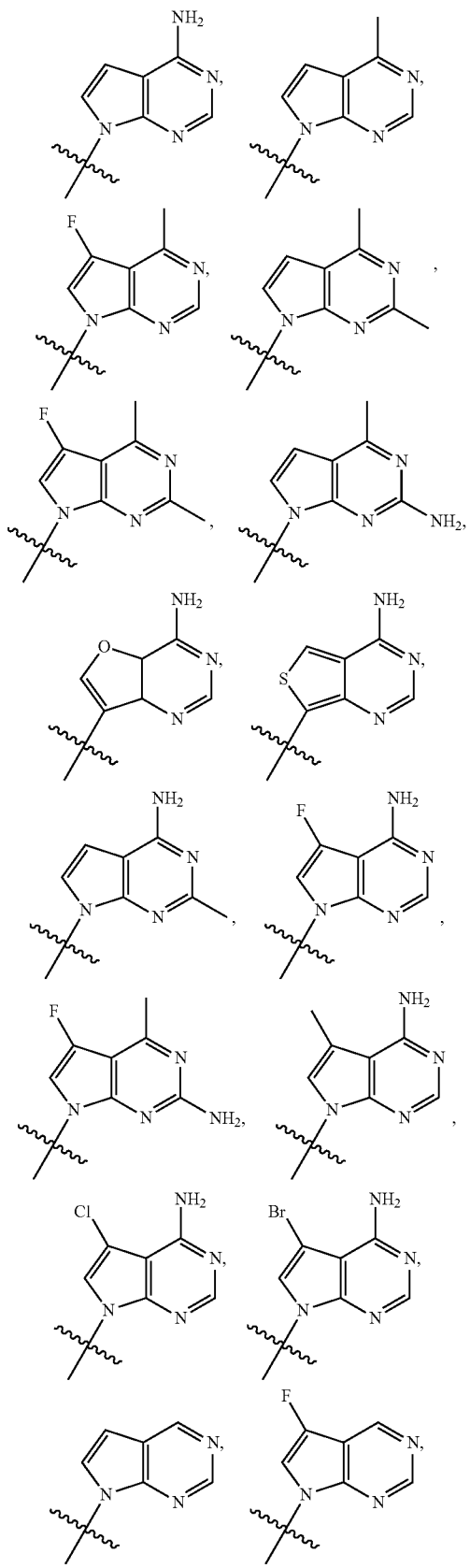
-continued
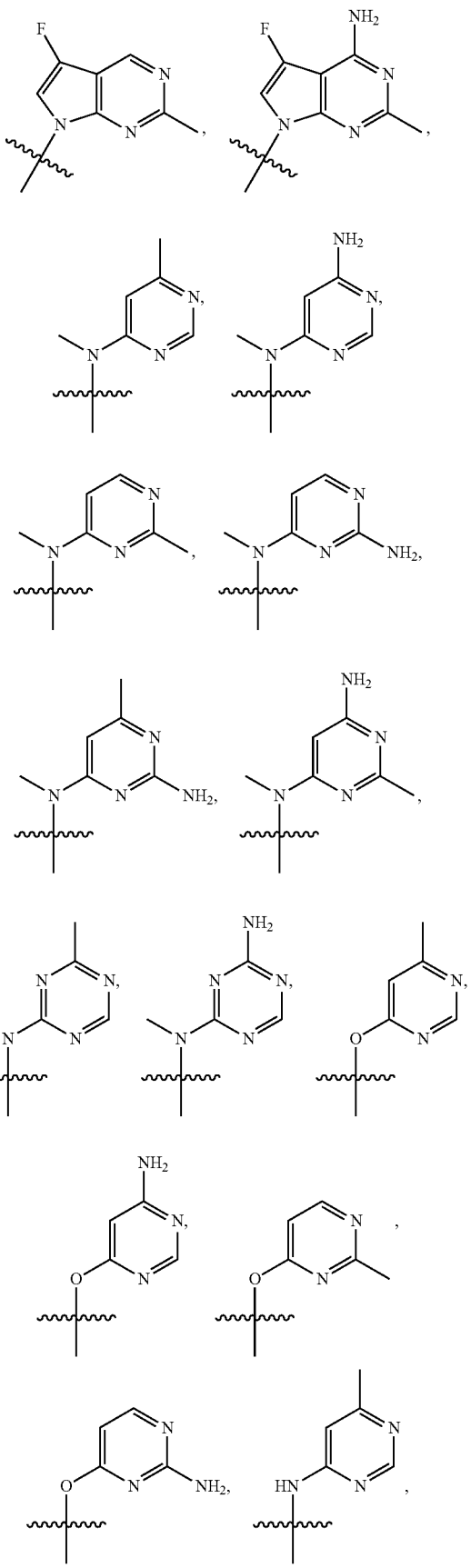

-continued
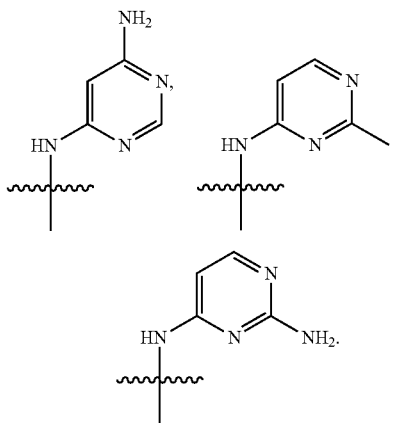
In certain embodiments:
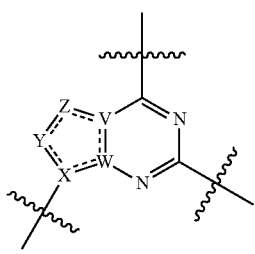
is selected from:
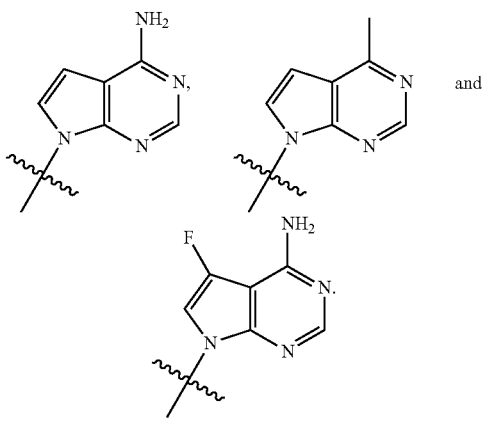
and
Further embodiments of the present invention include compounds as described herein where
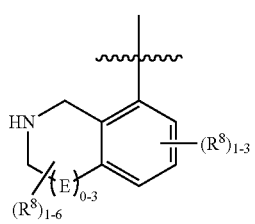
is selected from:
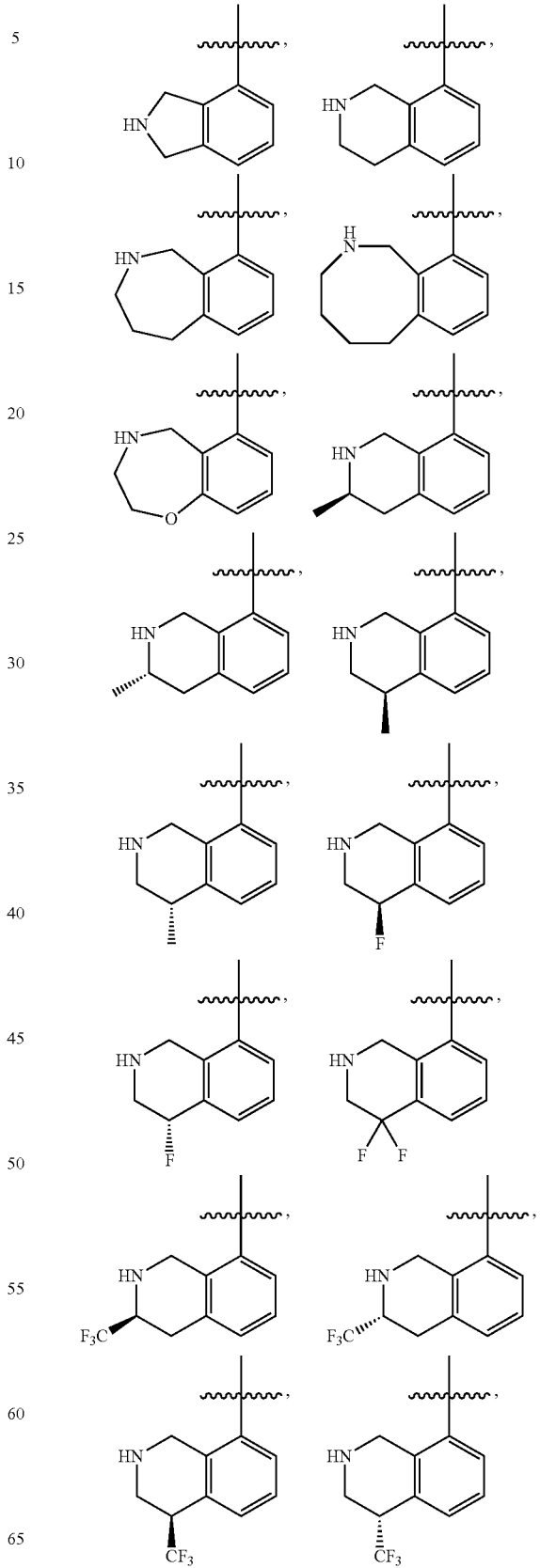

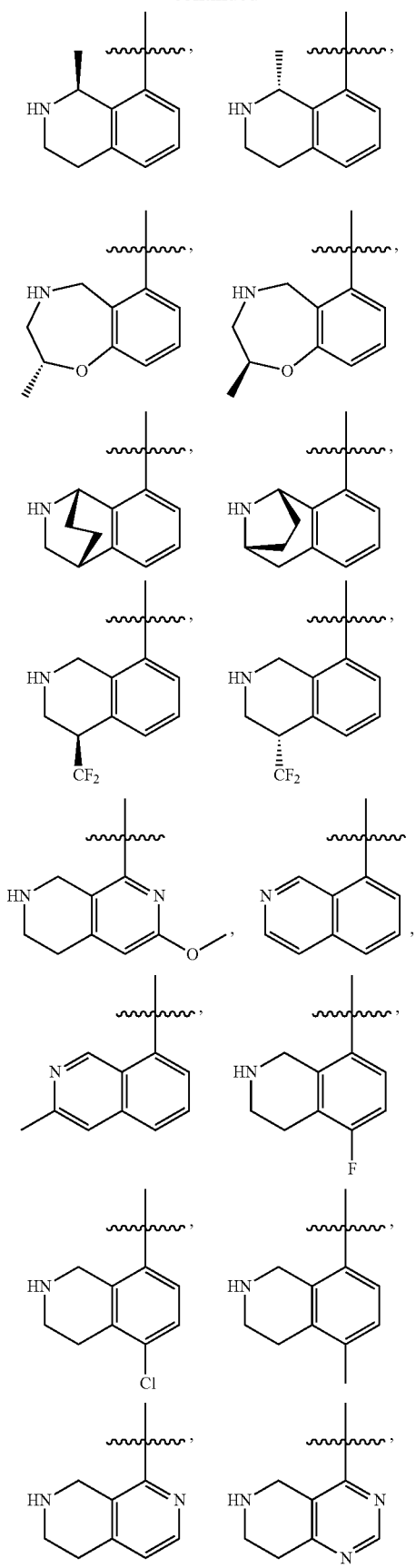
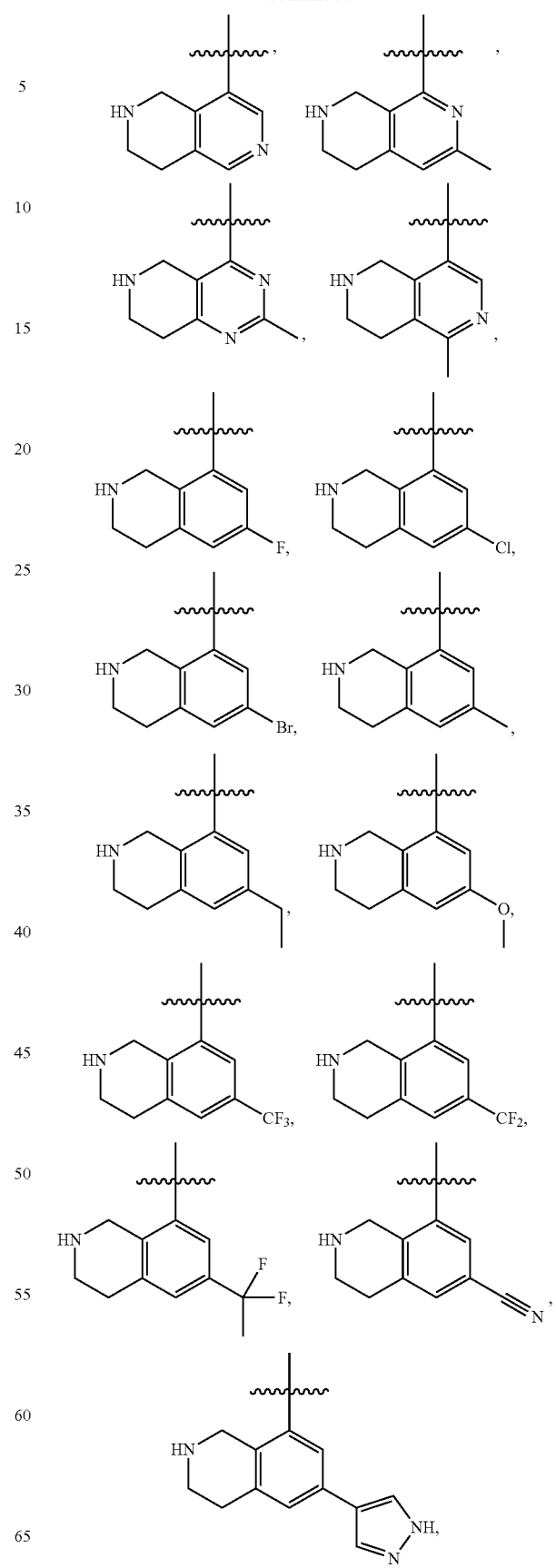

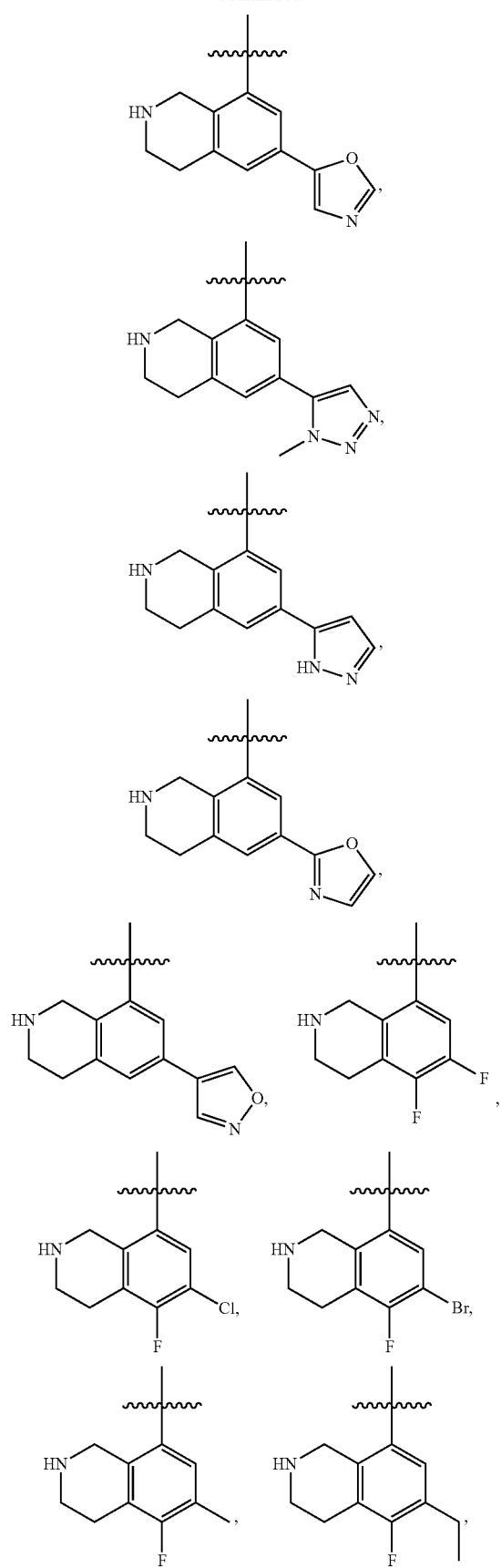
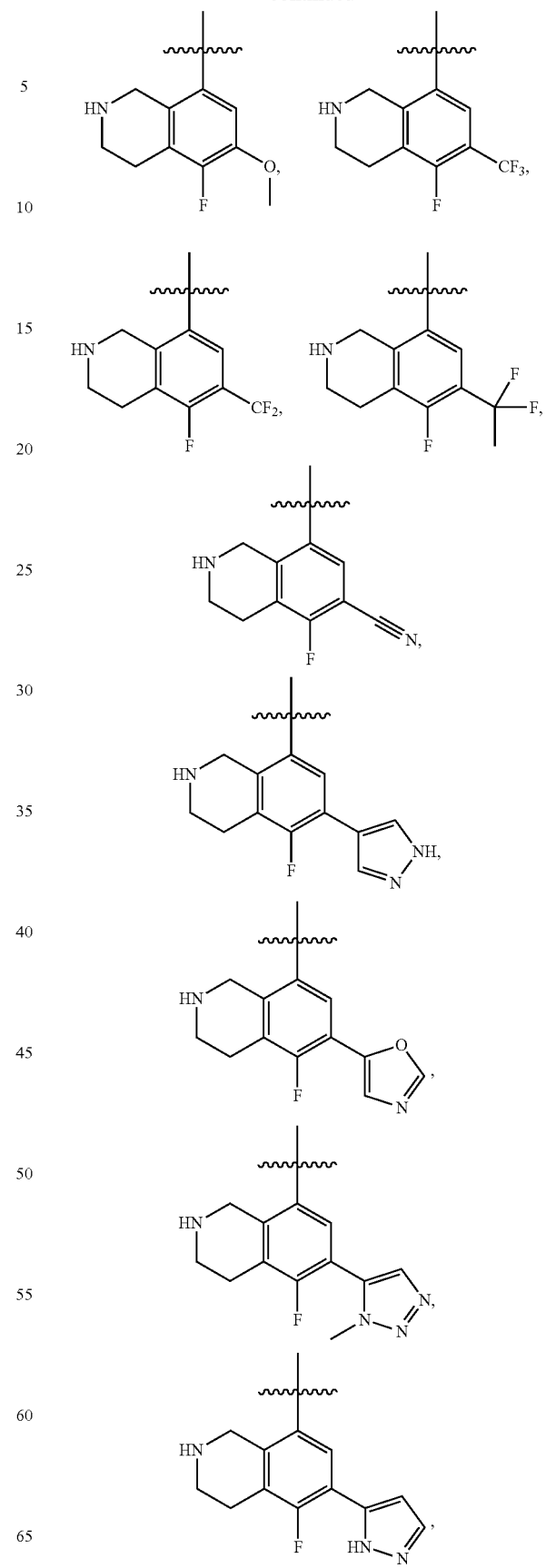

-continued
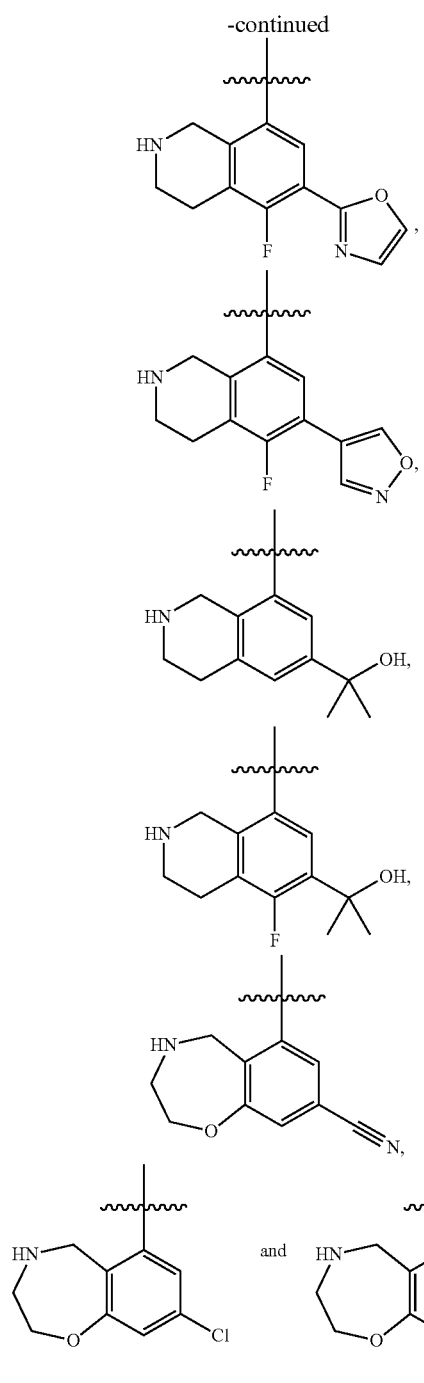
In certain embodiments
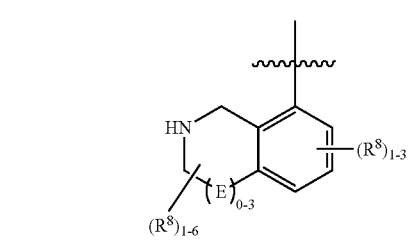
is
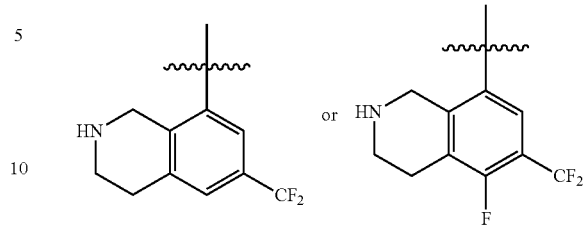
Further embodiments of the present invention include compounds selected from:
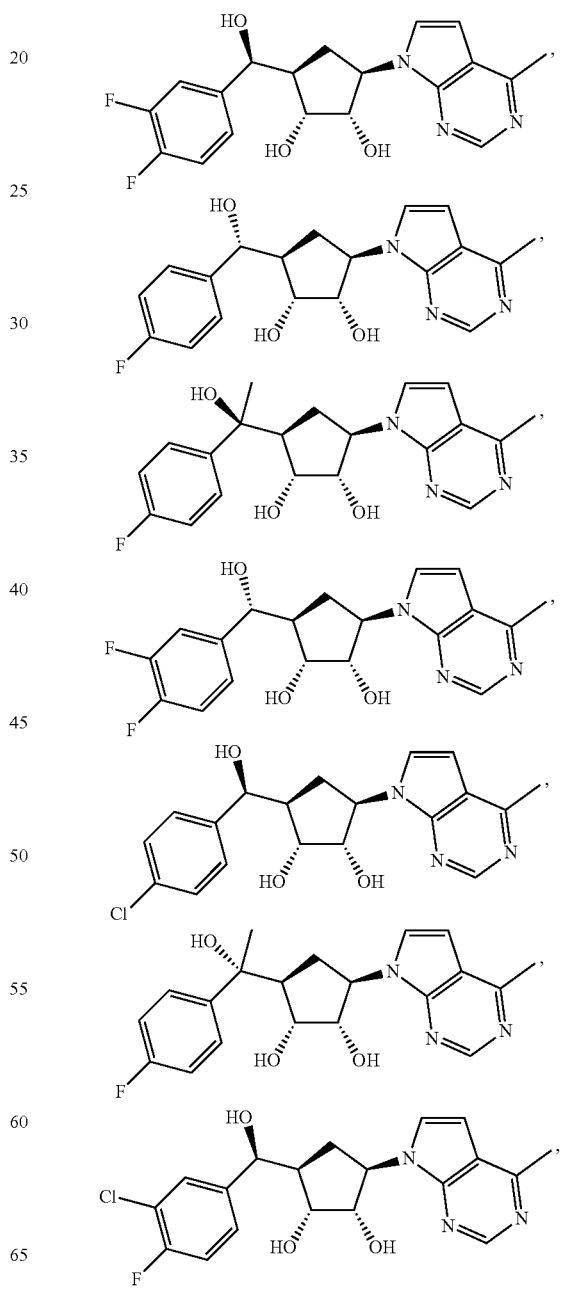

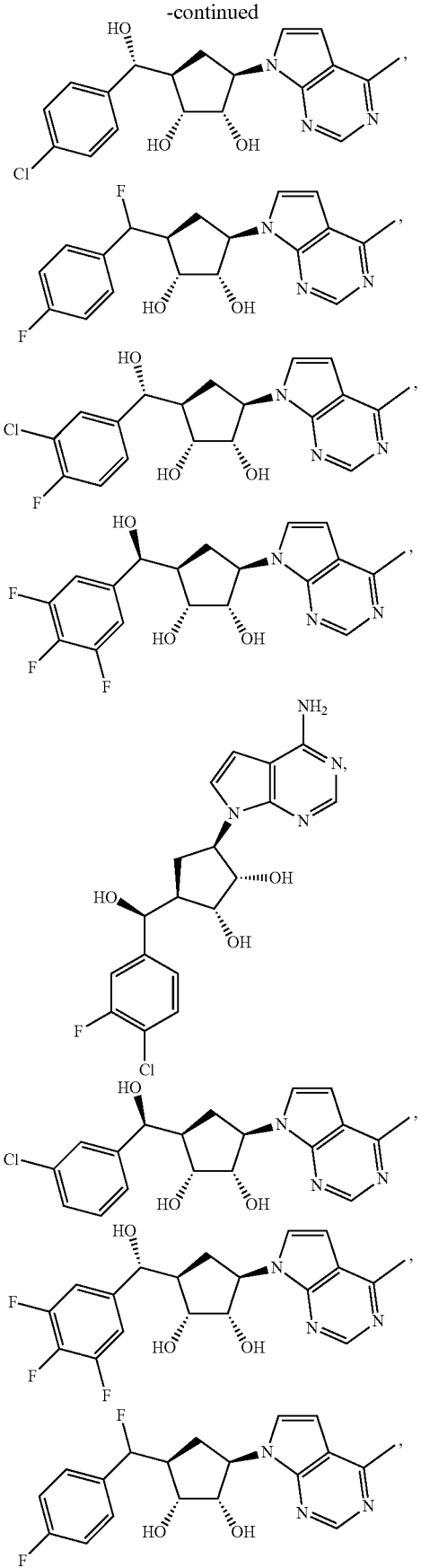
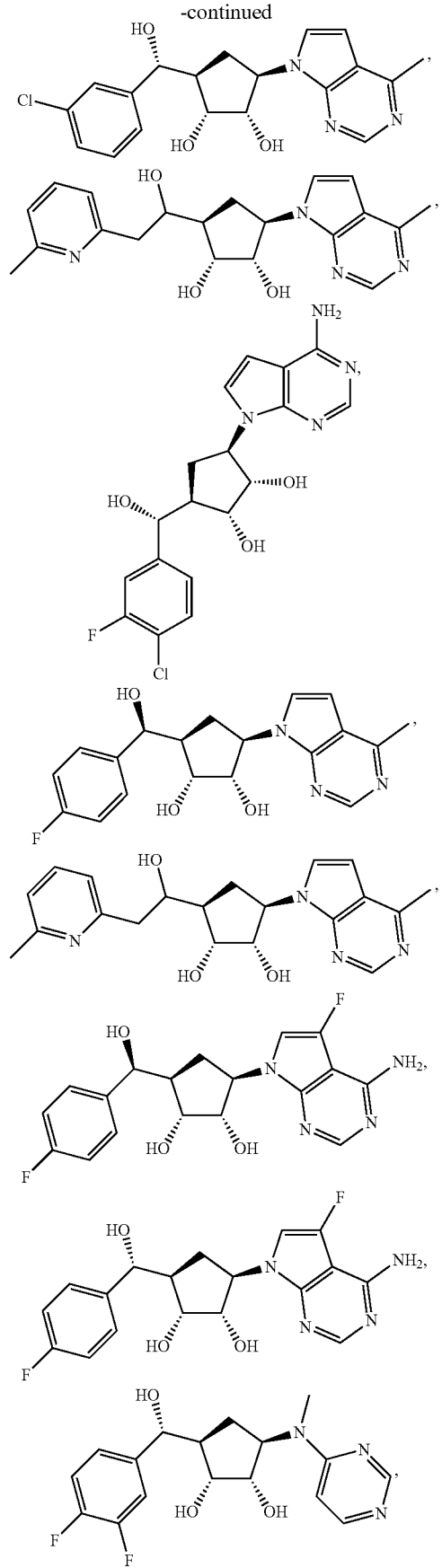

-continued
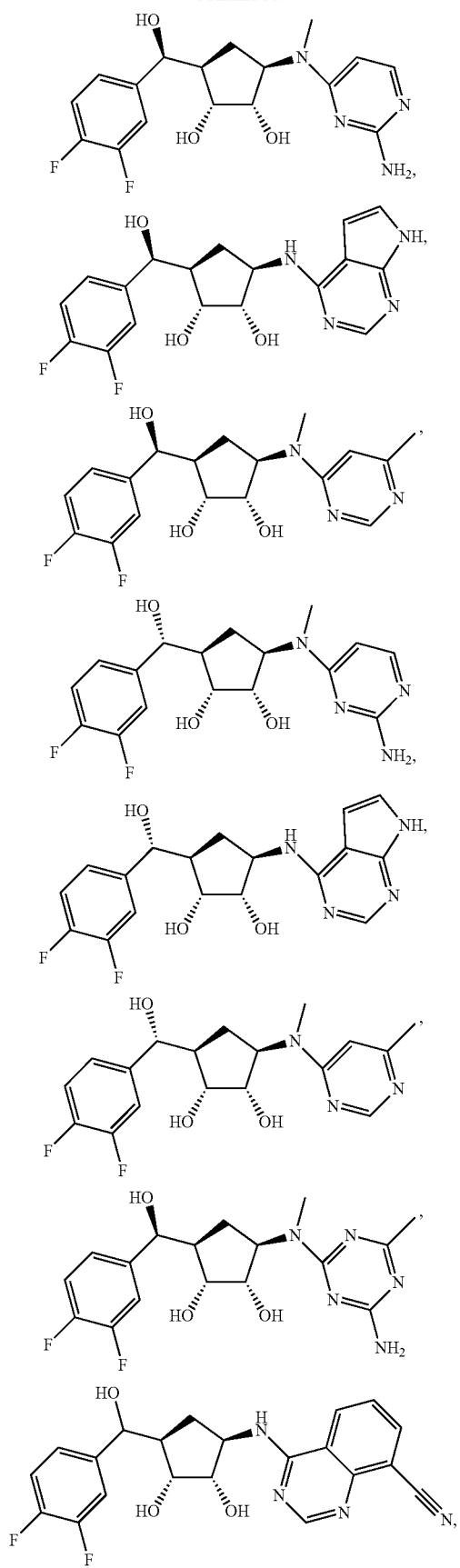
-continued
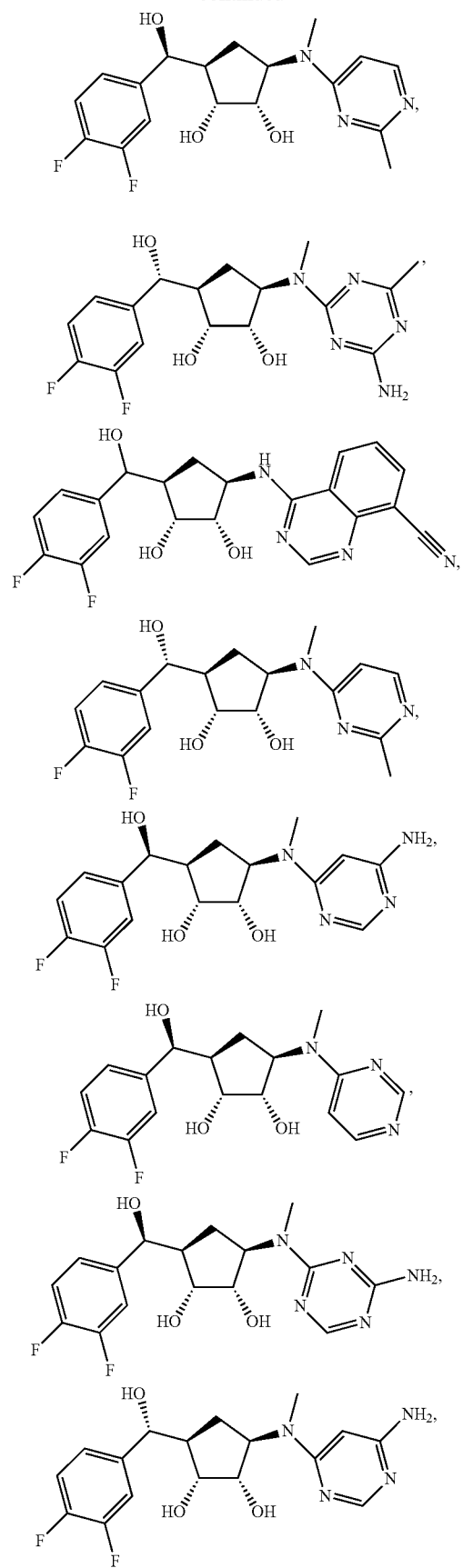

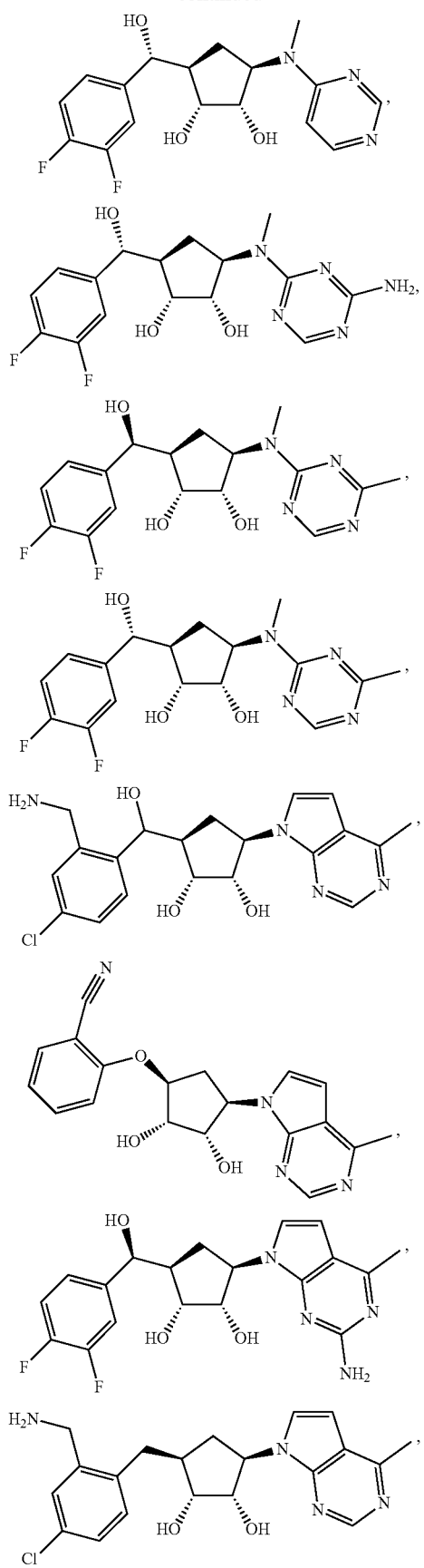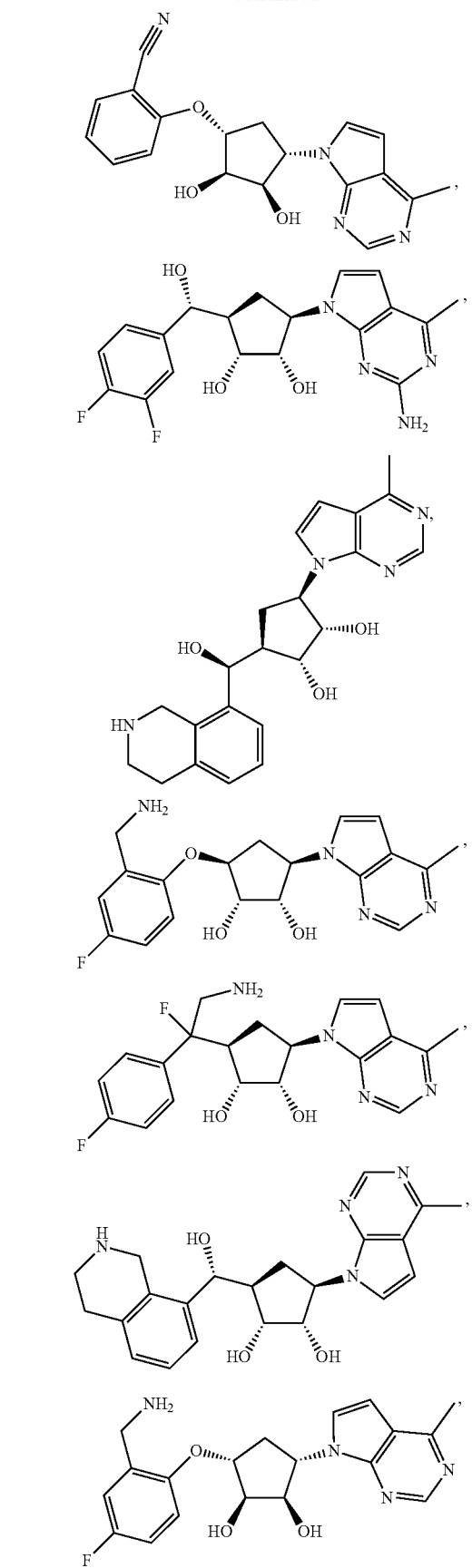

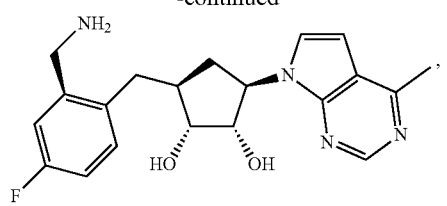
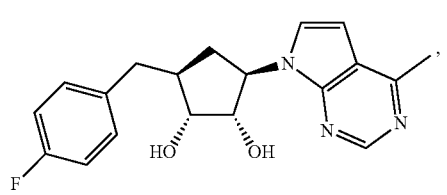
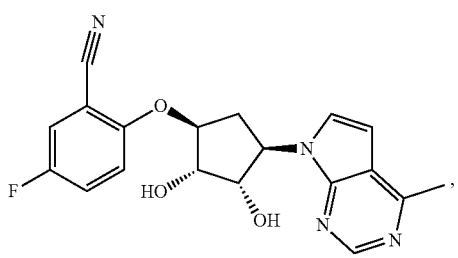
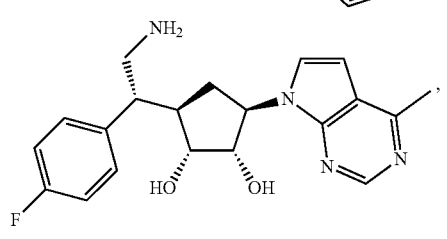
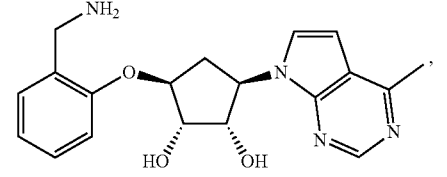
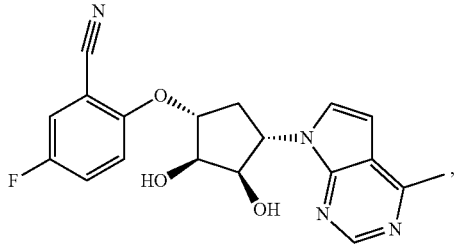
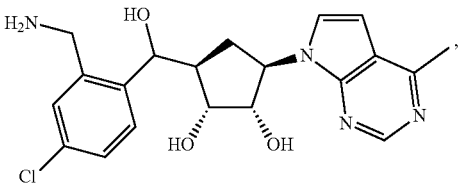
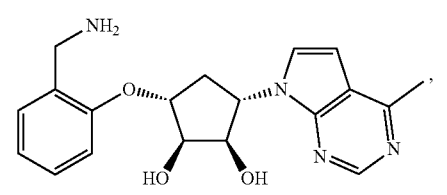
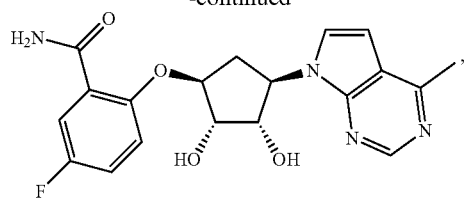
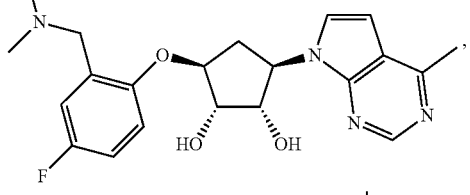
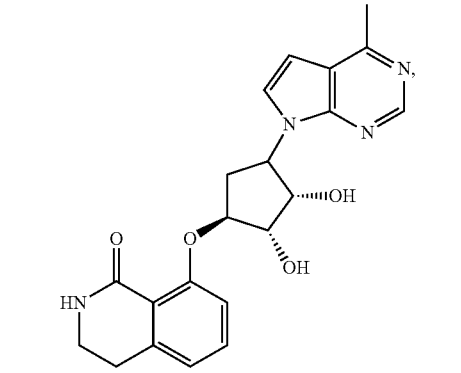
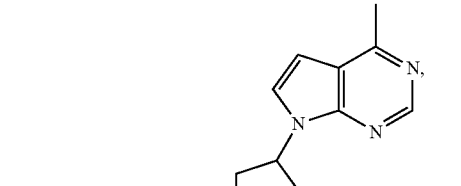
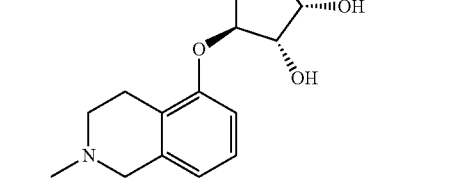
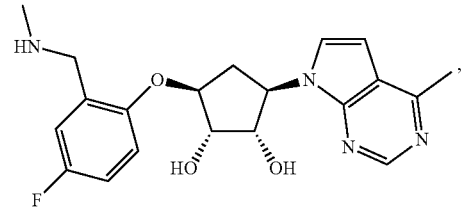
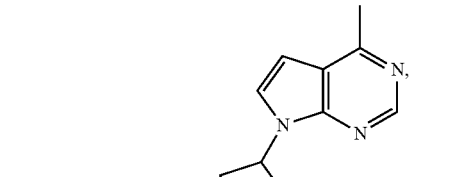
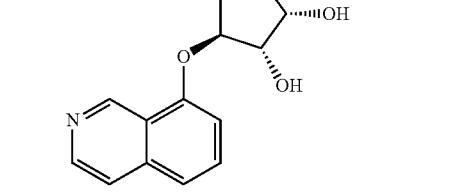

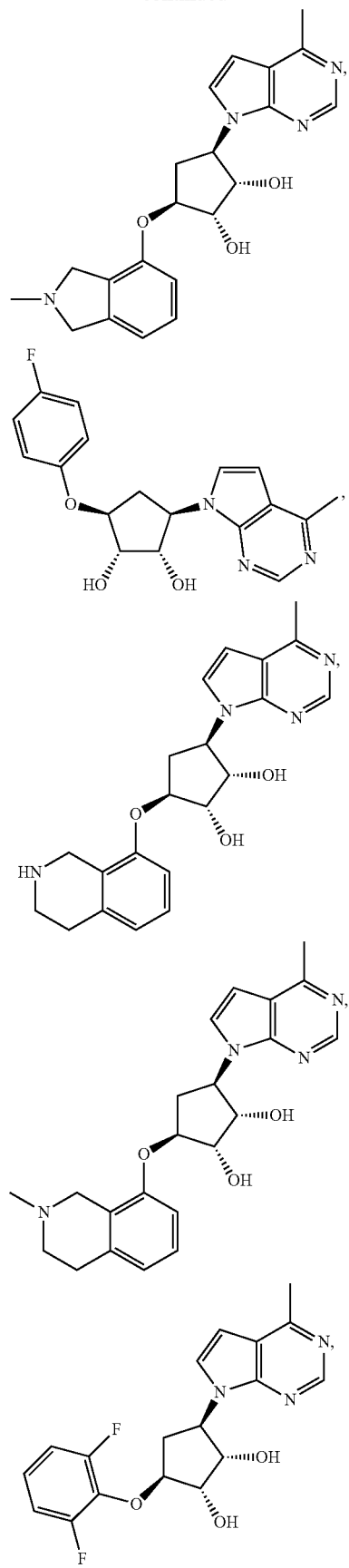
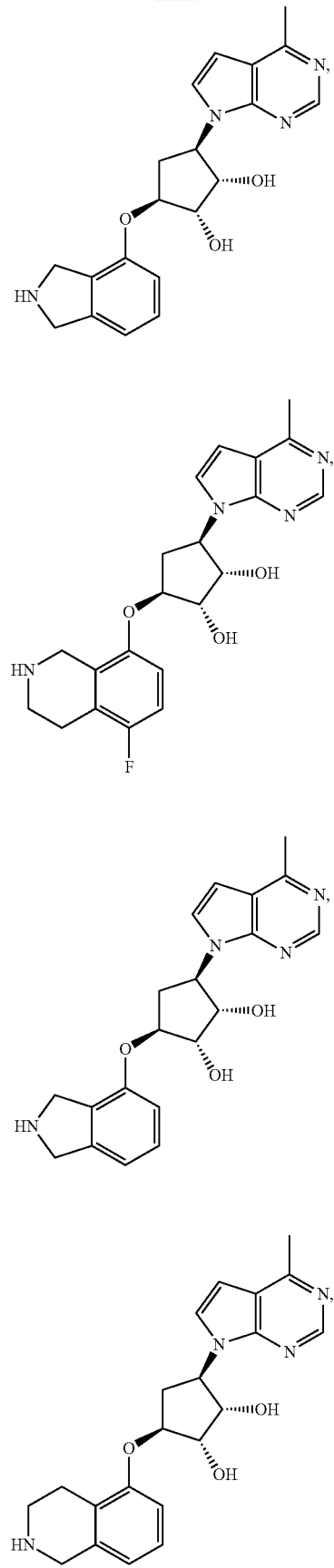

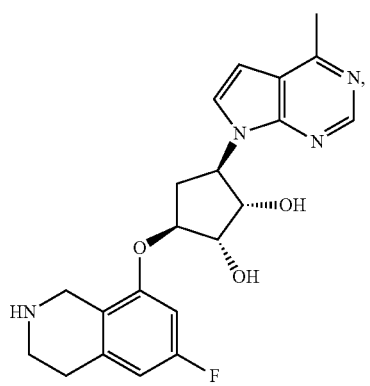
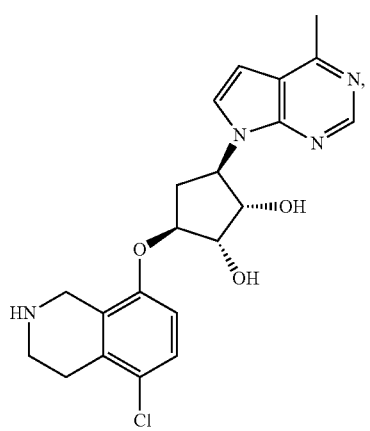
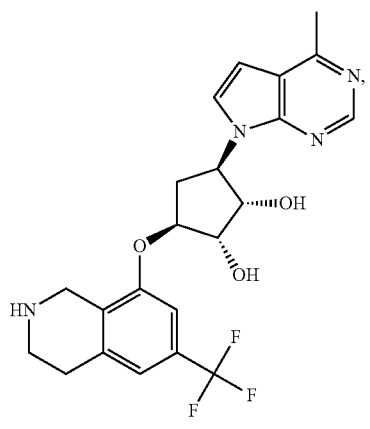
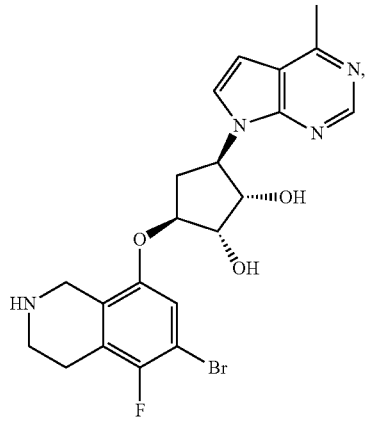
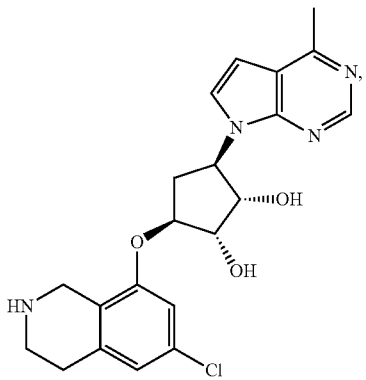
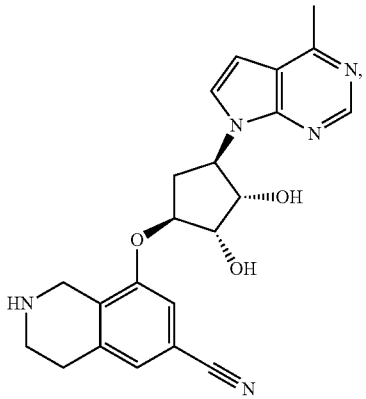
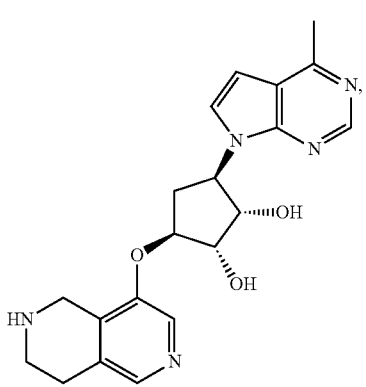
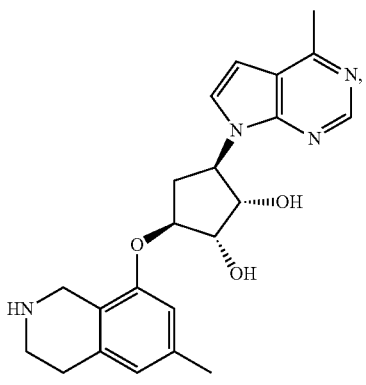

-continued
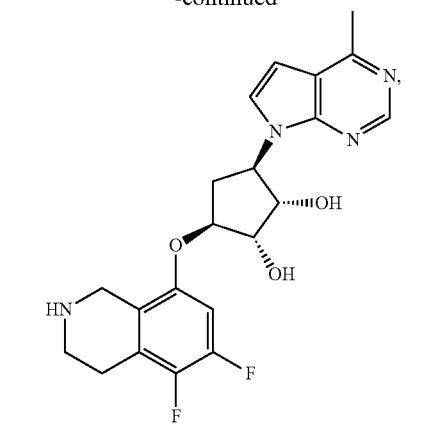
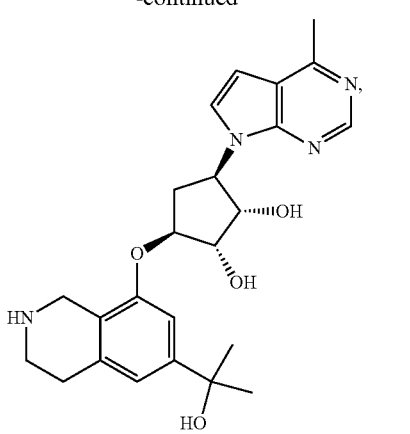
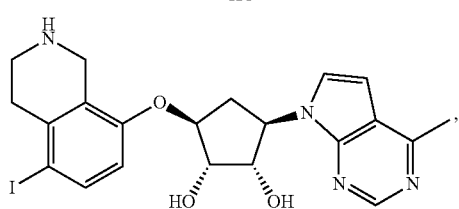
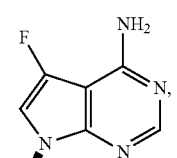
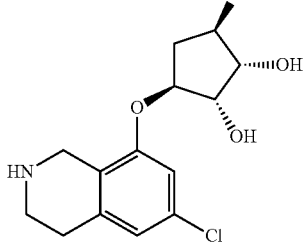
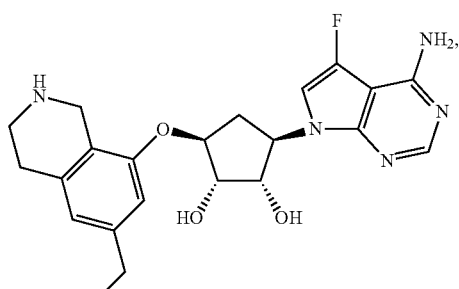
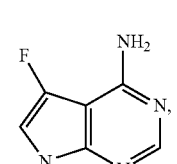
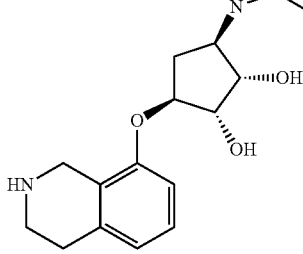

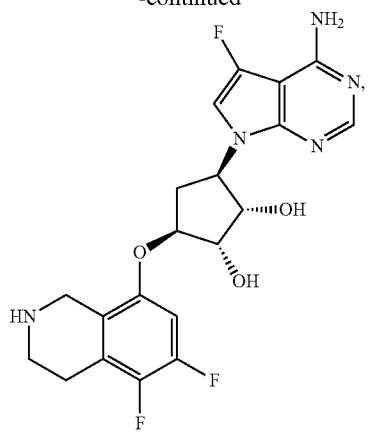
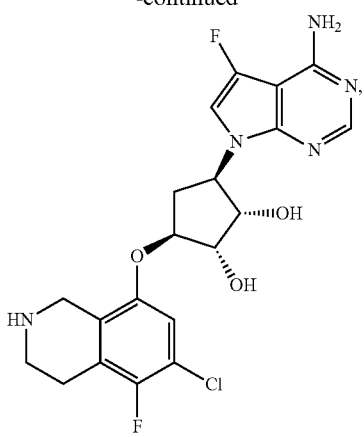

35
-continued
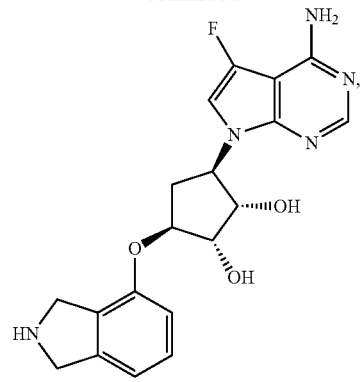
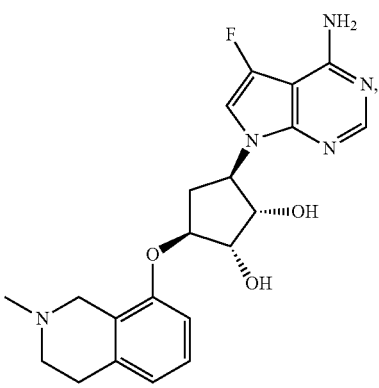
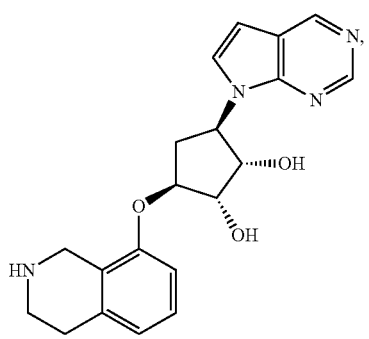
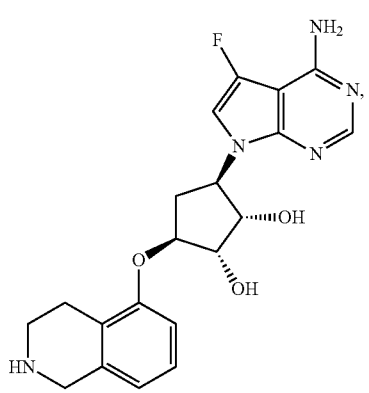
36
-continued
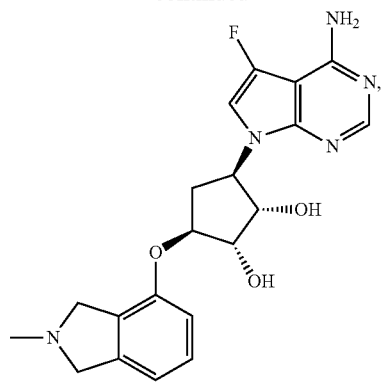
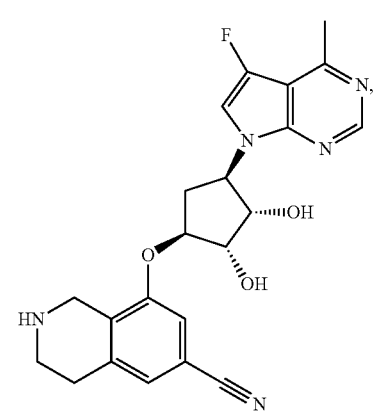
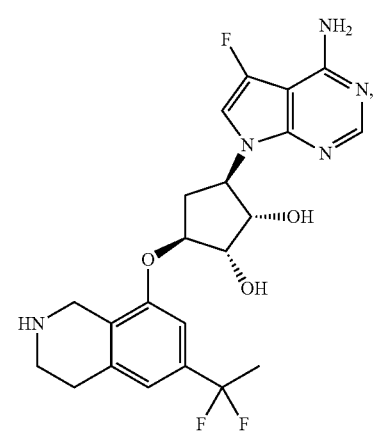
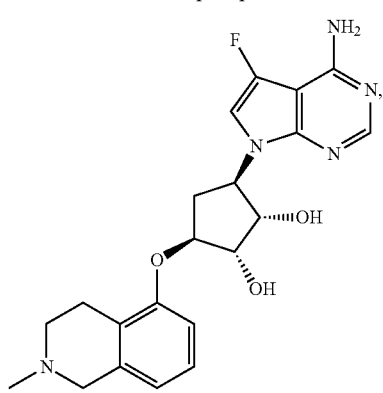

37
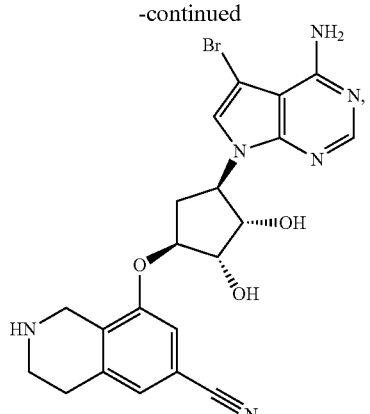
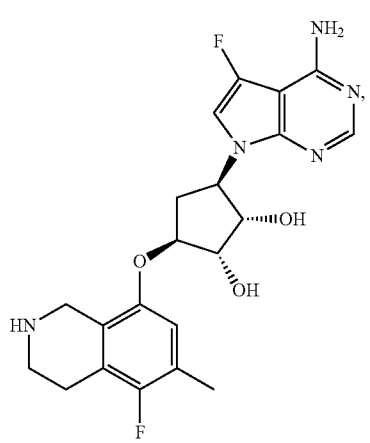
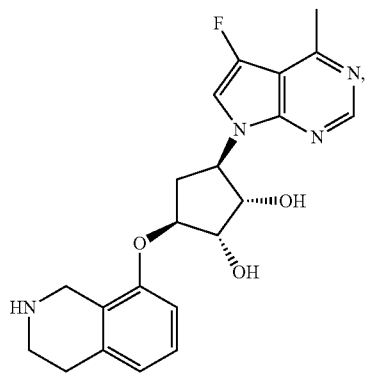
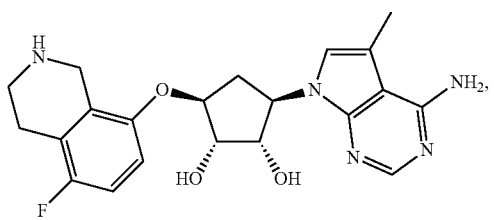
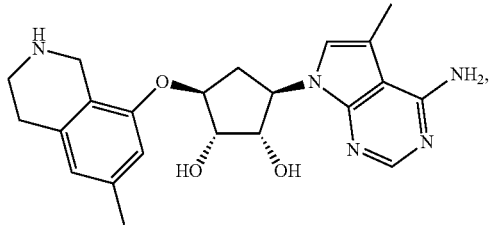
38
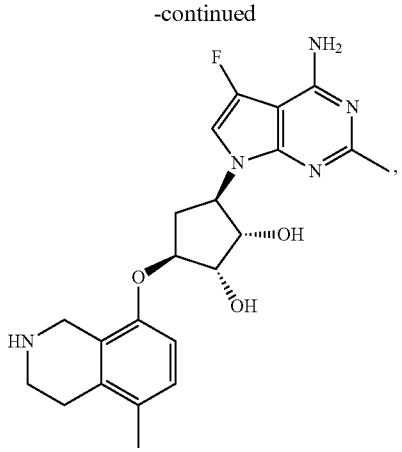
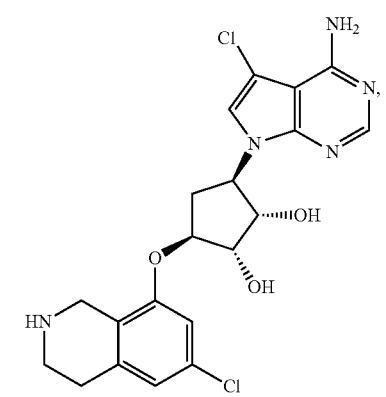
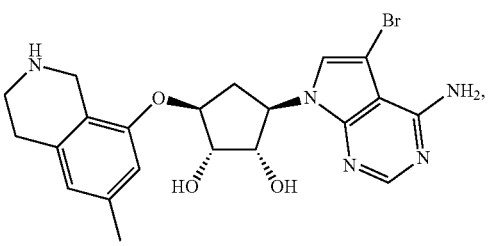
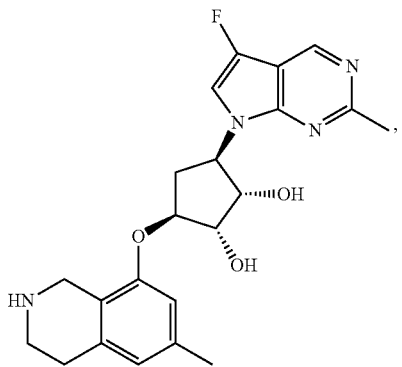

39
-continued
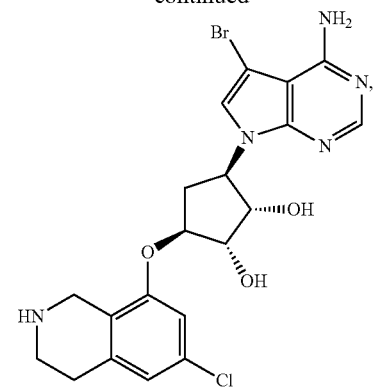
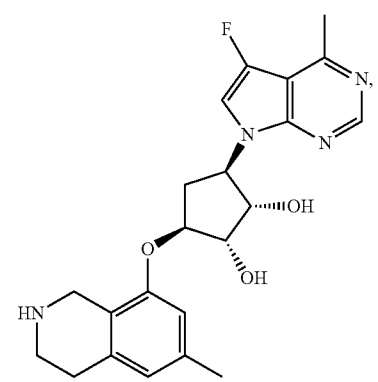
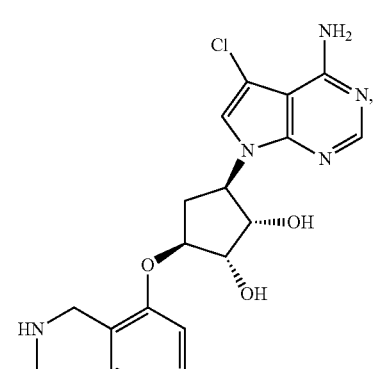
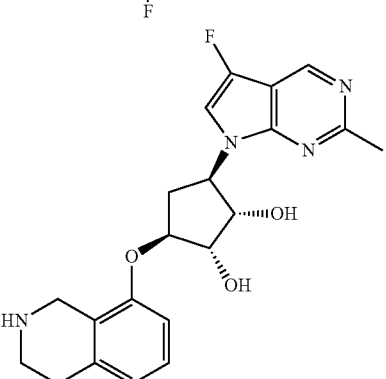
40
-continued
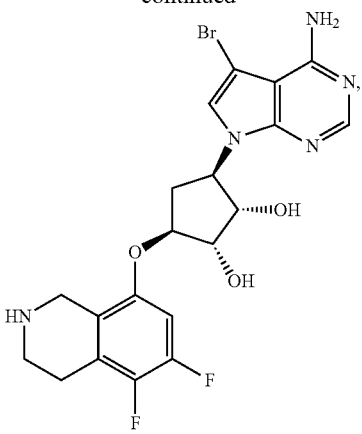
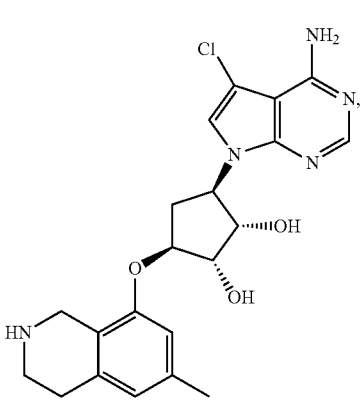
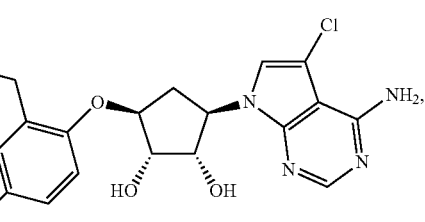
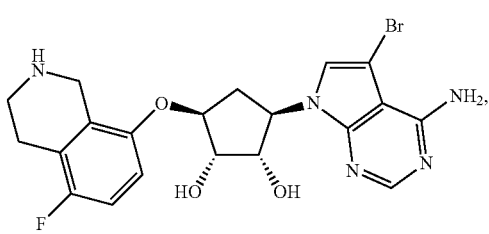
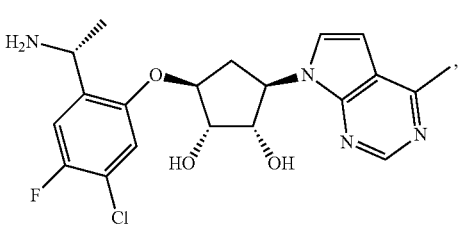

-continued
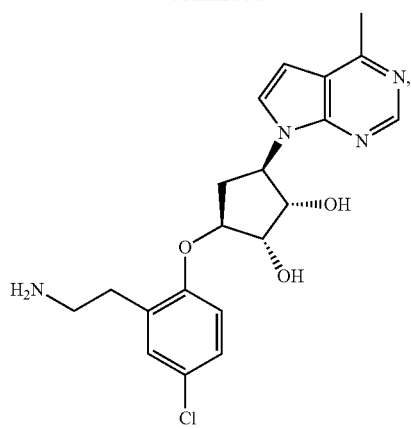
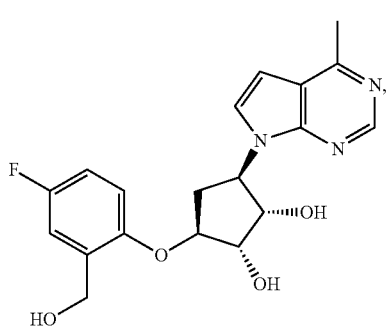
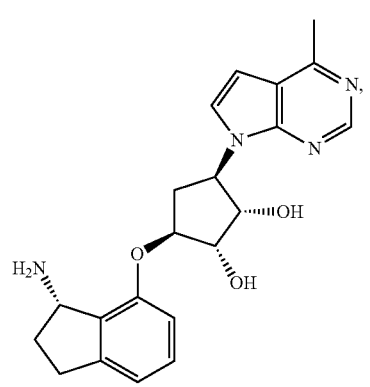
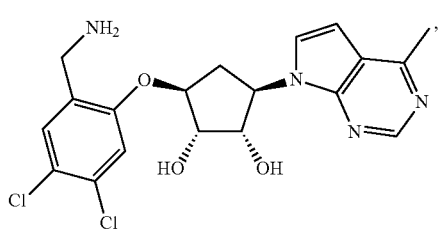
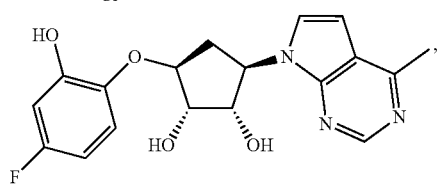
-continued
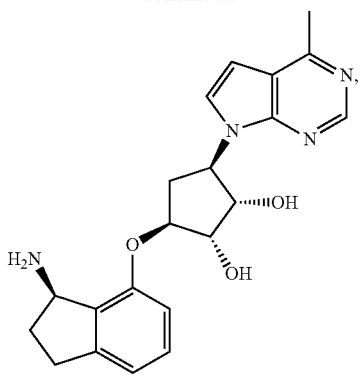
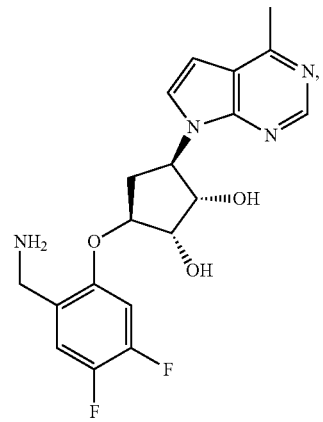

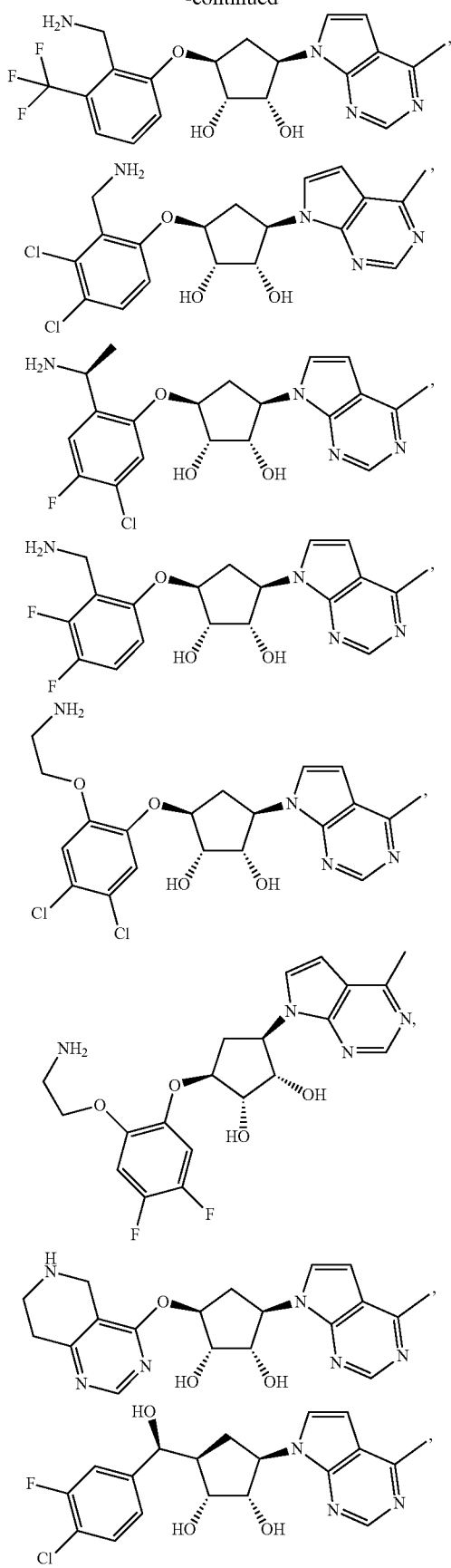
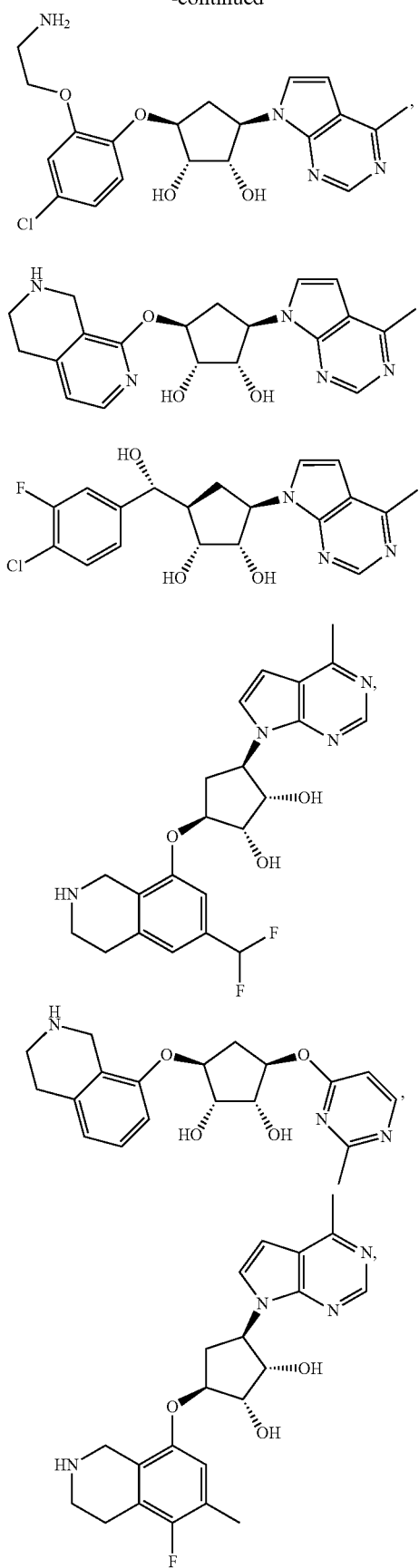

45
-continued
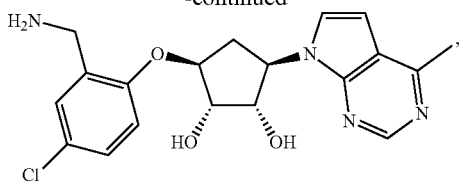
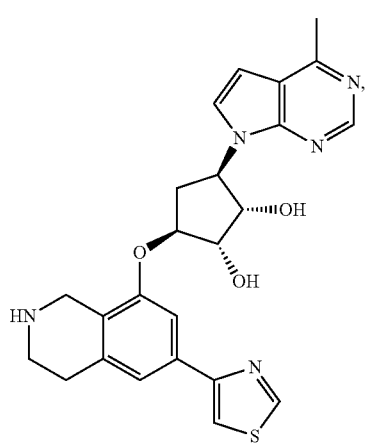
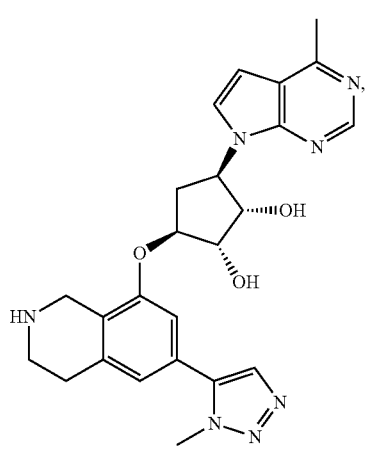
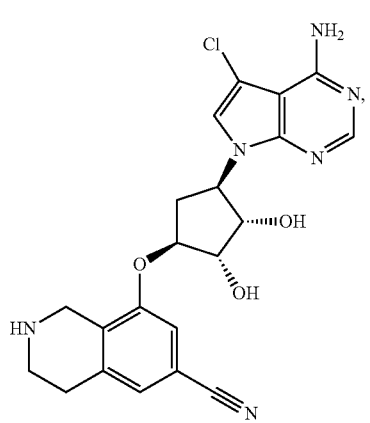
46
-continued
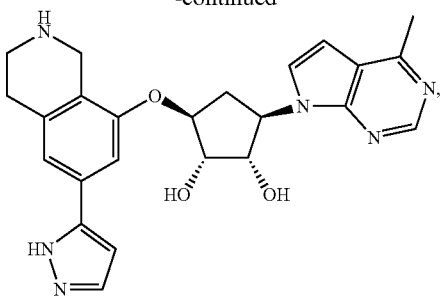
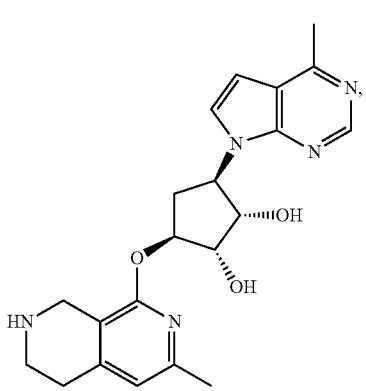
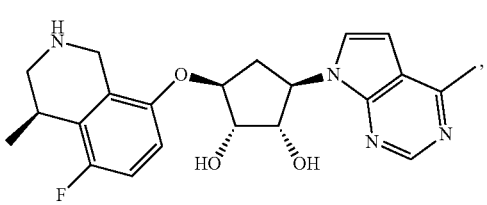
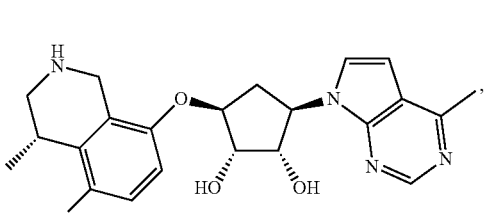
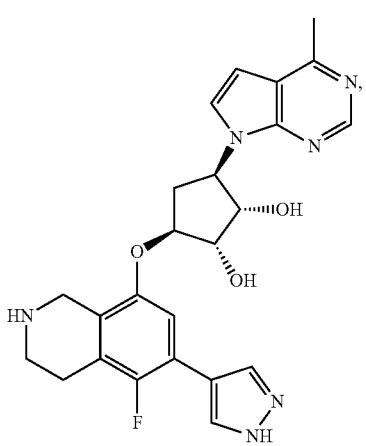

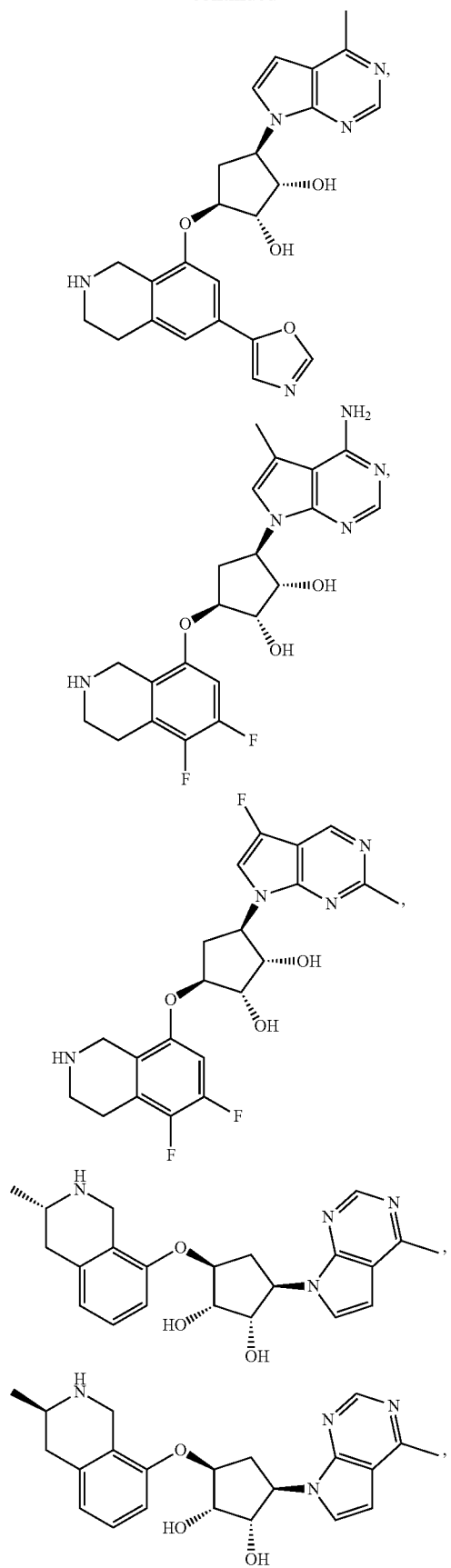
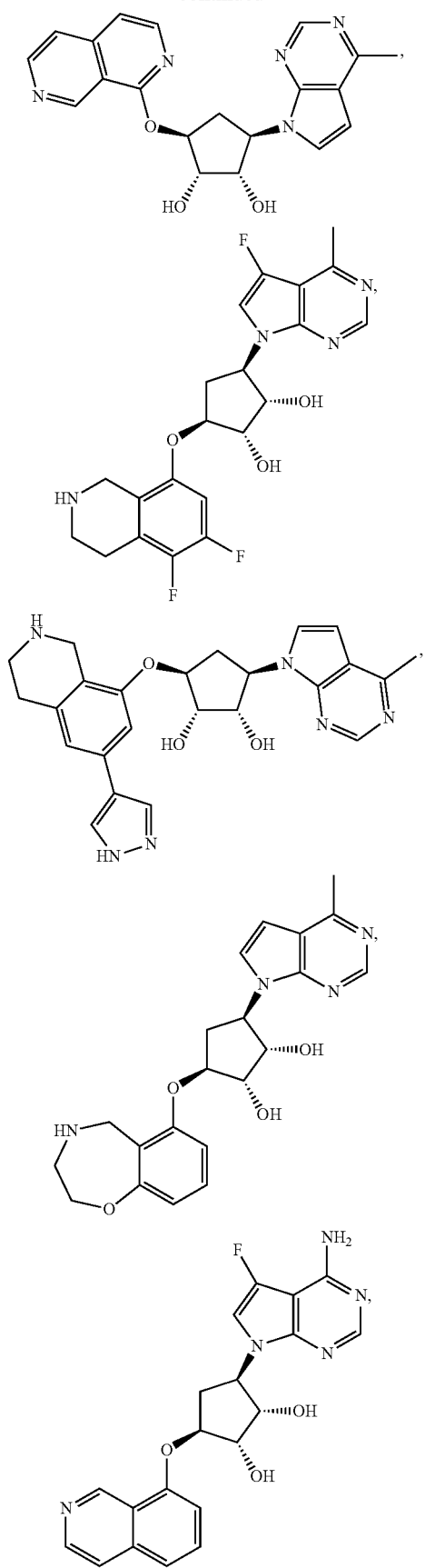

-continued
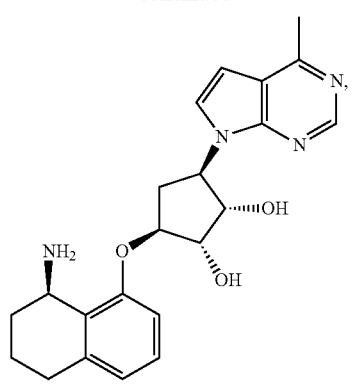
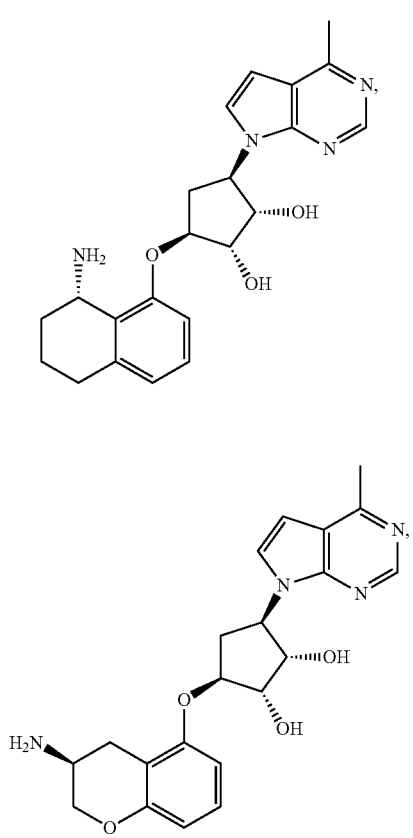
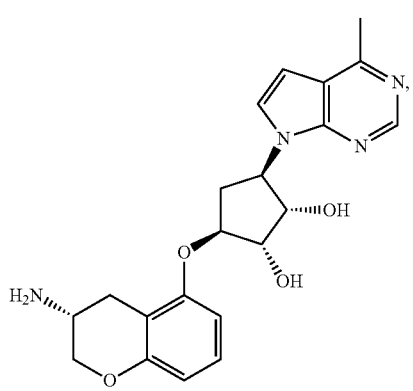
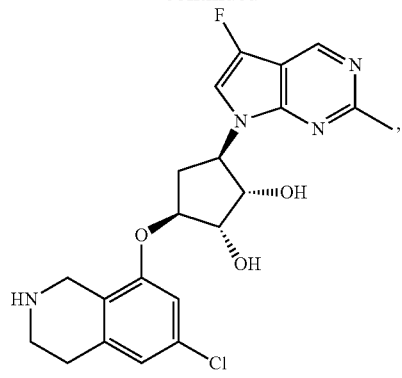
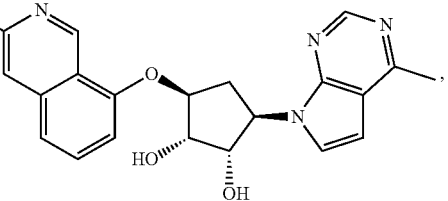
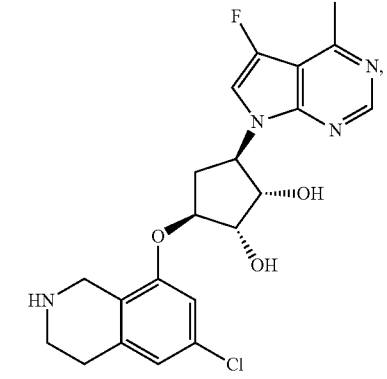
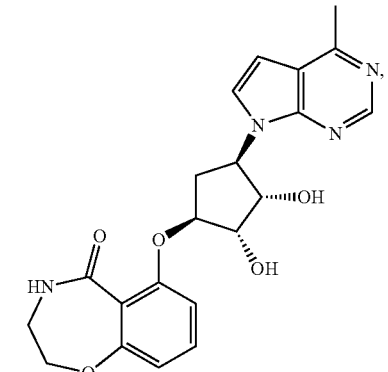
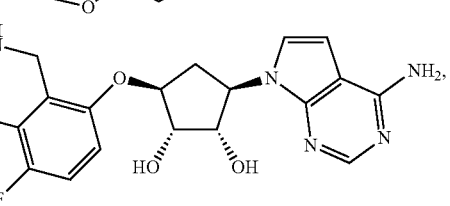

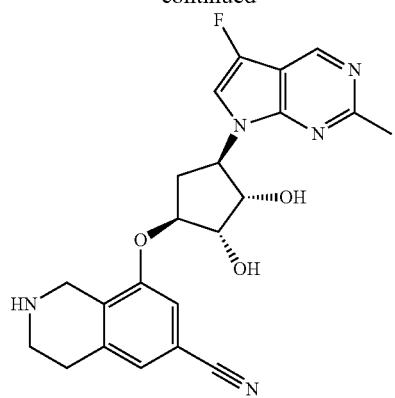
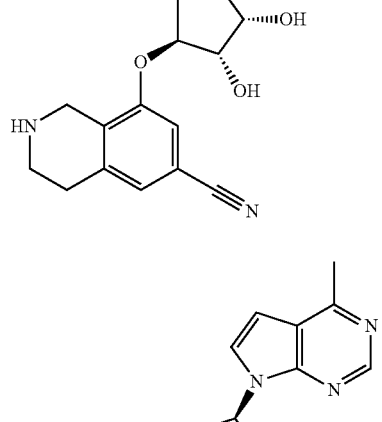
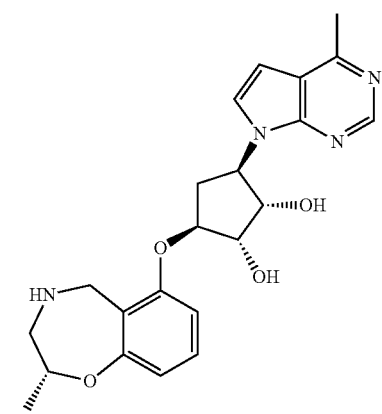
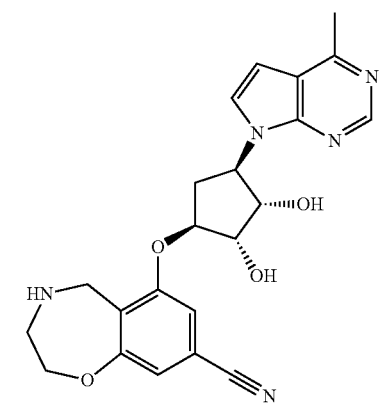
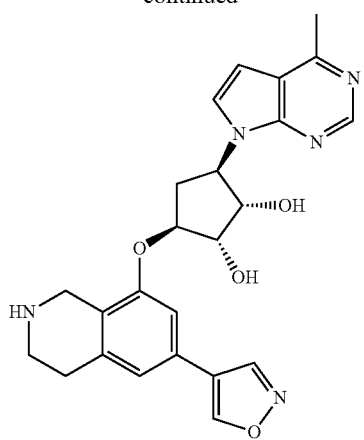
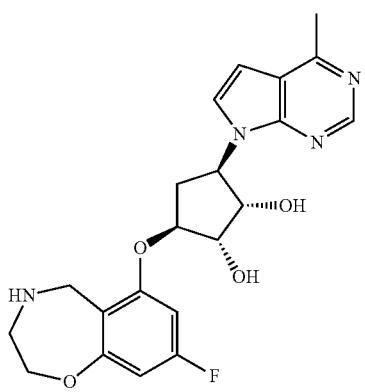
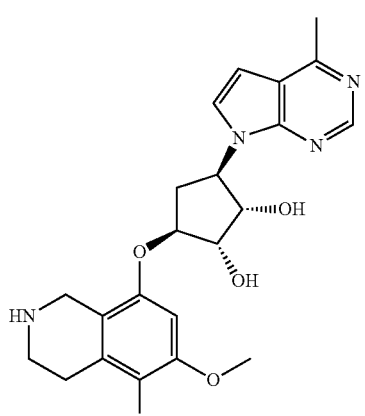
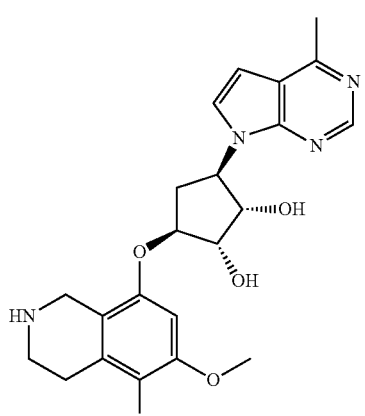

53
-continued
54
-continued
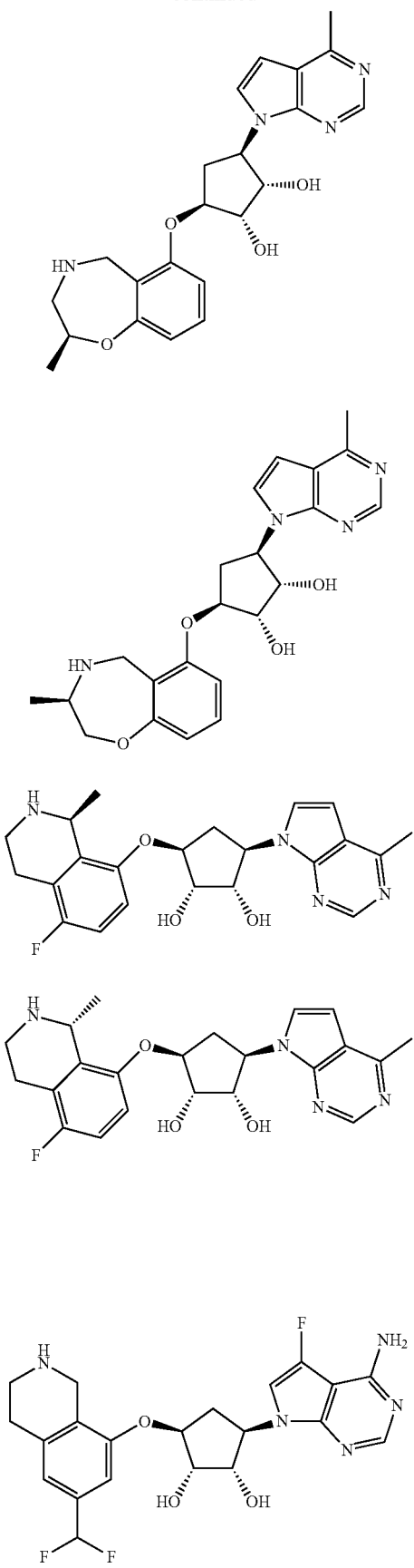
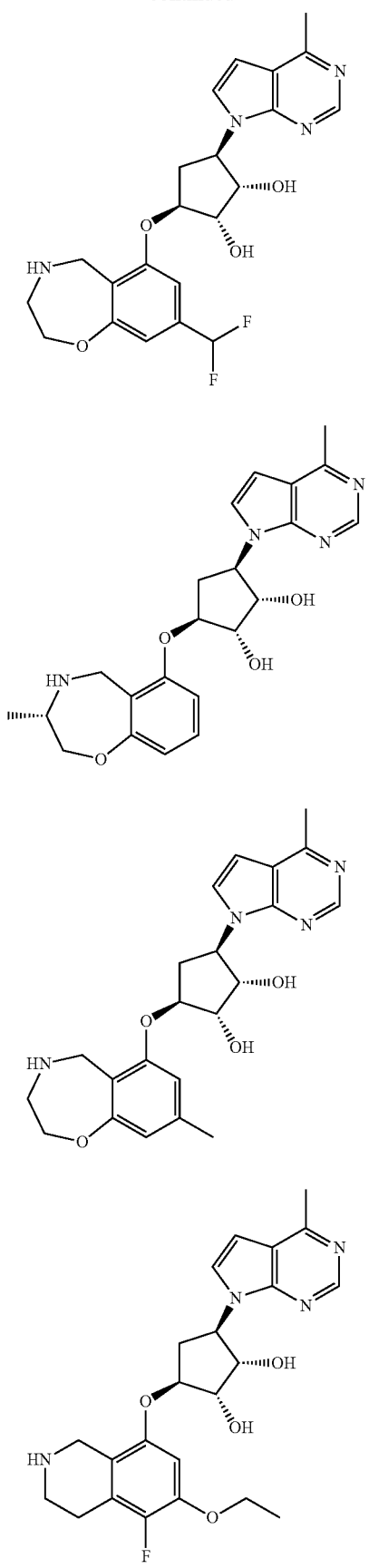 [SMILES: Cc1ncnc2c1ccn2[C@@H]1C[C@H](Oc2cc(C(F)F)cc3c2CNCCO3)[C@@H](O)[C@H]1O ; Cc1ncnc2c1ccn2[C@@H]1C[C@H](Oc2cccc3c2CN[C@@H](C)CO3)[C@@H](O)[C@H]1O ; Cc1cc2c(c(O[C@H]3C[C@@H](n4ccc5c(C)ncnc54)[C@H](O)[C@@H]3O)c1)CNCCO2 ; CCOc1cc(O[C@H]2C[C@@H](n3ccc4c(C)ncnc43)[C@H](O)[C@@H]2O)c2c(c1F)CCNC2]

55
-continued
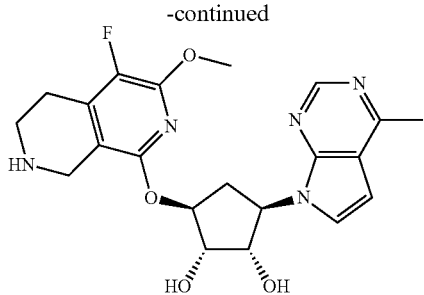
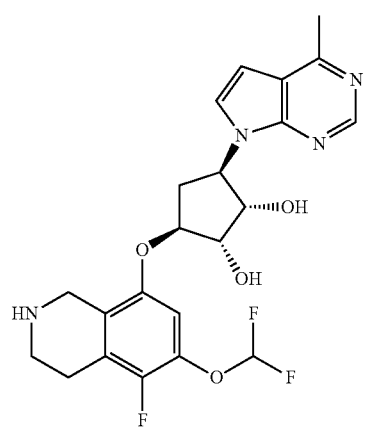
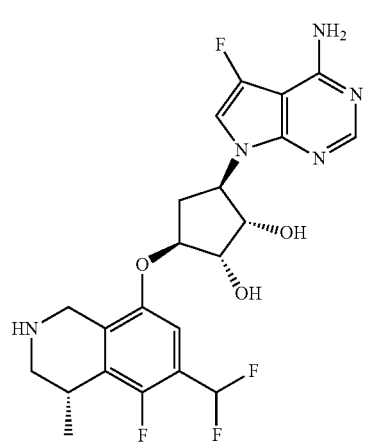
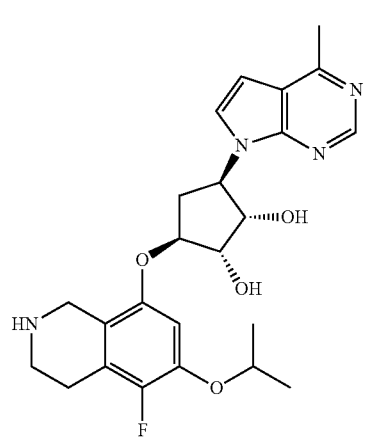
56
-continued
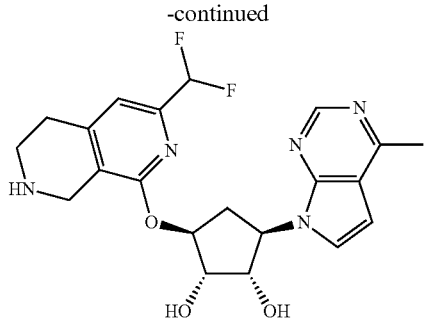
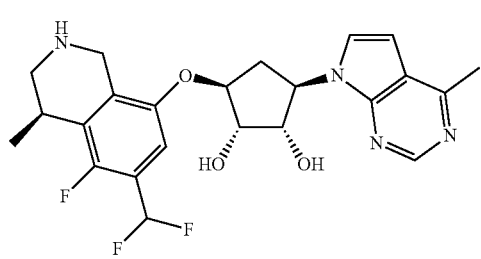
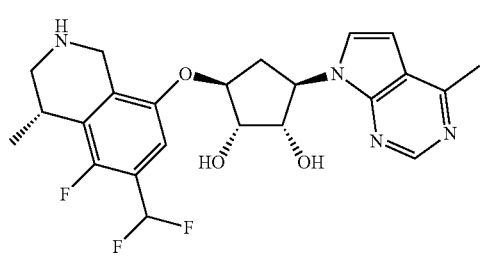
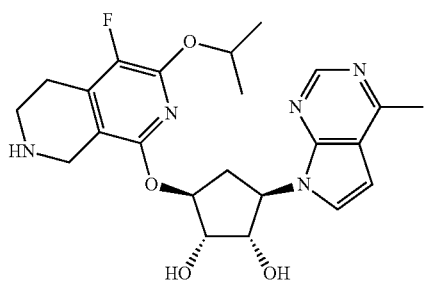
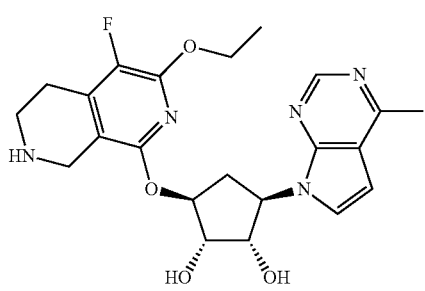

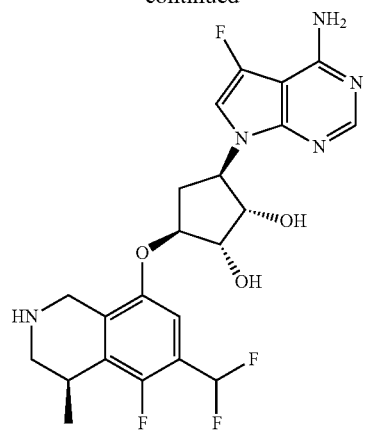
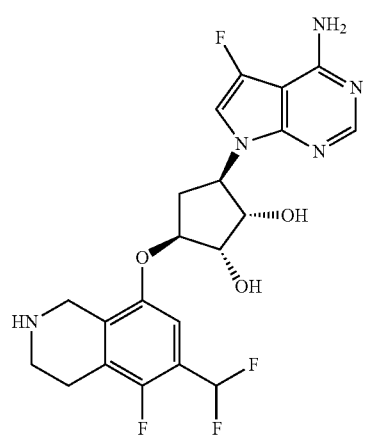 [SMILES: Nc1ncnc2c1c(F)cn2[C@@H]1C[C@H](Oc2cc(C(F)F)c(F)c3c2CNCC3)[C@@H](O)[C@H]1O]
or a pharmaceutically acceptable salt thereof.
In certain embodiments of the present invention the compound is selected from:

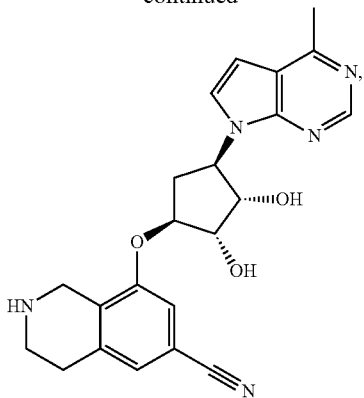
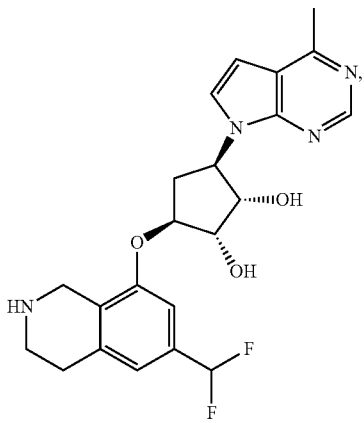
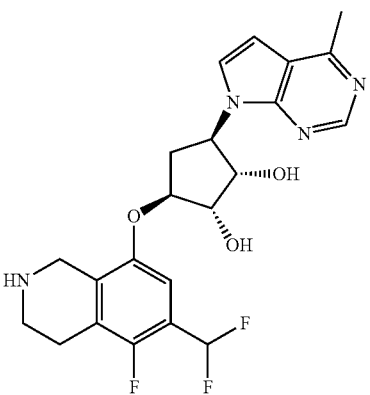

-continued
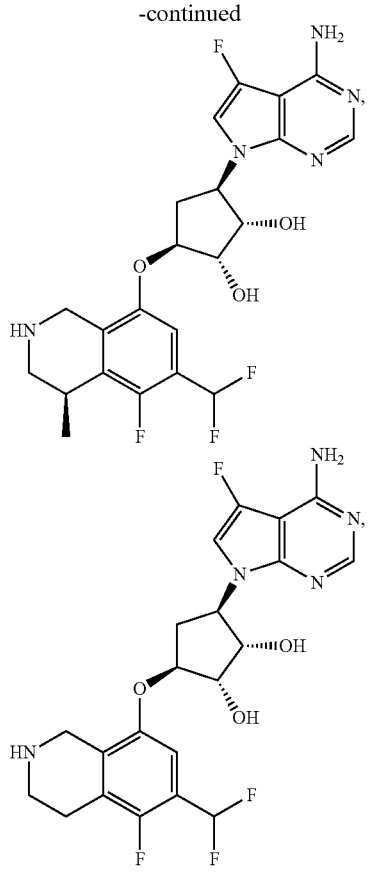
or a pharmaceutically acceptable salt thereof.
Further embodiments of the present invention include compounds selected from:
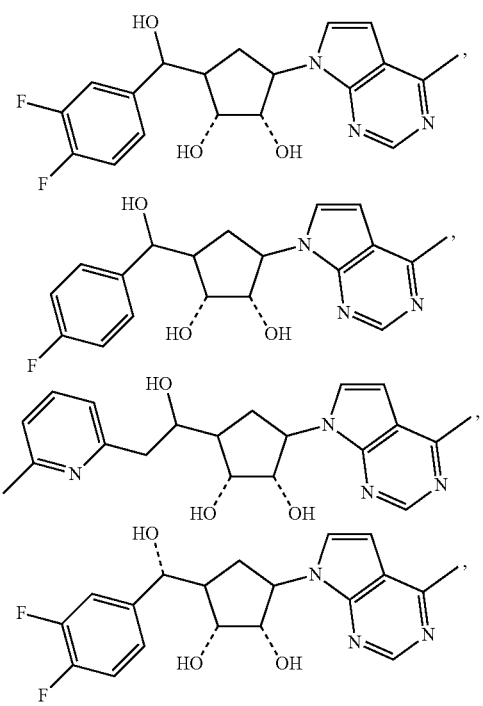
-continued
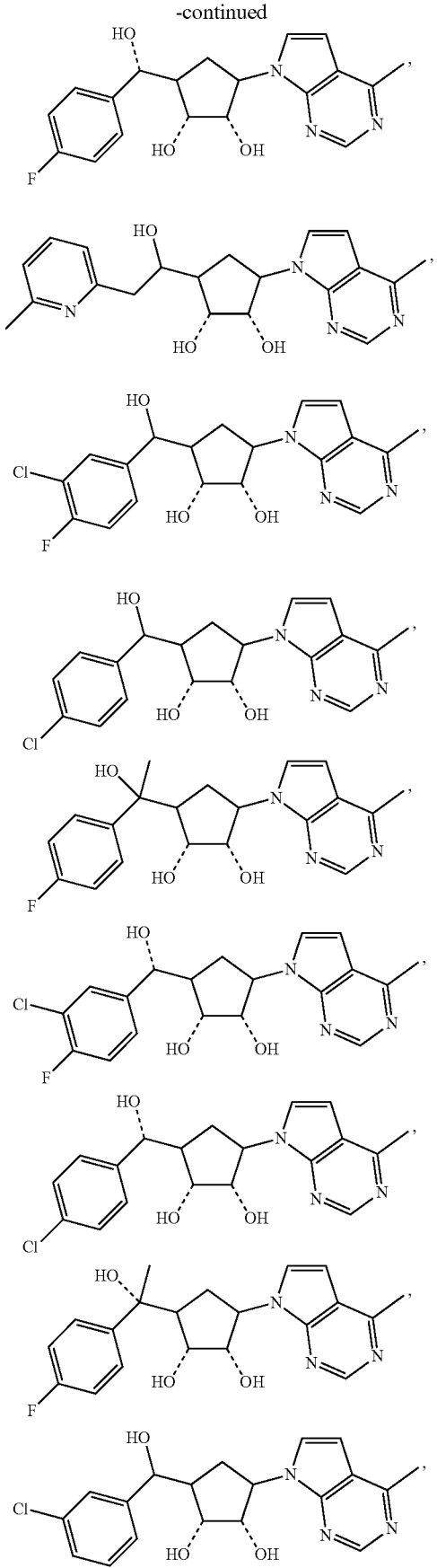

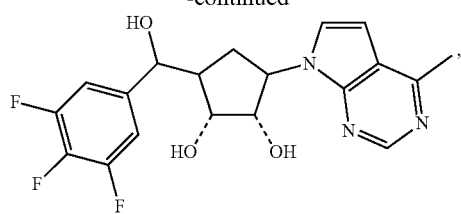
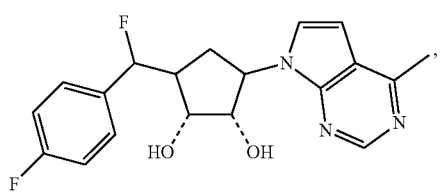
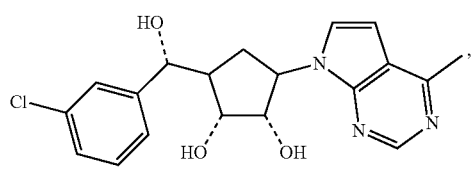
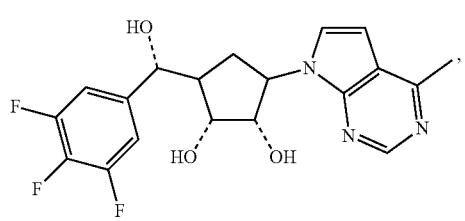
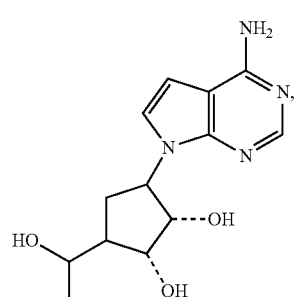
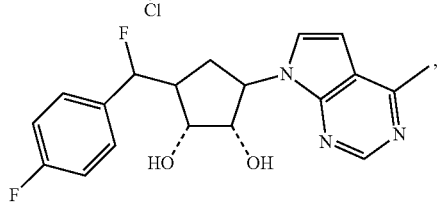
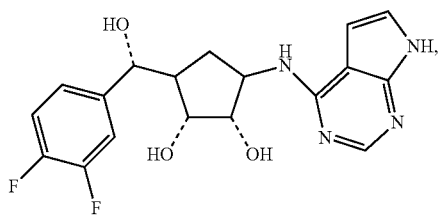
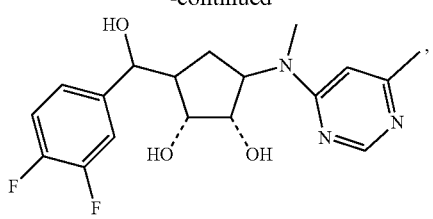
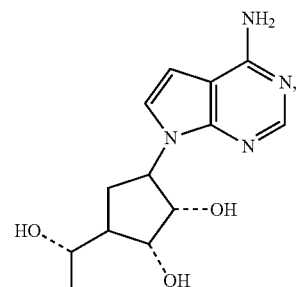
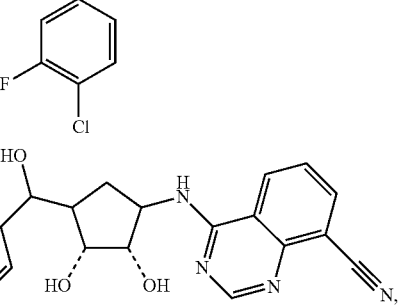
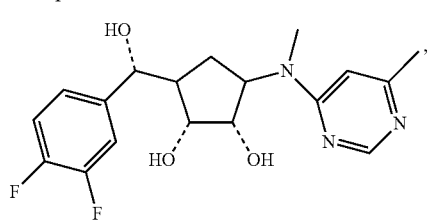
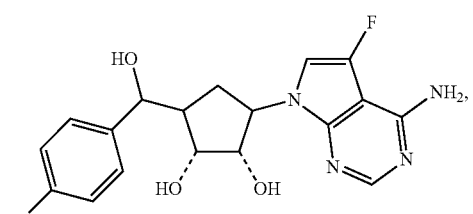
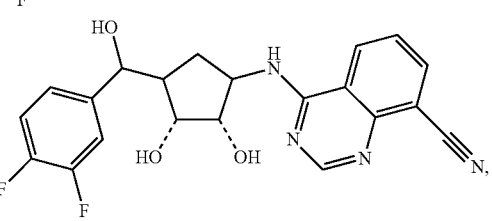
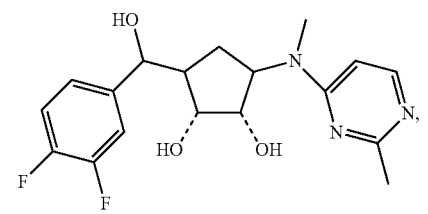

-continued
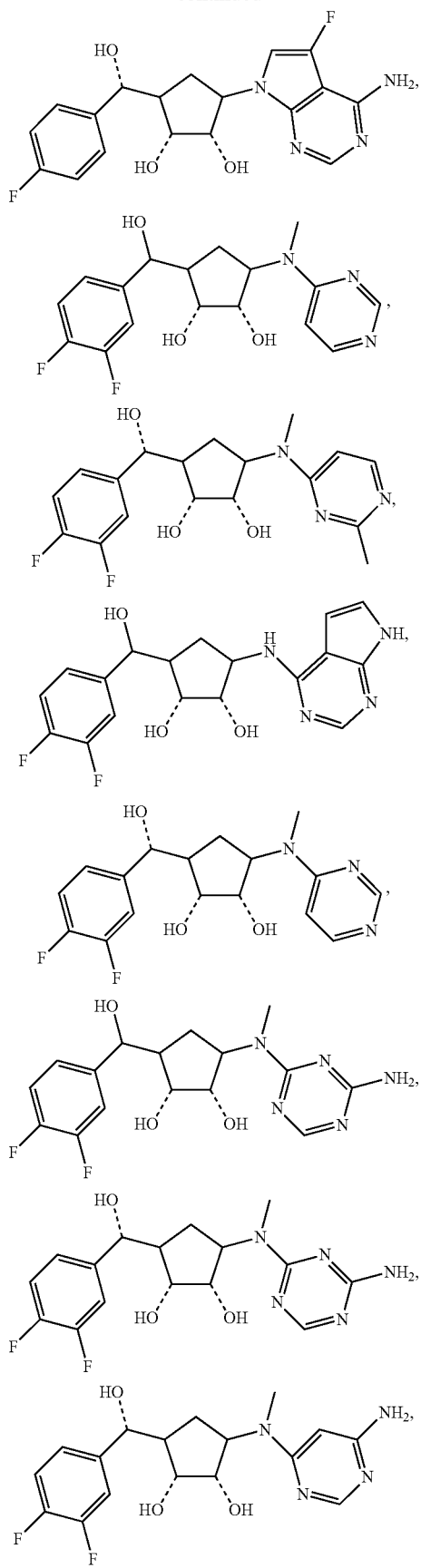
-continued
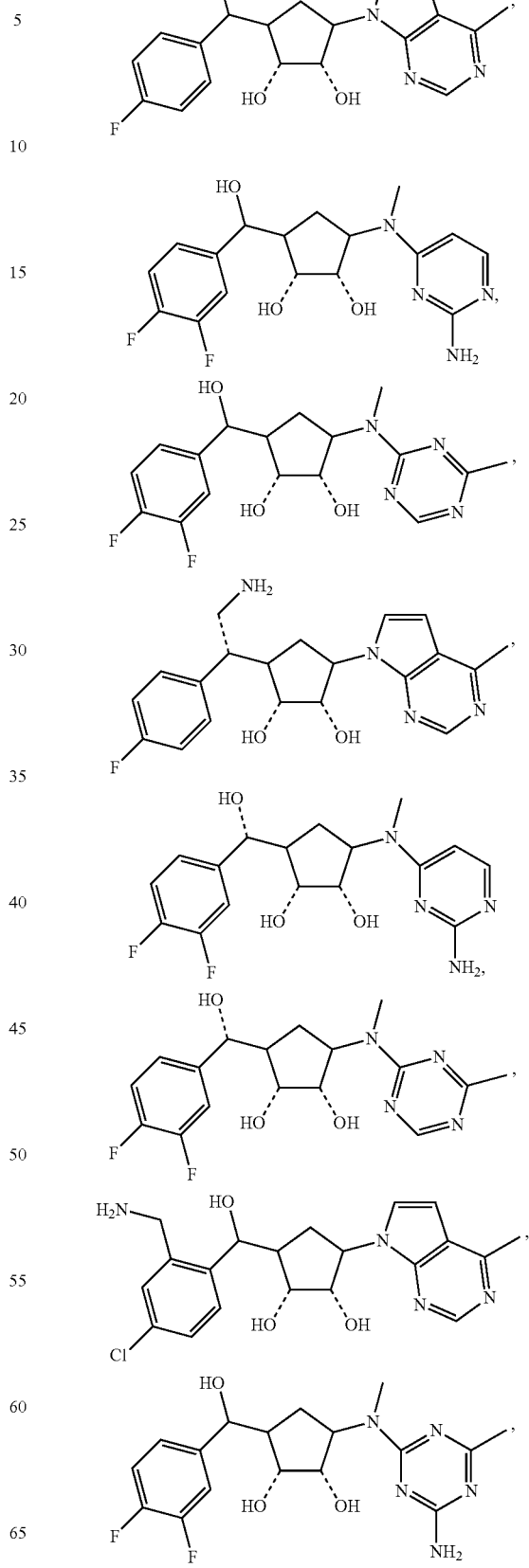

-continued
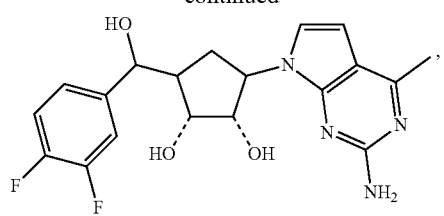
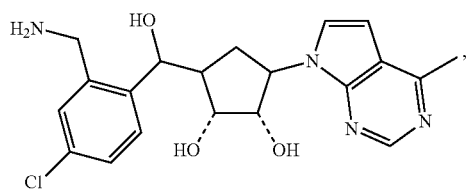
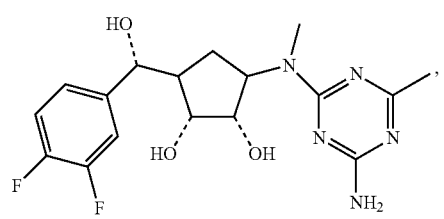
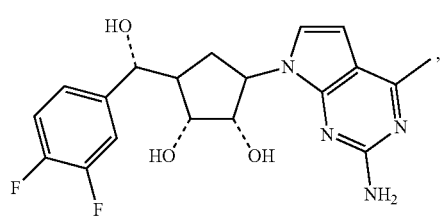
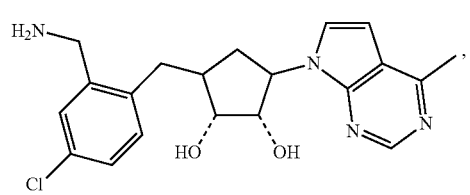
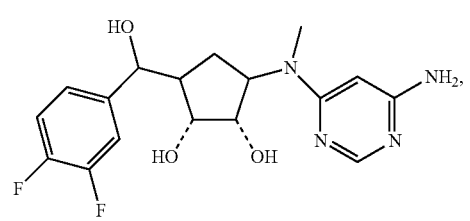
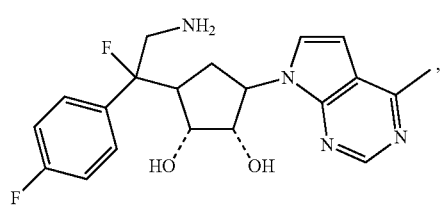
-continued
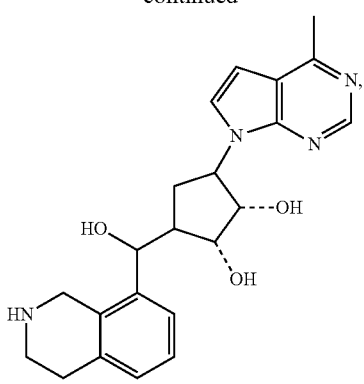
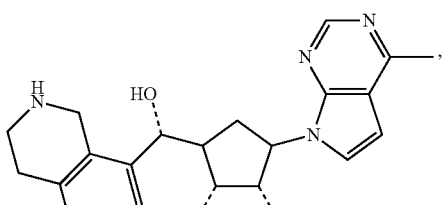
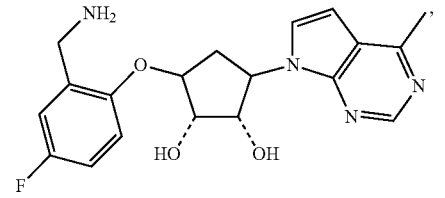
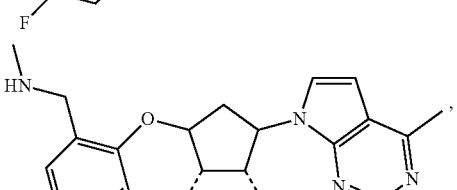
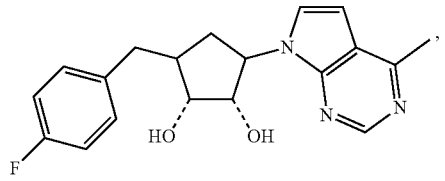
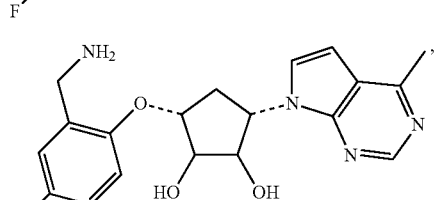

67
-continued
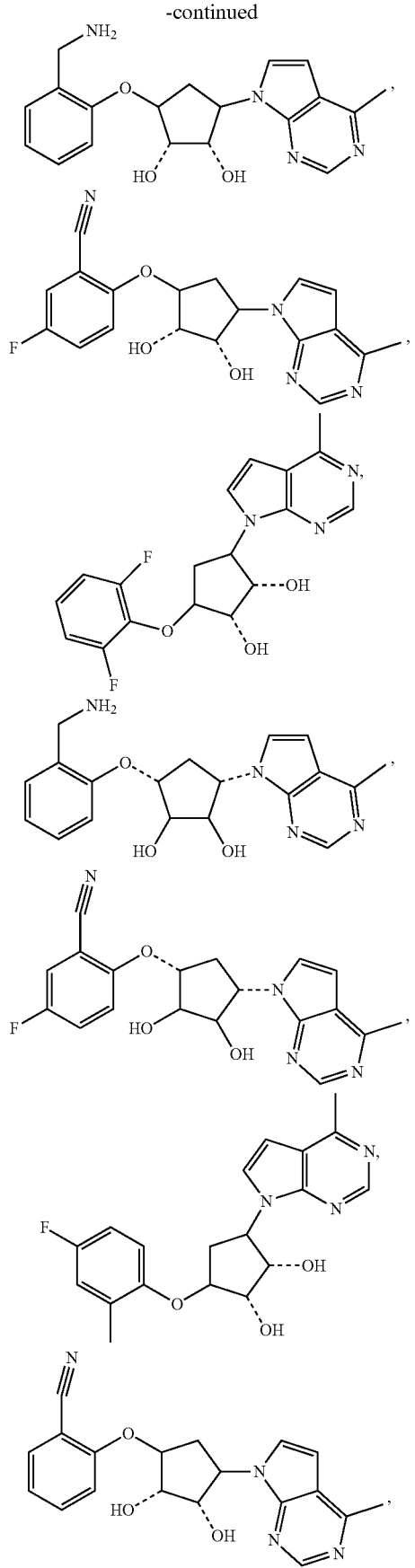
68
-continued
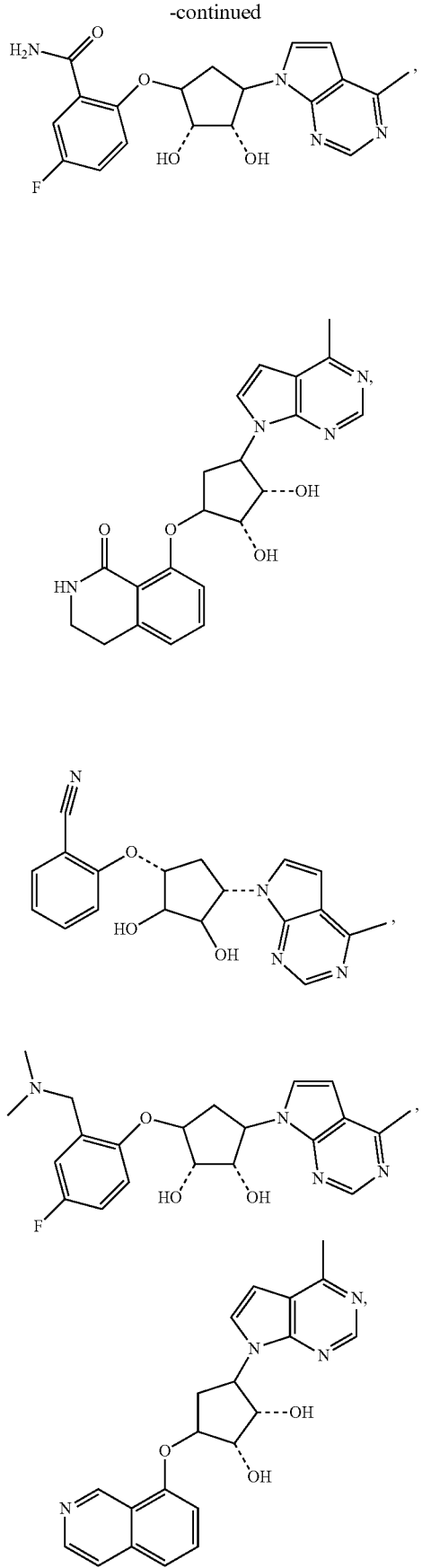

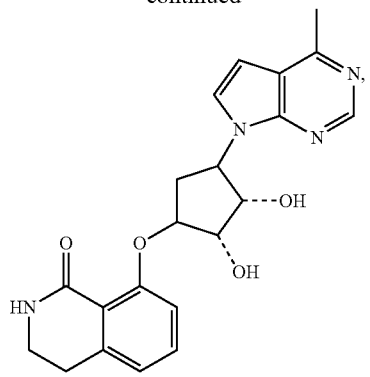
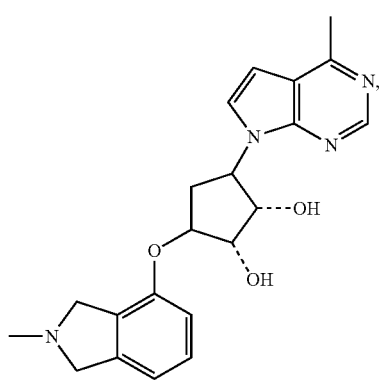
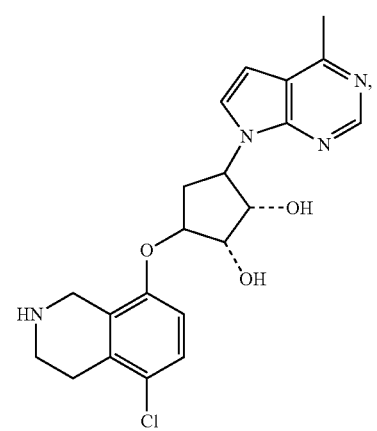
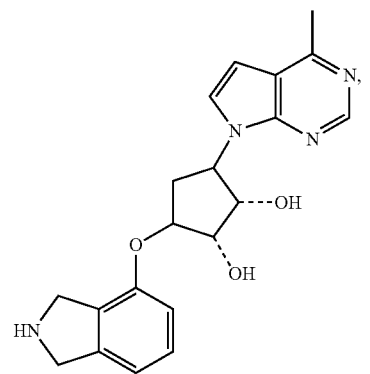
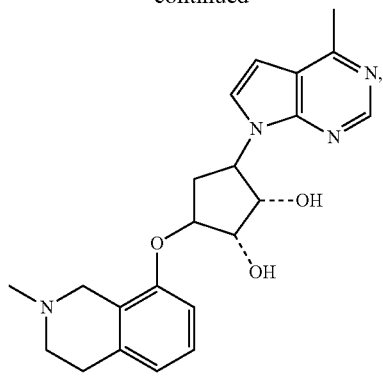
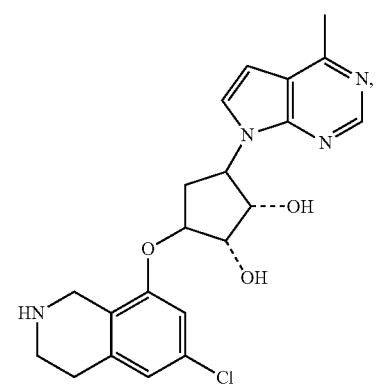
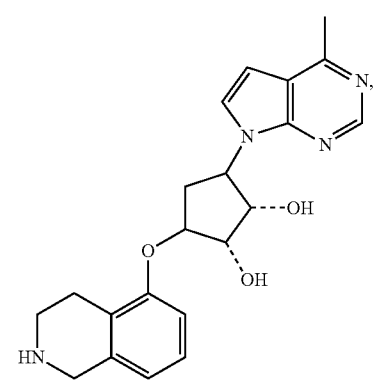
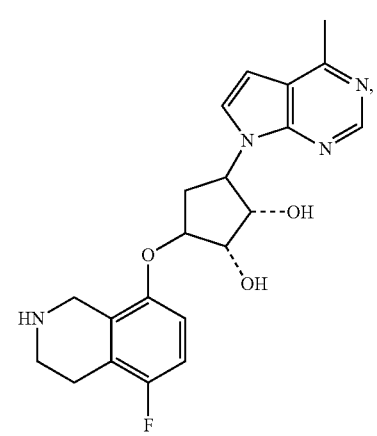

71
-continued
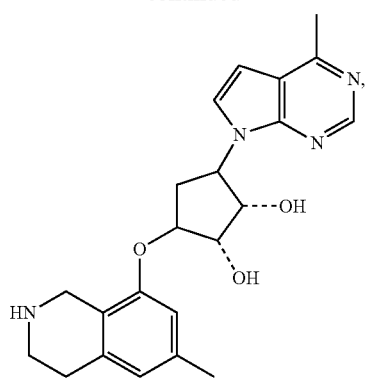

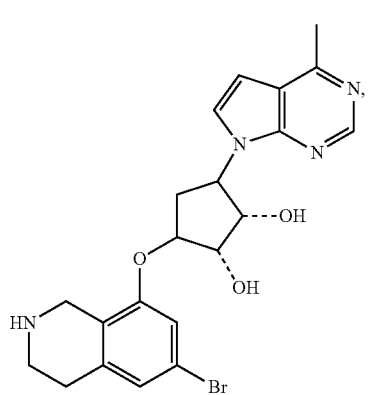
72
-continued
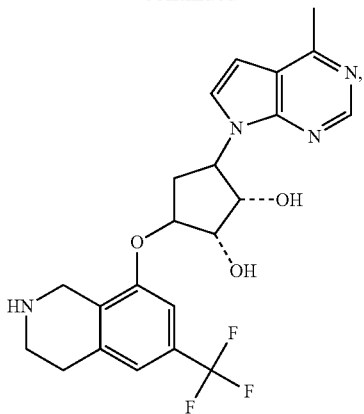
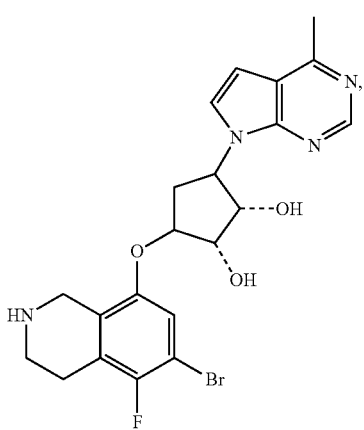
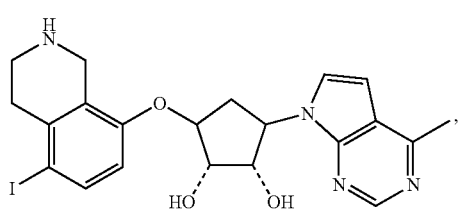
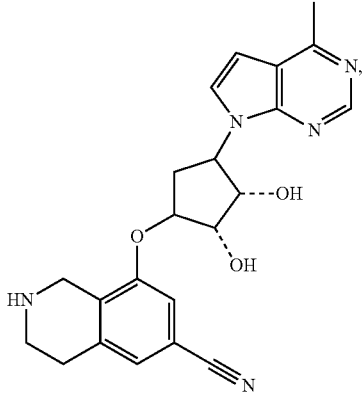

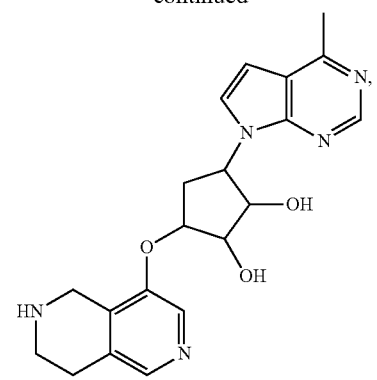
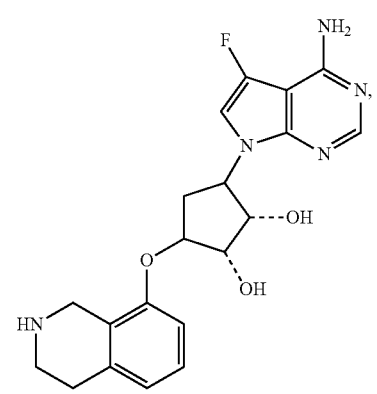
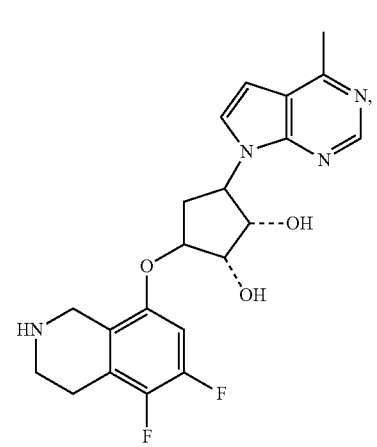
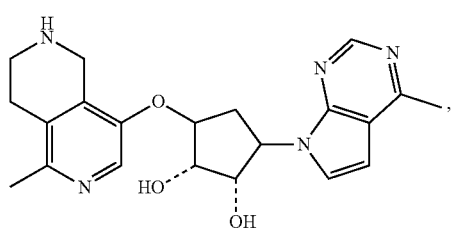
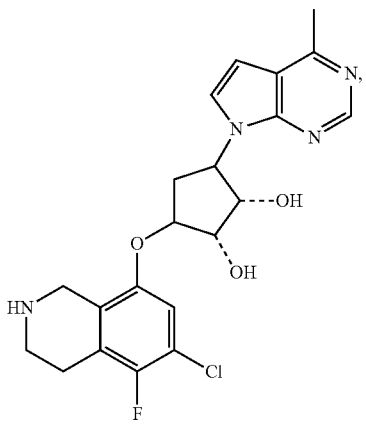
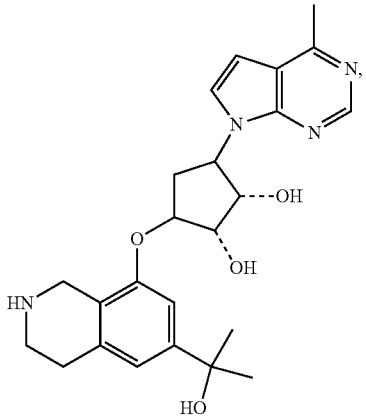
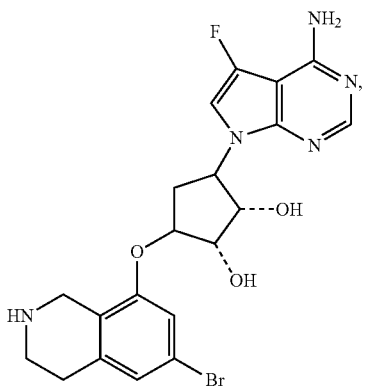

75
-continued
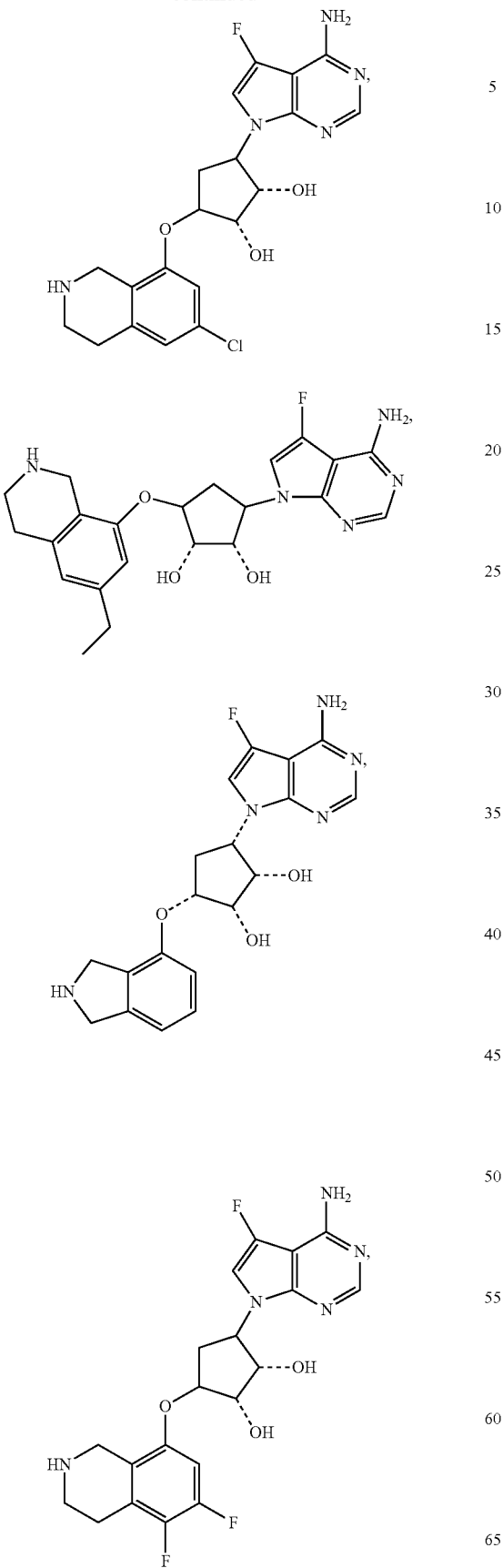
76
-continued
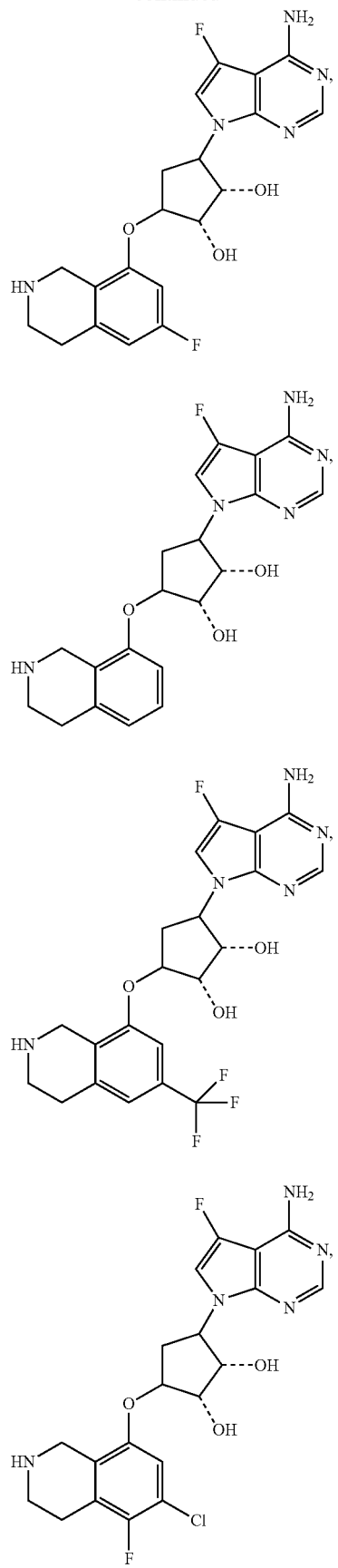

77
-continued
78
-continued
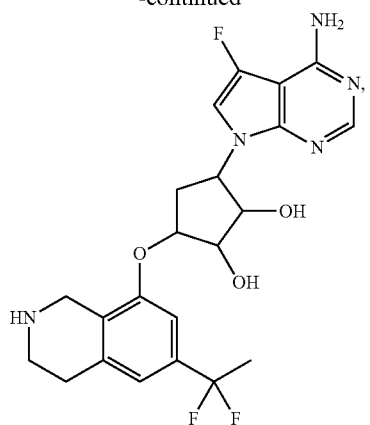
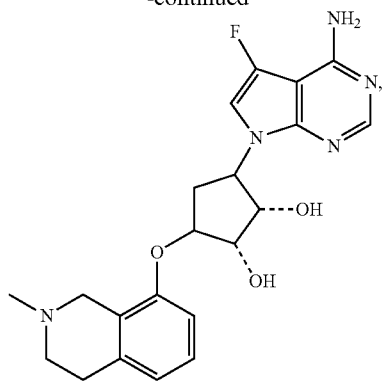
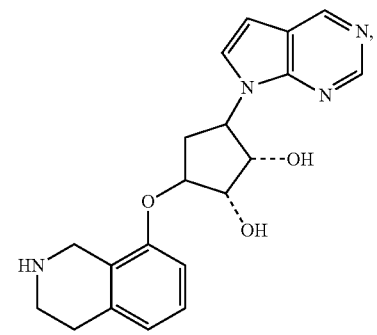
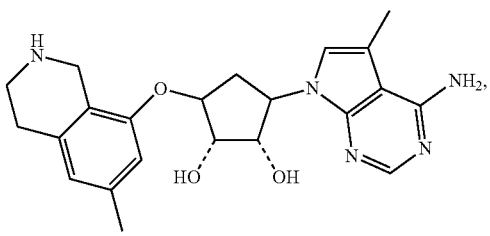
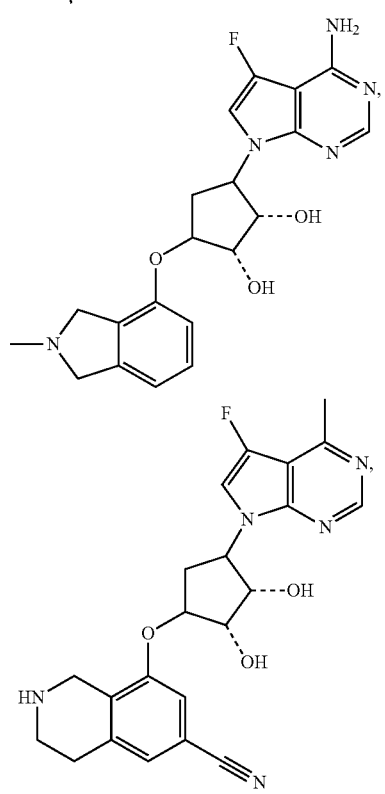

79
-continued
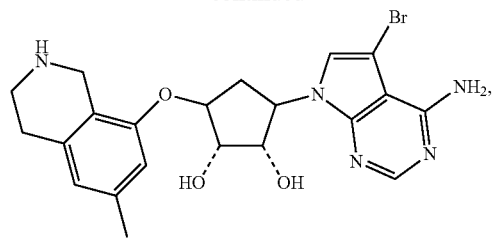
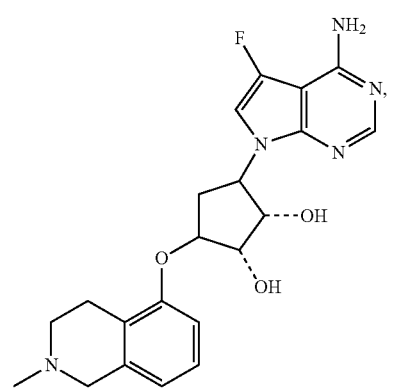
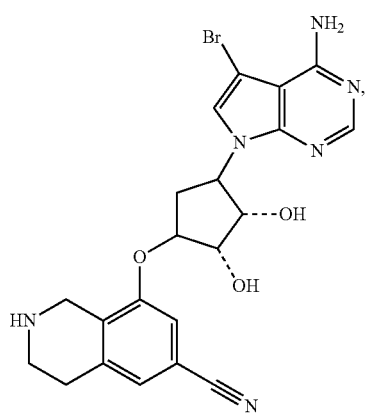
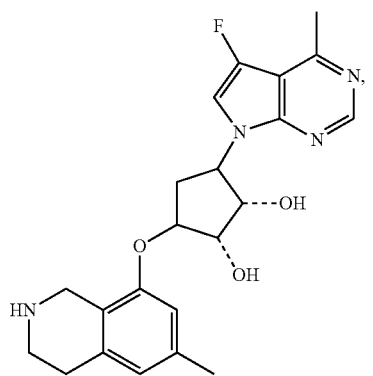
80
-continued
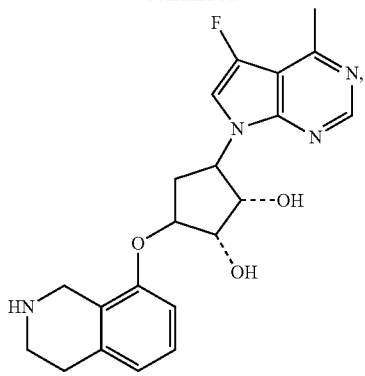
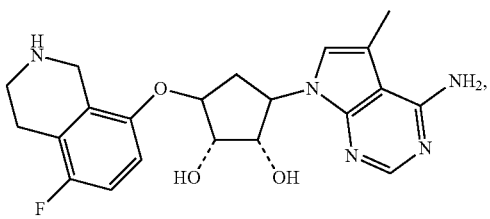
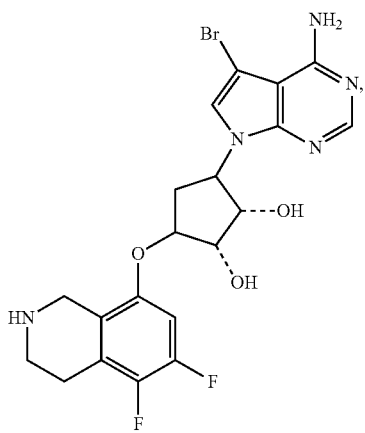
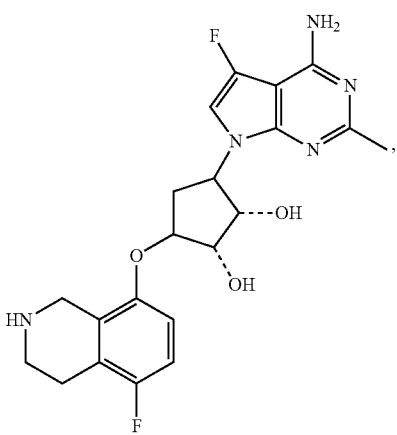

81
-continued
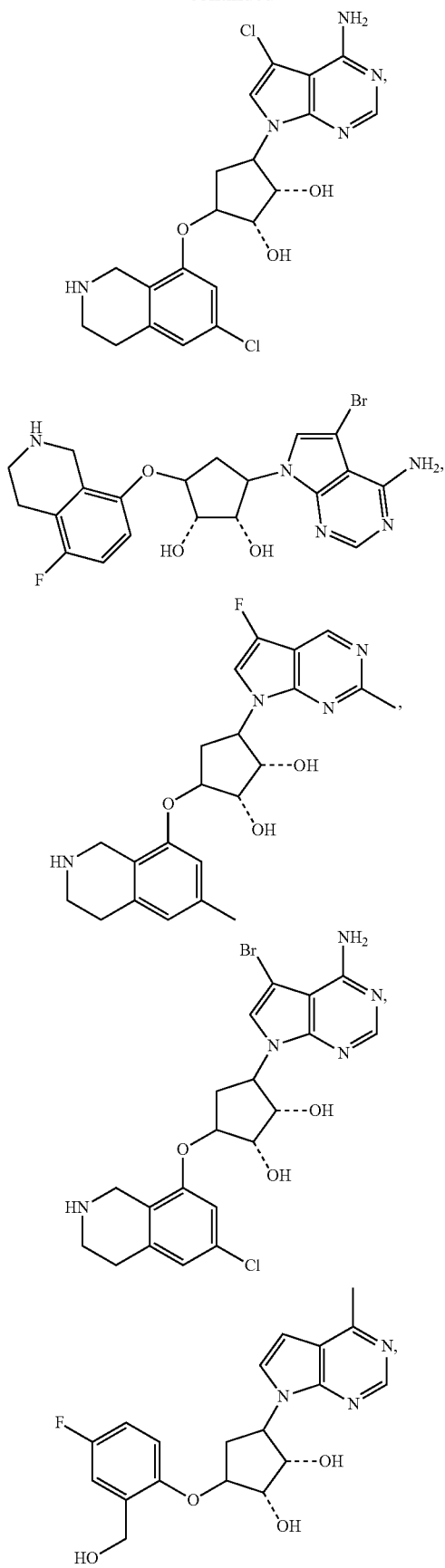
82
-continued
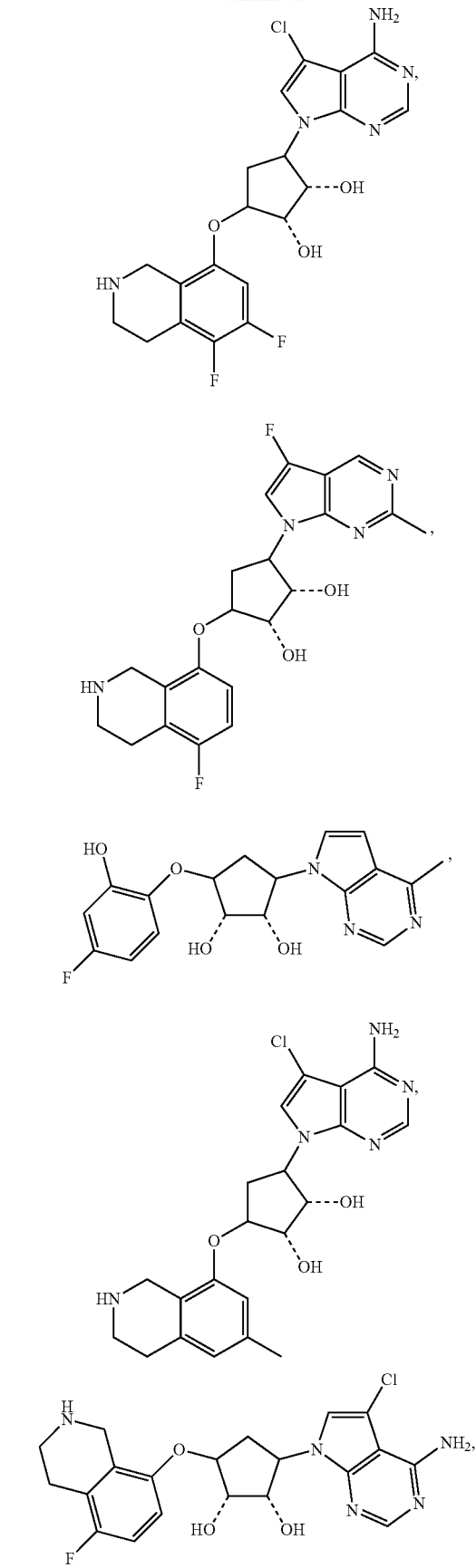

83
-continued
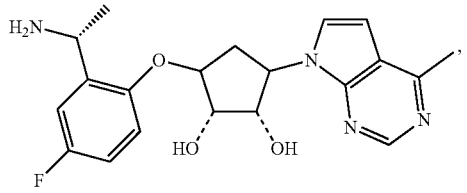
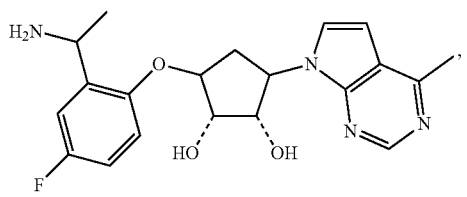
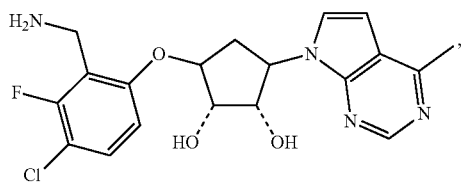
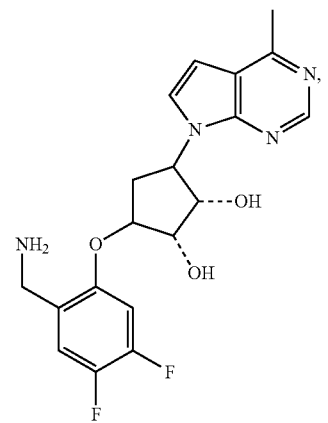
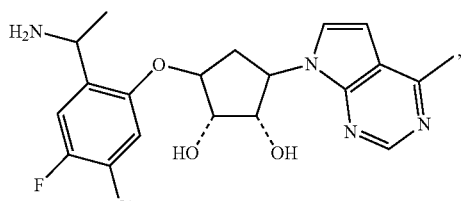
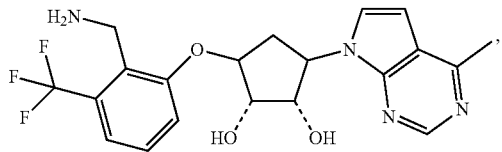
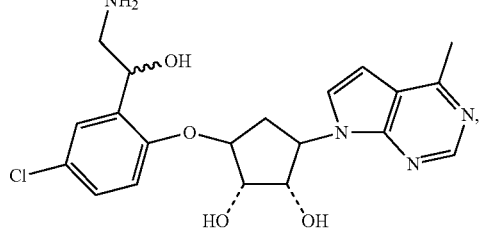
84
-continued
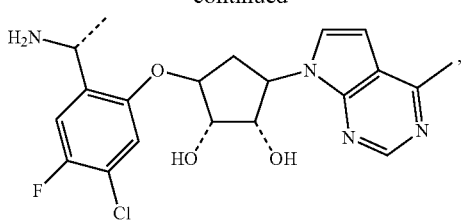
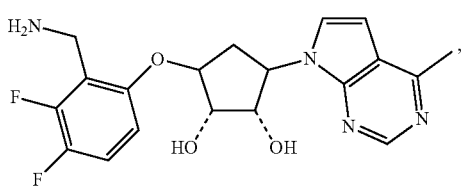
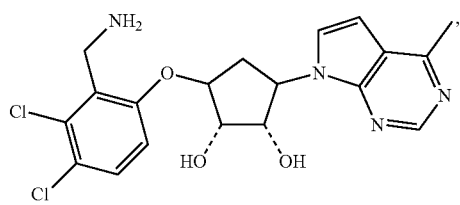
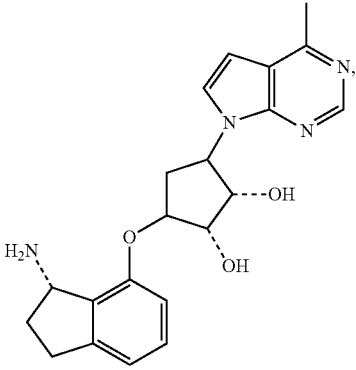
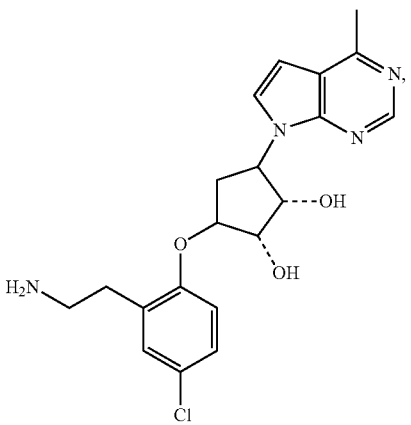
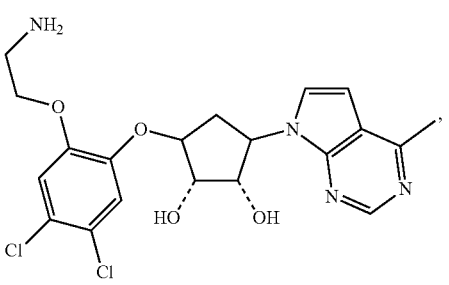

85
-continued
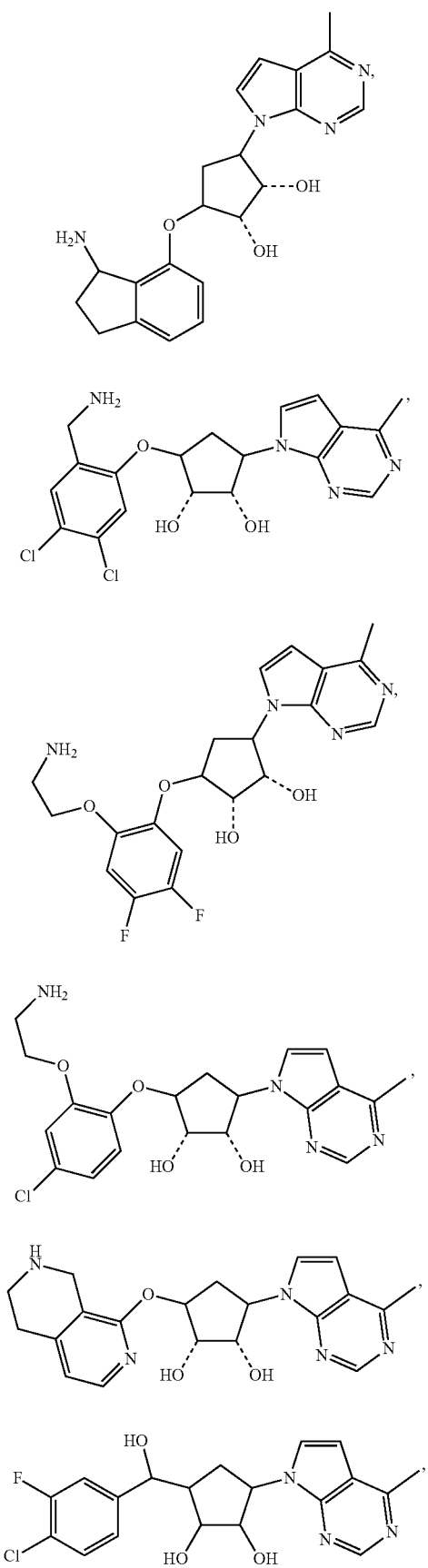
86
-continued
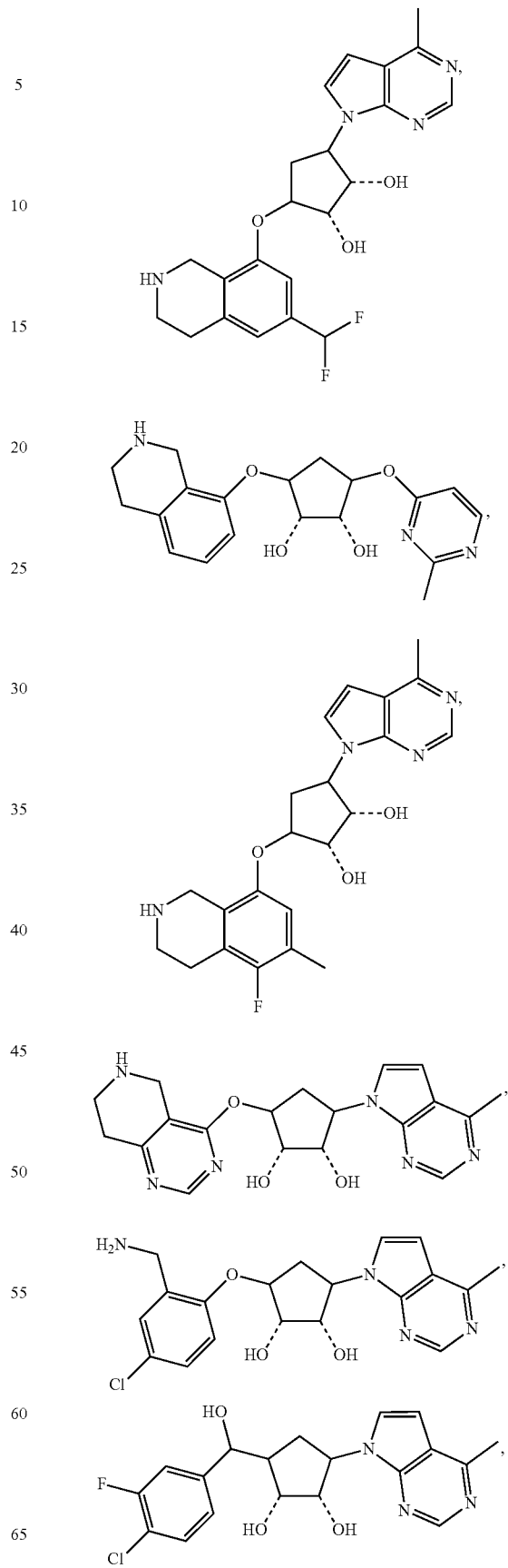

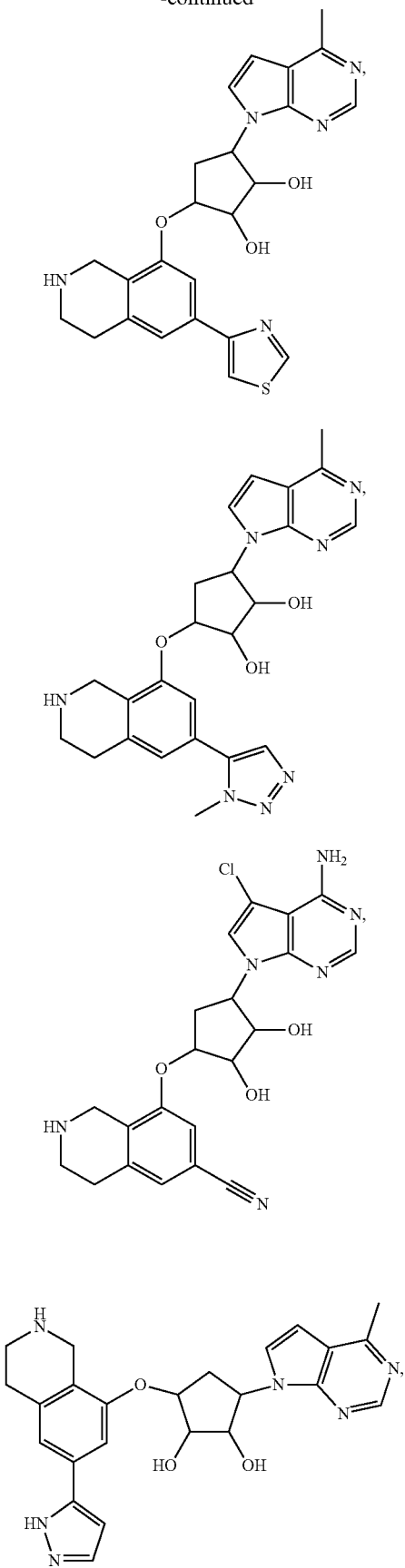
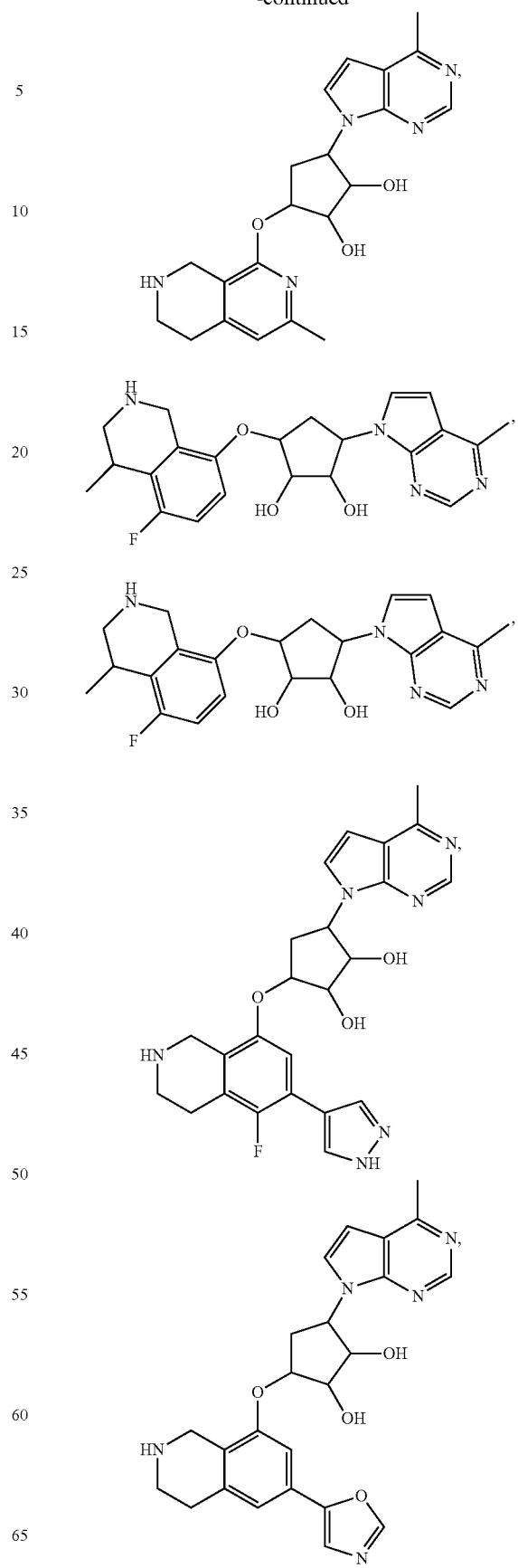

89
-continued
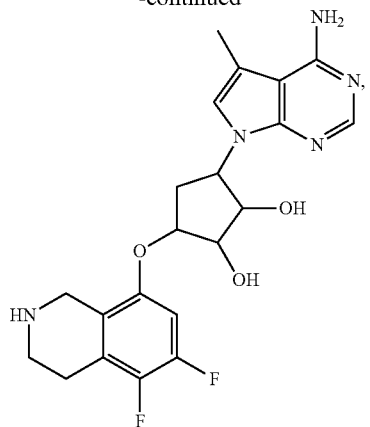
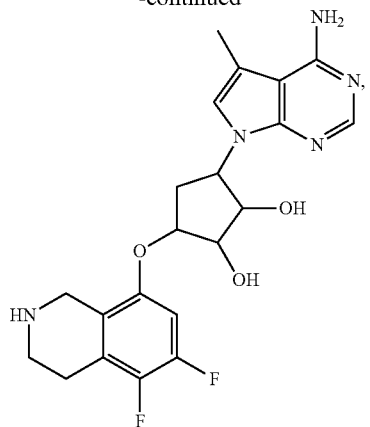
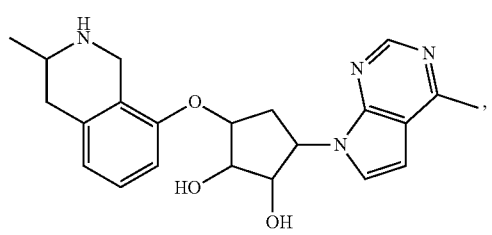
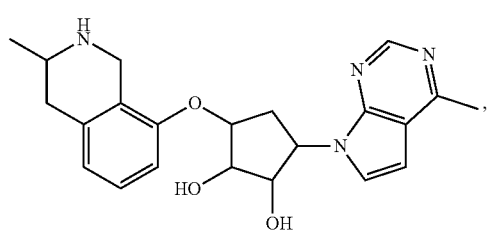
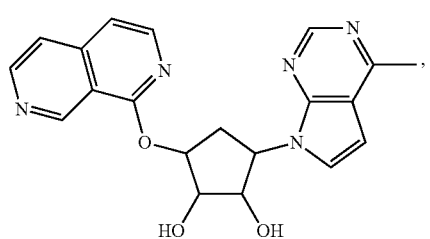
90
-continued
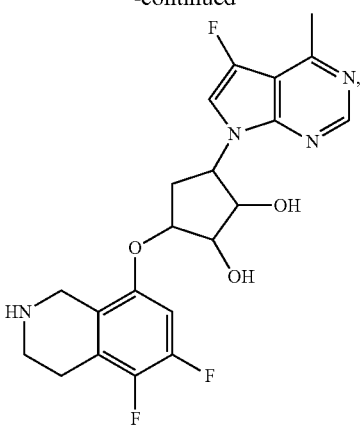
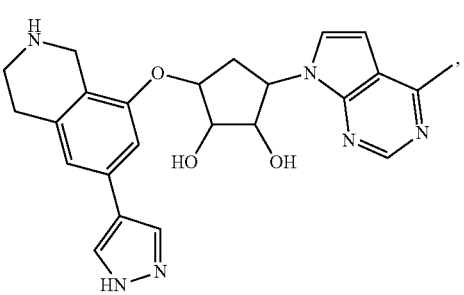
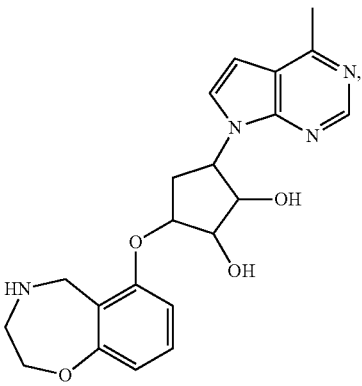

91
-continued
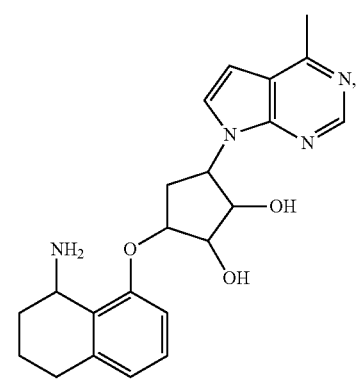
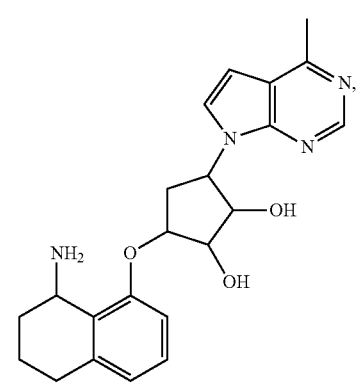
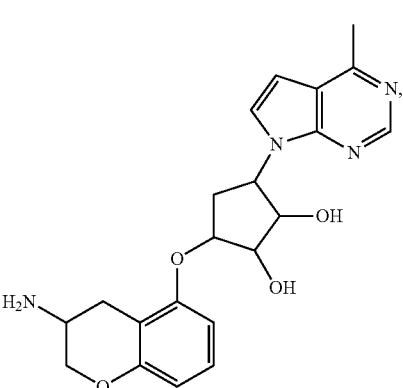
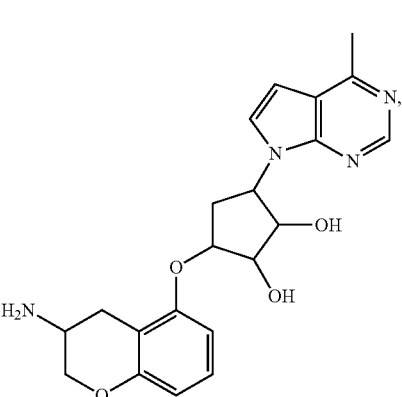
92
-continued
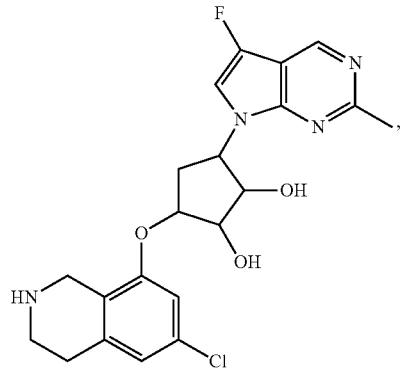
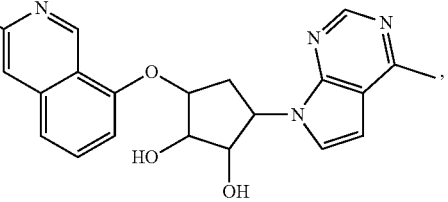
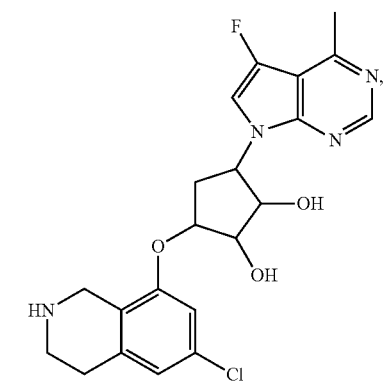
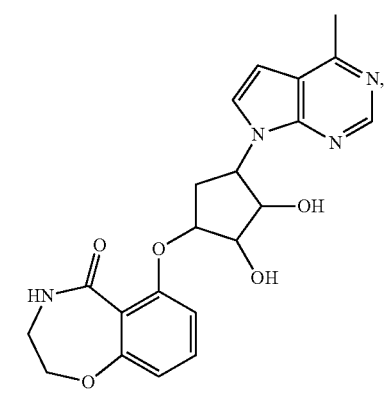
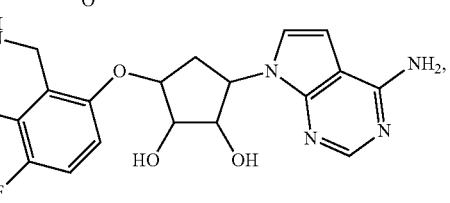

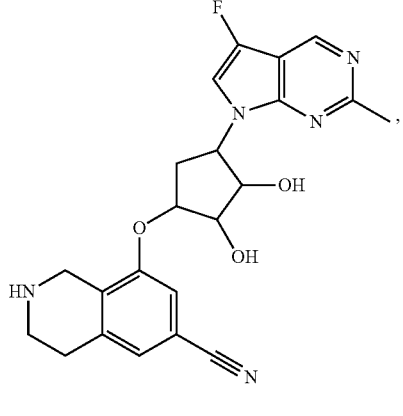
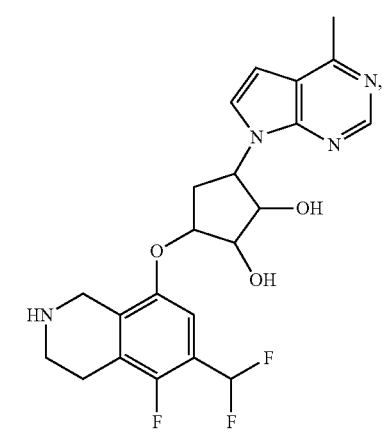
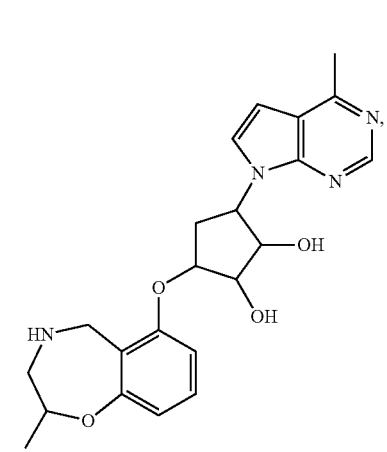
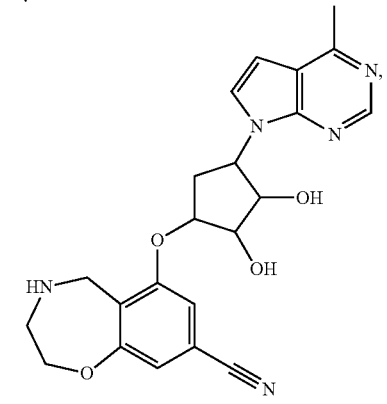
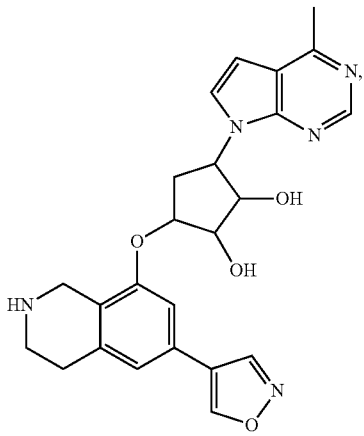
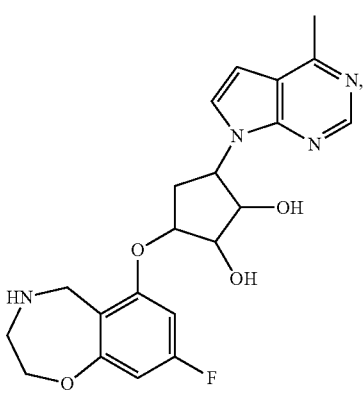
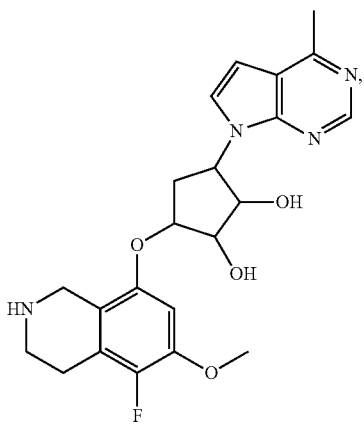
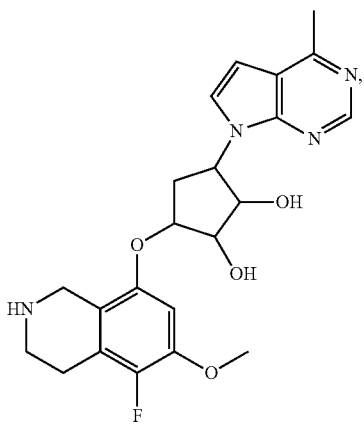

-continued
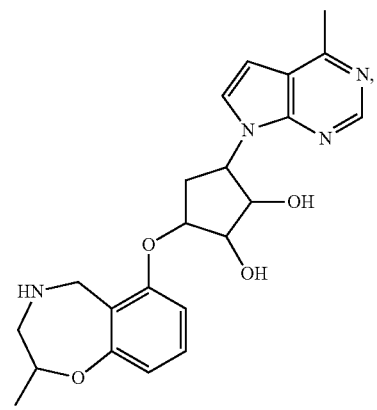
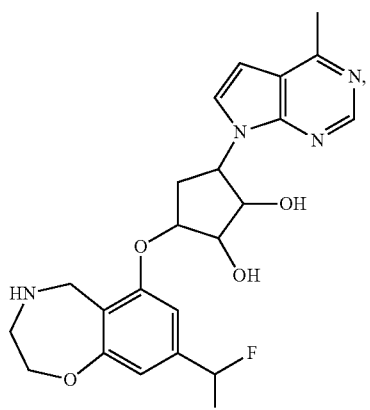
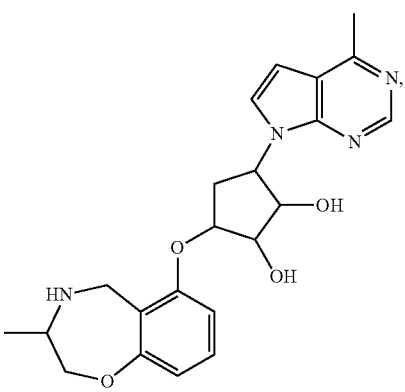
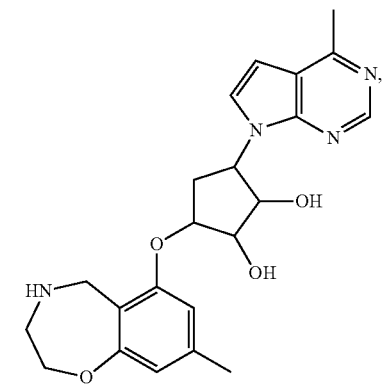
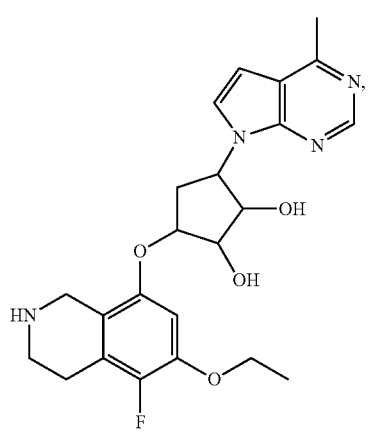

97
-continued
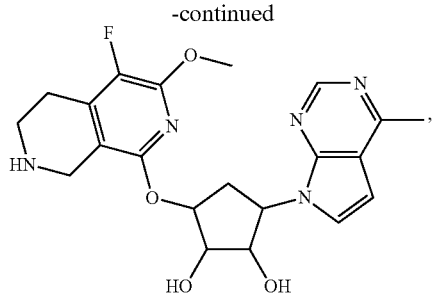
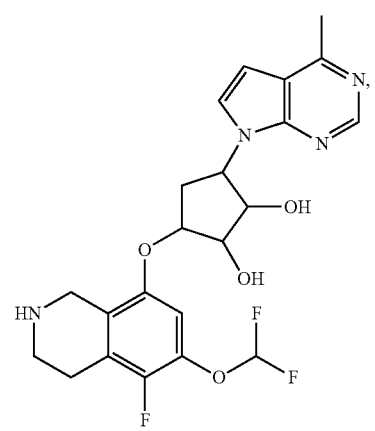
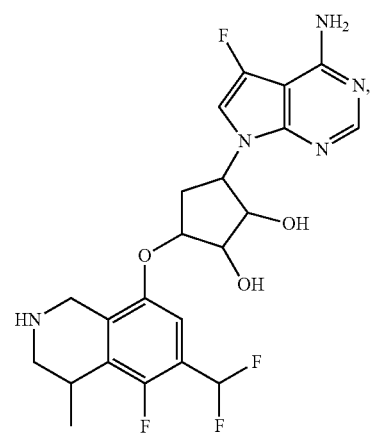 [SMILES: Nc1ncnc2c1c(F)cn2C1CC(Oc2cc(C(F)F)c(F)c3c2CNCC3)C(O)C1O]
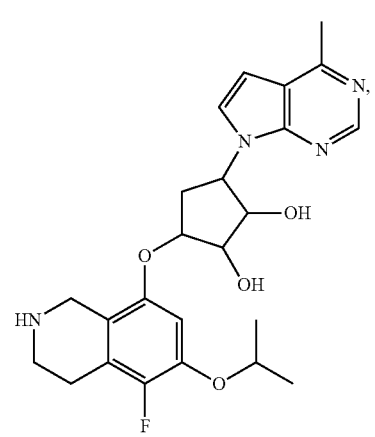
98
-continued
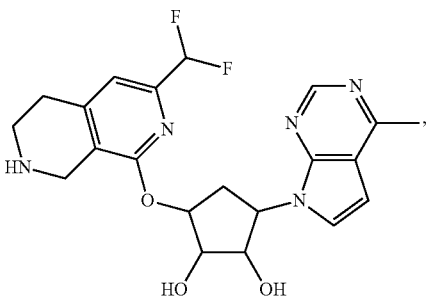
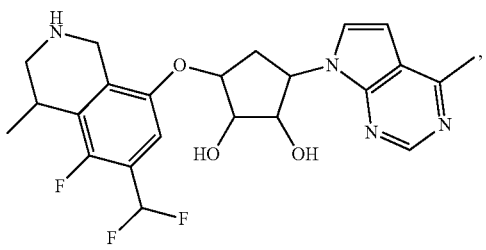
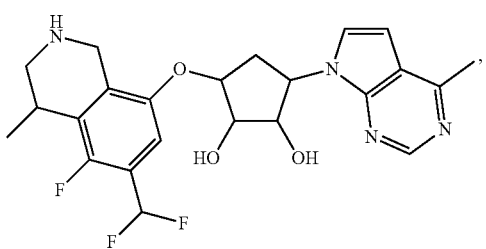
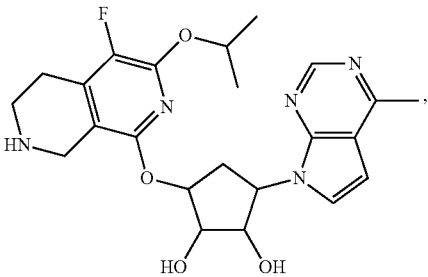
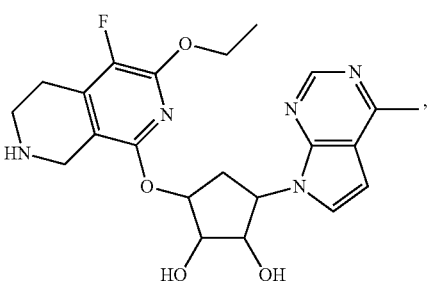

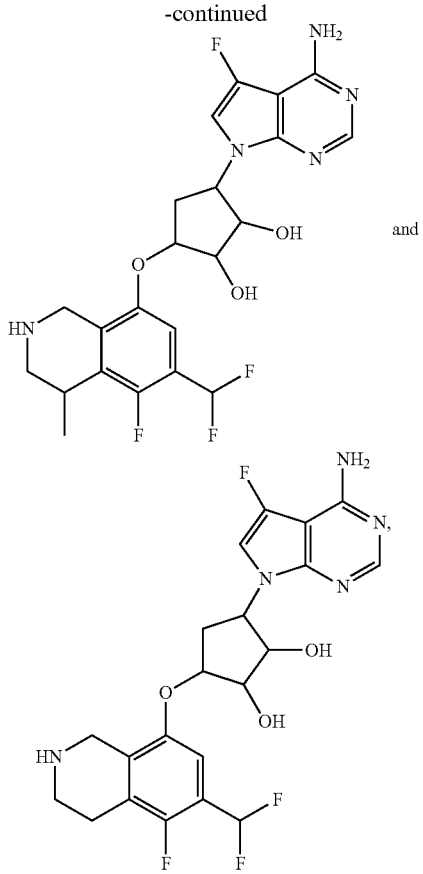

or a pharmaceutically acceptable salt thereof.

Also provided in the present invention are pharmaceutical compositions comprising a compound as described herein and a pharmaceutically acceptable carrier.

Additionally, provided in the present invention are methods of treating abnormal cell growth in a mammal comprising administering to the mammal a therapeutically effective amount of a compound as described herein. The abnormal cell growth is cancer. The cancer referred to herein may be lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

Further still, the present invention provides for the use of a compound as described herein for the preparation of a medicament useful in the treatment of abnormal cell growth in a mammal. The abnormal cell growth is cancer. The cancer referred to herein may be lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

The invention further provides for embodiments wherein:

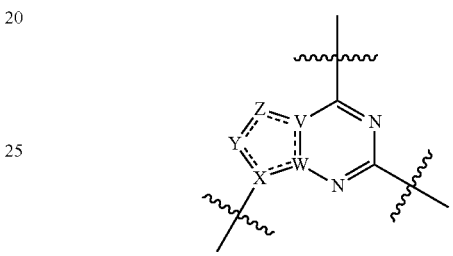

As found in formula I or formula II is selected from:

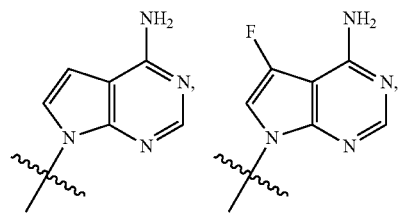

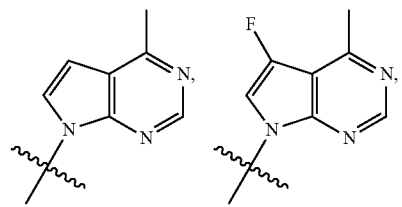

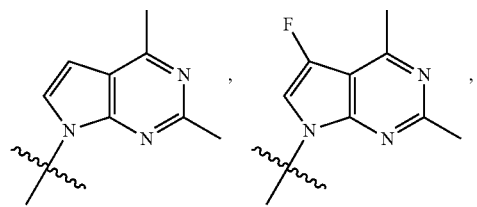

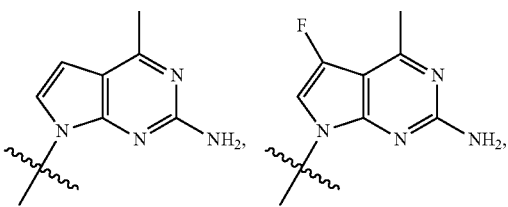

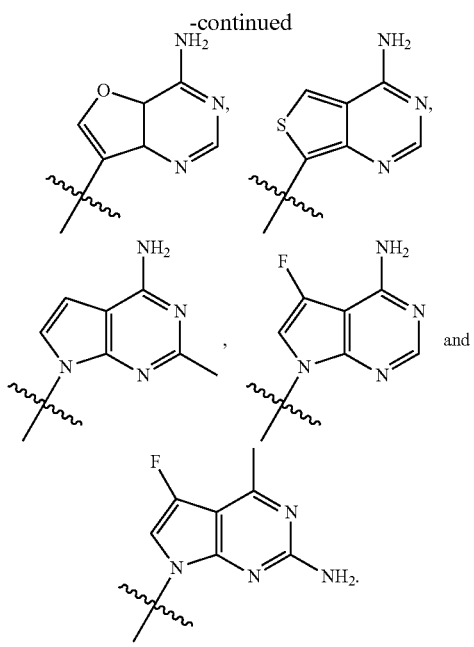

Additional embodiments of the invention include pharmaceutical composition comprising of a compound described herein or a pharmaceutically acceptable salt thereof, and a pharmaceutically acceptable carrier.

Additional embodiments of the invention include methods of treating abnormal cell growth in a mammal, the method comprising administering to the mammal a therapeutically effective amount of a compound described herein or a pharmaceutically acceptable salt thereof, and a pharmaceutically acceptable carrier.

Additional embodiments of the invention include such methods of treatment as are described herein, wherein the abnormal cell growth is cancer. In particular, such methods wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

There is also provided an embodiment of the invention which is the use of a compound described herein, or a pharmaceutically acceptable salt thereof for the preparation of a medicament useful in the treatment of abnormal cell growth in a mammal, particularly wherein the abnormal cell growth is cancer, and more particularly wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

In another embodiment, the invention provides a pharmaceutical composition comprising a compound of the invention or a pharmaceutically acceptable salt thereof, and a pharmaceutically acceptable carrier.

In another embodiment, the invention provides a method of treating abnormal cell growth in a mammal, including a human, the method comprising administering to the mammal a therapeutically effective amount of a compound of the invention or a pharmaceutically acceptable salt thereof. In another embodiment, the abnormal cell growth is cancer. In another embodiment, the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

Definitions

Unless otherwise stated, the following terms used in the specification and claims have the meanings discussed below. Variables defined in this section, such as R, X, n and the like, are for reference within this section only, and are not meant to have the same meaning as may be used outside of this definitions section. Further, many of the groups defined herein can be optionally substituted. The listing in this definitions section of typical substituents is exemplary and is not intended to limit the substituents defined elsewhere within this specification and claims.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

"Alkoxy" refers to —O-alkyl where alkyl is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl.

"Alkyl" refers to a saturated aliphatic hydrocarbon radical including straight chain and branched chain groups of 1 to 20 carbon atoms ("($C_1$-$C_{20}$)alkyl"), preferably 1 to 12 carbon atoms ("($C_1$-$C_{12}$)alkyl"), more preferably 1 to 8 carbon atoms ("($C_1$-$C_8$)alkyl"), or 1 to 6 carbon atoms ("($C_1$-$C_6$)alkyl"), or 1 to 4 carbon atoms ("($C_1$-$C_4$)alkyl"). Examples of alkyl groups include methyl, ethyl, propyl, 2-propyl, n-butyl, iso-butyl, tert-butyl, pentyl, neopentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl" for instance ($C_1$-$C_8$)haloalkyl, refers to an alkyl having one or more, halogen substituents. "Alkylene" refers to a di-valent form of alkyl.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like. "Alkynylene" refers to a di-valent form of alkynyl.

"Amino" refers to an —$NR^xR^y$ group, wherein $R^x$ and $R^y$ are both hydrogen.

"($C_6$-$C_{12}$)aryl" refers to an all-carbon monocyclic or fused-ring polycyclic groups of 6 to 12 carbon atoms having a completely conjugated pi-electron system. Similarly, "($C_5$-$C_{12}$)aryl" refers to an all-carbon monocyclic or fused-ring polycyclic groups of 5 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^xR^y$, with $R^x$ and $R^y$ as defined above.

"Cyano" refers to a —C≡N group. Cyano may be expressed as CN.

"($C_3$-$C_{10}$)cycloalkyl" refers to a 3 to 10 member all-carbon monocyclic ring, a 3 to 10 member all-carbon bicyclic ring, an all-carbon 5-member/6-member or 6-member/6-member fused bicyclic ring, a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system, and a bridged all-carbon ring system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —$NR^xR^y$, with $R^x$ and $R^y$ as defined above.

"Halogen" or the prefix "halo" refers to fluoro, chloro, bromo and iodo. Preferably halogen refers to fluoro or chloro.

"Heteroalkyl" refers to a straight chain or branched chain alkyl group of 1 to 20 carbon atoms, preferably 1 to 12 carbon atoms, more preferably 1 to 8 carbon atoms, or 1 to 6 carbon atoms, or 1 to 4 carbon atoms, wherein one, two or three of which carbon atoms are replaced by a heteroatom selected from from $NR^x$, N, O, and $S(O)_n$ (where n is 0, 1 or 2). Typically the heteroatoms, of there are more that one heteroatoms, are not adjacent to one another. Exemplary heteroalkyls include alkyl ethers, secondary and tertiary alkyl amines, amides, alkyl sulfides, and the like. The group may be a terminal group or a bridging group. As used herein, reference to the normal chain when used in the context of a bridging group refers to the direct chain of atoms linking the two terminal positions of the bridging group. As with "alkyl", typical substituent groups on "heteroalkyl" include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Heteroalkenyl" refers to a heteroalkyl possessing one or more carbon-carbon double bonds. "Heteroalkylene" refers to a di-valent form of heteroalkyl.

"Heteroalkenylene" refers to a di-valent form of heteroalkenyl.

"Heteroaryl" refers to a monocyclic or fused ring group of 5 to 12 carbon ring atoms containing one, two, three or four ring heteroatoms selected from from $NR^x$, N, O, and $S(O)_n$ (where n is 0, 1 or 2) and, in addition, having a completely conjugated pi-electron system. Preferred heteroaryl groups include ($C_2$-$C_7$)heteroaryl in accordance with the definition above. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —$NR^xR^y$ with $R^x$ and $R^y$ as defined above. A pharmaceutically acceptable heteroaryl is one that is sufficiently stable to be attached to a compound of the invention, formulated into a pharmaceutical composition and subsequently administered to a patient in need thereof.

Examples of typical monocyclic heteroaryl groups include, but are not limited to:

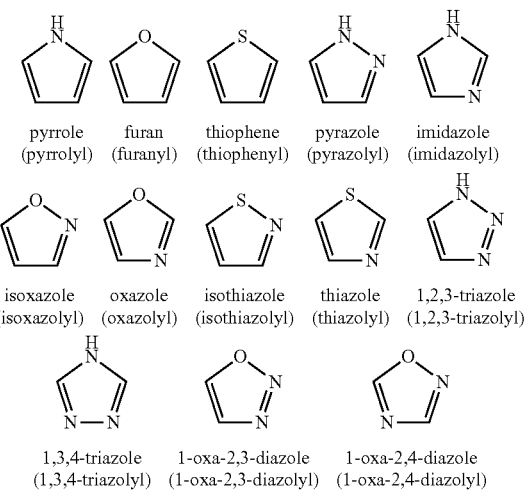

-continued

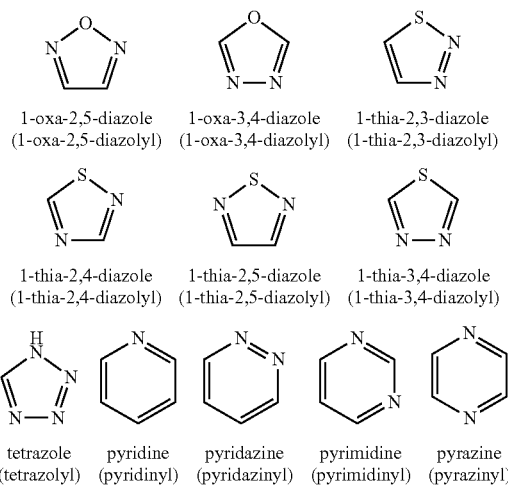

| 1-oxa-2,5-diazole (1-oxa-2,5-diazolyl) | 1-oxa-3,4-diazole (1-oxa-3,4-diazolyl) | 1-thia-2,3-diazole (1-thia-2,3-diazolyl) |
| 1-thia-2,4-diazole (1-thia-2,4-diazolyl) | 1-thia-2,5-diazole (1-thia-2,5-diazolyl) | 1-thia-3,4-diazole (1-thia-3,4-diazolyl) |
| tetrazole (tetrazolyl) | pyridine (pyridinyl) | pyridazine (pyridazinyl) | pyrimidine (pyrimidinyl) | pyrazine (pyrazinyl) |

Examples of suitable fused ring heteroaryl groups include, but are not limited to:

benzofuran (benzofuranyl)   benzothiophene (benzothiophenyl)   indole (indolyl)

benzimidazole (benzimidazolyl)   indazole (indazolyl)   benzotriazole (benzotriazolyl)

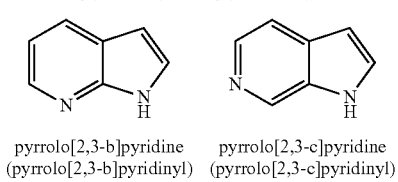

pyrrolo[2,3-b]pyridine (pyrrolo[2,3-b]pyridinyl)   pyrrolo[2,3-c]pyridine (pyrrolo[2,3-c]pyridinyl)

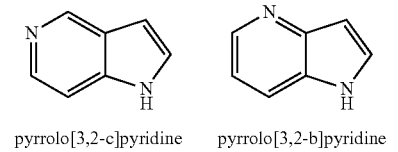

pyrrolo[3,2-c]pyridine (pyrrolo[3,2-c]pyridinyl)   pyrrolo[3,2-b]pyridine (pyrrolo[3,2-b]pyridinyl)

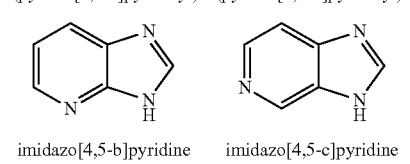

imidazo[4,5-b]pyridine (imidazo[4,5-b]pyridinyl)   imidazo[4,5-c]pyridine (imidazo[4,5-c]pyridinyl)

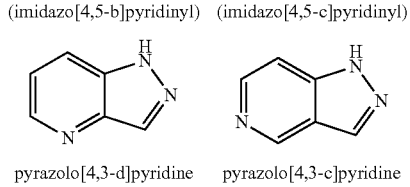

pyrazolo[4,3-d]pyridine (pyrazolo[4,3-d]pyidinyl)   pyrazolo[4,3-c]pyridine (pyrazolo[4,3-c]pyidinyl)

-continued

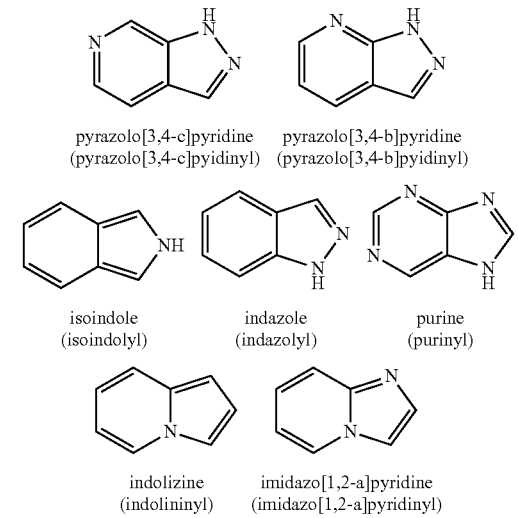

pyrazolo[3,4-c]pyridine (pyrazolo[3,4-c]pyidinyl)   pyrazolo[3,4-b]pyridine (pyrazolo[3,4-b]pyidinyl)

isoindole (isoindolyl)   indazole (indazolyl)   purine (purinyl)

indolizine (indolininyl)   imidazo[1,2-a]pyridine (imidazo[1,2-a]pyridinyl)

imidazo[1,5-a]pyridine (imidazo[1,5-a]pyridinyl)   pyrazolo[1,5-a]pyridine (pyrazolo[1,5-a]pyridinyl)

pyrrolo[1,2-b]pyridazine (pyrrolo[1-2,b]pyridazinyl)   imidazo[1,2-c]pyrimidine (imidazo[1,2-c]pyrimidinyl)

5H-pyrrolo[3,2-b]pyrazine   1H-pyrazolo[4,3-b]pyrazine 1H-pyrazolo[3,4-d]pyrimidine   7H-pyrrolo[2,3-d]pyrimidine quinoline (quinolinyl)   isoquinoline (isoquinolinyl)   cinnoline (cinnolinyl)

quinazoline (azaquinazoline)   quinoxaline (quinoxalinyl)   phthalazine (phthalazinyl)

1,6-naphthyridine (1,6-naphthyridinyl)   1,7-naphthyridine (1,7-naphthyridinyl)   1,8-naphthyridine (1,8-naphthyridinyl)

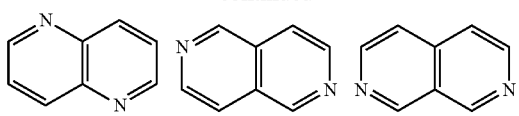

1,5-naphthyridine  2,6-naphthyridine  2,7-naphthyridine
(1,5-naphthyridinyl)  (2,6-naphthyridinyl)  (2,7-naphthyridinyl)

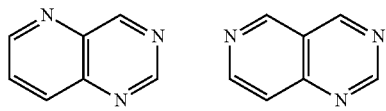

pyrido[3,2-d]pyrimidine  pyrido[4,3-d]pyrimidine
(pyrido[3,2-d]pyrimidinyl)  (pyrido[4,3-d]pyrimidinyl)

pyrido[3,4-d]pyrimidine  pyrido[2,3-d]pyrimidine
(pyrido[3,4-d]pyrimidinyl)  (pyrido[2,3-d]pyrimidinyl)

pyrido[2,3-b]pyrazine  pyrido[3,4-b]pyrazine
(pyrido[2,3-b]pyrazinyl)  (pyrido[3,4-b]pyrazinyl)

pyrimido[5,4-d]pyrimidine  pyrazino[2,3-b]pyrazine
(pyrimido[5,4-d]pyrimidinyl)  (pyrazino[2,3-b]pyrazinyl)

pyrimido[4,5-d]pyrimidine
(pyrimido[4,5-d]pyrimidinyl)

"Heterocyclyl" refers to a monocyclic or fused ring system having 3 to 12 ring atoms containing one, two, three or four ring heteroatoms selected from N, O, and $S(O)_n$ (where n is 0, 1 or 2), and 1-9 carbon atoms The rings may also have one or more double bonds. However, the rings do not have a completely conjugated pi-electron system. Preferred heterocycles include $(C_2-C_6)$heterocycles in accordance with the definition above. Examples of suitable saturated heteroalicyclic groups include, but are not limited to:

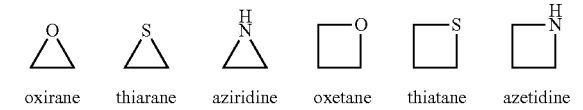

oxirane    thiarane   aziridine   oxetane    thiatane   azetidine
(oxiranyl) (thiaranyl) (aziridinyl) (oxetanyl) (thiatanyl) (azetidinyl)

tetrahydrofuran   tetrahydrothiophene   pyrrolidine
(tetrahydrofuranyl) (tetrahydrothiophenyl) (pyrrolidinyl)

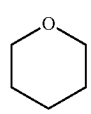 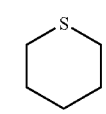 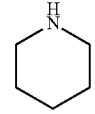

tetrahydropyran   tetrahydrothiopyran   piperidine
(tetrahydropyranyl) (tetrahydrothiopyranyl) (piperidinyl)

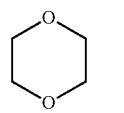 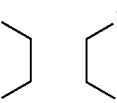 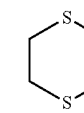

1,4-dioxane   1,4-oxathiane   morpholine   1,4-dithiane
(1,4-dioxanyl) (1,4-oxathianyl) (morpholinyl) (1,4-dithianyl)

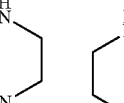

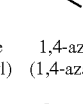 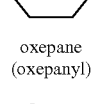 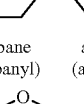

piperazine   1,4-azathiane   oxepane    thiepane   azepane
(piperazinyl) (1,4-azathianyl) (oxepanyl) (thiepanyl) (azepanyl)

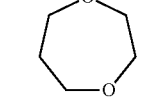 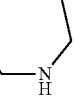

1,4-dioxepane   1,4-oxathiepane   1,4-oxaazepane
(1,4-dioxepanyl) (1,4-oxathiepanyl) (1,4-oxaazepanyl)

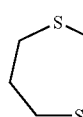 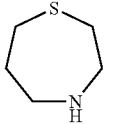 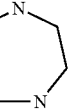

1,4-dithiepane   1,4-thieazepane   1,4-diazepane
(1,4-dithiepanyl) (1,4-thiezepanyl) (1,4-diazepanyl)

Examples of suitable partially unsaturated heteroalicyclic groups include, but are not limited to:

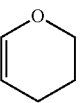 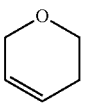 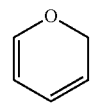

3,4-dihydro-2H-pyran   5,6-dihydro-2H-pyran   2H-pyran
(3,4-dihydro-2H-pyranyl) (5,6-dihydro-2H-pyranyl) (2H-pyranyl)

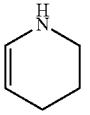 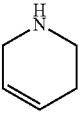

1,2,3,4-tetrahydropyridine   1,2,5,6-tetrahydropyridine
(1,2,3,4-tetrahydropyridinyl) (1,2,5,6-tetrahydropyridinyl)

The heterocyclyl group is optionally substituted with one or two substituents independently selected from halo, lower alkyl, lower alkyl substituted with carboxy, ester hydroxy, or mono or dialkylamino. Moreover, the heterocycle may contain bridging, including bridging between non-adjacent carbons on the heterocycle, with the bridge containing 1-2 carbons and 0-1 heteroatoms selected from selected from $NR^x$, O, and $S(O)_n$ (where n is 0, 1 or 2). "Hydroxy" or "hydroxyl" refers to an —OH group.

"In vitro" refers to procedures performed in an artificial environment such as, e.g., without limitation, in a test tube or culture medium.

"In vivo" refers to procedures performed within a living organism such as, without limitation, a mouse, rat or rabbit.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

"Organism" refers to any living entity comprised of at least one cell. A living organism can be as simple as, for example, a single eukariotic cell or as complex as a mammal, including a human being.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

reducing the size of the tumor;
inhibiting (that is, slowing to some extent, preferably stopping) tumor metastasis;
inhibiting to some extent (that is, slowing to some extent, preferably stopping) tumor growth, and
relieving to some extent (or, preferably, eliminating) one or more symptoms associated with the cancer.

"Treat", "treating" and "treatment" refer to a method of alleviating or abrogating a methyltransferase mediated cellular disorder and/or its attendant symptoms. With regard particularly to cancer, these terms simply mean that the life expectancy of an individual affected with a cancer will be increased or that one or more of the symptoms of the disease will be reduced.

DETAILED DESCRIPTION

General schemes for synthesizing the compounds of the invention can be found in the Examples section herein.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts). Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

Tosylate, hydrochloride and mesylate salts are of interest.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties. Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include:

(i) where the compound contains a carboxylic acid functionality —(COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—NH$_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where the compounds according to this invention have at least one chiral center, they may accordingly exist as enantiomers. Where the compounds possess two or more chiral centers, they may additionally exist as diastereomers. Similarly, where a compound of the invention contains a cyclopropyl group or other cyclic group where chirality exists, and alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or supercritical fluid chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration: The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patients, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration: Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

Ocular Administration: Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossedlinked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage: The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts: Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

For some of the steps described it may be necessary to protect potential reactive functions that are not wished to react, and to cleave said protecting groups in consequence. In such a case, any compatible protecting radical may be used. In particular methods of protection and deprotection such as those described by T. W. Greene (*Protective Groups in Organic Synthesis*, A. Wiley-Interscience Publication, 1981) or by P. J. Kocienski (*Protecting groups*, Georg Thieme Verlag, 1994), may be used.

All of the reactions herein and the preparations of novel starting materials used herein are conventional and appropriate reagents and reaction conditions for their performance or preparation as well as procedures for isolating the desired products will be well-known to those skilled in the art with reference to literature precedents and the examples and preparations hereto.

The following abbreviations may be used herein:

Ac (acetyl); AcCl (acetyl chloride); AcOH or HOAc (acetic acid); $Ac_2O$ (acetic anhydride); aq. (aqueous); Boc or boc (tert-butoxycarbonyl); ca. (about or approximately); $CDCl_3$ (deuterated chloroform); $CH_2Cl_2$ and/or DCM (dichloromethane); DAST (Diethylaminosulfur trifluoride); DCE (dichloroethane); DEA (diethylamine); DIBAL or DIBAL-H (diisobutylaluminum hydride); DIC (diisopropylcarbodiimide); DIPEA or Hunig's base (N,N-diisopropylethylamine); DMA (dimethylacetamide); DMF (dimethylformamide); DME (ethylene glycol); DMP (Dess-Martin Periodinane); DMAP (4-dimethylaminopyridine); DMSO (dimethylsulfoxide); DMSO-$d_6$ (deuterated dimethylsulfoxide); EDC or EDCI (1-ethyl-3-(3-dimethylaminopropyl)-carbodiimide); Et (ethyl); $Et_3N$ or TEA (triethylamine); EtOH (ethanol); EtOAc (ethyl acetate); $Et_2O$ (diethyl ether); g or gm (gram or grams); HATU (2-(7-aza-1H-benzotriazole-1-yl)-1,1,3,3-tetramethyluronium hexafluorophosphate); HBTU (o-(benzotriazole-1-yl)-1,1,3,3-tetramethyluronium hexafluorophosphate); HMPT (Tris(dimethylamino)phosphine); HPLC (high-performance liquid chromatography); HOBT (1-hydroxy benzotriazole); h or hr (hour or hours, as appropriate); iBu (isobutyl); IPA (iso-propyl alcohol); iPr (isopropyl); iPrOAc (isopropyl acetate); KHMDS (potassium bis(trimethylsilyl)amide); KOAc (potassium acetate); LCMS (liquid chromatography-mass spectrometry); LiHMDS (lithium bis(trimethylsilyl)amide); Me (methyl); MeOH (methanol); MeOD (deuterated methanol); MeCN (acetonitrile); m or min (minute or minutes, as appropriate); mg (milligram or milligrams); Ms (methylsulfonyl); MsCl (methanesulfonyl chloride); N (normal); NBS (N-Bromosuccinimide); NFSI (N-Fluorodibenzenesulfonimide); NMR (nuclear magnetic resonance); nBu (n-butyl); nBuLi (n-butyl lithium); nPr (n-propyl); Pd/C (palladium on carbon); $Pd_2(dba)_3$ (tris(dibenzylideneacetone)dipalladium(0)); Pd(dppf)$Cl_2$ ([1,1'-bis(diphenylphosphino)ferrocene]dichloropalladium(II)); Ph (phenyl); PTSA or pTSA (p-Toluene sulfonic acid); Rt (retention time); rt (room temperature); RuCl(p-cymene)[(R,R)-Ts-DPEN] ([N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium); s or sec (second or seconds, as appropriate); Selectfluor (N-Chloromethyl-N'-fluorotriethylenediammonium bis(tetrafluoroborate)); SEM (2-Trimethylsilylethoxymethoxy); SFC (supercritical fluid chromatography); Si-Thiol (silica 1-propanethiol); T3P (propylphosphonic anhydride); TBAF (tetrabutyl ammonium fluoride); TBDMSCl (t-butyl-dimethylsilyl chloride); TBME or MTBE (tert-butyl methyl ether); t-BuOH (2-methyl-2-propanol, tert-butanol or tert-butyl alcohol); TDA-1 (Tris[2-(2-methoxyethoxy)ethyl]amine or Tris(3,6-dioxaheptyl)amine); TEA, $NEt_3$ or $Et_3N$ (triethylamine); TFA (trifluoroacetic acid); THF (tetrahydrofuran); THP (tetrahydropyran); TLC (thin layer chromatography); TMS (trimethylsilyl); TMSCl (trimethylsilyl chloride); $TMSCF_3$ (Trimethyl(trifluoromethyl)silane); Tos or tosyl (4-toluenesulfonyl); TOSMIC (p-Toluenesulfonylmethyl isocyanide); UV (ultraviolet).

General Synthetic Scheme for Carbonucleoside Compounds

Scheme 1:

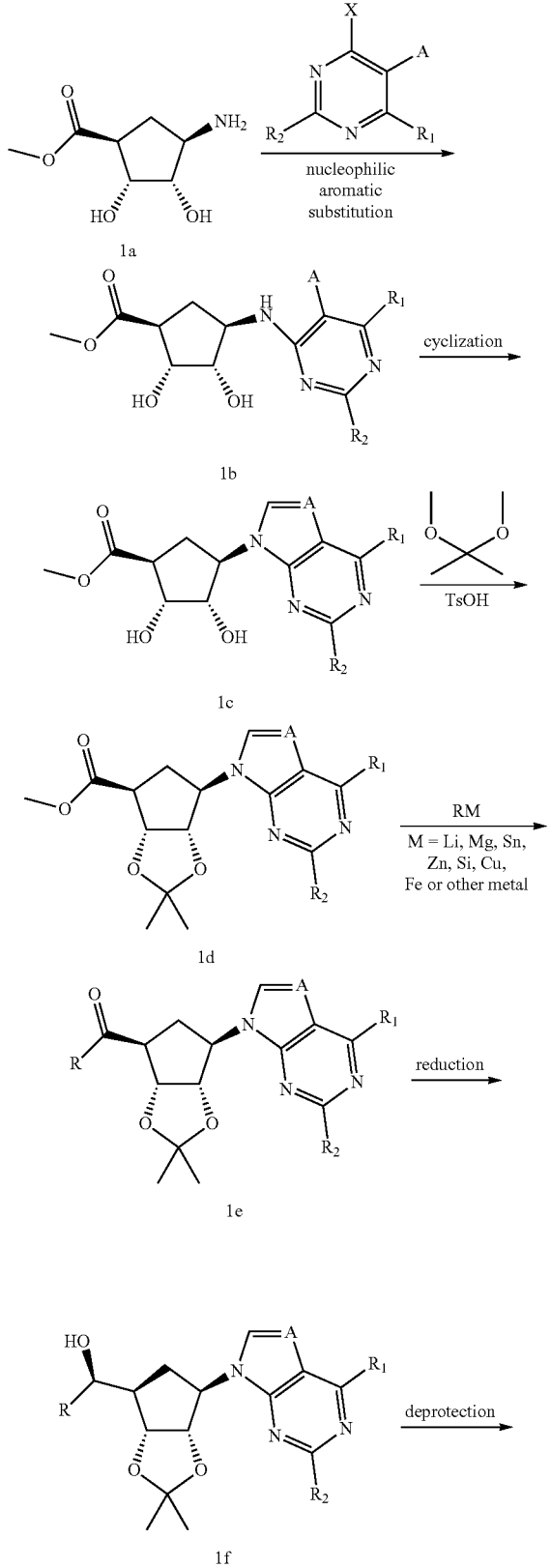

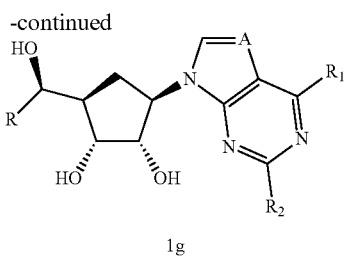

1g

As exemplified in Scheme 1, a compound such as 1a can be purchased or synthesized (*Chem. Rev.*, 2012, 112 (8), pp 4642-4686). Typically, methyl (1S,2R,3S,4R)-4-amino-2,3-dihydroxycyclopentane-1-carboxylate can react with an appropriately functionalized pyrimidine or other heterocycle to give compounds such as 1b. This reaction can be accomplished through standard nucleophilic aromatic substitution using conditions such as diisopropylethylamine or trimethylamine in DMSO, DMA or DMF or conditions using cesium fluoride in DMSO. Alternative reaction condition may include metal coupling reactions such as palladium couplings. Cyclization of compounds such as 1b to compounds such as 1c can occur under a variety of conditions including condensations or metal couplings depending on the atom type of A. Protection of the diol to produce 1d can be done using acetone or 2,2-dimethoxypropane in mild acid. Esters such as 1d are converted into alkyl and aryl ketones such as 1e using alkyl and aryl metal reagents such as alkyl and aryl Grignards (M=Mg), alkyl and aryl lithium reagents, alkyl and aryl cuprates, alkyl and aryl zincates as well as other organometal reagents. Typically these reactions are run in ethereal solvents such as THF, MeTHF, dioxane or similar solvent at temperatures ranging from −78° C. to 60° C. Alkyl and aryl ketones such as 1e can be converted to secondary alcohols such as 1f using reducing reagents such as NaBH4, LiBH4, LiAlH4, DIBAL and others. Typically these reactions can be run in a variety of solvents such as DCM, THF, MeOH, EtOH or others at varying temperatures. Alkyl and aryl ketones such as 1e can be preferentially converted to diastereomerically enriched secondary alcohols such as 1f using chiral reducing conditions such as RuCl(p-cymene)[(R,R)-Ts-DPEN] and sodium formate (*J. Org. Chem*, 2014, 79, 3238-3243). Typically, these reactions are done in EtOAc solvent and run at room temperature. Finally, compounds such as 1f can be deprotected to reveal the triol compounds such as 1g by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of the diastereomers of 1f or 1g may be carried out under standard methods known in the art such as chiral SFC or HPLC to afford single diastereomers.

Scheme 2:

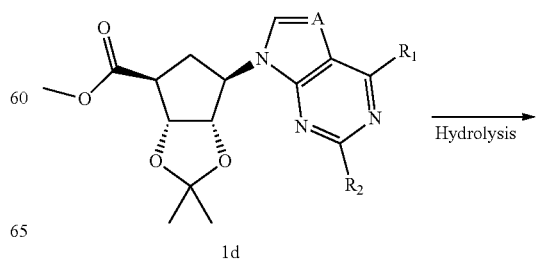

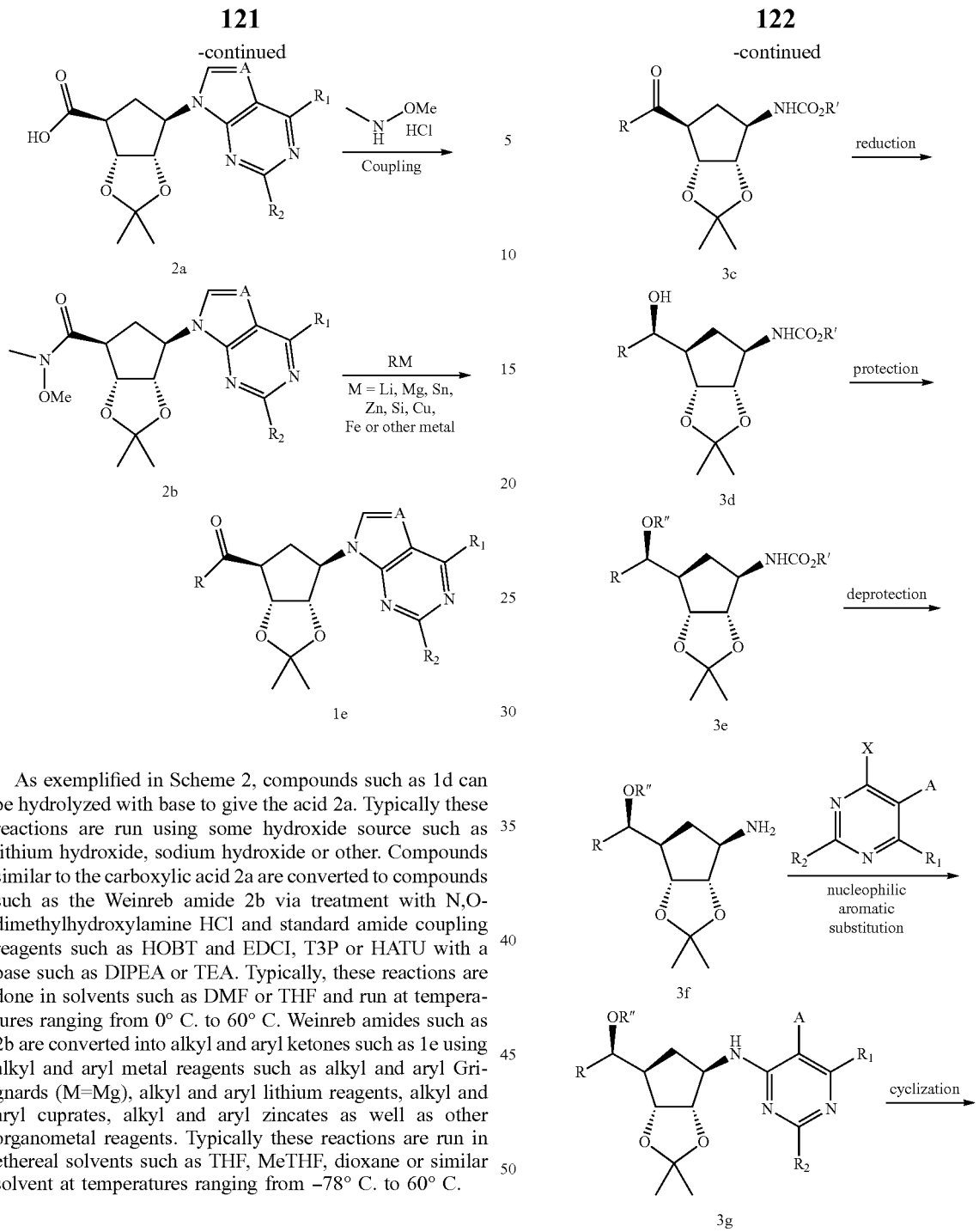

As exemplified in Scheme 2, compounds such as 1d can be hydrolyzed with base to give the acid 2a. Typically these reactions are run using some hydroxide source such as lithium hydroxide, sodium hydroxide or other. Compounds similar to the carboxylic acid 2a are converted to compounds such as the Weinreb amide 2b via treatment with N,O-dimethylhydroxylamine HCl and standard amide coupling reagents such as HOBT and EDCI, T3P or HATU with a base such as DIPEA or TEA. Typically, these reactions are done in solvents such as DMF or THF and run at temperatures ranging from 0° C. to 60° C. Weinreb amides such as 2b are converted into alkyl and aryl ketones such as 1e using alkyl and aryl metal reagents such as alkyl and aryl Grignards (M=Mg), alkyl and aryl lithium reagents, alkyl and aryl cuprates, alkyl and aryl zincates as well as other organometal reagents. Typically these reactions are run in ethereal solvents such as THF, MeTHF, dioxane or similar solvent at temperatures ranging from −78° C. to 60° C.

Scheme 3:

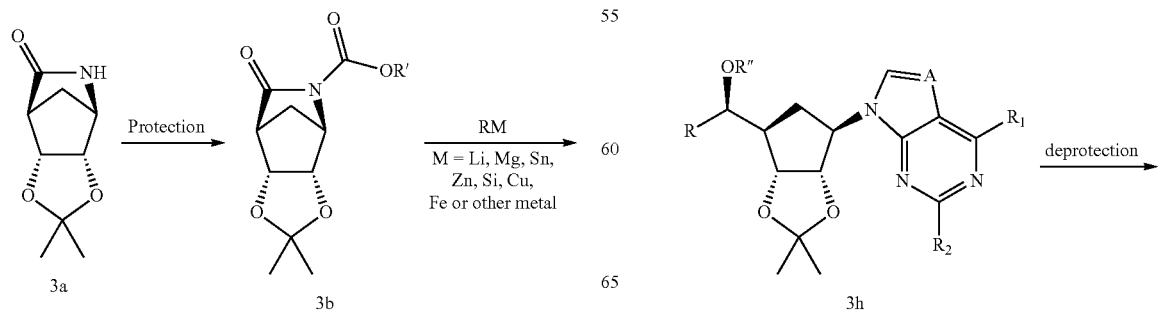

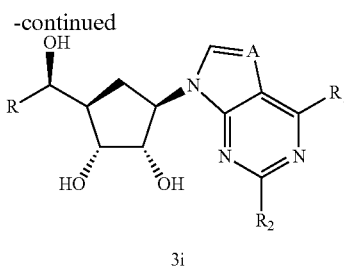

3i

As exemplified in Scheme 3, a compound such as 3a [(3aS,4R,7S,7aR)-2,2-dimethyltetrahydro-4,7-methano[1,3]dioxolo[4,5-c]pyridin-6(3aH)-one] can be purchased or synthesized (*Chem. Rev.*, 2012, 112 (8), 4642-4686) and can be protected as the carbamate using reagents such as Boc anhydride or benzoyl chloride resulting in lactams such as 3b. These activated lactams (3b) are converted into alkyl and aryl ketones such as 3c using alkyl and aryl metal reagents such as alkyl and aryl Grignards (M=Mg), alkyl and aryl lithium reagents, alkyl and aryl cuprates, alkyl and aryl zincates as well as other organometal reagents. Typically these reactions are run in ethereal solvents such as THF, MeTHF, dioxane or similar solvent at temperatures ranging from −78° C. to 60° C. Alkyl and aryl ketones such as 3c can be converted to secondary alcohols such as 3d using reducing reagents such as NaBH4, LiBH4, LiAlH4, DIBAL and others. Typically these reactions can be run in a variety of solvents such as DCM, THF, MeOH, EtOH or others at varying temperatures. Alkyl and aryl ketones such as 3c can be preferentially converted to diastereomerically enriched secondary alcohols such as 3d using chiral reducing conditions such as RuCl(p-cymene)[(S,S)-Ts-DPEN] and sodium formate (*J. Org. Chem*, 2014, 79, 3238-3243). Typically, these reactions are done in EtOAc solvent and run at room temperature. The resulting secondary alcohol such as 3d can be protected with a variety of reagents that provide orthogonal deprotection strategies to the carbamate installed earlier in the route. Such reagents include TMSCl, TESCl, TBDMSCl, TIPSCl, as well as others. Compounds such as 3e can be deprotected to give compounds such as 3f through a variety of methods depending on what carbamate is installed. Examples include using dilute trifluoroacetic acid solution in the case of Boc carbamate or hydrogenolysis with Pd catalyst and hydrogen gas in the case of benzoyl carbamate. Compounds such as 3f can react with appropriately substituted heterocycles in a nucleophilic aromatic substitution to yield compounds such as 3g. Such reactions are usually accomplished using organic bases such as diisopropylethylamine or trimethylamine in DMSO, DMA or DMF or conditions using cesium fluoride in DMSO. Alternative reaction condition may include metal coupling reactions such as palladium couplings. Cyclization of compounds such as 3g to compounds such as 3h can occur under a variety of conditions including condensations or metal couplings depending on the atom type of A. Finally, compounds such as 3h can be deprotected to reveal the triol compounds such as 3i by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of the diastereomers of 3d or any compound afterwards may be carried out under standard methods known in the art such as chiral SFC or HPLC to afford single diastereomers.

Scheme 4:

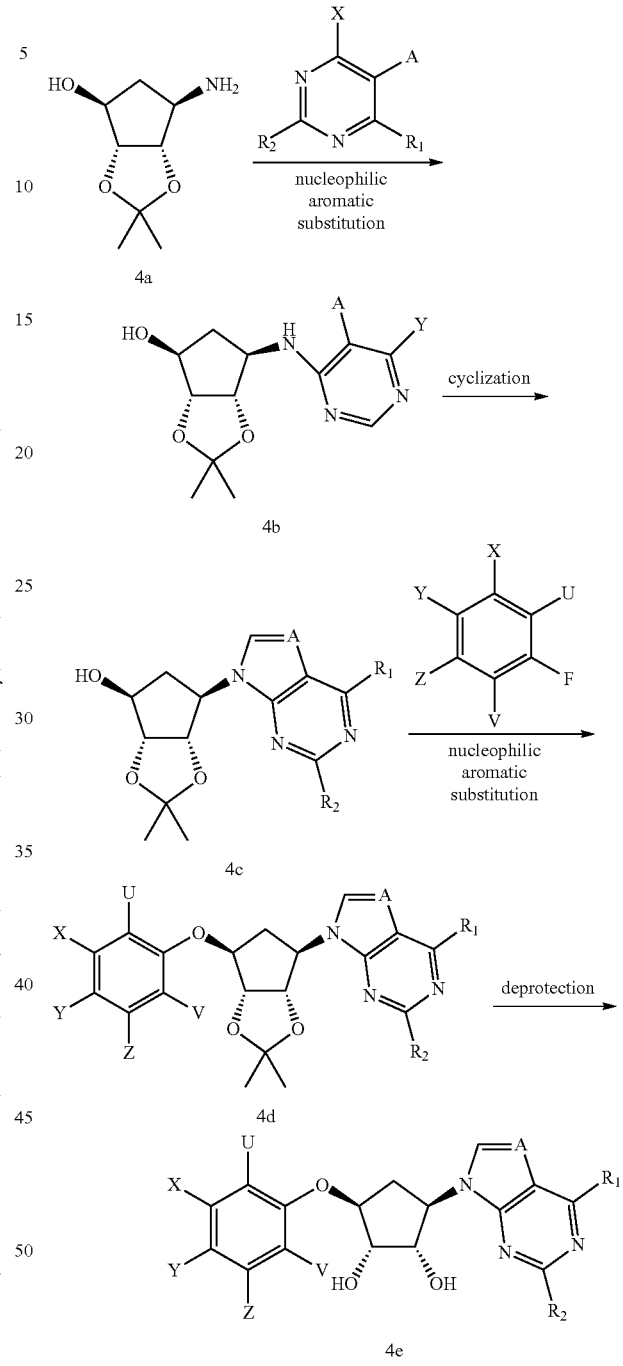

As exemplified in Scheme 4, a compound such as 4a [(3aR,4S,6R,6aS)-6-amino-2,2-dimethyltetrahydro-4H-cyclopenta[d][1,3]dioxol-4-ol] can be purchased or synthesized [*J. Perkin Trans. I*, 1985, 1437; *Tetrahedron Letters*, 2000, (41) 9537-9530]. Compounds such as 4a can undergo nucleophilic aromatic substitution with the appropriately substituted heterocycle to yield compounds such as 4b. Cyclization of compounds such as 4b to compounds such as 4c can occur under a variety of conditions including condensations or metal couplings depending on the atom type of A. Compounds such as 4c can undergo nucleophilic aromatic substitution with the appropriately substituted fluorobenzene to yield phenol ethers such as 4d.

Finally, compounds such as 4d can be deprotected to reveal the diol compounds such as 4e by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of the diastereomers of 4a or any compound afterwards may be carried out under standard methods known in the art such as chiral SFC or HPLC to afford single diastereomers.

Scheme 5:

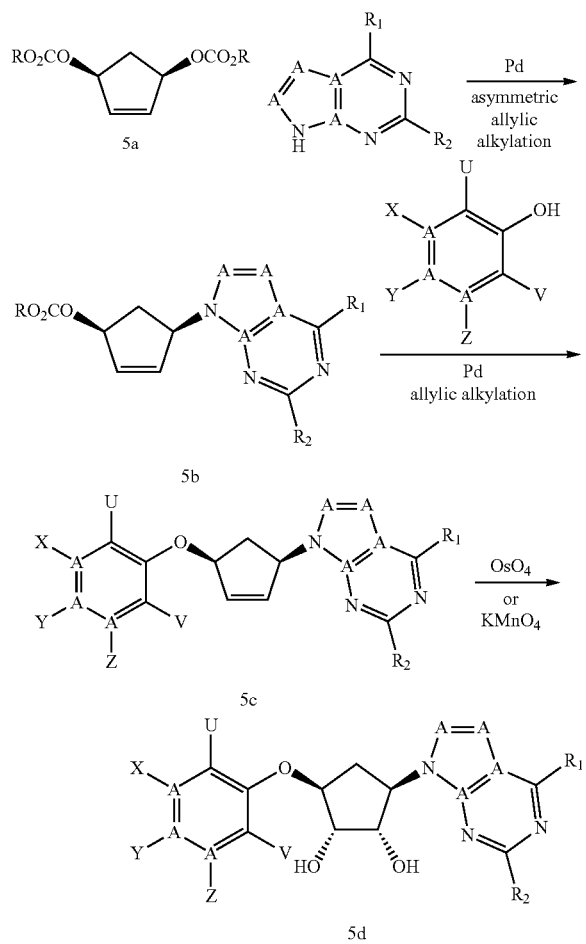

and ligands to form compounds such as 5c. Compounds such as 5c can be dihydroxylated to form diols such as 5d using reagents such as osmium tertroxide or potassium permanganate. Compounds at every step may be purified by standard techniques such as column chromatography, crystallization, reverse phase HPLC or SFC. If necessary, separation of the diastereomers of 5d may be carried out under standard methods known in the art such as chiral SFC or HPLC to afford single diastereomers.

Scheme 6:

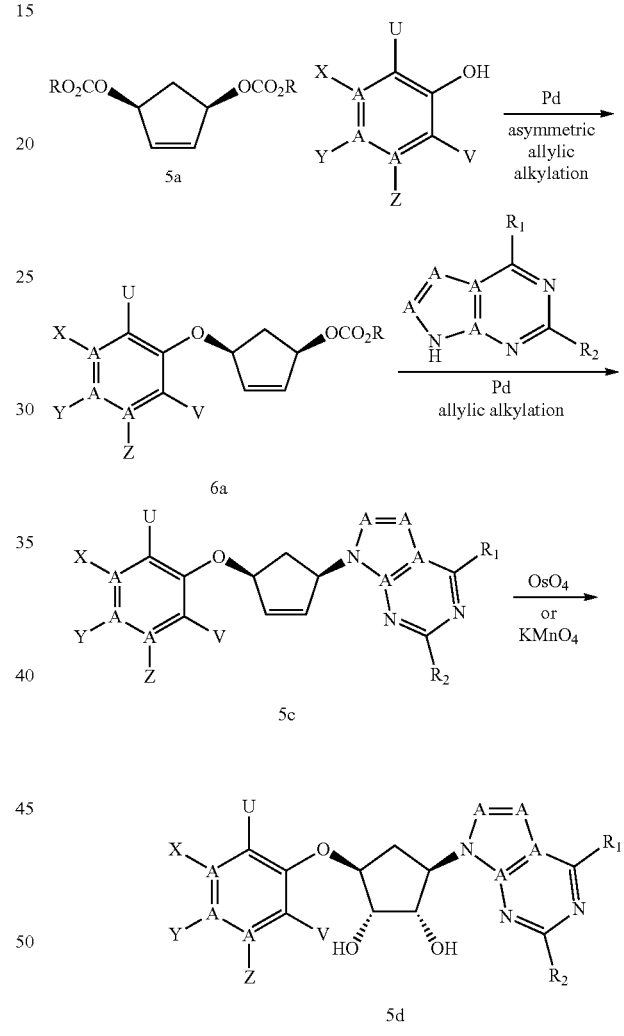

As exemplified in Scheme 5, compounds such as 5a can be purchased or synthesized (*Chemical Science,* 2010, 1, p 427; *Journal of the American Chemical Society,* 2000, 122, p 5947; *Organic Letters,* 2012, 14(9), p 2254). Compounds such as 5a can undergo asymmetric allylic alkylation with appropriately substituted heterocycles using a variety of palladium catalysts and chiral ligands to form compounds such as 5b. Compounds such as 5b can undergo allylic alkylation with appropriately substituted phenols or hydroxyheterocycles using a variety of palladium catalysts As exemplified in Scheme 6, compounds such as 5a can undergo asymmetric allylic alkylation with appropriately substituted phenols or hydroxyheterocycles using a variety of palladium catalysts and chiral ligands to form compounds such as 6a. Compounds such as 6a can undergo allylic alkylation with appropriately substituted heterocycles using a variety of palladium catalysts and ligands to form compounds such as 5c. Compounds such as 5c can be dihydroxylated to form diols such as 5d using reagents such as osmium tertroxide or potassium permanganate.

Scheme 7:

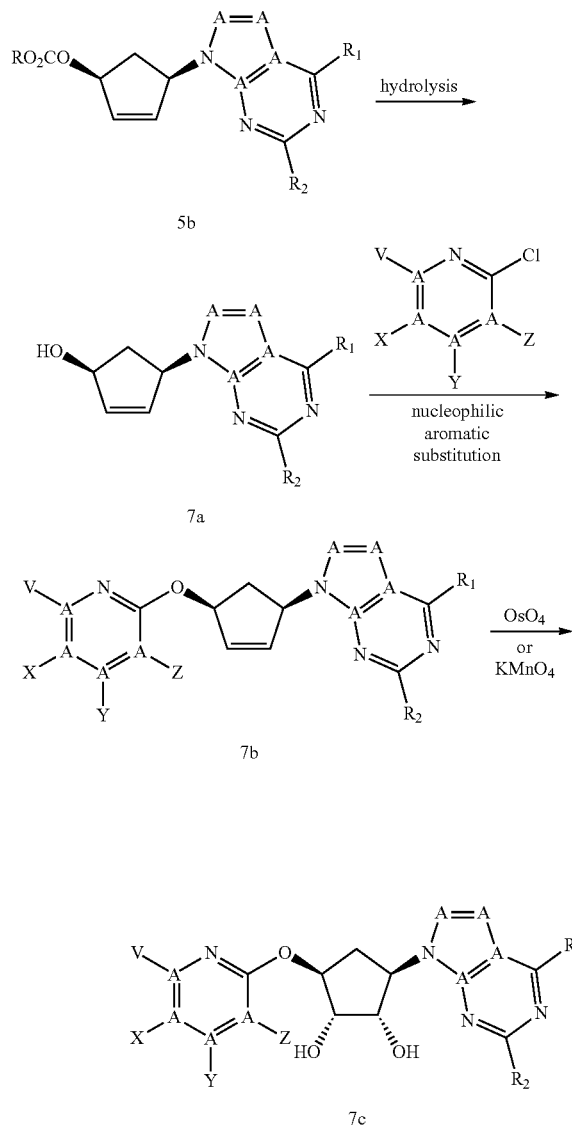

Scheme 8:

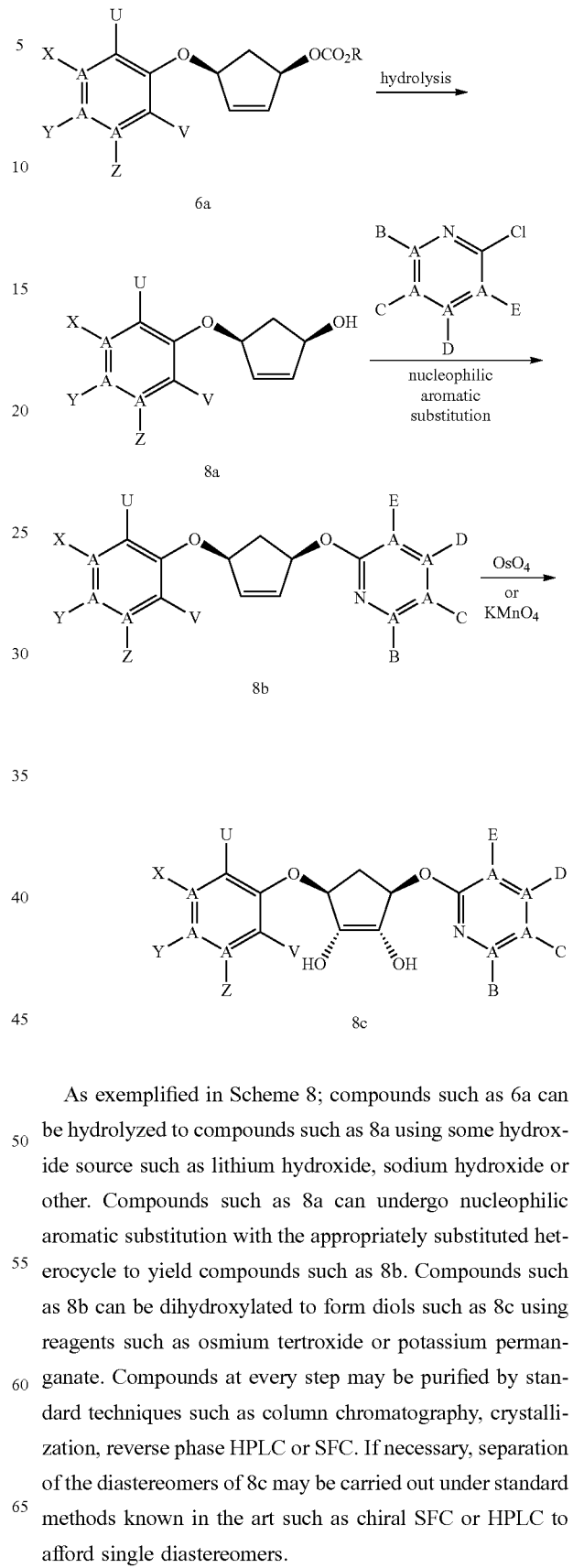

As exemplified in Scheme 7, compounds such as 5b can be hydrolyzed to compounds such as 7a using some hydroxide source such as lithium hydroxide, sodium hydroxide or other. Compounds such as 7a can undergo nucleophilic aromatic substitution with the appropriately substituted heterocycle to yield compounds such as 7b. Compounds such as 7b can be dihydroxylated to form diols such as 7c using reagents such as osmium tertroxide or potassium permanganate. Compounds at every step may be purified by standard techniques such as column chromatography, crystallization, reverse phase HPLC or SFC. If necessary, separation of the diastereomers of 7c may be carried out under standard methods known in the art such as chiral SFC or HPLC to afford single diastereomers.

As exemplified in Scheme 8; compounds such as 6a can be hydrolyzed to compounds such as 8a using some hydroxide source such as lithium hydroxide, sodium hydroxide or other. Compounds such as 8a can undergo nucleophilic aromatic substitution with the appropriately substituted heterocycle to yield compounds such as 8b. Compounds such as 8b can be dihydroxylated to form diols such as 8c using reagents such as osmium tertroxide or potassium permanganate. Compounds at every step may be purified by standard techniques such as column chromatography, crystallization, reverse phase HPLC or SFC. If necessary, separation of the diastereomers of 8c may be carried out under standard methods known in the art such as chiral SFC or HPLC to afford single diastereomers.

Example 1 (Scheme A): Synthesis of (1S,2R,3R, 5R)-3-((R)-1-hydroxyethyl)-5-(4-methyl-7H-pyrrolo [2,3-d]pyrimidin-7-yl)cyclopentane-1,2-diol (A-12)

Example 2 (Scheme A): Synthesis of (1S,2R,3R, 5R)-3-((S)-1-hydroxyethyl)-5-(4-methyl-7H-pyrrolo [2,3-d]pyrimidin-7-yl)cyclopentane-1,2-diol (A-13)

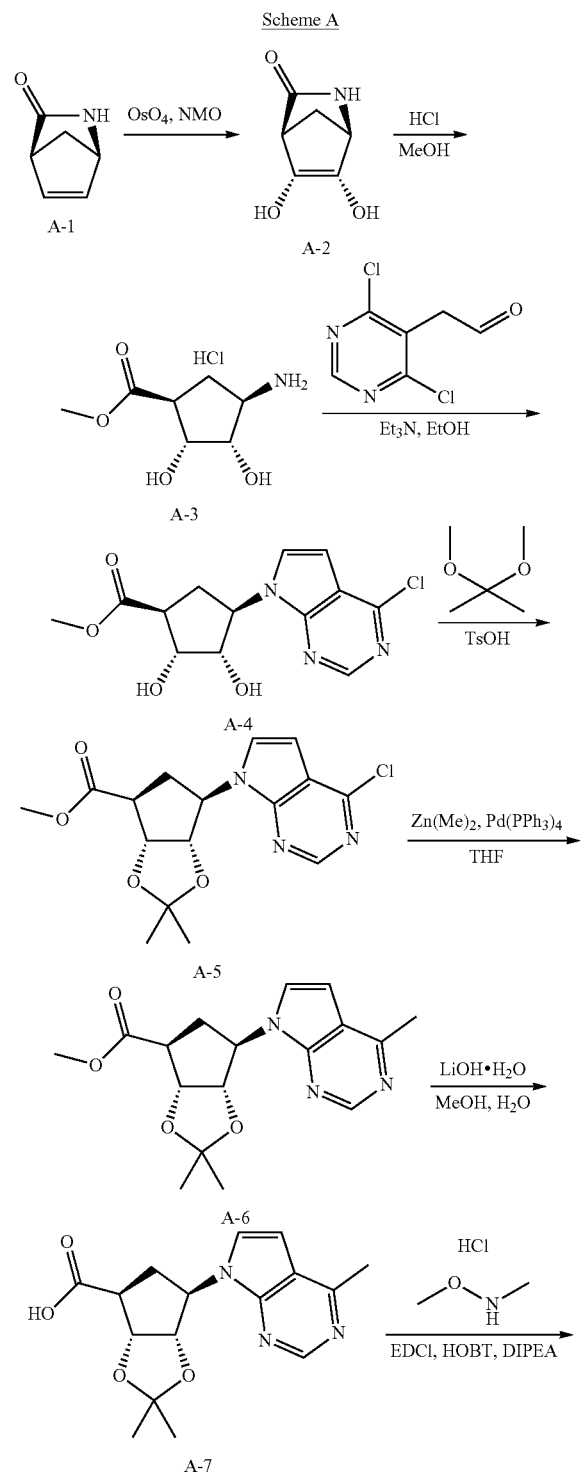

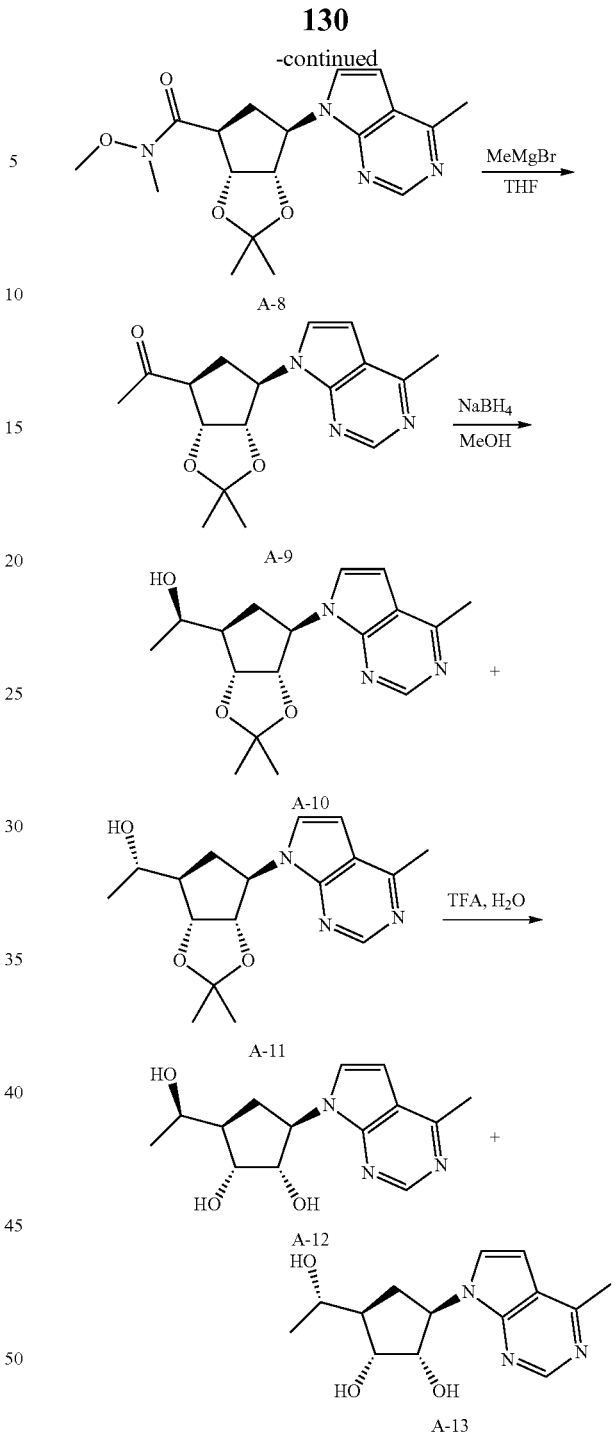

Step 1: Synthesis of (1R,4S,5R,6S)-5,6-dihydroxy-2-azabicyclo[2.2.1]heptan-3-one (A-2)

To a light yellow bi-phasic mixture of (1R,4S)-2-azabicyclo[2.2.1]hept-5-en-3-one A-1 (*Chemical Reviews*, 2012, 112 (8), pp 4642-4686) (100 g, 916 mmol) and NMO (118 g, 1.01 mol) in isoamyl alcohol (500 mL) and water (500 mL) was added 2.5% $OsO_4$ in t-BuOH (1.5 g, 5.9 mmol, 76 mL) at rt (15° C.). The mixture was heated at 70° C. for 2 hrs. The mixture was cooled to rt (15° C.). $NaHSO_3$ (12 g) was added and stirred at rt (15° C.) for 45 min. The mixture was concentrated in vacuo to afford crude (150 g) as dark solid which was purified by silica gel chromatography eluted with MeOH in DCM=10% to afford A-2 (90 g, 69%) as a light pink solid. $^1$H NMR (400 MHz, DMSO-$d_6$) δ ppm 7.54 (br. s., 1H), 5.00 (dd, J=21.3, 22.6 Hz, 2H), 3.81-3.64 (m, 2H), 3.43 (s, 1H), 2.25 (s, 1H), 1.93-1.67 (m, 2H)

Step 2: Synthesis of methyl(1S,2R,3S,4R)-4-amino-2,3-dihydroxycyclopentane-1-carboxylate-HCl (A-3)

Compound A-2 (33 g, 231 mmol) was added to 4N HCl in MeOH (500 mL) at rt (15° C.). The suspension was stirred at rt (15° C.) for 20 hrs. The mixture was concentrated in vacuo and the residue was suspended in DCM and filtered. The solid was washed with DCM and dried in vacuo to afford A-3 (45 g, 92%) as a white solid. LCMS [M+1] 176; $^1$H NMR (400 MHz, D$_2$O) δ ppm 4.27 (t, J=5.1 Hz, 1H), 4.04 (t, J=6.4 Hz, 1H), 3.72 (s, 3H), 3.55 (q, J=8.4 Hz, 1H), 2.97 (dt, J=5.0, 8.8 Hz, 1H), 2.49 (td, J=8.5, 13.8 Hz, 1H), 1.83 (td, J=9.2, 13.7 Hz, 1H)

Step 3: Synthesis of methyl(1S,2R,3S,4R)-4-(4-chloro-7H-pyrrolo[2,3-d]pyrimidin-7-yl)-2,3-dihydroxycyclopentane-1-carboxylate (A-4)

To a white suspension compound A-3 (42 g, 200 mmol) and 2-(4,6-dichloropyrimidin-5-yl)acetaldehyde (40 g, 209 mmol) in EtOH (400 mL) was added Et$_3$N (40.4 g, 400 mmol). The resulting yellow solution was stirred at reflux for 2 hrs. The mixture was concentrated in vacuo to about 100 mL. The residue was poured into NH$_4$Cl aq (500 mL) and extracted with EtOAc (200 mL×3). The extract was washed with brine (200 mL), dried over Na$_2$SO$_4$ and concentrated in vacuo to afford crude A-4 (60 g, >99%) as a red gum which was used in the next step directly. LCMS [M+1] 312

Step 4: Synthesis of methyl(3aR,4S,6R,6aS)-6-(4-chloro-7H-pyrrolo[2,3-d]pyrimidin-7-yl)-2,2-dimethyltetrahydro-4H-cyclopenta[d][1,3]dioxole-4-carboxylate (A-5)

To a solution of crude compound A-4 (60 g, 192 mmol) in 2,2-dimethoxypropane (300 mL) and acetone (300 mL) was added TsOH.H$_2$O (40 g, 212 mmol). The mixture was stirred at rt (15° C.) for 1 hr. The mixture was poured into NaHCO$_3$ aq (1000 mL) and extracted with EtOAc (500 mL). The extract was washed with brine, concentrated in vacuo to afford crude material which was purified by silica gel chromatography eluted with EtOAc in petroleum ether from 0-100% to afford A-5 (42 g, 62%) as a yellow gum which solidified upon standing. LCMS [M+1] 352; $^1$H NMR (400 MHz, CDCl$_3$) δ ppm 8.63 (s, 1H), 7.29 (d, J=3.5 Hz, 1H), 6.64 (d, J=3.8 Hz, 1H), 5.15-5.04 (m, 2H), 5.03-4.98 (m, 1H), 3.76 (s, 3H), 3.12 (ddd, J=5.3, 7.6, 10.7 Hz, 1H), 2.75-2.59 (m, 2H), 1.59 (s, 3H), 1.33 (s, 3H)

Step 5: Synthesis of methyl(3aR,4S,6R,6aS)-2,2-dimethyl-6-(4-methyl-7H-pyrrolo[2,3-d]pyrimidin-7-yl)tetrahydro-4H-cyclopenta[d][1,3]dioxole-4-carboxylate (A-6)

To a solution of A-5 (15 g, 42.6 mmol) in dry THF (125 mL) was added Pd(PPh$_3$)$_4$ (1.97 g, 1.71 mmol). To the resulting yellow solution was added 1M solution of Zn(Me)$_2$ (171 mL, 171 mmol). The mixture was degassed with N$_2$ four times. The yellow solution was heated at reflux for 3 hrs which changed to a dark solution. The mixture was poured into cooled NH$_4$Cl aq (200 mL) carefully and extracted with EtOAc (200 mL×3). The extract was washed with brine (200 mL), dried over Na$_2$SO$_4$ and concentrated in vacuo to afford crude (18 g) as a yellow gum. The crude material was purified by silica gel chromatography eluted with EtOAc in petroleum ether from 0 to 100% to A-6 (13.5 g, 96%) as a yellow gum. [α]$^{20}_D$ −21.57° (c=8.4 mg/mL, methanol). LCMS [M+1] 332; $^1$H NMR (400 MHz, DMSO-$d_6$) δ ppm 8.65 (s, 1H), 7.74 (d, J=3.5 Hz, 1H), 6.74 (d, J=3.8 Hz, 1H), 5.18-5.06 (m, 1H), 5.01-4.90 (m, 2H), 3.65 (s, 3H), 3.15-3.03 (m, 1H), 2.64 (s, 3H), 2.46-2.40 (m, 1H), 1.49 (s, 3H), 1.23 (s, 3H)

Step 6: Synthesis of (3aR,4S,6R,6aS)-2,2-dimethyl-6-(4-methyl-7H-pyrrolo[2,3-d]pyrimidin-7-yl)tetrahydro-4H-cyclopenta[d][1,3]dioxole-4-carboxylic acid (A-7)

A mixture of A-6 (13 g, 33 mmol) and LiOH (2.8 g, 66.7 mmol) in THF (100 mL)/H$_2$O (100 mL) was stirred at rt (15° C.) for 4 hrs. TLC (DCM/MeOH=10/1) showed most of SM was consumed. The mixture was diluted with water (50 mL) and washed with EtOAc (100 mL×2). To the aqueous layer was added H$_3$PO$_4$ (3.6 g, 37 mmol) and extracted with EtOAc/THF (50 mL/50 mL×5). The extract was dried over Na$_2$SO$_4$ and concentrated in vacuo to afford A-7 (8.9 g, 84%) as a yellow solid. LCMS [M+1] 318; $^1$H NMR (400 MHz, CDCl$_3$) δ ppm 8.77 (s, 1H), 7.26 (br. s, 1H), 6.59 (d, J=3.8 Hz, 1H), 5.25 (t, J=5.3 Hz, 1H), 5.14-4.98 (m, 2H), 3.18 (ddd, J=4.8, 7.8, 10.0 Hz, 1H), 2.77-2.60 (m, 5H), 1.60 (s, 3H), 1.35 (s, 3H)

Step 7: Synthesis of (3aR,4S,6R,6aS)—N-methoxy-N,2,2-trimethyl-6-(4-methyl-7H-pyrrolo[2,3-d]pyrimidin-7-yl)tetrahydro-4H-cyclopenta[d][1,3]dioxole-4-carboxamide (A-8)

To a suspension of crude A-7 (7 g, 22.1 mmol) and N,O-dimethylhydroxylamine-HCl (4.30 g, 44.1 mmol) in THF (140 mL) was added DIPEA (11.4 g, 88.2 mmol) and 50% T3P (28.1 g, 25.8 mL, 44.1 mmol) at rt (15° C.). The resulting red solution was stirred at rt (15° C.) for 20 hrs. LCMS showed the main peak was desired compound. The mixture was diluted with EtOAc and washed with NH$_4$Cl aq, NaHCO$_3$ aq, brine, dried over Na$_2$SO$_4$ and concentrated in vacuo to A-8 (7.3 g, 91.8%) as a yellow gum. [α]$^{20}_D$+27.30° (c=2.82 mg/mL, methanol); LCMS [M+1] 361; $^1$H NMR (400 MHz, CDCl$_3$) δ ppm 8.77 (s, 1H), 7.31 (d, J=3.5 Hz, 1H), 6.60 (d, J=3.5 Hz, 1H), 5.36-5.27 (m, 1H), 5.11-5.03 (m, 1H), 4.91 (dd, J=5.6, 7.2 Hz, 1H), 3.77 (s, 3H), 3.61-3.51 (m, 1H), 3.24 (s, 3H), 2.72 (s, 3H), 2.65-2.56 (m, 1H), 2.54-2.42 (m, 1H), 1.60 (s, 3H), 1.30 (s, 3H)

Step 8: Synthesis of 1-((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)ethan-1-one (A-9)

To a light yellow solution of A-8 (130 mg, 0.361 mmol) in THF (5.39 mL) was added MeMgBr (3.0 M solution in diethyl ether, 0.144 mL, 0.433 mmol) at 0° C. After the addition, the mixture was stirred at 0° C. for 40 min. The mixture was quenched with aq.NH$_4$Cl (40 mL) in an ice bath and extracted with EtOAc (30 mL×2). The extract was washed with brine (20 mL), dried over Na$_2$SO$_4$ and concentrated in vacuo to afford crude compound A-9 (110 mg, 97%) as a yellow oil and used as is in the next step.

Step 9: Synthesis of (R)-1-((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)ethan-1-ol (A-10) and (S)-1-((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)ethan-1-ol (A-11)

To a yellow solution of A-9 (110 mg, 0.349 mmol) in dry MeOH (6 mL) was added NaBH₄ (26 mg, 0.698 mmol) at 0° C. After addition, the mixture was stirred at 0° C. for 60 min. Then the reaction mixture was concentrated in vacuum to give a white solid (150 mg) which was separated by chiral SFC to give A-10 (62 mg, 56%) and A-11 (61 mg, 55%) and used as is.

Step 10: Synthesis of (1S,2R,3R,5R)-3-((R)-1-hydroxyethyl)-5-(4-methyl-7H-pyrrolo[2,3-d]pyrimidin-7-yl)cyclopentane-1,2-diol (A-12) and (1S,2R,3R,5R)-3-((S)-1-hydroxyethyl)-5-(4-methyl-7H-pyrrolo[2,3-d]pyrimidin-7-yl)cyclopentane-1,2-diol (A-13)

To a yellow suspension of A-10 (74 mg, 0.02 mmol) in H₂O (1 mL) was added TFA (1 mL) at 0° C. The mixture was stirred at room temperature (15° C.) for 2 hrs. Saturated aqueous K₂CO₃ (10 mL) was added into the mixture (0° C.) slowly until the pH 7-8. Purify by prep HPLC to give compound A-12 (34 mg, 53%). LCMS [M+1] 278; $^1$H NMR (400 MHz, MeOD-d₄) δ ppm 8.60 (s, 1H), 7.60 (d, J=3.8 Hz, 1H), 6.73 (d, J=3.5 Hz, 1H), 5.12-5.00 (m, 1H), 4.37 (dd, J=5.8, 9.3 Hz, 1H), 4.17 (dd, J=2.9, 5.6 Hz, 1H), 3.81 (quin, J=6.2 Hz, 1H), 2.71 (s, 3H), 2.31 (td, J=8.3, 12.7 Hz, 1H), 2.07 (ddt, J=2.8, 5.9, 9.0 Hz, 1H), 1.84 (ddd, J=9.3, 10.9, 12.7 Hz, 1H), 1.26 (d, J=6.3 Hz, 3H)

To a yellow suspension of A-11 (74 mg, 0.23 mmol) in H₂O (1.5 mL) was added TFA (1.5 mL) drop-wise at 0° C. Then the reaction mixture was stirred at room temperature (20° C.) for 2 hrs, then adjusted to pH=7 with 20% K₂CO₃. The aqueous phase was purified by prep HPLC to give A-13 (45 mg, 70%). LCMS [M+1] 278; $^1$H NMR (400 MHz, MeOD-d₄) δ ppm 8.59 (s, 1H), 7.61 (d, J=3.53 Hz, 1H), 6.72 (d, J=3.53 Hz, 1H), 5.03-5.12 (m, 1H), 3.92-4.30 (dd, J=8.60, 5.95 Hz, 1H), 3.92-4.03 (m, 2H), 2.70 (s, 3H), 2.28 (dt, J=12.57, 8.27 Hz, 1H), 2.06 (tt, J=8.71, 4.30 Hz, 1H), 1.88-1.99 (m, 1H), 1.22 (d, J=6.62 Hz, 3H)

Examples 3-16 were Prepared in Using Similar Chemistry in Scheme A Using the Appropriate Grignard Reagent for Step 8

| | | | |
|---|---|---|---|
| Example 3:<br>3,4-Difluorophenyl magnesium bromide | 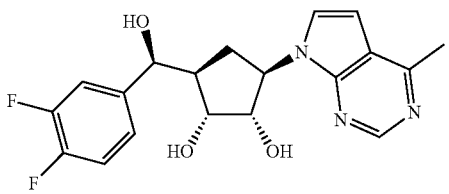 [SMILES: Cc1ncnc2c1ccn2[C@@H]1C[C@H]([C@H](O)c2ccc(F)c(F)c2)[C@@H](O)[C@H]1O] | 375.90<br>[M + 1] | (1S,2R,3R,5R)-3-[(S)-(3,4-difluorophenyl)(hydroxyl)methyl]-5-(4-methyl-7H-pyrrolo[2,3-d]pyrimidin-7-yl)cyclopentane-1,2-diol<br>$^1$H NMR (700 MHz, DMSO-d6) δ ppm 8.61 (s, 1 H) 7.65 (d, J = 3.74 Hz, 1 H) 7.39-7.45 (m, 1 H) 7.32-7.39 (m, 1 H) 7.19-7.28 (m, 1 H) 6.70 (d, J = 3.52 Hz, 1 H) 5.69 (d, J = 4.62 Hz, 1 H) 4.93-5.02 (m, 1 H) 4.80 (br. s., 1 H) 4.51-4.64 (m, 2 H) 4.23-4.35 (m, 1 H) 3.94 (d, J = 4.18 Hz, 1 H) 2.63 (s, 3 H) 2.20-2.30 (m, 1 H) 2.00 (dt, J = 12.93, 8.72 Hz, 1 H) 1.60 (ddd, J = 12.87, 10.78, 8.25 Hz, 1 H) |
| Example 4:<br>3,4-Difluorophenyl magnesium bromide | 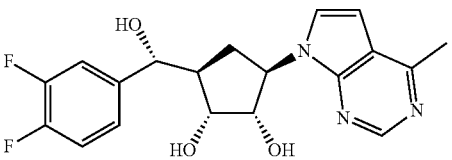 [SMILES: Cc1ncnc2c1ccn2[C@@H]1C[C@H]([C@@H](O)c2ccc(F)c(F)c2)[C@@H](O)[C@H]1O] | 375.90<br>[M + 1] | (1S,2R,3R,5R)-3-[(R)-(3,4-difluorophenyl)(hydroxy)methyl]-5-(4-methyl-7H-pyrrolo[2,3-d]pyrimidin-7-yl)cyclopentane-1,2-diol<br>$^1$H NMR (700 MHz, DMSO-d6) δ ppm 8.62 (s, 1 H) 7.68 (d, J = 3.74 Hz, 1 H) 7.32-7.41 (m, 2 H) 7.14-7.23 (m, 1 H) 6.73 (d, J = 3.52 Hz, 1 H) 5.68 (d, J = 4.40 Hz, 1 H) 4.90-4.98 (m, 1 H) 4.86 (br. s., 1 H) 4.80 (br. s., 1 H) 4.67 (br. s., 1 H) 4.23 (dd, J = 8.14, 5.72 Hz, 1 H) 3.85-3.94 (m, 1 H) 2.65 (s, 3H) 2.23 (tt, J = 8.72, 4.37 Hz, 1 H) 1.85 (dt, J = 12.98, 8.36 Hz, 1 H) 1.78 (dt, J = 12.87, 9.74 Hz, 1 H) |
| Example 5:<br>3-chloro-4-fluorophenyl magnesium bromide | 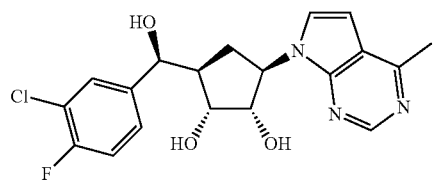 [SMILES: Cc1ncnc2c1ccn2[C@@H]1C[C@H]([C@H](O)c2ccc(F)c(Cl)c2)[C@@H](O)[C@H]1O] | 391.80<br>[M + 1] | (1S,2R,3R,5R)-3-[(S)-(3-chloro-4-fluorophenyl)(hydroxy)methyl]-5-(4-methyl-7H-pyrrolo[2,3-d]pyrimidin-7-yl)cyclopentane-1,2-diol<br>$^1$H NMR (700 MHz, DMSO-d6) δ ppm 8.60 (s, 1 H) 7.64 (d, J = 3.52 Hz, 1 H) 7.57 (dd, J = 7.26, 1.76 Hz, 1 H) 7.37-7.42 (m, 1 H) 7.32-7.37 (m, 1 H) 6.69 (d, J = 3.52 Hz, 1 H) 5.70 (d, J = 4.62 Hz, 1 H) 4.93-5.02 (m, 1 H) 4.80 (d, J = 6.82 Hz, 1 H) 4.58-4.62 (m, 1 H) 4.57 (d, J = 3.52 Hz, 1 H) 4.28 (dt, J = 9.57, 6.00 Hz, 1 H) 3.94 (br. s., 1 H) 2.63 (s, 3 H) 2.22-2.28 (m, 1 H) 2.00 (dt, J = 12.98, 8.80 Hz, 1 H) 1.60 (ddd, J = 12.87, 10.78, 8.25 Hz, 1 H) |

-continued

| | | | |
|---|---|---|---|
| Example 6: 3-chloro-4-fluorophenyl magnesium bromide | 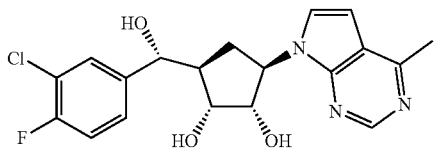 [SMILES: Cc1ncnc2c1ccn2[C@@H]1C[C@H]([C@@H](O)c2ccc(F)c(Cl)c2)[C@@H](O)[C@H]1O] | 391.85 [M + 1] | (1S,2R,3R,5R)-3-[(R)-(3-chloro-4-fluorophenyl) (hydroxy)methyl]-5-(4-methyl-7H-pyrrolo[2,3-d] pyrimidin-7-yl)cyclopentane-1,2-diol<br>$^1$H NMR (700 MHz, DMSO-d6) δ ppm 8.60 (s, 1 H) 7.66 (d, J = 3.52 Hz, 1 H) 7.52 (d, J = 6.82 Hz, 1 H) 7.30-7.38 (m, 2H) 6.71 (d, J = 3.52 Hz, 1 H) 5.68 (d, J = 4.62 Hz, 1 H) 4.90-4.98 (m, 1 H) 4.86 (br. s., 1 H) 4.80 (t, J = 4.51 Hz, 1 H) 4.66 (br. s., 1 H) 4.23 (br. s., 1 H) 3.88 (br. s., 1 H) 2.64 (s, 3 H) 2.19-2.27 (m, 1 H) 1.86 (dt, J = 12.82, 8.45 Hz, 1 H) 1.78 (dt, J = 12.87, 9.74 Hz, 1 H) |
| Example 7: 3-chlorophenyl magnesium bromide | 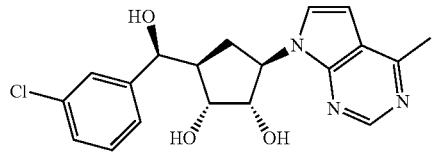 [SMILES: Cc1ncnc2c1ccn2[C@@H]1C[C@H]([C@H](O)c2cccc(Cl)c2)[C@@H](O)[C@H]1O] | 373.90 [M + 1] | (1S,2R,3R,5R)-3-[(S)-(3-chlorophenyl) (hydroxy)methyl]-5-(4-methyl-7H-pyrrolo[2,3-d] pyrimidin-7-yl)cyclopentane-1,2-diol<br>$^1$H NMR (700 MHz, DMSO-d6) δ ppm 8.53-8.63 (m, 1 H) 7.59-7.68 (m, 1 H) 7.44 (s, 1 H) 7.31-7.39 (m, 2 H) 7.23-7.31 (m, 1 H) 6.66-6.73 (m, 1 H) 5.66 (d, J = 4.62 Hz, 1 H) 4.93-5.03 (m, 1 H) 4.79 (d, J = 6.60 Hz, 1 H) 4.57-4.62 (m, 1 H) 4.55 (br. s., 1 H) 4.30 (d, J = 3.30 Hz, 1 H) 3.95 (br. s., 1 H) 2.58-2.67 (m, 3 H) 2.21-2.31 (m, 1 H) 1.96-2.05 (m, 1 H) 1.55-1.67 (m, 1 H) |
| Example 8: 3-chlorophenyl magnesium bromide | 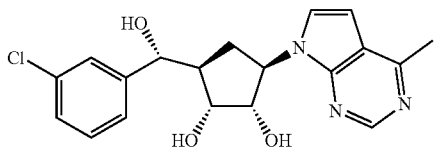 [SMILES: Cc1ncnc2c1ccn2[C@@H]1C[C@H]([C@@H](O)c2cccc(Cl)c2)[C@@H](O)[C@H]1O] | 373.80 [M + 1] | (1S,2R,3R,5R)-3-[(R)-(3-chlorophenyl) (hydroxy)methyl]-5-(4-methyl-7H-pyrrolo[2,3-d] pyrimidin-7-yl)cyclopentane-1,2-diol<br>$^1$H NMR (700 MHz, DMSO-d6) δ ppm 8.60 (s, 1 H) 7.67 (d, J = 3.74 Hz, 1 H) 7.39 (s, 1H) 7.32-7.37 (m, 1 H) 7.29-7.32 (m, 1 H) 7.27 (d, J = 7.70 Hz, 1 H) 6.71 (d. J = 3.52 Hz, 1 H) 5.65 (d, J = 4.84 Hz, 1 H) 4.90-4.98 (m, 1 H) 4.85 (br. s., 1 H) 4.81 (t, J = 4.40 Hz, 1 H) 4.67 (br. s., 1 H) 4.24 (br. s., 1 H) 3.91 (br. s., 1 H) 2.64 (s, 3 H) 2.24 (dt, J = 8.47, 4.35 Hz, 1 H) 1.81-1.88 (m, 1 H) 1.75-1.81 (m, 1 H) |
| Example 9: 3-fluorophenyl magnesium bromide | 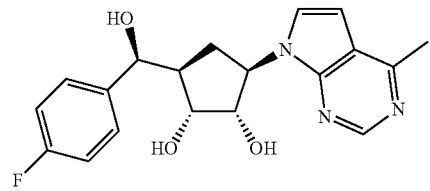 [SMILES: Cc1ncnc2c1ccn2[C@@H]1C[C@H]([C@H](O)c2ccc(F)cc2)[C@@H](O)[C@H]1O] | 357.85 [M + 1] | (1S,2R,3R,5R)-3-[(S)-(4-fluorophenyl) (hydroxy)methyl]-5-(4-methyl-7H-pyrrolo[2,3-d] pyrimidin-7-yl)cyclopentane-1,2-diol<br>$^1$H NMR (400 MHz, DMSO-d6) δ ppm 8.60 (s, 1 H) 7.62 (d. J = 3.55 Hz, 1 H) 7.42 (dd, J = 8.50, 5.81 Hz, 2 H) 7.13 (t, J = 8.93 Hz, 2 H) 6.68 (d, J = 3.55 Hz, 1 H) 5.51 (d, J = 4.52 Hz, 1 H) 4.91-5.05 (m, 1 H) 4.76 (d, J = 6.97 Hz, 1 H) 4.59 (dd, J = 6.79, 4.71 Hz, 1 H) 4.53 (d, J = 3.79 Hz, 1 H) 4.32 (dt, J = 9.60, 6.08 Hz, 1 H) 3.99 (br. s., 1 H) 2.63 (s, 3 H) 2.26 (q, J = 7.34 Hz, 1 H) 1.96 (dt, J = 12.72, 8.80 Hz, 1 H) 1.49-1.64 (m, 1 H) |
| Example 10: 3-fluorophenyl magnesium bromide | 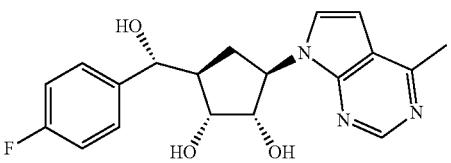 [SMILES: Cc1ncnc2c1ccn2[C@@H]1C[C@H]([C@@H](O)c2ccc(F)cc2)[C@@H](O)[C@H]1O] | 357.85 [M + 1] | (1S,2R,3R,5R)-3-[(R)-(4-fluorophenyl) (hydroxy)methyl]-5-(4-methyl-7H-pyrrolo[2,3-d] pyrimidin-7-yl)cyclopentane-1,2-diol<br>$^1$H NMR (700 MHz, DMSO-d6) δ ppm 8.57 (s, 1 H) 7.65 (d, J = 3.52 Hz, 1 H) 7.36 (t, J = 6.60 Hz, 2 H) 7.11 (t, J = 8.36 Hz, 2 H) 6.73 (d, J = 3.74 Hz, 1 H) 5.70 (br. s., 1 H) 4.93 (q, J = 9.02 Hz, 2 H) 4.78 (d, J = 4.40 Hz, 2 H) 4.19-4.26 (m, 2 H) 2.63 (s, 3 H) 2.18-2.28 (m, 1 H) 1.86 (dt, J = 13.04, 8.45 Hz, 1 H) 1.71-1.82 (m, 1 H) |
| Example 11: 4-chlorophenyl magnesium bromide | 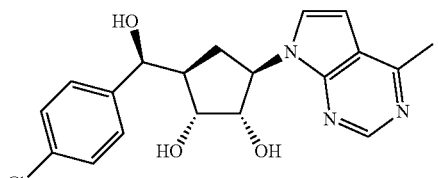 | 373.90 [M + 1] | (1S,2R,3R,5R)-3-[(S)-(4-chlorophenyl) (hydroxy)methyl]-5-(4-methyl-7H-pyrrolo[2,3-d] pyrimidin-7-yl)cyclopentane-1,2-diol<br>$^1$H NMR (400 MHz, DMSO-d6) δ ppm 1.58 (ddd, J = 12.90, 10.64,8.13 Hz, 1 H) 1.98 (dt, J = 12.93, 8.70 Hz, 1 H) 2.20-2.29 (m, 1 H) 2.58-2.66 (m, 3 H) 3.96 (d, J = 3.79 Hz, 1 H) 4.25-4.35 (m, 1 H) 4.52 (br. s., 1 H) 4.58 (d, J = 4.28 Hz, 1 H) 4.76 (br. s., 1 H) 4.91-5.04 (m, 1 H) 5.57 (br. s., 1 H) 6.70 (d, J = 3.55 Hz, 1 H) 7.32-7.45 (m, 4 H) 7.64 (d, J = 3.67 Hz, 1 H) 8.61 (s, 1 H) |

| Example 12: 4-chlorophenyl magnesium bromide | 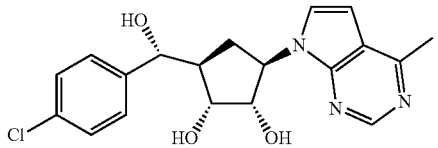 [SMILES: Cc1ncnc2c1ccn2[C@@H]1C[C@H]([C@@H](O)c2ccc(Cl)cc2)[C@@H](O)[C@H]1O] | 373.85 [M + 1] | (1S,2R,3R,5R)-3-[(R)-(4-chlorophenyl)(hydroxy)methyl]-5-(4-methyl-7H-pyrrolo[2,3-d]pyrimidin-7-yl)cyclopentane-1,2-diol<br>$^1$H NMR (400 MHz, DMSO-d6) δ ppm 1.73-1.92 (m, 2 H) 2.22 (tt, J = 8.67, 4.23 Hz, 1 H) 2.67 (s, 3 H) 3.84-3.96 (m, 1 H) 4.24 (dd, J = 8.44, 5.50 Hz, 1 H) 4.64 (br. s., 1 H) 4.73-4.89 (m, 2 H) 4.89-5.01 (m, 1 H) 5.56 (br. s., 1 H) 6.76 (d, J = 3.55 Hz, 1 H) 7.33-7.40 (m, 4 H) 7.71 (d, J = 3.55 Hz, 1 H) 8.65 (s, 1 H) |
|---|---|---|---|
| Example 13: 3,4,5-trifluorophenyl magnesium bromide | 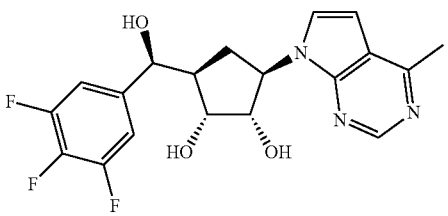 [SMILES: Cc1ncnc2c1ccn2[C@@H]1C[C@H]([C@H](O)c2cc(F)c(F)c(F)c2)[C@@H](O)[C@H]1O] | 393.90 [M + 1] | (1S,2R,3R,5R)-3-[(S)-hydroxy(3,4,5-trifluorophenyl)methyl]-5-(4-methyl-7H-pyrrolo[2,3-d]pyrimidin-7-yl)cyclopentane-1,2-diol<br>$^1$H NMR (700 MHz, DMSO-d6) δ ppm 8.53 (s, 1 H) 7.59 (d, J = 3.52 Hz, 1H) 7.21-7.29 (m, 2 H) 6.63 (d, J = 3.52 Hz, 1 H) 5.76 (d, J = 4.40 Hz, 1 H) 4.88-4.95 (m, 1 H) 4.74 (d, J = 6.82 Hz, 1 H) 4.48-4.56 (m, 2 H) 4.18 (dt, J = 9.52, 6.02 Hz, 1H) 3.84 (br. s., 1 H) 2.56 (s, 2 H) 2.15-2.23 (m, 1 H) 1.97 (dt, J = 12.82, 8.67 Hz, 1 H) 1.57 (ddd, J = 12.60, 10.95, 8.58 Hz, 1 H) |
| Example 14: 3,4,5-trifluorophenyl magnesium bromide | 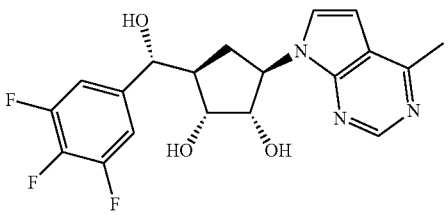 [SMILES: Cc1ncnc2c1ccn2[C@@H]1C[C@H]([C@@H](O)c2cc(F)c(F)c(F)c2)[C@@H](O)[C@H]1O] | 393.90 [M + 1] | (1S,2R,3R,5R)-3-[(R)-hydroxy(3,4,5-trifluorophenyl)methyl]-5-(4-methyl-7H-pyrrolo[2,3-d]pyrimidin-7-yl)cyclopentane-1,2-diol<br>$^1$H NMR (700 MHz, DMSO-d6) δ ppm 8.53 (s, 1 H) 7.58 (d, J = 3.52 Hz, 1 H) 7.21 (dd, J = 8.69, 6.93 Hz, 2 H) 6.64 (d, J = 3.52 Hz, 1 H) 5.75 (d, J = 4.84 Hz, 1 H) 4.86 (dt, J = 10.07, 8.39 Hz, 1 H) 4.81 (d, J = 6.60 Hz, 1 H) 4.75 (t, J = 4.62 Hz, 1 H) 4.61 (d, J = 4.62 Hz, 1 H) 4.15 (dt, J = 8.14, 6.16 Hz, 1 H) 3.85 (q, J = 4.40 Hz, 1 H) 2.57 (s, 2 H) 2.17 (dq, J = 8.80, 4.40 Hz, 1 H) 1.77 (dt, J = 12.98, 8.36 Hz, 1 H) 1.69 (dt, J = 12.87, 9.85 Hz, 1 H) |

Synthesis of (3,4,5-trifluorophenyl)magnesium bromide (for Example 13 & 14)

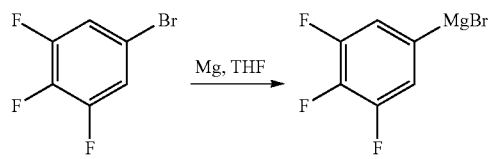

To a mixture of magnesium (264 mg, 11.0 mmol) and THF (5 mL) was added iodine (5.0 mg) and a solution of 5-bromo-1,2,3-trifluorobenzene (211 mg, 1 mmol) in THF (0.5 mL). The mixture was heated to 60° C., and a solution of 5-bromo-1,2,3-trifluorobenzene (1.9 g, 9 mmol) in THF (4.5 mL) was added by dropwise. The reaction was heated for two hours, the solution was cooled to room temperature and used directly in the next step.

Examples 15 & 16 (Scheme B) were Prepared in Using Similar Chemistry in Scheme A Using 2,6-dimethylpyridine and nBuLi in Step 8 in Place of Methylmagnesium Bromide Scheme B

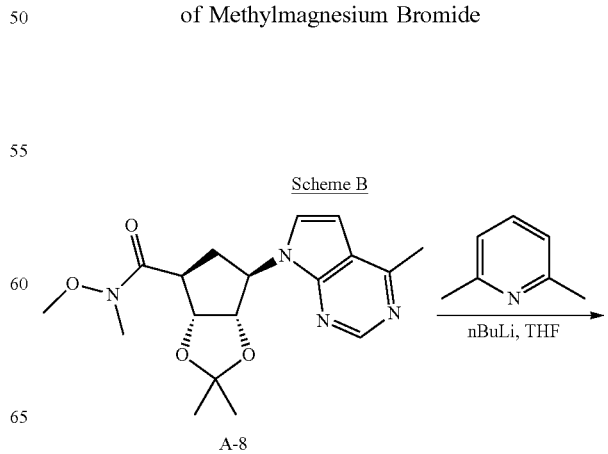

A-8

-continued

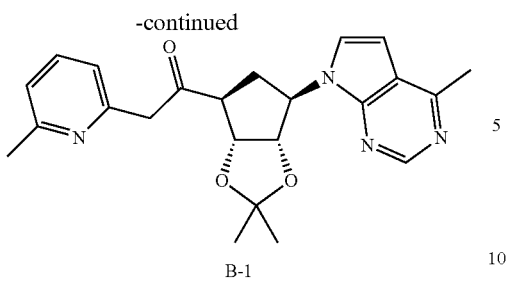

B-1

To a solution of 2.6-dimethyl pyridine (168 mg, 1.56 mmol) in dry THF (8 mL) at −75° C. was added n-BuLi (125 mg, 1.96 mmol, 1.22 mL, 1.6 M) dropwise, the temperature was maintained at about −70° C. The resulting suspension was stirred at −75° C. for 1 hr. A solution of A-8 (282 mg, 0.782 mmol) in dry THF (4 mL) was added at −75° C. dropwise. The resulting suspension was stirred at −75° C. and allowed to warm to r.t. and stirred overnight. THF was evaporated, the crude product was added H$_2$O and extracted with EtOAc, concentrated, purified by column chromatography with 5% MeOH/EtOAc to give 169 mg of B-1 (53% yield) as a yellow oil. LCMS [M+1] 407.15.

Example 17 (Scheme C): (1S,2R,3S,5R)-3-(1-hydroxycyclopropyl)-5-(4-methyl-7H-pyrrolo[2,3-d]pyrimidin-7-yl)cyclopentane-1,2-diol (C-2)

Scheme C

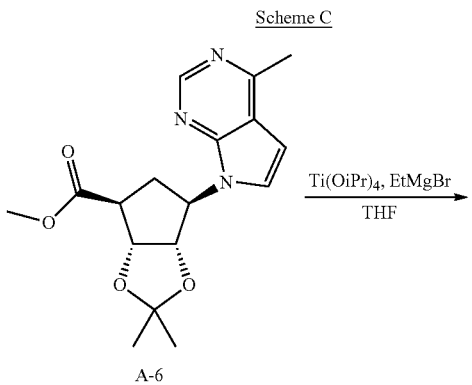

A-6

| Example 15 | 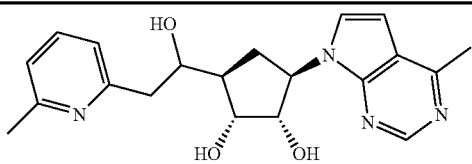 | 368.90 [M + 1] | (1S,2R,3R,5R)-3-[1-hydroxy-2-(6-methylpyridin-2-yl)ethyl]-5-(4-methyl-7H-pyrrolo[2,3-d]pyrimidin-7-yl)cyclopentane-1,2-diol<br>$^1$H NMR (700 MHz, DMSO-d6) δ ppm 8.55 (s, 1 H) 7.60 (d, J = 3.52 Hz, 1 H) 7.52 (t, J = 7.70 Hz, 1 H) 7.00 (d, J = 7.70 Hz, 1 H) 7.01 (d, J = 7.48 Hz, 1 H) 6.65 (d, J = 3.30 Hz, 1 H) 4.98-5.02 (m, 1 H) 4.92 (q, J = 8.80 Hz, 1 H) 4.73 (d, J = 5.72 Hz, 1 H) 4.66 (d, J = 3.08 Hz, 1 H) 4.06-4.12 (m, 1 H) 4.03 (dt, J = 11.33, 5.56 Hz, 1 H) 3.83 (q, J = 4.25 Hz, 1 H) 2.66-2.75 (m, 2 H) 2.58 (s, 3 H) 2.38 (s, 3 H) 2.09 (dt, J = 12.27, 8.06 Hz, 1 H) 1.84-1.89 (m, 1 H) 1.79-1.84 (m, 1 H) |
| --- | --- | --- | --- |
| Example 16 | 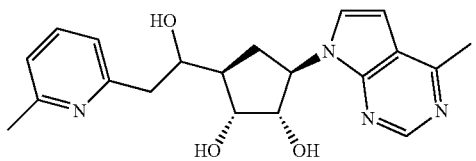 | 368.90 [M + 1] | (1S,2R,3R,5R)-3-[1-hydroxy-2-(6-methylpyridin-2-yl)ethyl]-5-(4-methyl-7H-pyrrolo[2,3-d]pyrimidin-7-yl)cyclopentane-1,2-diol<br>$^1$H NMR (700 MHz, DMSO-d6) δ ppm 8.59 (s, 1 H) 7.66 (d, J = 3.52 Hz, 1 H) 7.58 (t, J = 7.70 Hz, 1 H) 7.10 (d, J = 7.48 Hz, 1 H) 7.07 (d, J = 7.48 Hz, 1 H) 6.69 (d, J = 3.74 Hz, 1 H) 5.11 (d, J = 5.06 Hz, 1 H) 4.93-5.00 (m, 1 H) 4.79 (d, J = 6.82 Hz, 1 H) 4.72 (d, J = 3.08 Hz, 1 H) 4.20 dt, J = 9.19, 6.30 Hz, 1 H) 4.07-4.12 (m, 1 H) 3.85-3.90 (m, 1 H) 2.87 (dd, J = 13.64, 4.40 Hz, 1 H) 2.80 (dd, J = 13.86, 8.36 Hz, 1 H) 2.63 (s, 3 H) 2.43 (s, 3H) 2.13 (dt, J = 12.54, 8.36 Hz, 1 H) 1.95-2.03 (m, 1 H) 1.68-1.76 (m, 1 H) |

-continued

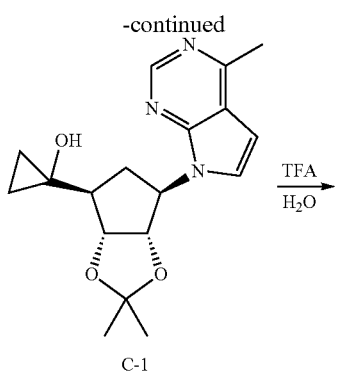

C-1

C-2

Step 1: Synthesis of 1-((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)cyclopropan-1-ol (C-1)

To a light yellow solution of A-6 (140 mg, 0.422 mmol) in dry THF (6.32 mL) was added Ti(OiPr)4 (168 mg, 0.591 mmol) and EtMgBr (3.0 M solution in diethyl ether, 0.845 mL, 2.53 mmol) at r.t (13° C.). After addition, the mixture was stirred at 13° C. for 10 min. The mixture was quenched with H$_2$O (50 mL) in an ice bath and extracted with EtOAc (30 mL×2). The extract was washed with brine (30 mL), dried over Na$_2$SO$_4$ and concentrated in vacuo to afford a crude residue which was purified by flash chromatography eluted with EtOAc/DCM 0-100% to give C-1 (90 mg, 65%) as a yellow solid. LCMS [M+1] 330; $^1$H NMR (400 MHz, CDCl$_3$) δ ppm 8.72 (s, 1H), 7.22 (d, J=3.5 Hz, 1H), 6.55 (d, J=3.8 Hz, 1H), 5.06-4.99 (m, 1H), 4.94 (dd, J=3.3, 6.3 Hz, 1H), 4.86 (d, J=5.8 Hz, 1H), 2.74 (s, 3H), 2.68-2.57 (m, 2H), 2.11 (d, J=3.0 Hz, 1H), 1.59 (s, 3H), 1.34 (s, 3H), 1.25 (d, J=3.8 Hz, 1H), 0.93 (d, 1H), 0.88-0.78 (m, 1H), 0.77-0.67 (m, 1H), 0.60-0.51 (m, 1H)

Step 2: Synthesis of (1S,2R,3S,5R)-3-(1-hydroxycyclopropyl)-5-(4-methyl-7H-pyrrolo[2,3-d]pyrimidin-7-yl)cyclopentane-1,2-diol (C-2)

To a suspension of C-1 (65 mg, 0.20 mmol) in H$_2$O (3 mL) was added TFA (3 mL) at 0° C. The mixture was stirred at rt (13° C.) for 1.5 hrs. The mixture was poured into 20% K$_2$CO$_3$ aq (50 mL) and extracted with EtOAc (30 mL×3). The extract was washed with brine (50 mL×2), dried over Na$_2$SO$_4$ and concentrated in vacuo to afford C-2 (50 mg, 88%) as a solid. LCMS [M+1] 290; $^1$H NMR (400 MHz, DMSO-d$_6$) δ ppm 8.60 (s, 1H), 7.66 (d, J=3.8 Hz, 1H), 6.70 (d, J=3.5 Hz, 1H), 5.32 (s, 1H), 5.03-4.93 (m, 1H), 4.77 (d, J=6.8 Hz, 1H), 4.61 (d, J=4.3 Hz, 1H), 4.19 (td, J=6.3, 8.9 Hz, 1H), 4.04-3.97 (m, 1H), 2.63 (s, 3H), 2.19 (td, J=8.5, 12.8 Hz, 1H), 1.93-1.82 (m, 1H), 1.63 (dt, J=3.0, 8.8 Hz, 1H), 0.67-0.60 (m, 1H), 0.57-0.48 (m, 2H), 0.46-0.39 (m, 1H)

Example 18 (Scheme D): (1S,2R,3S,5R)-3-(2-hydroxypropan-2-yl)-5-(4-methyl-7H-pyrrolo[2,3-d]pyrimidin-7-yl)cyclopentane-1,2-diol (D-2)

Scheme D

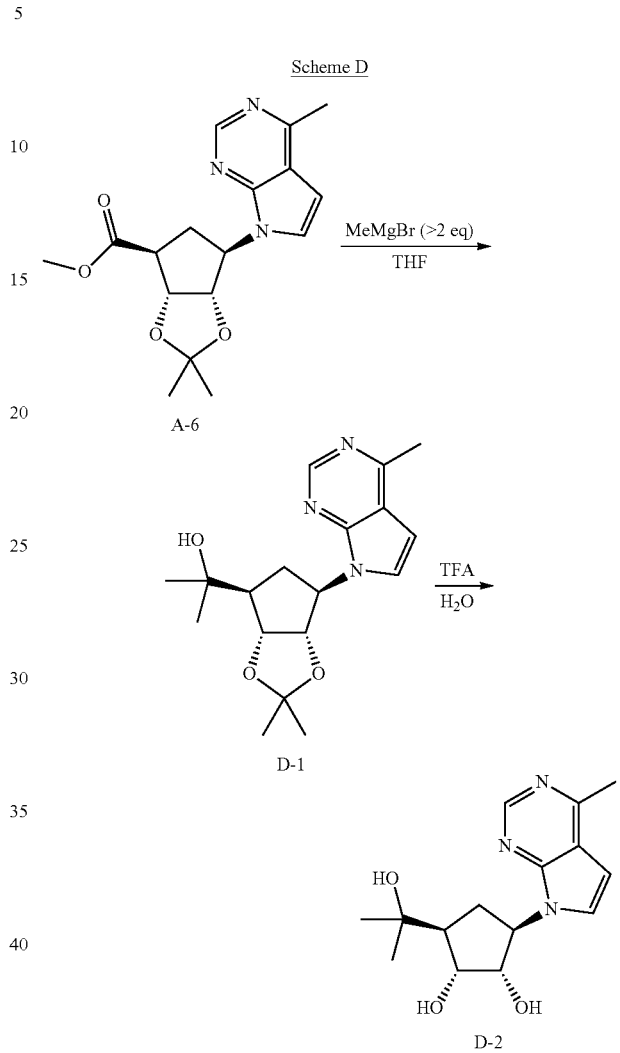

Step 1: Synthesis of 2-((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)propan-2-ol (D-1)

To a light yellow solution of A-6 (150 mg, 0.453 mmol) in dry THF (6.77 mL) was added MeMgBr (3.0 M solution in diethyl ether, 0.905 mL, 2.72 mmol) at r.t (13° C.). After addition, the mixture was stirred at 13° C. for 10 min. The mixture was quenched with H$_2$O (50 mL) in a ice bath and extracted with EtOAc (30 mL×2). The extract was washed with brine (30 mL), dried over Na$_2$SO$_4$ and concentrated in vacuo to afford crude compound (160 mg) as yellow oil which was purified by flash chromatography eluted with EtOAc/DCM 0-100% to give D-1 (120 mg, 80%) as a white solid. LCMS [M+1] 332; $^1$H NMR (400 MHz, CDCl$_3$) δ ppm 8.76 (s, 1H), 7.26 (d, J=3.8 Hz, 1H), 6.57 (d, J=3.5 Hz, 1H), 5.03 (ddd, J=6.0, 8.3, 10.8 Hz, 1H), 4.96-4.88 (m, 1H), 4.84 (dd, J=5.3, 7.3 Hz, 1H), 2.73 (s, 3H), 2.47-2.37 (m, 2H), 2.31-2.21 (m, 1H), 1.97 (s, 1H), 1.59 (s, 3H), 1.40 (s, 3H), 1.32 (s, 3H), 1.27 (s, 3H)

Step 2: Synthesis of (1S,2R,3S,5R)-3-(2-hydroxy-propan-2-yl)-5-(4-methyl-7H-pyrrolo[2,3-d]pyrimidin-7-yl)cyclopentane-1,2-diol (D-2)

To a suspension of D-1 (100 mg, 0.302 mmol) in $H_2O$ (5 mL) was added TFA (5 mL) at 0° C. The mixture was stirred at rt (13° C.) for 1.5 hrs. The mixture was poured into 20% $K_2CO_3$ aq (50 mL) and extracted with EtOAc (30 mL×3). The extract was washed with brine (50 mL×2), dried over $Na_2SO_4$ and concentrated in vacuo to afford D-2 (70 mg, 80%) as a yellow solid. LCMS [M+1] 292; $^1$H NMR (400 MHz, DMSO-$d_6$) δ ppm 8.60 (s, 1H), 7.65 (d, J=3.5 Hz, 1H), 6.69 (d, J=3.5 Hz, 1H), 4.92 (dt, J=7.3, 10.4 Hz, 1H), 4.73 (d, J=7.0 Hz, 1H), 4.53 (d, J=4.3 Hz, 1H), 4.32 (s, 1H), 4.08 (td, J=6.7, 9.7 Hz, 1H), 3.92 (t, J=6.3 Hz, 1H), 2.63 (s, 3H), 2.03 (td, J=7.8, 11.5 Hz, 1H), 1.88 (dt, J=2.3, 9.0 Hz, 1H), 1.84-1.73 (m, 1H), 1.19 (s, 3H), 1.08 (s, 3H)

Example 19 (Scheme E): (1S,2R,3S,5R)-3-[(1S)-1-(4-fluorophenyl)-1-hydroxyethyl]-5-(4-methyl-7H-pyrrolo[2,3-d]pyrimidin-7-yl)cyclopentane-1,2-diol (E-3)

Example 20 (Scheme E): (1S,2R,3S,5R)-3-[(1R)-1-(4-fluorophenyl)-1-hydroxyethyl]-5-(4-methyl-7H-pyrrolo[2,3-d]pyrimidin-7-yl)cyclopentane-1,2-diol (E-4)

Scheme E

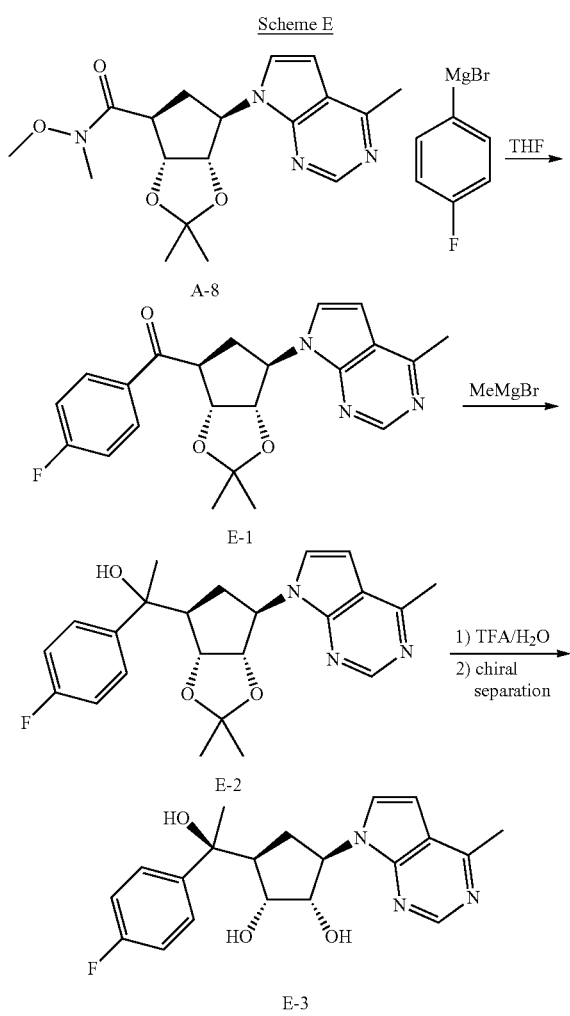

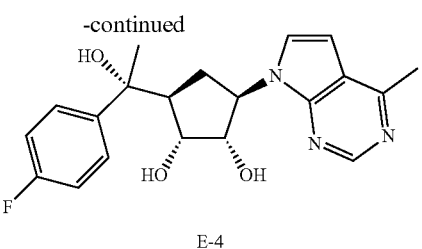

E-4

Step 1: Synthesis of ((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)(4-fluorophenyl)methanone (E-1)

Following a similar procedure to Step 8 in Scheme A using (4-fluorophenyl)magnesium bromide gave E-1 (240 mg, 95%). LCMS [M+1] 395.80. $^1$H NMR (400 MHz, CHLOROFORM-d) δ ppm 8.75 (s, 1H) 8.12 (dd, J=8.86, 5.44 Hz, 2H) 7.34 (dd, J=8.56, 5.50 Hz, 1H) 7.15-7.22 (m, 2H) 6.61 (d, J=3.67 Hz, 1H) 5.28-5.37 (m, 1H) 4.98-5.08 (m, 2H) 3.71 (br. s., 1H) 2.70-2.76 (m, 4H) 2.60-2.70 (m, 1H) 1.68 (s, 3H) 1.33 (s, 3H)

Step 2: Synthesis of 1-((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)-1-(4-fluorophenyl)ethan-1-ol (E-2)

To a solution of E-1 (66 mg, 0.17 mmol) in dry THF (6.0 mL, c=0.106 M) at 50° C. was added methylmagnesium bromide (99.5 mg, 0.835 mmol, 0.278 mL, 3.0 M), the resulting solution was stirred at 50° C. for 0.5 h. The mixture was added to std. $NH_4Cl$ (20 mL) slowly, the mixture was extracted with EtOAc (25 mL×3). The extract was washed with brine (25 mL), dried over $Na_2SO_4$ and concentrated in vacuum to give 70 mg of E-2 as a colorless oil. LCMS [M+1] 411.80.

Step 3: Synthesis of (1S,2R,3S,5R)-3-[(1S)-1-(4-fluorophenyl)-1-hydroxyethyl]-5-(4-methyl-7H-pyrrolo[2,3-d]pyrimidin-7-yl)cyclopentane-1,2-diol (E-3) and (1S,2R,3S,5R)-3-[(1R)-1-(4-fluorophenyl)-1-hydroxyethyl]-5-(4-methyl-7H-pyrrolo[2,3-d]pyrimidin-7-yl)cyclopentane-1,2-diol (E-4)

Following a similar procedure to Step 10 in Scheme A and subsequent separation by chiral SFC gave E-3 (19 mg, 31%). LCMS [M+1] 371.90. $^1$H NMR (700 MHz, DMSO-d6) δ ppm 8.61 (s, 1H) 7.61 (d, J=3.74 Hz, 1H) 7.54 (dd, J=8.58, 5.72 Hz, 2H) 7.13 (t, J=8.80 Hz, 2H) 6.72 (d, J=3.52 Hz, 1H) 5.26 (s, 1H) 4.97-5.06 (m, 1H) 4.70 (d, J=5.94 Hz, 1H) 4.17 (d, J=3.30 Hz, 1H) 4.04-4.12 (m, 1H) 3.54 (br. s., 1H) 2.64 (s, 3H) 2.39 (t, J=8.91 Hz, 1H) 2.19 (dt, J=12.54, 8.58 Hz, 1H) 1.95 (td, J=11.83, 8.91 Hz, 1H) 1.35 (s, 3H) and E-4 (12 mg, 19%). LCMS [M+1] 371.90. $^1$H NMR (700 MHz, DMSO-d6) δ ppm 8.51-8.59 (m, 1H) 7.52-7.59 (m, 1H) 7.40-7.47 (m, 2H) 7.02-7.10 (m, 2H) 6.65 (dd, J=3.52, 1.54 Hz, 1H) 5.24 (s, 1H) 4.78-4.88 (m, 2H) 4.67-4.74 (m, 1H) 4.10-4.19 (m, 2H) 2.57-2.65 (m, 3H) 2.35 (t, J=9.35 Hz, 1H) 1.54 (s, 3H) 1.39-1.51 (m, 2H)

Example 21 (Scheme F): (1S,2R,3S,5R)-3-[fluoro(4-fluorophenyl)methyl]-5-(4-methyl-7H-pyrrolo[2,3-d]pyrimidin-7-yl)cyclopentane-1,2-diol (F-3 Isomer A)

Example 22 (Scheme F): (1S,2R,3S,5R)-3-[fluoro(4-fluorophenyl)methyl]-5-(4-methyl-7H-pyrrolo[2,3-d]pyrimidin-7-yl)cyclopentane-1,2-diol (F-4 Isomer B)

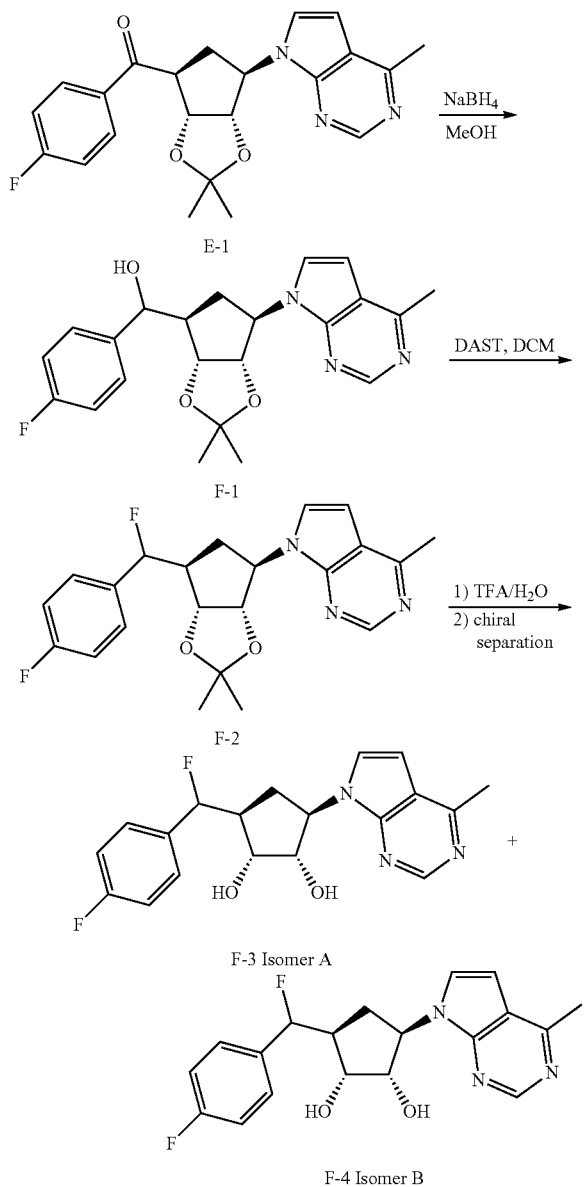

Step 1: Synthesis of ((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)(4-fluorophenyl)methanol (F-1)

Following a similar procedure to Step 8 in Scheme A gave F-1 (110 mg, 99%). LCMS [M+1] 398.15.

Step 2: Synthesis of 7-((3aS,4R,6S,6aR)-6-(fluoro(4-fluorophenyl)methyl)-2,2-dimethyltetrahydro-4H-cyclopenta[d][1,3]dioxol-4-yl)-4-methyl-7H-pyrrolo[2,3-d]pyrimidine (F-2)

To a solution of F-1 (110 mg, 0.277 mmol) in 5 mL DCM was added DAST (223 mg, 1.38 mmol), stirred at r.t. for 30 min. The reaction was quenched with std. NaHCO$_3$, the phases were separated and the aqueous phase was extracted with 3 portions of DCM. The organic phases were combined and washed with brine, concentrated to give crude F-2 which was used directly for next step. LCMS [M+1] 400.10.

Step 3: Synthesis of (1S,2R,3S,5R)-3-[fluoro(4-fluorophenyl)methyl]-5-(4-methyl-7H-pyrrolo[2,3-d]pyrimidin-7-yl)cyclopentane-1,2-diol Following a similar procedure to Step 10 in Scheme A and subsequent separation by chiral SFC gave F-3 Isomer A (7.7 mg, 7.8% two steps)

LCMS [M+1] 360.10. $^1$H NMR (700 MHz, DMSO-d6) δ ppm 1.40-1.49 (m, 1H) 1.91 (dt, J=12.87, 8.64 Hz, 1H) 2.55 (dd, J=17.39, 8.58 Hz, 1H) 2.62 (s, 3H) 4.07 (br. s., 1H) 4.36-4.48 (m, 1H) 4.91-5.02 (m, 3H) 5.59 (dd, J=1.00 Hz, 1H) 6.67 (d, J=3.30 Hz, 1H) 7.22 (t, J=8.58 Hz, 2H) 7.45-7.56 (m, 2H) 7.65 (d, J=3.30 Hz, 1H) 8.60 (s, 1H)

and F-4 Isomer B (1.3 mg, 1.3% two steps)

LCMS [M+1] 360.15. $^1$H NMR (400 MHz, DMSO-d6) δ ppm 1.84-1.94 (m, 1H) 2.09-2.16 (m, 1H) 2.64 (s, 3H) 3.83 (q, J=4.40 Hz, 1H) 4.24-4.35 (m, 1H) 4.80 (d, J=4.52 Hz, 1H) 4.89-5.04 (m, 2H) 5.72-5.83 (m, 1H) 6.71 (d, J=3.55 Hz, 1H) 7.20-7.30 (m, 2H) 7.47 (dd, J=8.13, 5.81 Hz, 2H) 7.66 (d, J=3.55 Hz, 1H) 8.61 (s, 1H)

Example 23 (Scheme G): (1R,2S,3R,5R)-3-(4-amino-7H-pyrrolo[2,3-d]pyrimidin-7-yl)-5-((S)-(4-chloro-3-fluorophenyl)(hydroxy)methyl)cyclopentane-1,2-diol (G-7)

Example 24 (Scheme G): (1R,2S,3R,5R)-3-(4-amino-7H-pyrrolo[2,3-d]pyrimidin-7-yl)-5-((R)-(4-chloro-3-fluorophenyl)(hydroxy)methyl)cyclopentane-1,2-diol (G-9)

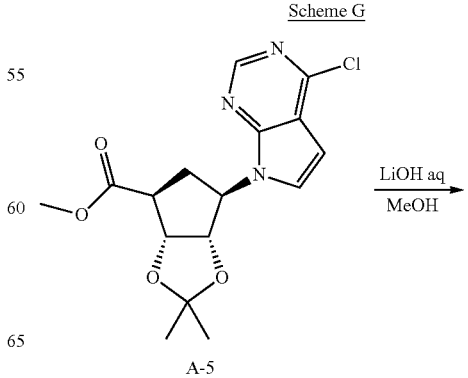

Scheme G

A-5

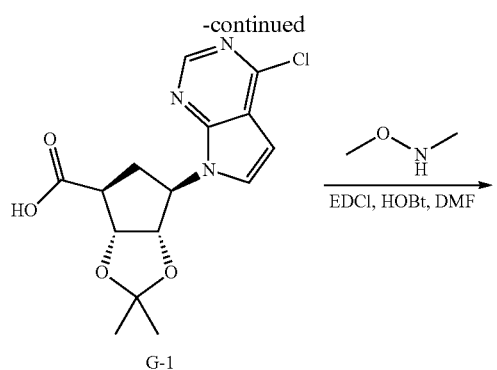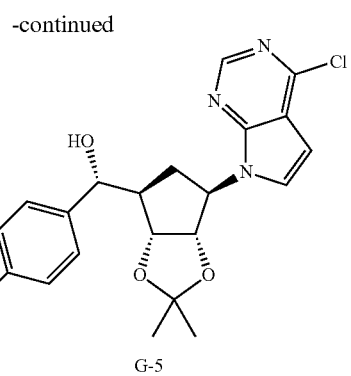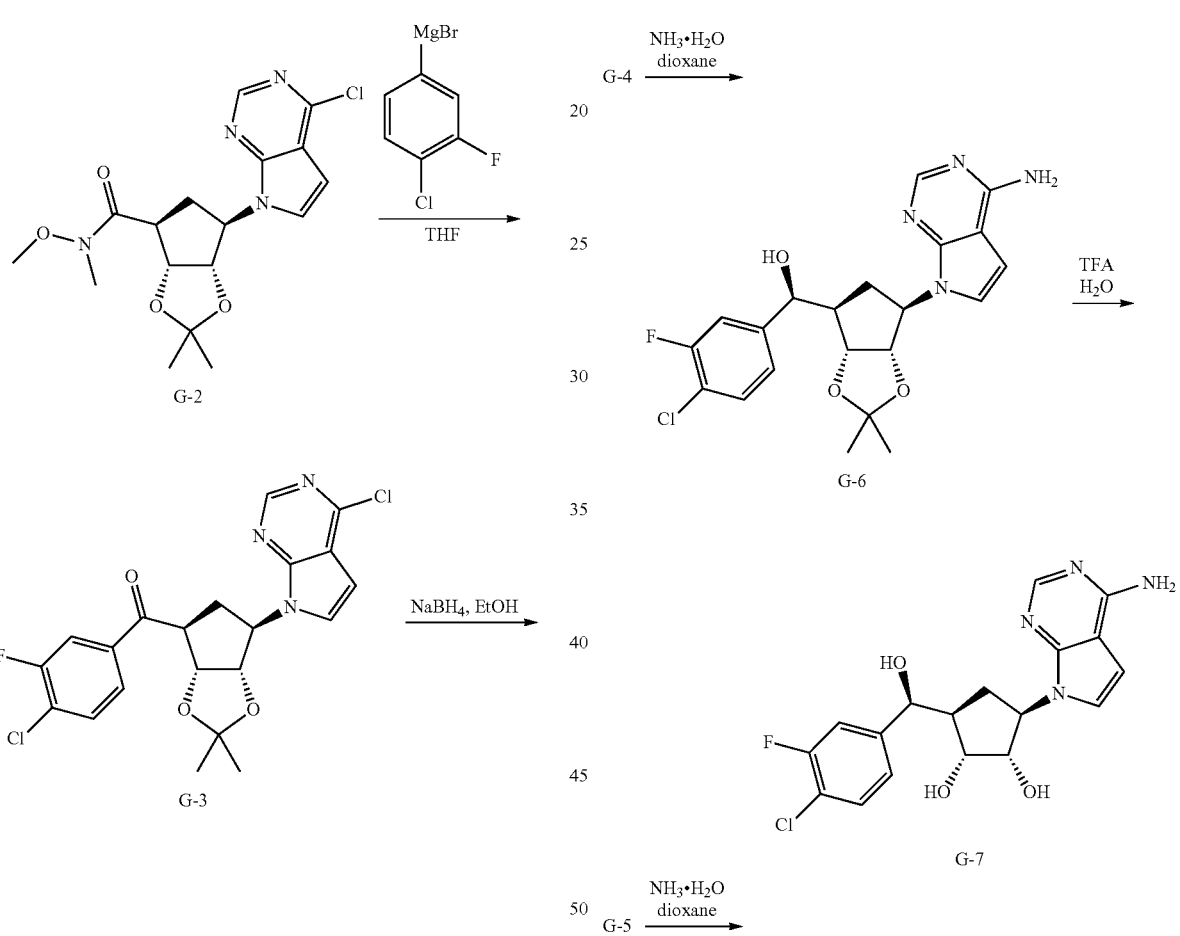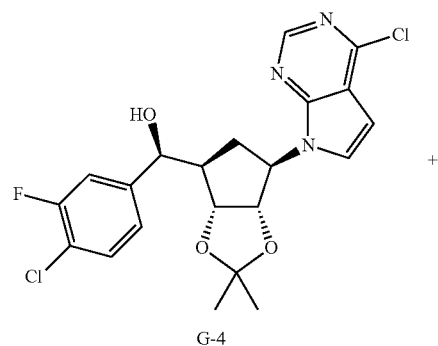

-continued

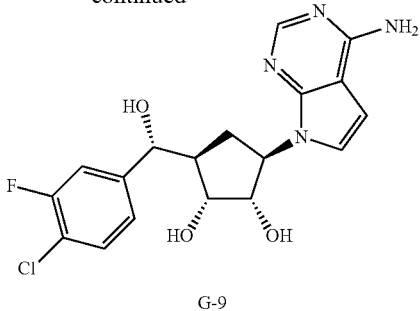

G-9

Step 1: Synthesis of (3aR,4S,6R,6aS)-6-(4-chloro-7H-pyrrolo[2,3-d]pyrimidin-7-yl)-2,2-dimethyltetrahydro-4H-cyclopenta[d][1,3]dioxole-4-carboxylic acid (G-1)

A mixture of A-5 (200 mg, 0.48 mmol) and LiOH (40.6 mg, 0.966 mmol) in THF (2 mL)/H$_2$O (2 mL) was stirred at rt (25° C.) for 2 hrs. The mixture was diluted with water (5 mL) and adjusted with 1N HCl to pH=2 and extracted with EtOAc (10 mL×2). The extract was dried over Na$_2$SO$_4$ and concentrated in vacuo to afford crude G-1 (200 mg) as yellow gum, used in the next step directly. LCMS [M+1] 338; $^1$H NMR (400 MHz, DMSO-d$_6$) δ ppm 8.65 (s, 1H), 7.97 (d, J=3.8 Hz, 1H), 6.72 (d, J=3.5 Hz, 1H), 5.17-5.07 (m, 1H), 5.01-4.90 (m, 2H), 3.03-2.93 (m, 1H), 2.60-2.53 (m, 2H), 1.49 (s, 3H), 1.23 (s, 3H)

Step 2: Synthesis of (3aR,4S,6R,6aS)-6-(4-chloro-7H-pyrrolo[2,3-d]pyrimidin-7-yl)-N-methoxy-N,2,2-trimethyltetrahydro-4H-cyclopenta[d][1,3]dioxole-4-carboxamide (G-2)

To a suspension of crude G-1 (200 mg, 461 mmol) and N,O-dimethylhydroxylamine—HCl (70 mg, 0.72 mmol) in THF (4 mL) was added DIPEA (186 mg, 1.44 mmol) and 50% T3P (458 mg, 0.42 mL, 1.5 mmol) at rt (15° C.). The resulting red solution was stirred at rt (15° C.) for 20 hrs. Some solid was formed in the reaction mixture. The mixture was poured into NaHCO$_3$ aq (15 mL) and extracted with EtOAc (10 mL×3). The extract was washed with brine (10 mL×2), dried over Na$_2$SO$_4$ and concentrated in vacuo to afford G-2 (150 mg, 82% in two steps) as yellow gum. LCMS [M+1] 381; $^1$H NMR (400 MHz, CDCl$_3$) δ ppm 8.66 (s, 1H), 7.42 (d, J=3.5 Hz, 1H), 6.67 (d, J=3.8 Hz, 1H), 5.27 (dd, J=5.1, 7.2 Hz, 1H), 5.06 (dd, J=5.0, 7.0 Hz, 1H), 4.92 (dd, J=5.5, 7.0 Hz, 1H), 3.78 (s, 3H), 3.64-3.51 (m, 1H), 3.25 (s, 3H), 2.70-2.42 (m, 2H), 1.61 (s, 3H), 1.32 (s, 3H)

Step 3: Synthesis of (4-chloro-3-fluorophenyl)((3aR,4S,6R,6aS)-6-(4-chloro-7H-pyrrolo[2,3-d]pyrimidin-7-yl)-2,2-dimethyltetrahydro-4H-cyclopenta[d][1,3]dioxol-4-yl)methanone (G-3)

To a solution of G-2 (150 mg, 0.394 mmol) in dry THF (3 mL) was added (4-chloro-3-fluorophenyl)magnesium bromide (3.1 mL, 1.54 mmol) at 0° C. The mixture was stirred at 0° C. for 3 hr. The mixture was quenched with NH$_4$Cl aq (20 mL) and diluted with EtOAc (10 mL×2). The organic layer was washed with brine (10 mL), dried over Na$_2$SO$_4$ and concentrated in vacuo to afford crude G-3 (250 mg, >99%) as a yellow oil which was used in the next step directly.

LCMS [M+1] 450

Step 4: Synthesis of (S)-(4-chloro-3-fluorophenyl)((3aR,4R,6R,6aS)-6-(4-chloro-7H-pyrrolo[2,3-d]pyrimidin-7-yl)-2,2-dimethyltetrahydro-4H-cyclopenta[d][1,3]dioxol-4-yl)methanol (G-4) and (R)-(4-chloro-3-fluorophenyl)((3aR,4R,6R,6aS)-6-(4-chloro-7H-pyrrolo[2,3-d]pyrimidin-7-yl)-2,2-dimethyltetrahydro-4H-cyclopenta[d][1,3]dioxol-4-yl)methanol (G-5)

To a solution of crude G-3 (150 mg, 0.4 mmol) in MeOH (5 mL) was added NaBH$_4$ (45 mg, 1.18 mmol) at 0° C. The mixture was stirred at 0° C. for 1 hr. The mixture was quenched with NH$_4$Cl aq (10 mL) and diluted with EtOAc (10 mL×3). The organic layer was washed with brine (10 mL), dried over Na$_2$SO$_4$ and concentrated in vacuo then purified by silica gel chromatography eluting with EtOAc in petroleum ether from 0 to 60% to afford G-4 (30 mg, 17%) and G-5 (50 mg, 28%) as a light yellow solid.
G-4: LCMS [M+1] 452
G-5: LCMS [M+1] 452

Step 5: Synthesis of (S)-((3aR,4R,6R,6aS)-6-(4-amino-7H-pyrrolo[2,3-d]pyrimidin-7-yl)-2,2-dimethyltetrahydro-4H-cyclopenta[d][1,3]dioxol-4-yl)(4-chloro-3-fluorophenyl)methanol (G-6)

A mixture of G-4 (30 mg, 0.0663 mmol) in dioxane/NH$_3$·H$_2$O (1 mL/1 mL) was heated at 120° C. under microwave for 2 h. LCMS showed most of SM was consumed and a good spot was formed. The mixture was concentrated in vacuo to afford crude G-6 (50 mg, >100%) as yellow solid, used in the next step directly. LCMS [M+1] 433

Step 6: Synthesis of (1R,2S,3R,5R)-3-(4-amino-7H-pyrrolo[2,3-d]pyrimidin-7-yl)-5-((S)-(4-chloro-3-fluorophenyl)(hydroxy)methyl)cyclopentane-1,2-diol (G-7)

A mixture of G-6 (30 mg, 0.0663 mmol) in TFA/H$_2$O (1 mL/1 mL) was stirred at rt (25° C.) for 1 hr. LCMS showed most of SM was consumed and main peak was desired compound. The mixture was poured into 20% K$_2$CO$_3$ aq (10 mL) and extracted with EtOAc (10 mL×2). The extract was washed with brine (10 mL×2), dried over Na$_2$SO$_4$ and concentrated in vacuo to afford crude material which was purified by prep-HPLC to afford G-7 (10 mg, 37%) as a white solid. LCMS [M+1] 393; $^1$H NMR (400 MHz, DMSO-d$_6$) δ ppm 8.01 (s, 1H), 7.52 (t, J=8.0 Hz, 1H), 7.35 (dd, J=1.6, 10.4 Hz, 1H), 7.27-7.18 (m, 2H), 6.92 (s, 2H), 6.55 (d, J=3.5 Hz, 1H), 5.74 (d, J=5.3 Hz, 1H), 4.85 (d, J=6.5 Hz, 1H), 4.84-4.73 (m, 2H), 4.62 (d, J=4.8 Hz, 1H), 4.24-4.10 (m, 1H), 3.91 (q, J=4.9 Hz, 1H), 2.21 (td, J=4.3, 8.5 Hz, 1H), 1.90-1.64 (m, 2H)

Compound G-9 was prepared from G-5 (10 mg, 37%) as a white solid in a similar method as G-7 was prepared from G-4.

G-9: LCMS [M+1] 393; $^1$H NMR (400 MHz, DMSO-d$_6$) δ ppm 8.02 (s, 1H), 7.54 (t, J=8.0 Hz, 1H), 7.40 (dd, J=1.6, 10.7 Hz, 1H), 7.30-7.24 (m, 1H), 7.21 (d, J=3.5 Hz, 1H), 6.92 (s, 2H), 6.54 (d, J=3.5 Hz, 1H), 5.76 (d, J=4.5 Hz, 1H), 4.87-4.76 (m, 2H), 4.61 (t, J=5.5 Hz, 1H), 4.51 (d, J=3.8 Hz, 1H), 4.28-4.19 (m, 1H), 3.93-3.88 (m, 1H), 2.23 (d, J=8.5 Hz, 1H), 2.06-1.94 (m, 1H), 1.66-1.52 (m, 1H)

Example 25 (Scheme H): (1R,2S,3R,5R)-3-(4-amino-5-fluoro-7H-pyrrolo[2,3-d]pyrimidin-7-yl)-5-[(S)-(4-fluorophenyl)(hydroxy)methyl]cyclopentane-1,2-diol (H-5)

Example 26 (Scheme H): (1R,2S,3R,5R)-3-(4-amino-5-fluoro-7H-pyrrolo[2,3-d]pyrimidin-7-yl)-5-[(R)-(4-fluorophenyl)(hydroxy)methyl]cyclopentane-1,2-diol (H-6)

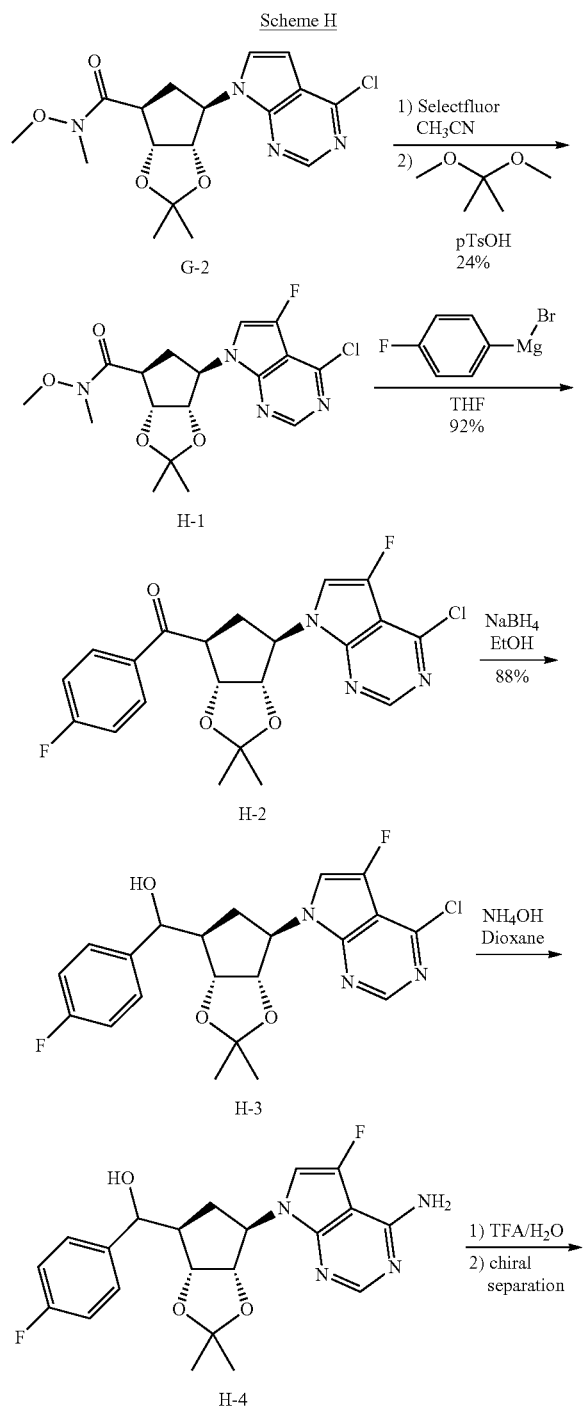

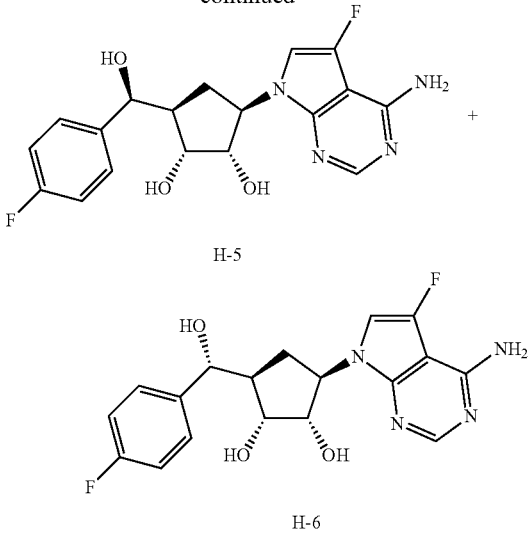

Step 1: Synthesis of (3aR,4S,6R,6aS)-6-(4-chloro-5-fluoro-7H-pyrrolo[2,3-d]pyrimidin-7-yl)-N-methoxy-N,2,2-trimethyltetrahydro-4H-cyclopenta[d][1,3]dioxole-4-carboxamide (H-1)

To a solution of G-2 (Scheme G) (400 mg, 1.05 mmol) in 20 mL anhydrous $CH_3CN$ was added selectfluor (558 mg, 1.58 mmol) and AcOH (10 ml). The mixture was heated at 70° C. for 6 hours in an atmosphere of $N_2$. The reaction mixture was concentrated, $H_2O$ and EtOAc were added, the aqueous was extracted 3 times with EtOAc. The organic layer was washed with brine, dried over $Na_2SO_4$, concentrated to give brown oil.

The above brown oil was added 2,2-dimethoxypropane (109 mg, 1.05 mmol, 3.50 mL, 0.3 M) and toluenesulfonic acid monohydrate (599 mg, 3.15 mmol), the yellow brown suspension was stirred vigorously at r.t. for 15 min. The reaction mixture was diluted with 50 mL $H_2O$, neutralized with solid $NaHCO_3$, the volatiles were carefully removed in vacuo and the resulting brown aqueous solution was extracted with EtOAc 3×20 mL, the organic was combined and concentrated, purified by column chromatography with 60% EtOAc/heptane to give 100 mg of H-1 (24% yield) as a colorless gum.

LCMS [M+1] 398.80. $^1$H NMR (400 MHz, CHLOROFORM-d) δ ppm 8.63 (s, 1H) 7.22 (d, J=2.57 Hz, 1H) 5.25-5.36 (m, 1H) 5.01 (dd, J=7.03, 4.95 Hz, 1H) 4.83 (dd, J=6.97, 5.50 Hz, 1H) 3.77 (s, 3H) 3.58 (d, J=7.34 Hz, 1H) 3.25 (s, 3H) 2.58-2.68 (m, 1H) 2.38-2.52 (m, 1H) 1.61 (s, 3H) 1.31 (s, 3H)

Step 2: Synthesis of ((3aR,4S,6R,6aS)-6-(4-chloro-5-fluoro-7H-pyrrolo[2,3-d]pyrimidin-7-yl)-2,2-dimethyltetrahydro-4H-cyclopenta[d][1,3]dioxol-4-yl)(4-fluorophenyl)methanone (H-2)

Following a similar procedure to step 8 in Scheme A using 4-fluorophenylmagnesium bromide and H-1 to give H-2 (100 mg, 92%).

LCMS [M+1] 433.70. $^1$H NMR (400 MHz, CHLOROFORM-d) δ ppm 8.62 (s, 1H) 8.07-8.16 (m, 2H) 7.14-7.23 (m, 3H) 5.25-5.37 (m, 1H) 4.98 (dd, J=6.91, 4.58 Hz, 1H)

4.86-4.93 (m, 1H) 4.03 (ddd, J=10.30, 7.79, 4.52 Hz, 1H) 2.58-2.76 (m, 2H) 1.67 (s, 3H) 1.32 (s, 3H)

Step 3: Synthesis of ((3aR,4R,6R,6aS)-6-(4-chloro-5-fluoro-7H-pyrrolo[2,3-d]pyrimidin-7-yl)-2,2-dimethyltetrahydro-4H-cyclopenta[d][1,3]dioxol-4-yl)(4-fluorophenyl)methanol (H-3)

Following a similar procedure to step 4 in Scheme G, H-2 was reduced to H-3 (88 mg, 88%).
LCMS [M+1] 435.70.

Step 4: Synthesis of ((3aR,4R,6R,6aS)-6-(4-amino-5-fluoro-7H-pyrrolo[2,3-d]pyrimidin-7-yl)-2,2-dimethyltetrahydro-4H-cyclopenta[d][1,3]dioxol-4-yl)(4-fluorophenyl)methanol (H-4)

Following a similar procedure to step 5 in Scheme G, H-3 was transformed to H-4 as crude for next step.
LCMS [M+1] 417.80.

Step 5: Synthesis of (1R,2S,3R,5R)-3-(4-amino-5-fluoro-7H-pyrrolo[2,3-d]pyrimidin-7-yl)-5-[(S)-(4-fluorophenyl)(hydroxy)methyl]cyclopentane-1,2-diol (H-5) and (1R,2S,3R,5R)-3-(4-amino-5-fluoro-7H-pyrrolo[2,3-d]pyrimidin-7-yl)-5-[(R)-(4-fluorophenyl)(hydroxy)methyl]cyclopentane-1,2-diol (H-6)

Following a similar procedure to step 6 in Scheme G and subsequent purification by chiral SFC, H-4 was deprotected and the isomers separated into H-5 and H-6 (26.5 mg, 35%).
H-5: LCMS [M+1] 376.90. $^1$H NMR (700 MHz, DMSO-d6) δ ppm 8.01 (s, 1H) 7.40 (dd, J=8.36, 5.72 Hz, 1H) 7.19 (s, 1H) 7.13 (t, J=8.80 Hz, 1H) 6.85 (br. s., 1H) 5.52 (d, J=4.62 Hz, 1H) 4.87 (q, J=9.68 Hz, 1H) 4.77 (d, J=6.82 Hz, 1H) 4.53 (dd, J=7.04, 4.62 Hz, 1H) 4.51 (d, J=3.52 Hz, 1H) 4.16 (dt, J=9.63, 5.97 Hz, 1H) 3.93 (br. s., 1H) 2.16-2.22 (m, 1H) 1.86 (dt, J=13.04, 8.78 Hz, 1H) 1.42 (ddd, J=12.98, 10.56, 8.14 Hz, 1H)
H-6: LCMS [M+1] 376.90. $^1$H NMR (700 MHz, DMSO-d6) δ ppm 8.01 (s, 1H) 7.37 (dd, J=8.47, 5.61 Hz, 1H) 7.23 (d, J=1.76 Hz, 1H) 7.12 (t, J=8.80 Hz, 1H) 6.87 (br. s., 1H) 5.51 (d, J=4.84 Hz, 1H) 4.82-4.88 (m, 1H) 4.79-4.82 (m, 1H) 4.76 (t, J=4.84 Hz, 1H) 4.58 (d, J=4.62 Hz, 1H) 4.10 (dt, J=8.36, 6.05 Hz, 1H) 3.80-3.86 (m, 1H) 2.17 (tt, J=8.64, 4.46 Hz, 1H) 1.79 (dt, J=13.09, 8.53 Hz, 1H) 1.68 (dt, J=12.93, 9.60 Hz, 1H)

Example 27 (Scheme I)—(1S,2R,3R,5R)-3-[(S)-(3,4-difluorophenyl)(hydroxy)methyl]-5-(7H-pyrrolo[2,3-d]pyrimidin-4-ylamino)cyclopentane-1,2-diol (I-12)

Example 28 (Scheme I)—(1S,2R,3R,5R)-3-[(R)-(3,4-difluorophenyl)(hydroxy)methyl]-5-(7H-pyrrolo[2,3-d]pyrimidin-4-ylamino)cyclopentane-1,2-diol (I-13)

Scheme I

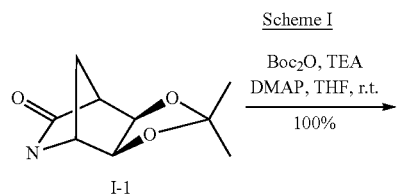

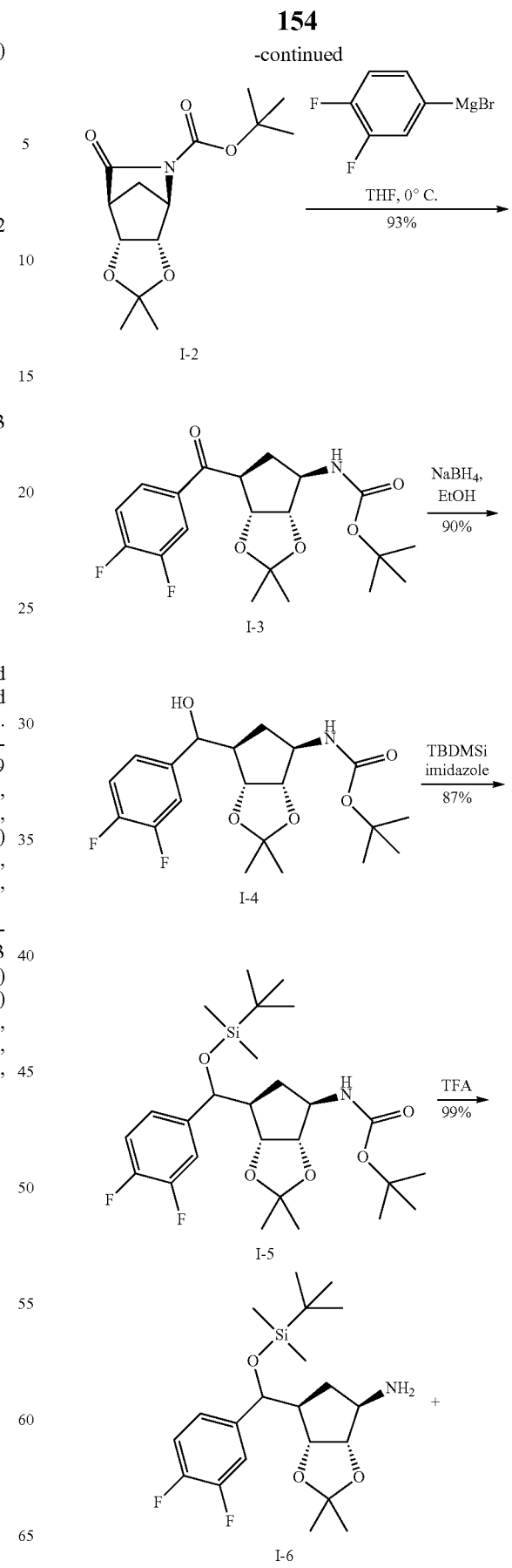

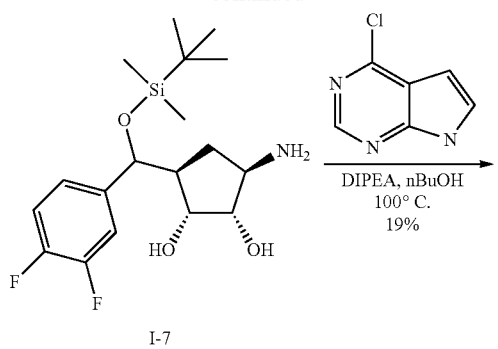

I-7

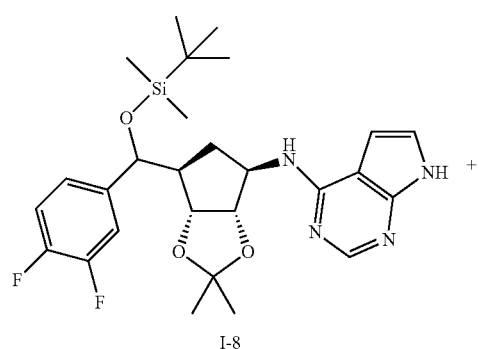

I-8

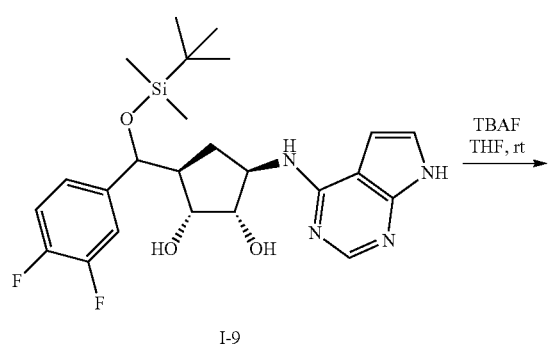

I-9

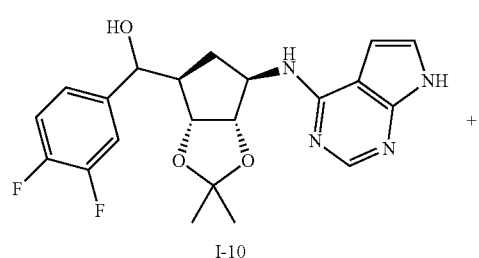

I-10

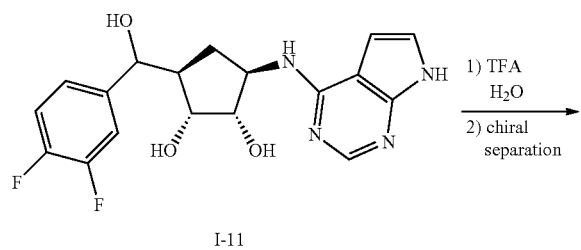

I-11

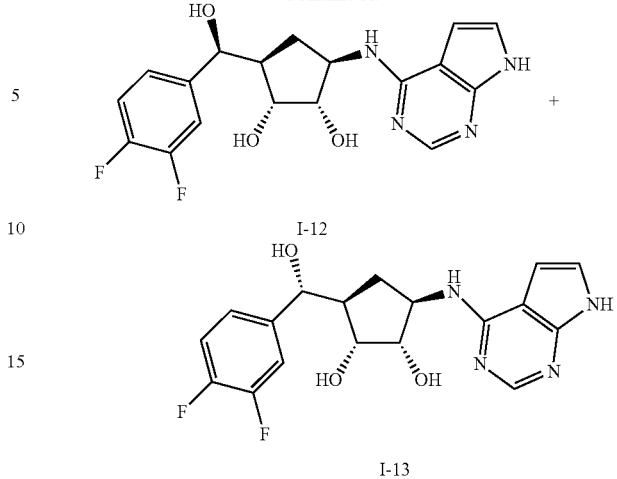

I-12

I-13

Step 1: Synthesis of tert-butyl(3aS,4R,7S,7aR)-2,2-dimethyl-6-oxotetrahydro-4,7-methano[1,3]dioxolo[4,5-c]pyridine-5(4H)-carboxylate (I-2)

To a solution of (3aS,4R,7S,7aR)-2,2-dimethyltetrahydro-4,7-methano[1,3]dioxolo[4,5-c]pyridin-6(3aH)-one I-1 (*Chemical Reviews*, 2012, 112 (8), pp 4642-4686) (5000 mg, 27.29 mmol) and Boc anhydride (7.15 g, 32.7 mmol) in THF (54.6 mL, c=0.5 M) was added triethylamine (3.31 g, 32.7 mmol, 4.56 mL) and DMAP (333 mg, 2.73 mmol). The reaction was stirred at r.t. for 3 hrs. The mixture was concentrated to a tan solid which was purified by column chromatography with 30% EtOAc/Heptane to give 7.9 g of I-2 (100% yield) as a white solid.

LCMS [M+1-tBu] 228. $^1$H NMR (400 MHz, CHLOROFORM-d) δ ppm 4.60 (d, J=5.4 Hz, 1H), 4.49 (d, J=5.4 Hz, 1H), 4.44 (s, 1H), 2.90 (s, 1H), 2.16-2.07 (m, 1H), 2.05-1.96 (m, 1H), 1.53 (s, 9H), 1.50 (s, 3H), 1.37 (s, 3H).

Step 2: Synthesis of tert-butyl((3aS,4R,6S,6aR)-6-(3,4-difluorobenzoyl)-2,2-dimethyltetrahydro-4H-cyclopenta[d][1,3]dioxol-4-yl)carbamate (I-3)

To a solution of I-2 (1.42 g, 5.00 mmol) in THF (10.0 mL, c=0.5 M) cooled in an ice-water bath was added 4-fluorophenylmagnesium bromide (997 mg, 5 mmol, 5.00 mL, 1 M). The reaction mixture was stirred at ice bath for 10 min, quenched by adding 50 mL MeOH and 50 mL std. NH$_4$Cl while cooling in ice bath. The aqueous layer was extracted with EtOAc, the organic layer was concentrated, purified by column chromatography with 30% EtOAc/heptane to give 4.15 g of I-3 (93% yield) as a white solid.

LCMS [M+1-Boc] 298. $^1$H NMR (400 MHz, CHLOROFORM-d) δ ppm 7.84-7.95 (m, 2H) 7.29-7.35 (m, 1H) 5.43 (br. s., 1H) 4.77 (d, J=5.50 Hz, 1H) 4.51 (d, J=5.62 Hz, 1H) 4.18 (br. s., 1H) 3.87 (d, J=8.68 Hz, 1H) 2.53 (d, J=6.85 Hz, 1H) 2.04 (d, J=13.94 Hz, 1H) 1.55 (s, 3H) 1.45 (s, 9H) 1.31 (s, 3H)

Step 3: Synthesis of tert-butyl((3aS,4R,6R,6aR)-6-((3,4-difluorophenyl)(hydroxy)methyl)-2,2-dimethyltetrahydro-4H-cyclopenta[d][1,3]dioxol-4-yl)carbamate (I-4)

To a solution of I-3 (4531 mg, 11.40 mmol) in EtOH (57.0 mL, c=0.2 M) was added NaBH$_4$ (2160 mg, 57.0 mmol), stirred at r.t. for 30 min. The reaction was quenched by adding std. NH₄Cl, extracted with EtOAc, the organic layers were concentrated, purified by column chromatography eluting with 50% EtOAc/heptane to give 4120 mg of I-4 (90% yield) as a white solid. LCMS [M+1-Boc] 300.

Step 4: Synthesis of tert-butyl((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)carbamate (I-5)

To a solution of I-4 (4300 mg, 10.77 mmol) and imidazole (2200 mg, 32.3 mmol) in DMF (53.8 mL, c=0.2 M) was added t-butyldimethylsilyl chloride (4870 mg, 32.3 mmol). The mixture was stirred at r.t. overnight. Additional TBSCl (1620 mg, 10.8 mmol) was added and stirred at r.t. overnight. The reaction mixture was quenched with H₂O and extracted with EtOAc (×3). The organic layer was dried over Na₂SO₄, concentrated, purified by column chromatography with 15-20% EtOAc/heptane to give 5.27 g of I-5 (87% yield) as a colorless oil which solidified upon vacuum. LCMS [M+1-Boc] 414.

Step 5: Synthesis of mixture of (3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-amine (I-6) and (1R,2S,3R,5S)-3-amino-5-(((tert-butyldimethylsilyl)oxy)(3,4-difluorophenyl)methyl)cyclopentane-1,2-diol (I-7)

I-5 (1250 mg, 2.433 mmol) in TFA (5.0 mL, c=0.5 M) was stirred at r.t. for 10-15 min. The reaction mixture was added EtOAc and neutralized with std. NaHCO₃ until pH about 7, the aqueous layer was extracted with EtOAc, the organic was combined and dried over Na₂SO₄, concentrated to give 1 g (99% yield) as a light yellow oil as a mixture of the two compounds I-6 and I-7.

Step 6: Synthesis of mixture of N-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-7H-pyrrolo[2,3-d]pyrimidin-4-amine (I-8) and (1R,2S,3R,5S)-3-((7H-pyrrolo[2,3-d]pyrimidin-4-yl)amino)-5-(((tert-butyldimethylsilyl)oxy)(3,4-difluorophenyl)methyl)cyclopentane-1,2-diol (I-9)

To the above compounds I-6 and I-7 (154 mg, 0.372 mmol) in 4 mL nBuOH solution was added 4-chloro-7H-pyrrolo[2,3-d]pyrimidine (85.8 mg, 0.559 mmol) and DIPEA (96.3 mg, 0.745 mmol, 0.123 mL), heated at 100° C. for 2 days. The reaction mixture was cooled to r.t., EtOAc was added. The organic layer was washed with H₂O three times and then brine, dried over Na₂SO₄, concentrated, purified by column chromatography eluting from 80% EtOAc/heptane to 10% EtOAc/MeOH to give 35.3 mg (19% yield) of a mixture of two compounds I-8 and I-9 as a brown oil.

Step 7: Synthesis of mixture of ((3aR,4R,6R,6aS)-6-((7H-pyrrolo[2,3-d]pyrimidin-4-yl)amino)-2,2-dimethyltetrahydro-4H-cyclopenta[d][1,3]dioxol-4-yl)(3,4-difluorophenyl)methanol (I-10) and (1R,2S,3R,5R)-3-((7H-pyrrolo[2,3-d]pyrimidin-4-yl)amino)-5-((3,4-difluorophenyl)(hydroxy)methyl)cyclopentane-1,2-diol (I-11)

To a mixture of the above compounds I-8 and I-9 (49 mg, 0.10 mmol) in 1 mL THF was added TBAF (39.2 mg, 0.150 mmol, 0.15 mL, 1.0 M) dropwise, stirred at r.t. for 0.5 h, concentrated and used crude for next step.

Step 8: Synthesis of (1S,2R,3R,5R)-3-[(S)-(3,4-difluorophenyl)(hydroxy)methyl]-5-(7H-pyrrolo[2,3-d]pyrimidin-4-ylamino)cyclopentane-1,2-diol (I-12) and (1S,2R,3R,5R)-3-[(R)-(3,4-difluorophenyl)(hydroxy)methyl]-5-(7H-pyrrolo[2,3-d]pyrimidin-4-ylamino)cyclopentane-1,2-diol (I-13)

A mixture of above compounds I-10 and I-11 (42 mg, 0.10 mmol) was dissolved in TFA/H₂O (1 mL/1 mL) and stirred at rt for 2 h. After completion, the mixture was concentrated to give crude oil, which was dissolved in H₂O, washed with EtOAc (1 mL×2). The water layer was lyophilized and the mixture separated by supercritical CO₂ fluid chromatography to give (1S,2R,3R,5R)-3-[(S)-(3,4-difluorophenyl)(hydroxy)methyl]-5-(7H-pyrrolo[2,3-d]pyrimidin-4-ylamino)cyclopentane-1,2-diol I-12 (5.88 mg, 15%) and (1S,2R,3R,5R)-3-[(R)-(3,4-difluorophenyl)(hydroxy)methyl]-5-(7H-pyrrolo[2,3-d]pyrimidin-4-ylamino)cyclopentane-1,2-diol I-13 (5.72 mg, 15%).

I-12: LCMS [M+1] 376.90. ¹H NMR (700 MHz, DMSO-d6) δ ppm 1.06-1.12 (m, 1H) 1.88-1.96 (m, 1H) 2.15-2.21 (m, 1H) 2.88 (q, J=6.83 Hz, 1H) 3.77 (t, J=6.15 Hz, 1H) 3.88 (br. s., 1H) 4.24-4.32 (m, 1H) 4.47 (d, J=5.98 Hz, 1H) 6.53 (br. s., 1H) 7.06 (br. s., 1H) 7.15 (br. s., 1H) 7.25-7.36 (m, 3H) 7.99 (br. s., 1H)

I-13: LCMS [M+1] 376.90. ¹H NMR (700 MHz, DMSO-d6) δ ppm 1.32-1.40 (m, 1H) 1.81 (dt, J=12.55, 8.07 Hz, 1H) 2.10-2.20 (m, 1H) 2.88 (q, J=6.83 Hz, 1H) 3.75-3.81 (m, 1H) 3.83 (br. s., 1H) 4.18-4.31 (m, 1H) 4.73 (br. s., 1H) 6.55 (br. s., 1H) 7.07 (br. s., 1H) 7.14 (br. s., 1H) 7.24-7.41 (m, 3H) 8.00 (br. s., 1H)

Examples 29 and 30 were Prepared in Using Similar Chemistry in Scheme I Using 4-chloroquinazoline-8-carbonitrile in Step 6 in Place of 4-chloro-7H-pyrrolo[2,3-d]pyrimidine

| Example 29 Isomer A | 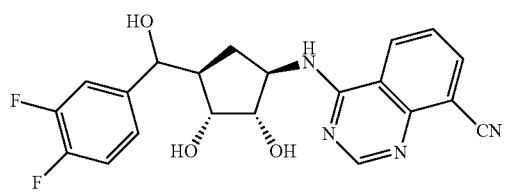 [SMILES: N#Cc1cccc2c(N[C@@H]3C[C@H](C(O)c4ccc(F)c(F)c4)[C@@H](O)[C@H]3O)ncnc12] | LCMS 412.85. | 4-({(1R;2S;3R;4R)-4-[(3;4-difluorophenyl)(hydroxy)methyl]-2;3-dihydroxycyclopentyl}amino)quinazoline-8-carbonitrile ¹H NMR (700 MHz, DMSO-d6) δ ppm 1.40 (dt, J = 13.11, 8.82 Hz, 1 H) 1.85 (dt, J = 13.15, 8.20 Hz, 1 H) 2.17 (dt, J = 8.80, 4.31 Hz, 1 H) 3.86 (q, J = 4.61 Hz, 1 H) 3.88-3.95 (m, 1 H) 4.43 (t, J = 7.69 Hz, 1 H) 4.75 (t, J = 4.10 Hz, 1 H) 7.09-7.16 (m, 1 H) 7.22-7.32 (m, 2 H) 7.58 (t, J = 7.86 Hz, 1 H) 8.21 (d, J = 7.34 Hz, 1 H) 8.38 (d, J = 7.34 Hz, 1 H) 8.40-8.46 (m, 2 H) |

| Example 30 Isomer B | 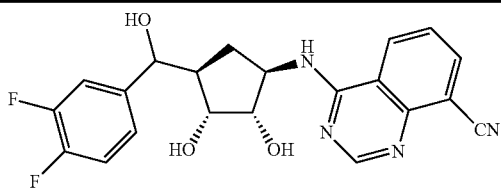 | LCMS [M + 1] 412.85. | 4-({(1R;2S;3R;4R)-4-[(3;4-difluorophenyl)(hydroxy)methyl]-2;3-dihydroxycyclopentyl}amino)quinazoline-8-carbonitrile<br>¹H NMR (700 MHz, DMSO-d6) δ ppm 1.13-1.18 (m, 1 H) 1.92-1.99 (m, 1 H) 2.16-2.25 (m, 1H) 3.92 (br. s., 2 H) 4.42-4.52 (m, 2 H) 7.11-7.15 (m, 1 H) 7.22-7.26 (m, 1 H) 7.26-7.30 (m, 1 H) 7.55-7.60 (m, 1 H) 8.21 (dd, J = 7.34, 1.20 Hz, 1 H) 8.40-8.44 (m, 2 H) |

Example 31 (Scheme J)—(1S,2R,3R,5R)-3-[(S)-(3,4-difluorophenyl)(hydroxy)methyl]-5-[methyl(pyrimidin-4-yl)amino]cyclopentane-1,2-diol (J-5)

Example 32 (Scheme J)—(1S,2R,3R,5R)-3-[(R)-(3;4-difluorophenyl)(hydroxy)methyl]-5-[methyl(pyrimidin-4-yl)amino]cyclopentane-1,2-diol (J-5)

Scheme J

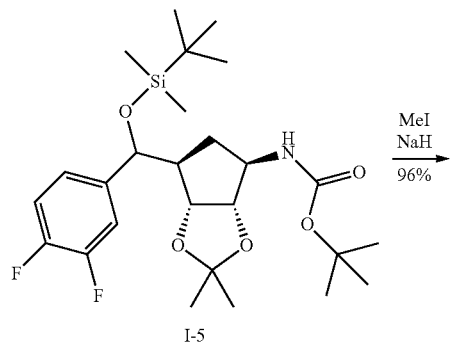

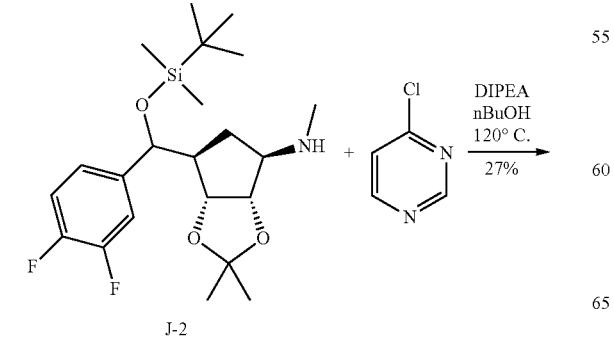

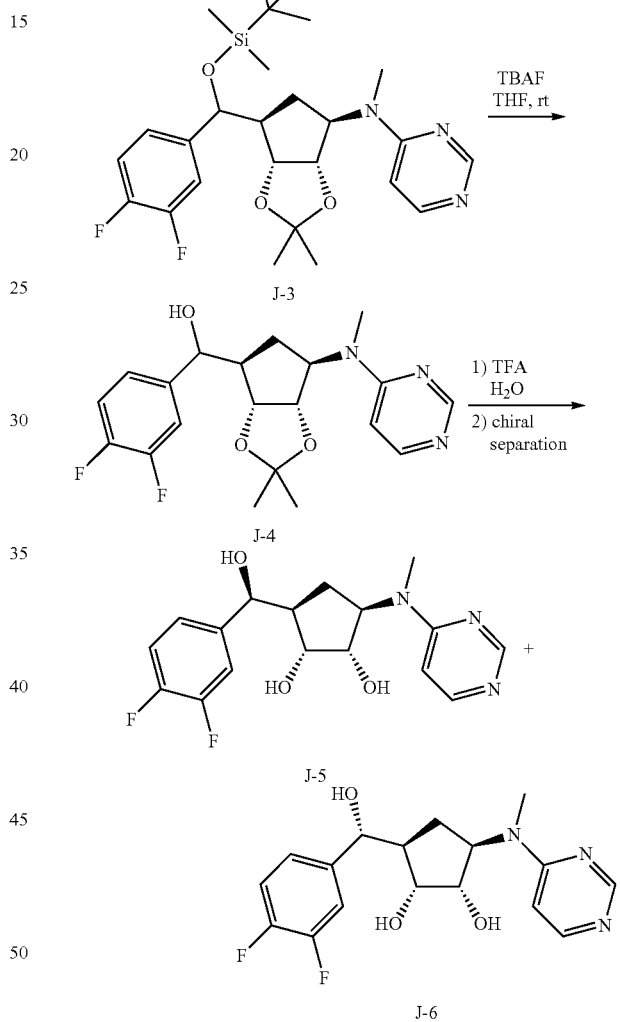

Step 1: Synthesis of tert-butyl((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)(methyl)carbamate (J-1)

Sodium hydride (304 mg, 7.59 mmol) was added in portions to a solution of I-5 (1300 mg, 2.531 mmol) in DMF (15 mL, 0.1 M) under an atmosphere of nitrogen, after 5 min, iodomethane (1080 mg, 7.59 mmol) was added, stirred at r.t. for 30 min. The reaction mixture was added H₂O, extracted with EtOAc, concentrated and purified by column chromatography with 20% EtOAc/heptane to give 1290 mg of J-1 (96% yield) as a colorless oil, LCMS [M+1-Boc] 428.1.

Step 2: Synthesis of (3aS,4R,6S,6aR)-6-(((tert-butyldimethylsilyl)oxy)(3,4-difluorophenyl)methyl)-N,2,2-trimethyltetrahydro-4H-cyclopenta[d][1,3]dioxol-4-amine (J-2)

J-1 (967 mg, 1.83 mmol) in TFA (5.0 mL, c=0.1 M) was stirred at r.t. for 10-15 min. The reaction mixture was added EtOAc and std. NaHCO$_3$ to neutralize to pH about 7, extracted with EtOAc, the organic layer was dried over Na$_2$SO$_4$, concentrated to give colorless oil.

The above oil was dissolved in acetone dimethyl acetal (10 mL, c=0.1 M), toluene-4-sulfonic acid (349 mg, 1.83 mmol) was added, stirred at r.t. for 15 min. The reaction mixture was added std NaHCO$_3$, extracted with EtOAc, the organic layer was washed with brine, dried over Na$_2$SO$_4$, concentrated to give 0.78 g of J-2 (99% yield) as a light yellow oil. LCMS [M+1] 428.15.

Step 3: Synthesis of N-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-N-methylpyrimidin-4-amine (J-3)

The mixture of J-2 (200 mg, 0.468 mmol), 4-chloropyrimidine (64.3 mg, 0.561 mmol) and DIPEA (121 mg, 0.935 mmol, 0.155 mL) in n-butanol (2.0 mL, c=0.2 M) was heated at 120° C. overnight. The reaction mixture was cooled to r.t., the solvent was removed. The residue was added EtOAc, washed with H$_2$O 3 times and then brine, dried over Na$_2$SO$_4$ and concentrated, purified by column chromatography with 70% EtOAc/heptane to give 64 mg of J-3 (27% yield) as a brown oil. LCMS [M+1] 506.20.

Step 4: Synthesis of (3,4-difluorophenyl)((3aR,4R,6R,6aS)-2,2-dimethyl-6-(methyl(pyrimidin-4-yl)amino)tetrahydro-4H-cyclopenta[d][1,3]dioxol-4-yl)methanol (J-4)

Followed similar procedure as step 7 in Scheme I, J-3 was deprotected to give J-4 as crude for the next step. LCMS [M+1] 392.15.

Step 5: Synthesis of (1S,2R,3R,5R)-3-[(S)-(3,4-difluorophenyl)(hydroxy)methyl]-5-[methyl(pyrimidin-4-yl)amino]cyclopentane-1,2-diol (J-5) and (1S,2R,3R,5R)-3-[(R)-(3;4-difluorophenyl)(hydroxy)methyl]-5-[methyl(pyrimidin-4-yl)amino]cyclopentane-1,2-diol (J-6)

Followed similar procedure as step 8 in Scheme I, J-4 (50 mg, 0.13 mmol) was deprotected to give J-5 (19.73 mg, 44%) and J-6 (3.14 mg, 7%).

J-5: LCMS [M+1] 351.90. $^1$H NMR (700 MHz, DMSO-d6) δ ppm 1.18-1.31 (m, 1H) 1.63 (d, J=9.68 Hz, 1H) 2.08-2.19 (m, 1H) 2.90 (br. s., 3H) 3.73-3.82 (m, 1H) 3.90 (dd, J=9.35, 5.17 Hz, 1H) 4.38 (br. s., 1H) 4.49 (d, J=5.94 Hz, 1H) 4.63 (br. s., 1H) 5.60 (br. s., 1H) 6.57-6.69 (m, 1H) 7.21 (br. s., 1H) 7.31-7.42 (m, 2H) 8.02-8.14 (m, 1H) 8.41 (br. s., 1H)

J-6: LCMS [M+1] 351.90. $^1$H NMR (700 MHz, DMSO-d6) δ ppm 1.42 (br. s., 2H) 2.10 (br. s., 1H) 2.90 (br. s., 3H) 3.76 (br. s., 1H) 3.86-3.97 (m, 1H) 4.54 (br. s., 1H) 4.65 (br. s., 1H) 4.70-4.78 (m, 1H) 5.58 (br. s., 1H) 6.63 (br. s., 1H) 7.17 (br. s., 1H) 7.28-7.40 (m, 2H) 8.09 (br. s., 1H) 8.41 (br. s., 1H)

Examples 33-36 were Prepared in Following Similar Chemistry in Scheme J Using the Chloropyrimidine Listed in Step 3

| | | | |
|---|---|---|---|
| Example 33 4-chloro-6-methylpyrimidine | 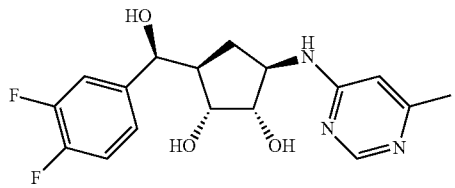 | LCMS [M + 1] 366.1 | (1S,2R,3R,5R)-3-[(S)-(3,4-difluorophenyl)(hydroxy)methyl]-5-[methyl(6-methylpyrimidin-4-yl)amino]cyclopentane-1,2-diol $^1$H NMR (700 MHz, DMSO-d6) δ ppm 1.18-1.31 (m, 1 H) 1.61 (d, J = 10.34 Hz, 1 H) 2.13 (d, J = 7.04 Hz, 1 H) 2.22 (s, 3 H) 2.88 (br. s., 3 H) 3.77 (br. s., 1 H) 3.84-3.94 (m, 1 H) 4.32-4.41 (m, 1 H) 4.49 (t, J = 5.06 Hz, 1 H) 4.61 (br. s., 1 H) 5.61 (d, J = 4.40 Hz, 1 H) 6.49 (br. s., 1 H) 7.15-7.23 (m, 1 H) 7.32-7.43 (m, 2 H) 8.28 (s, 1 H) |
| Example 34 4-chloro-6-methylpyrimidine | 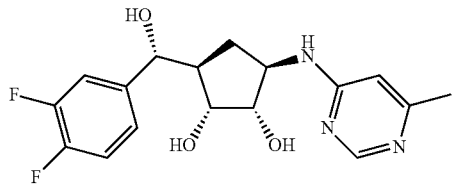 | LCMS [M + 1] 366.1 | (1S,2R,3R,5R)-3-[(R)-(3,4-difluorophenyl)(hydroxy)methyl]-5-[methyl(6-methylpyrimidin-4-yl)amino]cyclopentane-1,2-diol $^1$H NMR (700 MHz, DMSO-d6) δ ppm 1.40 (t, J = 9.24 Hz, 2 H) 2.09 (dt, J = 8.14, 4.29 Hz, 1 H) 2.22 (s, 3 H) 2.89 (br. s., 3 H) 3.71-3.78 (m, 1 H) 3.86-3.95 (m, 1 H) 4.46-4.54 (m, 1 H) 4.62 (br. s., 1 H) 4.73 (t, J = 4.40 Hz, 1 H) 5.58 (d, J = 4.62 Hz, 1 H) 6.50 (br. s., 1 H) 7.16 (br. s., 1 H) 7.29-7.39 (m, 2 H) 8.28 (s, 1 H) |
| Example 35 4-chloro-2-methylpyrimidine | 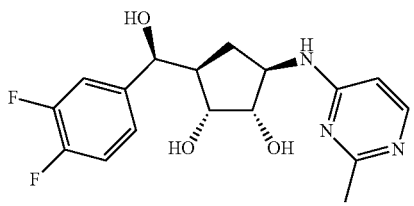 | LCMS [M + 1] 365.90 | (1S,2R,3R,5R)-3-[(S)-(3,4-difluorophenyl)(hydroxy)methyl]-5-[methyl(2-methylpyrimidin-4-yl)amino]cyclopentane-1,2-diol $^1$H NMR (700 MHz, DMSO-d6) δ ppm 1.17-1.32 (m, 1 H) 1.57-1.68 (m, 1 H) 2.08-2.19 (m, 1 H) 2.31 (br. s., 3 H) 2.88 (br. s., 3 H) 3.77 (br. s., 1 H) 3.84-3.94 (m, 1 H) 4.37 (br. s., 1 H) 4.49 (br. s., 1 H) 4.63 (br. s., 1 H) 5.61 (br. s., 1 H) 6.43 (br. s., 1 H) 7.21 (br. s., 1 H) 7.37 (d, J = 8.58 Hz, 2 H) 7.99 (br. s., 1 H) |

| Example 36 4-chloro-2-methylpyrimidine | 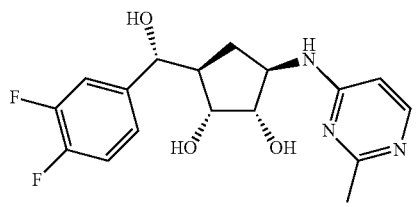 | LCMS [M + 1] 365.90 | (1S,2R,3R,5R)-3-[(R)-(3,4-difluorophenyl)(hydroxy)methyl]-5-[methyl(2-methylpyrimidin-4-yl)amino]cyclopentane-1,2-diol<br>¹H NMR (700 MHz, DMSO-d6) δ ppm 1.35-1.48 (m, 2 H) 2.10 (tt, J = 8.53, 4.24 Hz, 1 H) 2.31 (s, 3 H) 2.89 (br. s., 3 H) 3.71-3.79 (m, 1 H) 3.91 (dt, J = 8.42, 6.02 Hz, 1 H) 4.52 (d, J = 3.96 Hz, 1 H) 4.65 (br. s., 1 H) 4.73 (t, J = 4.51 Hz, 1 H) 5.59 (d, J = 4.62 Hz, 1 H) 6.43 (d, J = 5.06 Hz, 1 H) 7.12-7.19 (m, 1 H) 7.29-7.38 (m, 2 H) 7.99 (d, J = 5.94 Hz, 1 H) |
|---|---|---|---|

Example 37 (Scheme K)—(1R,2S,3R,5R)-3-[(4-amino-1,3,5-triazin-2-yl)(methyl)amino]-5-[(S)-(3,4-difluorophenyl)(hydroxy)methyl]cyclopentane-1,2-diol (K-4)

Example 38 (Scheme K)—(1R,2S,3R,5R)-3-[(4-amino-1,3,5-triazin-2-yl)(methyl) amino]-5-[(R)-(3,4-difluorophenyl)(hydroxy)methyl]cyclopentane-1,2-diol (K-5)

Scheme K

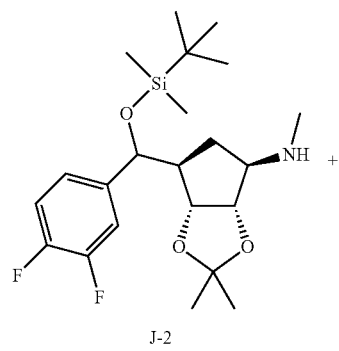

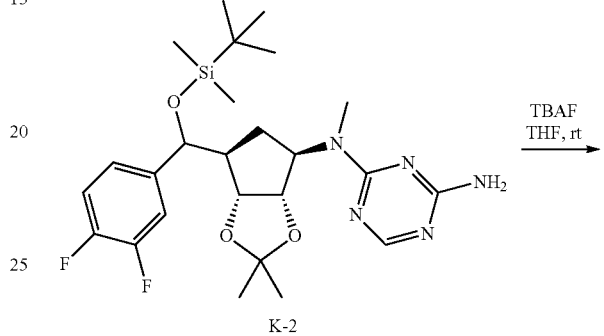

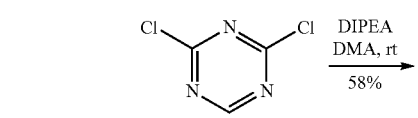

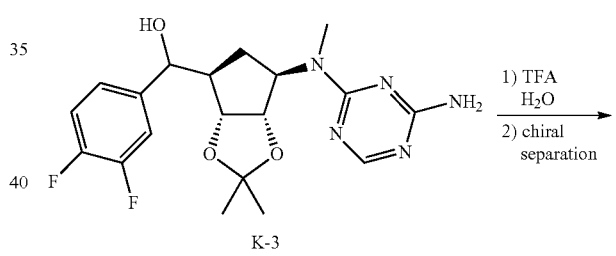

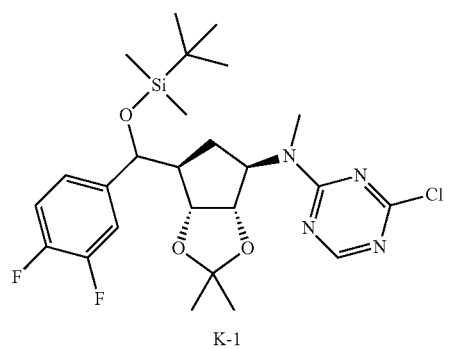

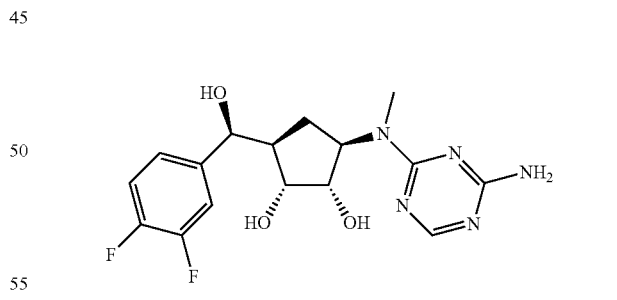

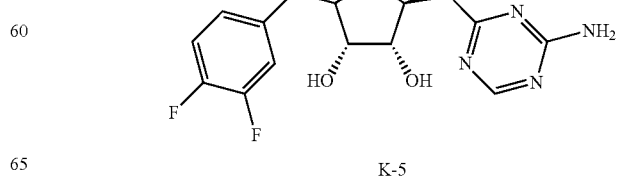

Step 1: Synthesis of N-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-4-chloro-N-methyl-1,3,5-triazin-2-amine (K-1)

Following a similar procedure to step 3 in Scheme J using 2,4-dichloro-[1,3,5]triazine with J-2 generated K-1 (267 mg, 58%).

Step 2: Synthesis of N2-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-N2-methyl-1,3,5-triazine-2,4-diamine (K-2)

Following a similar procedure to step 5 in Scheme G, K-1 was converted to K-2 (86 mg, 81%). LCMS [M+1] 522.

Step 3: Synthesis of ((3aR,4R,6R,6aS)-6-((4-amino-1,3,5-triazin-2-yl)(methyl)amino)-2,2-dimethyl tetrahydro-4H-cyclopenta[d][1,3]dioxol-4-yl)(3,4-difluorophenyl)methanol (K-3)

Following a similar procedure to step 4 in Scheme J, K-2 was deprotected with TBAF to give K-3 as crude for the next step.

Step 4: Synthesis of (1R,2S,3R,5R)-3-[(4-amino-1,3,5-triazin-2-yl)(methyl)amino]-5-[(S)-(3,4-difluorophenyl)(hydroxy)methyl]cyclopentane-1,2-diol (K-4) and (1R,2S,3R,5R)-3-[(4-amino-1,3,5-triazin-2-yl)(methyl)amino]-5-[(3R)-(3,4-difluorophenyl)(hydroxy)methyl]cyclopentane-1,2-diol (K-5)

Following a similar procedure to step 5 in Scheme J with subsequent separation with chiral SFC, K-3 was converted to K-4 (12 mg, 20%) and K-5 (48 mg, 80%).

K-4: LCMS [M+1] 367.90. $^1$H NMR (400 MHz, DMSO-d6) δ ppm 1.12-1.23 (m, 1H) 1.52-1.64 (m, 1H) 2.08 (br. s., 1H) 2.96 (d, J=9.78 Hz, 3H) 3.78 (br. s., 1H) 3.87 (br. s., 1H) 4.48 (d, J=5.38 Hz, 1H) 4.94 (br. s., 1H) 5.55 (br. s., 1H) 6.95 (s, 1H) 7.08 (br. s, 2H) 7.21 (br. s, 1H) 7.30-7.45 (m, 2H) 8.07 (br. s., 1H)

K-5: LCMS [M+1] 367.90. $^1$H NMR (700 MHz, DMSO-d6) δ ppm 1.31-1.45 (m, 2H) 2.05 (br. s., 1H) 2.93 (m, 3H) 3.72 (br. s., 1H) 3.90 (br. s., 1H) 4.65-4.72 (m, 1H) 4.86 (d, J=15.03 Hz, 1H) 7.14 (br. s., 1H) 7.25-7.35 (m, 2H) 7.98 (br. s., 1H) 8.30 (br. s., 2H)

Examples 39-42 were Prepared in Following Similar Chemistry in Scheme K Using 2,4-dichloropyrimidine (Examples 39 & 40) or 2,4-dichloro-6-methyl-1,3,5-triazine (Examples 41 & 42) Listed in Step 1

| | | LCMS [M + 1] | |
|---|---|---|---|
| Example 39 2,4-dichloropyrimidine | 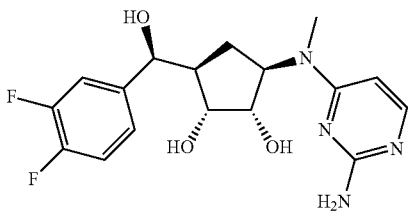 [SMILES: CN(c1ccnc(N)n1)[C@@H]1C[C@H]([C@H](O)c2ccc(F)c(F)c2)[C@@H](O)[C@H]1O] | 366.90 | (1R,2S,3R,5R)-3-[(2-aminopyrimidin-4-yl)(methyl)amino]-5-((S)-(3,4-difluorophenyl)(hydroxy)methyl]cyclopentane-1,2-diol $^1$H NMR (700 MHz, DMSO-d6) δ ppm 1.17-1.22 (m, 1 H) 1.53-1.60 (m, 1 H) 2.06-2.11 (m, 1 H) 2.81 (br. s., 3 H) 3.75 (br. s., 1 H) 3.84-3.89 (m, 1 H) 4.32 (d, J = 3.08 Hz, 1 H) 4.48 (t, J = 5.28 Hz, 1 H) 4.60 (d, J = 5.94 Hz, 1 H) 5.59 (d, J = 4.62 Hz, 1 H) 5.81 (s, 2 H) 5.87 (d, J = 5.94 Hz, 1 H) 7.20 (br. s., 1 H) 7.32-7.40 (m, 2 H) 7.67 (d, J = 5.72 Hz, 1 H) |
| Example 40 2,4-dichloropyrimidine | 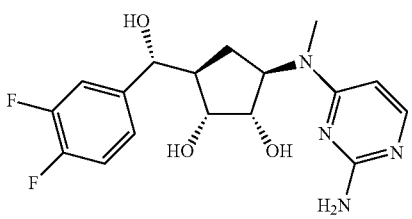 [SMILES: CN(c1ccnc(N)n1)[C@@H]1C[C@H]([C@@H](O)c2ccc(F)c(F)c2)[C@@H](O)[C@H]1O] | 366.90 | (1R,2S,3R,5R)-3-[(2-aminopyrimidin-4-yl)(methyl)amino]-5-[(R)-(3,4-difluorophenyl)(hydroxy)methyl]cyclopentane-1,2-diol $^1$H NMR (700 MHz, DMSO-d6) δ ppm 1.30-1.44 (m, 2 H) 2.05 (dt, J = 8.25, 4.24 Hz, 1 H) 2.82 (br. s., 3 H) 3.74 (br. s., 1 H) 3.88 (br. s., 1 H) 4.48 (br. s., 1 H) 4.62 (br. s., 1 H) 4.72 (br. s., 1 H) 5.57 (d, J = 4.40 Hz, 1 H) 5.81 (br. s., 2 H) 5.87 (d, J = 5.06 Hz, 1 H) 7.09-7.19 (m, 1 H) 7.28-7.38 (m, 2 H) 7.67 (br. s., 1 H) |
| Example 41 2,4-dichloro-6-methyl-1,3,5-triazine | 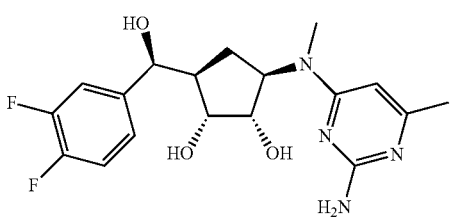 [SMILES: Cc1cc(N(C)[C@@H]2C[C@H]([C@H](O)c3ccc(F)c(F)c3)[C@@H](O)[C@H]2O)nc(N)n1] | 381.90 | (1R,2S,3R,5R)-3-[(4-amino-6-methyl-1,3,5-triazin-2-yl)(methyl)amino]-5-[(S)-(3,4-difluorophenyl)(hydroxy)methyl]cyclopentane-1,2-diol $^1$H NMR (700 MHz, DMSO-d6) δ ppm 1.18 (d, J = 13.66 Hz, 1 H) 1.49-1.59 (m, 1 H) 2.12 (d, J = 14.69 Hz, 4 H) 2.91 (d, J = 19.81 Hz, 3 H) 3.79 (br. s., 1 H) 3.88 (br. s., 1 H) 4.46 (br. s., 1 H) 4.88 (br. s., 1 H) 7.16 (br. s., 1 H) 7.23-7.36 (m, 2 H) |
| Example 42 2,4-dichloro-6-methyl-1,3,5-triazine | 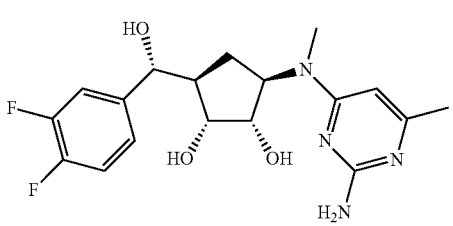 [SMILES: Cc1cc(N(C)[C@@H]2C[C@H]([C@@H](O)c3ccc(F)c(F)c3)[C@@H](O)[C@H]2O)nc(N)n1] | 381.90 | (1R,2S,3R,5R)-3-[(4-amino-6-methyl-1,3,5-triazin-2-yl)(methyl)amino]-5-[(R)-(3,4-difluorophenyl)(hydroxy)methyl]cyclopentane-1,2-diol $^1$H NMR (700 MHz, DMSO-d6) δ ppm 1.31-1.45 (m, 2 H) 2.07 (d, J = 18.62 Hz, 4 H) 2.82-2.96 (m, 3 H) 3.72 (br. s., 1 H) 3.87 (br. s., 1 H) 4.68 (br. s., 1 H) 4.94-4.78 (m, 1 H) 6.37 (br. s., 2 H) 7.13 (br. s., 1 H) 7.22-7.34 (m, 2 H) |

Example 43 (Scheme L)—(1R,2S,3R,5R)-3-[(6-aminopyrimidin-4-yl)(methyl)amino]-5-[(S)-(3,4-difluorophenyl)(hydroxy)methyl]cyclopentane-1,2-diol (L-4)

Example 44 (Scheme L)—(1R,2S,3R,5R)-3-[(6-aminopyrimidin-4-yl)(methyl)amino]-5-[(R)-(3,4-difluorophenyl)(hydroxy)methyl]cyclopentane-1,2-diol (L-5)

Scheme L

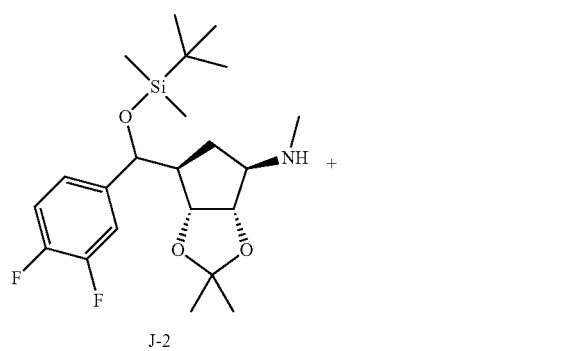

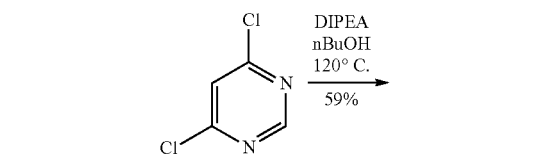

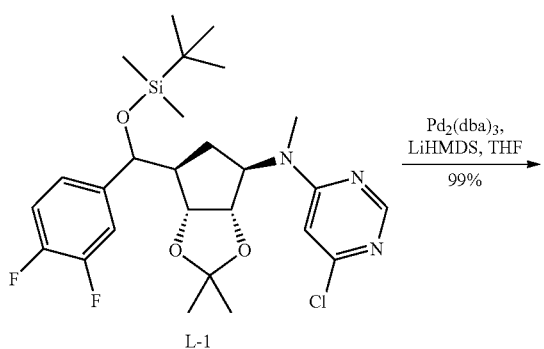

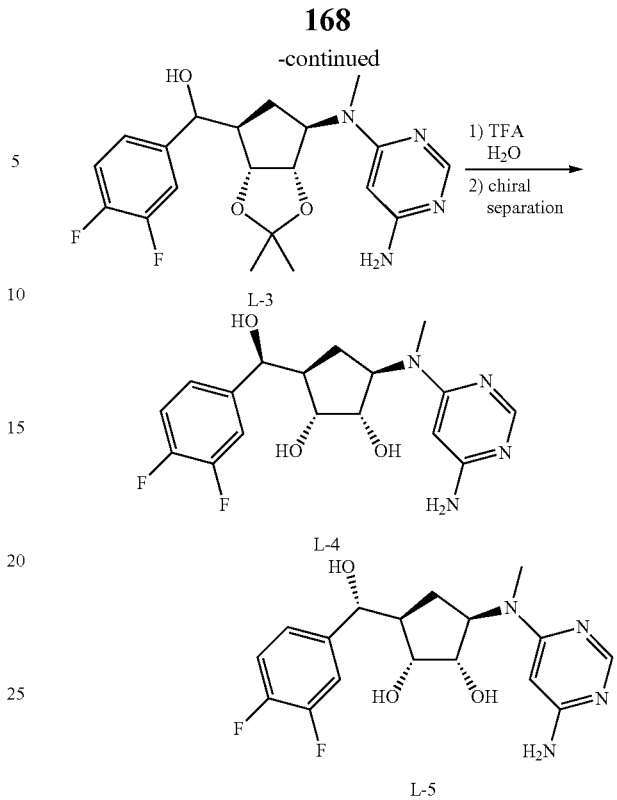

Step 1: Synthesis of N-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-6-chloro-N-methylpyrimidin-4-amine (L-1)

Following a similar procedure to step 1 in Scheme K, J-2 was treated with 4,6-dichloropyrimidine in n-butanol and DIPEA to give L-1 (188 mg, 60%). LCMS [M+1] 540.20.

Step 2: Synthesis of N4-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-N4-methylpyrimidine-4,6-diamine (L-2)

To a solution of L-1 (188 mg, 0.348 mmol) in THF (10 mL, c=0.035 M) was added tris(dibenzylideneacetone)dipalladium (41.4 mg, 0.045 mmol) and dicyclohexyl(2-phenylphenyl)phosphane (33.7 mg, 0.092 mmol), capped and purged with nitrogen, then LHMDS (153 mg, 0.905 mmol, 0.90 mL, 1.0 M) was added, heated at 75° C. for 18 h. The reaction was cooled to r.t., diluted with water and EtOAc, the layers were separated. The organic phase was dried over Na$_2$SO$_4$, filtered and concentrated. The product was purified by column chromatography with 80%-100% EtOAc/heptane to give 180 mg of L-2 (99% yield) as a light yellow oil. LCMS [M+1] 521.30.

Step 3: Synthesis of ((3aR,4R,6R,6aS)-6-((6-aminopyrimidin-4-yl)(methyl)amino)-2,2-dimethyl tetrahydro-4H-cyclopenta[d][1,3]dioxol-4-yl)(3,4-difluorophenyl)methanol (L-3)

Following a similar procedure as step 3 in Scheme K, L-2 was treated with TBAF to give L-3 as crude for the next step. LCMS [M+1] 407.20.

Step 4: Synthesis of (1R,2S,3R,5R)-3-[(6-aminopyrimidin-4-yl)(methyl)amino]-5-[(S)-(3,4-difluorophenyl)(hydroxy)methyl]cyclopentane-1,2-diol (L-4) and (1R,2S,3R,5R)-3-[(6-aminopyrimidin-4-yl)(methyl) amino]-5-[(R)-(3,4-difluorophenyl)(hydroxy)methyl]cyclopentane-1,2-diol (L-5)

Following a similar procedure as step 4 in Scheme K, L-3 was treated with TFA in water. L-4 (31 mg, 25%) and L-5 (11 mg, 9%) were isolated after workup and purification by chiral SFC.

L-4: LCMS [M+1] 366.90. $^1$H NMR (700 MHz, DMSO-d6) δ ppm 1.13-1.26 (m, 1H) 1.55 (dt, J=12.60, 8.56 Hz, 1H) 2.04-2.13 (m, 1H) 2.77 (s, 2H) 3.71-3.79 (m, 1H) 3.81-3.88 (m, 1H) 4.27-4.35 (m, 1H) 4.47 (t, J=5.28 Hz, 1H) 4.55 (d, J=5.72 Hz, 1H) 5.47 (s, 1H) 5.58 (d, J=4.62 Hz, 1H) 6.03 (br. s., 2H) 7.15-7.23 (m, 1H) 7.30-7.40 (m, 2H) 7.86 (s, 1H)

L-5: LCMS [M+1] 366.90. $^1$H NMR (700 MHz, DMSO-d6) δ ppm 1.29-1.42 (m, 2H) 1.99-2.09 (m, 1H) 2.78 (br. s., 3H) 3.74 (br. s., 1H) 3.86 (d, J=7.04 Hz, 1H) 4.41-4.49 (m, 1H) 4.52-4.60 (m, 1H) 4.72 (br. s., 1H) 5.47 (s, 1H) 5.56 (d, J=3.96 Hz, 1H) 6.03 (br. s., 1H) 7.15 (br. s., 1H) 7.28-7.38 (m, 2H) 7.86 (s, 1H)

Example 46 (Scheme M)—(1S,2R,3R,5R)-3-[(S)-(3,4-difluorophenyl)(hydroxy)methyl]-5-[methyl(4-methyl-1,3,5-triazin-2-yl)amino]cyclopentane-1,2-diol (M-4)

Example 47 (Scheme M)—(1S,2R,3R,5R)-3-[(R)-(3,4-difluorophenyl)(hydroxy)methyl]-5-[methyl(4-methyl-1,3,5-triazin-2-yl)amino]cyclopentane-1,2-diol (M-5)

Scheme M

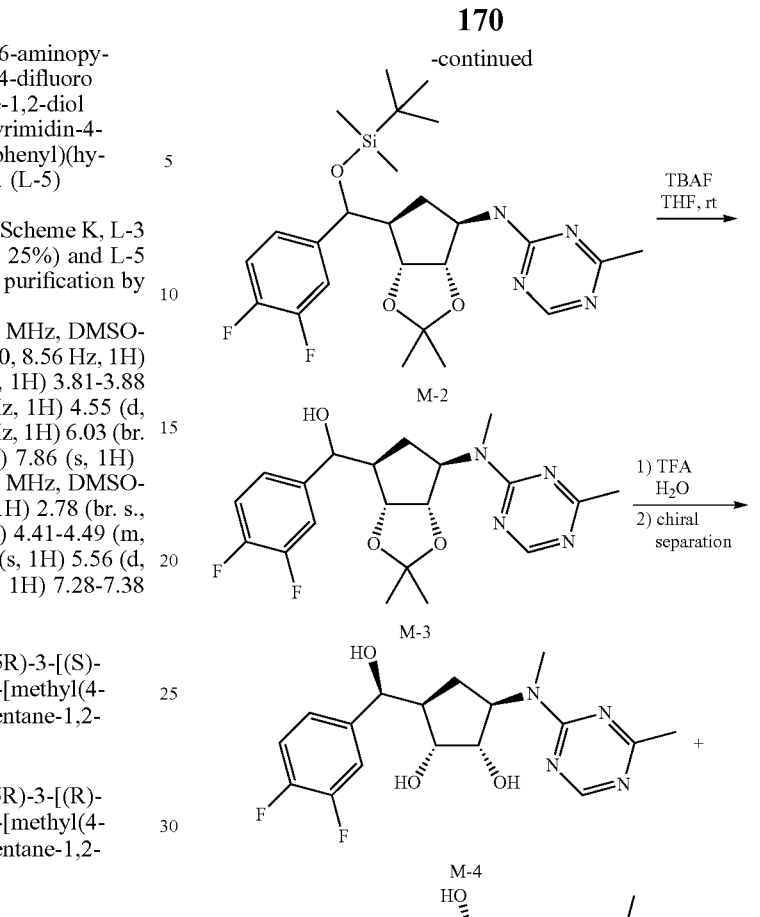

Step 1: Synthesis of N-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-4-chloro-N-methyl-1,3,5-triazin-2-amine (M-1)

The reaction mixture of J-2 (360 mg, 0.842 mmol), 2,4-dichloro-[1,3,5] triazine (152 mg, 1.01 mmol) and DIPEA (218 mg, 1.68 mmol, 0.279 mL) in DMA (5 mL, 0.16 M) was stirred at r.t. for 5 hrs. The rxn mixture was added EtOAc, washed with H$_2$O 3 times and then brine. The organic layer was dried over Na$_2$SO$_4$ and concentrated, purified by column chromatography with 20% EtOAc/heptane to give 267 mg of M-1 (58.6% yield) as a colorless oil. LCMS [M+1] 541.

Step 2: Synthesis of N-((3aS,4R,6S,6aR)-6-(((tert-butyldimethylsilyl)oxy)(3,4-difluorophenyl)methyl)-2,2-dimethyltetrahydro-4H-cyclopenta[d][1,3]dioxol-4-yl)-N,4-dimethyl-1,3,5-triazin-2-amine (M-2)

M-2 (176 mg, 99%) was made from M-1 following a similar procedure to step 5 in Scheme A. LCMS [M+1] 521.

Step 3: Synthesis of (3,4-difluorophenyl)((3aR,4R, 6R,6aS)-2,2-dimethyl-6-(methyl(4-methyl-1,3,5-triazin-2-yl)amino)tetrahydro-4H-cyclopenta[d][1,3]dioxol-4-yl)methanol (M-3)

Following a similar procedure as step 3 in Scheme K, M-2 was treated with TBAF to give M-3 as crude for the next step. LCMS [M+1] 407.

Step 4: Synthesis of (1S,2R,3R,5R)-3-((S)-(3,4-difluorophenyl)(hydroxy)methyl)-5-(methyl(4-methyl-1,3,5-triazin-2-yl)amino)cyclopentane-1,2-diol (M-4) and (1S,2R,3R,5R)-3-((R)-(3,4-difluorophenyl)(hydroxy)methyl)-5-(methyl(4-methyl-1,3,5-triazin-2-yl)amino)cyclopentane-1,2-diol (M-5)

Following a similar procedure as step 4 in Scheme K, M-3 was treated with TFA in water. M-4 (78.97 mg, 64%) and M-5 (24.48 mg, 20%) were isolated after subsequent workup and purification by chiral SFC.

M-4: LCMS [M+1] 366.90. ¹H NMR (400 MHz, DMSO-d6) δ ppm 1.26-1.34 (m, 1H) 1.56-1.69 (m, 1H) 2.13 (br. s., 1H) 2.24-2.32 (m, 3H) 3.00 (s, 3H) 3.78 (br. s., 1H) 3.91 (br. s., 1H) 4.33 (d, J=15.89 Hz, 1H) 4.48 (br. s., 1H) 4.60 (br. s., 1H) 4.92-5.04 (m, 1H) 5.56 (d, J=4.40 Hz, 1H) 7.22 (d, J=4.52 Hz, 1H) 7.30-7.43 (m, 2H) 8.39 (d, J=14.67 Hz, 1H)

M-5: LCMS [M+1] 366.90. ¹H NMR (700 MHz, DMSO-d6) δ ppm 1.36-1.48 (m, 2H) 2.09 (br. s., 1H) 2.27 (d, J=23.74 Hz, 3H) 2.98 (d, J=4.10 Hz, 3H) 3.73 (br. s., 1H) 3.90 (m, 1H) 4.70 (br. s., 1H) 4.93 (t, J=9.99 Hz, 1H) 7.15 (br. s., 1H) 7.31 (d, J=9.39 Hz, 2H) 8.34 (d, J=33.65 Hz, 1H)

Example 48 (Scheme N)—(1R,2S,3R,5R)-3-(2-amino-4-methyl-7H-pyrrolo[2,3-d]pyrimidin-7-yl)-5-[(S)-(3,4-difluorophenyl)(hydroxy)methyl]cyclopentane-1,2-diol (N-5)

Example 49 (Scheme N)—(1R,2S,3R,5R)-3-(2-amino-4-methyl-7H-pyrrolo[2,3-d]pyrimidin-7-yl)-5-[(R)-(3,4-difluorophenyl)(hydroxy)methyl]cyclopentane-1,2-diol (N-6)

Scheme N

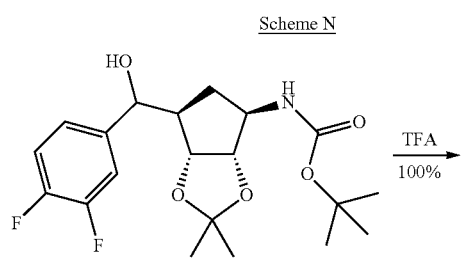

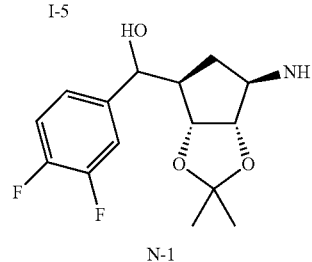

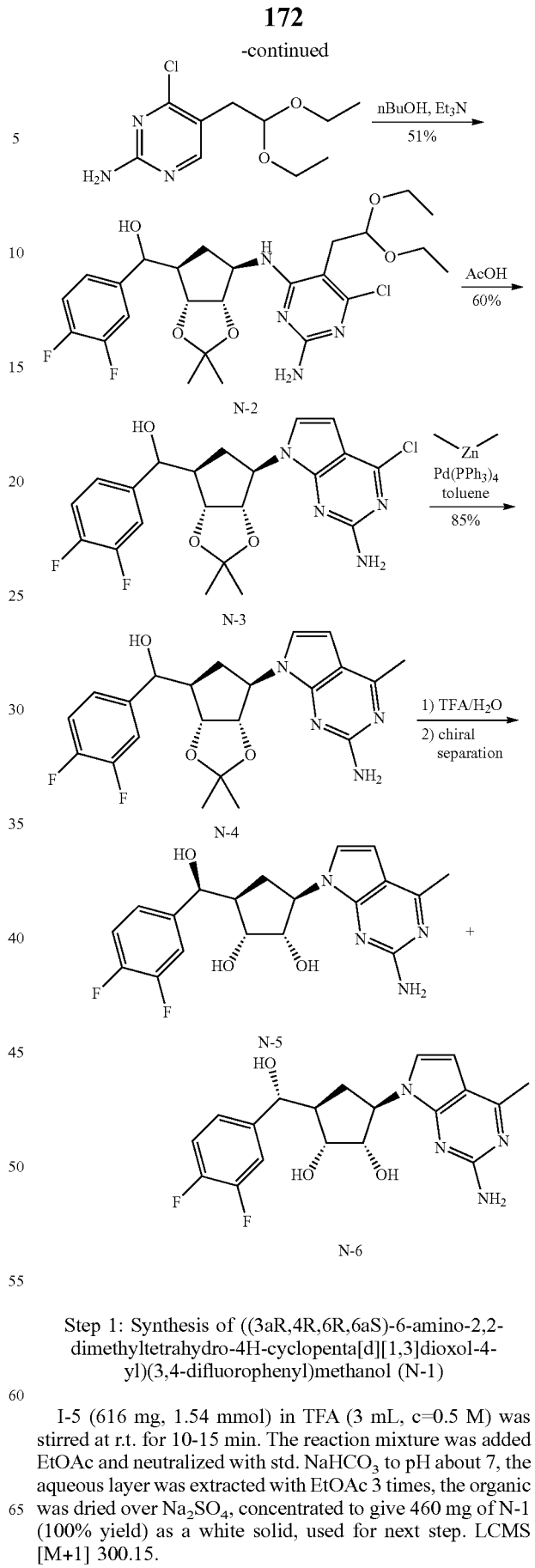

Step 1: Synthesis of ((3aR,4R,6R,6aS)-6-amino-2,2-dimethyltetrahydro-4H-cyclopenta[d][1,3]dioxol-4-yl)(3,4-difluorophenyl)methanol (N-1)

I-5 (616 mg, 1.54 mmol) in TFA (3 mL, c=0.5 M) was stirred at r.t. for 10-15 min. The reaction mixture was added EtOAc and neutralized with std. NaHCO₃ to pH about 7, the aqueous layer was extracted with EtOAc 3 times, the organic was dried over Na₂SO₄, concentrated to give 460 mg of N-1 (100% yield) as a white solid, used for next step. LCMS [M+1] 300.15.

Step 2: Synthesis of ((3aR,4R,6R,6aS)-6-((2-amino-6-chloro-5-(2,2-diethoxyethyl)pyrimidin-4-yl)amino)-2,2-dimethyltetrahydro-4H-cyclopenta[d][1,3]dioxol-4-yl)(3,4-difluorophenyl)methanol (N-2)

The mixture of N-1 (214 mg, 0.714 mmol), 4,6-dichloro-5-(2,2-diethoxyethyl)pyrimidin-2-amine (200 mg, 0.714 mmol), and triethylamine (289 mg, 2.86 mmol) in 10 mL nBuOH was heated at 135° C. in a sealed tube for 40 hrs. The reaction mixture was cooled to r.t., concentrated, $H_2O$ was added, extracted with EtOAc, the product was purified by column chromatography with 50-60% EtOAc/heptane to give 200 mg of N-2 (51% yield) as a yellow solid. LCMS [M+1] 543.20.

Step 3: Synthesis of ((3aR,4R,6R,6aS)-6-(2-amino-4-chloro-7H-pyrrolo[2,3-d]pyrimidin-7-yl)-2,2-dimethyltetrahydro-4H-cyclopenta[d][1,3]dioxol-4-yl)(3,4-difluorophenyl)methanol (N-3)

N-2 (200 mg, 0.368 mmol) was added to acetic acid (15 mL, c=0.025 M), the solution was heated at 100° C. for 1 h. The volatiles were removed in vacuo, the residue was added EtOAc, neutralized with std. $NaHCO_3$, the layers were separated and the aqueous was extracted with EtOAc 3 times. The organic layer was concentrated, purified by column chromatography with 50% EtOAc/heptane to give 100 mg of N-3 (60% yield) as an off white solid. LCMS [M+1] 451.10.

Step 4: Synthesis of ((3aR,4R,6R,6aS)-6-(2-amino-4-methyl-7H-pyrrolo[2,3-d]pyrimidin-7-yl)-2,2-dimethyltetrahydro-4H-cyclopenta[d][1,3]dioxol-4-yl)(3,4-difluorophenyl)methanol (N-4)

Following a similar procedure to step 5 in Scheme A, N-3 was converted to N-4 (69 mg, 85%). LCMS [M+1] 431.15.

Step 5: Synthesis of (1R,2S,3R,5R)-3-(2-amino-4-methyl-7H-pyrrolo[2,3-d]pyrimidin-7-yl)-5-[(S)-(3,4-difluorophenyl)(hydroxy)methyl]cyclopentane-1,2-diol (N-5) and (1R,2S,3R,5R)-3-(2-amino-4-methyl-7H-pyrrolo[2,3-d]pyrimidin-7-yl)-5-[(R)-(3,4-difluorophenyl)(hydroxy)methyl]cyclopentane-1,2-diol (N-6)

Following a similar procedure as step 4 in Scheme K, N-4 was treated with TFA in water. N-5 (14.6 mg, 23%) and N-6 (6.6 mg, 11%) were isolated after subsequent workup and purification by chiral SFC.

N-5: LCMS [M+1] 390.85. $^1$H NMR (700 MHz, DMSO-d6) δ ppm 7.35-7.40 (m, 1H) 7.29-7.35 (m, 1H) 7.21 (br. s., 1H) 7.07 (d, J=3.74 Hz, 1H) 6.38 (d, J=3.52 Hz, 1H) 5.90 (s, 2H) 5.74 (d, J=4.40 Hz, 1H) 4.83 (d, J=6.60 Hz, 1H) 4.71-4.79 (m, 1H) 4.51-4.58 (m, 2H) 4.15-4.21 (m, 1H) 3.90 (br. s., 1H) 2.38 (s, 3H) 2.18 (d, J=7.92 Hz, 1H) 1.83-1.93 (m, 1H) 1.44 (d, J=10.34 Hz, 1H)

N-6: LCMS [M+1] 390.90. $^1$H NMR (700 MHz, DMSO-d6) δ ppm 7.29-7.36 (m, 2H) 7.16 (br. s., 1H) 7.12 (d, J=3.52 Hz, 1H) 6.40 (d, J=3.30 Hz, 1H) 5.89 (s, 2H) 5.76 (br. s., 1H) 4.86 (d, J=5.94 Hz, 1H) 4.76 (t, J=4.62 Hz, 1H) 4.73 (q, J=8.88 Hz, 1H) 4.68 (br. s., 1H) 4.08-4.12 (m, 1H) 3.83-3.86 (m, 1H) 2.39 (s, 3H) 2.16 (dt, J=8.53, 4.21 Hz, 1H) 1.76 (dt, J=12.98, 8.47 Hz, 1H) 1.57-1.64 (m, 1H)

Example 50 (Scheme O)—(1S,2R,3S,5R)-3-[2-amino-1-fluoro-1-(4-fluorophenyl)ethyl]-5-(4-methyl-7H-pyrrolo[2,3-d]pyrimidin-7-yl)cyclopentane-1,2-diol (O-5)

Example 51 (Scheme O)—(1S,2R,3R,5R)-3-[(1S)-2-amino-1-(4-fluorophenyl)ethyl]-5-(4-methyl-7H-pyrrolo[2,3-d]pyrimidin-7-yl)cyclopentane-1,2-diol (O-6)

Example 52 (Scheme O)—(1S,2R,3R,5R)-3-[(1R)-2-amino-1-(4-fluorophenyl)ethyl]-5-(4-methyl-7H-pyrrolo[2,3-d]pyrimidin-7-yl)cyclopentane-1,2-diol (O-7)

Scheme O

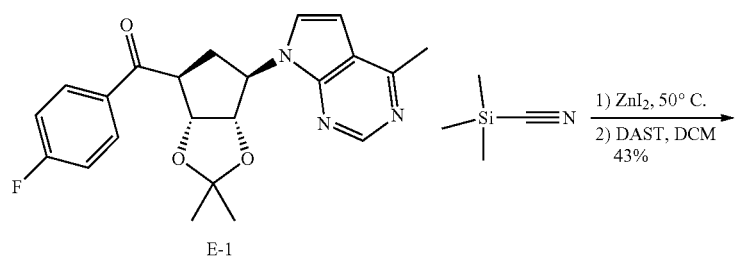

E-1

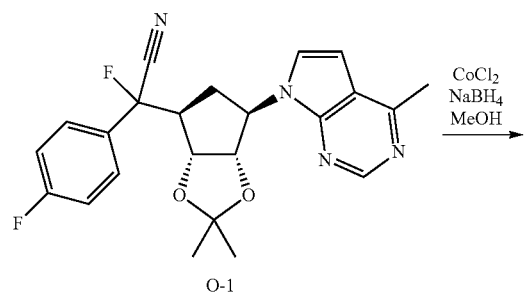

O-1

-continued

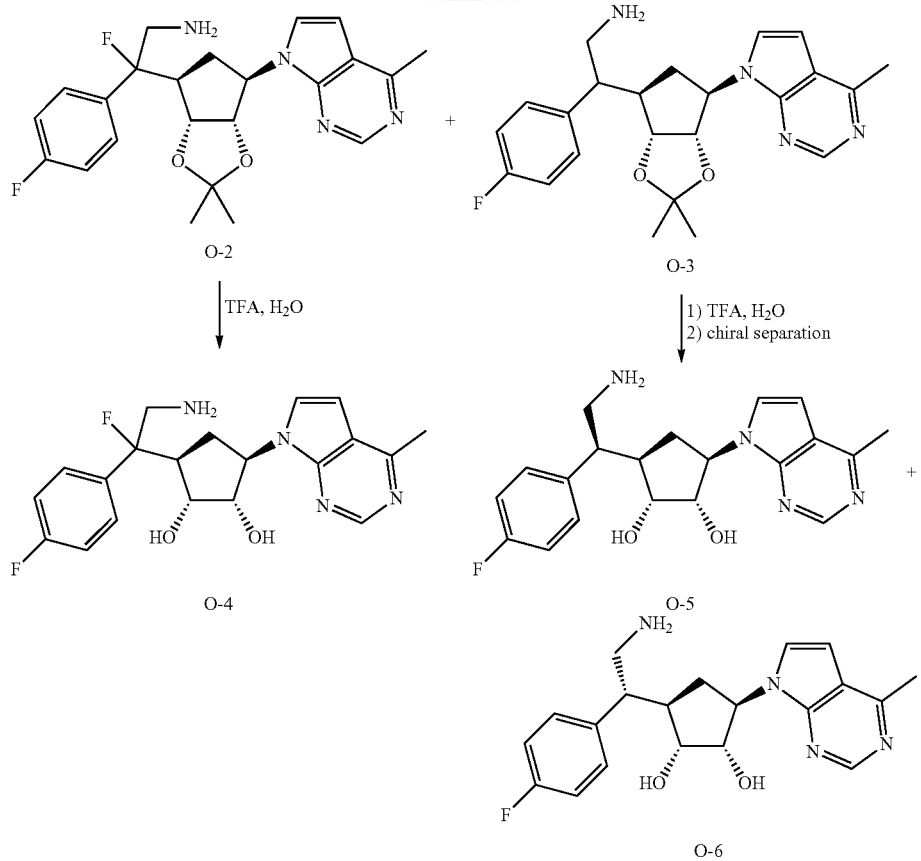

Step 1: Synthesis of 2-((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)-2-fluoro-2-(4-fluorophenyl)acetonitrile (O-1)

To a mixture of E-1 (175 mg, 0.443 mmol) and zinc(II) iodide (2.12 mg, 0.00664 mmol) in a sealable tube was added anhydrous 2 mL $CH_2Cl_2$, followed by trimethylsilyl cyanide (0.25 mL) under nitrogen. The reaction was sealed and heated at 50° C. for 2 days. The resulting mixture was cooled in an ice bath, DAST (78.5 mg, 0.487 mmol) was added dropwise, stirred at r.t. for 15 min. The reaction mixture was washed with $H_2O$, 0.5 N HCl, std. $NaHCO_3$, brine and concentrated. The product was purified by column chromatography with 50% EtOAc/heptane to give 80 mg of O-1 (43% yield) as a yellow oil. LCMS [M+1] 425.10.

Step 2: Synthesis of 2-((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)-2-fluoro-2-(4-fluorophenyl)ethan-1-amine (O-2) and 2-((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)-2-(4-fluorophenyl)ethan-1-amine (O-3)

O-1 (70 mg, 0.16 mmol) was dissolved in 0.5 mL MeOH. Cobalt (II) chloride hexahydrate (118 mg, 0.495 mmol) was added and the mixture was cooled in an ice bath. $NaBH_4$ (32.8 mg, 0.825 mmol) was added and the reaction stirred at 0° C. for 0.5 h. The reaction mixture was quenched by std. $NH_4Cl$, extracted with EtOAc, the organic layer was washed with brine, concentrated, purified by prep TLC plate with 5% MeOH/$CH_2Cl_2$ to give 20 mg of O-2 (28% yield) as a yellow oil, (LCMS [M+1] 429.10) and 22 mg of O-3 (32% yield) as a yellow oil. (LCMS [M+1] 411.20)

Step 3: Synthesis of (1S,2R,3S,5R)-3-[2-amino-1-fluoro-1-(4-fluorophenyl)ethyl]-5-(4-methyl-7H-pyrrolo[2,3-d]pyrimidin-7-yl)cyclopentane-1,2-diol (O-4)

Following a similar procedure as step 4 in Scheme K, O-2 was treated with TFA in water. O-4 (1.2 mg, 6.6%) was isolated after subsequent workup and purification by SFC.
LCMS [M+1] 388.90. $^1H$ NMR (400 MHz, METHANOL-d4) δ ppm 1.62-1.73 (m, 1H) 1.81 (s, 3H) 2.54-2.73 (m, 4H) 4.17 (br. s., 1H) 4.76-4.94 (m, 2H) 6.59 (d, J=3.42 Hz, 1H) 7.04 (t, J=8.68 Hz, 2H) 7.29-7.42 (m, 3H) 8.46 (s, 1H)

Step 4: Synthesis of (1S,2R,3R,5R)-3-[(1S)-2-amino-1(4-fluorophenyl)ethyl]-5-(4-methyl-7H-pyrrolo[2,3-d]pyrimidin-7-yl)cyclopentane-1,2-diol (O-5) and (1S,2R,3R,5R)-3-[(1R)-2-amino-1-(4-fluorophenyl)ethyl]-5-(4-methyl-7H-pyrrolo[2,3-d]pyrimidin-7-yl)cyclopentane-1,2-diol (O-6)

Following a similar procedure as step 4 in Scheme K, O-3 was treated with TFA in water. O-5 (5.4 mg, 27%) and O-6 (3.7 mg, 19%) were isolated after subsequent workup and purification by chiral SFC.

O-5: LCMS [M+1] 370.90. $^1$H NMR (400 MHz, METHANOL-d4) δ ppm 1.42-1.57 (m, 1H) 1.65-1.79 (m, 1H) 2.24 (br. s., 1H) 2.49-2.68 (m, 3H) 2.83 (br. s., 1H) 2.96-3.10 (m, 1H) 3.31 (d, J=13.20 Hz, 1H) 4.02 (t, J=5.81 Hz, 1H) 4.27 (t, J=6.79 Hz, 1H) 4.75 (br. s., 1H) 6.56 (d, J=3.18 Hz, 1H) 6.98 (t, J=8.38 Hz, 2H) 7.13-7.28 (m, 2H) 7.31 (d, J=2.93 Hz, 1H) 8.45 (s, 1H)

O-6: LCMS [M+1] 370.90. $^1$H NMR (400 MHz, METHANOL-d4) δ ppm 1.78 (d, J=9.29 Hz, 1H) 2.26-2.40 (m, 2H) 2.53-2.67 (m, 4H) 2.91-3.00 (m, 1H) 3.24-3.25 (m, 1H) 3.67-3.78 (m, 1H) 4.19-4.32 (m, 1H) 4.82-4.89 (m, 1H) 6.60 (d, J=3.67 Hz, 1H) 7.08 (t, J=8.68 Hz, 2H) 7.27-7.40 (m, 3H) 8.44-8.52 (m, 1H)

Example 53 (Scheme P)—(1S,2R,3R,5R)-3-((S)-(2-(aminomethyl)-4-chlorophenyl)(hydroxy)methyl)-5-(4-methyl-7H-pyrrolo[2,3-d]pyrimidin-7-yl)cyclopentane-1,2-diol (P-8)

Example 54 (Scheme P)—(1S,2R,3R,5R)-3-((R)-(2-(aminomethyl)-4-chlorophenyl)(hydroxy)methyl)-5-(4-methyl-7H-pyrrolo[2,3-d]pyrimidin-7-yl)cyclopentane-1,2-diol (P-9)

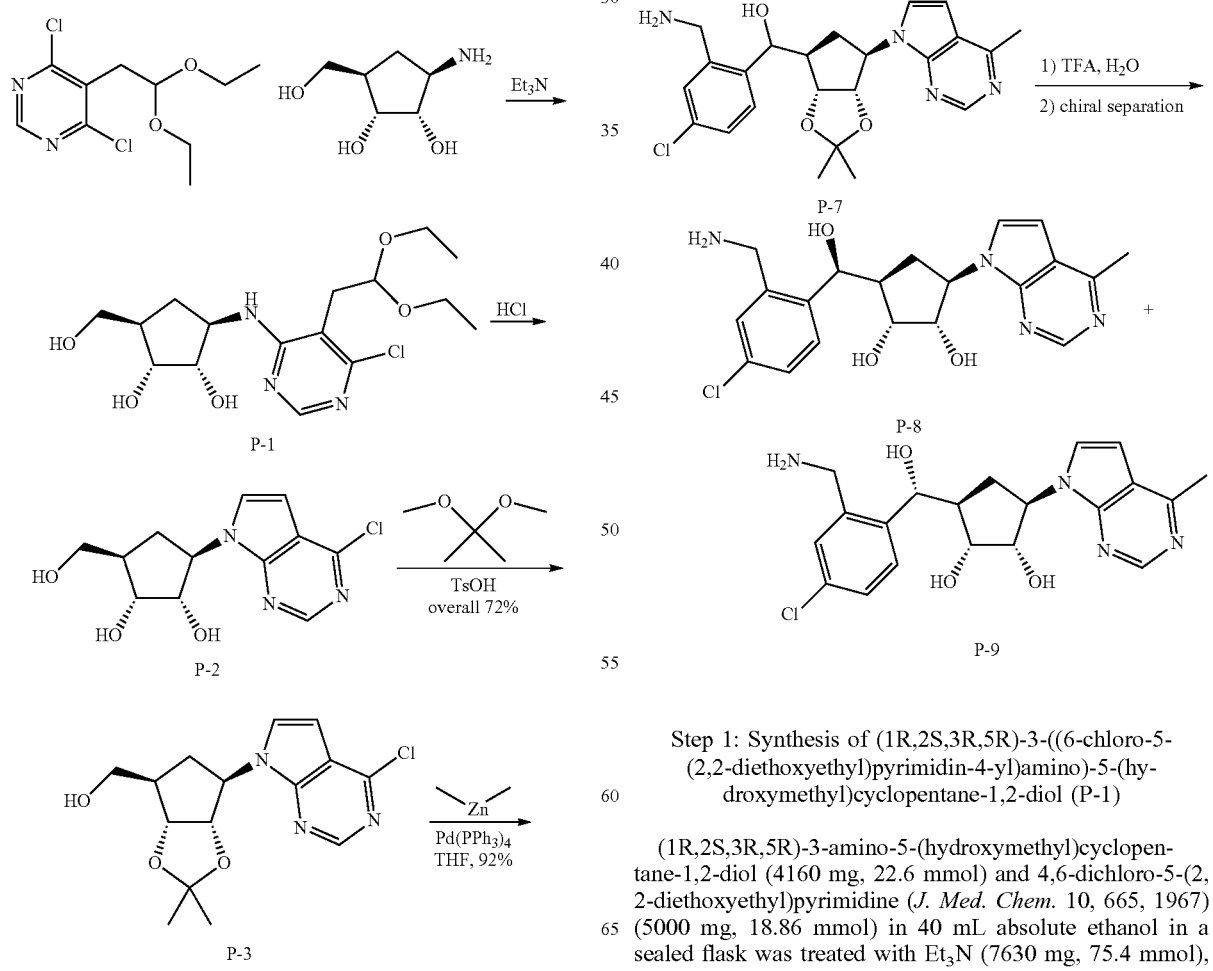

Step 1: Synthesis of (1R,2S,3R,5R)-3-((6-chloro-5-(2,2-diethoxyethyl)pyrimidin-4-yl)amino)-5-(hydroxymethyl)cyclopentane-1,2-diol (P-1)

(1R,2S,3R,5R)-3-amino-5-(hydroxymethyl)cyclopentane-1,2-diol (4160 mg, 22.6 mmol) and 4,6-dichloro-5-(2,2-diethoxyethyl)pyrimidine (*J. Med. Chem.* 10, 665, 1967) (5000 mg, 18.86 mmol) in 40 mL absolute ethanol in a sealed flask was treated with Et$_3$N (7630 mg, 75.4 mmol), heated at 80° C. for 18 hrs. The reaction mixture was cooled in an ice bath, the solid was filtered and the mother liquor was concentrated to give P-1 as a brown slurry which was used directly for next step. LCMS [M+1] 375.80.

Step 2: Synthesis of (1R,2S,3R,5R)-3-(4-chloro-7H-pyrrolo[2,3-d]pyrimidin-7-yl)-5-(hydroxymethyl)cyclopentane-1,2-diol (P-2)

The suspension of P-1 (7088 mg, 18.86 mmol) in 30 mL dioxane, was treated with 10 mL 1 N HCl, heated at 80° C. for 30 min. The reaction mixture was neutralized with NH$_4$OH to pH 7 and the volatiles were removed in vacuo to afford P-2 as a brown slurry which was used directly for next step. LCMS [M+1] 283.85.

Step 3: Synthesis of ((3aR,4R,6R,6aS)-6-(4-chloro-7H-pyrrolo[2,3-d]pyrimidin-7-yl)-2,2-dimethyltetrahydro-4H-cyclopenta[d][1,3]dioxol-4-yl)methanol (P-3)

P-2 (5350 mg, 18.86 mmol) and 2,2-dimethoxypropane (50 mL, c=0.38 M) was treated with p-toluenesulphonic acid monohydrate (7170 mg, 37.7 mmol) and the yellow brown suspension was adjusted to pH 4-5, stirred vigorously at r.t. for 15 min. The reaction mixture was diluted with 100 mL H$_2$O, neutralized with solid NaHCO$_3$. The volatiles were carefully removed in vacuo and the resulting brown aqueous solution was extracted with 20% isopropanol/DCM, the organic was combined, concentrated, purified by column chromatography with 50% EtOAc/DCM to 100% EtOAc to give 4.4 g of P-3 as a yellow gum (72% overall yield).
LCMS [M+1] 324.10. $^1$H NMR (400 MHz, CHLOROFORM-d) δ ppm 8.63 (s, 1H) 7.33 (d, J=3.55 Hz, 1H) 6.63 (d, J=3.67 Hz, 1H) 4.94-5.06 (m, 2H) 4.72 (dd, J=6.66, 4.46 Hz, 1H) 3.85-3.92 (m, 1H) 3.78-3.85 (m, 1H) 2.43-2.56 (m, 2H) 2.28-2.42 (m, 1H) 2.09 (br. s., 1H) 1.55-1.64 (m, 3H) 1.33 (s, 3H)

Step 4: Synthesis of ((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)methanol (P-4)

Following a similar procedure to step 5 in Scheme A, P-3 was converted to P-4 (930 mg, 88%).
LCMS [M+1] 304.15. $^1$H NMR (400 MHz, CHLOROFORM-d) δ ppm 1.25 (s, 3H) 1.53 (s, 3H) 2.21-2.34 (m, 2H) 2.38-2.47 (m, 2H) 2.75 (s, 3H) 3.75 (br. s., 1H) 3.80 (br. s., 1H) 4.65 (dd, J=6.66, 4.10 Hz, 1H) 4.86-5.00 (m, 2H) 6.57 (br. s., 1H) 7.25 (br. s., 1H) 8.71 (s, 1H)

Step 5: Synthesis of (3aR,4S,6R,6aS)-2,2-dimethyl-6-(4-methyl-7H-pyrrolo[2,3-d]pyrimidin-7-yl)tetrahydro-4H-cyclopenta[d][1,3]dioxole-4-carbaldehyde (P-5)

EDC HCl (3110 mg, 16.2 mmol) was added to a solution of P-4 (1230 mg, 4.055 mmol) in anhydrous dimethyl sulfoxide (22.5 mL, c=0.18 M). Pyridine (641 mg, 8.11 mmol) was added followed by TFA (462 mg, 4.05 mmol), stirred at r.t. for 1.5 h. The reaction mixture was diluted with H$_2$O, extracted with EtOAc twice, the combined organic was washed with H$_2$O 3 times, brine, dried over Na$_2$SO$_4$, filtered and concentrated to give P-5 (950 mg) as a brown oil (78% yield).
LCMS [M+1] 302.15. $^1$H NMR (400 MHz, CHLOROFORM-d) δ ppm 1.28 (s, 3H) 1.53 (s, 3H) 2.47-2.57 (m, 1H) 2.58-2.69 (m, 1H) 2.85 (s, 3H) 3.13 (td, J=8.68, 4.28 Hz, 1H) 4.94 (dd, J=6.60, 4.16 Hz, 1H) 5.04 (td, J=8.04, 4.34 Hz, 1H) 5.14 (dd, J=6.42, 4.22 Hz, 1H) 6.66 (d, J=3.42 Hz, 1H) 7.26 (br. s., 1H) 8.73 (s, 1H) 9.80 (s, 1H)

Step 6: Synthesis of 5-chloro-2-(((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)(hydroxy)methyl)benzonitrile (P-6)

To a solution of 5-chloro-2-iodobenzonitrile (1570 mg, 5.97 mmol) in dry THF (29.9 mL, c=0.2 M) at −78° C. was added isopropylmagnesium chloride (1080 mg, 7.47 mmol, 5.74 mL, 1.3 M). The resulting solution was stirred at −78° C. for 15 min, P-5 (900 mg, 2.99 mmol) in THF (5.0 mL) was added dropwise. The reaction mixture was transferred to an ice bath, allowed to warm up to r.t. and stirred overnight. The reaction was then quenched with std. NH$_4$Cl, extracted with EtOAc 3 times; the organic layers were combined, washed with brine, dried over Na$_2$SO$_4$, concentrated and purified by column chromatography with 5% MeOH/DCM to give P-6 (700 mg) as a yellow oil. LCMS [M+1] 439.10.

Step 7: Synthesis of (2-(aminomethyl)-4-chlorophenyl)((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)methanol (P-7)

To a solution of P-6 (200 mg, 0.456 mmol) in MeOH (5 mL, c=0.09 M) was added cobalt(II) chloride hexahydrate (545 mg, 2.28 mmol), and NaBH$_4$ (181 mg, 4.56 mmol). The reaction mixture was stirred at r.t. for 0.5 h, then quenched with std. NH$_4$Cl. The aqueous was saturated with solid NaCl and extracted with 20% isopropyl alcohol/DCM multiple times. The organic layers were concentrated and purified by preparative HPLC to give 50 mg of P-7 as a colorless oil (13% two steps). LCMS [M+1] 443.10.

Step 8: Synthesis of (1S,2R,3R,5R)-3-((S)-(2-(aminomethyl)-4-chlorophenyl)(hydroxy)methyl)-5-(4-methyl-7H-pyrrolo[2,3-d]pyrimidin-7-yl)cyclopentane-1,2-diol (P-8) and (1S,2R,3R,5R)-3-((R)-(2-(aminomethyl)-4-chlorophenyl)(hydroxy)methyl)-5-(4-methyl-7H-pyrrolo[2,3-d]pyrimidin-7-yl)cyclopentane-1,2-diol (P-9)

Following a similar procedure as step 4 in Scheme K, P-7 was treated with TFA in water. P-8 (5.5 mg, 12% yield) and P-9 (0.2 mg, 0.4% yield) were isolated after subsequent workup and purification by chiral SFC. LCMS [M+1] 403.00.

Example 55 (Scheme Q)—(1S,2R,3S,5R)-3-(2-(aminomethyl)-4-chlorobenzyl)-5-(4-methyl-7H-pyrrolo[2,3-d]pyrimidin-7-yl)cyclopentane-1,2-diol (Q-4)

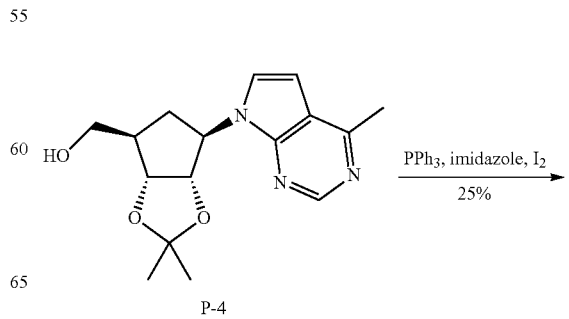

P-4

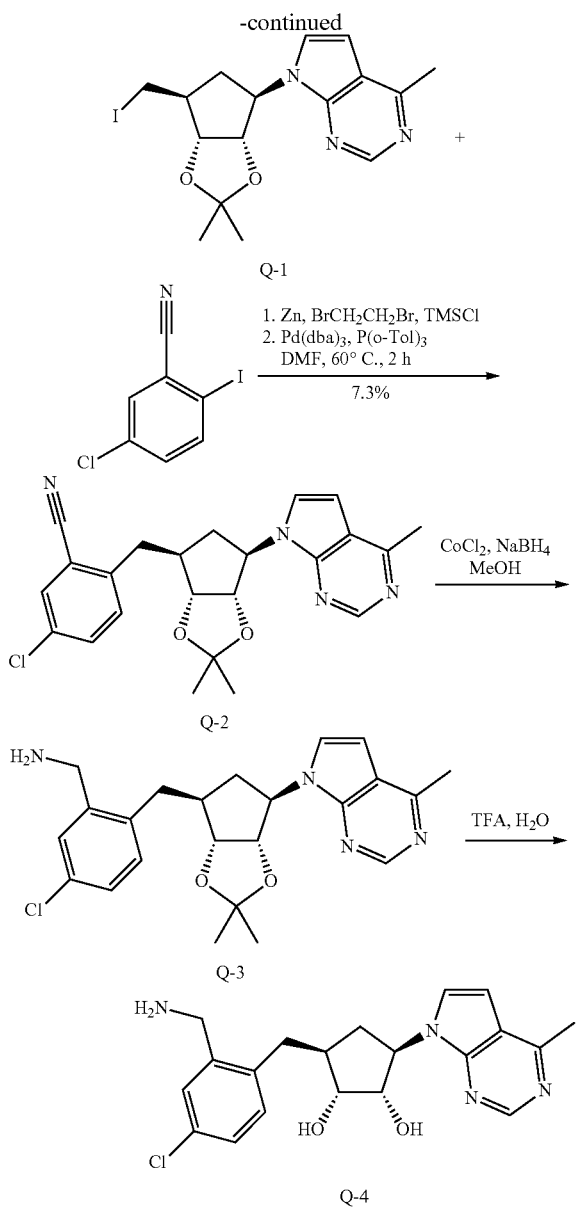

1H) 2.80 (s, 3H) 3.41 (dd, J=10.03, 6.72 Hz, 1H) 3.50 (dd, J=10.09, 4.83 Hz, 1H) 4.56 (t, J=6.11 Hz, 1H) 5.02-5.13 (m, 2H) 6.64 (d, J=3.55 Hz, 1H) 7.28 (d, J=3.55 Hz, 1H) 8.79 (s, 1H)

Step 2: Synthesis of 5-chloro-2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)methyl)benzonitrile (Q-2)

To a suspension of zinc (318 mg, 4.87 mmol) in dry degassed DMF (8.11 mL, c=0.1 M) was added 1,2-dibromoethane (33 mg, 0.17 mmol, 15 uL) under nitrogen. The mixture was heated with a heat gun for about 30 sec until the gas started to evolve from the solution indicating the activation of zinc. The mixture was allowed to cool to r.t. TMSCl (19 mg, 0.18 mmol, 23 uL) was added and the reaction was stirred at r.t. for 15 min followed by the addition of a solution of Q-1 (335 mg, 0.811 mmol) in dry degassed DMF (1 mL). The resulting mixture was heated at 60° C. for 5 min, then stirred at r.t. for 30 min. After allowing the zinc solids to settle, the reaction mixture was filtered through a syringe filter into a mixture of 5-chloro-2-iodobenzonitrile (214 mg, 0.812 mmol), Pd$_2$(dba)$_3$ (37.2 mg, 0.0406 mmol) and tri-o-tolylphosphine (49.4 mg, 0.162 mmol) in 1 mL dry degassed DMF. The reaction mixture was flushed with nitrogen, and stirred at 80° C. for 2 h. After cooling to r.t., the reaction mixture was partitioned between H$_2$O (30 mL) and EtOAc (30 mL). The organic phase was separated, washed with H$_2$O (3×30 mL) and brine (1×30 mL), dried over Na$_2$SO$_4$, concentrated and purified by column chromatography with 70% EtOAc/heptane to give 25 mg of Q-2 (7.3% yield).

LCMS [M+1] 423.10. $^1$H NMR (400 MHz, CHLOROFORM-d) δ ppm 1.29 (s, 3H) 1.56 (s, 3H) 2.21-2.38 (m, 2H) 2.48-2.60 (m, 1H) 2.78 (s, 3H) 2.95-3.04 (m, 1H) 3.24 (dd, J=14.18, 6.72 Hz, 1H) 4.62 (t, J=6.72 Hz, 1H) 4.92-5.01 (m, 1H) 5.04 (dd, J=7.09, 5.38 Hz, 1H) 6.61 (d, J=3.67 Hz, 1H) 7.25 (d, J=3.67 Hz, 1H) 7.36 (d, J=8.31 Hz, 1H) 7.52 (dd, J=8.44, 2.20 Hz, 1H) 7.60 (d, J=2.20 Hz, 1H) 8.76 (s, 1H)

Step 3: Synthesis of (5-chloro-2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)methyl)phenyl)methanamine (Q-3)

Following a similar procedure as step 7 in Scheme P, Q-2 was reduced to Q-3 as crude for the next step. LCMS [M+1] 427.10.

Step 4: Synthesis of (1S,2R,3S,5R)-3-(2-(aminomethyl)-4-chlorobenzyl)-5-(4-methyl-7H-pyrrolo[2,3-d]pyrimidin-7-yl)cyclopentane-1,2-diol (Q-4)

Following a similar procedure as step 4 in Scheme K, Q-3 was treated with TFA in water. Q-4 (9.5 mg, 35%) was isolated after subsequent workup and purification by chiral SFC.

Q-4: LCMS [M+1] 386.85. $^1$H NMR (700 MHz, DMSO-d6) δ ppm 1.48-1.56 (m, 1H) 1.97-2.04 (m, 1H) 2.11 (br. s., 1H) 2.53-2.60 (m, 5H) 2.91 (dd, J=14.09, 5.72 Hz, 1H) 3.68-3.78 (m, 2H) 4.29 (t, J=6.23 Hz, 1H) 4.84 (q, J=8.37 Hz, 1H) 6.63 (d, J=3.42 Hz, 1H) 7.09-7.17 (m, 2H) 7.41 (br. s., 1H) 7.62 (d, J=2.22 Hz, 1H) 8.53 (s, 1H)

Step 1: Synthesis of 7-((3aS,4R,6S,6aR)-6-(iodomethyl)-2,2-dimethyltetrahydro-4H-cyclopenta[d][1,3]dioxol-4-yl)-4-methyl-7H-pyrrolo[2,3-d]pyrimidine (Q-1)

The solution of triphenylphosphine (529 mg, 1.98 mmol) and imidazole (135 mg, 1.98 mmol) in methylene chloride (8.24 mL, c=0.2 M) was added I$_2$ (502 mg, 1.98 mmol) followed by dropwise addition of P-4 (500 mg, 1.65 mmol) in 2 mL methylene chloride. The resulting reaction mixture was stirred at r.t. overnight, and then diluted with water (20 mL), extracted with methylene chloride (3×20 mL). The combined organic layers were dried over Na$_2$SO$_4$, concentrated and purified by column chromatography with 60% EtOAc/heptane to give 280 mg of Q-1 as a yellow oil (25% yield).

LCMS [M+1] 414.00. $^1$H NMR (400 MHz, CHLOROFORM-d) δ ppm 1.33 (s, 3H) 1.60 (s, 3H) 2.26-2.37 (m, 1H) 2.40 (dd, J=11.55, 5.93 Hz, 1H) 2.59 (dt, J=12.29, 6.08 Hz,

Example 56 (Scheme R)—(1S,2R,3R,5R)-3-((S)-hydroxy(1,2,3,4-tetrahydroisoquinolin-8-yl)methyl)-5-(4-methyl-7H-pyrrolo[2,3-d]pyrimidin-7-yl)cyclopentane-1,2-diol (R-7)

Example 57 (Scheme R)—(1S,2R,3R,5R)-3-((R)-hydroxy(1,2,3,4-tetrahydroisoquinolin-8-yl)methyl)-5-(4-methyl-7H-pyrrolo[2,3-d]pyrimidin-7-yl)cyclopentane-1,2-diol (R-8)

Scheme R

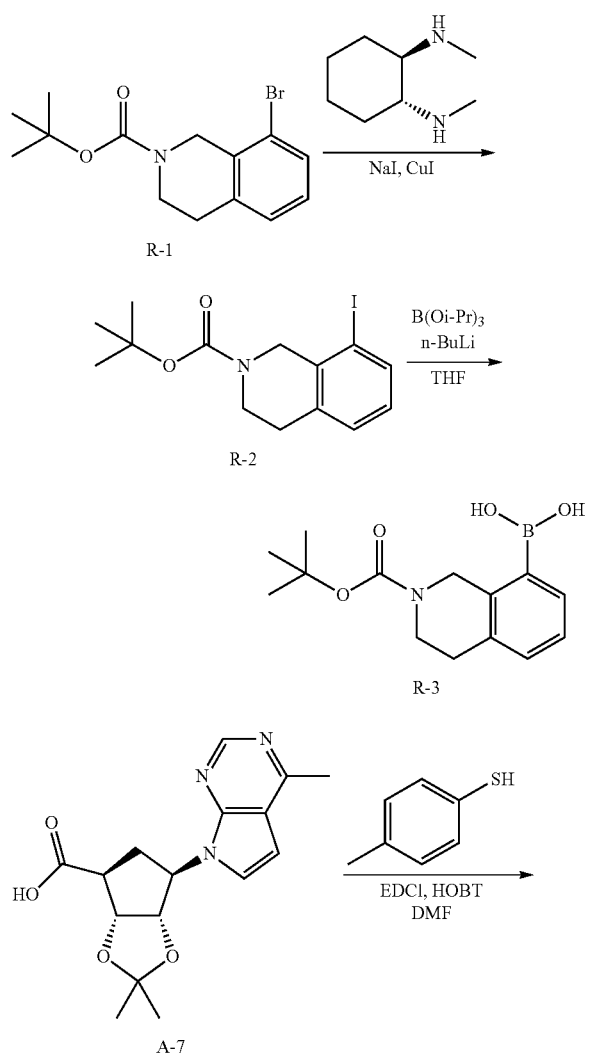

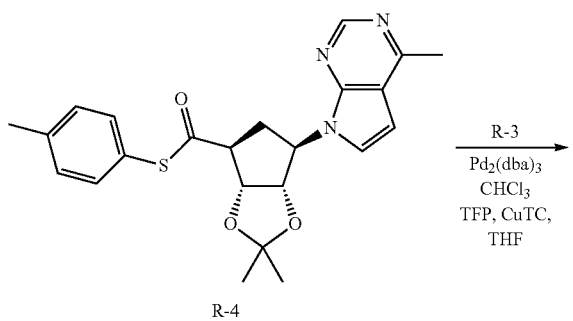

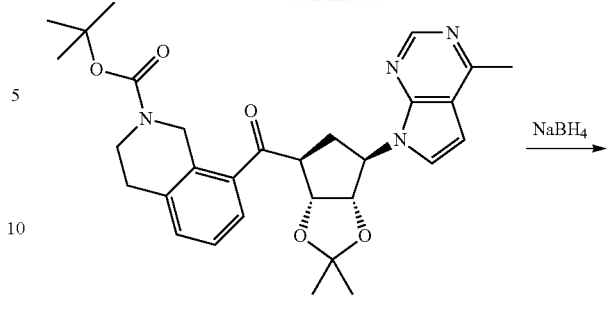

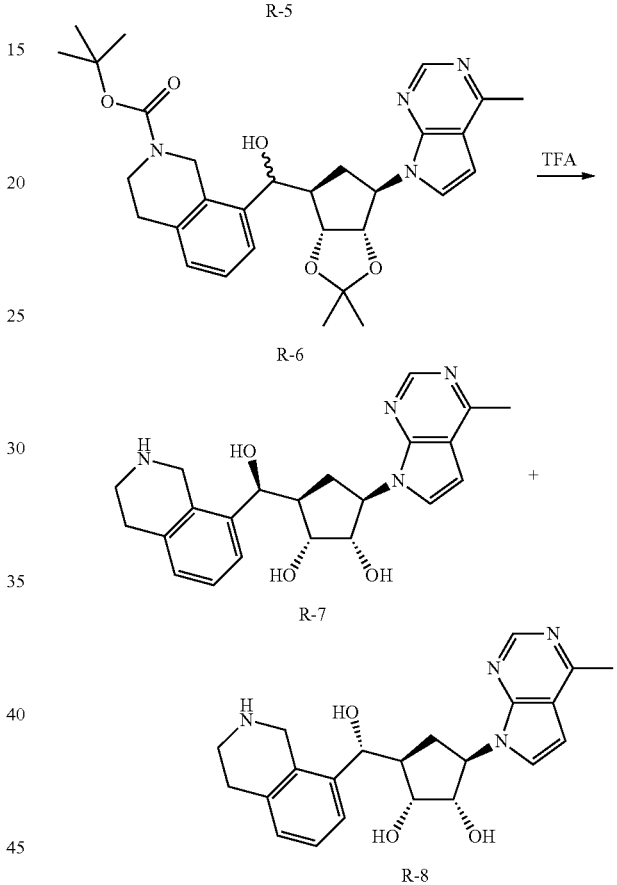

Step 1: Synthesis of tert-butyl 8-iodo-3,4-dihydroisoquinoline-2(1H)-carboxylate (R-2)

A mixture of tert-butyl 8-bromo-3,4-dihydroisoquinoline-2(1H)-carboxylate (R-1) (1100 mg, 3.52 mmol), NaI (4.76 g, 31.8 mmol), CuI (402 mg, 2.12 mmol) and trans-N,N-dimethylcyclohexane (602 mg, 4.22 mmol) in dioxane (20 mL) was purged with $N_2$ for 10 min. The resulting yellow suspension was stirred at 110° C. in a sealed tube for 48 hrs. The reaction was diluted with petroleum ether (50 mL) and filtered. The filtrate was concentrated in vacuo and residue was purified by silica gel chromatography eluted with EtOAC in petroleum ether from 0 to 20% to afford R-2 (1200 mg, 94.8%) as a light yellow gum. LCMS [M+1-tBu] 304; $^1$H NMR (400 MHz, CDCl$_3$) δ ppm 7.70 (d, J=7.8 Hz, 1H), 7.45-7.39 (m, 1H), 7.12 (d, J=7.5 Hz, 1H), 6.88 (s, 1H), 4.44 (br. s., 2H), 3.62 (t, J=5.5 Hz, 2H), 2.81 (d, J=4.8 Hz, 2H), 1.50 (s, 9H)

Step 2: Synthesis of (2-(tert-butoxycarbonyl)-1,2,3,4-tetrahydroisoquinolin-8-yl)boronic acid (R-3)

To a solution of R-2 (250 mg, 0.696 mmol) and triisopropyl borate (262 mg, 0.321 mmol) in dry THF (8 mL) was added 2.5 M n-BuLi (0.418 mL, 1.04 mmol) at −60° C. the mixture was stirred at −60 0° C. for 30 min. The mixture was poured into $NH_4Cl$ aq (15 mL) and extracted with EtOAc (10 mL×3). The extract was dried over $Na_2SO_4$ and concentrated in vacuo to afford crude. The crude was purified by silica gel chromatography eluted with MeOH in DCM from 0 to 10% to afford R-3 (180 mg, 93%) as a light yellow gum which was used in the next step directly.

Step 3: Synthesis of S-(p-tolyl)(3aR,4S,6R,6aS)-2,2-dimethyl-6-(4-methyl-7H-pyrrolo[2,3-d]pyrimidin-7-yl)tetrahydro-4H-cyclopenta[d][1,3]dioxole-4-carbothioate (R-4)

To compound A-7 (270 mg, 0.851 mmol) in THF was added 4-methylbenzenethiol (211 mg, 1.7 mmol), DIPEA (440 mg, 3.4 mmol) and T3P (1.08 g, 1.7 mmol) at rt (15° C.). The mixture was stirred at rt 5-10° C. for 2 days. The mixture was poured into $NaHCO_3$ aq (20 mL) and extracted with EtOAc (10 mL×2). The extract was washed with brine (15 mL) and concentrated in vacuo, then purified by silica gel chromatography eluted with EtOAc in petroleum ether from 0 to 100% to afford R-4 (320 mg, 89%) as a white solid. LCMS [M+1] 424

Step 4: Synthesis of tert-butyl 8-((3aR,4S,6R,6aS)-2,2-dimethyl-6-(4-methyl-7H-pyrrolo[2,3-d]pyrimidin-7-yl)tetrahydro-4H-cyclopenta[d][1,3]dioxole-4-carbonyl)-3,4-dihydroisoquinoline-2(1H)-carboxylate (R-5)

A mixture of R-4 (125 mg, 0.3 mmol) and R-3 (180 mg, 0.32 mmol), CuTC (90 mg, 0.47 mmol), $Pd_2(dba)_3$.$CHCl_3$ (31 mg, 0.03 mmol) and TFP (20.6 mg, 0.0886 mmol) in dry THF (5 mL) was degassed with $N_2$ four times. The mixture was stirred at 50° C. in a sealed tube for 16 hours. The mixture was diluted with EtOAc (10 mL) and filtered. The filtrate was concentrated in vacuo to dryness. The residue was purified by silica gel chromatography eluted with EtOAc in petroleum ether from 0 to 100% to afford R-5 (70 mg, 40%) as a white solid. LCMS [M+1] 533

Step 5: Synthesis of tert-butyl 8-(((3aR,4R,6R,6aS)-2,2-dimethyl-6-(4-methyl-7H-pyrrolo[2,3-d]pyrimidin-7-yl)tetrahydro-4H-cyclopenta[d][1,3]dioxol-4-yl)(hydroxy)methyl)-3,4-dihydroisoquinoline-2(1H)-carboxylate (R-6)

To a solution of R-5 (70 mg, 0.131 mmol) in MeOH (2 mL) was added $NaBH_4$ (86.9 mg, 2.30 mmol) at rt 15° C. The mixture was stirred at rt 15° C. for 30 min. The mixture was diluted with water (10 mL) and extracted with EtOAc (10 mL×3). The extract was washed with brine (10 mL), dried over $Na_2SO_4$ and concentrated in vacuo to afford crude R-6 (60 mg, 85%) as a light yellow solid.

Step 6: Synthesis of (1S,2R,3R,5R)-3-((S)-hydroxy(1,2,3,4-tetrahydroisoquinolin-8-yl)methyl)-5-(4-methyl-7H-pyrrolo[2,3-d]pyrimidin-7-yl)cyclopentane-1,2-diol (R-7) and (1S,2R,3R,5R)-3-((R)-hydroxy(1,2,3,4-tetrahydroisoquinolin-8-yl)methyl)-5-(4-methyl-7H-pyrrolo[2,3-d]pyrimidin-7-yl)cyclopentane-1,2-diol (R-8)

To compound R-6 (60 mg, 0.1 mmol) was added TFA/$H_2O$ (1 mL/1 mL, cooled to 0° C. previously). The mixture was stirred at rt (15° C.) for 3 hrs. The mixture was concentrated in vacuo to afford crude which was purified by SFC. After SFC, the products were re-purified by prep TLC to obtain R-7 (4.5 mg, 13%) and R-8 (3.5 mg, 9%) as white solids.

R-7: LCMS [M+1] 395; $^1$H NMR (400 MHz, MeOD-$d_4$) δ ppm 8.63 (s, 1H), 7.59 (d, J=3.8 Hz, 1H), 7.42 (d, J=7.5 Hz, 1H), 7.21 (t, J=7.5 Hz, 1H), 7.06 (d, J=7.3 Hz, 1H), 6.73 (d, J=3.8 Hz, 1H), 5.09-5.01 (m, 1H), 4.81 (d, J=7.0 Hz, 1H), 4.64 (dd, J=5.3, 9.5 Hz, 1H), 4.31 (dd, J=2.0, 5.5 Hz, 1H), 4.29-4.16 (m, 2H), 3.21-3.06 (m, 2H), 2.92 (d, J=4.0 Hz, 2H), 2.72 (s, 3H), 2.56-2.47 (m, 1H), 2.22 (td, J=8.8, 13.1 Hz, 1H), 1.83 (ddd, J=8.3, 10.7, 13.1 Hz, 1H)

R-8: LCMS [M+1] 395; $^1$H NMR (400 MHz, MeOD-$d_4$) δ ppm 8.63 (s, 1H), 7.72 (d, J=3.8 Hz, 1H), 7.42 (d, J=8.0 Hz, 1H), 7.23-7.17 (m, 1H), 7.07 (d, J=7.5 Hz, 1H), 6.77 (d, J=3.8 Hz, 1H), 5.12-5.04 (m, 2H), 4.48-4.42 (m, 1H), 4.30-4.15 (m, 2H), 4.14-4.10 (m, 1H), 3.24-3.18 (m, 2H), 3.00-2.94 (m, 2H), 2.74 (s, 3H), 2.45-2.36 (m, 1H), 2.20-2.14 (m, 1H) 2.09-1.99 (m, 1H)

Example 58 (Scheme S)—(1S,2R,3S,5R)-3-(4-fluorobenzyl)-5-(4-methyl-7H-pyrrolo[2,3-d]pyrimidin-7-yl)cyclopentane-1,2-diol (S-1)

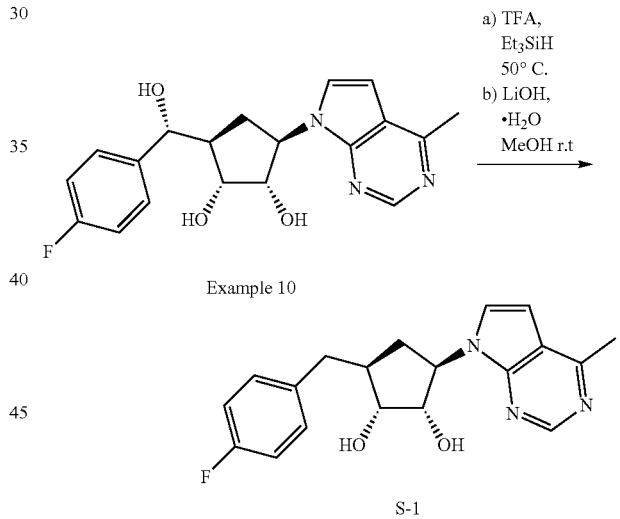

A mixture of (1S,2R,3R,5R)-3-((R)-(4-fluorophenyl)(hydroxy)methyl)-5-(4-methyl-7H-pyrrolo[2,3-d]pyrimidin-7-yl)cyclopentane-1,2-diol (Example 10) (30 mg, 0.084 mmol), trifluoroacetic acid (302 ul) and triethylsilane (268 ul, 1.68 mmol) was heated to 50° C. for 2 hours. The reaction mixture was concentrate to an oil then lithiumhydroxide monohydrate (20 mg, 0.48 mmol) and methanol (1 ml) were added and stirred at r.t. for 45 min. The reaction mixture was concentrated to remove methanol then partitioned between water and EtOAc. The EtOAc layer was washed with brine, dried with $Na_2SO_4$, filtered and concentrated to give S-1 as an oil in 52% yield.

LCMS-APCI(+): MH+=342, $^1$H NMR (700 MHz, DMSO-d6) δ ppm 8.58 (s, 1H), 7.64 (d, J=3.5 Hz, 1H), 7.25 (dd, J=5.9, 8.1 Hz, 2H), 7.08 (t, J=8.8 Hz, 2H), 6.68 (d, J=3.5 Hz, 1H), 4.98-4.84 (m, 2H), 4.77 (d, J=4.4 Hz, 1H), 4.44-4.23 (m, 1H), 3.82-3.75 (m, 1H), 2.92 (dd, J=6.6, 13.6 Hz, 1H), 2.68-2.57 (m, 4H), 2.26-2.12 (m, 1H), 2.06 (td, J=8.3, 13.0 Hz, 1H), 1.60-1.41 (m, 1H)

Example 59 (Scheme T)—(+/−)-(1S,2S,3S,5R)-3-methoxy-5-(4-methyl-7H-pyrrolo[2,3-d]pyrimidin-7-yl)cyclopentane-1,2-diol (T-5)

Example 60 (Scheme T)—(1S,2S,3S,5R)-3-methoxy-5-(4-methyl-7H-pyrrolo[2,3-d]pyrimidin-7-yl)cyclopentane-1,2-diol (T-6)

Example 61 (Scheme T)—(1R,2R,3R,5S)-3-methoxy-5-(4-methyl-7H-pyrrolo[2,3-d]pyrimidin-7-yl)cyclopentane-1,2-diol (T-7)

Scheme T

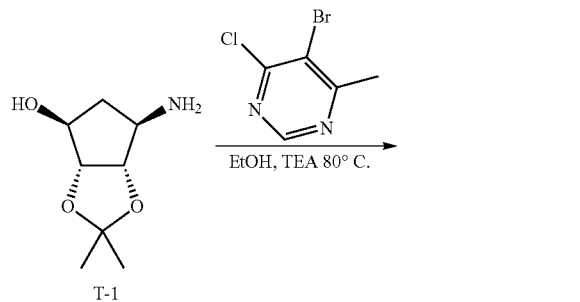

T-1

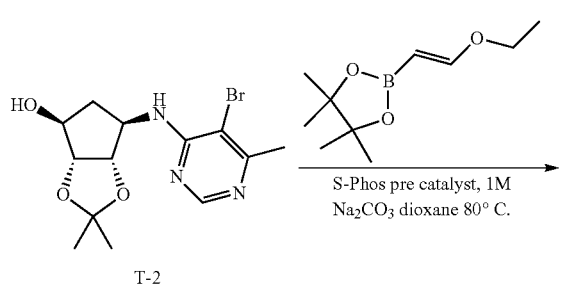

T-2

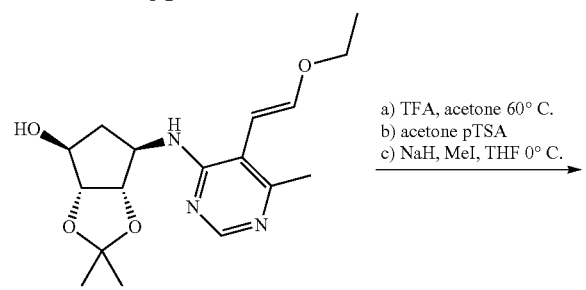

T-3

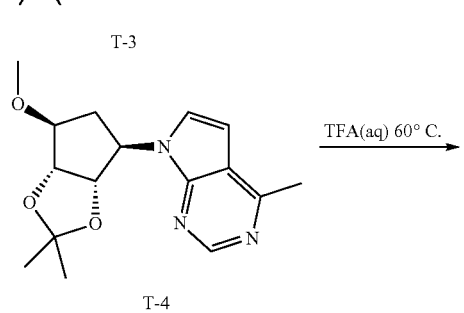

T-4

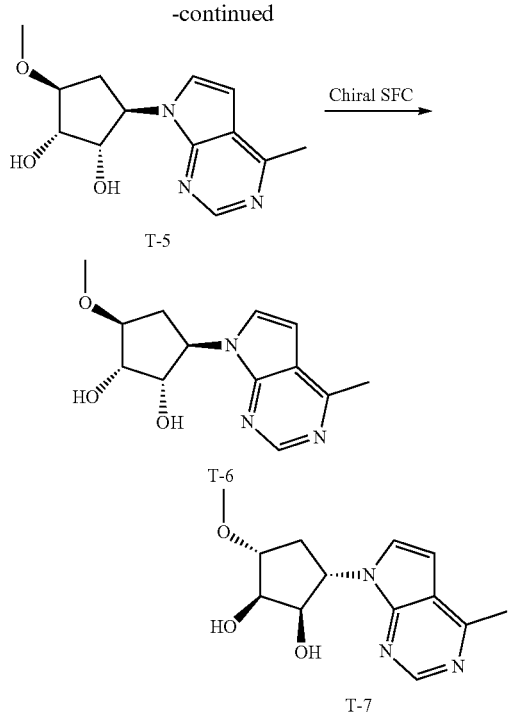

Step 1: (+/−)-(3aR,4S,6R,6aS)-6-((5-bromo-6-methylpyrimidin-4-yl)amino)-2,2-dimethyltetrahydro-4H-cyclopenta[d][1,3]dioxol-4-ol. (T-2)

A mixture of (+/−)-(3aR,4S,6R,6aS)-6-amino-2,2-dimethyltetrahydro-4H-cyclopenta[d][1,3]dioxol-4-ol (T-1) (786 mg, 4.54 mmol), 5-bromo-4-chloro-6-methylpyrimidine (1.04 g, 4.99 mmol) and trimethylamine (0.822 ml, 5.9 mmol) in ethanol (9.0 ml, 0.5 M) was heated to 80° C. for 20 hours. The crude reaction mixture was concentrated to a solid then purified by silica gel chromatography with a gradient of 0% to 100% EtOAc in heptane to give T-2 as white solid, 1.35 g (87% yield).

LCMS-ESI(+): MH+=344/346, $^1$H NMR (400 MHz, METHANOL-d4) δ ppm 8.29 (s, 1H), 4.60 (d, J=6.4 Hz, 1H), 4.56-4.52 (m, 1H), 4.51-4.47 (m, 1H), 4.22 (d, J=3.9 Hz, 1H), 2.33-2.23 (m, 1H), 1.76 (d, J=14.2 Hz, 1H), 1.41 (s, 3H), 1.27 (s, 3H).

Step 2: Synthesis of (+/−)-(3aR,4S,6R,6aS)-6-((5-((E)-2-ethoxyvinyl)-6-methylpyrimidin-4-yl)amino)-2,2-dimethyltetrahydro-4H-cyclopenta[d][1,3]dioxol-4-ol. (T-3)

To a solution of T-2 (2.06 g, 5.98 mmol) and (E)-2-(2-ethoxyvinyl)-4,4,5,5-tetramethyl-1,3,2-dioxaborolane (1.19 g, 5.98 mmol) in dioxane (19.9 ml, 0.3 M) was vacuum flushed with nitrogen then 2N sodium carbonate (aq) (8.98 ml) was added followed by S-Phos pre-catalyst (136 mg, 0.180 mmol). The resulting mixture was heated to 80° C. for 23 hours. The reaction mixture was cooled to r.t. then diluted with EtOAc and water. The organic layer was washed with brine, dried with Na$_2$SO$_4$, filtered and concentrated to an oil then purified by silica gel chromatography eluting with a gradient of 0% to 100% EtOAc in heptane to give T-3 as a white solid, 1.21 g (60% yield).

LCMS-ESI(+): MH+=336, $^1$H NMR (400 MHz, DMSO-d6) δ ppm 8.23 (s, 1H), 6.66 (d, J=13.2 Hz, 1H), 6.38 (d, J=8.6 Hz, 1H), 5.63 (d, J=2.4 Hz, 1H), 5.32 (d, J=13.2 Hz, 1H), 4.50-4.33 (m, 3H), 4.07 (br. s., 1H), 3.87 (q, J=6.9 Hz, 2H), 2.24 (s, 3H), 2.12 (td, J=5.2, 13.6 Hz, 1H), 1.62 (d, J=13.9 Hz, 1H), 1.34 (s, 3H), 1.25 (t, J=7.0 Hz, 3H), 1.18 (s, 3H)

Step 3: Synthesis of (+/−)-7-((3aS,4R,6S,6aR)-6-methoxy-2,2-dimethyltetrahydro-4H-cyclopenta[d][1,3]dioxol-4-yl)-4-methyl-7H-pyrrolo[2,3-d]pyrimidine. (T-4)

A mixture of (+/−)-(3aR,4S,6R,6aS)-6-((5-((E)-2-ethoxyvinyl)-6-methylpyrimidin-4-yl)amino)-2,2-dimethyl-tetrahydro-4H-cyclopenta[d][1,3]dioxol-4-ol (111 mg, 0.331 mmol) and trifluoroacetic acid (127 ul, 1.65 mmol) in acetone (3.31 ml, 0.1 M) was heated to 60° C. for 43 hours. The reaction mixture was concentrated to an oil then azeotroped with toluene. The crude oil was dissolved in acetone (3.31 ml) then DMP (81 ul, 0.662 mmol) and PTSA (3.1 mg, 0.016 mmol) was added. The mixture was stirred at r.t. for 48 hours. The reaction mixture was concentrated to an oil then re-dissolved in EtOAc. The EtOAc layer was washed with saturated NaHCO$_3$(aq), brine, dried with Na$_2$SO$_4$, filtered and concentrated to an oil. The crude mixture was purified by silica gel chromatography eluting a gradient of 0% to 100% EtOAc in heptane to give (3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-ol as a white solid, 76 mg (79% yield, 80% pure).

To a suspension of (3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-ol (76 mg, 80% pure) in 2-methyl-tetrahydrofuran (1 ml) at r.t. was added 60% sodium hydride (26 mg). After 15 minutes methyl iodide (200 ul) was added. After 1 hour more methyl iodide (200 ul) was added and the mixture was stirred at r.t. for 3 more hours. The reaction mixture was quenched with saturated ammonium chloride (aq) then extracted with EtOAc. The EtOAc layer was washed with brine, dried with Na$_2$SO$_4$, filtered and concentrated to an oil. The crude oil was purified by silica gel chromatography eluting with a gradient of 0% to 100% EtOAc in heptane to give (+/−)-7-((3aS,4R,6S,6aR)-6-methoxy-2,2-dimethyltetrahydro-4H-cyclopenta[d][1,3]dioxol-4-yl)-4-methyl-7H-pyrrolo[2,3-d]pyrimidine as a colorless oil, 39 mg (39% yield).

LCMS-ESI(+): MH+=304, $^1$H NMR (400 MHz, CHLOROFORM-d) δ ppm 8.77 (s, 1H), 7.43 (d, J=3.7 Hz, 1H), 6.53 (d, J=3.7 Hz, 1H), 5.30 (ddd, J=2.6, 5.3, 7.8 Hz, 1H), 4.84 (dd, J=2.1, 6.2 Hz, 1H), 4.71 (d, J=6.4 Hz, 1H), 3.94 (t, J=4.2 Hz, 1H), 3.41 (s, 3H), 2.80-2.65 (m, 4H), 2.24 (td, J=4.6, 14.5 Hz, 1H), 1.54 (s, 3H), 1.30 (s, 3H).

Step 4: Synthesis of (+/−)-(1S,2S,3S,5R)-3-methoxy-5-(4-methyl-7H-pyrrolo[2,3-d]pyrimidin-7-yl)cyclopentane-1,2-diol (T-5), (1S,2S,3S,5R)-3-methoxy-5-(4-methyl-7H-pyrrolo[2,3-d]pyrimidin-7-yl)cyclopentane-1,2-diol (T-6) and (1R,2R,3R,5S)-3-methoxy-5-(4-methyl-7H-pyrrolo[2,3-d]pyrimidin-7-yl)cyclopentane-1,2-diol (T-7)

A mixture of T-4 (39 mg, 0.13 mmol) and 50% aqueous TFA (800 ul) was heated to 60° C. for 2 hours. The reaction mixture was concentrated to an oil then purified by SFC (3HOP column) to give (+/−)-(1S,2S,3S,5R)-3-methoxy-5-(4-methyl-7H-pyrrolo[2,3-d]pyrimidin-7-yl)cyclopentane-1,2-diol (T-5) as a white solid, 25 mg (75% yield).

T-5: LCMS-APCI(+): MH+=264, $^1$H NMR (400 MHz, CHLOROFORM-d) δ ppm 8.61 (s, 1H), 7.31 (d, J=3.7 Hz, 1H), 6.59 (d, J=3.4 Hz, 1H), 4.95 (q, J=8.6 Hz, 1H), 4.54-4.39 (m, 1H), 4.23 (d, J=4.9 Hz, 1H), 3.87 (t, J=5.4 Hz, 1H), 3.47 (s, 3H), 2.98-2.81 (m, 1H), 2.71 (s, 3H), 2.09 (ddd, J=5.1, 9.0, 13.8 Hz, 1H).

T-5 was resolved by chiral SFC (Lux Cellulose-4 4.6×100 mm 3u column, 30% MeOH/DEA @ 120 bar, 4 mL/min) to give (1S,2S,3S,5R)-3-methoxy-5-(4-methyl-7H-pyrrolo[2,3-d]pyrimidin-7-yl)cyclopentane-1,2-diol (T-6) as a white solid, 6 mg (19% yield).

T-6: LCMS-APCI(+): MH+=264, $^1$H NMR (700 MHz, DMSO-d6) δ ppm 8.61 (s, 1H), 7.60 (d, J=3.5 Hz, 1H), 6.70 (d, J=3.5 Hz, 1H), 5.11-4.83 (m, 3H), 4.40-4.26 (m, 1H), 3.91 (br. s., 1H), 3.61 (t, J=4.8 Hz, 1H), 3.31 (s, 3H), 2.63 (s, 3H), 2.56 (td, J=8.0, 14.0 Hz, 1H), 1.77 (ddd, J=4.8, 9.1, 13.8 Hz, 1H)

and (1R,2R,3R,5S)-3-methoxy-5-(4-methyl-7H-pyrrolo[2,3-d]pyrimidin-7-yl)cyclopentane-1,2-diol (T-7) as a white solid, 6 mg (19% yield).

T-7: LCMS-APCI(+): MH+=264, 1H NMR (700 MHz, DMSO-d6) δ ppm 8.61 (s, 1H), 7.60 (d, J=3.5 Hz, 1H), 6.70 (d, J=3.5 Hz, 1H), 5.07-4.92 (m, 3H), 4.38-4.25 (m, 1H), 3.91 (br. s., 1H), 3.66-3.52 (m, 1H), 3.31 (s, 3H), 2.63 (s, 3H), 2.56 (td, J=8.1, 13.8 Hz, 1H), 1.76 (ddd, J=4.6, 8.9, 13.8 Hz, 1H)

Example 62 (Scheme U)—(1S,2S,3S,5R)-3-(2-(aminomethyl)phenoxy)-5-(4-methyl-7H-pyrrolo[2,3-d]pyrimidin-7-yl)cyclopentane-1,2-diol (U-6)

Example 63 (Scheme U)—(1R,2R,3R,5S)-3-(2-(aminomethyl)phenoxy)-5-(4-methyl-7H-pyrrolo[2,3-d]pyrimidin-7-yl)cyclopentane-1,2-diol (U-7)

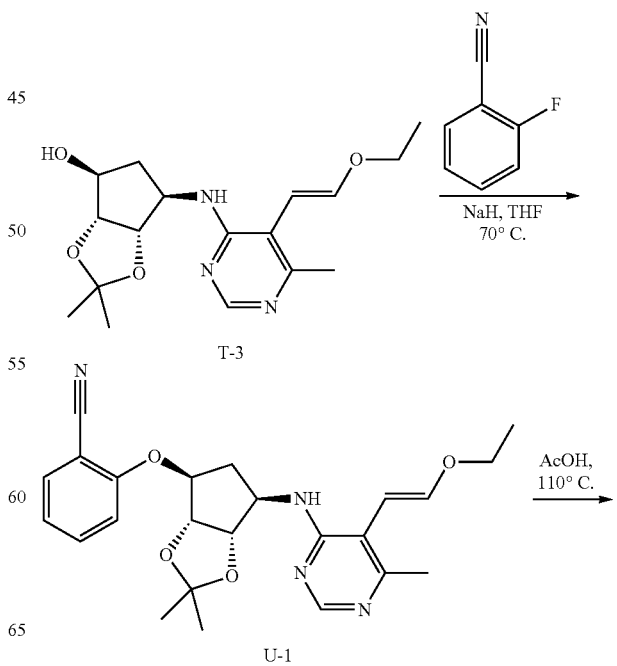

Scheme U

-continued

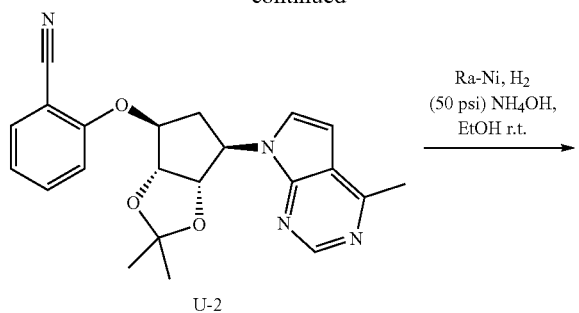

U-2

Ra-Ni, H₂
(50 psi) NH₄OH,
EtOH r.t.
→

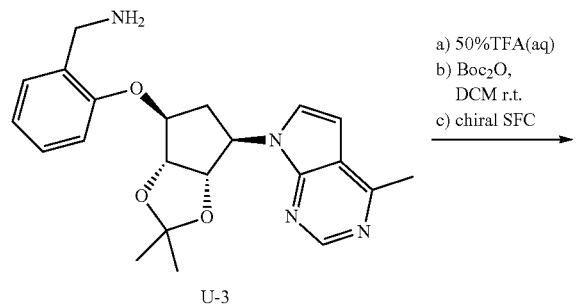

U-3 a) 50%TFA(aq)
b) Boc₂O,
   DCM r.t.
c) chiral SFC
→

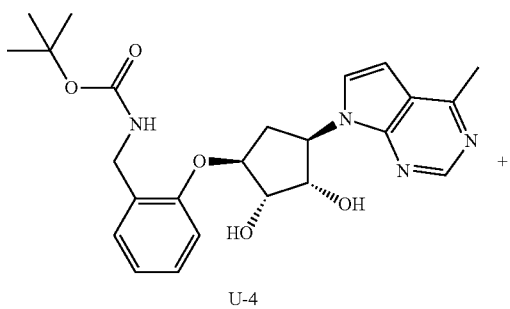

U-4

+

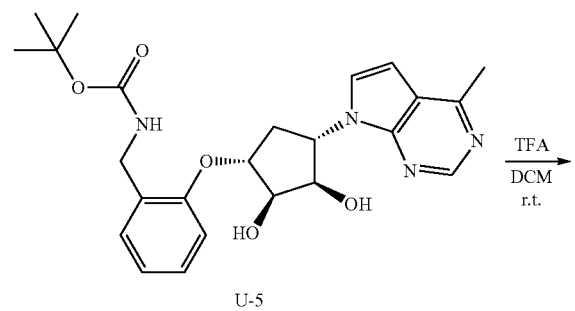

U-5

TFA
DCM
r.t.
→

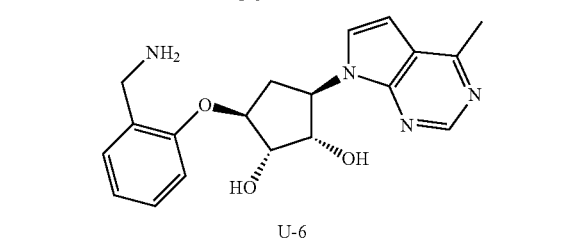

U-6

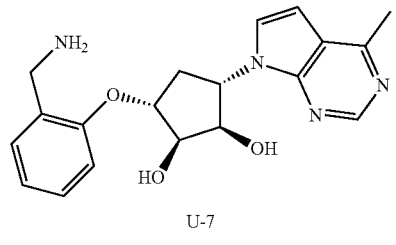

U-7

Step 1: Synthesis of 2-(((3aR,4S,6R,6aS)-6-((5-((E)-2-ethoxyvinyl)-6-methylpyrimidin-4-yl)amino)-2,2-dimethyltetrahydro-4H-cyclopenta[d][1,3]dioxol-4-yl)oxy)benzonitrile. (U-1)

To a mixture of T-3 (181 mg, 0.54 mmol) and 2-fluorobenzonitrile (57.4 ul, 65.4 mg, 0.54 mmol) in THF (1.8 ml, 0.3 M) at r.t. was added 60% sodium hydride (45.3 mg, 1.13 mmol). After stirring for 5 minutes the reaction mixture was heated to 70° C. for 6 hours. The reaction mixture was cooled to r.t. then quenched with saturated NH₄Cl(aq), diluted with water and extracted with EtOAc. The EtOAc layer was washed with brine, dried with MgSO4, filtered then concentrated to an oil. The crude oil was purified by silica gel chromatography eluting with 0-100% EtOAc-Heptane to give U-1 as an amber oil, 210 mg (89% yield).

LCMS-ESI(+): MH+=437, ¹H NMR (400 MHz, CHLOROFORM-d) δ ppm 8.48 (s, 1H), 7.68-7.49 (m, 2H), 7.19-6.98 (m, 2H), 6.47 (d, J=13.2 Hz, 1H), 5.45 (d, J=7.6 Hz, 1H), 5.41 (d, J=13.2 Hz, 1H), 4.82-4.69 (m, 4H), 3.86 (q, J=6.8 Hz, 2H), 2.70 (td, J=6.1, 15.0 Hz, 1H), 2.35 (s, 3H), 2.13 (d, J=15.2 Hz, 1H), 1.51 (s, 3H), 1.32 (s, 3H), 1.26 (t, J=7.0 Hz, 4H).

Step 2: 2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)benzonitrile. (U-2)

A solution of U-1 (210 mg, 0.481 mmol in acetic acid (4.81 ml, 0.1 M) was heated to 110° C. for 19 hours. The reaction mixture was concentrated to an oil then purified by silica gel chromatography eluting with 0-100% EtOAc-Heptane to give U-2 as a dark amber glass, 166 mg (88% yield).

LCMS-ESI(+): MH+=391, ¹H NMR (400 MHz, CHLOROFORM-d) δ ppm 8.79 (s, 1H), 7.69 (d, J=3.4 Hz, 1H), 7.65-7.51 (m, 2H), 7.13 (d, J=8.6 Hz, 1H), 7.07 (t, J=7.6 Hz, 1H), 6.66 (d, J=3.7 Hz, 1H), 5.48 (dd, J=3.2, 6.8 Hz, 1H), 5.01 (d, J=4.6 Hz, 1H), 4.95 (dd, J=2.7, 6.1 Hz, 1H), 4.86 (d, J=5.9 Hz, 1H), 3.06 (td, J=7.6, 14.7 Hz, 1H), 2.74 (s, 3H), 2.57 (d, J=14.9 Hz, 1H), 1.62 (s, 4H), 1.34 (s, 4H).

Step 3: Synthesis of (2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)phenyl)methanamine (U-3)

A mixture of U-2 (139 mg, 0.356 mmol) in ethanol (7.12 ml, 0.05 M) was added 28% NH₄OH (3 ml) and Raney Nickel (70 mg, 1.2 mmol). The mixture was hydrogenated at 50 psi in a stainless steel bomb for 24 hours. The reaction mixture was filtered through celite then the filtrate was concentrated to an oil and purified by silica gel chromatography eluting with 0-100% MeOH in EtOAc to give U-3 as a colorless oil, 81 mg (58% yield).

LCMS-APCI(+): MH+=395, ¹H NMR (400 MHz, METHANOL-d4) δ ppm 8.64 (s, 1H), 7.62 (d, J=3.7 Hz, 1H), 7.34-7.23 (m, 2H), 7.12 (d, J=8.6 Hz, 1H), 6.96 (t, J=7.5 Hz, 1H), 6.75 (d, J=3.7 Hz, 1H), 5.28 (dt, J=3.5, 7.0 Hz, 1H), 5.19 (dd, J=3.4, 6.4 Hz, 1H), 4.94 (d, J=6.4 Hz, 1H), 4.87 (t, J=5.9 Hz, 1H), 3.72 (br. s., 2H), 2.95 (td, J=7.0, 14.1 Hz, 1H), 2.73 (s, 3H), 2.65-2.54 (m, 1H), 1.60 (s, 3H), 1.35 (s, 3H).

193

Step 4: Synthesis of tert-butyl(2-(((1S,2S,3S,4R)-2, 3-dihydroxy-4-(4-methyl-7H-pyrrolo[2,3-d]pyrimidin-7-yl)cyclopentyl)oxy)benzyl)carbamate (U-4) and tert-butyl(2-(((1R,2R,3R,4S)-2,3-dihydroxy-4-(4-methyl-7H-pyrrolo[2,3-d]pyrimidin-7-yl)cyclopentyl)oxy)benzyl)carbamate (U-5)

A solution of the U-3 (81 mg, 0.21 mmol) in 50% TFA (aq) (600 ul) was stirred at r.t for 16 hours. The reaction mixture was then concentrated to an oil. A mixture of the crude oil and Boc₂O (30.8 mg, 1.41 mmol) in DCM 30.8 mg, 0.141 mmol) was stirred at r.t. for 6 hours. The reaction mixture was concentrated then purified by silica gel chromatography eluting with 40 to 100% EtOAc in heptane then 0-20% MeOH in EtOAc to give racemic mixture of U-4 and U-5 as a colorless oil, 73 mg. The enantiomers were separated by chiral SFC (Chiralpak IC-3 4.6×100 mm 3u column, 30% MeOH @ 120 bar, 4 mL/min) to give U-4 (25.4 mg, 40% yield) and U-5 (24.4 mg, 38% yield) as white solids.

U-4: LCMS-ESI(+): MH+=455, ¹H NMR (400 MHz, METHANOL-d4) δ ppm 8.52 (s, 1H), 7.51 (br. s., 1H), 7.23-7.09 (m, 2H), 6.92 (d, J=8.1 Hz, 1H), 6.84 (t, J=7.5 Hz, 1H), 6.64 (d, J=3.7 Hz, 1H), 5.15 (q, J=8.6 Hz, 1H), 4.67-4.58 (m, 2H), 4.34-4.15 (m, 2H), 4.11 (d, J=4.4 Hz, 1H), 2.90 (ddd, J=7.3, 9.4, 14.5 Hz, 1H), 2.61 (s, 3H), 2.24-2.08 (m, 1H), 1.33 (s, 9H). [α]D22=+61.3° (c=0.1, MeOH).

U-5: LCMS-ESI(+): MH+=455, ¹H NMR (400 MHz, METHANOL-d4) δ ppm 8.62 (s, 1H), 7.61 (br. s., 1H), 7.33-7.17 (m, 2H), 7.02 (d, J=8.1 Hz, 1H), 6.94 (t, J=7.3 Hz, 1H), 6.74 (d, J=3.7 Hz, 1H), 5.25 (q, J=9.0 Hz, 1H), 4.74 (d, J=7.1 Hz, 2H), 4.43-4.25 (m, 2H), 4.21 (d, J=4.4 Hz, 1H), 3.00 (ddd, J=7.3, 9.5, 14.7 Hz, 1H), 2.71 (s, 3H), 2.38-2.12 (m, 1H), 1.43 (s, 9H). [α]D22=−86.1° (c=0.1, MeOH)

Step 5: Synthesis of (1S,2S,3S,5R)-3-(2-(aminomethyl)phenoxy)-5-(4-methyl-7H-pyrrolo[2,3-d]pyrimidin-7-yl)cyclopentane-1,2-diol (U-6)

A mixture of U-4 (24 mg, 0.053 mmol) and trifluoroacetic acid (120 mg, 1.06 mmol) in DCM (0.176 ml, 0.3 M) was stirred at r.t. for 3 hours then concentrated to an oil and purified by SFC (ZymorSpher Pyridine Diol 150×21.2 mm column with 20-40% MeOH @ 5%/min, 100 bar, 60 mL/min.) to give U-6 as a white solid, 6.54 mg (35% yield).
LCMS-APCI(+): MH+=355, 1H NMR (700 MHz, DMSO-d6) δ ppm 8.62 (s, 1H), 7.66 (d, J=2.2 Hz, 1H), 7.37 (d, J=7.0 Hz, 1H), 7.28 (t, J=7.5 Hz, 1H), 7.07 (d, J=7.9 Hz, 1H), 6.96 (t, J=7.0 Hz, 1H), 6.72 (d, J=2.6 Hz, 1H), 5.12 (q, J=8.8 Hz, 1H), 4.61 (d, J=3.1 Hz, 1H), 4.06 (br. s., 1H), 2.94-2.75 (m, 1H), 2.64 (s, 3H), 2.03 (t, J=9.7 Hz, 1H)

Step 6: Synthesis of (1R,2R,3R,5S)-3-(2-(aminomethyl)phenoxy)-5-(4-methyl-7H-pyrrolo[2,3-d]pyrimidin-7-yl)cyclopentane-1,2-diol (U-7)

U-7 was prepared in a similar manner to U-6 staring from U-5 to give a white solid, 9 mg (50% yield).
LCMS-APCI(+): MH+=355, 1H NMR (700 MHz, DMSO-d6) δ ppm 8.63 (s, 1H), 7.66 (d, J=3.5 Hz, 1H), 7.39 (d, J=7.5 Hz, 1H), 7.36 (t, J=7.7 Hz, 1H), 7.13 (d, J=8.4 Hz, 1H), 7.00 (t, J=7.5 Hz, 1H), 6.72 (d, J=3.5 Hz, 1H), 5.19-5.04 (m, 2H), 4.63 (d, J=4.4 Hz, 2H), 4.08 (d, J=4.4 Hz, 1H), 4.06 (s, 2H), 2.87 (td, J=8.3, 14.2 Hz, 1H), 2.64 (s, 3H), 2.06 (ddd, J=4.0, 9.5, 13.9 Hz, 1H)

194

Example 64 (Scheme V)—2-(((1S,2S,3S,4R)-2,3-dihydroxy-4-(4-methyl-7H-pyrrolo[2,3-d]pyrimidin-7-yl)cyclopentyl)oxy)benzonitrile (V-1)

Example 65 (Scheme V)—2-(((1R,2R,3R,4S)-2,3-dihydroxy-4-(4-methyl-7H-pyrrolo[2,3-d]pyrimidin-7-yl)cyclopentyl)oxy)benzonitrile (V-2)

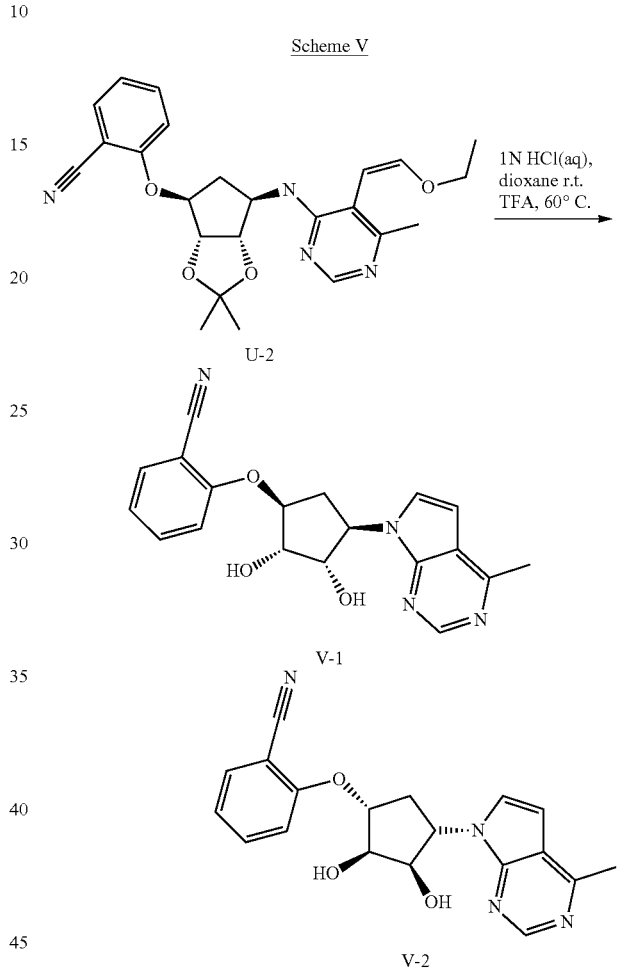

Scheme V

Step 1: Synthesis of 2-(((1S,2S,3S,4R)-2,3-dihydroxy-4-(4-methyl-7H-pyrrolo[2,3-d]pyrimidin-7-yl) cyclopentyl)oxy)benzonitrile (V-1) and 2-(((1R,2R,3R,4S)-2,3-dihydroxy-4-(4-methyl-7H-pyrrolo[2,3-d]pyrimidin-7-yl)cyclopentyl)oxy)benzonitrile (V-2)

V-1 (9.5 mg, 47% yield) and V-2 (9.4 mg, 47% yield) were prepared from U-2 in a similar manner to step 5 in Scheme U.
V-1: LCMS-ESI(+): MH+=351, ¹H NMR (400 MHz, METHANOL-d4) δ ppm 8.68 (br. s., 1H), 7.75 (d, J=3.7 Hz, 1H), 7.71-7.60 (m, 2H), 7.30 (d, J=8.6 Hz, 1H), 7.12 (t, J=7.6 Hz, 1H), 6.82 (d, J=3.7 Hz, 1H), 5.36 (q, J=8.5 Hz, 1H), 4.89 (d, J=6.1 Hz, 1H), 4.71 (dd, J=4.6, 8.3 Hz, 1H), 4.23 (d, J=4.2 Hz, 1H), 3.16-3.01 (m, 1H), 2.75 (s, 3H), 2.18 (ddd, J=2.4, 7.6, 14.7 Hz, 1H).
V-2: LCMS-ESI(+): MH+=351, ¹H NMR (400 MHz, METHANOL-d4) δ ppm 8.73 (br. s., 1H), 7.79 (d, J=3.7 Hz, 1H), 7.72-7.61 (m, 1H), 7.31 (d, J=8.6 Hz, 1H), 7.12 (t, J=7.6 Hz, 1H), 6.87 (d, J=3.7 Hz, 1H), 5.43-5.31 (m, 1H), 4.90 (d, J=5.9 Hz, 1H), 4.72 (dd, J=4.6, 8.6 Hz, 1H), 4.23 (d, J=4.4 Hz, 1H), 3.16-3.01 (m, 1H), 2.77 (s, 2H), 2.19 (ddd, J=2.3, 7.6, 14.8 Hz, 1H)

Example 66 (Scheme W)—(1S,2S,3S,5R)-3-(2-(aminomethyl)-4-fluorophenoxy)-5-(4-methyl-7H-pyrrolo[2,3-d]pyrimidin-7-yl)cyclopentane-1,2-diol (W-5)

Example 67 (Scheme W)—(1R,2R,3R,5S)-3-(2-(aminomethyl)-4-fluorophenoxy)-5-(4-methyl-7H-pyrrolo[2,3-d]pyrimidin-7-yl)cyclopentane-1,2-diol. (W-6)

Scheme W

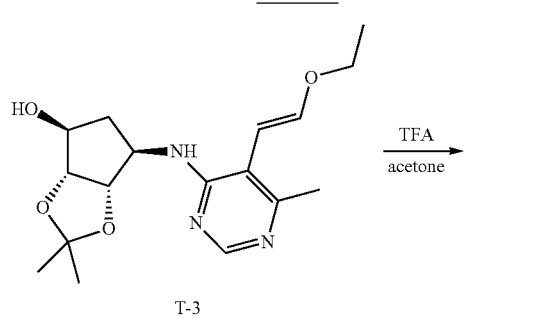

T-3

TFA acetone

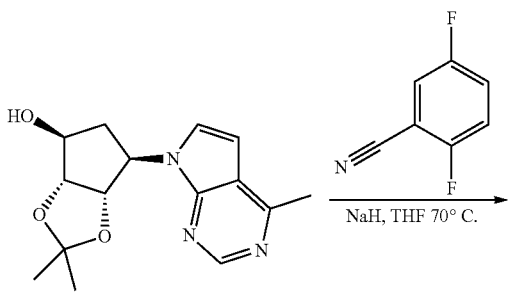

W-1

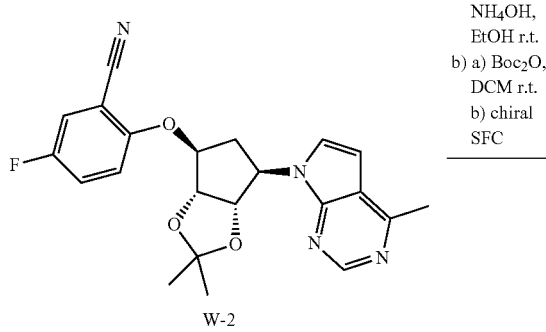

W-2 a) Ra-Ni H₂ (50 psi) NH₄OH, EtOH r.t.
b) a) Boc₂O, DCM r.t.
b) chiral SFC

-continued

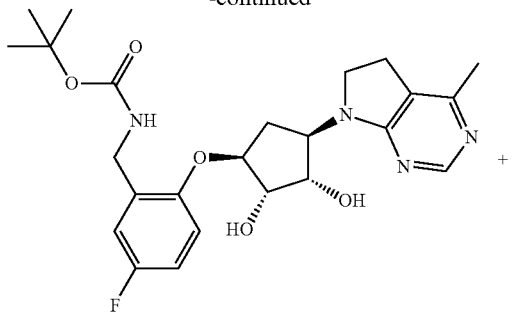

W-3

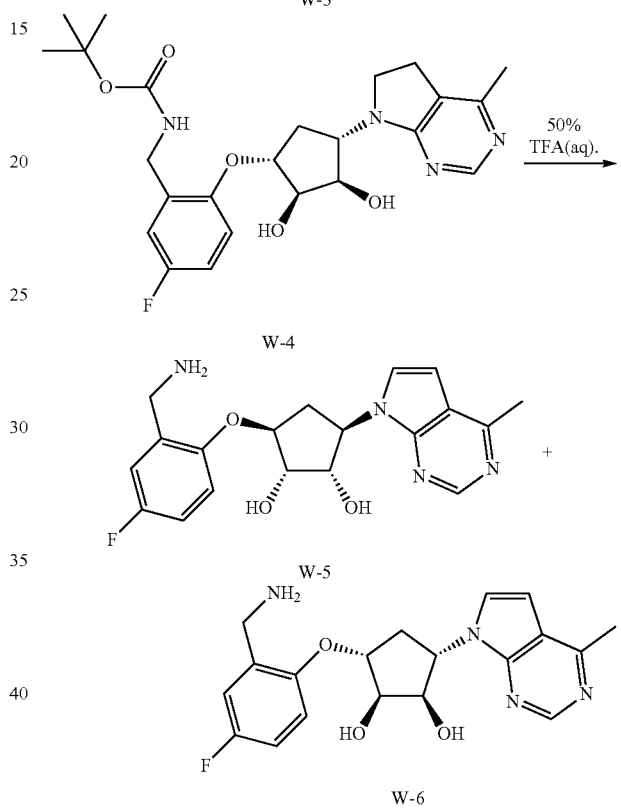

Step 1: Synthesis of (3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-ol (W-1)

A mixture of T-3 (111 mg, 0.331 mmol) and trifluoroacetic acid (127 ul, 1.65 mmol) in acetone (3.31 ml, 0.1 M) was heated to 60° C. for 43 hours. The reaction mixture was concentrated to an oil then dissolved in EtOAc. The EtOAc layer was washed with saturated NaHCO₃(aq), brine, dried with Na₂SO₄, filtered and concentrated to an oil. The crude mixture was purified by silica gel chromatography eluting a gradient of 0% to 100% EtOAc in heptane to give W-1 as a white solid, 76 mg (79% yield, 80% pure).

Step 1: Synthesis of 2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorobenzonitrile (W-2)

To a mixture of W-1 (67.1 mg, 0.2 mmol) and 2,5-difluorobenzonitrile (55.0 mg, 0.395 mmol, 55.0 uL) in THF (1.01 mL, c=0.3 M) at r.t. was added 60% sodium hydride (24.3 mg, 0.608 mmol). After stirring for 3 minutes the reaction mixture was heated to 70° C. for 6 hours then quenched with saturated NH$_4$Cl(aq) then diluted with EtOAc and water. The EtOAc layer was washed with brine, dried with Na$_2$SO$_4$ filtered then concentrated to an oil. The oil was purified by silica gel chromatography eluting with 0-100% EtOAc in heptane to give W-2 as a white foam, 101 mg (81% yield).

LCMS-ESI(+): MH+=409, 1H NMR (400 MHz, CHLOROFORM-d) δ ppm 1.34 (s, 3H) 1.61 (s, 3H) 2.59 (d, J=15.41 Hz, 1H) 2.78 (s, 3H) 3.05 (dt, J=15.16, 7.34 Hz, 1H) 4.84 (d, J=6.36 Hz, 1H) 4.86-4.92 (m, 1H) 5.04 (d, J=4.40 Hz, 1H) 5.35-5.53 (m, 1H) 6.68 (d, J=3.18 Hz, 1H) 7.11 (dd, J=9.78, 3.67 Hz, 1H) 7.32 (d, J=7.58 Hz, 2H) 7.66 (br. s., 1H) 8.80 (s, 1H).

Step 2: Synthesis of tert-butyl(2-(((1S,2S,3S,4R)-2,3-dihydroxy-4-(4-methyl-7H-pyrrolo[2,3-d]pyrimidin-7-yl)cyclopentyl)oxy)-5-fluorobenzyl)carbamate (W-3) and tert-butyl(2-(((1R,2R,3R,4S)-2,3-dihydroxy-4-(4-methyl-7H-pyrrolo[2,3-d]pyrimidin-7-yl)cyclopentyl)oxy)-5-fluorobenzyl)carbamate (W-4)

To a mixture of W-2 (101 mg, 0.247 mmol) in ethanol (7.0 mL) was added 28% ammonium hydroxide (3.0 mL) and Raney Nickel (70 mg, 1.2 mmol). The mixture was hydrogenated at 50 psi in a stainless steel bomb for 24 hours. The reaction mixture was filtered through celite then concentrated to a foam.

To this crude amine was added boc anhydride (54 mg, 0.247 mmol) in DCM (3 ml, 0.3 M) and stirred at r.t. for 2 hours. This was concentrated to a foam and purified by silica gel chromatography to give a racemic mixture of W-3 and W-4 as a colorless oil, 104 mg 982% yield). The enantiomers were separated by chiral SFC (Chiralpak AS-3 4.6×100 mm 3u column, 8% MeOH+10 mM NH3 @ 120 bar, 4 mL/min) to give W-3 (34.2 mg, 27% yield) and W-4 (35.9 mg, 28% yield) as white solids.

W-3: LCMS-ESI(+): MH+=513, $^1$H NMR (400 MHz, CHLOROFORM-d) δ ppm 8.86-8.76 (m, 1H), 7.45 (br. s., 1H), 7.02 (d, J=8.6 Hz, 1H), 6.95 (d, J=5.1 Hz, 2H), 6.67 (d, J=3.2 Hz, 1H), 5.35 (br. s., 1H), 5.07 (d, J=3.7 Hz, 1H), 4.89-4.71 (m, 3H), 4.21 (br. s., 1H), 2.98 (td, J=7.2, 14.7 Hz, 1H), 2.81 (s, 3H), 2.54 (d, J=15.2 Hz, 1H), 1.61 (s, 3H), 1.50-1.38 (m, 10H), 1.34 (s, 3H), [α]D22=+28.2° (c=0.1, MeOH)

W-4: LCMS-ESI(+): MH+=513 ~80% pure.

Step 3: Synthesis of (1S,2S,3S,5R)-3-(2-(aminomethyl)-4-fluorophenoxy)-5-(4-methyl-7H-pyrrolo[2,3-d]pyrimidin-7-yl)cyclopentane-1,2-diol. (W-5)

A mixture of W-3 (34 mg, 0.066 mmol) in a mixture of 50% TFA(aq) (0.4 ml) was stirred at r.t. for 3 hours then concentrated and purified by SFC (ZymorSpher Pyridine Diol 150×21.2 mm column with 20-40% MeOH @ 5%/min, 100 bar, 60 mL/min.) to give W-5 as a white solid, 16.5 mg (67% yield).

LCMS-ESI(+): MH+=373, $^1$H NMR (400 MHz, DMSO-d6) δ ppm 8.63 (s, 1H), 7.65 (d, J=3.7 Hz, 1H), 7.28 (dd, J=2.6, 9.2 Hz, 1H), 7.21-7.03 (m, 2H), 6.72 (d, J=3.4 Hz, 1H), 5.19-4.98 (m, 2H), 4.69-4.48 (m, 2H), 4.06 (d, J=4.6 Hz, 1H), 4.00 (s, 2H), 2.95-2.76 (m, 1H), 2.64 (s, 3H), 2.04 (ddd, J=4.0, 9.5, 13.8 Hz, 1H)

Step 4: Synthesis of (1R,2R,3R,5S)-3-(2-(aminomethyl)-4-fluorophenoxy)-5-(4-methyl-7H-pyrrolo[2,3-d]pyrimidin-7-yl)cyclopentane-1,2-diol. (W-6)

W-6 was prepared from W-4 in a similar manner to step 3 in Scheme W to give a white solid, 17.2 mg (70% yield).

LCMS-ESI(+): MH+=373, $^1$H NMR (400 MHz, DMSO-d6) δ ppm 8.63 (s, 1H), 7.65 (d, J=3.7 Hz, 1H), 7.28 (dd, J=2.6, 9.2 Hz, 1H), 7.21-7.07 (m, 2H), 6.72 (d, J=3.4 Hz, 1H), 5.18-5.02 (m, 2H), 4.69-4.54 (m, 2H), 4.06 (d, J=4.6 Hz, 1H), 4.01 (s, 2H), 2.94-2.74 (m, 1H), 2.64 (s, 3H), 2.04 (ddd, J=4.2, 9.5, 13.7 Hz, 1H).

Example 68 (Scheme X)—2-(((1S,2S,3S,4R)-2,3-dihydroxy-4-(4-methyl-7H-pyrrolo[2,3-d]pyrimidin-7-yl)cyclopentyl)oxy)-5-fluorobenzonitrile (X-2)

Example 69 (Scheme X)—2-(((1R,2R,3R,4S)-2,3-dihydroxy-4-(4-methyl-7H-pyrrolo[2,3-d]pyrimidin-7-yl)cyclopentyl)oxy)-5-fluorobenzonitrile (X-3)

Scheme X

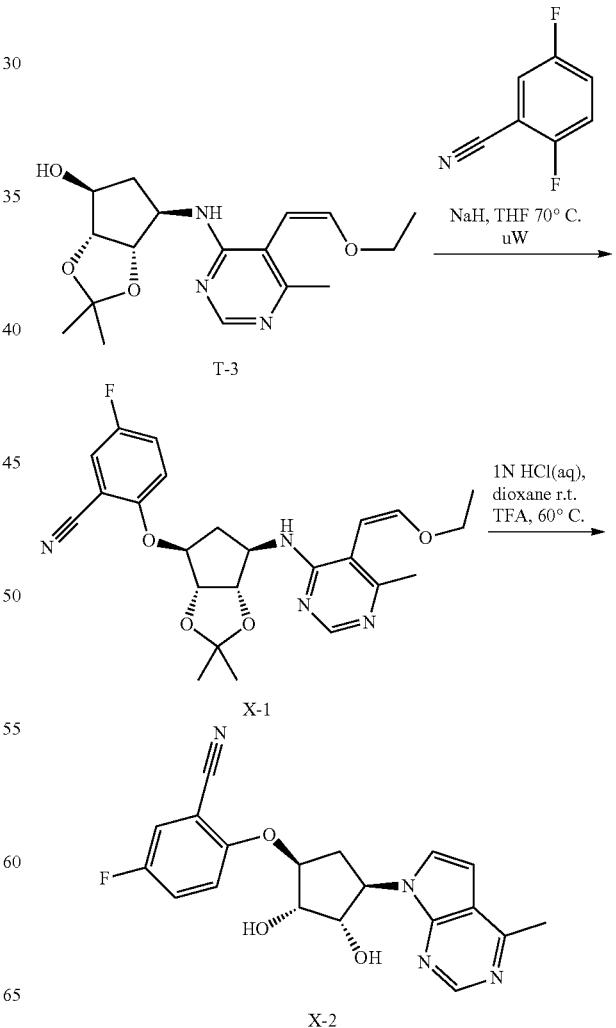

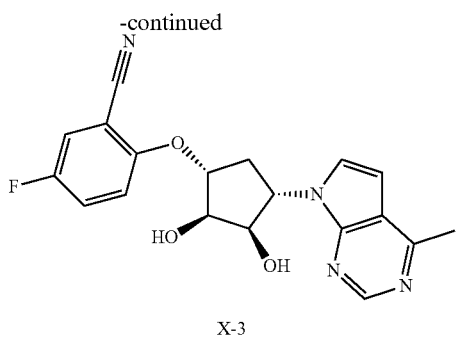

X-3

Step 1: Synthesis of 2-(((3aR,4S,6R,6aS)-6-((5-((Z)-2-ethoxyvinyl)-6-methylpyrimidin-4-yl)amino)-2,2-dimethyltetrahydro-4H-cyclopenta[d][1,3]dioxol-4-yl)oxy)-5-fluorobenzonitrile. (X-1)

A mixture of T-3 (67.1 mg, 0.2 mmol) and O-fluorobenzonitrile (25.5 ul, 0.240 mmol) in THF (0.67 ml, 0.3 M) at r.t. was added 60% sodium hydride (16.8 mg, 0.42 mmol). The mixture was then heated to 70° C. in a microwave reactor for 30 minutes. The reaction mixture was quenched with saturated NH₄Cl(aq) then diluted with water and extracted with EtOAc. The EtOAc was washed with brine, dried with Na₂SO₄, filtered and concentrated to an oil then purified by silica gel chromatography eluting with 0-100% EtOAc/Heptane to give X-1 as an amber oil, 58 mg (64% yield).

LCMS-ESI(+): MH+=455, ¹H NMR (400 MHz, CHLOROFORM-d) δ ppm 8.47 (s, 1H), 7.35-7.28 (m, 2H), 7.16-7.06 (m, 1H), 6.47 (d, J=13.2 Hz, 1H), 5.43 (d, J=7.3 Hz, 1H), 5.39 (d, J=13.2 Hz, 1H), 4.81-4.65 (m, 4H), 3.87 (q, J=7.0 Hz, 2H), 2.69 (td, J=6.1, 14.9 Hz, 1H), 2.34 (s, 3H), 2.11 (d, J=14.9 Hz, 1H), 1.50 (s, 3H), 1.31 (s, 2H), 1.27 (t, J=7.0 Hz, 3H).

Step 2: Synthesis of 2-(((1S,2S,3S,4R)-2,3-dihydroxy-4-(4-methyl-7H-pyrrolo[2,3-d]pyrimidin-7-yl)cyclopentyl)oxy)-5-fluorobenzonitrile (X-2) and 2-(((1R,2R,3R,4S)-2,3-dihydroxy-4-(4-methyl-7H-pyrrolo[2,3-d]pyrim din-7-yl)cyclopentyl)oxy)-5-fluorobenzonitrile (X-3)

A mixture of the X-1 (58 mg, 0.13 mmol) and 1N HCl(aq) (255 ul, 0.255 mmol) in 1,4-dioxane (0.382 ml, 0.15 M) was stirred at r.t. for 24 hours. Trifluoroacetic acid (200 ul) was added and the mixture was stirred at r.t for 48 hours then heated to 60° C. for 6 hours. The reaction mixture was concentrated to an oil then partitioned between EtOAc and and water. Saturated NaHCO₃(aq) was added and the EtOAc layer was washed with brine, dried with Na₂SO₄, filtered then concentrated to a white solid, 44 mg. The enantiomers were separated by chiral SFC (Lux Cellulose-2 4.6×100 mm 3u column, 30% MeOH @ 120 bar, 4 mL/min) to give X-2 (17 mg, 36% yield) and X-3 (16.2 mg, 35% yield) as white solids.

X-2: LCMS-ESI(+): MH+=369, ¹H NMR (400 MHz, DMSO-d6) δ ppm 8.64 (s, 1H), 7.79 (dd, J=3.1, 8.2 Hz, 1H), 7.70 (d, J=3.4 Hz, 1H), 7.65-7.51 (m, 2H), 7.40 (dd, J=4.2, 9.3 Hz, 1H), 6.76 (d, J=3.4 Hz, 1H), 5.41 (br. s., 1H), 5.15 (q, J=8.9 Hz, 1H), 4.77 (br. s., 1H), 4.53 (br. s., 1H), 4.05 (br. s., 1H), 2.97-2.75 (m, 1H), 2.65 (s, 3H), 2.11-1.93 (m, 1H), [α]D22=+47.3° (c=0.1, MeOH).

X-3: LCMS-ESI(+): MH+=369, ¹H NMR (400 MHz, METHANOL-d4) δ ppm 7.72 (d, J=3.4 Hz, 1H), 7.51 (dd, J=2.9, 7.6 Hz, 1H), 7.47-7.38 (m, 1H), 7.32 (dd, J=4.0, 9.2 Hz, 1H), 6.80 (d, J=3.4 Hz, 1H), 5.33 (q, J=8.6 Hz, 1H), 4.85 (br. s., 1H), 4.71 (dd, J=4.8, 8.2 Hz, 1H), 4.22 (d, J=3.9 Hz, 1H), 3.12-2.97 (m, 1H), 2.74 (br. s., 3H), 2.26-2.12 (m, 1H), [α]D22=−53.5° (c=0.1, MeOH).

Example 70 (Scheme Y)—2-(((1S,2S,3S,4R)-2,3-dihydroxy-4-(4-methyl-7H-pyrrolo[2,3-d]pyrimidin-7-yl)cyclopentyl)oxy)-5-fluorobenzamide (Y-3)

Scheme Y

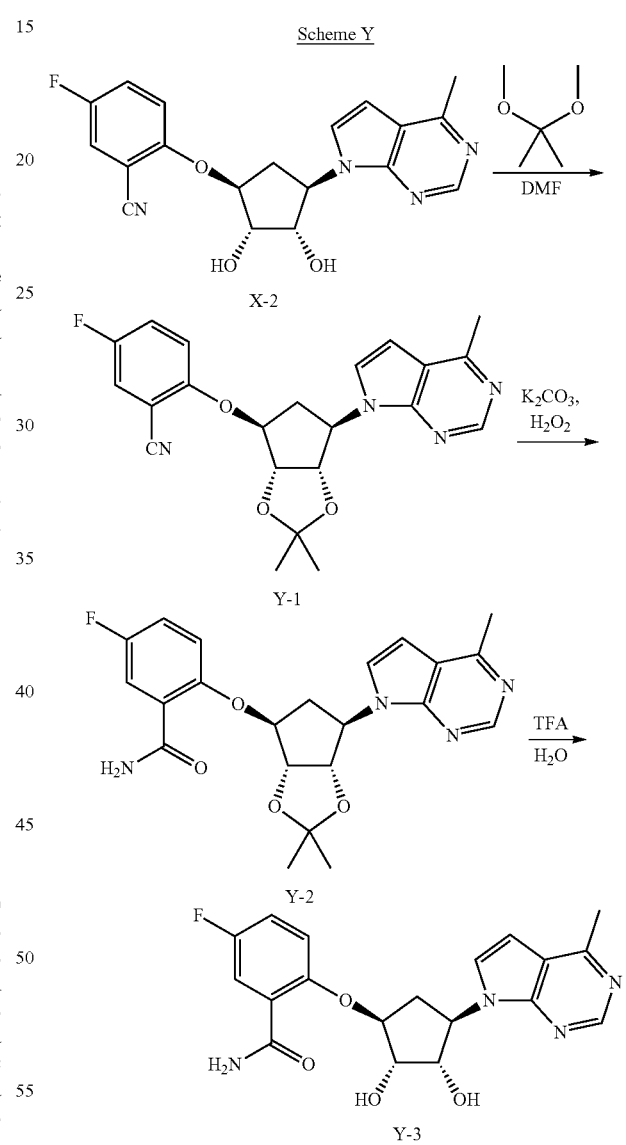

Step 1—Synthesis of 2-(((3aR,4S,6R,6aS)-2,2-dimethyl-6-(4-methyl-7H-pyrrolo[2,3-d]pyrimidine-7-yl)tetrahydro-4H-cyclopenta[d][1,3]dioxol-4-yl)oxy)-5-fluorobenzonitrile (Y-1)

To a suspension of X-2 (4 g, 9.8 mmol) in dimethoxypropane (60 mL)/DMF (20 mL) was added TsOH.H₂O (2990 mg, 15.75 mmol) at rt (20° C.). The resulting solution was stirred at rt (20° C.) for 24 hrs. The mixture was purified directly by silica gel chromatography eluted with EtOAc in petroleum ether from 0 to 100% to afford Y-1 (2.2 g, 55%) as a white solid. LCMS 409 [M+1]; $^1$H NMR (400 MHz, CDCl$_3$) δ ppm 8.77 (s, 1H), 7.60 (d, J=3.8 Hz, 1H), 7.33-7.25 (m, 2H), 7.15-7.06 (m, 1H), 6.63 (d, J=3.5 Hz, 1H), 5.44 (ddd, J=2.5, 5.0, 7.8 Hz, 1H), 5.02 (dd, J=2.3, 6.0 Hz, 1H), 4.90-4.85 (m, 1H), 4.82 (d, J=6.3 Hz, 1H), 3.04 (ddd, J=6.8, 8.0, 15.1 Hz, 1H), 2.72 (s, 3H), 2.63-2.53 (m, 1H), 1.60 (s, 3H), 1.33 (s, 3H)

Step 2—Synthesis of 2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorobenzamide (Y-2)

To a solution of Y-1 (50 mg, 0.12 mmol) in DMSO (0.25 mL) was added K$_2$CO$_3$ (20 mg, 0.15 mmol), followed by H$_2$O$_2$ (0.25 mL) drop-wise at ice-water, then the reaction can be warmed to room temperature for 2 h, in which gas was observed. To the reaction mixture was added water and extracted with EtOAc two times. The organic layer was dried over sodium sulfate, filtered, and the residue was purified by prep-TLC to give Y-2 (36 mg, 69%) and used as is in the next step.

Step 3—Synthesis of 2-(((1S,2S,3S,4R)-2,3-dihydroxy-4-(4-methyl-7H-pyrrolo[2,3-d]pyrimidin-7-yl)cyclopentyl)oxy)-5-fluorobenzamide (Y-3)

To a suspension of Y-2 (42 mg, 0.1 mmol) in H$_2$O (0.3 mL) was added TFA (0.3 mL) drop-wise at 0° C. Then the reaction mixture was stirred at room temperature (20° C.) for 16 h. The reaction was then adjusted to pH 7 with 20% K$_2$CO$_3$ in which solid was formed, then filtered, and washed with water and MTBE. The solid was dried to give Y-3 (32 mg, 84%). LCMS 387 [M+1]; $^1$H NMR (400 MHz, MeOD-d$_4$) δ ppm 8.63 (s, 1H), 7.62-7.65 (m, 1H), 7.60 (d, J=3.8 Hz, 1H), 7.24-7.30 (m, 2H), 6.75 (d, J=3.5 Hz, 1H), 5.16 (q, J=8.8 Hz, 1H), 4.82-4.87 (m, 2H), 4.27 (d, J=4.8 Hz, 1H), 3.02 (ddd, J=14.6, 9.6, 7.4 Hz, 1H), 2.73 (s, 3H), 2.42 ppm (ddd, J=13.7, 9.2, 4.3 Hz, 1H)

Example 71 (Scheme Z)—(1S,2S,3S,5R)-3-(2-((dimethylamino)methyl)-4-fluorophenoxy)-5-(4-methyl-7H-pyrrolo[2,3-d]pyrimidin-7-yl)cyclopentane-1,2-diol (8)

Scheme Z

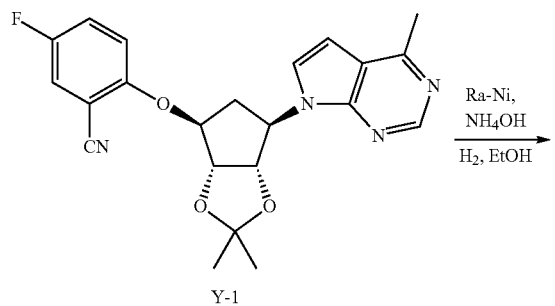

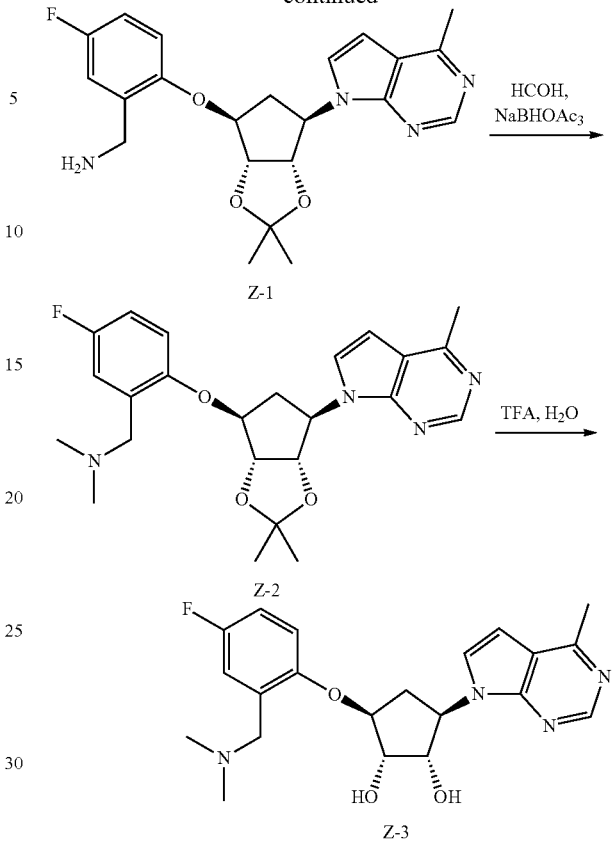

Step 1—Synthesis of (2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorophenyl)methanamine (Z-1)

A mixture of Y-1 (500 mg, 1.22 mmol) and Ra—Ni (100 mg) in EtOH (30 mL)/NH$_3$.H$_2$O (3 mL) was de-gassed with H$_2$ four times. The mixture was stirred at rt (20° C.) under H$_2$ balloon for 20 hrs then allowed to stand at rt for 20 hrs. The mixture was filtered and concentrated in vacuo to afford Z-1 (510 mg, >99%) as a light yellow gum. LCMS [M+1] 413; $^1$H NMR (400 MHz, CDCl$_3$) δ ppm 8.79 (s, 1H), 7.37 (d, J=3.5 Hz, 1H), 7.05 (dd, J=2.4, 8.7 Hz, 1H), 6.99-6.88 (m, 2H), 6.58 (d, J=3.8 Hz, 1H), 5.33 (ddd, J=2.6, 5.5, 8.0 Hz, 1H), 5.05 (dd, J=2.9, 6.1 Hz, 1H), 4.88-4.80 (m, 1H), 4.80-4.75 (m, 1H), 3.76 (br. s., 2H), 3.06-2.89 (m, 1H), 2.73 (s, 3H), 2.62-2.47 (m, 1H), 1.61 (s, 3H), 1.34 (s, 3H)

Step 2—Synthesis of 1-(2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorophenyl)-N,N-dimethylmethanamine (Z-2)

A mixture of Z-1 (100 mg, 0.24 mmol), 37% CH$_2$O (59 mg, 0.73 mmol) and NaBHOAc$_3$ (206 mg, 0.970 mmol) in THF (2 mL) was stirred at rt for 2 hrs. The mixture was poured into NaHCO$_3$ aq (10 mL) and extracted with EtOAc (10 mL×3). The extract was washed with brine (10 mL), dried over Na$_2$SO$_4$ and concentrated in vacuo to afford Z-2 (100 mg, 94%) as a colorless gum. LCMS 441 [M+1]; $^1$H NMR (400 MHz, CDCl$_3$) δ ppm 8.79 (s, 1H), 7.49 (d, J=3.8

Hz, 1H), 7.14-7.08 (m, 1H), 7.01-6.86 (m, 2H), 6.55 (d, J=3.5 Hz, 1H), 5.37 (t, J=2.8 Hz, 1H), 5.02 (d, J=4.0 Hz, 1H), 4.83 (d, J=6.3 Hz, 1H), 4.77 (dd, J=3.3, 5.8 Hz, 1H), 3.33 (s, 2H), 2.97 (d, J=8.0 Hz, 1H), 2.73 (s, 3H), 2.54 (d, J=13.8 Hz, 1H), 2.23 (s, 6H), 1.60 (s, 3H), 1.33 (s, 3H)

Step 3—Synthesis of (1S,2S,3S,5R)-3-(2-((dimethylamino)methyl)-4-fluorophenoxy)-5-(4-methyl-7H-pyrrolo[2,3-d]pyrimidin-7-yl)cyclopentane-1,2-diol (Z-3)

To TFA/H$_2$O (1 mL/2 mL) was added Z-2 (100 mg, 0.23 mmol) at rt. The mixture was stirred at rt for 1 hr. The mixture was poured into 20% K$_2$CO$_3$ (10 mL). The mixture was washed saturated with NaCl and extracted with EtOAc/THF (20 mL/20 mL) twice. The extract was washed with concentrated in vacuo. The residue was dissolved in CH$_3$CN/H$_2$O (10 mL/50 mL) and lyophilized to afford Z-3 (70 mg, 77%) as a white solid. LCMS 404 [M+1]; $^1$H NMR (400 MHz, DMSO-d$_6$) δ ppm 8.61 (s, 1H), 7.69 (d, J=3.8 Hz, 1H), 7.13 (d, J=8.5 Hz, 1H), 7.05 (d, J=5.5 Hz, 2H), 6.72 (d, J=3.5 Hz, 1H), 5.36 (br. s., 1H), 5.16-5.09 (m, 2H), 4.60-4.49 (m, 2H), 4.01 (d, J=3.3 Hz, 1H), 3.57-3.48 (m, 1H), 3.44 (br. s., 1H), 2.90-2.78 (m, 1H), 2.63 (s, 3H), 2.23 (s, 6H), 1.96-1.86 (m, 1H)

Example 72 (Scheme AA)—(1S,2S,3S,5R)-3-(4-fluoro-2-((methylamino)methyl)phenoxy)-5-(4-methyl-7H-pyrrolo[2,3-d]pyrimidin-7-yl)cyclopentane-1,2-diol (11)

Scheme AA

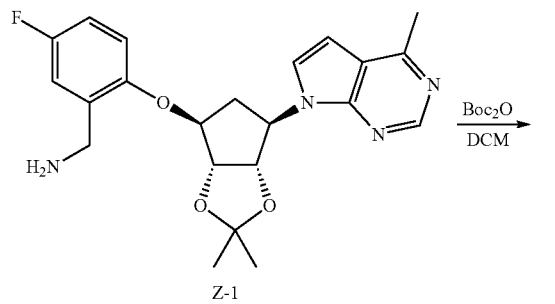

Z-1

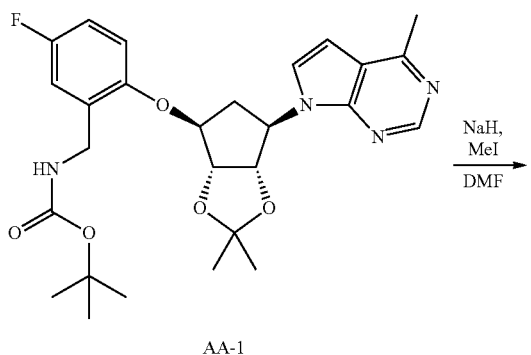

AA-1

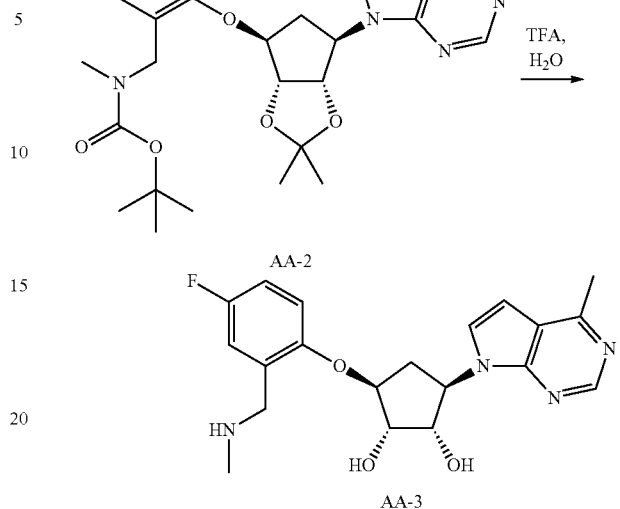

AA-2

AA-3

Step 1—Synthesis of tert-butyl(2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorobenzyl)carbamate (AA-1)

To a solution of Z-1 (140 mg, 0.34 mmol) and Et$_3$N (34 mg, 0.34 mmol) in DCM (5 mL) was added Boc$_2$O (74 mg, 0.34 mmol) at rt (20° C.). The mixture was stirred at rt (20° C.) for 1 hr. The mixture was purified by silica gel chromatography eluted with EtOAC in petroleum ether from 0 to 100% to afford AA-1 (140 mg, 81%) as a colorless oil. LCMS 513 [M+1]; $^1$H NMR (400 MHz, CDCl$_3$) δ ppm 8.78 (s, 1H), 7.33 (s, 1H), 7.00 (d, J=8.8 Hz, 1H), 6.93 (d, J=5.2 Hz, 2H), 6.58 (d, J=3.6 Hz, 1H), 5.30-5.28 (m, 1H), 5.06-5.05 (m, 1H), 4.81 (d, J=6 Hz, 2H), 4.76-4.75 (m, 1H), 4.18 (d, J=3.2 Hz, 1H), 2.98-2.90 (m, 1H), 2.71 (s, 3H), 2.54-2.50 (m, 1H), 1.55 (s, 3H), 1.44 (s, 9H), 1.24 (s, 3H)

Step 2—Synthesis of tert-butyl(2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorobenzyl)(methyl)carbamate (AA-2)

To a solution of AA-1 (140 mg, 0.27 mmol) in dry DMF (3 mL) was added 60% NaH (16.4 mg, 0.41 mmol) at rt (0° C.). The mixture was stirred at rt (20° C.) for 1 hr. CH$_3$I (56 mg, 0.4 mmol) was added to the mixture and stirred at rt (20° C.) for 20 hrs. The mixture was poured into NH$_4$Cl aq (10 mL) and extracted with EtOAc (5 mL×3). The extract was washed with brine (5 mL), dried over Na$_2$SO$_4$ and concentrated in vacuo to afford crude material (200 mg) as a brown oil which was purified by silica gel chromatography eluted with EtOAc in petroleum ether from 0 to 100% to afford AA-2 (100 mg, 70%) as a colorless gum. LCMS 527 [M+1]

Step 3—Synthesis of (1S,2S,3S,5R)-3-(4-fluoro-2-((methylamino)methyl)phenoxy)-5-(4-methyl-7H-pyrrolo[2,3-d]pyrimidin-7-yl)cyclopentane-1,2-diol (AA-3)

To TFA/H$_2$O (1 mL/2 mL) was added AA-2 (89 mg, 0.169 mmol) at rt. The mixture was stirred at rt for 2 hrs, then poured into 20% K$_2$CO$_3$ aq (5 mL). The mixture was extracted with EtOAc (10 mL×3). The extract was washed with brine (10 mL×2), dried over Na$_2$SO$_4$, filtered and concentrated in vacuo. The residue was dissolved in CH$_3$CN/H$_2$O (4 mL/10 mL) and lyophilized to afford AA-3 (55 mg, 84%) as a white solid. LCMS 387 [M+1]; $^1$H NMR (400 MHz, DMSO-d$_6$) δ ppm 8.62 (s, 1H), 7.67 (d, J=3.8 Hz, 1H), 7.23-7.14 (m, 1H), 7.08-6.98 (m, 2H), 6.73 (d, J=3.8 Hz, 1H), 5.12 (q, J=9.1 Hz, 2H), 4.57 (br. s., 2H), 4.02 (d, J=4.8 Hz, 1H), 3.71 (s, 2H), 2.92-2.77 (m, 1H), 2.65 (s, 3H), 2.34 (s, 3H), 2.03-1.93 (m, 1H)

Example 73 (Scheme BB)—(1S,2S,3S,5R)-3-(4-fluorophenoxy)-5-(4-methyl-7H-pyrrolo[2,3-d]pyrimidin-7-yl)cyclopentane-1,2-diol (BB-4)

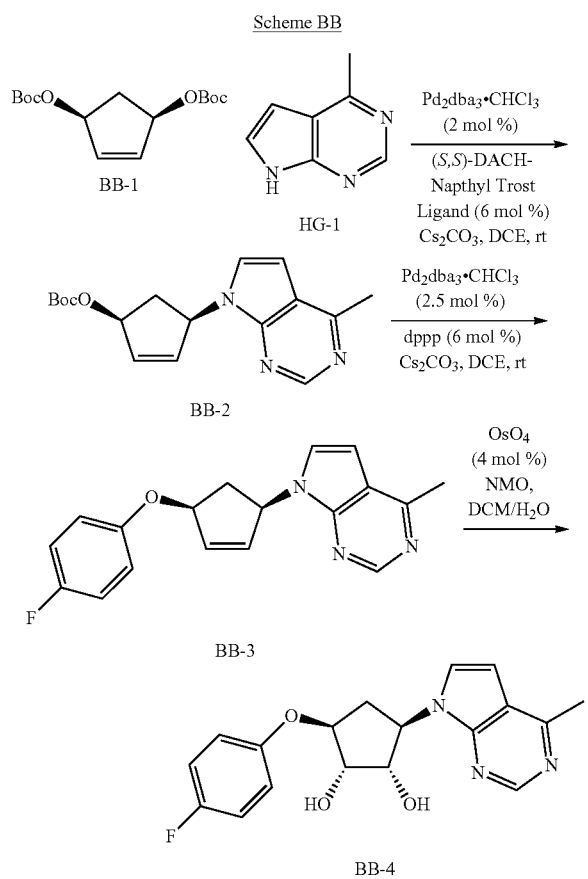

Step 1: Synthesis of tert-butyl-((1S,4R)-4-(4-methyl-7H-pyrrolo[2,3-d]pyrimidin-7-yl)cyclopent-2-en-1-yl)-carbonate (BB-2)

Vial A: To an oven dried reaction vial, equipped with a magnetic stirbar and cooled under a stream of argon, was added Tris(benzylideneacetone)dipalladium(0)chloroform adduct (78.7 mg, 0.0760 mmol) and (S,S)-DACH-Naphthyl Trost Ligand (MFCD02684552) (180 mg, 0.228 mmol). The vial was vacuum purged with argon under dynamic vacuum and DCE (7.5 mL), which had been sparged with argon for 30 minutes. The solution was stirred for 30 minutes at rt at which point a bright orange solution of ligated catalyst was obtained. At this stage Vial B was prepared.

Vial B: To an oven dried reaction vial, equipped with a magnetic stirbar and cooled under a stream of argon, was added 4-methyl-7H-pyrrolo[2,3-d]pyrimidine (HG-1) (506 mg, 3.8 mmol), di-tert-butyl-((1R,3S)-cyclopent-4-ene-1,3-diyl)-bis(carbonate) (BB-1) (prepared as reported in *J. Am. Chem. Soc.* 2006, 128, 6054-6055) (1.37 g, 4.56 mmol), and cesium carbonate (1.36 g, 4.18 mmol). The vial was vacuum purged with argon under dynamic vacuum and DCE (7.5 mL), which had been sparged with argon for 30 minutes, was added followed by the addition of the contents of Vial A via airtight syringe. The reaction was stirred under argon at rt for 48 hours. The reaction was transferred to a separatory funnel with DCM. The solution was washed with 2 portions water and 1 portion brine. A small amount of 1M HCl was used to dissipate the emulsion in the last wash. The organic phase was dried (MgSO$_4$), filtered, and concentrated under vacuum. The crude residue was purified via flash column chromatography (40 g SiO$_2$, Isco, 100% Hept. to 100% EtOAc, 20 mL fractions) to afford the compound BB-2 (814 mg, 68%, >99% ee) as a brown gum which solidified upon standing. LCMS [M+H]=316 observed; Chiral LCMS (Chiralcel OJ-3 4.6×100 mm 3µ column, 4% MeOH+10 nM NH$_3$ @ 120 bar, 4 mL/min) peak 1 @ 0.63 min., peak 2 @ 0.77 min., observed major peak @ 0.65 min, 99.8:0.2% by MS area; $^1$H NMR (400 MHz, CHLOROFORM-d) δ ppm 8.78 (s, 1H), 7.32-7.22 (m, 1H), 6.60 (d, J=3.7 Hz, 1H), 6.35-6.23 (m, 1H), 6.10 (d, J=5.4 Hz, 1H), 6.00 (br. s., 1H), 5.66-5.57 (m, 1H), 3.21-3.07 (m, 1H), 2.75 (s, 3H), 1.89 (d, J=14.9 Hz, 1H), 1.57-1.46 (m, 9H).

Step 2: Synthesis of 7-((1R,4S)-4-(4-fluorophenoxy)cyclopent-2-en-1-yl)-4-methyl-7H-pyrrolo[2,3-d]pyrimidine (BB-3)

To a scintillation vial, equipped with a magnetic stirbar, was added BB-2 (56.8 mg, 0.180 mmol), 4-fluorophenol (22.2 mg, 0.198 mmol), diphenylphosphinopropane (dppp) (4.5 mg, 0.0108 mmol), tris(dibenzylideneacetone)dipalladium(0)chloroform adduct (4.7 mg, 0.0045 mmol), and cesium carbonate (64.6 mg, 0.198 mmol). The vial was purged with argon under dynamic vacuum followed by the addition of DCE (0.9 mL) which had been sparged with argon for 30 minutes. The reaction was stirred at rt under argon for 2.5 hours. The reaction was taken up with DCM and loaded directly onto a pre-packed silica column. The crude residue was purified via flash column chromatography (12 g SiO2, Isco, 100% Hept. to 100% EtOAc, 9 mL fractions) to afford the compound BB-3 (38.8 mg, 70% yield) as a colorless gum. LCMS [M+H]=310 observed; $^1$H NMR (400 MHz, CHLOROFORM-d) δ ppm 8.77 (s, 1H), 7.34 (d, J=3.55 Hz, 1H), 6.92-7.04 (m, 2H), 6.80-6.92 (m, 2H), 6.57 (d, J=3.55 Hz, 1H), 6.37 (d, J=5.38 Hz, 1H), 6.14 (d, J=4.03 Hz, 1H), 5.97-6.09 (m, 1H), 5.17-5.34 (m, 1H), 3.02-3.18 (m, 1H), 2.56-2.91 (m, 3H), 1.97 (td, J=3.35, 14.70 Hz, 1H).

Step 3: Synthesis of (1S,2S,3S,5R)-3-(4-fluorophenoxy)-5-(4-methyl-7H-pyrrolo[2,3-d]pyrimidin-7-yl)cyclopentane-1,2-diol (BB-4)

To a scintillation vial, equipped with a magnetic stirbar and containing BB-3 (38.8 mg, 0.125 mmol), was added DCM (0.73 mL) and water (0.03 mL). To the solution was added 4-Methylmorpholine-N-oxide (NMO) (44.1 mg, 0.376 mmol) followed by the dropwise addition of osmium tetraoxide (32 µL, 0.005 mmol) as a 4 wt % solution in water. The reaction was stirred at rt for 8 hours. The reaction was quenched with 1M NaHSO$_3$ aq., stirred for 30 minutes and transferred to a separatory funnel with DCM. The solution was further diluted with water and the product was extracted with 4 portions of a 3:1 mixture of CHCl$_3$/i-PrOH. The combined organic extracts were dried (MgSO4), filtered, and concentrated under vacuum to afford the crude product as a white solid. The crude residue was purified via preparative HPLC (Lux Cellulose-1 4.6×100 mm 3µ column, 15% MeOH @ 120 bar, 4 mL/min) to afford the compound BB-4 (30.4 mg, 71%, >99% de) as a white solid. LCMS [M+H]=344 observed; [α]$^{22}$D=−36.0° (c=0.1, MeOH); $^1$H NMR (400 MHz, METHANOL-d4) δ ppm 8.61 (s, 1H), 7.58 (d, J=3.67 Hz, 1H), 6.94-7.09 (m, 4H), 6.75 (d, J=3.67 Hz, 1H), 5.27 (q, J=8.64 Hz, 1H), 4.58-4.68 (m, J=3.67 Hz, 2H), 4.17 (d, J=4.89 Hz, 1H), 2.96 (ddd, J=7.15, 9.32, 14.46 Hz, 1H), 2.71 (s, 3H), 2.09 (ddd, J=3.85, 8.53, 14.03 Hz, 1H). 19F NMR (377 MHz, METHANOL-d4) δ ppm=−125.65 (s, 1F).

Examples 74-77 were Prepared Using the Chemistry Depicted in Scheme BB and Employing the Appropriate Commercial Phenol Reagent for Step 2

| | | | |
|---|---|---|---|
| Example 74: 2,6-difluorophenyl | 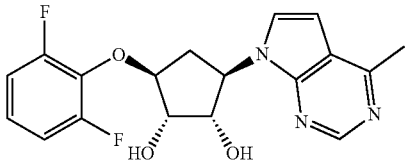 [SMILES: Cc1ncnc2c1ccn2[C@@H]1C[C@H](Oc2c(F)cccc2F)[C@@H](O)[C@H]1O] | 362 LCMS [M + 1] | (1S,2S,3S,5R)-3-(2,6-difluorophenoxy)-5-(4-methyl-7H-pyrrolo[2,3-d]pyrimidin-7-yl)cyclopentane-1,2-diol<br>$^1$H NMR (400 MHz, METHANOL-d4) δ ppm 8.64 (s, 1H), 7.70 (d, J = 4.02 Hz, 1H), 7.18-7.02 (m, 3H), 6.82 (d, J = 3.51 Hz, 1H), 5.39-5.31 (m, 1H), 4.75 (m, 1H), 4.68 (m, 1H), 4.23 (m, 1H), 3.03-2.94 (m, 1H), 2.75 (s, 3H), 2.19 (dd, J = 14.8, 5.3 Hz, 1H). |
| Example 75: 4-fluoro-2-methylphenol | 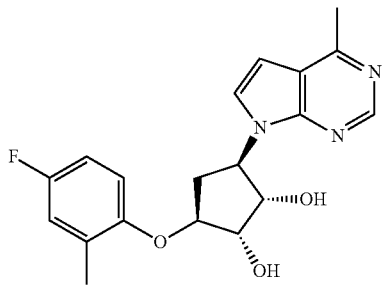 [SMILES: Cc1cc(F)ccc1O[C@H]1C[C@@H](n2ccc3c(C)ncnc32)[C@H](O)[C@@H]1O] | 358 LCMS [M + 1] | (1S,2S,3S,5R)-3-(4-fluoro-2-methylphenoxy)-5-(4-methyl-7H-pyrrolo[2,3-d]pyrimidin-7-yl)cyclopentane-1,2-diol<br>$^1$H NMR (400 MHz, MeOD-d$_4$) δ 8.63 (s, 1H), 7.59 (d, J = 3.8 Hz, 1H), 6.96 (td, J = 9.5, 4.0 Hz, 2H), 6.85-6.91 (m, 1H), 6.78 (d, J = 3.5 Hz, 1H), 5.29 (q, J = 8.8 Hz, 1H), 4.64-4.73 (m, 2H), 4.21 (d, J = 4.5 Hz, 1H), 3.01 (ddd, J = 14.6, 9.5, 7.0 Hz, 1H), 2.73 (s, 3H), 2.31 (s, 3H), 2.16 ppm (ddd, J = 14.5, 8.5, 3.4 Hz, 1H) |
| Example 76 8-hydroxy-3,4-dihydroisoquinolin-1(2H)-one | 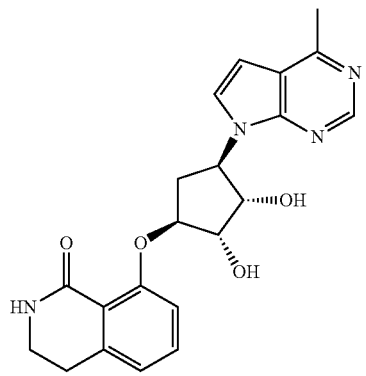 [SMILES: Cc1ncnc2c1ccn2[C@@H]1C[C@H](Oc2cccc3c2C(=O)NCC3)[C@@H](O)[C@H]1O] | 395 LCMS [M + 1] | 8-(((1S,2S,3S,4R)-2,3-dihydroxy-4-(4-methyl-7H-pyrrolo[2,3-d]pyrimidin-7-yl)cyclopentyl)oxy)-3,4-dihydroisoquinolin-1(2H)-one<br>$^1$H NMR (400 MHz, MeOD-d$_4$) δ ppm 8.60 (s, 1H), 7.97 (d, J = 4.0 Hz, 1H), 7.42 (t, J = 8.0 Hz, 1H), 7.08 (d, J = 8.8 Hz, 1H), 6.91 (d, J = 7.3 Hz, 1H), 6.75 (d, J = 3.8 Hz, 1H), 5.47-5.33 (m, 1H), 4.83-4.71 (m, 2H), 4.24 (d, J = 3.8 Hz, 1H), 3.42 (t, J = 6.5 Hz, 2H), 3.06-2.98 (m, 1H), 2.97-2.90 (m, 2H), 2.71 (s, 3H), 2.11-2.02 (m, 1H) |
| Example 77 isoquinolin-8-ol | 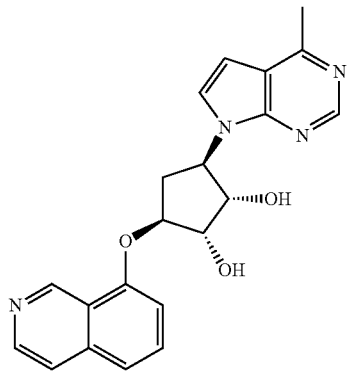 [SMILES: Cc1ncnc2c1ccn2[C@@H]1C[C@H](Oc2cccc3ccncc23)[C@@H](O)[C@H]1O] | 377 LCMS [M + 1] | (1S,2S,3S,5R)-3-(isoquinolin-8-yloxy)-5-(4-methyl-7H-pyrrolo[2,3-d]pyrimidin-7-yl) cyclopentane-1,2-diol<br>$^1$H NMR (400 MHz, DMSO-d$_6$) δ ppm 9.69 (br s, 1H), 8.62 (s, 1H), 8.56 (br d, J = 4.5 Hz, 1H), 7.83 (br d, J = 5.5 Hz, 1H), 7.79 (d, J = 3.5 Hz, 1H), 7.72 (t, J = 8.0 Hz, 1H), 7.53 (d, J = 8.0 Hz, 1H), 7.24 (d, J = 7.8 Hz, 1H), 6.76 (d, J = 3.5 Hz, 1H), 5.50 (br s, 1H), 5.20 (q, J = 1.0 Hz, 2H), 4.89-4.83 (m, 1H), 4.72-4.66 (m, 1H), 4.18 (br d, J = 4.3 Hz, 1H), 3.02-2.91 (m, 1H), 2.66 (s, 3H), 2.24-2.14 (m, 1H) |

Example 78 (Scheme CC)—(1S,2S,3S,5R)-3-((6-chloro-5-fluoro-1,2,3,4-tetrahydroisoquinolin-8-yl)oxy)-5-(4-methyl-7H-pyrrolo[2,3-d]pyrimidin-7-yl)cyclopentane-1,2-diol (CC-3)

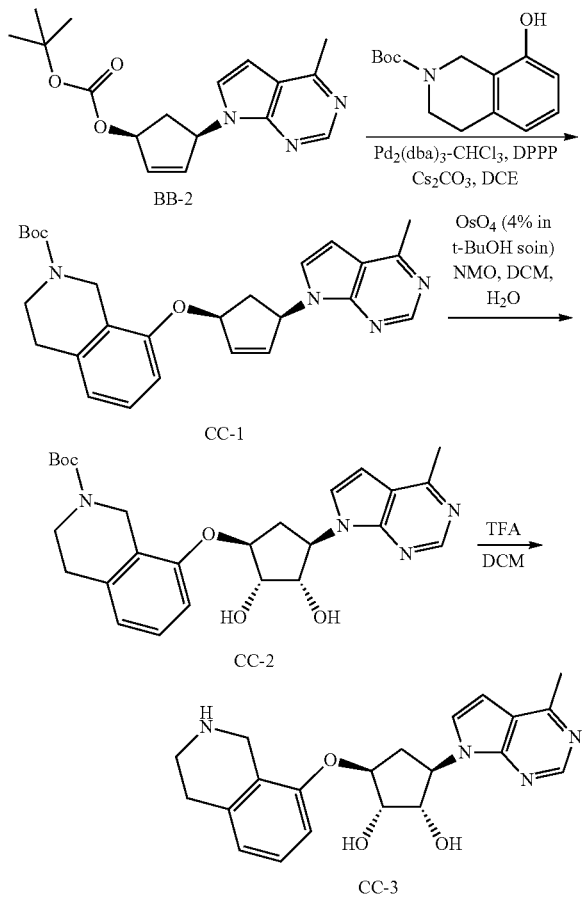

Step 1—Synthesis of tert-butyl 8-(((1S,4R)-4-(4-methyl-7H-pyrrolo[2,3-d]pyrimidin-7-yl)cyclopent-2-en-1-yl)oxy)-3,4-dihydroisoquinoline-2(1H)-carboxylate (CC-1)

To a mixture of BB-2 (600 mg, 1.9 mmol) and tert-butyl 8-hydroxy-3,4-dihydroisoquinoline-2(1H)-carboxylate (474 mg, 1.9 mmol), Cs$_2$CO$_3$(682 mg, 2.09 mmol) and DPPP (47.1 mg, 0.11 mmol) in DCE (15 mL) was sparged with N$_2$ for 40 min. To the mixture was added Pd$_2$(dba)$_3$.CHCl$_3$ (49 mg, 0.048 mmol) under N$_2$. The reaction was sparged with N$_2$ for 5 min then stirred at rt (20° C.) under N$_2$ for 40 min. The mixture was purified immediately (solution purified directly) by silica gel chromatography eluted with petroleum ether/EtOAc=8/1 to 1/1 then DCM/MeOH=12/1 to afford CC-1 (735 mg, 87%) as a yellow gum. LCMS [M+1] 447; $^1$H NMR (400 MHz, CDCl$_3$) δ ppm 8.77 (s, 1H), 7.33 (d, J=3.5 Hz, 1H), 7.13 (t, J=7.9 Hz, 1H), 6.79-6.72 (m, 2H), 6.62-6.52 (m, 1H), 6.44-6.33 (m, 1H), 6.21-6.11 (m, 1H), 6.09-6.01 (m, 1H), 5.41-5.33 (m, 1H), 4.71-4.40 (m, 2H), 3.71-3.48 (m, 2H), 3.22-3.12 (m, 1H), 2.82 (br. s., 2H), 2.73 (s, 3H), 1.98 (d, J=15.1 Hz, 1H), 1.51 (s, 9H)

Step 2—Synthesis of tert-butyl 8-(((1S,2S,3S,4R)-2,3-dihydroxy-4-(4-methyl-7H-pyrrolo[2,3-d]pyrimidin-7-yl)cyclopentyl)oxy)-3,4-dihydroisoquinoline-2(1H)-carboxylate (CC-2)

To a mixture of CC-1 (730 mg, 1.63 mmol) in DCM (15 mL)/H$_2$O (0.5 mL) was added NMO (575 mg, 4.9 mmol) and OsO$_4$ (4% in t-BuOH, 832 mg, 0.12 mmol). The mixture was stirred at rt (25° C.) for 3 hrs. Na$_2$SO$_3$ (500 mg) and water (20 mL) was added. The mixture was stirred at rt for 1 hr then the mixture was filtered. The filtrate was diluted with water (50 mL) and extracted with EtOAc (50 mL×2). The extract washed with brine (50 mL), dried over Na$_2$SO$_4$ and concentrated in vacuo and purified with silica gel chromatography eluted with MeOH in DCM from 0 to 10% to afford CC-2 (560 mg, 71%) as a white solid. LCMS [M+1] 481; $^1$H NMR (400 MHz, CDCl$_3$) δ ppm 8.67 (s, 1H), 7.24 (d, J=3.8 Hz, 1H), 7.18 (t, J=7.9 Hz, 1H), 6.90 (d, J=8.0 Hz, 1H), 6.80 (d, J=7.8 Hz, 1H), 6.60 (d, J=3.3 Hz, 1H), 5.08-4.94 (m, 1H), 4.87-4.76 (m, 1H), 4.61-4.39 (m, 3H), 4.37-4.28 (m, 1H), 3.76-3.55 (m, 2H), 3.46-3.31 (m, 1H), 3.20-3.04 (m, 1H), 2.86-2.79 (m, 2H), 2.73 (s, 3H), 2.48-2.30 (m, 1H), 1.48 (s, 9H)

Step 3—Synthesis of (1S,2S,3R,5S)-3-(4-methyl-7H-pyrrolo[2,3-d]pyrimidin-7-yl)-5-((1,2,3,4-tetrahydroisoquinolin-8-yl)oxy)cyclopentane-1,2-diol (CC-3)

To a solution of CC-2 (560 mg, 1.17 mmol) in DCM (15 mL) was added TFA (4.5 mL) at 0° C. The reaction mixture was stirred at 0° C. for 1 hour. The reaction mixture was evaporated and dissolved in water (30 mL) and K$_2$CO$_3$ (1 g) was added. The mixture was diluted with brine (30 mL) and extracted with EtOAc/THF (1/1, 30 mL×3). The extract was washed with brine (30 mL×2), dried over Na$_2$SO$_4$, filtered and concentrated in vacuo to afford CC-3 (400 mg, 90%) as a white solid. LCMS [M+1] 381; $^1$H NMR (400 MHz, DMSO-d$_6$) δ ppm 8.64 (s, 1H), 7.62 (d, J=3.8 Hz, 1H), 7.11-7.02 (m, 1H), 6.81 (d, J=8.3 Hz, 1H), 6.73 (d, J=3.5 Hz, 1H), 6.68 (d, J=7.5 Hz, 1H), 5.33 (br. s., 1H), 5.19-5.08 (m, 2H), 4.56 (br. s., 2H), 3.99 (br. s., 1H), 3.85 (s, 2H), 2.93 (t, J=5.8 Hz, 2H), 2.90-2.81 (m, 1H), 2.70-2.66 (m, 2H), 2.65 (s, 3H), 1.98-1.86 (m, 1H)

Examples 79 & 80 were Prepared Using the Chemistry Depicted in Scheme CC and Employing the Appropriate Commercial NBoc-Protected Phenol Reagent for Step 1

| Example 79<br>tert-butyl 4-hydroxyisoindoline-2-carboxylate | 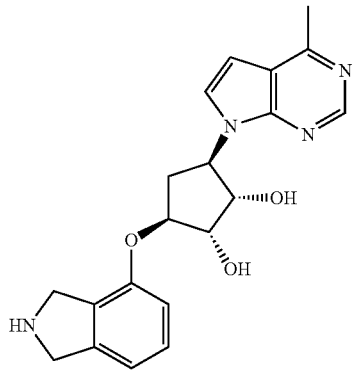 [SMILES: Cc1ncnc2c1ccn2[C@@H]1C[C@H](Oc2cccc3c2CNC3)[C@@H](O)[C@H]1O] | 367 LCMS [M + 1] | (1S,2S,3S,5R)-3-(2,3-dihydro-1H-isoindol-4-yloxy)-5-(4-methyl-7H-pyrrolo[2;3-d]pyrimidin-7-yl)cyclopentane-1,2-diol<br>$^1$H NMR (400 MHz, MeOD-$d_4$) δ ppm 8.63 (s, 1H), 8.43-8.33 (m, 1H), 7.59 (d, J = 3.5 Hz, 1H), 7.45-7.36 (m, 1H), 7.13-7.08 (m, 1H), 7.07-7.01 (m, 1H), 6.77 (d, J = 3.8 Hz, 1H), 5.28-5.19 (m, 1H), 4.82-4.78 (m, 1H), 4.76-4.71 (m, 1H), 4.67 (d, J = 4.8 Hz, 4H), 4.24 (d, J = 3.8 Hz, 1H), 3.08-2.94 (m, 1H), 2.73 (s, 3H), 2.28-2.15 (m, 1H) |
| --- | --- | --- | --- |
| Example 80<br>tert-butyl 5-hydroxy-3,4-dihydroisoquinoline-2(1H)-carboxylate | 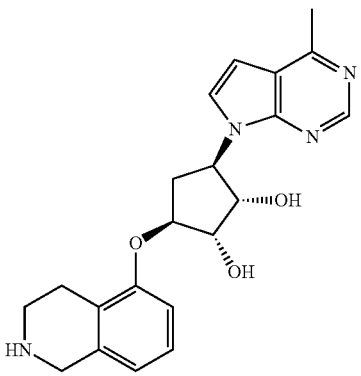 [SMILES: Cc1ncnc2c1ccn2[C@@H]1C[C@H](Oc2cccc3c2CCNC3)[C@@H](O)[C@H]1O] | 381 LCMS [M + 1] | (1S,2S,3R,5S)-3-(4-methyl-7H-pyrrolo[2,3-d]pyrimidin-7-yl)-5-((1,2,3,4-tetrahydroisoquinolin-5-yl)oxy)cyclopentane-1,2-diol<br>$^1$H NMR (400 MHz, DMSO-$d_6$) δ ppm 8.64 (s, 1H), 7.64 (d, J = 3.5 Hz, 1H), 7.26-7.18 (m, 1H), 6.99 (d, J = 8.0 Hz, 1H), 6.82 (d, J = 7.8 Hz, 1H), 6.73 (d, J = 3.5 Hz, 1H), 5.40 (br. s., 1H), 5.19-5.08 (m, 2H), 4.66-4.54 (m, 2H), 4.22 (s, 2H), 4.02 (br. s., 1H), 2.96-2.83 (m, 3H), 2.65 (s, 3H), 2.01-1.90 (m, 1H) |

Example 81 (Scheme DD)—(1S,2S,3R,5S)-3-(4-methyl-7H-pyrrolo[2,3-d]pyrimidin-7-yl)-5-[(2-methyl-1,2,3,4-tetrahydroisoquinolin-5-yl)oxy]cyclopentane-1,2-diol (DD-1)

Scheme DD

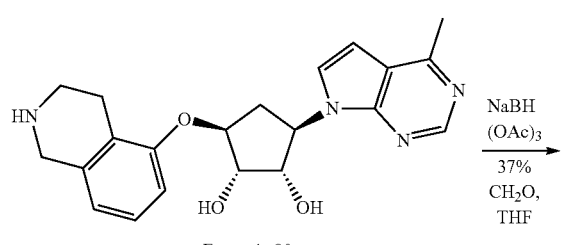

Example 80

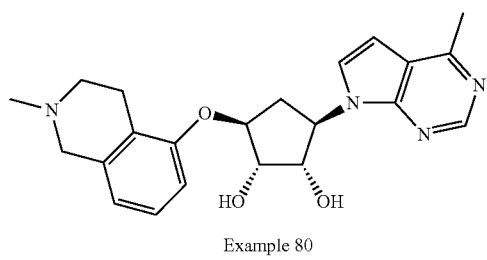

Example 80

Step 1: Synthesis of (1S,2S,3R,5S)-3-(4-methyl-7H-pyrrolo[2,3-d]pyrimidin-7-yl)-5-[(2-methyl-1,2,3,4-tetrahydroisoquinolin-5-yl)oxy]cyclopentane-1,2-diol (DD-1)

A mixture of compound Example 80 (42 mg, 0.11 mmol), 37% CH$_2$O (26.9 mg, 0.331 mmol) and NaBHOAc$_3$ (93.6 mg, 0.442 mmol) in THF (1.2 mL) was stirred at rt for 2 hrs. The mixture was poured into NaHCO$_3$ aq (10 mL) and extracted with EtOAc (20 mL×4). The extract was dried over Na$_2$SO$_4$ and concentrated in vacuo to afford the residue (50 mg) as a white solid which was purified by prep-TLC (DCM:MeOH=10:1 with NH$_3$.H$_2$O) to give DD-1 (35 mg, 80%) as a white solid. LCMS 395 [M+1]; $^1$H NMR (400 MHz, DMSO-$d_6$) δ ppm 8.63 (s, 1H), 7.63 (d, J=3.5 Hz, 1H), 7.16 (t, J=8.0 Hz, 1H), 6.92 (d, J=8.5 Hz, 1H), 6.75-6.69 (m, 2H), 5.36 (d, J=3.8 Hz, 1H), 5.18-5.09 (m, 2H), 4.64-4.54 (m, 2H), 4.02 (br. s., 1H), 3.83 (br. s., 2H), 2.99 (br. s., 2H), 2.92-2.82 (m, 3H), 2.65 (s, 3H), 2.58 (br. s., 3H), 1.95 (ddd, J=3.8, 9.5, 13.8 Hz, 1H)

Example 82 & 83 was Made in a Similar Fashion from Example 79 & 78 Respectively

| Example 82 | 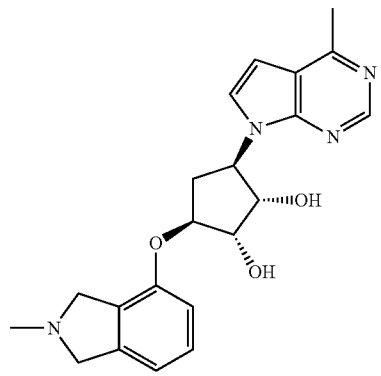 [SMILES: Cc1ncnc2c1ccn2[C@@H]1C[C@H](Oc2cccc3c2CN(C)C3)[C@@H](O)[C@H]1O] | 381 [M + 1] | (1S,2S,3S,5R)-3-(2-methyl-2,3-dihydro-1H-isoindol-4-yl)oxy]-5-(4-methyl-7H-pyrrolo[2,3-d]pyrimidin-7-yl)cyclopentane-1,2-diol<br>$^1$H NMR (400 MHz, MeOD-d$_4$) δ ppm 8.62 (s, 1H), 7.56 (d, J = 3.8 Hz, 1H), 7.21 (t, J = 7.9 Hz,1H), 6.89 (dd, J = 7.8, 14.1 Hz, 2H), 6.77 (d, J = 3.8 Hz, 1H), 5.29 (q, J = 8.7 Hz, 1H), 4.73 (ddd, J = 1.8, 3.5, 7.0 Hz, 1H), 4.65 (dd, J = 4.8, 8.8 Hz, 1H), 4.18 (d, J = 4.5 Hz, 1H), 3.97 (d, J = 12.5 Hz, 4H), 3.00 (ddd, J = 7.0, 9.5, 14.6 Hz, 1H), 2.71 (s, 3H), 2.62 (s, 3H), 2.15-2.07 (m, 1H) |
| --- | --- | --- | --- |
| Example 83 | 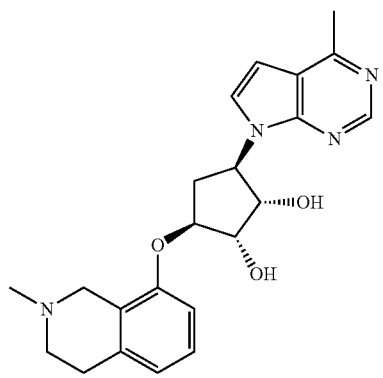 [SMILES: Cc1ncnc2c1ccn2[C@@H]1C[C@H](Oc2cccc3c2CN(C)CC3)[C@@H](O)[C@H]1O] | 395 [M + 1] | (1S,2S,3S,5R)-3-((2-methyl-1,2,3,4-tetrahydroisoquinolin-8-yl)oxy)-5-(4-methyl-7H-pyrrolo[2,3-d]pyrimidin-7-yl)cyclopenlane-1,2-diol<br>$^1$H NMR (400 MHz, MeOD-d$_4$) δ ppm 8.62 (s, 1H), 7.57 (d, J = 3.8 Hz, 1H), 7.22 (t, J = 8.0 Hz, 1H), 6.93 (d, J = 7.8 Hz, 1H), 6.84 (d, J = 7.5 Hz, 1H), 6.76 (d, J = 3.8 Hz, 1H), 5.23 (q, J = 8.9 Hz, 1H), 4.74-4.68 (m, 2H), 4.20 (d, J = 5.5 Hz, 1H), 4.05 (s, 2H), 3.19-3.12 (m, 2H), 3.10-3.05 (m, 2H), 3.00 (ddd, J = 7.0, 9.3, 14.3 Hz, 1H), 2.83 (s, 3H), 2.72 (s, 3H), 2.24-2.15 (m, 1H) |

Synthesis of tert-butyl 6-fluoro-8-hydroxy-3,4-dihydroisoquinoline-2(1H)-carboxylate (TP-1)

Scheme EE

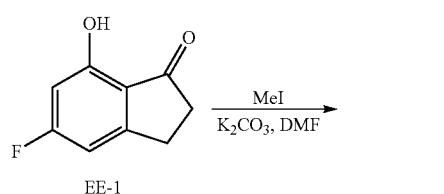

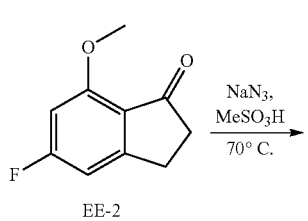

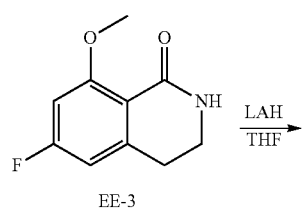

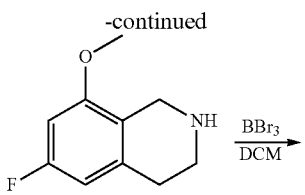

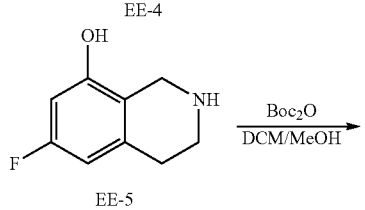

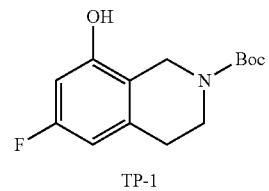

Step 1—Synthesis of 5-fluoro-7-methoxy-2,3-dihydro-1H-inden-1-one (EE-2)

To a solution of 5-fluoro-7-hydroxy-2,3-dihydro-1H-inden-1-one (prepared in a similar manner as *Bio. Med. Chem Letters*, 20, 1004-1007, 2010) (1 g, 6.02 mmol) and K$_2$CO$_3$ (2.5 g, 18 mmol) in dry DMF (10 mL) was added MeI (1710 mg, 12.0 mmol) at 0° C. After the addition, the reaction was stirred at 25° C. for 4 hours. The reaction mixture was partitioned between EtOAc and H₂O. The aqueous layer was extracted with EtOAc. The combined organic layers was washed with brine, dried over Na₂SO₄ and concentrated to afford EE-2 (1 g, 92%) as a yellow solid. LCMS 181 [M+1]; ¹H NMR (400 MHz, CDCl₃) δ ppm 6.73-6.69 (m, 1H), 6.51 (dd, J=2.0, 11.3 Hz, 1H), 3.94 (s, 3H), 3.13-3.03 (m, 2H), 2.73-2.65 (m, 2H)

Step 2—Synthesis of 6-fluoro-8-methoxy-3,4-dihydroisoquinolin-1(2H)-one (EE-3)

To a solution of EE-2 (950 mg, 5.27 mmol) in 1,2-DCE/MeSO₃H (38 mL/29 mL) at 0° C. was added portion-wise NaN₃ (1.4 mg, 21.1 mmol). After addition, the mixture was stirred at 70° C. for 16 hrs. The mixture was cooled to 0° C., adjusted to pH 7-8 with addition of aqueous NaHCO₃ (sat). The mixture was extracted with DCM (15 mL×2), dried over Na₂SO₄, filtered and concentrated to give EE-3 (1.15 g, 74%) as a brown solid. LCMS 196 [M+1]; ¹H NMR (400 MHz, DMSO-d₆) δ ppm 7.70 (br. s., 1H), 6.85 (dd, J=2.4, 11.9 Hz, 1H), 6.73 (dd, J=2.4, 8.9 Hz, 1H), 3.76 (s, 3H), 3.21 (dt, J=3.5, 6.3 Hz, 2H), 2.80 (t, J=6.3 Hz, 2H)

Step 3—Synthesis of 6-fluoro-8-methoxy-1,2,3,4-tetrahydroisoquinoline (EE-4)

Compound EE-4 was prepared from EE-3 in a similar method as step 5 in Scheme FF to give crude EE-4 (455 mg, >99%) as a yellow oil and used directly in the next step. LCMS 182 [M+1]; ¹H NMR (400 MHz, DMSO-d₆) δ ppm 6.63 (dd, J=2.3, 11.3 Hz, 1H), 6.48 (dd, J=2.3, 9.5 Hz, 1H), 3.75 (s, 3H), 3.67-3.61 (m, 2H), 2.85 (t, J=5.8 Hz, 2H), 2.61 (t, J=5.6 Hz, 2H)

Step 4—Synthesis of 6-fluoro-1,2,3,4-tetrahydroisoquinolin-8-ol (EE-5)

Compound EE-5 was prepared from EE-4 in a similar method as step 6 in Scheme FF to give crude EE-5 (228 mg, 54%) as a yellow solid. LCMS 168 [M+1]; ¹H NMR (400 MHz, DMSO-d₆) δ ppm 6.39-6.28 (m, 2H), 3.63 (s, 2H), 2.85 (t, J=5.8 Hz, 2H), 2.63-2.57 (m, 2H)

Step 5—Synthesis of tert-butyl 6-fluoro-8-hydroxy-3,4-dihydroisoquinoline-2(1H)-carboxylate (TP-1)

Compound TP-1 was prepared from EE-5 in a similar method as step 7 in Scheme FF to give TP-1 (182 mg, 50%) as a yellow solid. MS 212 [M-56+1]; ¹H NMR (400 MHz, DMSO-d₆) δ ppm 10.11 (s, 1H), 6.45 (d, J=10.5 Hz, 2H), 4.29 (s, 2H), 3.51 (m, J=5.8 Hz, 2H), 2.69 (m, J=5.6 Hz, 2H), 1.43 (s, 9H)

Synthesis of tert-butyl 5-fluoro-8-hydroxy-3,4-dihydroisoquinoline-2(1H)-carboxylate (TP-2)

Scheme FF

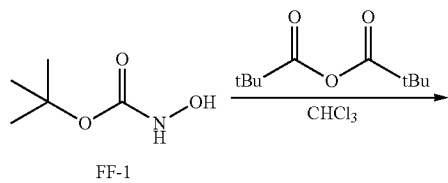

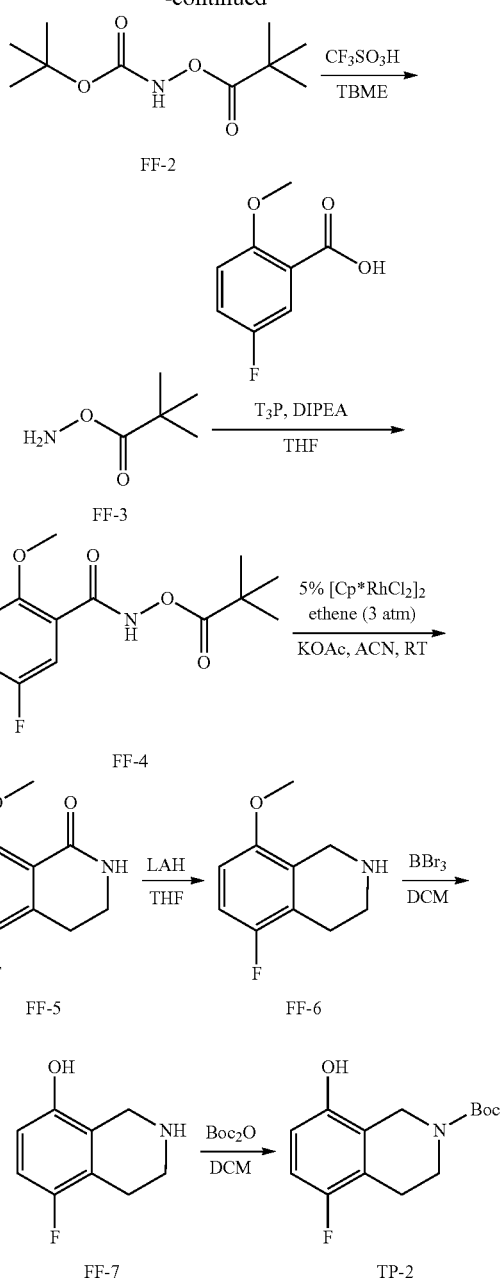

Step 1—Synthesis of tert-butyl(pivaloyloxy)carbamate (FF-2)

To a solution of compound FF-1 (20 g, 150 mmol) in CHCl₃ (200 mL) was slowly added pivalic anhydride (34 g, 180 mmol) in an ice bath and then stirred at 70° C. for 16 h. The reaction solution was diluted with DCM (200 mL) and washed with saturated NaHCO₃ (200 mL×2) until pH-7. The organic layer was dried over Na₂SO₄, filtered and concentrated under reduced pressure to afford a light yellow oil. The crude product was crystallized with petroleum ether (20 mL) to afford FF-2 (18 g, 55%) as a white solid. ¹H NMR (400 MHz, CDCl₃) δ ppm 7.8 (br. s., 1H), 1.5 (s, 9H), 1.3 (s, 9H)

Step 2—Synthesis of O-pivaloylhydroxylamine (FF-3)

To a solution of FF-2 (16 g, 70 mmol) in TBME (32 mL) was added $CF_3SO_3H$ (10.6 g, 70.7 mmol) at 0° C. The reaction solution was stirred at 15° C. for 2 h. The reaction mixture was evaporated to give the crude product FF-3 (20 g, >99%) as a white solid and used directly in the next reaction.

Step 3—Synthesis of 5-fluoro-2-methoxy-N-(pivaloyloxy)benzamide (FF-4)

To a solution of 5-fluoro-2-methoxybenzoic acid (4.50 g, 26.4 mmol) in THF (90.0 mL) was added T3P (19 g, 29.1 mmol) at 0° C. After the addition, the reaction mixture was stirred for 30 min at 25° C. To the reaction mixture was added DIPEA (13.8 mL, 8.82 mmol) followed by FF-3 (7.28 g, 29.1 mmol). After the addition, the reaction mixture was stirred at 25° C. for 16 hours. The reaction mixture was filtered and the filtrate was partitioned between EtOAc and $H_2O$. The organic layer was separated, dried over $Na_2SO_4$ and concentrated to afford the crude product which was purified via flash column chromatography (EtOAc: petroleum ether=1~100%, then MeOH:DCM=1%~10%) to afford FF-4 (9 g, >99%) as a white solid and used directly in the next reaction.

Step 4—Synthesis of 5-fluoro-8-methoxy-3,4-dihydroisoquinolin-1(2H)-one (FF-5)

A suspension of FF-4 (8.00 g, 28.0 mmol), KOAc (6.06 g, 61.7 mmol) and $[Cp^*RhCl_2]_2$ (867 mg, 1.40 mmol) in MeCN (100 mL) in a vessel was purged with $N_2$ for 5 min and then cooled to −40° C. with dry ice/acetone. Ethylene was purged into the vessel for 30 min then sealed and stirred at 25° C. for 16 h. The dark red suspension was filtered and the filtrate cake was washed with $CH_3CN$. The combined filtrate was concentrated to afford the crude product which was purified via flash column chromatography (EtOAc: Petroleum ether=1%~100%, then MeOH:DCM=1~8%) to afford FF-5 (4.62 g, 84%) as a yellow solid. $^1H$ NMR (400 MHz, DMSO-$d_6$) δ ppm 7.85 (br. s., 1H), 7.32 (t, J=9.0 Hz, 1H), 6.99 (dd, J=4.3, 9.3 Hz, 1H), 3.76 (s, 3H), 3.31-3.22 (m, 2H), 2.79 (t, J=6.3 Hz, 2H)

Step 5—Synthesis of 5-fluoro-8-methoxy-1,2,3,4-tetrahydroisoquinoline (FF-6)

To a solution of FF-5 (4.66 g, 23.9 mmol) in dry THF (240 mL) was added LiAlH4 (3.62 g, 95.5 mmol) portion-wise. After the addition, the reaction mixture was heated at 65° C. (reflux) for 2 hours. The reaction mixture was quenched with 4 mL of $H_2O$. The mixture was distilled in EtOAc and filtered. The filtrate cake was washed with EtOAc. The filtrate was dried over $Na_2SO_4$ and concentrated to afford the crude product which was purified via flash column chromatography (MeOH:DCM=1~8%) to afford FF-6 (2.9 g, 66%) as a yellow gum. $^1H$ NMR (400 MHz, DMSO-$d_6$) δ ppm 6.92 (t, J=9.2 Hz, 1H), 6.73 (dd, J=4.4, 8.9 Hz, 1H), 3.73 (s, 3H), 3.69 (s, 2H), 2.88 (t, J=5.8 Hz, 2H), 2.55 (t, J=5.8 Hz, 2H)

Step 6—Synthesis of 5-fluoro-1,2,3,4-tetrahydroisoquinolin-8-ol (FF-7)

To a solution of FF-6 (2.86 g, 15.8 mmol) in DCM (28.6 mL) was added $BBr_3$ (2.86 mL, 30.3 mmol) at −10° C. drop-wise. After the addition, the reaction mixture was stirred at 0° C. for 2 hours. The reaction mixture was cooled to −10° C. and quenched with MeOH. The resulting mixture was diluted in $H_2O$, basified with sat. $K_2CO_3$ to pH 9~10 and then extracted with EtOAc (50 mL×3). The combined organic layers were washed with brine, dried over $Na_2SO_4$ and concentrated to afford the crude product which was purified via flash column chromatography (MeOH:DCM=1:10) to afford FF-7 (1.0 g, 38%) as a yellow solid. $^1H$ NMR (400 MHz, DMSO-$d_6$) δ ppm 9.24 (br. s., 1H), 6.76 (t, J=9.0 Hz, 1H), 6.55 (dd, J=4.6, 8.7 Hz, 1H), 3.69 (s, 2H), 2.90 (t, J=5.9 Hz, 2H), 2.54 (t, J=6.4 Hz, 2H)

Step 7—Synthesis of tert-butyl 5-fluoro-8-hydroxy-3,4-dihydroisoquinoline-2(1H)-carboxylate (TP-2)

To a solution of FF-7 (1.0 g, 6 mmol) in DCM (25.00 mL) and MeOH (5 mL) was added $Boc_2O$ (1.4 g, 6.6 mmol) followed by $Et_3N$ (2.08 mL, 15.0 mmol) at 0° C. After the addition, the reaction mixture was stirred at 25° C. for 16 hours. The reaction mixture was acidified with aq. citric acid to pH 3-4 and the resulting mixture was partitioned between DCM and $H_2O$. The organic layer was separated and the aqueous layer was extracted with DCM. The combined organic layers were washed with sat. $NaHCO_3$, brine, dried over $Na_2SO_4$ and concentrated to afford the crude product which was purified via flash column chromatography (MeOH:DCM=1:10) to afford the TP-2 (744 mg, 47%) as a white solid. MS 212 [M-55+1]; $^1H$ NMR (400 MHz, DMSO-$d_6$) δ ppm 9.55 (s, 1H), 6.83 (t, J=9.0 Hz, 1H), 6.62 (dd, J=4.6, 8.9 Hz, 1H), 4.32 (s, 2H), 3.52 (t, J=5.9 Hz, 2H), 2.63 (t, J=5.6 Hz, 2H), 1.41 (s, 9H)

The Procedures Above in Scheme FF were Used to Synthesis the Hydroxytetrahydroisoquinoline Intermediates TP-3 through TP-7.

| | | | |
|---|---|---|---|
| TP-3 | (structure: 6-Cl, 8-OH tetrahydroisoquinoline-N-Boc) | 228 LCMS = [M − 55 + 1] | tert-butyl 6-chloro-8-hydroxy-3,4-dihydroisoquinoline-2(1H)-carboxylate $^1H$ NMR (400 MHz, DMSO-$d_6$) δ ppm 10.13 (s, 1H), 6.68 (s, 2H), 4.29 (s, 2H), 3.53-3.45 (t, J = 5.6 Hz, 2H), 2.74-2.64 (t, J = 5.5 Hz, 2H), 1.42 (s, 9H) |
| TP-4 | (structure: 6-CF3, 8-OH tetrahydroisoquinoline-N-Boc) | 262 LCMS = [M − 55 + 1] | tert-butyl 8-hydroxy-6-(trifluoromethyl)-3,4-dihydroisoquinoline-2(1H)-carboxylate $^1H$ NMR (400 MHz, DMSO-$d_6$) δ ppm 10.36 (br. s., 1H), 7.00-6.96 (s, 1H), 6.95-6.91 (s, 1H), 4.40 (s, 2H), 3.55 (t, J = 5.8 Hz, 2H), 2.79 (t, J = 5.6 Hz, 2H), 1.44 (s, 9H) |

| | | | |
|---|---|---|---|
| TP-5 | 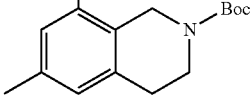 | 208 LCMS = [M − 55 + 1] | tert-butyl 8-hydroxy-6-methyl-3,4-dihydroisoquinoline-2(1H)-carboxylate <br> $^1$H NMR (400 MHz, CDCl$_3$) δ ppm 6.58-6.51 (m, 1H), 6.46 (s, 1H), 4.51 (br. s., 2H), 3.64-3.60 (m, 2H), 2.80-2.76 (m, 2H), 2.25 (s, 3H), 1.51 (s, 9H) |
| TP-6 | 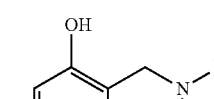 | 230 LCMS = [M − 55 + 1] | tert-butyl 5,6-difluoro-8-hydroxy-3,4-dihydroisoquinoline-2(1H)-carboxylate <br> $^1$H NMR (400 MHz, DMSO-d$_6$) δ ppm 10.04 (s, 1H), 6.63(dd, J = 6.8, 12.3 Hz, 1H), 4.30 (s, 2H), 3.60-3.50 (t, J = 5.8 Hz, 2H), 2.75-2.65 (t, J = 5.9 Hz, 2H), 1.42 (s, 9H) |
| TP-7 | 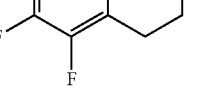 | 320 LCMS = [M − 55 + 1] | tert-butyl 8-hydroxy-5-iodo-3,4-dihydroisoquinoline-2(1H)-carboxylate <br> $^1$H NMR (400 MHz, DMSO-d$_6$) δ ppm 9.93 (s, 1H), 7.50 (d, J = 8.3 Hz, 1H), 6.54 (d, J = 8.5 Hz, 1H), 4.32 (s, 2H), 3.59-3.49 (m, 2H), 2.57 (t, J = 5.8 Hz, 2H), 1.42 (s, 9H) |

Synthesis of tert-butyl 8-hydroxy-6-(2-hydroxypropan-2-yl)-3,4-dihydroisoquinoline-2(1H)-carboxylate (TP-9)

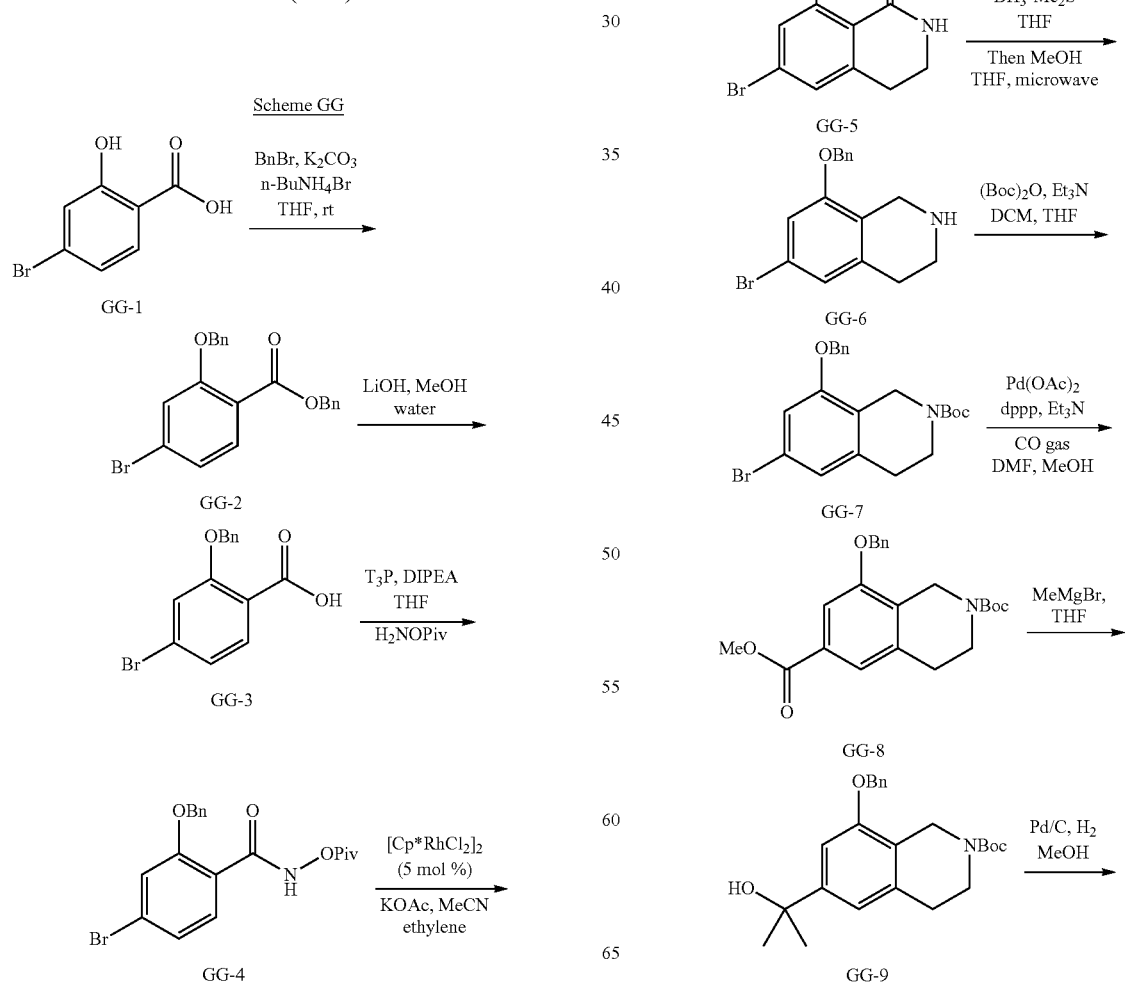

-continued

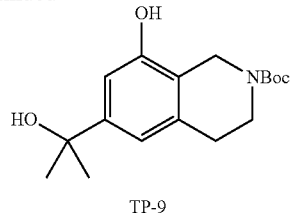

TP-9

Step 1: Synthesis of benzyl 2-(benzyloxy)-4-bromobenzoate (GG-2)

To a solution of the salicyclic acid GG-1 (50 g, 230 mmol) in THF (1000 mL) was added potassium carbonate (95.5 g, 691 mmol), tetrabutyl ammonium bromide (14.9 g, 46.1 mmol) and benzyl bromide (95.8 g, 576 mmol). The reaction was stirred at 20° C. for 16 hours. The solution was filtered and concentrated under vacuum to afford the desired product GG-2 as a crude brown solid (150 g). This material was used in the next step without further purification. TLC (PE./EA=10:1, Rf~0.5)

Step 2: Synthesis of 2-(benzyloxy)-4-bromobenzoic acid (GG-3)

To a solution of GG-2 (140 g, 352 mmol, crude, ~53% of purity) in MeOH/water/DCM (500 mL/500 mL/500 mL) was added lithium hydroxide (44.4 g, 1060 mmol) at 10° C. The reaction was stirred at 70° C. for 16 hours. The solution was concentrated under vacuum and a yellow solid precipitated from the solution. The solids were filtered and the filter cake was washed with water (50 mL×2). The yellow solid was acidified with 1N HCl to pH=2. Yellow solid was filtered and dried in an infrared oven to give compound GG-3 (43.3 g, 40%) as a yellow solid. $^1$NMR (400 MHz, DMSO-d6) δ ppm 12.76 (bs, 1H), 7.61 (d, J=8.3 Hz, 1H), 7.52-7.47 (m, 2H), 7.44 (d, J=1.8 Hz, 1H), 7.43-7.38 (m, 2H), 7.37-7.31 (m, 1H), 7.23 (dd, J=1.8, 8.3 Hz, 1H), 5.25 (s, 2H).

Step 3: Synthesis of 2-(benzyloxy)-4-bromo-N-(pivaloyloxy)-benzamide (GG-4)

To a solution of GG-3 (31.2 g, 101.58 mmol) in THF (630 mL) was added T$_3$P (71.1 g, 112 mmol) at 0° C. After the addition, the reaction mixture was stirred for 30 minutes at 25° C. To the above solution was added DIPEA (78.8 g, 609 mmol) followed by O-pivaloylhydroxylamine (28 g, 112 mmol). After the addition, the reaction mixture was stirred at 25° C. for 2 hours. The solution was transferred to a separatory funnel with EtOAc (500 mL) and washed with 1 portion water (300 mL), 1 portion citric acid aq. (300 mL), 1 portion sat. NaHCO$_3$, and 1 portion brine (300 mL). The organic layer was dried over Na$_2$SO$_4$, filtered, and concentrated under vacuum. The crude residue was purified via flash column chromatography (silica gel, petroleum ether: EtOAc=7:1) to afford compound GG-4 (30.4 g, 74%) as a yellow solid. $^1$H NMR (400 MHz, DMSO-d6) δ ppm 10.74 (s, 1H), 8.06 (d, J=8.5 Hz, 1H), 7.52-7.35 (m, 5H), 7.28 (d, J=1.5 Hz, 1H), 7.26 (d, J=1.8 Hz, 1H), 7.23 (d, J=1.5 Hz, 1H), 5.27 (s, 2H), 1.34 (s, 9H)

Step 4: Synthesis of 8-(benzyloxy)-6-bromo-1-oxo-3,4-dihydroisoquinolin-2(1H)-yl pivalate (GG-5)

A suspension of GG-4 (40.7 g, 100.18 mmol), KOAc (10.8 g, 110 mmol) and Cp$_2$RhCl$_2$ (3.1 g, 5.01 mmol) in MeCN (1300 mL) was cooled to 0° C. and the solution was sparged with ethylene gas for 45 minutes. The vessel was sealed and stirred at 10° C. for 16 hours. The reaction suspension was filtered and the cake was washed with 2 portions of a 5:1 mixture of DCM/MeOH (100 mL). The filtrate was concentrated under reduced pressure to give the crude product (50 g) as a yellow solid. The crude residue was purified via flash column chromatography (silica gel, DCM:MeOH=40:1) to afford compound GG-5 (28 g, 84%) as a yellow solid. LCMS [M+H+Na] 356 observed; $^1$H NMR (400 MHz, DMSO-d$_6$) δ ppm 7.79 (t, J=3.1 Hz, 1H) 7.53-7.59 (m, 2H) 7.35-7.42 (m, 2H) 7.30-7.34 (m, 1H) 7.26 (d, J=2.0 Hz, 1H) 7.15 (d, J=2.0 Hz, 1H) 5.20 (s, 2H) 3.25 (td, J=6.1, 3.6 Hz, 2H) 2.83 (t, J=6.3 Hz, 2H).

Step 5: Synthesis of 8-(benzyloxy)-6-bromo-3,4-dihydroisoquinolin-1(2H)-one (GG-6)

To a mixture of GG-5 (36.5 g, 110 mmol) in anhydrous THF (700 mL) was added BH$_3$.Me$_2$S (10M, 33 mL, 330 mmol) at 0° C. dropwise under N$_2$. After the addition, the reaction was stirred at 5° C. for 12 hours. At this stage, the reaction mixture was heated at 78° C. (reflux) for 3 hours to drive completion. The reaction was allowed to cool gradually to rt and carefully quenched with 70 mL of MeOH at 0° C. The solution was concentrated then taken up in THF (2 mL) and MeOH (10 mL) and transferred to a microwave vial. The solution was heated at 120° C. in a microwave reactor for 1 hour. The solution was concentrated to afford a black solid. The crude residue was purified via flash column chromatography (120 g silica gel×3, MeOH/DCM=10%~20%) to afford compound GG-6 (8.28 g, 24%) as a brown solid. LCMS [M+H] 319 observed; $^1$H NMR (400 MHz, DMSO-d$_6$) δ ppm 8.99 (br. s, 1H) 7.37-7.50 (m, 5H) 7.23 (d, J=1.3 Hz, 1H) 7.11 (d, J=1.3 Hz, 1H) 5.21 (s, 2H) 4.11 (s, 2H) 2.97 (t, J=5.9 Hz, 2H).

Step 6: Synthesis of tert-butyl 8-(benzyloxy)-6-bromo-3,4-dihydroisoquinoline-2(1H)-carboxylate (GG-7)

To a mixture of GG-6 (10.99 g, 34.537 mmol) in DCM (110 mL) and THF (22 mL) were added Et$_3$N (10.5 g, 104 mmol) and (Boc)$_2$O (11.3 g, 51.8 mmol) at 10° C. The reaction was stirred at 10° C. for 16 hours. The mixture was concentrated under vacuum to give the crude product as black gum. The crude residue was purified by flash column chromatography (120 g of silica gel, EtOAc/Petroleum ether from 4% to 7%) to afford compound GG-7 (9.9 g, 68.5%) as yellow gum. LCMS [M+H-Boc] 319 observed; $^1$H NMR (400 MHz, CHLOROFORM-d) δ ppm 7.48-7.30 (m, 5H), 6.98-6.88 (m, 2H), 5.15-4.96 (m, 2H), 4.60-4.44 (m, 2H), 3.71-3.54 (m, 2H), 2.88-2.71 (m, 2H), 1.50 (s, 9H).

Step 7: Synthesis of 2-(tert-butyl) 6-methyl 8-(benzyloxy)-3,4-dihydroisoquinoline-2,6(1H)-dicarboxylate (GG-8)

A mixture of GG-7 (600 mg, 1.43 mmol), DPPP (296 mg, 0.717 mmol), TEA (435 mg, 4.30 mmol) and Pd(OAc)$_2$ (161 mg, 0.717 mmol) in MeOH (20 mL) and DMF (20 mL) was heated at 120° C. under 22 bar of carbon monoxide for 24 hours. The mixture was concentrated under vacuum and transferred to a separatory funnel with EtOAc. The solution was washed with 5 portions brine, dried over sodium sulfate, filtered, and concentrated under vacuum. The crude residue was purified via flash column chromatography (12 g, silica gel, 20% EtOAc/petroleum ether) to afford compound GG-8 (440 mg, 77% yield) as a white solid. $^1$H NMR (400 MHz, CHLOROFORM-d) δ ppm 7.54-7.28 (m, 7H), 5.22-5.08 (m, 2H), 4.67-4.54 (m, 2H), 3.91 (s, 3H), 3.70-3.57 (m, 2H), 2.93-2.77 (m, 2H), 1.50 (s, 9H).

Step 8: Synthesis of tert-butyl 8-(benzyloxy)-6-(2-hydroxypropan-2-yl)-3,4-dihydroisoquinoline-2(1H)-carboxylate (GG-9)

To a colorless solution of GG-8 (327 mg, 0.823 mmol) in dry THF (15 mL) was added MeMgBr (3.0 M solution in diethyl ether, 1.65 mL, 4.94 mmol) dropwise at 0° C. The mixture was stirred at 17° C. for 1.5 hours. The solution was cooled to 0° C. and quenched with water (10 mL). The solution was transferred to a separatory funnel with EtOAc and the phases were separated. The aqueous phase was extracted with 2 portions EtOAc (20 mL). the combined organic extracts were washed with 1 portion brine (30 mL), dried over sodium sulfate, filtered, and concentrated under vacuum. The crude residue was purified via flash column chromatography (silica gel, 12 g, petroleum ether:EA=3:1) to afford compound GG-9 (320 mg, 98%) as colorless gum. $^1$H NMR (400 MHz, CHLOROFORM-d) δ ppm 7.29-7.49 (m, 5H) 6.97 (s, 1H) 6.84 (s, 1H) 5.12 (br. s., 2H) 4.58 (s, 2H) 3.65 (br. s., 2H) 2.82 (br. s., 2H) 1.57 (s, 6H) 1.49 (s, 9H).

Step 9: Synthesis of tert-butyl 8-hydroxy-6-(2-hydroxypropan-2-yl)-3,4-dihydroisoquinoline-2(1H)-carboxylate (TP-9)

A mixture of GG-9 (290 mg, 0.73 mmol) and Pd/C (105 mg) in MeOH (10 mL) was stirred at 15° C. for 5 hours under a balloon of hydrogen. The mixture was filtered through a pad of Celite and the filtrate concentrated under vacuum. The crude residue was purified via flash column chromatography (4 g, silica gel, 60% EtOAc/petroleum ether) to afford compound TP-9 (144 mg, 64%) as a white solid. 1H NMR (400 MHz, CHLOROFORM-d) δ ppm 6.91 (br. s., 1H), 6.76 (s, 1H), 4.53 (br. s., 2H), 3.63 (br. s., 2H), 2.80 (br. s., 2H), 1.55 (s, 6H), 1.50 (s, 9H).

A Sequence Consisting of Steps 1-6 & 9 from Scheme GG were Used to Synthesis the Hydroxytetrahydroisoquinoline Intermediates TP-8 (Scheme III), TP-10-12 from the Appropriate Salicyclic Acid.

| | | | | |
|---|---|---|---|---|
| TP-8 (see Scheme III) 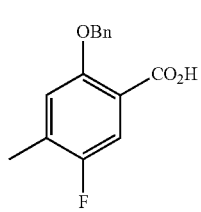 | | 226 LCMS = [M − 55 + 1] | tert-butyl 5-fluoro-8-hydroxy-6-methyl-3,4-dihydroisoquinoline-2(1H)-carboxylate $^1$H NMR (400 MHz, MeOD) δ ppm 6.45 (d, J = 6.3 Hz, 1H), 4.40 (s, 2H), 3.66-3.50 (m, 2H), 2.70 (t, J = 5.9 Hz, 2H), 2.14 (d, J = 1.5 Hz, 3H), 1.50-1.47 (m, 9H) | |
| TP-10 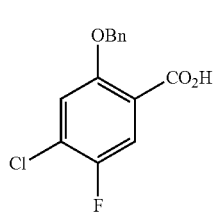 [SMILES: O=C(O)c1cc(F)c(Cl)cc1OCc1ccccc1] | 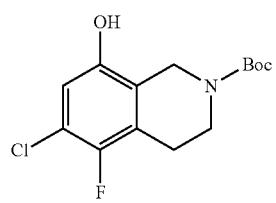 [SMILES: CC(C)(C)OC(=O)N1CCc2c(F)c(Cl)cc(O)c2C1] | 246 LCMS = [M − 55 + 1] | tert-butyl 6-chloro-5-fluoro-8-hydroxy-3,4-dihydroisoquinoline-2(1H)-carboxylate $^1$H NMR (400 MHz, DMSO-d$_6$) δ ppm 10.06 (s, 1H), 6.76 (d, J = 6.3 Hz, 1H), 4.31 (s, 2H), 3.54 (t, J = 5.8 Hz, 2H), 2.69 (t, J = 5.8 Hz, 2H), 1.42 (s, 9H) | |
| TP-11 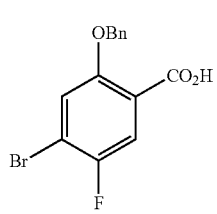 | 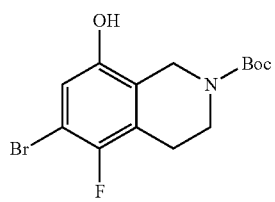 [SMILES: CC(C)(C)OC(=O)N1CCc2c(F)c(Br)cc(O)c2C1] | | tert-butyl 6-bromo-5-fluoro-8-hydroxy-3,4-dihydroisoquinoline-2(1H)-carboxylate $^1$H NMR (400 MHz, DMSO-d$_6$) δ ppm 10.04 (s, 1H), 6.88 (d, J = 5.8 Hz, 1H), 4.30 (s, 2H), 3.54 (t, J = 5.8 Hz, 2H), 2.69 (t, J = 5.9 Hz, 2H), 1.42 (s, 9H) | |
| TP-12 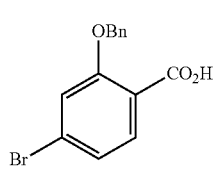 [SMILES: O=C(O)c1ccc(Br)cc1OCc1ccccc1] | 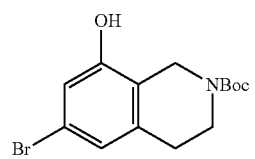 | 272 LCMS = [M − 55 + 1] | tert-butyl 6-bromo-8-hydroxy-3,4-dihydroisoquinoline-2(1H)-carboxylate ; $^1$H NMR (400 MHz, CDCl$_3$) δ ppm 6.94-6.66 (m, 2H), 4.46 (m, 2H), 3.61 (t, J = 5.6 Hz, 2H), 2.76 (m, 2H), 1.51 (s, 9H) | |

225

Synthesis of tert-butyl 6-ethyl-8-hydroxy-3,4-dihydroisoquinoline-2(1H)-carboxylate (TP-13)

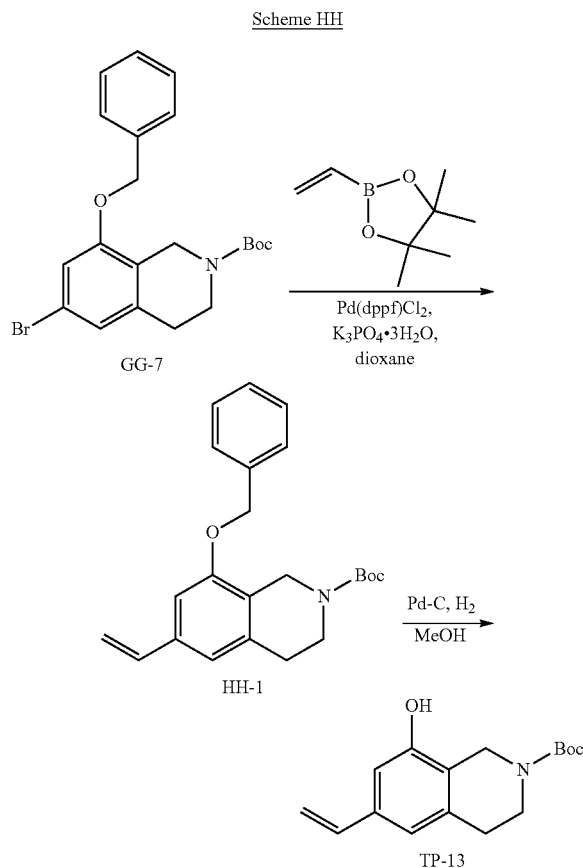

Step 1—Synthesis of tert-butyl 8-(benzyloxy)-6-vinyl-3,4-dihydroisoquinoline-2(1H)-carboxylate (HH-1)

A mixture of GG-7 (530 mg, 1.27 mmol) and 4,4,5,5-tetramethyl-2-vinyl-1,3,2-dioxaborolane (410 mg, 2.67 mmol), K$_3$PO$_4$·3H$_2$O (675 mg, 2.53 mmol), PdCl$_2$(dppf) (93 mg, 0.013 mmol) in dioxane (20 mL) and H$_2$O (5 mL) was degassed with N$_2$ heated at 100° C. for 2 hours. The mixture was purified by pre-TLC (Petroleum Ether/EtOAc=8/1) to afford HH-1 (370 mg, 80%) as a colorless gum. LCMS 266 [M-Boc+1]; $^1$H NMR (400 MHz, CDCl$_3$) δ ppm 7.51-7.28 (m, 5H), 6.83 (d, J=12.0 Hz, 2H), 6.65 (dd, J=10.9, 17.4 Hz, 1H), 5.69 (d, J=17.6 Hz, 1H), 5.22 (d, J=10.8 Hz, 1H), 5.12 (br. s., 2H), 4.58 (br. s., 2H), 3.73-3.56 (m, 2H), 2.90-2.73 (m, 2H), 1.50 (s, 9H)

Step 2—Synthesis of tert-butyl 6-ethyl-8-hydroxy-3,4-dihydroisoquinoline-2(1H)-carboxylate (TP-13)

A mixture of HH-1 (370 mg, 1.01 mmol) and Pd/C (370 mg) in MeOH (20 mL) was degassed with H$_2$ and stirred at 50° C. under H$_2$ (50 psi) for 24 hrs. The mixture was filtered and the filtrate was concentrated in vacuo to afford crude material which was purified by silica gel chromatography eluted with EtOAc in petroleum ether from 0 to 20% to afford TP-12 (210 mg, 75%) as a white solid. LCMS 222

226

[M-55+1]; $^1$H NMR (400 MHz, CDCl$_3$) δ ppm 6.57 (br. s., 1H), 6.48 (s, 1H), 4.51 (br. s., 2H), 3.63 (br. s., 2H), 2.78 (br. s, 2H), 2.62-2.45 (q, J=7.5 Hz, 2H), 1.50 (s, 9H), 1.20 (t, J=7.5 Hz, 3H)

Synthesis of tert-butyl 6-(difluoromethyl)-8-hydroxy-3,4-dihydroisoquinoline-2(1H)-carboxylate (TP-14)

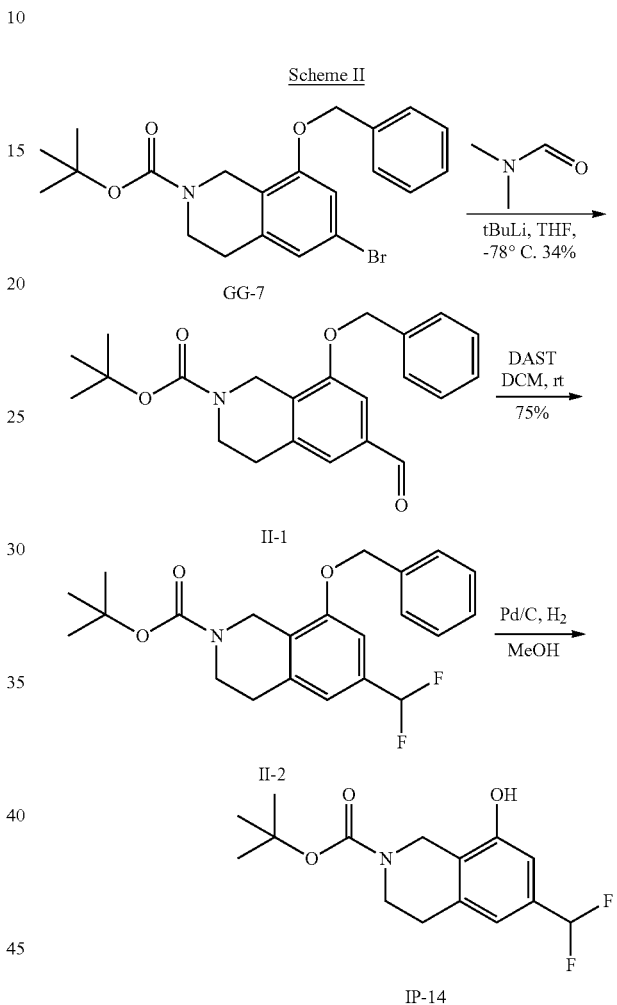

Step 1: Synthesis of tert-butyl 8-(benzyloxy)-6-formyl-3,4-dihydroisoquinoline-2(1H)-carboxylate (II-1)

GG-7 (1000 mg, 2.390 mmol) in an oven dried two necked flask equipped with a thermometer was dissolved in tetrahydrofuran (22.0 mL, c=0.109 M), cooled to −78° C., tert-butyllithium (459 mg, 7.17 mmol, 4.22 mL, 1.7 M) was added slowly under N$_2$ while maintaining the internal temperature around −70° C., stirred at −78° C. for 30 min, N,N-dimethyl formamide (262 mg, 3.59 mmol) was added dropwise and stirred at −78° C. for 1.5 h. The reaction was quenched by std. NH$_4$Cl at −78° C., extracted with EtOAc 3 times. The organic layers were combined, washed with brine, dried over Na$_2$SO$_4$, concentrated and purified by column chromatography with 15% EtOAc/heptane to give II-1 (300 mg, 34% yield) as a colorless oil.

LCMS [M+1-Boc] 268.10. ¹H NMR (400 MHz, CHLOROFORM-d) δ ppm 1.51 (s, 9H) 2.91 (t, J=5.38 Hz, 2H) 3.68 (t, J=5.69 Hz, 2H) 4.65 (s, 2H) 5.17 (br. s., 2H) 7.29 (d, J=9.05 Hz, 2H) 7.31-7.37 (m, 1H) 7.40 (t, J=7.27 Hz, 2H) 7.43-7.48 (m, 2H) 9.92 (s, 1H)

Step 2: Synthesis of tert-butyl 8-(benzyloxy)-6-(difluoromethyl)-3,4-dihydroisoquinoline-2(1H)-carboxylate (II-2)

To a solution of II-1 (300 mg, 0.816 mmol) in DCM (16.3 mL, c=0.05 M) at 0° C. was added (diethylamino)sulfur trifluoride (1320 mg, 8.16 mmol, 1070 uL). The reaction was removed from the ice bath and stirred at r.t. overnight. The reaction was diluted with DCM and quenched with std. NaHCO₃, stirred at r.t. until CO₂ evolution ceased. The layers were separated and the aqueous was extracted with DCM. The organic layer was dried over Na₂SO₄ and concentrated, purified by column chromatography with 15% EtOAc/heptane to give II-2 (240 mg, 75% yield) as a clear oil.

LCMS [M+1-Boc] 290.10. ¹H NMR (400 MHz, CHLOROFORM-d) δ ppm 1.51 (s, 9H) 2.86 (t, J=5.26 Hz, 2H) 3.66 (t, J=5.62 Hz, 2H) 4.61 (s, 2H) 5.13 (br. s., 2H) 6.58 (t, J=57.22 Hz, 1H) 6.92 (d, J=8.31 Hz, 2H) 7.31-7.48 (m, 5H)

Step 3: Synthesis of tert-butyl 6-(difluoromethyl)-8-hydroxy-3,4-dihydroisoquinoline-2(1H)-carboxylate (TP-14)

To a solution of II-2 (240 mg, 0616 mmol) in methanol (10 mL) was added palladium on carbon (66 mg, 0.616 mmol). The reaction solution was degassed and back filled with hydrogen gas. The mixture was fitted with a hydrogen balloon and stirred at rt overnight. The reaction was filtered, the solvents removed in vacuo and the material purified by column chromatography with 20% EtOAc/heptane to give TP-14 (175 mg, 95% yield) as a white solid.

LCMS [M+1-tBu] 242. ¹H NMR (400 MHz, CHLOROFORM-d) δ ppm 1.52 (s, 9H) 2.84 (br. s., 2H) 3.66 (t, J=5.81 Hz, 2H) 4.56 (br. s., 2H) 6.53 (t, J=57.22 Hz, 1H) 6.76 (s, 1H) 6.84 (br. s., 1H)

Synthesis of tert-butyl 6-(1,1-difluoroethyl)-8-hydroxy-3,4-dihydroisoquinoline-2(1H)-carboxylate (TP-15)

Scheme JJ

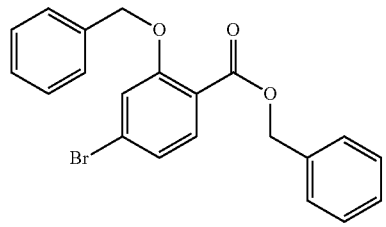

GG-2

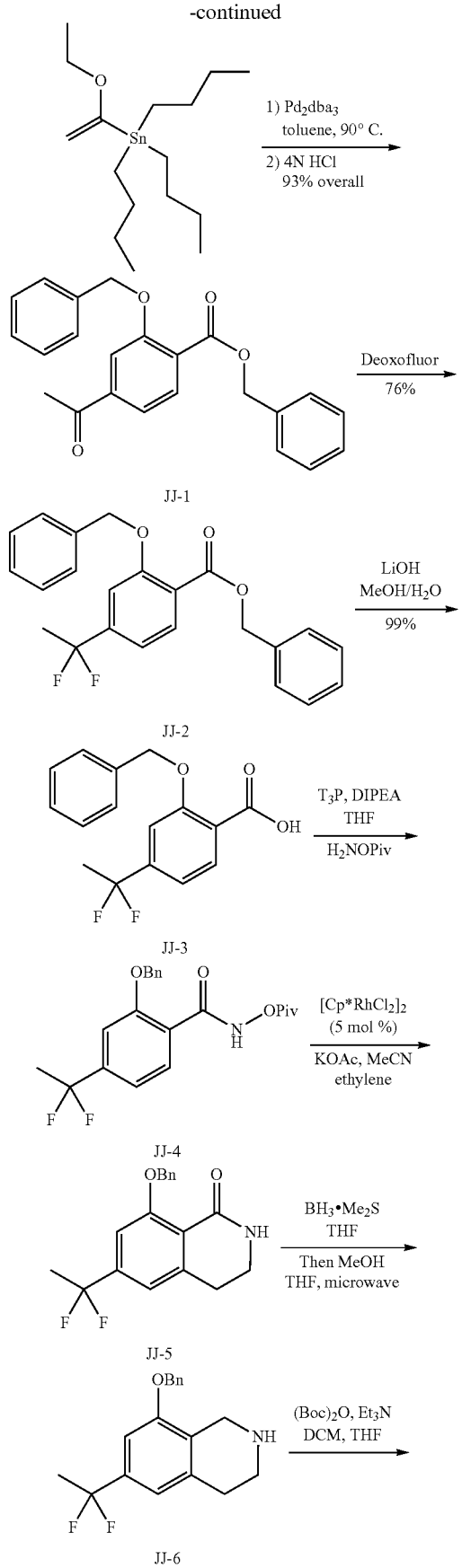

229

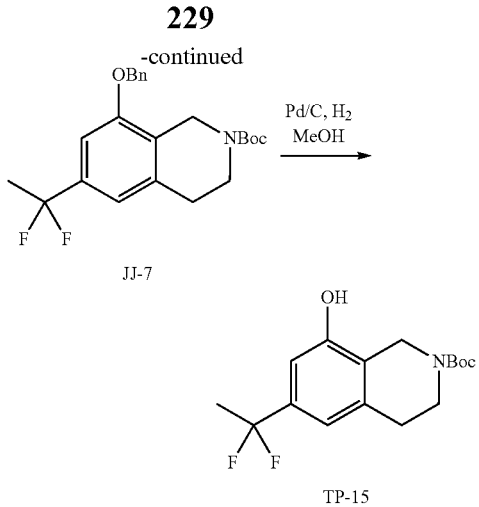

Step 1: Synthesis of benzyl 4-acetyl-2-(benzyloxy)benzoate (JJ-1)

The mixture of GG-2 (8544 mg, 21.51 mmol), tributyl (1-ethoxyvinyl)tin (8160 mg, 22.6 mmol), $Pd_2(dba)_3$ (394 mg, 0.430 mmol) and 2,2'-bis(diphenylphosphino)-1,1'-binaphthyl (536 mg, 0.860 mmol) in toluene (108 mL, c=0.2 M) was degassed and heated at 90° C. for 18 h. Toluene was removed and the crude was carried to next step.

The crude was dissolved in THF (108 mL, c=0.20 M), hydrochloric acid (6670 mg, 183 mmol, 45.7 mL, 4.0 M) was added, stirred at r.t. for 2 hrs. The organic solvent was removed; $H_2O$ was added, extracted with EtOAc 3 times. The organic layers were combined, washed with brined, dried over $Na_2SO_4$, filtered and concentrated, purified with silica gel chromatography eluted with 15% EtOAc/heptane to give 7180 mg yellow oil.

LCMS [M+1] 361.10. $^1$H NMR (400 MHz, CHLOROFORM-d) δ ppm 2.60 (s, 3H) 5.23 (s, 2H) 5.37 (s, 2H) 7.29-7.42 (m, 8H) 7.45 (d, J=6.85 Hz, 2H) 7.54 (dd, J=8.01, 1.28 Hz, 1H) 7.62-7.65 (m, 1H) 7.90 (d, J=7.95 Hz, 1H)

Step 2: Synthesis of benzyl 2-(benzyloxy)-4-(1,1-difluoroethyl)benzoate (JJ-2)

JJ-1 (7.380 g, 20.48 mmol) was added deoxofluor (22.7 g, 102 mmol). The reaction mixture was heated to 80° C. for 4.5 hrs, cooled to r.t., poured into std. $NaHCO_3$, and after $CO_2$ evolution ceased, the aqueous was extracted with EtOAc 3 times. The organic layer was concentrated under vacuum, purified by column chromatography with 10% EtOAc/heptane to give JJ-2 (5.94 g, 76% yield) as a colorless oil which solidified upon vacuum.

$^1$H NMR (400 MHz, CHLOROFORM-d) δ ppm 1.89 (t, J=18.16 Hz, 3H) 5.19 (s, 2H) 5.36 (s, 2H) 7.12 (d, J=8.07 Hz, 1H) 7.17 (s, 1H) 7.29-7.42 (m, 8H) 7.45 (d, J=6.72 Hz, 2H) 7.89 (d, J=8.07 Hz, 1H)

Step 3: Synthesis of 2-(benzyloxy)-4-(1,1-difluoroethyl)benzoic acid (JJ-3)

Following a similar procedure as step 2 in Scheme GG, JJ-2 was hydrolyzed to JJ-3 (4.49 g, 99%) as white solid.

$^1$H NMR (400 MHz, DMSO-d6) δ ppm 1.97 (t, J=18.89 Hz, 3H) 5.26 (s, 2H) 7.19 (d, J=7.95 Hz, 1H) 7.29-7.36 (m, 2H) 7.40 (t, J=7.34 Hz, 2H) 7.51 (d, J=7.21 Hz, 2H) 7.71 (d, J=7.95 Hz, 1H) 12.89 (br. s., 1H)

230

Step 4-8: Synthesis of tert-butyl 6-(1,1-difluoroethyl)-8-hydroxy-3,4-dihydroisoquinoline-2(1H)-carboxylate (TP-15)

Following similar procedures as step 3 in Scheme GG (1.30 g, 70%), step 4 in Scheme GG (684 mg, 65%), steps 5 in Scheme FF and step 6 in Scheme GG (575 mg, 77%), step 9 in Scheme GG (400 mg, 90%), JJ-3 was converted to TP-15.

LCMS [M+1-Boc] 214.10. $^1$H NMR (400 MHz, CHLOROFORM-d) δ ppm 1.52 (s, 9H) 1.87 (t, J=18.10 Hz, 3H) 2.83 (br. s., 2H) 3.65 (t, J=5.69 Hz, 2H) 4.56 (br. s., 2H) 6.76 (s, 1H) 6.83 (br. s., 1H)

Synthesis of tert-butyl 8-hydroxy-3,4-dihydro-2,6-naphthyridine-2(1H)-carboxylate (TP-16)

Scheme KK

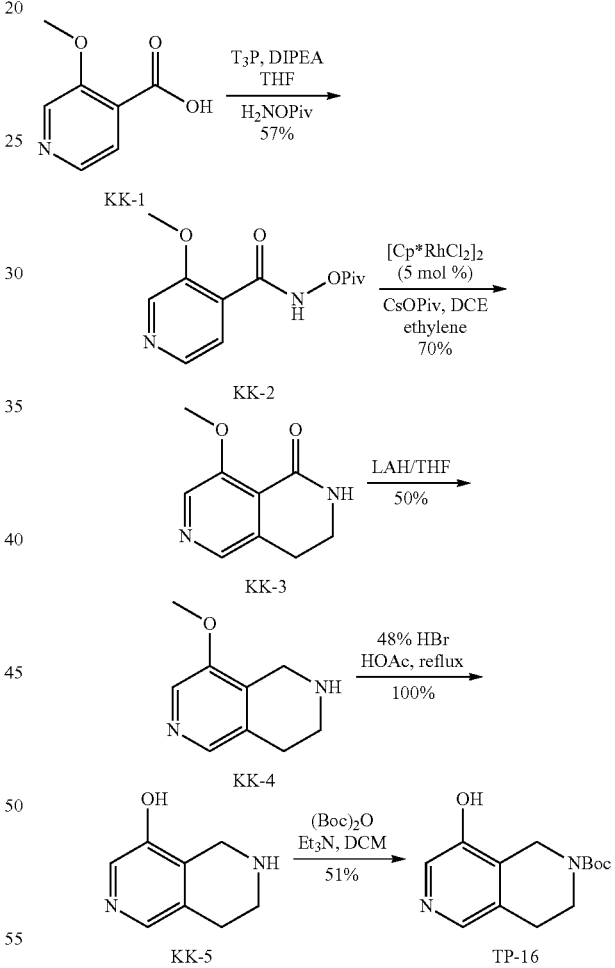

Step 1-3: Synthesis of 8-methoxy-1,2,3,4-tetrahydro-2,6-naphthyridine (KK-4)

Following similar procedures as step 3 in Scheme GG (939 mg, 57%), step 4 in Scheme GG using cesium pivolate and dichloroethane in place of potassium acetate and acetonitrile (290 mg, 70%), and steps 5 in Scheme FF (136 mg, 50%), KK-1 was converted to KK-4.

LCMS [M+1] 165.10. $^1$H NMR (400 MHz, CHLOROFORM-d) δ ppm 2.77 (t, J=5.81 Hz, 2H) 3.11 (t, J=5.81 Hz, 2H) 3.90 (s, 3H) 3.94 (s, 2H) 8.03 (d, J=2.93 Hz, 2H)

Step 4: Synthesis of 5,6,7,8-tetrahydro-2,6-naphthyridin-4-ol (KK-5)

KK-4 (136.0 mg, 0.828 mmol) in 5 mL 48% HBr and 3 mL glacial acetic acid was sealed and refluxed at 120° C. for 4 days. The reaction was cooled to RT, concentrated off the acetic acid by azeotroping from heptanes 3 times, neutralized by careful addition of 5 N NaOH until pH around 9. Rotavaporated to remove most $H_2O$, added MeOH, dried packed with silica gel. The product was purified by column chromatography with 10% MeOH/DCM with 0.5% $NH_4OH$ to give KK-5 (124 mg, 100%). LCMS [M+1] 151.10.

Step 5: Synthesis of tert-butyl 8-hydroxy-3,4-dihydro-2,6-naphthyridine-2(1H)-carboxylate (TP-16)

Following similar procedures as step 6 in Scheme GG, KK-5 was converted to TP-16 (106 mg, 51%).
LCMS [M-55+1] 228. $^1$H NMR (400 MHz, DMSO-$d_6$) δ ppm 10.13 (s, 1H), 6.68 (s, 2H), 4.29 (s, 2H), 3.53-3.45 (t, J=5.6 Hz, 2H), 2.74-2.64 (t, J=5.5 Hz, 2H), 1.42 (s, 9H)

Synthesis of tert-butyl 8-hydroxy-5-methyl-3,4-dihydro-2,6-naphthyridine-2(1H)-carboxylate (TP-17)

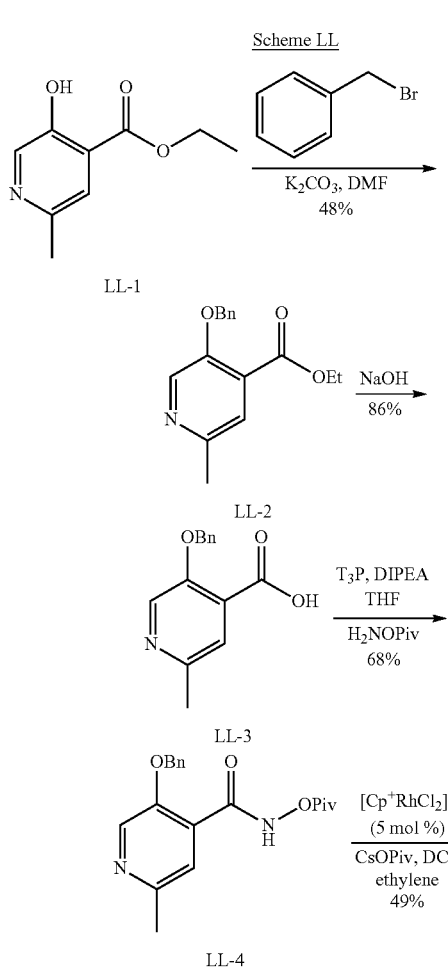

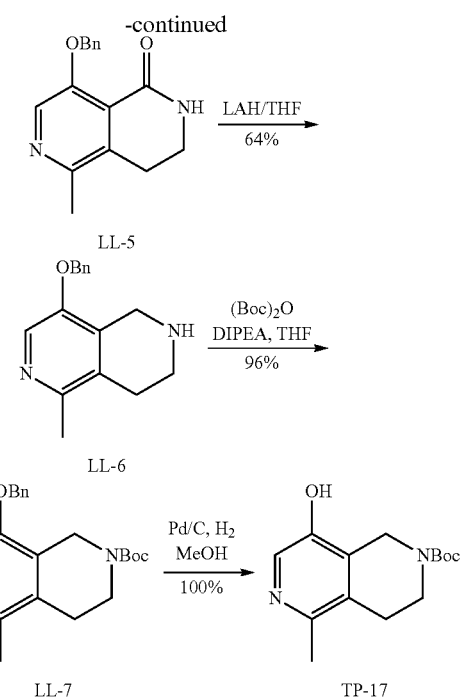

Step 1: Synthesis of (5-(benzyloxy)-2-methylpyridin-4-yl)(ethoxy)methanol (LL-2)

Ethyl 5-hydroxy-2-methylisonicotinate (LL-1) (synthesis described in WO10100475) (2190 mg, 17.22 mmol) and N-benzyl bromide (3540 mg, 20.7 mmol), $K_2CO_3$ (4810 mg, 34.4 mmol) in 20 mL DMF was heated at 80° C. overnight. After the reaction mixture cooled to r.t., EtOAc was added, washed with $H_2O$ 3 times. The organic layer was concentrated, purified by column chromatography with 30% EtOAc/heptane to give LL-2 (16 g, 48% yield) as a brown solid.
LCMS [M+1] 272.10. $^1$H NMR (400 MHz, CHLOROFORM-d) δ ppm 1.37 (t, J=7.15 Hz, 3H) 2.54 (s, 3H) 4.39 (q, J=7.13 Hz, 2H) 5.23 (s, 2H) 7.34 (d, J=7.09 Hz, 1H) 7.36-7.43 (m, 2H) 7.44-7.51 (m, 3H) 8.35 (s, 1H)

Step 2: Synthesis of (5-(benzyloxy)-2-methylpyridin-4-yl)methanediol (LL-3)

To a solution of LL-2 (2160 mg, 7.961 mmol) in 20 mL MeOH was added sodium hydroxide (1590 mg, 39.8 mmol, 7.96 mL, 5.0 M), and the reaction was heated at 50° C. for 4 hrs. The mixture was cooled to r.t., MeOH was evaporated, $H_2O$ was added, neutralized with 1 N HCl to pH about 4, the yellow solid crashed out which was filtered and rinsed with $H_2O$ to give LL-3 (1.66 g, 86% yield).
LCMS [M+1] 244.10. $^1$H NMR (400 MHz, DMSO-d6) δ ppm 2.42 (s, 3H) 5.27 (s, 2H) 7.33 (d, J=7.21 Hz, 1H) 7.35-7.43 (m, 3H) 7.44-7.52 (m, 2H) 8.41 (s, 1H)

Step 3-7:—Synthesis of tert-butyl 8-hydroxy-5-methyl-3,4-dihydro-2,6-naphthyridine-2(1H)-carboxylate (TP-17)

Following similar procedures as step 3 in Scheme GG (1.60 g, 68%), step 4 in Scheme GG using cesium pivolate and dichloroethane in place of potassium acetate and acetonitrile (620 mg, 49%), steps 5 in Scheme FF (366 mg, 64%), step 6 in Scheme GG (483 mg, 96%), and step 9 in Scheme GG (386 mg, 100%), LL-3 was converted to TP-17.
$^1$H NMR (400 MHz, CHLOROFORM-d) δ ppm 1.51 (s, 9H) 2.41 (s, 3H) 2.71 (t, J=5.38 Hz, 2H) 3.69 (t, J=5.75 Hz, 2H) 4.59 (s, 2H) 7.95 (s, 1H)

Synthesis of tert-butyl 6-cyano-8-hydroxy-3,4-dihydroisoquinoline-2(1H)-carboxylate (TP-18)

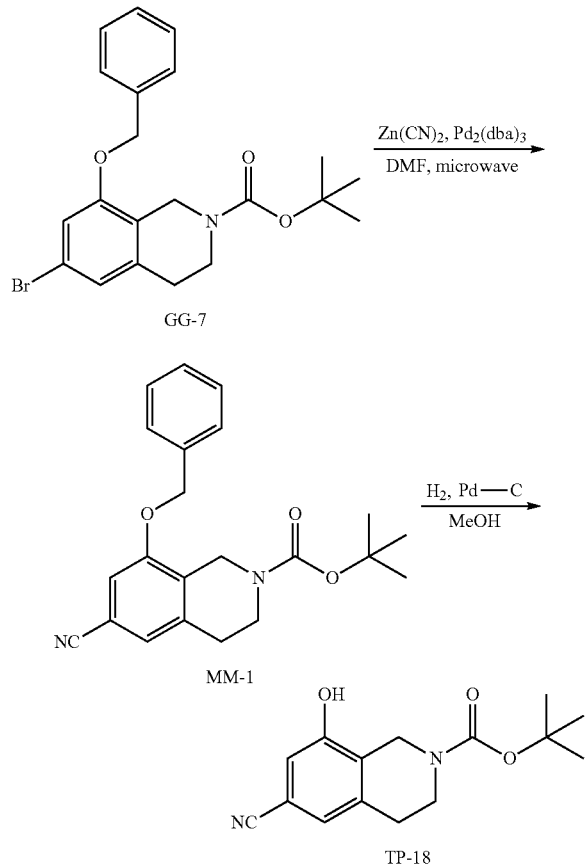

Step 1: Synthesis of tert-butyl 8-(benzyloxy)-6-cyano-3,4-dihydroisoquinoline-2(1H)-carboxylate (MM-1)

Compound GG-7 (700 mg, 1.67 mmol) was dissolved in DMF (5.00 mL). $Zn(CN)_2$ (236 mg, 2.01 mmol) was added to the above solution. The reaction solution was degassed for 2 min. $Pd(PPh_3)_4$ (580 mg, 0.502 mmol) was added to the above mixture. The reaction mixture was degassed with $N_2$ for 3 min. Then the reaction mixture was heated by microwave at 150° C. for 30 min. The reaction solution became black from yellow. The reaction solution was cooled and diluted with EtOAc/$H_2O$ (8 mL/8 mL), then the mixture was filtered, and the filtrate was extracted. The organic layer was separated, dried and evaporated to give the crude product which was purified by flash chromatography with petroleum ether/EtOAc from 0-25% to give MM-1 (350 mg, 57%) as a white solid. LCMS 265 [M-Boc]$^+$; $^1$H NMR (400 MHz, DMSO-$d_6$) δ ppm 7.52-7.32 (m, 6H), 7.29 (s, 1H), 5.22 (br. s., 2H), 4.53-4.40 (m, 2H), 3.54 (t, J=5.6 Hz, 2H), 2.79 (t, J=5.5 Hz, 2H), 1.41 (s, 9H)

Step 2: Synthesis of tert-butyl 6-cyano-8-hydroxy-3,4-dihydroisoquinoline-2(1H)-carboxylate (TP-18)

Compound MM-1 (320 mg, 0.878 mmol) was dissolved in MeOH (3 mL). Pd/C (93 mg, 0.44 mmol) was added to the reaction solution and degassed by $H_2$ balloon three times, and stirred under $H_2$ balloon at 20° C. for 1 hour. DCM (5 mL) was added to the above mixture, the reaction mixture was filtered and concentrated to give the crude product, which was purified by flash chromatography with petroleum ether/EtOAc from 0-50% to give TP-18 as a white solid (125 mg, 51.9%). LCMS [219-tBu]$^+$; $^1$H NMR (400 MHz, CDCl$_3$) δ ppm 7.45-7.28 (m, 1H), 7.10-6.95 (m, 1H), 6.87 (br. s., 1H), 4.57 (br. s., 2H), 3.66 (t, J=5.9 Hz, 2H), 2.82 (br. s., 2H), 1.53 (s, 9H)

Examples 84-98 were Made in a Similar Fashion to Example 78 in Scheme CC Using the Appropriate NBoc-Protected Tetrahydroisoquinoline in Step 1

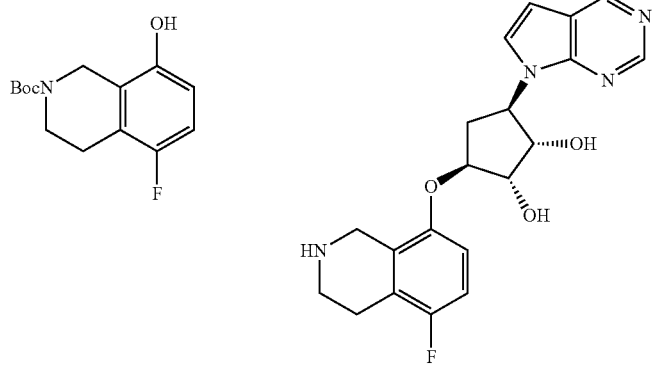

| Example 84 TP-2 | | 399 [M + 1] | (1S,2S,3S,5R)-3-((5-fluoro-1,2,3,4-tetrahydroisoquinolin-8-yl)oxy)-5-(4-methyl-7H-pyrrolo[2,3-d]pyrimidin-7-yl)cyclopentane-1,2-diol $^1$H NMR (400 MHz, DMSO-$d_6$) δ ppm 8.63 (s, 1H), 7.62 (d, J = 3.5 Hz, 1H), 6.96-6.89 (m, 1H), 6.86-6.80 (m, 1H), 6.72 (d, J = 3.5 Hz, 1H), 5.31 (d, J = 3.8 Hz, 1H), 5.16-5.06 (m, 2H), 4.59-4.49 (m, 2H), 4.00-3.95 (m, 1H), 3.82 (s, 2H), 2.91 (t, J = 5.8 Hz, 2H), 2.88-2.77 (m, 1H), 2.64 (s, 3H), 2.57 (t, J = 5.8 Hz, 2H), 1.92 (ddd, J = 3.8, 9.3, 13.6 Hz, 1H) |
|---|---|---|---|

-continued

| | | | |
|---|---|---|---|
| Example 85 TP-1 | 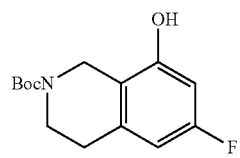 [SMILES: CC(C)(C)OC(=O)N1CCc2cc(F)cc(O)c2C1] | 399 [M + 1] | (1S,2S,3S,5R)-3-((6-fluoro-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, MeOD-d$_4$) δ ppm 8.61 (s, 1H), 7.55 (d, J = 3.5 Hz, 1H), 6.75 (d, J = 3.8 Hz, 1H), 6.68 (dd, J = 2.3, 10.8 Hz, 1H), 6.49 (dd, J = 2.1, 9.2 Hz, 1H), 5.24 (q, J = 8.8 Hz, 1H), 4.74-4.63 (m, 2H), 4.17 (d, J = 4.8 Hz, 1H), 3.93 (s, 2H), 3.06 (t, J = 5.9 Hz, 2H), 3.03-2.94 (m, 1H), 2.80 (t, J = 5.8 Hz, 2H), 2.22-2.10 (m, 1H) |
| | 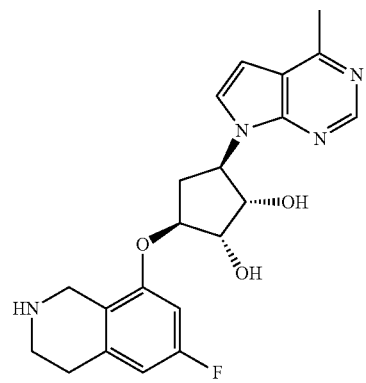 [SMILES: Cc1ncnc2c1ccn2[C@@H]1C[C@H](Oc2cc(F)cc3c2CNCC3)[C@@H](O)[C@H]1O] | | |
| Example 86 TP-19 | 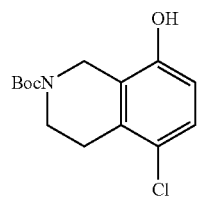 [SMILES: CC(C)(C)OC(=O)N1CCc2c(Cl)ccc(O)c2C1] | 415 [M + 1] | (1S,2S,3S,5R)-3-((5-chloro-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, MeOD-d$_4$) δ ppm 8.64 (s, 1H), 7.57 (d, J = 4.0 Hz, 1H), 7.25 (d, J = 9.0 Hz, 1H), 6.92 (d, J = 8.5 Hz, 1H), 6.77 (d, J = 3.5 Hz, 1H), 5.25 (q, J = 9.0 Hz, 1H), 4.72 (dd, J = 4.8, 8.3 Hz, 2H), 4.20 (d, J = 4.5 Hz, 1H), 4.03 (s, 2H), 3.16 (t, J = 6.0 Hz, 2H), 3.07-2.91 (m, 1H), 2.83 (t, J = 5.8 Hz, 2H), 2.74 (s, 3H), 2.27-2.05 (m, 1H) |
| | 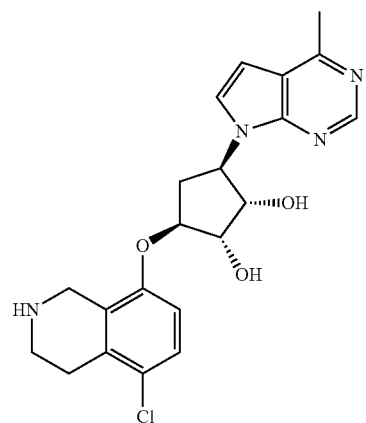 [SMILES: Cc1ncnc2c1ccn2[C@@H]1C[C@H](Oc2ccc(Cl)c3c2CNCC3)[C@@H](O)[C@H]1O] | | |
| Example 87 TP-3 | 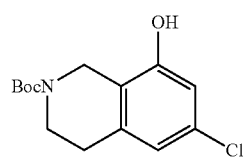 [SMILES: CC(C)(C)OC(=O)N1CCc2cc(Cl)cc(O)c2C1] | 415 [M + 1] | (1S,2S,3S(5R)-3-((6-chloro-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400MHz, DMSO-d$_6$) δ ppm 8.62 (s, 1H), 7.62 (d, J = 3.8 Hz, 1H), 6.92 (s, 1H), 6.76 (s, 1H), 6.72 (d, J = 3.5 Hz, 1H), 5.41-5.35 (m, 1H), 5.10 (d, J = 9.3 Hz, 2H), 4.63-4.44 (m, 2H), 3.99-3.91 (m, 1H), 3.78 (s, 2H), 2.93-2.78 (m, 3H), 2.69-2.59 (m, 4H), 2.02-1.88 (m, 1H) |
| | 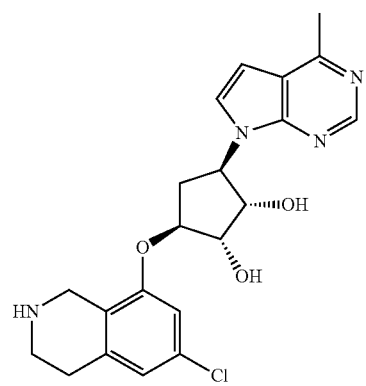 [SMILES: Cc1ncnc2c1ccn2[C@@H]1C[C@H](Oc2cc(Cl)cc3c2CNCC3)[C@@H](O)[C@H]1O] | | |
| Example 88 TP-5 | 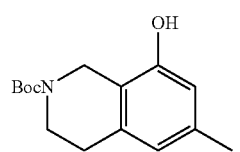 | 395 [M + 1] | (1S,2S,3R,5S)-3-(4-methyl-7H-pyrrolo[2,3-d]pyrimidin-7-yl)-5-(6-methyl-1,2,3,4-tetrahydroisoquinolin-8-yl)oxy]cyclopentane-1,2-diol<br>$^1$H NMR (400 MHz, MeOD-d$_4$) δ ppm 8.64 (s, 1H), 7.56 (d, J = 3.8 Hz, 1H), 6.77 (d, J = 3.8 Hz, 1H), 6.70-6.66 (s, 1H), 6.61-6.55 (s, 1H), 5.34-5.23 (m, 1H), 473-4.66 (m, 2H), 4.22-4.16 (m, 1H), 3.96 (s, 2H), 3.07-3.06 (m, 3H), 2.84-2.76 (m, 2H), 2.73 (s, 3H), 2.30 (s, 3H), 2.18-2.07 (m, 1H) |
| | 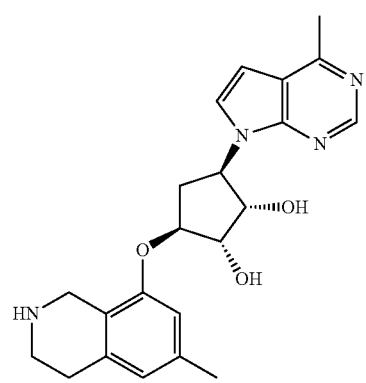 [SMILES: Cc1cc2c(c(O[C@H]3C[C@@H](n4ccc5c(C)ncnc54)[C@H](O)[C@@H]3O)c1)CNCC2] | | |

| | | | |
|---|---|---|---|
| Example 89 TP-12 | 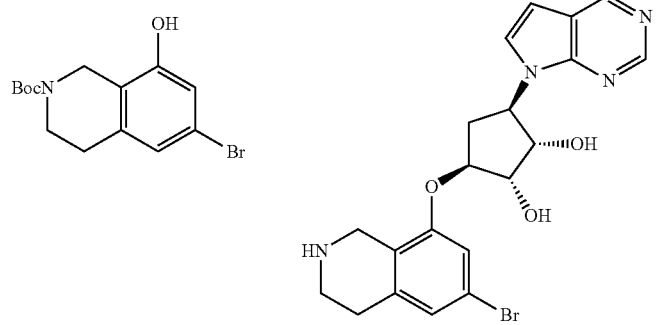 | 459 [M + 1] | (1S,2S,3S,5R)-3-((6-bromo-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, MeOD-d$_4$) δ ppm 8.63 (s, 1H), 7.57 (d, J = 3.5 Hz, 1H), 7.13 (s, 1H), 7.05-6.94 (m, 1H), 6.76 (d, J = 3.8 Hz, 1H), 5.22 (q, J = 9.0 Hz, 1H), 4.76-4.67 (m, 2H), 4.24-4.14 (m, 1H), 4.09 (s, 2H), 3.23 (t, J = 6.0 Hz, 2H), 3.00 (ddd, J = 7.3, 9.3, 14.3 Hz, 1H), 2.95-2.86 (m, 2H), 2.73 (s, 3H), 2.32-2.15 (m, 1H) |
| Example 90 TP-4 | 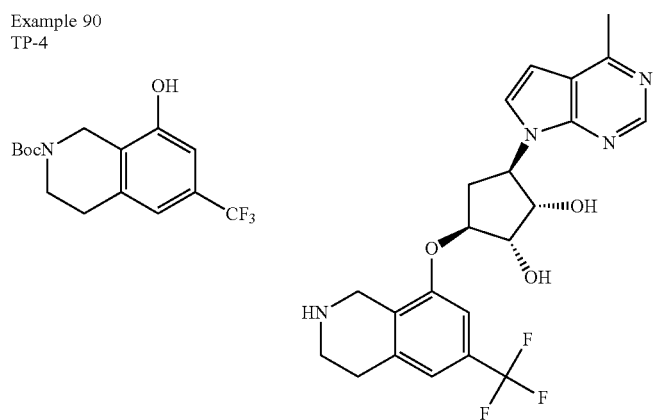 | 449 [M + 1] | (1S,2S,3R,5S)-3-(4-methyl-7H-pyrrolo[2,3-d]pyrimidin-7-yl)-5-((6-(trifluoromethyl)-1,2,3,4-tetrahydroisoquinolin-8-yl)oxy)cyclopentane-1,2-diol<br>$^1$H NMR (400 MHz, MeOD-d$_4$) δ ppm 8.62 (s, 1H), 7.57 (d, J = 3.5 Hz, 1H), 7.13 (s, 1H), 7.07 (s, 1H), 6.75 (d, J = 3.8 Hz, 1H), 5.23 (q, J = 9.0 Hz, 1H), 4.76 (dd, J = 2.6, 4.6 Hz, 1H), 4.72 (dd, J = 4.9, 8.9 Hz, 1H), 4.18 (d, J = 5.0 Hz, 1H), 4.03 (s, 2H), 3.12-3.06 (m, 2H), 3.00 (ddd, J = 7.3, 9.3, 14.3 Hz, 1H), 2.88 (t, J = 5.6 Hz, 2H), 2.71 (s, 3H), 2.27-2.17 (m, 1H) |
| Example 91 TP-18 | 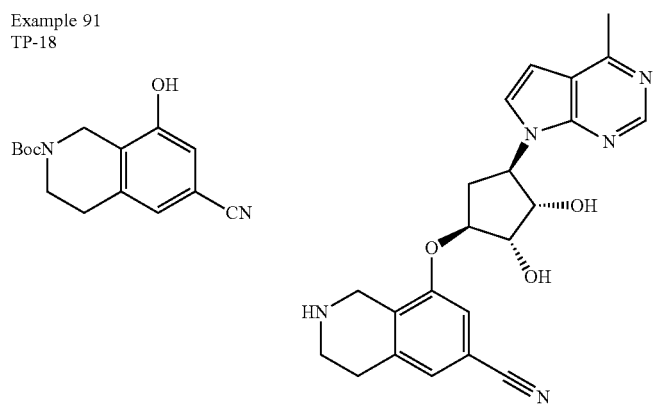 | 428 [M + 23] | 8-(((1S,2S,3S,4R)-2,3-dihydroxy-4-(4-methyl-7H-pyrrolo[2,3-d]pyrimidin-7-yl)cyclopentyl)oxy)-1,2,3,4-tetrahydroisoquinoline-6-carbonitrile<br>$^1$H NMR (400 MHz, MeOD-d$_4$) δ ppm 8.64 (s, 1H), 7.58 (d, J = 3.5 Hz, 1H), 7.24 (s, 1H), 7.17 (s, 1H), 6.77 (d, J = 3.8 Hz, 1H), 5.29-5.19 (m, 1H), 4.80-4.69 (m, 2H), 4.19 (d, J = 4.5 Hz, 1H), 4.03 (s, 2H), 3.10-3.07 (m, 2H), 3.05-2.97 (m, 1H), 2.90-2.84 (m, 2H), 2.74 (s, 3H), 2.27-2.23 (m, 1H) |
| Example 92 TP-6 | 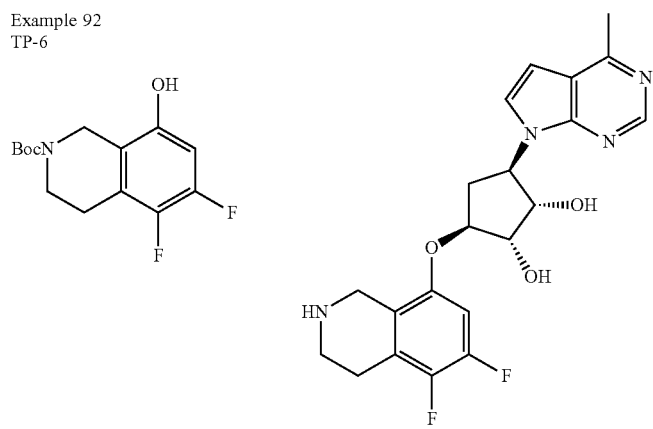 | 417 [M + 1] | (1S,2S,3S,5R)-3-((5,6-difluoro-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, MeOD-d$_4$) δ ppm 8.62 (s, 1H), 7.55 (d, J = 3.8 Hz, 1H), 7.02 (dd, J = 6.9, 12.2 Hz, 1H), 6.75 (d, J = 3.5 Hz, 1H), 5.21-5.11 (m, 1H), 4.76-4.70 (m, 1H), 4.70-4.63 (m, 1H), 4.22-4.15 (m, 3H), 3.37 (t, J = 6.3 Hz, 2H), 3.03-2.90 (m, 3H), 2.72 (s, 3H), 2.31-2.21 (m, 1H) |

| Example 93 TP-10 | 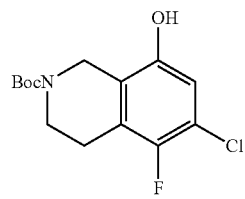 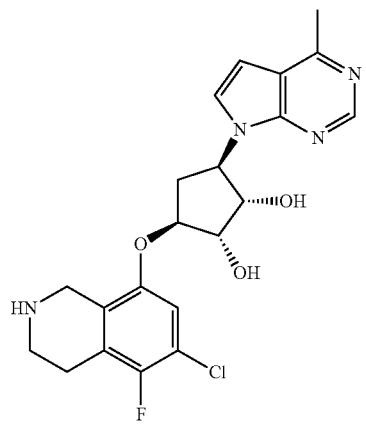 [SMILES: Cc1ncnc2c1ccn2[C@@H]1C[C@H](Oc2cc(Cl)c(F)c3c2CNCC3)[C@@H](O)[C@H]1O] | 433 [M + 1] | (1S,2S,3S,5R)-3-((6-chloro-5-fluoro-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, DMSO-d$_6$) δ ppm 8.63 (s, 1H), 7.63 (d, J = 3.5 Hz, 1H), 7.14 (d, J = 6.3 Hz, 1H), 6.72 (d, J = 3.8 Hz, 1H), 5.41 (d, J = 3.0 Hz, 1H), 5.21-4.96 (m, 2H), 4.65-4.46 (m, 2H), 4.06-3.90 (m, 3H), 3.08 (t, J = 5.8 Hz, 2H), 2.91-2.78 (m, 1H), 2.77-2.69 (m, 2H), 2.64 (s, 3H), 2.04-1.90 (m, 1H) |
|---|---|---|---|
| Example 94 TP-11 | 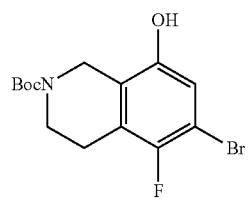 [SMILES: CC(C)(C)OC(=O)N1CCc2c(F)c(Br)cc(O)c2C1] 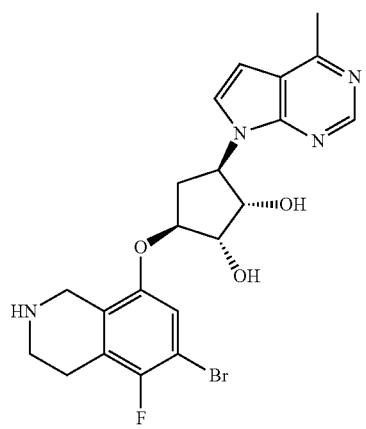 [SMILES: Cc1ncnc2c1ccn2[C@@H]1C[C@H](Oc2cc(Br)c(F)c3c2CNCC3)[C@@H](O)[C@H]1O] | 477 [M + 1] | (1S,2S,3S,5R)-3-((6-bromo-5-fluoro-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, DMSO-d$_6$) δ ppm 8.63 (s, 1H), 7.63 (d, J = 3.76 Hz, 1H), 7.22 (d, J = 5.52 Hz, 1H), 6.72 (s, 1H), 5.40 (d, J = 3.76 Hz, 1H), 5.01-5.17 (m, 2H), 4.51-4.62 (m, 2H), 3.88-4.01 (m, 3H), 3.06 (t, J = 5.90 Hz, 2H), 2.78-2.87 (m, 1H), 2.71 (t, J = 5.27 Hz, 2H), 2.64 (s, 3H), 2.00-1.95 (m, 1H) |
| Example 95 TP-16 | 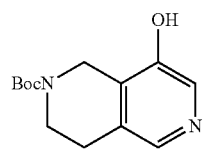 [SMILES: CC(C)(C)OC(=O)N1CCc2cncc(O)c2C1] 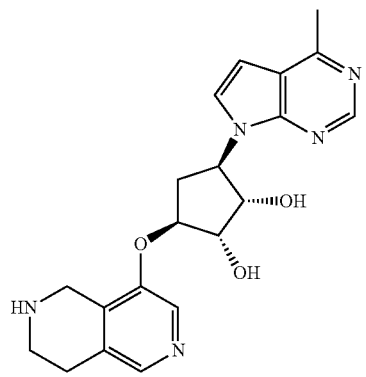 [SMILES: Cc1ncnc2c1ccn2[C@@H]1C[C@H](Oc2cncc3c2CNCC3)[C@@H](O)[C@H]1O] | 382.1 [M + 1] | (1S,2S,3R,5S)-3-(4-methyl-7H-pyrrolo[2,3-d]pyrimidin-7-yl)-5-((5,6,7,8-tetrahydro-2,6-naphthyridin-4-yl)oxy)cyclopentane-1,2-diol<br>$^1$H NMR (400MHz, DMSO-d$_6$) δ ppm 8.63 (s, 1H), 8.19 (s, 1H), 8.03 (s, 1H), 7.64 (d, J = 3.8 Hz, 1H), 6.72 (d, J = 3.5 Hz, 1H), 5.43 (d, J = 4.3 Hz, 1H), 5.17-5.06 (m, 2H), 4.71 (br. s., 1H), 4.62-4.53 (m, 1H), 4.04-3.97 (m, 3H), 3.10 (br. s., 2H), 2.95-2.83 (m, 1H), 2.78 (br. s., 2H), 2.64 (s, 3H), 2.08- 1.94 (m, 1H) |
| Example 96 TP-17 | 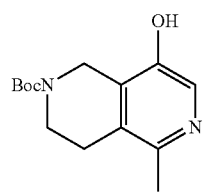 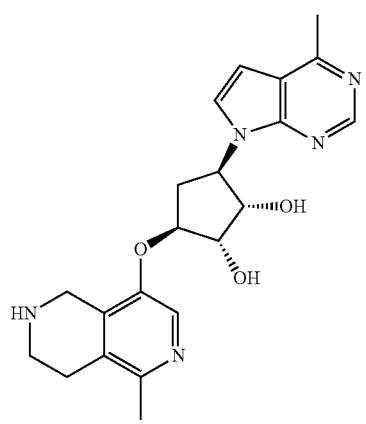 [SMILES: Cc1ncc(O[C@H]2C[C@@H](n3ccc4c(C)ncnc43)[C@H](O)[C@@H]2O)c2c1CCNC2] | 396.1 [M + 1] | (1S,2S,3S,5R)-3-((1-methyl-5,6,7,8-tetrahydro-2,6-naphthyridin-4-yl)oxy)-5-(4-methyl-7H-pyrrolo[2,3-d]pyrimidin-7-yl)cyclopentane-1,2-diol<br>$^1$H NMR (400MHz, METHANOL-d$_4$) δ ppm 8.62 (s, 1H), 8.03 (s, 1H), 7.56 (d, J = 3.8 Hz, 1H), 6.75 (d, J = 3.5 Hz, 1H), 5.29-5.12 (m, 1H), 4.75 (ddd, J = 4.8, 9.0, 13.6 Hz, 2H), 4.20 (d, J = 4.3 Hz, 1H), 4.09 (s, 2H), 3.22 (t, J = 6.0 Hz, 2H), 3.05-2.94 (m, 1H), 2.79 (t, J = 5.8 Hz. 2H), 2.72 (s, 3H), 2.40 (s, 3H), 2.30-2.19 (m, 1H) |

| Example 97 TP-9 | 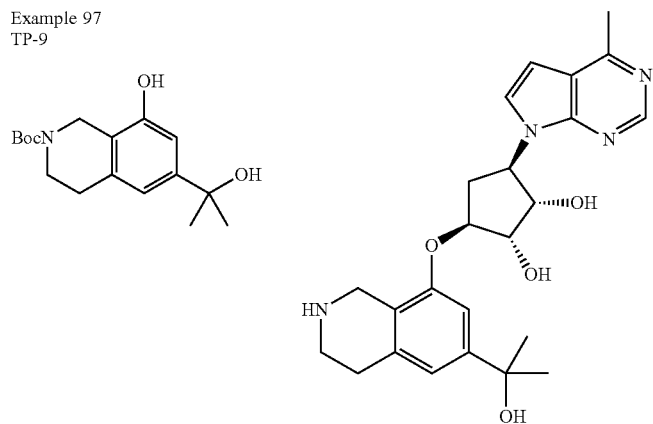 | 439 observed [M +H] | (1S,2S,3S,5R)-3-((6-(2-hydroxypropan-2-yl)-1,2,3,4-tetrahydroisoquinolin-8-yl)oxy)-5-(4-methyl-7H-pyrrolo[2,3-d]pyrimidin-7-yl)cyclopentane-1,2-diol<br>¹H NMR (400 MHz, METHANOL-d₄) δ ppm 8.64 (s, 1H) 7.57 (d, J = 3.5 Hz, 1H) 7.00 (s, 1H) 6.88 (s, 1H) 6.77 (d, J = 3.5 Hz, 1H) 5.29 (q, J = 8.8 Hz, 1H) 4.73 (s, 2H) 4.22 (d. J = 4.8 Hz, 1H) 4.02 (s, 2H) 3.12 (t, J = 5.9 Hz, 2H) 3.03 (ddd, J = 14.6, 9.5, 7.0 Hz, 1H) 2.87 (t, J = 5.8 Hz, 2H) 2.73 (s, 3H) 2.17 (ddd, J = 14.3, 8.4, 3.6 Hz, 1H) 1.53 (s, 6H) |
| --- | --- | --- | --- |
| Example 98 TP-7 | 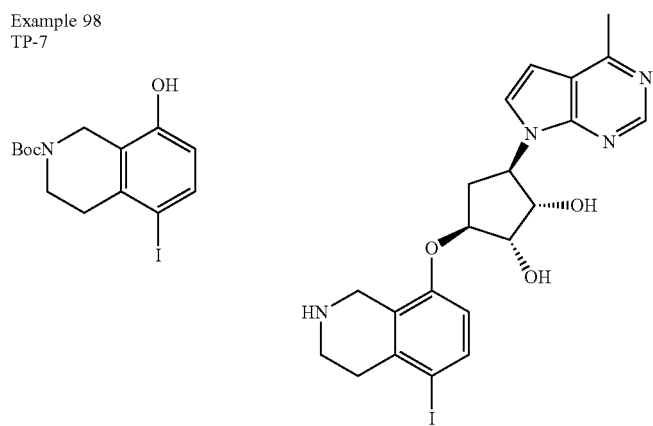 | 507 M + 1 | (1S,2S,3S,5R)-3-((5-iodo-1,2,3,4-tetrahydroisoquinolin-8-yl)oxy)-5-(4-methyl-7H-pyrrolo[2,3-d]pyrimidin-7-yl)cyclopentane-1,2-diol<br>¹H NMR (400 MHz, DMSO-d₆) δ ppm 8.64 (s, 1H), 7.71 (d, J = 8.4 Hz, 1H), 7.62 (s, 1H), 6.80 (d, J = 8.8 Hz, 1H), 6.71 (s, 1H), 5.38 (s, 1H), 5.19-5.02 (m, 2H), 4.60-4.55 (m, 2H), 4.08-3.93 (m, 3H), 3.18 (s, 2H), 2.91-2.78 (m, 1H), 2.64 (br. s, 4H), 2.00-1.96 (m, 1H) |

Example 99 (Scheme NN)—(1S,2S,3R,5S)-3-(4-amino-5-fluoro-7H-pyrrolo[2,3-d]pyrimidin-7-yl)-5-((1,2,3,4-tetrahydroisoquinolin-8-yl)oxy)cyclopentane-1,2-diol (NN-5)

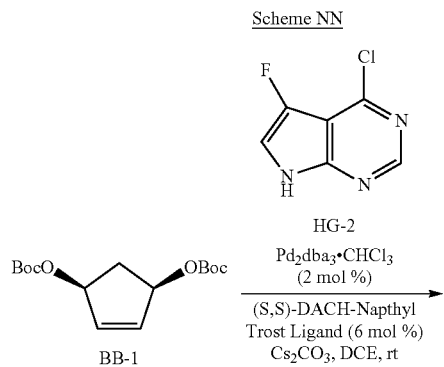

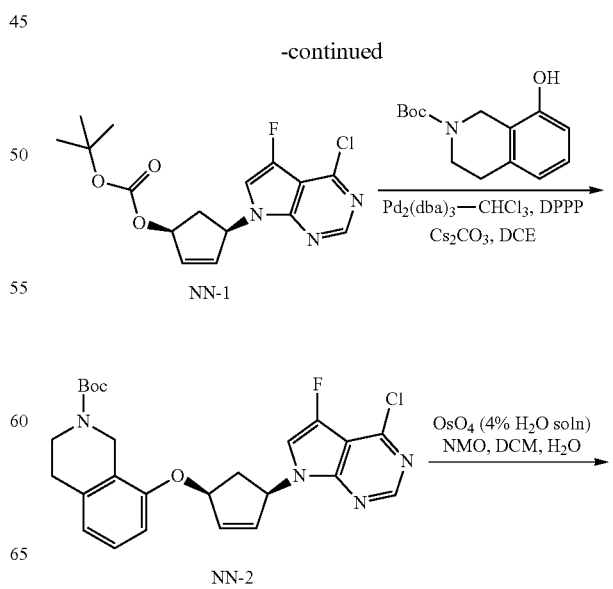

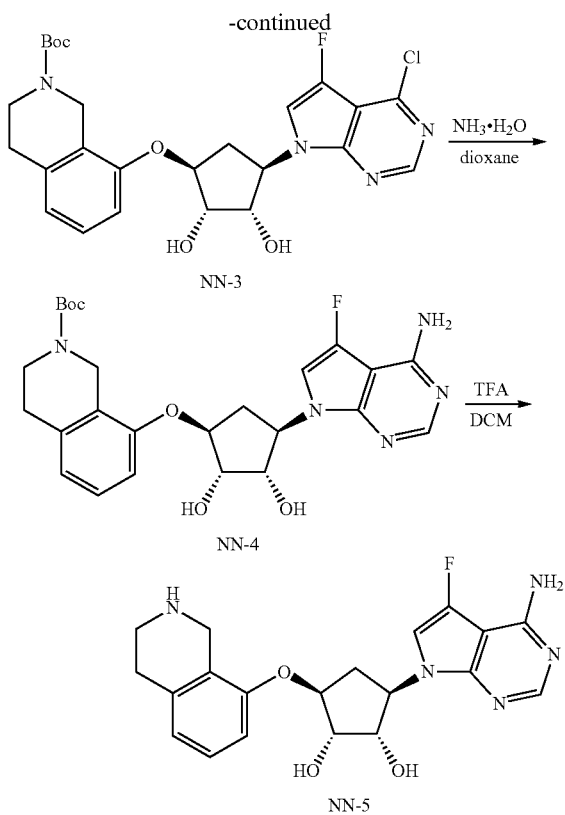

Step 1—Synthesis of tert-butyl((1S,4R)-4-(4-chloro-5-fluoro-7H-pyrrolo[2,3-d]pyrimidin-7-yl)cyclopent-2-en-1-yl) carbonate (NN-1)

Vial A: To a dry round bottom flask (purged with $N_2$) was added (S,S)-DACH-Naphthyl Trost Ligand (1.13 g, 1.43 mmol) and $Pd_2(dba)_3 \cdot CHCl_3$ (493 mg, 0.48 mmol). The vial was purged with $N_2$ four times and DCE (50 mL, sparged with $N_2$ for 30 min) was added. The black solution was stirred for 30 min at 12° C. at which point a red-brown solution was obtained.

Vial B: To a dry round bottom flask (purged with $N_2$) was added BB-1 (7155 mg, 23.82 mmol), 4-chloro-5-fluoro-7H-pyrrolo[2,3-d]pyrimidine (4.5 g, 26.23 mmol) and $Cs_2CO_3$ (8.54 g, 26.2 mmol). The vial was purged with $N_2$ five times and DCE (50 mL) was added, followed by the addition of the contents of Vial A via syringe. The reaction stirred at 12° C. under $N_2$ for 24 hours.

The reaction mixture was filtered and concentrated to a brown gum. The crude residue was purified by flash biotage (120 g, silica gel, EtOAc/petroleum ether=15%) to give NN-1 (6.4 g, 76%) as an off-white solid. LCMS [M+1] 354; $^1$H NMR (400 MHz, $CDCl_3$) δ ppm 8.62 (s, 1H), 7.08 (d, J=2.5 Hz, 1H), 6.35-6.29 (m, 1H), 6.10-6.00 (m, 2H), 5.63-5.55 (m, 1H), 3.11 (td, J=7.8, 15.4 Hz, 1H), 1.87 (td, J=3.8, 15.0 Hz, 1H), 1.52 (s, 9H)

Step 2—Synthesis of tert-butyl 8-(((1S,4R)-4-(4-chloro-5-fluoro-7H-pyrrolo[2,3-d]pyrimidin-7-yl)cyclopent-2-en-1-yl)oxy)-3,4-dihydroisoquinoline-2(1H)-carboxylate (NN-2)

To a dry microwave vial (purged with $N_2$) was added NN-1 (200 mg, 0.57 mmol), tert-butyl 8-hydroxy-3,4-dihydroisoquinoline-2(1H)-carboxylate(141 mg, 0.57 mmol), $Cs_2CO_3$ (203 mg, 0.622 mmol), $Pd_2(dba)_3 \cdot CHCl_3$ (15 mg, 0.014 mmol) and DPPP (14 mg, 0.03 mmol). Then the vial was purged with $N_2$ three times and DCE (2.6 mL, sparged with $N_2$ for 30 mins) was added. The black mixture was stirred at 20° C. for 1 hour. Then the reaction mixture was directly purified by prep-TLC (petroleum ether:EtOAc=4:1) to give NN-2 (260 mg, 95%) as a white foam.

LCMS [M+23] 507; $^1$H NMR (400 MHz, $CDCl_3$) δ ppm 8.63 (s, 1H), 7.16 (d, J=2.0 Hz, 1H), 7.14-7.09 (m, 1H), 6.79 (d, J=7.3 Hz, 1H), 6.74 (d, J=7.5 Hz, 1H), 6.46-6.40 (m, 1H), 6.15-6.06 (m, 2H), 5.37-5.31 (m, 1H), 4.74-4.42 (m, 2H), 3.75-3.54 (m, 2H), 3.19-3.10 (m, 1H), 2.87-2.79 (m, 2H), 1.97 (d, J=14.6 Hz, 1H), 1.51 (s, 9H)

Step 2—Synthesis of tert-butyl 8-(((1S,2S,3S,4R)-4-(4-chloro-5-fluoro-7H-pyrrolo[2,3-d]pyrimidin-7-yl)-2,3-dihydroxycyclopentyl)oxy)-3,4-dihydroisoquinoline-2(1H)-carboxylate (NN-3)

To a mixture of NN-2 (260 mg, 0.536 mmol) in DCM (9 mL)/$H_2O$ (0.3 mL) was added NMO (188 mg, 1.61 mmol) and $OsO_4$ (4% in t-BuOH, 204 mg, 0.0322 mmol) at 20° C. The black mixture was stirred at 20° C. for 2 hours. The mixture was diluted with DCM (10 mL) and quenched by sat. $Na_2SO_3$ (5 mL) and separated. The aqueous layer was extracted with DCM (10 mL). The combined organic layer was washed with brine (10 mL), dried over $Na_2SO_4$, filtered and concentrated and purified by ISCO (12 g, silica gel, EtOAc:petroleum ether=1:1) to yield NN-3 (230 mg, 83%) as a colorless gum.

LCMS [M+23] 541; $^1$H NMR (400 MHz, $CDCl_3$) δ ppm 8.62 (s, 1H), 7.17 (t, J=8.0 Hz, 1H), 7.13 (d, J=2.5 Hz, 1H), 6.86-6.79 (m, 2H), 5.21-5.05 (m, 1H), 5.02-4.75 (m, 2H), 4.67-4.56 (m, 1H), 4.53-4.42 (m, 2H), 4.37-4.29 (m, 1H), 3.72-3.57 (m, 2H), 3.32-2.99 (m, 2H), 2.87-2.78 (m, 2H), 2.33-2.22 (m, 1H), 1.50-1.44 (m, 9H)

Step 3—Synthesis of tert-butyl 8-(((1S,2S,3S,4R)-4-(4-amino-5-fluoro-7H-pyrrolo[2,3-d]pyrimidin-7-yl)-2,3-dihydroxycyclopentyl)oxy)-3,4-dihydroisoquinoline-2(1H)-carboxylate (NN-4)

A solution of NN-3 (105 mg, 0.202 mmol) in $NH_3 \cdot H_2O$ and dioxane (2.8 mL/2.8 mL) was sealed in a steel tube at 90° C. for 15 hours. The reaction was concentrated to give NN-4 (101 mg, >99%) as a yellow gum and used directly in the next step. LCMS [M+23] 522

Step 4—Synthesis of (1S,2S,3R,5S)-3-(4-amino-5-fluoro-7H-pyrrolo[2,3-d]pyrimidin-7-yl)-5-((1,2,3,4-tetrahydroisoquinolin-8-yl)oxy)cyclopentane-1,2-diol (NN-5)

To a light yellow solution of NN-4 (101 mg, 0.202 mmol) in DCM (5 mL) was added TFA (1 mL) dropwise at 0° C. The yellow solution mixture was stirred at 20° C. for 2 hours. The mixture was concentrated MeOH (4 mL) was added to the residue and basified by solid $K_2CO_3$ to pH 7-8. The mixture was filtered and concentrated purified by prep-HPLC to give NN-5 (35 mg, 39%) as a light yellow solid.

LCMS [M+1] 400; $^1$H NMR (400 MHz, MeOD) δ ppm 8.09 (s, 1H), 7.35-7.23 (m, 1H), 7.15-7.06 (m, 1H), 7.03-6.96 (m, 1H), 6.94-6.83 (m, 1H), 5.16-5.07 (m, 1H), 4.75-4.68 (m, 1H), 4.63-4.55 (m, 1H), 4.37 (s, 2H), 4.22-4.16 (m, 1H), 3.54-3.44 (m, 2H), 3.17-3.08 (m, 2H), 3.04-2.92 (m, 1H), 2.16-2.02 (m, 1H)

Examples 100-111 were Made in a Similar Fashion to Example 99 in Scheme NN Using the Appropriate NBoc-Protected Tetrahydroisoquinoline in Step 2

| Example 100 TP-2 | 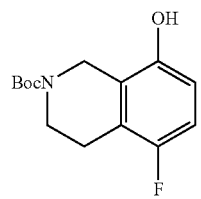 [SMILES: CC(C)(C)OC(=O)N1CCc2c(F)ccc(O)c2C1] 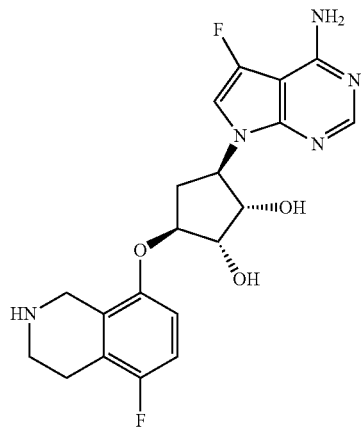 [SMILES: Nc1ncnc2c1c(F)cn2[C@@H]1C[C@H](Oc2ccc(F)c3c2CNCC3)[C@@H](O)[C@H]1O] | 418 [M + 1] | (1S,2S,3R,5S)-3-(4-amino-5-fluoro-7H-pyrrolo[2,3-d]pyrimidin-7-yl)-5-((5-fluoro-1,2,3,4-tetrahydroisoquinolin-8-yl)oxy)cyclopentane-1,2-diol<br>$^1$H NMR (400 MHz, MeOD-d$_4$) δ ppm 8.09 (s, 1H), 7.08 (d, J = 2.0 Hz, 1H), 7.02-6.83 (m, 2H), 5.13 (q, J = 8.8 Hz, 1H), 4.68-4.62 (m, 1H), 4.55 (dd, J = 5.0, 8.8 Hz, 1H), 4.15 (d, J = 5.5 Hz, 1H), 4.13 (s, 2H), 3.26 (t, J = 6.0 Hz, 2H), 3.01-2.92 (m, 1H), 2.89 (t, J = 6.1 Hz, 2H), 2.04 (ddd, J = 4.3, 9.1, 14.0 Hz, 1H) |
| --- | --- | --- | --- |
| Example 101 TP-12 | 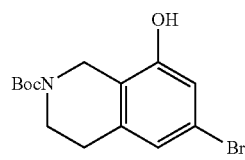 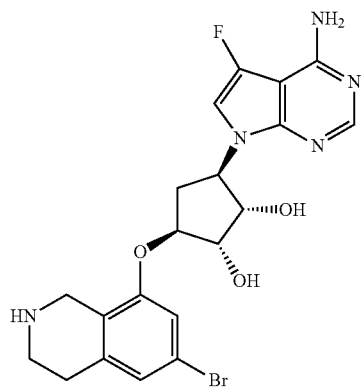 | 478 [M + 1] | (1S,2S,3R,5S)-3-(4-amino-5-fluoro-7H-pyrrolo[2,3-d]pyrimidin-7-yl)-5-((6-bromo-1,2,3,4-tetrahydroisoquinolin-8-yl)oxy)cyclopentane-1,2-diol<br>$^1$H NMR (400 MHz, MeOD-d$_4$) δ ppm 8.08 (s, 1H), 7.17-7.10 (m, 1H), 7.09-7.05 (m, 1H), 7.04-7.00 (m, 1H), 5.10 (q, J = 8.8 Hz, 1H), 4.69-4.63 (m, 1H), 4.57-4.51 (m, 1H), 4.16-4.06 (m, 3H), 3.29-3.24 (m, 2H), 2.99-2.89 (m, 3H), 2.13-2.02 (m, 1H) |
| Example 102 TP-3 | 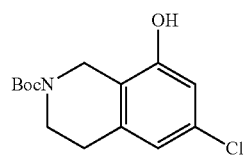 [SMILES: CC(C)(C)OC(=O)N1CCc2cc(Br)cc(O)c2C1] 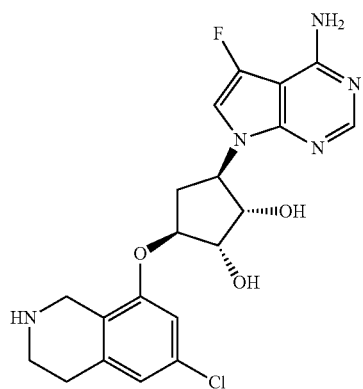 | 434 [M + 1] | (1S,2S,3R,5S)-3-(4-amino-5-fluoro-7H-pyrrolo[2,3-d]pyrimidin-7-yl)-5-((6-chloro-1,2,3,4-tetrahydroisoquinolin-8-yl)oxy)cyclopentane-1,2-diol<br>$^1$H NMR (400 MHz, MeOD-d$_4$) δ ppm 8.08 (s, 1H), 7.07 (d, J = 4.0 Hz, 2H), 6.93 (s, 1H), 5.07 (q, J = 8.8 Hz, 1H), 4.72-4.63 (m, 1H), 4.60-4.53 (m, 1H), 4.28 (s, 2H), 4.16-4.12 (m, 1H), 3.44 (t, J = 6.1 Hz, 2H), 3.06 (t, J = 6.3 Hz, 2H), 2.99-2.88 (m, 1H), 2.19-2.04 (m, 1H) |

-continued

| | | | |
|---|---|---|---|
| Example 103 TP-6 | 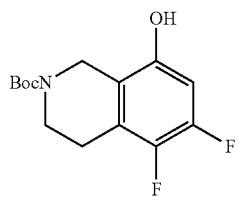 [SMILES: CC(C)(C)OC(=O)N1CCc2c(F)c(F)cc(O)c2C1] 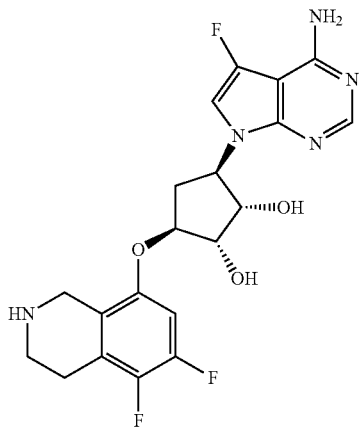 [SMILES: Nc1ncnc2c1c(F)cn2[C@@H]1C[C@H](Oc2cc(F)c(F)c3c2CNCC3)[C@@H](O)[C@H]1O] | 436 [M + 1] | (1S,2S,3R,5S)-3-(4-amino-5-fluoro-7H-pyrrolo[2,3-d]pyrimidin-7-yl)-5-((5,6-difluoro-1,2,3,4-tetrahydroisoquinolin-8-yl)oxy)cyclopentane-1,2-diol<br>$^1$H NMR (400 MHz, MeOD-d$_4$) δ ppm 8.07 (s, 1H), 7.07 (d, J = 2.0 Hz, 1H), 7.03 (dd, J = 6.7, 12.2 Hz, 1H), 5.06 (q, J = 9.0 Hz, 1H), 4.63 (td, J = 2.6, 4.8 Hz, 1H), 4.55 (dd, J = 5.3, 8.8 Hz, 1H), 4.20 (s, 2H), 4.13 (d, J = 4.0 Hz, 1H), 3.40 (t, J = 6.3 Hz, 2H), 3.01 (t, J = 6.0 Hz, 2H), 2.93 (td, J = 8.2, 14.3 Hz, 1H), 2.09 (ddd, J = 4.8, 9.3, 14.1 Hz, 1H) |
| Example 104 TP-4 | 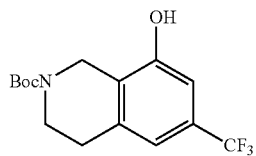 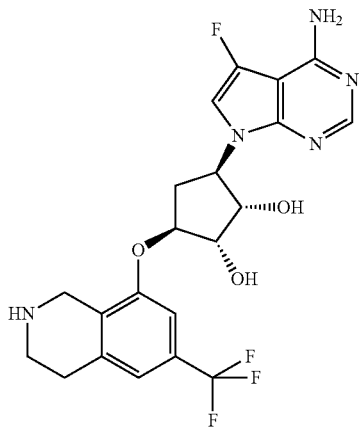 [SMILES: Nc1ncnc2c1c(F)cn2[C@@H]1C[C@H](Oc2cc(C(F)(F)F)cc3c2CNCC3)[C@@H](O)[C@H]1O] | 468 [M + 1] | (1S,2S,3R,5S)-3-(4-amino-5-fluoro-7H-pyrrolo[2,3-d]pyrimidin-7-yl)-5-((6-(trifluoromethyl)-1,2,3,4-tetrahydroisoquinolin-8-yl)oxy)cyclopentane-1,2-diol<br>$^1$H NMR (400 MHz, MeOD-d$_4$) δ ppm 8.08 (s, 1H), 7.12 (s, 1H), 7.08 (d, J = 2.3 Hz, 1H), 7.06 (s, 1H), 5.14 (q, J = 9.3 Hz, 1H), 4.74-4.67 (m, 1H), 4.52 (dd, J = 5.0, 8.8 Hz, 1H), 4.13 (d, J = 5.5 Hz, 1H), 3.98 (s, 2H), 3.09-3.04 (m, 2H), 2.95 (ddd, J = 7.3, 9.2, 14.4 Hz, 1H), 2.88-2.83 (m, 2H), 2.06 (ddd, J = 4.1, 9.0, 13.7 Hz, 1H) |
| Example 105 TP-5 | 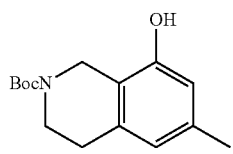 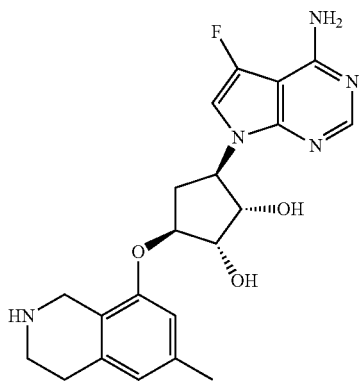 [SMILES: Cc1cc2c(c(O[C@H]3C[C@@H](n4cc(F)c5c(N)ncnc54)[C@H](O)[C@@H]3O)c1)CNCC2] | 414 [M + 1] | (1S,2S,3R,5S)-3-(4-amino-5-fluoro-7H-pyrrolo[2,3-d]pyrimidin-7-yl)-5-((6-methyl-1,2,3,4-tetrahydroisoquinolin-8-yl)oxy)cyclopentane-1,2-diol<br>$^1$H NMR (400 MHz, DMSO-d$_6$) δ ppm 8.05 (s, 1H), 7.20 (s, 1H), 6.92 (br. s., 2H), 6.66 (s, 1H), 6.53 (s, 1H), 5.06-4.98 (m, 1H), 4.50 (br. s., 1H), 4.41-4.37 (m, 1H), 3.95-3.92 (m, 1H), 3.88 (br. s., 2H), 3.05-2.95 (m, 3H), 2.84-2.67 (m, 2H), 2.23 (s, 3H), 1.84-1.73 (m, 1H) |

-continued

| | | | |
|---|---|---|---|
| Example 106 TP-13 | 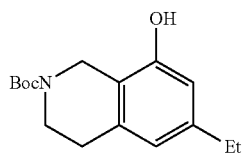 | 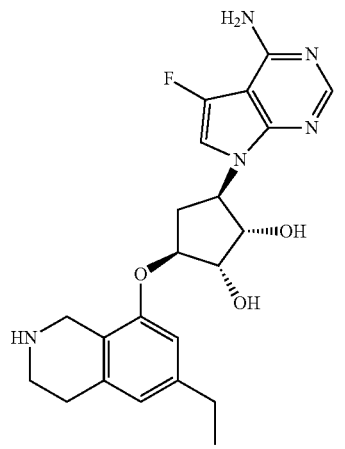 [SMILES: CCc1cc2c(c(O[C@H]3C[C@@H](n4cc(F)c5c(N)ncnc54)[C@H](O)[C@@H]3O)c1)CNCC2] | 428 [M + 1] | (1S,2S,3R,5S)-3-(4-amino-5-fluoro-7H-pyrrolo[2,3-d]pyrimidin-7-yl)-5-((6-ethyl-1,2,3,4-tetrahydroisoquinolin-8-yl)oxy)cyclopentane-1,2-diol<br>¹H NMR (400 MHz, MeOD-d₄) δ ppm 8.14 (s, 1H), 7.22 (d, J = 2.0 Hz, 1H), 6.85 (s, 1H), 6.74 (s, 1H), 5.17 (q, J = 9.0 Hz, 1H), 4.74-4.66 (m, 1H), 4.56 (dd, J = 4.9, 8.9 Hz, 1H), 4.30 (s, 2H), 4.15 (d, J = 5.0 Hz, 1H), 3.47 (t, J = 6.4 Hz, 2H), 3.07 (t, J = 6.1 Hz, 2H), 3.02-2.92 (m, 1H), 2.64 (q, J = 7.4 Hz, 2H), 2.12-2.02 (m, 1H), 1.23 (t, J = 7.7 Hz, 3H) |
| Example 107 TP-1 | 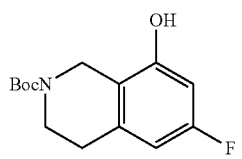 | 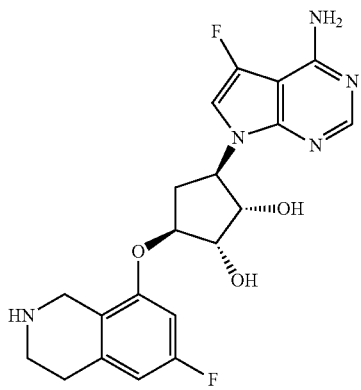 [SMILES: Nc1ncnc2c1c(F)cn2[C@@H]1C[C@H](Oc2cc(F)cc3c2CNCC3)[C@@H](O)[C@H]1O] | 418 [M + 1] | (1S,2S,3R,5S)-3-(4-amino-5-fluoro-7H-pyrrolo[2,3-d]pyrimidin-7-yl)-5-((6-fluoro-1,2,3,4-tetrahydroisoquinolin-8-yl)oxy)cyclopentane-1,2-diol<br>¹H NMR (400 MHz, MeOD-d₄) δ ppm 8.16 (s, 1H), 7.27 (d, J = 2.0 Hz, 1H), 6.86 (dd, J = 2.3, 10.8 Hz, 1H), 6.67 (d, J = 9.3 Hz, 1H), 5.21-5.12 (m, 1H), 4.68 (t, J = 5.3 Hz, 1H), 4.56 (dd. J = 5.0, 9.0 Hz, 1H), 4.30 (s, 2H), 4.15 (d, J = 4.8 Hz, 1H), 3.48 (t, J = 6.3 Hz, 2H), 3.10 (t, J = 6.0 Hz, 2H), 3.02-2.91 (m, 1H), 2.12 (ddd, J = 4.6, 9.5, 14.0 Hz, 1H) |
| Example 108 TP-10 | 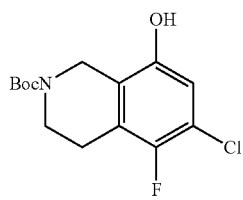 | 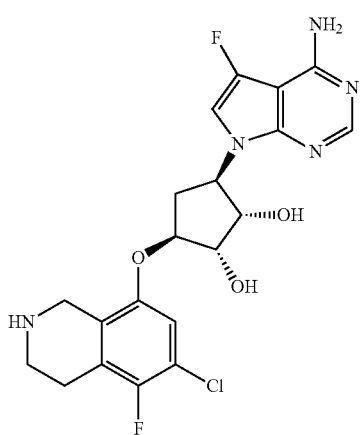 [SMILES: Nc1ncnc2c1c(F)cn2[C@@H]1C[C@H](Oc2cc(Cl)c(F)c3c2CNCC3)[C@@H](O)[C@H]1O] | 452 [M + 1] | (1S,2S,3R,5S)-3-(4-amino-5-fluoro-7H-pyrrolo[2,3-d]pyrimidin-7-yl)-5-((6-chloro-5-fluoro-1,2,3,4-tetrahydroisoquinolin-8-yl)oxy)cyclopentane-1,2-diol<br>¹H NMR (400 MHz, MeOD-d₄) δ ppm 8.08 (s, 1H), 7.08 (d, J = 2.0 Hz, 1H), 7.01 (d, J = 6.0 Hz, 1H), 5.16-5.09 (m, 1H), 4.63-4.58 (m, 1H), 4.53-4.47 (m, 1H), 4.14-4.08 (m, 1H), 3.92 (s, 2H), 3.07 (t, J = 5.9 Hz, 2H), 2.98-2.88 (m, 1H), 2.82-2.73 (m, 2H), 2.07-1.97 (m, 1H) |

| | | | |
|---|---|---|---|
| Example 109 TP-11 | 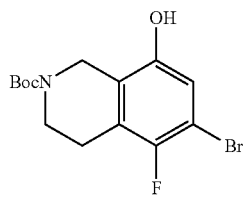 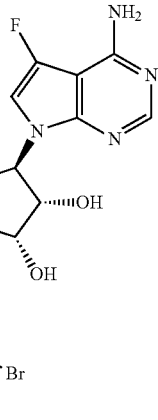 | 496 [M + 1] | (1S,2S,3R,5S)-3-(4-amino-5-fluoro-7H-pyrrolo[2,3-d]pyrimidin-7-yl)-5-((6-bromo-5-fluoro-1,2,3,4-tetrahydroisoquinolin-8-yl)oxy)cyclopentane-1,2-diol<br>$^1$H NMR (400 MHz, MeOD) δ ppm 8.09 (s, 1H), 7.04-7.20 (m, 2H), 5.13 (m, J = 9.00 Hz, 1H), 4.59-4.68 (m, 1H), 4.52 (m, J = 8.80 Hz, 1H), 4.13 (d, J = 4.77 Hz, 1H), 3.95 (s, 2H), 3.11 (m, J = 6.00 Hz, 2H), 2.87-3.03 (m, 1H), 2.81 (m, J = 5.80 Hz, 2H), 1.97-2.13 (m, 1H) |
| Example 110 tert-butyl 4-hydroxyisoindoline-2-carboxylate | 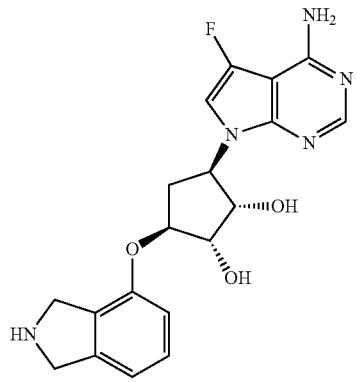 [SMILES: Nc1ncnc2c1c(F)cn2[C@@H]1C[C@H](Oc2cccc3c2CNC3)[C@@H](O)[C@H]1O] | 386 [M + 1] | (1S,2S,3R,5S)-3-(4-amino-5-fluoro-7H-pyrrolo[2,3-d]pyrimidin-7-yl)-5-(2,3-dihydro-1H-isoindol-4-yloxy)cyclopentane-1,2-diol<br>$^1$H NMR (400 MHz, MeOD-$d_4$) δ ppm 8.09 (s, 1H), 7.45-7.38 (m, 1H), 7.14-7.07 (m, 2H), 7.07-7.01 (m, 1H), 5.18-5.08 (m, 1H), 4.78-4.72 (m, 1H), 4.66 (s, 4H), 4.58-4.52 (m, 1H), 4.20-4.15 (m, 1H), 3.03-2.92 (m, 1H), 2.13-2.02 (m, 1H) |
| Example 111 tert-butyl 5-hydroxy-3,4-dihydroisoquinoline-2(1H)-carboxylate | 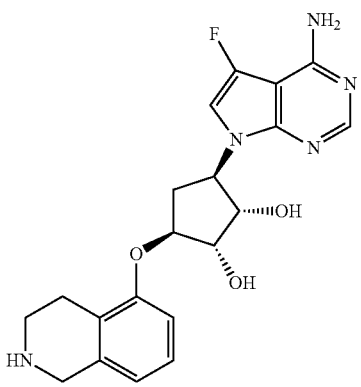 [SMILES: Nc1ncnc2c1c(F)cn2[C@@H]1C[C@H](Oc2cccc3c2CCNC3)[C@@H](O)[C@H]1O] | 400 [M + 1] | (1S,2S,3R,5S)-3-(4-amino-5-fluoro-7H-pyrrolo[2,3-d]pyrimidin-7-yl)-5-((1,2,3,4-tetrahydroisoquinolin-5-yl)oxy)cyclopentane-1,2-diol<br>$^1$H NMR (400 MHz, MeOD-$d_4$) δ ppm 8.09 (s, 1H), 7.29 (t, J = 7.8 Hz, 1H), 7.08 (d, J = 2.0 Hz, 1H), 7.04 (d, J = 8.5 Hz, 1H), 6.86 (d, J = 7.8 Hz, 1H), 5.22-5.09 (m, 2H), 4.74-4.68 (m, 1H), 4.57 (dd, J = 5.0, 8.5 Hz, 1H), 4.37 (s, 2H), 4.18 (d, J = 4.0 Hz, 1H), 3.56 (t, J = 6.5 Hz, 2H), 3.10 (t, J = 6.5 Hz, 2H), 3.04-2.93 (m, 1H), 2.11-1.98 (m, 1H) |
| Example 112 TP-15 | 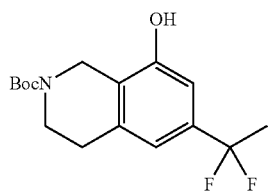 [SMILES: CC(C)(C)OC(=O)N1CCc2cc(C(C)(F)F)cc(O)c2C1] 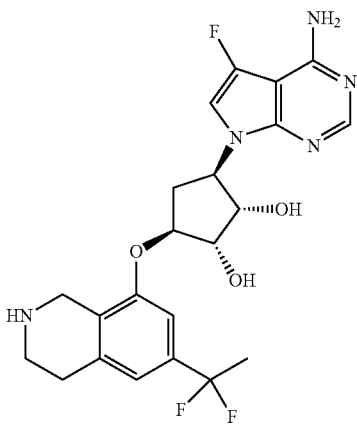 [SMILES: CC(F)(F)c1cc2c(c(O[C@H]3C[C@@H](n4cc(F)c5c(N)ncnc54)[C@H](O)[C@@H]3O)c1)CNCC2] | | (1S,2S,3R,5S)-3-(4-amino-5-fluoro-7H-pyrrolo[2,3-d]pyrimidin-7-yl)-5-((6-(1,1-difluoroethyl)-1,2,3,4-tetrahydroisoquinolin-8-yl)oxy)cyclopentane-1,2-diol<br>$^1$H NMR (400 MHz, MeOD) δ ppm 8.29 (s, 1H), 7.51 (d, J = 2.3 Hz, 1H), 7.14 (s, 1H), 7.10 (s, 1H), 5.27 (q, J = 9.0 Hz, 1H), 4.79-4.75 (m, 1H), 4.60 (dd, J = 5.0, 9.0 Hz, 1H), 4.39 (s, 2H), 4.17 (d, J = 4.8 Hz, 1H), 3.52 (t, J = 6.3 Hz, 2H), 3.17 (t, J = 6.0 Hz, 2H), 3.00 (ddd, J = 7.7, 9.0, 14.2 Hz, 1H), 2.17 (ddd, J = 4.1, 9.7, 14.1 Hz, 1H), 1.93 (t, J = 18.3 Hz, 3H) |

| Example 113 TP-8 | 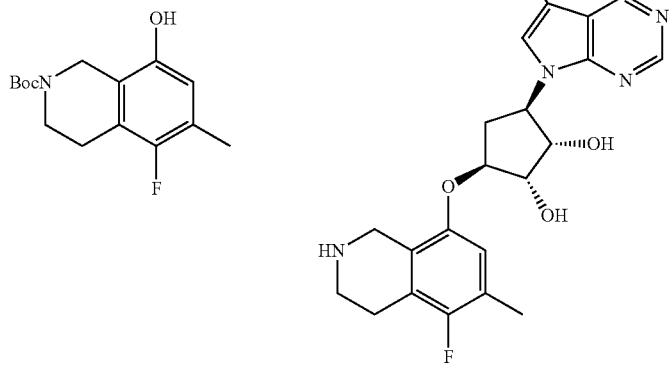 | 432 [M + 1] | (1S,2S,3R,5S)-3-(4-amino-5-fluoro-7H-pyrrolo[2,3-d]pyrimidin-7-yl)-5-((5-fluoro-6-methyl-1,2,3,4-tetrahydroisoquinolin-8-yl)oxy)cyclopentane-1,2-diol<br>$^1$H NMR with formic acid (400 MHz, MeOD-d$_4$) δ ppm 8.50 (br s, 1H), 8.07 (s, 1H), 7.07 (d, J = 2.3 Hz, 1H), 6.88 (d, J = 6.3 Hz, 1H), 5.07 (q, J = 8.7 Hz, 1H), 4.67-4.61 (m, 1H), 4.55 (dd, J = 5.0, 8.8 Hz, 1H), 4.28 (s, 2H), 4.16-4.11 (m, 1H), 3.49-3.41 (m, 2H), 3.01 (t, J = 6.1 Hz, 2H), 2.96-2.87 (m, 1H), 2.27 (d, J = 1.8 Hz, 3H), 2.10-2.01 (m, 1H) |
|---|---|---|---|

Example 114 (Scheme OO)—(1S,2S,3R,5S)-3-(4-amino-5-fluoro-7H-pyrrolo[2,3-d]pyrimidin-7-yl)-5-((2-methyl-1,2,3,4-tetrahydroisoquinolin-8-yl)oxy)cyclopentane-1,2-diol (OO-1)

Step 1—Synthesis of (1S,2S,3R,5S)-3-(4-amino-5-fluoro-7H-pyrrolo[2,3-d]pyrimidin-7-yl)-5-((2-methyl-1,2,3,4-tetrahydroisoquinolin-8-yl)oxy)cyclopentane-1,2-diol (OO-1)

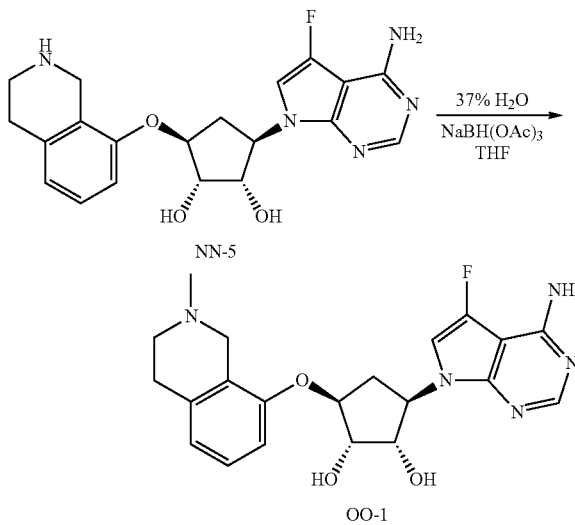

Scheme OO

A mixture of NN-5 (100 mg, 0.25 mmol), 37% CH$_2$O (31 mg, 0.38 mmol) and NaBH(OAc)$_3$ (212 mg, 1.0 mmol) in THF (6 mL) was stirred at 20° C. for 2 hrs. The mixture was filtered and sent to prep-HPLC to give OO-1 (65 mg, 53%) as a light yellow solid. LCMS 414 [M+1]; $^1$H NMR (400 MHz, MeOD-d$_4$) δ ppm 8.10 (s, 1H), 7.34-7.27 (m, 1H), 7.16-7.10 (m, 1H), 7.03-6.97 (m, 1H), 6.94-6.88 (m, 1H), 5.18-5.09 (m, 1H), 4.75-4.68 (m, 1H), 4.59-4.53 (m, 1H), 4.42-4.34 (m, 2H), 4.21-4.16 (m, 1H), 3.55-3.46 (m, 2H), 3.23-3.16 (m, 2H), 3.08 (s, 3H), 3.04-2.92 (m, 1H), 2.16-2.03 (m, 1H)

Examples 115 & 116 were Made Using Similar Procedures to Scheme OO from Examples 110 & 111 Respectively

| Example 115 | 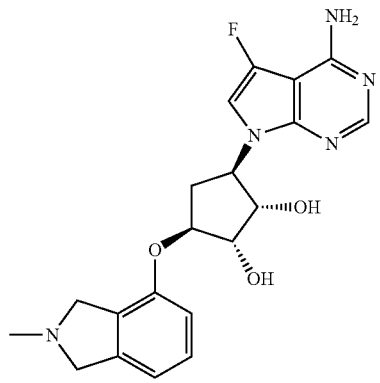 [SMILES: CN1Cc2cccc(O[C@H]3C[C@@H](n4cc(F)c5c(N)ncnc54)[C@H](O)[C@@H]3O)c2C1] | 400 [M + 1] | (1S,2S,3R,5S)-3-(4-amino-5-fluoro-7H-pyrrolo[2,3-d]pyrimidin-7-yl)-5-[(2-methyl-2,3-dihydro-1H-isoindol-4-yl)oxy]cyclopentane-1,2-diol<br>$^1$H NMR (400 MHz, MeOD-d$_4$) δ ppm 8.09 (s, 1H), 7.41 (t, J = 7.9 Hz, 1H), 7.15-7.06 (m, 2H), 7.02 (d, J = 7.5 Hz, 1H), 5.21-5.10 (m, 1H), 4.77-4.70 (m, 1H), 4.66 (d, J = 5.5 Hz, 4H), 4.53 (dd, J = 5.1, 8.7 Hz, 1H), 4.18 (d, J = 5.0 Hz, 1H), 3.11 (s, 3H), 2.98 (ddd, J = 7.4, 9.0, 14.4 Hz, 1H), 2.05 (ddd, J = 4.3, 9.3, 14.1 Hz, 1H) |
|---|---|---|---|

| | | | |
|---|---|---|---|
| Example 116 | 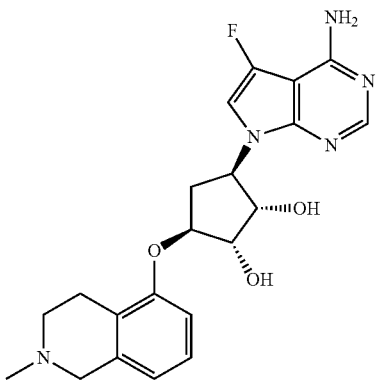 [SMILES: CN1CCc2c(cccc2O[C@H]2C[C@@H](n3cc(F)c4c(N)ncnc43)[C@H](O)[C@@H]2O)C1] | 414 [M + 1] | (1S,2S,3R,5S)-3-(4-amino-5-fluoro-7H-pyrrolo[2,3-d]pyrimidin-7-yl)-5-((2-methyl-1,2,3,4-tetrahydroisoquinolin-5-yl)oxy)cyclopentane-1,2-diol<br>$^1$H NMR (400 MHz, MeOD-d$_4$) δ ppm 8.09 (s, 1H), 7.27 (t, J = 8.0 Hz, 1H), 7.08 (d, J = 2.0 Hz, 1H), 7.01 (d, J = 8.3 Hz, 1H), 6.82 (d, J = 7.8 Hz, 1H), 5.22-5.10 (m, 1H), 4.71 (br. s., 1H), 4.56 (dd, J = 4.9, 8.7 Hz, 1H), 4.23 (br. s., 2H), 4.18 (d, J = 4.5 Hz, 1H), 3.46-3.37 (m, 2H), 3.10 (t, J = 6.1 Hz, 2H), 2.99 (ddd, J = 7.5, 9.2, 14.4 Hz, 1H), 2.93 (s, 3H), 2.05 (s, 1H) |

Synthesis of 5-fluoro-2-methyl-7H-pyrrolo[2,3-d]pyrimidine (HG-3)

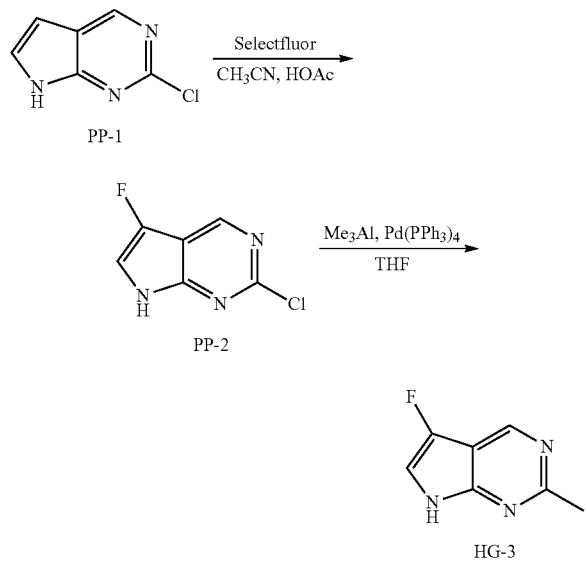

Step 1—Synthesis of 2-chloro-5-fluoro-7H-pyrrolo[2,3-d]pyrimidine (PP-2)

To a solution of 2-chloro-7H-pyrrolo[2,3-d]pyrimidine (PP-1) (8.5 g, 55 mmol) and selectfluor (29.4 g, 83.0 mmol) in CH$_3$CN (500 mL) was added AcOH (100 mL) under N$_2$. The mixture was stirred at 70° C. for 16 hours. The color of the reaction became orange from yellow. The reaction concentrated and azeotroped with toluene (30 mL×3). Then the solid was diluted with CH$_2$Cl$_2$/EtOAc (1/1, 200 mL) and stirred at room temperature (25° C.) for 16 hrs and filtered. The filtrate was concentrated and washed with DCM to afford crude material as a brown solid. MBTE was added and stirred overnight and filtered to afford PP-2 (1.5 g, 15%) as a yellow solid. LCMS 172 [M+1]; $^1$H NMR (400 MHz, MeOD-d$_4$) δ ppm 8.89 (d, J=0.8 Hz, 1H), 7.31 (d, J=2.5 Hz, 1H)

Step 2—Synthesis of 5-fluoro-2-methyl-7H-pyrrolo[2,3-d]pyrimidine (HG-3)

Pd(PPh$_3$)$_4$ (835 mg, 0.723 mmol) was added to a solution PP-2 (2.48 g, 14.46 mmol) in dry THF (36 mL) at 10° C. The suspension was degassed with N$_2$. A solution of Me$_3$Al (2M, 14.5 mL, 28.9 mmol) was added to the above mixture at −10° C. slowly. After the addition, the mixture was heated at 70° C. for 16 hours. The reaction mixture was added to ice-water carefully. The mixture was diluted with EtOAc and filtered through celite. The filtrate was partitioned between EtOAc and H$_2$O. The organic layer was separated and washed with brine, dried over Na$_2$SO$_4$ and concentrated to afford the crude product and purified via flash column (MeOH:DCM=1%~7.5%) to afford the product HG-3 (1.2 g, 55%) as a yellow solid. LCMS 152 [M+1]; $^1$H NMR (400 MHz, MeOD-d$_4$) δ ppm 11.76 (br. s., 1H), 8.96 (s, 1H), 7.44 (t, J=2.5 Hz, 1H), 2.63 (s, 3H)

Synthesis of 5-fluoro-4-methyl-7H-pyrrolo[2,3-d]pyrimidine (HG-4)

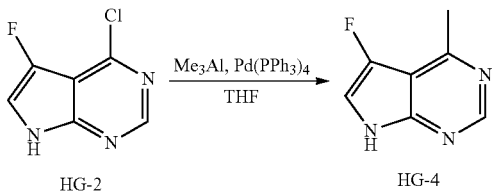

To Pd(PPh₃)₄ (2 g, 1.75 mmol) was added a solution of HG-2 (7.5 g, 43.7 mmol) in dry THF (75 mL). The suspension was degassed with N₂. A solution of AlMe₃ (43.7 mL, 87.5 mmol, 2M) was added to the above mixture at ice-water. After the addition, the yellow solution was heated at 80° C. for 16 h. The reaction mixture was quenched with ice and aqueous Rochelle salt. The mixture was partitioned between EtOAc and H₂O. The mixture was filtered and the filtrate cake was washed with EtOAc (100 mL×3). The organic layer was separated and dried over Na₂SO₄ and concentrated then purified via flash column (MeOH:DCM=1%~4%) to afford the product. The product was triturated in DCM and filtered. The filtrate cake was washed with TBME and collected to afford the product HG-4 (2.00 g, 30%) as a yellow solid. The filtrate was concentrated purified via flash column (MeOH:DCM=1%~5%) to afford the product. LCMS 152 [M+1]; ¹H NMR (400 MHz, MeOD-d₄) δ ppm 11.89 (br. s., 1H), 8.62 (s, 1H), 7.48 (t, J=2.5 Hz, 1H), 2.70 (s, 3H)

Synthesis of 4-chloro-5-fluoro-2-methyl-7H-pyrrolo[2,3-d]pyrimidine (HG-5)

Step 1—Synthesis of 4-chloro-2-methyl-7H-pyrrolo[2,3-d]pyrimidine (RR-2)

A mixture of 2-methyl-3,7-dihydro-4H-pyrrolo[2,3-d]pyrimidin-4-one (RR-1) (2.7 g, 18.1 mmol) in POCl₃ (35 mL) was heated at reflux for 4 hours. The mixture was cooled to 20° C. and concentrated. To the residue was added ice-water (20 mL) and basified by solid Na₂CO₃ to pH-8. The mixture was extracted with EtOAc (60 mL×2). The combined organic layers were washed with brine (100 mL), dried over Na₂SO₄, filtered and concentrated to yield RR-2 (2.4 g, 78%) as an off-white solid. LCMS 168 [M+1]; ¹H NMR (400 MHz, CDCl₃) δ ppm 10.70-10.41 (m, 1H), 7.36-7.29 (m, 1H), 6.67-6.56 (m, 1H), 2.81 (s, 3H)

Step 2—Synthesis of 4-chloro-5-fluoro-2-methyl-7H-pyrrolo[2,3-d]pyrimidine (HG-5)

A mixture of RR-2 (2.35 g, 14 mmol) and Selectfluor (7.45 g, 21 mmol) in CH₃CN (110 mL) and AcOH (22 mL) was stirred at 70° C. under N₂ for 16 hours in which the reaction became brown from pink. The mixture was concentrated and azeotroped toluene (50 ml×2). The filtrate was concentrated and purified by prep-HPLC to give HG-5 (600 mg, 23%) as a yellow solid. LCMS 186 [M+1]; ¹H NMR (400 MHz, MeOD-d₄) δ ppm 12.27-12.18 (m, 1H), 7.62-7.56 (m, 1H), 2.61 (s, 3H)

Examples 117-119 were Made in a Similar Fashion to CC-3 (Example 78) Using the Appropriate Pyrrolopyrimidine in Step 1 of Scheme BB and the Appropriate N-Boc Protected Tetrahydroisoquinoline in Step 1 of Scheme CC Scheme RR

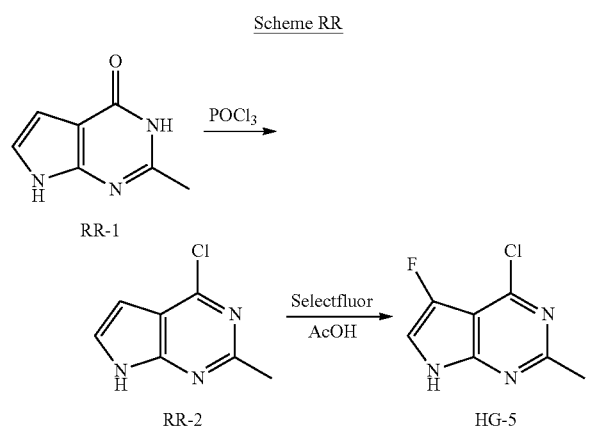

| Example 117 | | 399 [M + 1] | (1S,2S,3R,5S)-3-(5-fluoro-4-methyl-7H-pyrrolo[2,3-d]pyrimidin-7-yl)-5-((1,2,3,4-tetrahydroisoquinolin-8-yl)oxy)cyclopentane-1,2-diol ¹H NMR (400 MHz, MeOD-d₄) δ ppm 8.62 (s, 1H), 8.50 (br. s., 1H), 7.44 (d, J = 1.5 Hz, 1H), 7.27 (t, J = 7.8 Hz, 1H), 6.97 (d, J = 8.5 Hz, 1H), 6.88 (d, J = 7.5 Hz, 1H), 5.23 (q, J = 9.0 Hz, 1H), 4.74-4.69 (m, 1H), 4.69-4.62 (m, 1H), 4.36 (s, 2H), 4.18 (d, J = 4.5 Hz, 1H), 3.47 (t, J = 6.0 Hz, 2H), 3.10 (t, J = 6.0 Hz, 2H), 3.04-2.90 (m, 1H), 2.78 (s, 3H), 2.21-2.07 (m, 1H) |
|---|---|---|---|
| 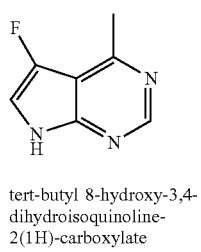 tert-butyl 8-hydroxy-3,4-dihydroisoquinoline-2(1H)-carboxylate 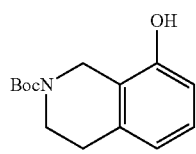 [SMILES: CC(C)(C)OC(=O)N1CCc2cccc(O)c2C1] | 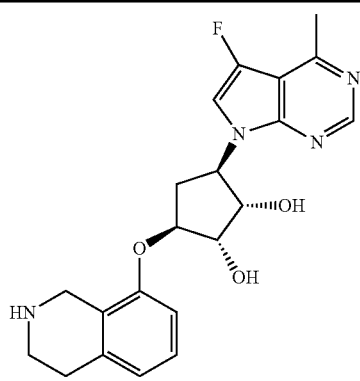 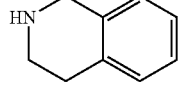 | | |

| Example 118<br>7H-pyrrolo[2,3-d]pyrimidine<br>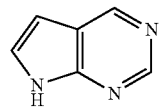<br><br>tert-butyl 8-hydroxy-3,4-dihydroisoquinoline-2(1H)-carboxylate<br>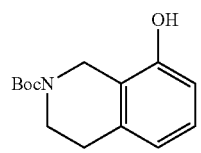 [SMILES: CC(C)(C)OC(=O)N1CCc2cccc(O)c2C1] | 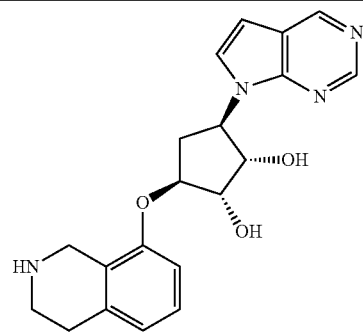 | 367<br>[M + 1] | (1S,2S,3R,5S)-3-(7H-pyrrolo[2,3-d]pyrimidin-7-yl)-5-((1,2,3,4-tetrahydroisoquinolin-8-yl)oxy)cyclopentane-1,2-diol<br>$^1$H NMR (400 MHz, DMSO-d$_6$) δ ppm 9.00 (s, 1H), 8.79 (s, 1H), 7.70 (d, J = 3.6 Hz, 1H), 7.12-7.03 (m, 1H), 6.87-6.78 (d, J = 8.0, 1H), 6.78-6.62 (m, 2H), 5.39-5.32 (m, 1H), 5.21-5.07 (m, 2H), 4.63-4.51 (m, 2H), 4.02-3.97 (m, 1H), 3.93-3.81 (m, 2H), 3.00-2.91 (m, 2H), 2.90-2.82 (m, 1H), 2.71-2.68 (m, 1H), 2.00-1.89 (m, 1H) |
| Example 119<br>HG-4<br>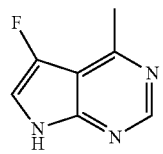<br><br>TP-18<br>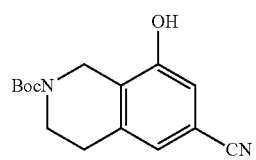 | 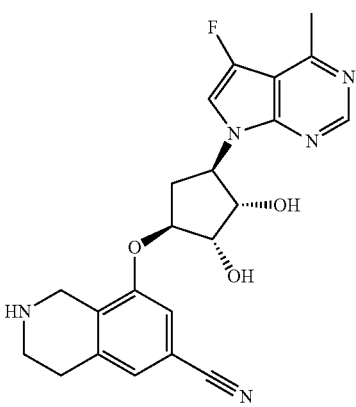 [SMILES: Cc1ncnc2c1c(F)cn2[C@@H]1C[C@H](Oc2cc(C#N)cc3c2CNCC3)[C@@H](O)[C@H]1O] | 424<br>[M + 1] | 8-(((1S,2S,3S,4R)-4-(5-fluoro-4-methyl-7H-pyrrolo[2,3-d]pyrimidin-7-yl)-2,3-dihydroxycyclopentyl)oxy)-1,2,3,4-tetrahydroisoquinoline-6-carbonitrile<br>$^1$H NMR with formic acid (400 MHz, DMSO-d$_6$) δ ppm 8.66 (s, 1H), 8.28 (s, 1H), 7.71 (s, 1H), 7.28 (s, 1H), 7.20 (s, 1H), 5.14 (q, J = 9.6 Hz, 1H), 4.63-4.60 (m, 1H), 4.45 (dd, J = 4.8, 9.0 Hz, 1H), 3.96 (d, J = 4.8 Hz, 1H), 3.89 (s, 2H), 2.95-2.90 (m, 2H), 2.88-2.80 (m, 1H), 2.70-2.67 (m, 5H), 1.95-1.90 (m, 1H) |

Examples 120 was Made in a Similar Fashion to NN-5 (Example 99) Using the Appropriate Pyrrolopyrimidine in Step 1 of Scheme BB and the Appropriate N-Boc Protected Tetrahydroisoquinoline in Step 1 of Scheme NN

| Example 120<br>5-bromo-4-chloro-7H-pyrrolo[2,3-d]pyrimidine<br>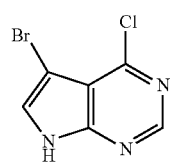<br><br>TP-18<br>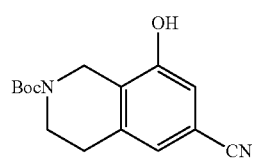 | 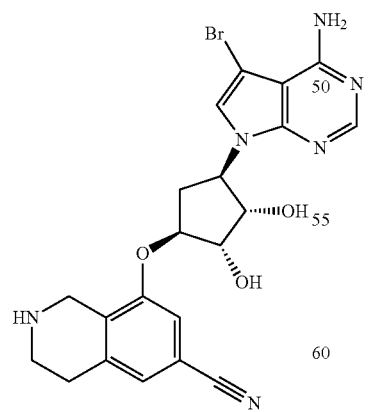 [SMILES: N#Cc1cc2c(c(O[C@H]3C[C@@H](n4cc(Br)c5c(N)ncnc54)[C@H](O)[C@@H]3O)c1)CNCC2] | 485<br>[M + 1] | 8-(((1S,2S,3S,4R)-4-(4-amino-5-bromo-7H-pyrrolo[2,3-d]pyrimidin-7-yl)-2,3-dihydroxycyclopentyl)oxy)-1,2,3,4-tetrahydroisoquinoline-6-carbonitrile<br>$^1$H NMR (400 MHz, MeOD-d$_4$) δ ppm 8.12 (s, 1H), 7.39 (s, 1H), 7.38 (s, 1H), 7.31 (s, 1H), 5.05 (q, J = 9.2 Hz, 1H), 4.81-4.74 (m, 1H), 4.67 (dd, J = 4.9, 8.9 Hz, 1H), 4.38 (s, 2H), 4.18 (br d, J = 4.3 Hz, 1H), 3.48 (t, J = 6.0 Hz, 2H), 3.13 (br t, J = 5.9 Hz, 2H), 3.03-2.93 (m, 1H), 2.26-2.19 (m, 1H) |

Example 121 (Scheme SS)—(1S,2S,3R,5S)-3-(4-amino-5-methyl-7H-pyrrolo[2,3-d]pyrimidin-7-yl)-5-((5-fluoro-1,2,3,4-tetrahydroisoquinolin-8-yl)oxy)cyclopentane-1,2-diol (SS-5)

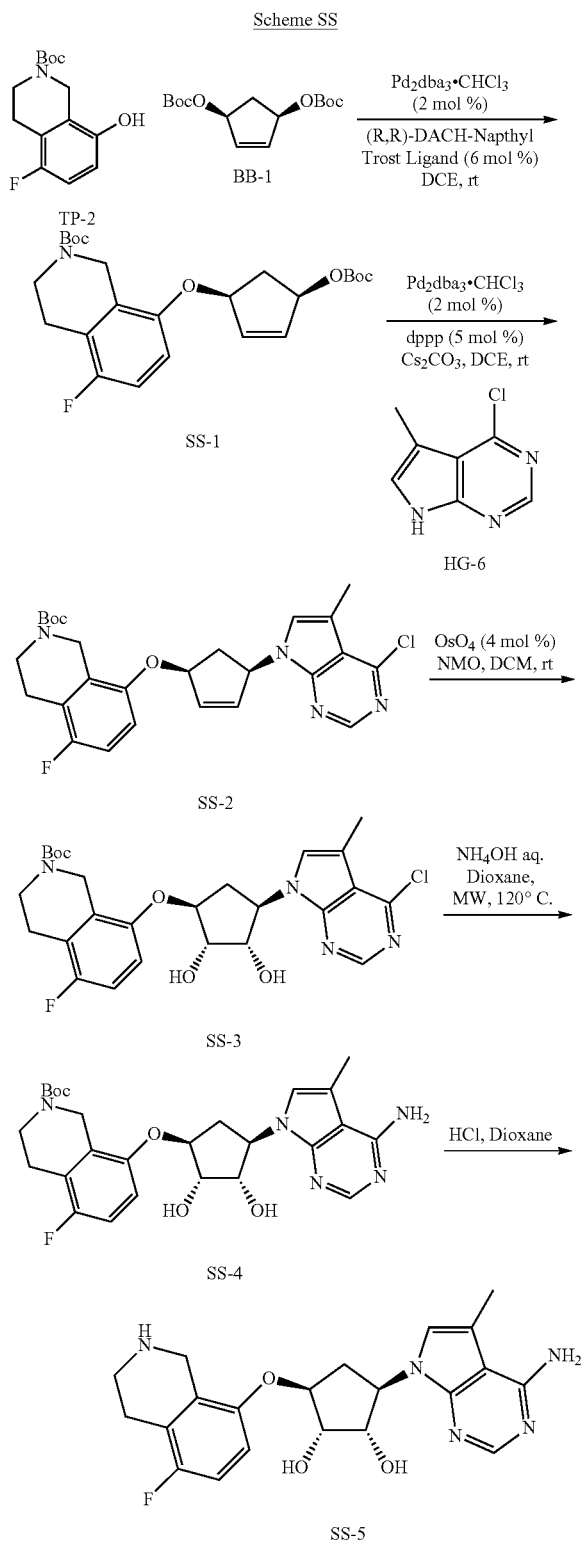

Step 1: Synthesis of tert-butyl 8-(((1S,4R)-4-((tert-butoxycarbonyl)oxy)cyclopent-2-en-1-yl)oxy)-5-fluoro-3,4-dihydroisoquinoline-2(1H)-carboxylate (SS-1)

Vial A: To an oven dried reaction vial, equipped with a magnetic stirbar and cooled under a stream of argon, was added Tris(benzylideneacetone)dipalladium(0)chloroform adduct (62 mg, 0.060 mmol) and MFCD02684551 (R,R)-DACH-Naphthyl Trost Ligand (142 mg, 0.180 mmol). The vial was vacuum purged with argon under dynamic vacuum and DCE (5.0 mL), which had been sparged with argon for 30 minutes, was added. The solution was stirred for 30 minutes at rt at which point a bright orange solution of ligated catalyst was obtained. At this stage Vial B was prepared.

Vial B: To an oven dried reaction vial, equipped with a magnetic stirbar and cooled under a stream of argon, was added TP-2 (800 mg, 2.99 mmol), and di-tert-butyl-((1R,3S)-cyclopent-4-ene-1,3-diyl)-bis(carbonate) (BB-1) (prepared as reported in *J. Am. Chem. Soc.* 2006, 128, 6054-6055) (1.08 g, 3.59 mmol). The vial was vacuum purged with argon under dynamic vacuum and DCE (5.0 mL), which had been sparged with argon for 30 minutes, was added followed by the addition of the contents of Vial A via airtight syringe. The reaction was stirred under argon at rt for 12 hours. The reaction was concentrated under vacuum and purified via flash column chromatography (24 g SiO2, Isco, 100% Hept. to 100% EtOAc, 20 mL fractions) to afford SS-1 (1.33 g, >95%) as a pale yellow solid. LCMS [M+H-Boc-isobutylene]=294 observed; 1H NMR (400 MHz, CHLOROFORM-d) δ ppm 6.84 (t, J=8.8 Hz, 1H), 6.65 (dd, J=4.3, 8.9 Hz, 1H), 6.20 (td, J=1.5, 5.7 Hz, 1H), 6.17-6.11 (m, 1H), 5.46 (t, J=5.9 Hz, 1H), 5.09 (t, J=5.6 Hz, 1H), 4.57-4.40 (m, 2H), 3.72-3.54 (m, 2H), 3.02 (td, J=7.4, 14.5 Hz, 1H), 2.77 (t, J=5.7 Hz, 2H), 1.94 (td, J=4.5, 14.4 Hz, 1H), 1.50 (d, J=1.6 Hz, 18H).

Step 2: Synthesis of tert-butyl 8-(((1S,4R)-4-(4-chloro-5-methyl-7H-pyrrolo[2,3-d]pyrimidin-7-yl)cyclopent-2-en-1-yl)oxy)-5-fluoro-3,4-dihydroisoquinoline-2(1H)-carboxylate (SS-2)

To a scintillation vial, equipped with a magnetic stirbar, was added HG-6 (113 mg, 0.674 mmol), SS-1 (303 mg, 0.674 mmol), diphenylphosphinopropane (dppp) (13.9 mg, 0.034 mmol), tris(dibenzylideneacetone)dipalladium(0) chloroform adduct (14 mg, 0.014 mmol) and cesium carbonate (242 mg, 0.741 mmol). The vial was purged with argon under dynamic vacuum followed by the addition of DCE (2.25 mL) which had been sparged with argon for 30 minutes. The reaction was stirred at rt under argon for 1.5 hours. The reaction was transferred to a separatory funnel with DCM and diluted with water. The phases were separated and the aqueous phase was extracted with 2 portions DCM. The combined organic phases were dried (MgSO4), filtered, and concentrated under vacuum. The crude residue was purified via flash column chromatography (12 g SiO2, Isco, 100% Hept. to 100% EtOAc, 9 mL fractions) to afford SS-2 (287.6 mg, 86%) as a colorless gum. LCMS [M+H]=499 observed; 1H NMR (400 MHz, CHLOROFORM-d) δ ppm 8.57 (s, 1H), 7.14 (s, 1H), 6.86 (t, J=8.8 Hz, 1H), 6.68 (dd, J=3.7, 8.4 Hz, 1H), 6.37 (d, J=5.4 Hz, 1H), 6.11 (d, J=4.4 Hz, 1H), 6.06-5.96 (m, 1H), 5.33-5.25 (m, 1H), 4.69-4.41 (m, 2H), 3.75-3.55 (m, 2H), 3.22-3.03 (m, 1H), 2.79 (t, J=5.4 Hz, 2H), 2.49 (s, 3H), 1.95 (td, J=3.6, 14.8 Hz, 1H), 1.51 (s, 9H).

Step 3: Synthesis of tert-butyl 8-(((1S,2S,3S,4R)-4-(4-chloro-5-methyl-7H-pyrrolo[2,3-d]pyrimidin-7-yl)-2,3-dihydroxycyclopentyl)oxy)-5-fluoro-3,4-dihydroisoquinoline-2(1H)-carboxylate (SS-3)

To a scintillation vial, equipped with a magnetic stirbar and containing SS-2 (278 mg, 0.557 mmol), was added DCM (2.79 mL). To the solution was added 4-Methylmorpholine-N-oxide (NMO) (0.13 mL, 0.613 mmol) as a 50 wt % solution in water followed by the dropwise addition of osmium tetraoxide (100 µL, 0.022 mmol) as a 4 wt % solution in water. The reaction was stirred at rt for 4 hours. The reaction was transferred to a separatory funnel with DCM, diluted with water and further diluted with 1M NaHSO3. The phases were separated and the aqueous phase was extracted with 3 portions of DCM. The combined organic extracts were dried (MgSO4), filtered, and concentrated under vacuum. The crude residue was purified via flash column chromatography (12 g SiO2, Isco, 100% Hept. to 100% EtOAc, 9 mL fractions) to afford SS-3 (169 mg, 57%) as a white solid. LCMS [M+H]=533 observed; 1H NMR (400 MHz, CHLOROFORM-d) δ ppm 8.49 (s, 1H), 7.09 (br. s., 1H), 6.89 (t, J=8.8 Hz, 1H), 6.81 (dd, J=4.2, 8.8 Hz, 1H), 5.03 (q, J=8.9 Hz, 1H), 4.73 (t, J=5.2 Hz, 1H), 4.55 (dd, J=5.2, 8.1 Hz, 1H), 4.53-4.40 (m, 2H), 4.30 (d, J=4.5 Hz, 1H), 3.73-3.54 (m, 2H), 3.13-2.97 (m, 1H), 2.79 (t, J=5.7 Hz, 2H), 2.49 (s, 3H), 2.31 (ddd, J=4.6, 9.4, 14.1 Hz, 1H), 1.48 (br. s., 9H).

Step 4: Synthesis of tert-butyl 8-(((1S,2S,3S,4R)-4-(4-amino-5-methyl-7H-pyrrolo[2,3-d]pyrimidin-7-yl)-2,3-dihydroxycyclopentyl)oxy)-5-fluoro-3,4-dihydroisoquinoline-2(1H)-carboxylate (SS-4)

To a reaction vial, equipped with a magnetic stirbar, was added SS-3 (159 mg, 0.298 mmol) as a solution in dioxane (0.8 mL) and ammonium hydroxide (0.8 mL, 5.00 mmol). The reaction was placed in a microwave reactor and heated to 120° C. for 6 hours. The solution was transferred to a separatory funnel with DCM and diluted with water. The phases were separated and the aqueous phase was extracted with 3 portions of a 3:1 mixture of DCM:IPA. The combined organic extracts were dried (MgSO4), filtered, and concentrated under vacuum. The crude residue was purified via flash column chromatography (12 g SiO2, Isco, 100% Hept. to 10% MeOH/EtOAc, 9 mL fractions) to afford SS-4 (98.4 mg, 64%) as a white solid. LCMS [M+H]=514 observed; [α]$^{22}$D=-70.0° (C=0.1, MeOH); 1H NMR (400 MHz, CHLOROFORM-d) δ ppm 8.13 (s, 1H), 6.98-6.81 (m, 2H), 6.76 (br. s., 1H), 5.32 (br. s., 2H), 4.93-4.80 (m, 1H), 4.73 (t, J=5.3 Hz, 1H), 4.54 (br. s., 1H), 4.44 (d, J=16.8 Hz, 2H), 4.25 (br. s., 1H), 3.75-3.51 (m, 2H), 3.11-2.92 (m, 1H), 2.79 (t, J=5.5 Hz, 2H), 2.43 (s, 3H), 2.38-2.25 (m, 1H), 1.48 (br. s., 9H).

Step 5: Synthesis of (1S,2S,3R,5S)-3-(4-amino-5-methyl-7H-pyrrolo[2,3-d]pyrimidin-7-yl)-5-((5-fluoro-1,2,3,4-tetrahydroisoquinolin-8-yl)oxy)cyclopentane-1,2-diol (SS-5)

To a scintillation vial, equipped with a magnetic stirbar and containing SS-4 (79.4 mg, 0.155 mmol), was added dioxane (0.4 mL). To the solution was added hydrochloric acid (0.4 mL) as a 4M solution in dioxane and the reaction was stirred at rt for 17 hours. The reaction was quenched with half saturated NaHCO₃ aqueous and transferred to a separatory funnel with DCM. The phases were separated and the aqueous phase was extracted with 3 portions of 3:1 mixture of DCM/IPA. The combined organic extracts were dried (MgSO4), filtered, and concentrated under vacuum. The isolated material was dissolved in a minimum amount of methanol and diluted with water. The sample was frozen and lyophilized overnight to afford SS-5 (51.3 mg, 80%) as a white solid. LCMS [M+H] 414 observed; 1H NMR (400 MHz, METHANOL-d4) δ ppm 8.03 (s, 1H), 6.98 (d, J=1.0 Hz, 1H), 6.93-6.81 (m, 2H), 5.07 (q, J=8.7 Hz, 1H), 4.62 (ddd, J=1.8, 4.0, 7.0 Hz, 1H), 4.51 (dd, J=5.0, 8.5 Hz, 1H), 4.17-4.11 (m, 1H), 3.98 (s, 2H), 3.10 (t, J=6.0 Hz, 2H), 2.93 (ddd, J=7.3, 9.3, 14.5 Hz, 1H), 2.77 (t, J=5.9 Hz, 2H), 2.43 (d, J=1.1 Hz, 3H), 1.99 (ddd, J=4.0, 8.4, 13.8 Hz, 1H); 19F NMR (376 MHz, METHANOL-d4) d=-131.36 (s, 1F).

Examples 122-129 were Made in a Similar Fashion to SS-5 (Example 121) Using the Appropriate N-Boc Protected Tetrahydroisoquinoline in Step 1 S and the Appropriate Pyrrolopyrimidine in Step 2 of Scheme SS

| Example 122 TP-5 | | | 410 M + 1 | (1S,2S,3R,5S)-3-(4-amino-5-methyl-7H-pyrrolo[2,3-d]pyrimidin-7-yl)-5-((6-methyl-1,2,3,4-tetrahydroisoquinolin-8-yl)oxy)cyclopentane-1,2-diol ¹H NMR (400 MHz, MeOD-d₄) δ ppm 8.05 (s, 1H), 6.99 (s, 1H), 6.70 (s, 1H), 6.61 (s, 1H), 5.17-5.06 (m, 1H), 4.71-4.64 (m, 1H), 4.53 (dd, J = 8.53, 4.77 Hz, 1H), 4.16 (d, J = 4.27 Hz, 1H), 3.99 (s, 2H), 3.12 (d, J = 5.90 Hz, 2H), 2.97 (dd, J = 14.50, 9.50, 7.20 Hz, 1H), 2.83 (t, J = 5.77 Hz, 2H), 2.45 (s, 3H), 2.30 (s, 3H), 2.04-1.93 (m, 1H) |
|---|---|---|---|---|
| 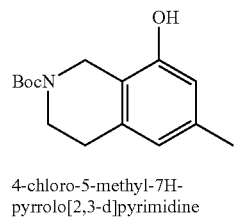 4-chloro-5-methyl-7H-pyrrolo[2,3-d]pyrimidine 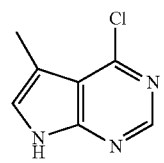 | 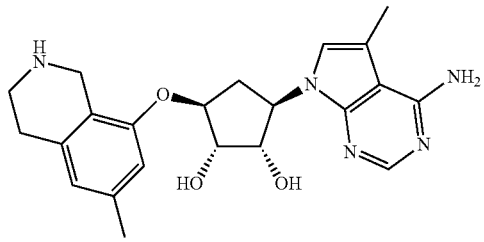 [SMILES: Cc1cc2c(c(O[C@H]3C[C@@H](n4cc(C)c5c(N)ncnc54)[C@H](O)[C@@H]3O)c1)CNCC2] | | | |

| Example 123 TP-5 | 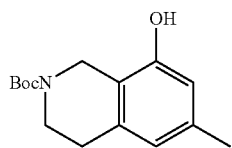 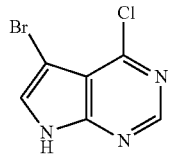 5-bromo-4-chloro-7H-pyrrolo[2,3-d]pyrimidine | 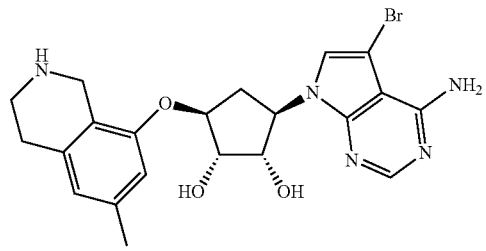 [SMILES: Cc1cc2c(c(O[C@H]3C[C@@H](n4cc(Br)c5c(N)ncnc54)[C@H](O)[C@@H]3O)c1)CNCC2] | 474 M + 1 | (1S,2S,3R,5S)-3-(4-amino-5-bromo-7H-pyrrolo[2,3-d]pyrimidin-7-yl)-5-((6-methyl-1,2,3,4-tetrahydroisoquinolin-8-yl)oxy)cyclopentane-1,2-diol<br>¹H NMR (400 MHz, MeOD-d₄) δ ppm 8.12 (s, 1H), 7.35 (s, 1H), 6.77 (s, 1H), 6.67 (s, 1H), 5.11 (q, J = 9.0 Hz, 1H), 4.69 (ddd, J = 1.6, 4.0, 7.2 Hz, 1H), 4.62 (dd, J = 4.8, 8.8 Hz, 1H), 4.18-4.13 (m, 3H), 3.31-3.27 (m, 2H), 3.03-2.92 (m, 3H), 2.33 (s, 3H), 2.14-2.06 (m, 1H) |
|---|---|---|---|---|
| Example 124 TP-5 | 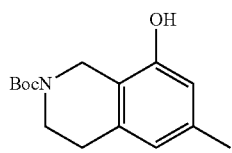 HG-4 (step 4 is skipped) 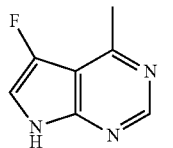 | 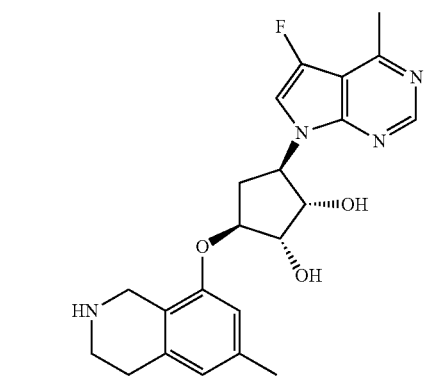 [SMILES: Cc1cc2c(c(O[C@H]3C[C@@H](n4cc(F)c5c(C)ncnc54)[C@H](O)[C@@H]3O)c1)CNCC2] | 413 M + 1 | (1S,2S,3R,5S)-3-(5-fluoro-4-methyl-7H-pyrrolo[2,3-d]pyrimidin-7-yl)-5-((6-methyl-1,2,3,4-tetrahydroisoquinolin-8-yl)oxy)cyclopentane-1,2-diol<br>¹H NMR (400 MHz, MeOD-d₄) δ ppm 8.65 (s, 1H), 7.43 (d, J = 2.0 Hz, 1H), 6.81 (s, 1H), 6.70 (s, 1H), 5.25 (q, J = 9.0 Hz, 1H), 4.71 (dt, J = 2.3, 3.6 Hz, 1H), 4.69-4.64 (m, 1H), 4.26 (s, 2H), 4.17 (d, J = 4.8 Hz, 1H), 3.39 (t, J = 6.1 Hz, 2H), 3.04-2.95 (m, 3H), 2.80 (s, 3H), 2.34 (s, 3H), 2.20-2.11 (m, 1H) |
| Example 125 TP-6 | 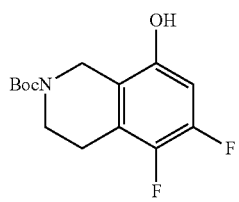 [SMILES: CC(C)(C)OC(=O)N1CCc2c(F)c(F)cc(O)c2C1] 5-bromo-4-chloro-7H-pyrrolo[2,3-d]pyrimidine 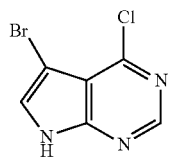 | 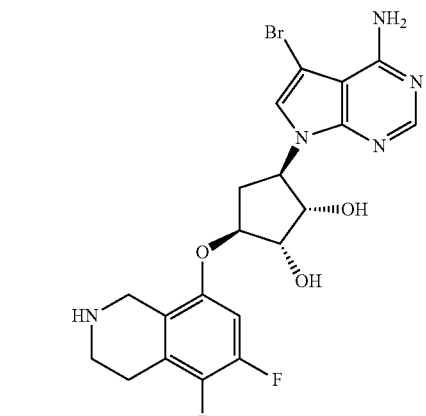 | 497 [M + 1] | (1S,2S,3R,5S)-3-(4-amino-5-bromo-7H-pyrrolo[2,3-d]pyrimidin-7-yl)-5-((5,6-difluoro-1,2,3,4-tetrahydroisoquinolin-8-yl)oxy)cyclopentane-1,2-diol<br>¹H NMR (400 MHz, MeOD-d₄) δ ppm 8.10 (s, 1H), 7.35 (s, 1H), 6.87 (dd, J = 6.8, 12.5 Hz, 1H), 5.09 (q, J = 8.8 Hz, 1H), 4.58-4.51 (m, 2H), 4.13 (d, J = 5.0 Hz, 1H), 3.90 (s, 2H), 3.12-3.01 (m, 2H), 3.00-2.90 (m, 1H), 2.78 (t, J = 5.8 Hz, 2H), 2.13-2.00 (m, 1H) |

-continued

| Example 126 TP-2 | 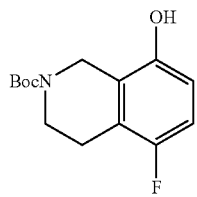 [SMILES: CC(C)(C)OC(=O)N1CCc2c(F)ccc(O)c2C1] 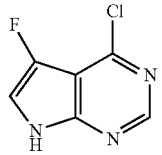 [SMILES: Fc1c[nH]c2ncnc(Cl)c12] HG-5 | 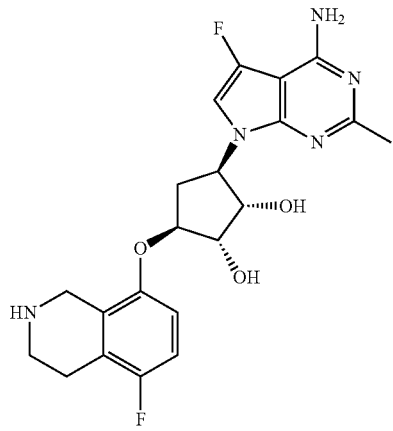 [SMILES: Cc1nc(N)c2c(F)cn([C@@H]3C[C@H](Oc4ccc(F)c5c4CNCC5)[C@@H](O)[C@H]3O)c2n1] | 432 [M + 1] | (1S,2S,3R,5S)-3-(4-amino-5-fluoro-2-methyl-7H-pyrrolo[2,3-d]pyrimidin-7-yl)-5-((5-fluoro-1,2,3,4-tetrahydroisoquinolin-8-yl)oxy)cyclopentane-1,2-diol<br>$^1$H NMR (400 MHz, DMSO-d$_6$) δ ppm 9.07 (br. s., 2H), 7.27 (br. s., 1H), 7.15 (t, J = 9.2 Hz, 1H), 6.99 (dd, J = 4.1, 9.2 Hz, 1H), 5.38 (br. s., 1H), 5.18 (br. s., 1H), 5.08 (q, J = 9.0 Hz, 1H), 4.53 (br. s., 1H), 4.39-4.30 (m, 1H), 4.21 (br. s., 2H), 3.95 (br. s., 1H), 2.95-2.88 (m, 2H), 2.83-2.73 (m, 1H), 2.53-2.51 (m, 3H), 2.40 (s, 3H), 1.74 (ddd, J = 4.4, 9.3, 13.7 Hz, 1H) |
| --- | --- | --- | --- | --- |
| Example 127 TP-5 | 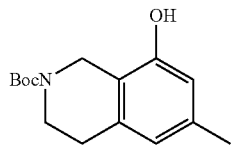 HG-3 (step 4 is skipped) 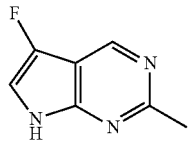 | 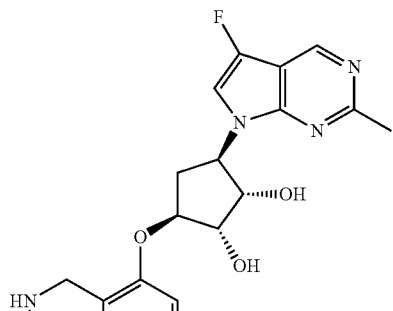 | 413 [M + 1] | (1S,2S,3R,5S)-3-(5-fluoro-2-methyl-7H-pyrrolo[2,3-d]pyrimidin-7-yl)-5-((6-methyl-1,2,3,4-tetrahydroisoquinolin-8-yl)oxy)cyclopentane-1,2-diol<br>$^1$H NMR (400 MHz, MeOD-d$_4$) δ ppm 8.90 (s, 1H), 7.39 (s, 1H), 6.76 (s, 1H), 6.66 (s, 1H), 5.35 (q, J = 9.2 Hz, 2H), 4.58 (dd, J = 4.9, 8.7 Hz, 1H), 4.17 (d, J = 4.3 Hz, 1H), 4.12 (s, 2H), 3.25 (t, J = 6.0 Hz, 2H), 3.06-2.95 (m, 1H), 2.92 (t, J = 5.9 Hz, 2H), 2.74 (s, 3H), 2.33 (s, 3H), 2.13-2.04 (m, 1H) |
| Example 128 TP-6 | 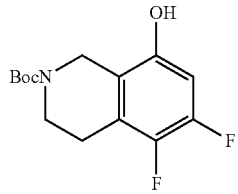 [SMILES: CC(C)(C)OC(=O)N1CCc2c(F)c(F)cc(O)c2C1] 4,5-dichloro-7H-pyrrolo[2,3-d]pyrimidine 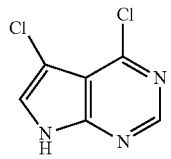 [SMILES: Clc1c[nH]c2ncnc(Cl)c12] | 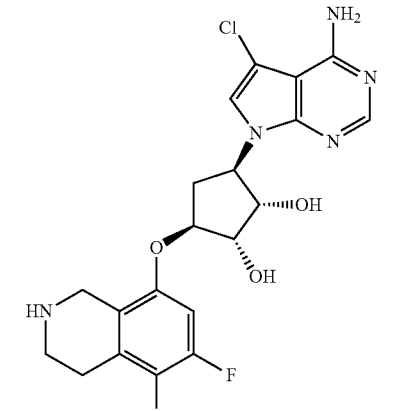 | 452 [M + 1] | (1S,2S,3R,5S)-3-(4-amino-5-chloro-7H-pyrrolo[2,3-d]pyrimidin-7-yl)-5-((5,6-difluoro-1,2,3,4-tetrahydroisoquinolin-8-yl)oxy)cyclopentane-1,2-diol<br>1H NMR (400 MHz, MeOD-d4) δ ppm 8.09 (s, 1H), 7.29 (s, 1H), 6.89 (dd, J = 6.7, 12.4 Hz, 1H), 5.15-5.01 (m, 1H), 4.60-4.50 (m, 2H), 4.16-4.07 (m, 1H), 3.94 (s, 2H), 3.11 (t, J = 6.0 Hz, 2H), 2.99-2.88 (m, 1H), 2.81 (t, J = 5.8 Hz, 2H), 2.12-2.02 (m, 1H) |

| Example 129 TP-5 | 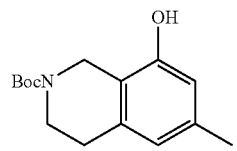<br>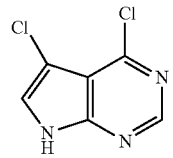 [SMILES: Clc1c[nH]c2ncnc(Cl)c12]4,5-dichloro-7H-pyrrolo[2,3-d]pyrimidine | 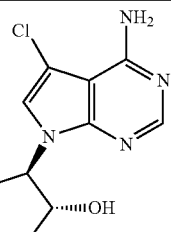<br>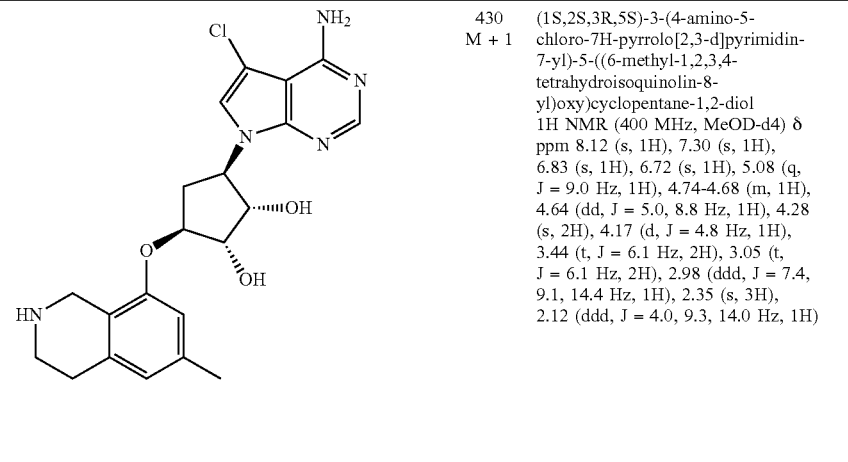 | 430 M + 1 | (1S,2S,3R,5S)-3-(4-amino-5-chloro-7H-pyrrolo[2,3-d]pyrimidin-7-yl)-5-((6-methyl-1,2,3,4-tetrahydroisoquinolin-8-yl)oxy)cyclopentane-1,2-diol<br>1H NMR (400 MHz, MeOD-d4) δ ppm 8.12 (s, 1H), 7.30 (s, 1H), 6.83 (s, 1H), 6.72 (s, 1H), 5.08 (q, J = 9.0 Hz, 1H), 4.74-4.68 (m, 1H), 4.64 (dd, J = 5.0, 8.8 Hz, 1H), 4.28 (s, 2H), 4.17 (d, J = 4.8 Hz, 1H), 3.44 (t, J = 6.1 Hz, 2H), 3.05 (t, J = 6.1 Hz, 2H), 2.98 (ddd, J = 7.4, 9.1, 14.4 Hz, 1H), 2.35 (s, 3H), 2.12 (ddd, J = 4.0, 9.3, 14.0 Hz, 1H) |

Examples 130-132 were Prepared Using the Chemistry Depicted in Scheme SS by Employing the Appropriate Tetrahydroisoquinoline for Step 1 and Pyrrolopyrimidine for Step 2. In a Modification to Step 5, Trifluoroacetic Acid (TFA) was Used for the Deprotection Example 130 (Scheme TT)—(1S,2S,3R,5S)-3-(4-amino-5-chloro-7H-pyrrolo[2,3-d]pyrimidin-7-yl)-5-((6-chloro-1,2,3,4-tetrahydroisoquinolin-8-yl)oxy)cyclopentane-1,2-diol (TT-2)

Scheme TT

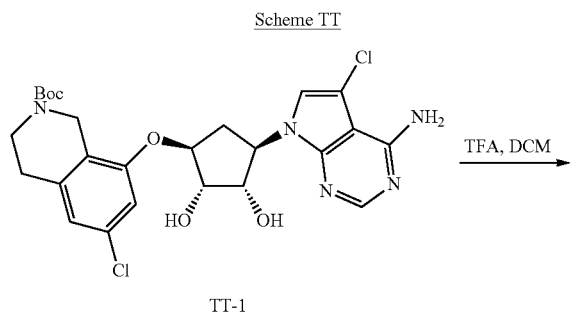

To a cooled solution of TT-1 (50.0 mg, 0.091 mmol) in DCM (2.0 mL) was added TFA (0.50 mL). The yellow solution was stirred at 15° C. for 1 hour. The reaction was concentrated under vacuum to give the crude product and the pH of the solution was adjusted to 7-8 using saturated NaHCO₃ aq. (2 mL). Then FA (1%) aq. (2 mL) was added to the reaction solution. The mixture was purified by prep-HPLC and the desired fractions were combined and lyophilized to afford TT-2 (35.0 mg, 86%) as white solid.

| Example 130 TP-3 | 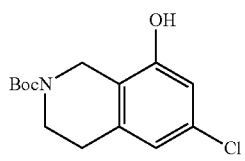 [SMILES: CC(C)(C)OC(=O)N1CCc2cc(Cl)cc(O)c2C1]<br>4,5-dichloro-7H-pyrrolo[2,3-d]pyrimidine | 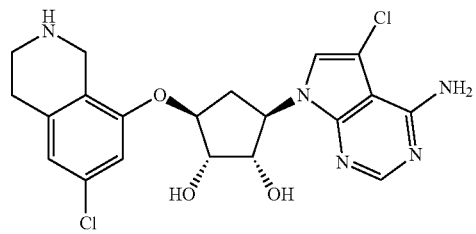 | 450 observed [M +H] | (1S,2S,3S,5R)-3-((6-chloro-1,2,3,4-tetrahydroisoquinolin-8-yl)oxy)-5-(4,5-dichloro-7H-pyrrolo[2,3-d]pyrimidin-7-yl)cyclopentane-1,2-diol<br>1H NMR (400 MHz, DMSO-d6) δ ppm 8.04 (s, 1H), 7.38 (s, 1H), 7.01-6.89 (m, 2H), 4.92 (q, J = 9.0 Hz, 1H), 4.56 (d, J = 5.3 Hz, 1H), 4.47 (dd, J = 4.9, 9.2 Hz, 1H), 4.13 (s, 2H), 3.95 (d, J = 4.8 Hz, 1H), 3.29 (t, J = 6.1 Hz, 2H), 2.94 (t, J = 5.9 Hz, 2H), 2.86-2.76 (m, 1H), 1.89 (ddd, J = 3.9, 9.5, 13.7 Hz, 1H) |

| Example 131 TP-3 | 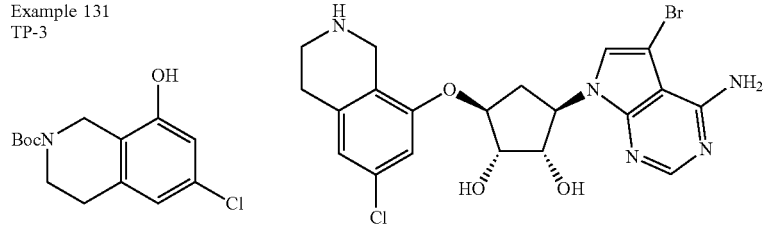 | 495 observed [M +H] | (1S,2S,3R,5S)-3-(5-bromo-4-chloro-7H-pyrrolo[2,3-d]pyrimidin-7-yl)-5-((6-chloro-1,2,3,4-tetrahydroisoquinolin-8-yl)oxy)cyclopentane-1,2-diol<br>1H NMR (400 MHz, DMSO-d6) δ ppm 8.10 (s, 1H), 7.53 (s, 1H), 6.92 (d, J = 1.5 Hz, 1H), 6.85-6.57 (m, 2H), 5.36 (br. s., 1H), 5.16 (br. s., 1H), 4.99 (q, J = 9.2 Hz, 1H), 4.58-4.51 (m, 1H), 4.50-4.42 (m, 1H), 3.93 (d, J = 5.0 Hz, 1H), 3.79 (s, 2H), 2.91 (t, J = 5.8 Hz, 2H), 2.84-2.73 (m, 1H), 2.70-2.62 (m, 2H), 1.96- 1.84 (m, 1H) |
|---|---|---|---|
| 4,5-dichloro-7H-pyrrolo[2,3-d]pyrimidine<br>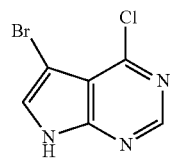 [SMILES: Clc1c[nH]c2ncnc(Cl)c12] | | | |
| Example 132 TP-2 | 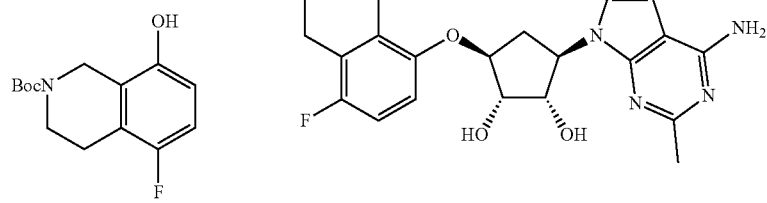 | 417 observed [M +H] | (1S,2S,3S,5R)-3-((5-fluoro-1,2,3,4-tetrahydroisoquinolin-8-yl)oxy)-5-(5-fluoro-2-methyl-7H-pyrrolo[2,3-d]pyrimidin-7-yl)cyclopentane-1,2-diol<br>1H NMR (400 MHz, METHANOL-d4) δ ppm 8.87 (d, J = 0.8 Hz, 1H), 7.38 (d, J = 2.3 Hz, 1H), 6.92-6.81 (m, 2H), 5.37-5.27 (m, 1H), 4.65-4.60 (m, 1H), 4.56 (t, J = 8.9 Hz, 1H), 4.14 (d, J = 5.0 Hz, 1H), 3.96 (s, 2H), 3.10-3.04 (m, J = 6.0, 6.0 Hz, 2H), 3.01-2.91 (m, J = 7.2, 9.4, 14.6 Hz, 1H), 2.79-2.73 (m, J = 6.0, 6.0 Hz, 2H), 2.72 (s, 3H), 2.11-2.03 (m,1H) |
| HG-3 (Step 4 is skipped)<br>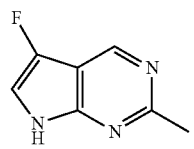 | | | |

Examples 133 & 134 were Prepared Using the Chemistry Depicted in Scheme SS by Employing the Appropriate Tetrahydroisoquinoline for Step 1 and Pyrrolopyrimidine for Step 2. In a Modification to the General Procedure for Step 4, HOBt was Employed as a Catalyst as Described in Scheme UU Synthesis of tert-butyl 8-(((1S,2S,3S,4R)-4-(4-amino-5-chloro-7H-pyrrolo[2,3-d]pyrimidin-7-yl)-2,3-dihydroxycyclopentyl)oxy)-5-fluoro-3,4-dihydroisoquinoline-2(1H)-carboxylate (UU-2)

Scheme UU

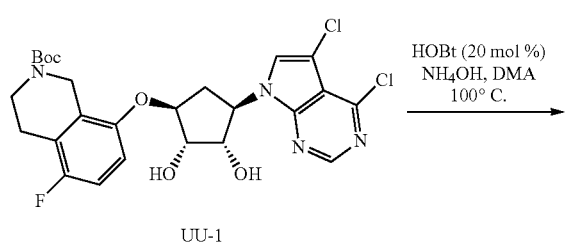

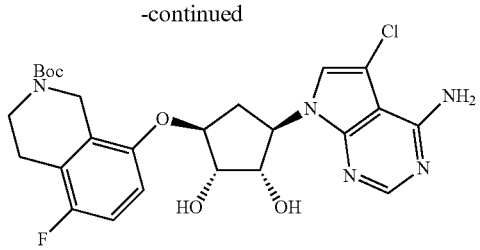

To a reaction vial, equipped with a magnetic stirbar, was added UU-1 (147 mg, 0.266) as a solution in DMA (2.5 mL) followed by the addition of HOBt.hydrate (8.13 mg, 0.053 mmol). To the solution was added ammonium hydroxide (1.0 mL, 7.96 mmol). The vial was sealed with a teflon cap and placed in a heating block. The reaction was heated at 100° C. for 19 hours. The solution was transferred to a separatory funnel with DCM and diluted with water. The phases were separated and the aqueous phase was extracted with 3 portions of DCM. The combined organic extracts were dried (MgSO4), filtered, and concentrated under vacuum. The crude residue was purified via flash column chromatography (4 g SiO2, Isco, 100% Hept. to 10% MeOH/EtOAc, 9 mL fractions). Fractions containing product were collected and concentrated under vacuum. The material was lyophilized to afford the product, containing minor impurities, as an off-white solid (140.7 mg, 99%). The material was used in step 5, employing TFA/DCM for the deprotection as depicted in scheme TT, without further purification.

| Example 133 TP-2 | 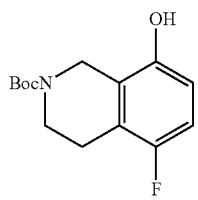 [SMILES: CC(C)(C)OC(=O)N1CCc2c(F)ccc(O)c2C1] 4,5-dichloro-7H-pyrrolo[2,3-d]pyrimidine  | 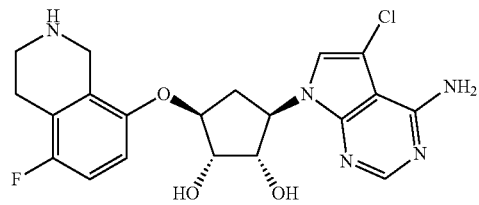 [SMILES: Nc1ncnc2c1c(Cl)cn2[C@@H]1C[C@H](Oc2ccc(F)c3c2CNCC3)[C@@H](O)[C@H]1O] | 434 observed [M +H] | (1S,2S,3R,5S)-3-(4-amino-5-chloro-7H-pyrrolo[2,3-d]pyrimidin-7-yl)-5-((5-fluoro-1,2,3,4-tetrahydroisoquinolin-8-yl)oxy)cyclopentane-1,2-diol 1H NMR (700 MHz, DMSO-d6) δ ppm 8.08 (br. s., 1H), 7.44 (s, 1H), 6.97-6.89 (m, 1H), 6.82 (d, J = 4.6 Hz, 1H), 5.26 (br. s., 1H), 5.11 (br. s., 1H), 4.99 (q, J = 8.6 Hz, 1H), 4.55-4.39 (m, 2H), 3.94 (br. s., 1H), 3.83 (br. s., 2H), 2.93 (br. s., 2H), 2.84-2.70 (m, 2H), 2.58 (br. s., 2H), 1.92-1.82 (m, 1H). |
| --- | --- | --- | --- | --- |
| Example 134 TP-2 | 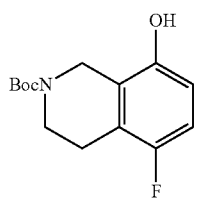 [SMILES: CC(C)(C)OC(=O)N1CCc2c(F)ccc(O)c2C1] 5-bromo-4-chloro-7H-pyrrolo[2,3-d]pyrimidine  | 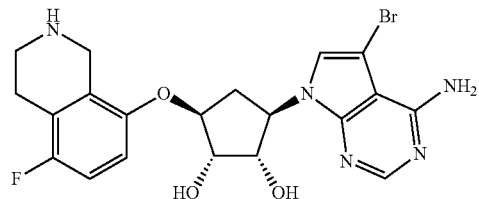 [SMILES: Nc1ncnc2c1c(Br)cn2[C@@H]1C[C@H](Oc2ccc(F)c3c2CNCC3)[C@@H](O)[C@H]1O] | 478 observed [M +H] | (1S,2S,3R,5S)-3-(4-amino-5-bromo-7H-pyrrolo[2,3-d]pyrimidin-7-yl)-5-((5-fluoro-1,2,3,4-tetrahydroisoquinolin-8-yl)oxy)cyclopentane-1,2-diol 1H NMR (700 MHz, DMSO-d6) δ ppm (s, 1H), 7.49 (s, 1H), 6.94-6.88 (m, 1H), 6.84-6.77 (m, 1H), 5.25 (br. s., 1H), 5.15-5.05 (m, 1H), 4.99 (d, J = 9.0 Hz, 1H), 4.47 (d, J = 3.3 Hz, 2H), 3.94 (br. s., 1H), 3.81 (br. s., 2H), 2.92 (br. s., 2H), 2.80-2.70 (m, 1H), 2.58 (br. s., 2H), 1.86 (br. s., 1H), |

Example 135 (Scheme VV)—(1S,2S,3S,5R)-3-(4-fluoro-2-(hydroxymethyl)phenoxy)-5-(4-methyl-7H-pyrrolo[2,3-d]pyrimidin-7-yl)cyclopentane-1,2-diol (2)

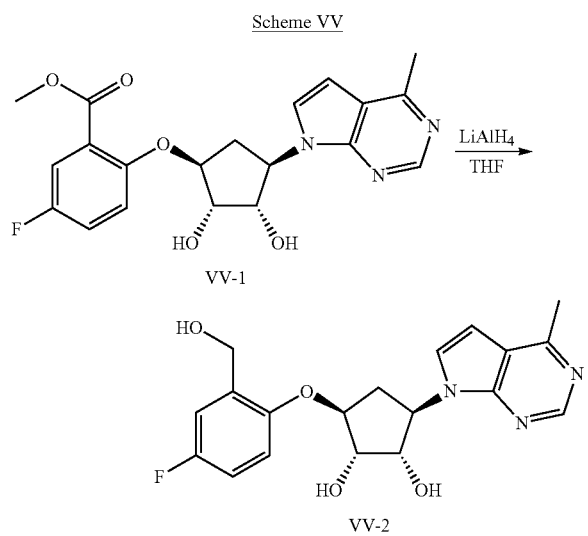

Compound VV-1 was prepared using procedures from steps 2 and 3 from Scheme BB starting from BB-2 and using commercially available methyl 5-fluoro-2-hydroxybenzoate. To a solution of VV-1 (90 mg, 0.22 mmol) in dry THF (5 mL) was added LiAlH$_4$ (30 mg, 0.79 mmol) at 0° C. for 2 hours. H$_2$O (30 mL) was added to the reaction mixture and the mixture was extracted with EtOAc (30 mL×4). The organic layer was washed with brine, dried over Na$_2$SO$_4$ and concentrated in vacuo to a residue that was purified by prep-TLC giving VV-2 (60 mg, 72%) as a white solid. LCMS 374 [M+1]; $^1$H NMR (400 MHz, DMSO-d$_6$) δ ppm 8.62 (s, 1H), 7.65 (d, J=3.8 Hz, 1H), 7.18 (d, J=9.0 Hz, 1H), 7.04-6.99 (m, 2H), 6.72 (d, J=3.5 Hz, 1H), 5.32 (d, J=3.8 Hz, 1H), 5.23 (t, J=5.6 Hz, 1H), 5.16-5.07 (m, 2H), 4.58 (d, J=5.8 Hz, 2H), 4.56-4.50 (m, 2H), 3.99 (br. s., 1H), 2.88-2.78 (m, 1H), 2.64 (s, 3H), 1.97-1.87 (m, 1H)

Example 136 (Scheme WW)—(1S,2S,3S,5R)-3-(4-fluoro-2-hydroxyphenoxy)-5-(4-methyl-7H-pyrrolo[2,3-d]pyrimidin-7-yl)cyclopentane-1,2-diol (WW-6)

Scheme WW

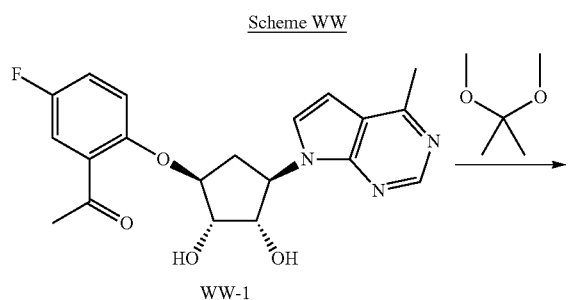

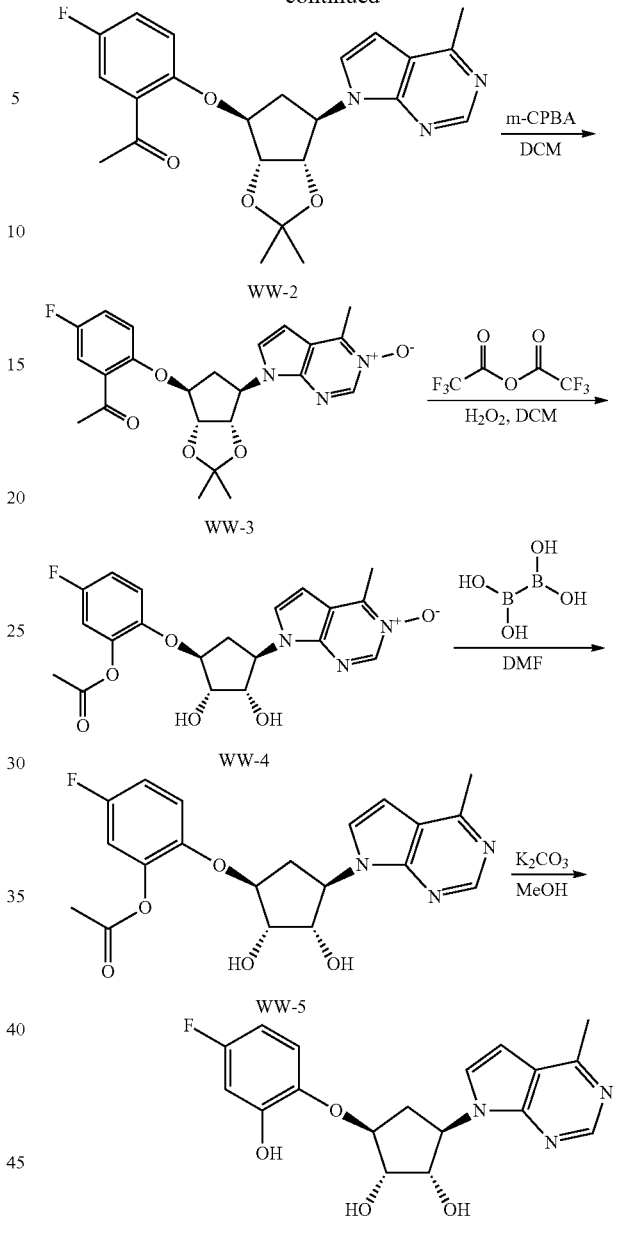

Step 1—Synthesis of 1-(2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorophenyl)ethan-1-one (WW-2)

Compound WW-1 was prepared using procedures from steps 2 and 3 from Scheme BB starting from BB-2 and using commercially available 1-(5-fluoro-2-hydroxyphenyl)ethan-1-one. To a stirred white suspension solution of WW-1 (1.06 g, 2.75 mmol) in acetone (6 mL) was added 2,2-dimethoxypropane (16 mL) and p-toluenesulfonic acid (523 mg, 2.75 mmol) at r.t (25° C.). The reaction was stirred at 25° C. for 15 hrs. Aqueous NaHCO$_3$ was added to the reaction mixture until the pH reached 8.0. Then the mixture was extracted with EtOAc (15 mL×5). The organic layers were separated, dried and evaporated to give the crude product, which was purified by chromatography, eluted with MeOH/DCM 0-5% to give WW-2 (1.06 g, 91%) as a white solid. The material was used directly in the next step.

Step 2—Synthesis of 7-((3aS,4R,6S,6aR)-6-(2-acetyl-4-fluorophenoxy)-2,2-dimethyltetrahydro-4H-cyclopenta[d][1,3]dioxol-4-yl)-4-methyl-7H-pyrrolo[2,3-d]pyrimidine 3-oxide (WW-3)

Compound WW-2 (1.03 g, 2.42 mmol) was dissolved in DCM (15 mL). Then m-CPBA (1.97 g, 9.68 mmol) was added to the above mixture. The reaction mixture was heated at 40° C. for 16 hours. The mixture was cooled to 25° C. Then the mixture was diluted with DCM (15 mL) and then saturated sodium thiosulfate (15 mL) was added the organic layer was separated. The organic layer was washed with saturated NaHCO$_3$ (20 mL), dried over Na$_2$SO$_4$, filtered and purified by flash chromatography eluted with from 0-10% MeOH/DCM to give WW-3 (600 mg, 56%) as a yellow oil and used directly in the next step.

Step 3—Synthesis of 7-((1R,2S,3S,4S)-4-(2-acetoxy-4-fluorophenoxy)-2,3-dihydroxycyclopentyl)-4-methyl-7H-pyrrolo[2,3-d]pyrimidine 3-oxide (WW-4)

Trifluoroacetic anhydride (3.56 g, 16.9 mmol) was cooled to −10° C. for about 10-20 min and 30% H$_2$O$_2$ (457 mg, 3.13 mL) was added drop-wise and stirred for 10 min (maintaining the temperature between 0 and −10° C.). To this mixture was added compound WW-3 (570 mg, 1.29 mmol) in DCM (5 mL) drop-wise and stirred at 25° C. for 10-30 min. Saturated Na$_2$S2O$_3$/NaHCO$_3$ aq (15 mL) was added to the above mixture and stirred at 25° C. for 10 min. The reaction solution was extracted with DCM (10 mL×2), dried and evaporated to give the crude WW-4 (540 mg, >99%) as a yellow oil. LCMS 418 [M+1]

Step 4—Synthesis of 2-(((1S,2S,3S,4R)-2,3-dihydroxy-4-(4-methyl-7H-pyrrolo[2,3-d]pyrimidin-7-yl)cyclopentyl)oxy)-5-fluorophenyl acetate (WW-5)

Compound WW-4 (540 mg, 1.22 mmol) was dissolved in DMF (1 mL). Then hypodiboric acid (658 mg, 7.34 mmol) was added to the above mixture and stirred at 25° C. for 30 min. The reaction solution of WW-5 was used directly for the next step without further purification. LCMS 402 [M+1]

Step 5—Synthesis of (1S,2S,3S,5R)-3-(4-fluoro-2-hydroxyphenoxy)-5-(4-methyl-7H-pyrrolo[2,3-d]pyrimidin-7-yl)cyclopentane-1,2-diol (WW-6)

A solution of compound WW-5 (490 mg, 1.11 mmol) in DMF was added MeOH (2 mL). K$_2$CO$_3$ (2.30 g, 16.6 mmol) was added to the above mixture. The reaction mixture was stirred at 25° C. for 2 hours. The solvent was evaporated and the crude product was purified by prep-HPLC to give WW-6 (62 mg, 16%) as a white solid. LCMS 360 [M+1]; $^1$H NMR (400 MHz, DMSO-d$_6$) δ ppm 9.53 (s, 1H), 8.63 (s, 1H), 7.75 (d, J=3.5 Hz, 1H), 7.01 (dd, J=5.9, 8.9 Hz, 1H), 6.75 (d, J=3.8 Hz, 1H), 6.68 (d, J=3.0 Hz, 1H), 6.66 (d, J=3.0 Hz, 1H), 6.56 (dt, J=3.0, 8.7 Hz, 1H), 5.26 (d, J=3.0 Hz, 1H), 5.16 (q, J=8.9 Hz, 1H), 5.07 (d, J=6.8 Hz, 1H), 4.54 (br. s., 2H), 4.00 (br. s., 1H), 2.83-2.74 (m, 1H), 2.65 (s, 3H), 1.97-1.90 (m, 1H)

Example 137 (Scheme XX)—(1S,2S,3S,5R)-3-(2-((R)-1-aminoethyl)-4-fluorophenoxy)-5-(4-methyl-7H-pyrrolo[2,3-d]pyrimidin-7-yl)cyclopentane-1,2-diol (XX-3)

Example 138 (Scheme XX)—(1S,2S,3S,5R)-3-(2-((S)-1-aminoethyl)-4-fluorophenoxy)-5-(4-methyl-7H-pyrrolo[2,3-d]pyrimidin-7-yl)cyclopentane-1,2-diol (XX-4)

Scheme XX

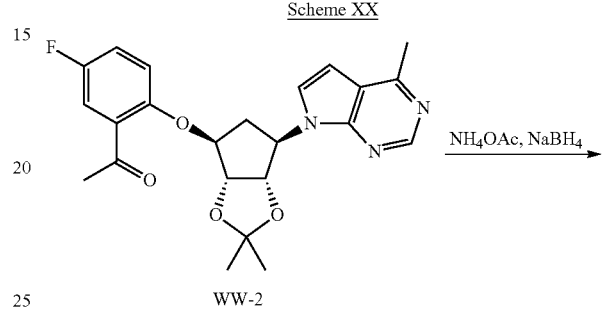

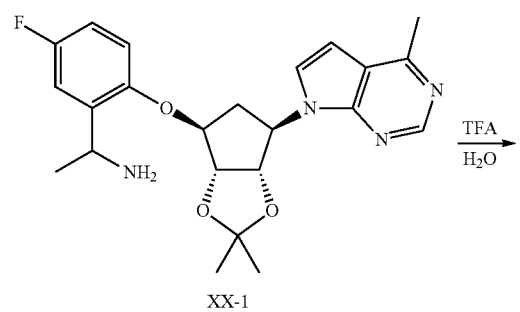

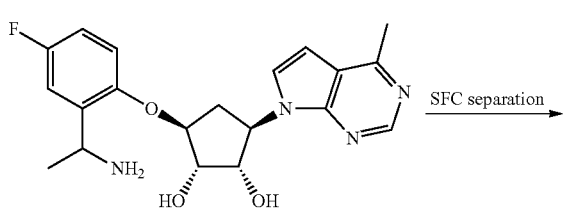

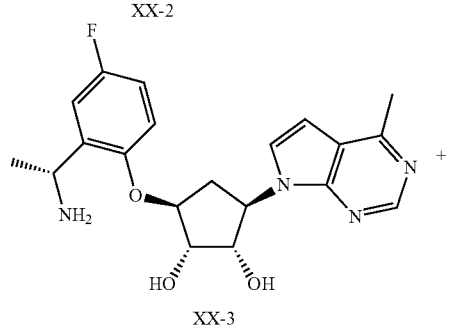

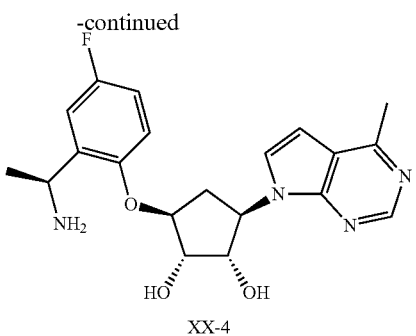

XX-4

Step 1—Synthesis of 1-(2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluorophenyl)ethan-1-amine (XX-1)

Compound WW-2 (100 mg, 0.235 mmol) was dissolved in MeOH (1 mL). Then NH$_4$OAc (181 mg, 2.35 mmol) was added to the above mixture and stirred at 25° C. for 1 hour. Then NaBH$_3$CN (89 mg, 1.41 mmol) was added and heated to 80° C. for 16 hour. The mixture was cooled to 25° C., then 1 mL saturated NaHCO$_3$ was added and stirred 25° C. for 10 min. The reaction mixture was extracted with DCM (5 mL×3), separated, dried and evaporated to give crude material which was purified by prep-TLC (MeOH/DCM 0-10%) to afford XX-1 (35 mg, 35%) as a colorless oil and used directly in the next step.

Step 2—Synthesis of (1S,2S,3S,5R)-3-(2-(1-aminoethyl)-4-fluorophenoxy)-5-(4-methyl-7H-pyrrolo[2,3-d]pyrimidin-7-yl)cyclopentane-1,2-diol (XX-2)

To compound XX-1 (100 mg, 0.234 mmol) in H$_2$O (0.5 mL) was added TFA (0.5 mL) at 0° C. The mixture was stirred at 0° C. for 60 min. The pH of the reaction solution was adjusted to pH=9 by addition of saturated K$_2$CO$_3$ aq. The final solution was separated by prep-HPLC, to give 90 mg of the XX-2 (90 mg, 99%) as a white solid.

Step 3—Separation of (1S,2S,3S,5R)-3-(2-((R)-1-aminoethyl)-4-fluorophenoxy)-5-(4-methyl-7H-pyrrolo[2,3-d]pyrimidin-7-yl)cyclopentane-1,2-diol (XX-3) and (1S,2S,3S,5R)-3-(2-((S)-1-aminoethyl)-4-fluorophenoxy)-5-(4-methyl-7H-pyrrolo[2,3-d]pyrimidin-7-yl)cyclopentane-1,2-diol (XX-4)

Separation of Compound XX-2 by Chiral SFC
XX-3: LCMS 370 [M-NH$_2$]; $^1$H NMR (400 MHz, DMSO-d$_6$) δ ppm 8.61 (s, 1H), 7.61 (d, J=3.7 Hz, 1H), 7.29 (dd, J=3.0, 10.0 Hz, 1H), 7.03-6.90 (m, 2H), 6.72 (d, J=3.7 Hz, 1H), 5.34 (br. s., 1H), 5.18-5.01 (m, 2H), 4.61-4.49 (m, 2H), 4.33 (q, J=6.4 Hz, 1H), 4.01 (d, J=4.5 Hz, 1H), 2.94-2.79 (m, 1H), 2.64 (s, 3H), 2.00 (ddd, J=4.0, 9.4, 13.8 Hz, 2H), 1.25 (d, J=6.5 Hz, 3H)

XX-4: LCMS 370 [M-NH$_2$]; $^1$H NMR (400 MHz, DMSO-d$_6$) δ ppm 8.62 (s, 1H), 7.60 (d, J=3.7 Hz, 1H), 7.29 (dd, J=3.0, 10.0 Hz, 1H), 7.04-6.87 (m, 2H), 6.71 (d, J=3.5 Hz, 1H), 5.35 (br. s., 1H), 5.20-5.03 (m, 2H), 4.63-4.46 (m, 2H), 4.33 (q, J=6.6 Hz, 1H), 4.02 (d, J=4.3 Hz, 1H), 2.91-2.78 (m, 1H), 2.64 (s, 3H), 2.04-1.91 (m, 2H), 1.26 (d, J=6.6 Hz, 3H)

Examples 139-142 were Made in a Similar Fashion as XX-3 & XX-4 Starting from BB-2 and the Appropriate Phenolic Ketone. The Sequence Starts with Steps 2 (Allylic Alkylation) & 3 (Dihydroxylation) from Scheme BB Followed by Step 1 (Acetonide Formation) from Scheme WW and then Steps 1 (Reductive Amination), 2 (Deprotection) and 3 (Chiral Separation) in Scheme XX

| Example 139 1-(4-chloro-5-fluoro-2-hydroxyphenyl)ethan-1-one | 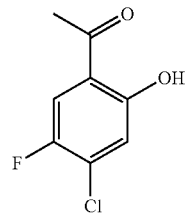 | 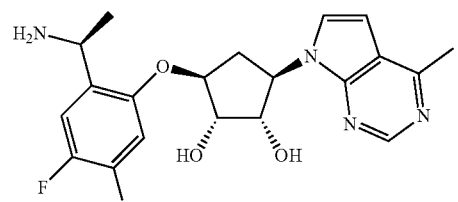 | 421 [M + 1] | (1S,2S,3S,5R)-3-(2-((S)-1-aminoethyl)-5-chloro-4-fluorophenoxy)-5-(4-methyl-7H-pyrrolo[2,3-d]pyrimidin-7-yl)cyclopentane-1,2-diol $^1$H NMR (400 MHz, MeOD-d$_4$) δ ppm 8.61 (s, 1H), 7.55 (d, J = 3.5 Hz, 1H), 7.31 (d, J = 10.0 Hz, 1H), 7.20 (d, J = 6.3 Hz, 1H), 6.75 (d, J = 3.5 Hz, 1H), 5.16 (q, J = 9.0 Hz, 1H), 4.80-4.73 (m, 1H), 4.72-4.64 (m, 1H), 4.49-4.39 (m, 1H), 4.22 (d, J = 5.0 Hz, 1H), 3.04-2.92 (m, 1H), 2.72 (s, 3H), 2.36-2.25 (m, 1H), 1.44 (d, J = 6.8 Hz, 3H) |
|---|---|---|---|---|
| Example 140 1-(4-chloro-5-fluoro-2-hydroxyphenyl)ethan-1-one | 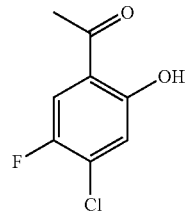 | 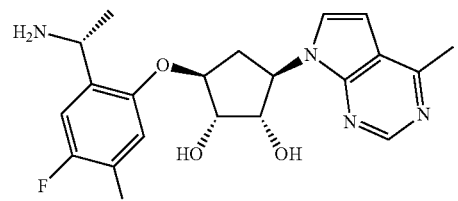 | 421 [M + 1] | (1S,2S,3S,5R)-3-(2-((R)-1-aminoethyl)-5-chloro-4-fluorophenoxy)-5-(4-methyl-7H-pyrrolo[2,3-d]pyrimidin-7-yl)cyclopentane-1,2-diol $^1$H NMR (400 MHz, MeOD-d$_4$) δ ppm 8.62 (s, 1H), 7.56 (d, J = 3.5 Hz, 1H), 7.31 (d, J = 10.0 Hz, 1H), 7.19 (d, J = 6.0 Hz, 1H), 6.75 (d, J = 3.8 Hz, 1H), 5.17 (q, J = 9.0 Hz, 1H), 4.79 (dd, J = 5.0, 8.8 Hz, 1H), 4.69 (br. s., 1H), 4.42 (q, J = 6.8 Hz, 1H), 4.20 (d, J = 4.8 Hz, 1H), 3.06-2.93 (m, 1H), 2.72 (s, 3H), 2.41-2.28 (m, 1H), 1.45 (d, J = 6.8 Hz, 3H) |

-continued

| | | | |
|---|---|---|---|
| Example 141<br>7-hydroxy-2,3-dihydro-1H-inden-1-one<br>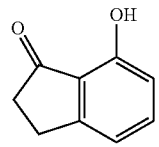 [SMILES: O=C1CCc2cccc(O)c21] | 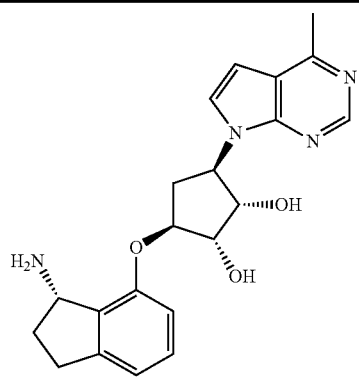 | 364<br>[M − NH₂] | (1S,2S,3S,5R)-3-(((S)-3-amino-2,3-dihydro-1H-inden-4-yl)oxy)-5-(4-methyl-7H-pyrrolo[2,3-d]pyrimidin-7-yl)cyclopentane-1,2-diol<br>¹H NMR (400 MHz, DMSO-d₆) δ ppm 8.63 (s, 1H), 7.67 (d, J = 3.5 Hz, 1H), 7.21-7.06 (m, 1H), 6.86-6.77 (m, 2H), 6.71 (d, J = 3.5 Hz, 1H), 5.40 (br. s., 1H), 5.15-5.04 (m, 2H), 4.65-4.57 (m, 2H), 4.51-4.45 (m, 1H), 4.04 (d, J = 4.5 Hz, 1H), 3.03-2.93 (m, 1H), 2.90-2.79 (m, 1H), 2.70 (ddd, J = 5.8, 9.1, 15.5 Hz, 1H), 2.64 (s, 3H), 2.34-2.22 (m, 1H), 2.15-1.81 (m, 2H), 1.76-1.65 (m, 1H) |
| Example 142<br>7-hydroxy-2,3-dihydro-1H-inden-1-one<br>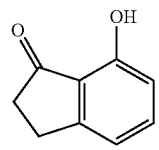 [SMILES: O=C1CCc2cccc(O)c21] | 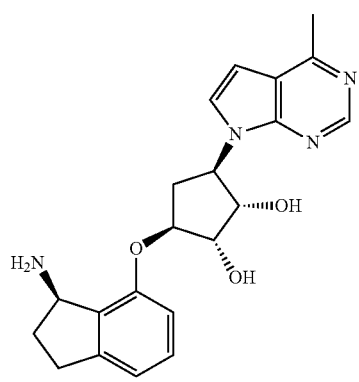 [SMILES: Cc1ncnc2c1ccn2[C@@H]1C[C@H](Oc2cccc3c2[C@H](N)CC3)[C@@H](O)[C@H]1O] | 364<br>[M − NH₂] | (1S,2S,3S,5R)-3-(((R)-3-amino-2,3-dihydro-1H-inden-4-yl)oxy)-5-(4-methyl-7H-pyrrolo[2,3-d]pyrimidin-7-yl)cyclopentane-1,2-diol<br>¹H NMR (400 MHz, DMSO-d₆) δ ppm 8.60 (s, 1H), 7.70 (d, J = 3.5 Hz, 1H), 7.12 (t, J = 7.8 Hz, 1H), 6.86-6.75 (m, 2H), 6.69 (s, 1H), 5.37 (br. s., 1H), 5.23-5.03 (m, 2H), 4.66-4.55 (m, 2H), 4.48 (dd, J = 4.5, 7.5 Hz, 1H), 4.02 (d, J = 4.3 Hz, 1H), 3.02-2.93 (m, 1H), 2.90-2.80 (m, 1H), 2.76-2.66 (m, 1H), 2.66-2.59 (m, 3H), 2.28 (dt, J = 8.2, 13.6 Hz, 1H), 2.06- 1.97 (m, 1H), 1.77-1.64 (m, 1H) |

Example 143 (Scheme YY)—(1S,2S,3S,5R)-3-(2-(aminomethyl)-4-chloro-3-fluorophenoxy)-5-(4-methyl-7H-pyrrolo[2,3-d]pyrimidin-7-yl)cyclopentane-1,2-diol (YY-6)

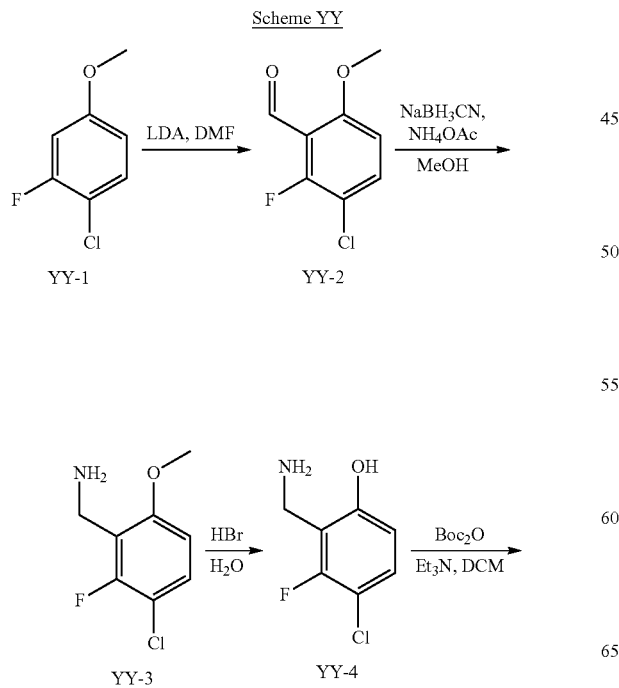

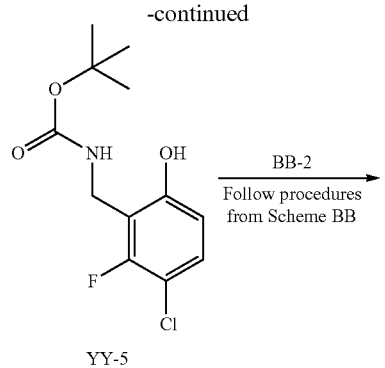

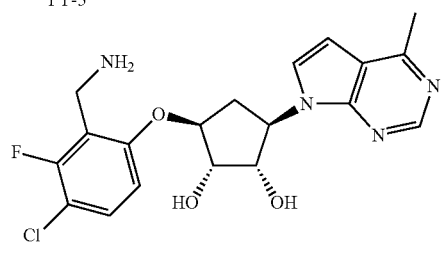

Step 1—Synthesis of 3-chloro-2-fluoro-6-methoxybenzaldehyde (YY-2)

To a solution of 4-chloro-3-fluoroanisole (YY-1) (250 mg, 1.56 mmol) in anhydrous THF was added LDA (0.86 mL, 2M, 1.71 mmol) drop-wise under N₂, at −78° C. and stirred at −78° C. for 30 min under N₂. To the above solution was added DMF (125 mg, 1.71 mmol) at −78° C. under N₂ and the resulting mixture was stirred at −78° C. for 20 min. The reaction was quenched by sat. NH₄Cl at −78° C. The resulting mixture was warmed to 25° C. The mixture was partitioned between EtOAc and H₂O. The organic layer was separated and the aqueous layer was extracted with EtOAc. The combined organic layers were washed with brine, dried over Na₂SO₄ and concentrated to afford the crude product. The crude product was purified via flash column (EtOAc: petroleum ether=1%-12%) to afford YY-2 (178 mg, 61%) as a white solid. ¹H NMR (400 MHz, CDCl₃) δ ppm 10.41 (d, J=1.3 Hz, 1H), 7.54 (dd, J=8.0, 9.0 Hz, 1H), 6.76 (dd, J=1.5, 9.0 Hz, 1H), 3.95 (s, 3H)

Step 2—Synthesis of (3-chloro-2-fluoro-6-methoxyphenyl)methanamine (YY-3)

To a solution of YY-2 (400 mg, 2.12 mmol) in anhydrous MeOH (20.0 mL) was added NH₄OAc (1.63 g, 21.2 mmol). The mixture was stirred at 25° C. for 1 hour. To the above solution was added NaCNBH₃ (533 mg, 8.48 mmol) at 25° C. The resulting mixture was stirred for 16 hours at 25° C. The reaction mixture was partitioned between EtOAc and H₂O. The organic layer was separated, washed with brine, dried over Na₂SO₄ and concentrated to afford the crude product which was purified via flash column (MeOH: DCM=1%-15%) to afford YY-3 (270 mg, 67%) as a yellow gum. ¹H NMR (400 MHz, DMSO-d₆) δ ppm 7.35 (t, J=8.8 Hz, 1H), 6.78 (d, J=9.0 Hz, 1H), 3.77 (s, 3H), 3.70 (s, 2H)

Step 3—Synthesis of 2-(aminomethyl)-4-chloro-3-fluorophenol (YY-4)

To a solution of YY-3 (180 mg, 0.949 mmol) in H₂O (15.0 mL) was added aq.HBr (1.50 mL) drop-wise at 0° C. under N₂. After the addition, the reaction was heated at reflux (110° C.) and stirred for 6 hours. The reaction mixture was cooled to 0° C., diluted in H₂O, and neutralized with sat. NaOH. The aqueous layer was extracted with EtOAc. The organic layer was washed with brine, dried over Na₂SO₄ and concentrated to afford the crude product which was purified via pre-TLC (MeOH:DCM=1:10) to afford YY-4 (50 mg, 30%) as white solid. ¹H NMR (400 MHz, DMSO-d₆) δ ppm 7.18 (t, J=8.9 Hz, 1H), 6.52 (dd, J=1.5, 8.8 Hz, 1H), 3.92 (d, J=1.3 Hz, 2H)

Step 4—Synthesis of tert-butyl(3-chloro-2-fluoro-6-hydroxybenzyl)carbamate (YY-5)

To a solution of YY-4 (50.0 mg, 0.285 mmol) in DCM (5.00 mL) and MeOH (1.0 mL) was added Boc₂O (68.4 mg, 0.313 mmol) followed by Et₃N (72 mg, 0.71 mmol) at 0° C. After the addition, the reaction mixture was stirred at 25° C. for 16 hours. The reaction mixture was acidified by sat. citric acid to pH 5-6. The mixture was partitioned between DCM and H₂O. The organic layer was separated and the aqueous layer was extracted with DCM. The combined organic layer was washed with sat.NaHCO₃ and brine, dried over Na₂SO₄ and concentrated to afford the crude product which was purified via pre-TLC (EtOAc: Petroleum ether=1:2) to afford YY-5 (45 mg, 57%) as a white solid. ¹H NMR (400 MHz, DMSO-d₆) δ ppm 10.22 (s, 1H), 7.27 (t, J=8.4 Hz), 7.02 (br. s, 1H), 6.67 (d, J=9.2 Hz), 4.14 (s, 2H), 1.37 (s, 9H)

Step 5—Synthesis of (1S,2S,3S,5R)-3-(2-(aminoethyl)-4-chloro-3-fluorophenoxy)-5-(4-methyl-7H-pyrrolo[2,3-d]pyrimidin-7-yl)cyclopentane-1,2-diol (YY-6)

Compound YY-6 was synthesized using YY-5 and BB-2 following procedures steps 2 & 3 in Scheme BB.
LCMS 407 [M+1]; ¹H NMR (400 MHz, DMSO-d₆+D₂O) δ ppm 8.57 (s, 1H), 7.61 (d, J=3.5 Hz, 1H), 7.56 (t, J=8.7 Hz, 1H), 7.00 (d, J=9.0 Hz, 1H), 6.72 (br. s., 1H), 5.14-4.99 (m, 1H), 4.64 (br. s., 1H), 4.59 (dd, J=4.6, 9.4 Hz, 1H), 4.08 (s, 3H), 2.90-2.78 (m, 1H), 2.62 (s, 3H), 2.06 (t, J=10.4 Hz, 1H)

Example 144-146 were Made in a Similar Fashion as YY-6 Starting with the Appropriate Anisole Reagent and Following Steps 3 & 4 in Scheme YY

| Example 144 2-methoxy-6-(trifluoromethyl) phenyl)methanamine 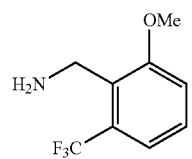 | 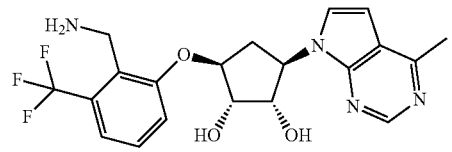 [SMILES: Cc1ncnc2c1ccn2[C@@H]1C[C@H](Oc2cccc(C(F)(F)F)c2CN)[C@@H](O)[C@H]1O] | 423 [M + 1] | (1S,2S,3S,5R)-3-(2-(aminomethyl)-3-(trifluoromethyl)phenoxy)-5-(4-methyl-7H-pyrrolo[2,3-d]pyrimidin-7-yl)cyclopentane-1,2-diol ¹H NMR (400 MHz, DMSO-d₆) δ ppm = 8.60 (s, 1H), 7.71 (d, J = 3.5 Hz, 1H), 7.56-7.48 (m, 1H), 7.47-7.40 (m, 1H), 7.33 (d, J = 7.8 Hz, 1H), 6.71 (d, J = 3.5 Hz, 1H), 5.11 (q, J = 9.3 Hz, 1H), 4.71 (br. s., 1H), 4.65 (dd, J = 4.9, 9.2 Hz, 1H), 4.13 (d, J = 4.3 Hz, 1H), 4.02 (br. s., 2H), 2.97-2.82 (m, 1H), 2.64 (s, 3H), 2.11 (ddd, J = 4.3, 9.7, 13.7 Hz, 1H) |
| --- | --- | --- | --- |
| Example 145 (2,3-difluoro-6-methoxyphenyl) methanamine 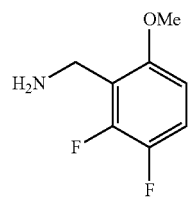 [SMILES: COc1ccc(F)c(F)c1CN] | 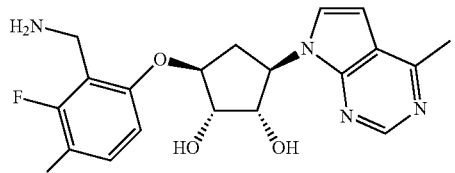 | 391 [M + 1] | (1S,2S,3S,5R)-3-(2-(aminomethyl)-3,4-difluorophenoxy)-5-(4-methyl-7H-pyrrolo[2,3-d]pyrimidin-7-yl)cyclopentane-1,2-diol ¹H NMR (400 MHz, DMSO-d₆) δ ppm 8.61 (s, 1H), 7.68 (s, 1H), 7.31-7.20 (m, 1H), 6.90-6.83 (m, 1H), 6.72 (d, J = 3.5 Hz, 1H), 5.54-5.25 (m, 1H), 5.17-5.03 (m, 2H), 4.68-4.55 (m, 2H), 4.07-4.01 (m, 1H), 3.77 (d, J = 1.3 Hz, 2H), 2.90-2.79 (m, 1H), 2.64 (s, 3H), 2.10-1.99 (m, 1H) |

| Example 146 2-(5-chloro-2-methoxyphenyl)ethan-1-amine 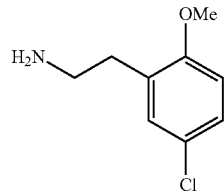 [SMILES: COc1ccc(Cl)cc1CCN] | 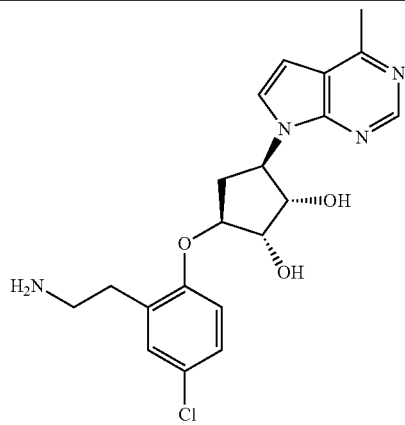 | 403 [M + 1] | (1S,2S,3S,5R)-3-(2-(2-aminoethyl)-4-chlorophenoxy)-5-(4-methyl-7H-pyrrolo[2,3-d]pyrimidin-7-yl)cyclopentane-1,2-diol <br> $^1$H NMR (400 MHz, DMSO-d$_6$ + D$_2$O) δ ppm 8.59 (s, 1H), 7.58 (d, J = 3.8 Hz, 1H), 7.23-7.16 (m, 2H), 7.00 (d, 8.5 Hz, 1H), 6.72 (d, J = 3.8 Hz, 1H), 5.16-5.01 (m, 1H), 4.62-4.46 (m, 2H), 3.99 (d, J = 5.3 Hz, 1H), 2.91-2.81 (m, 1H), 2.79-2.68 (m, 2H), 2.62 (s, 2H), 2.00-1.88 (m, 1H) |
Example 147 (Scheme ZZ)—(1S,2S,3S,5R)-3-(2-(aminomethyl)-4,5-dichlorophenoxy)-5-(4-methyl-7H-pyrrolo[2,3-d]pyrimidin-7-yl)cyclopentane-1,2-diol (ZZ-7)
Scheme ZZ
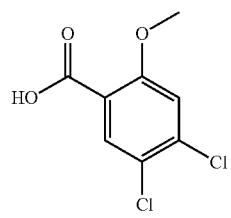
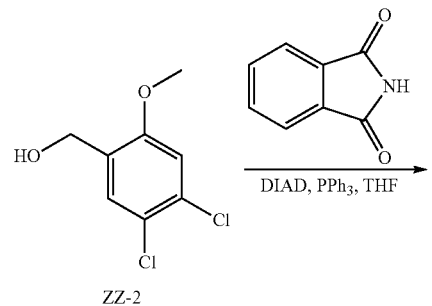
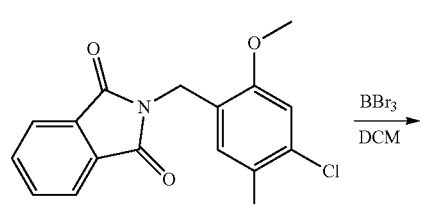
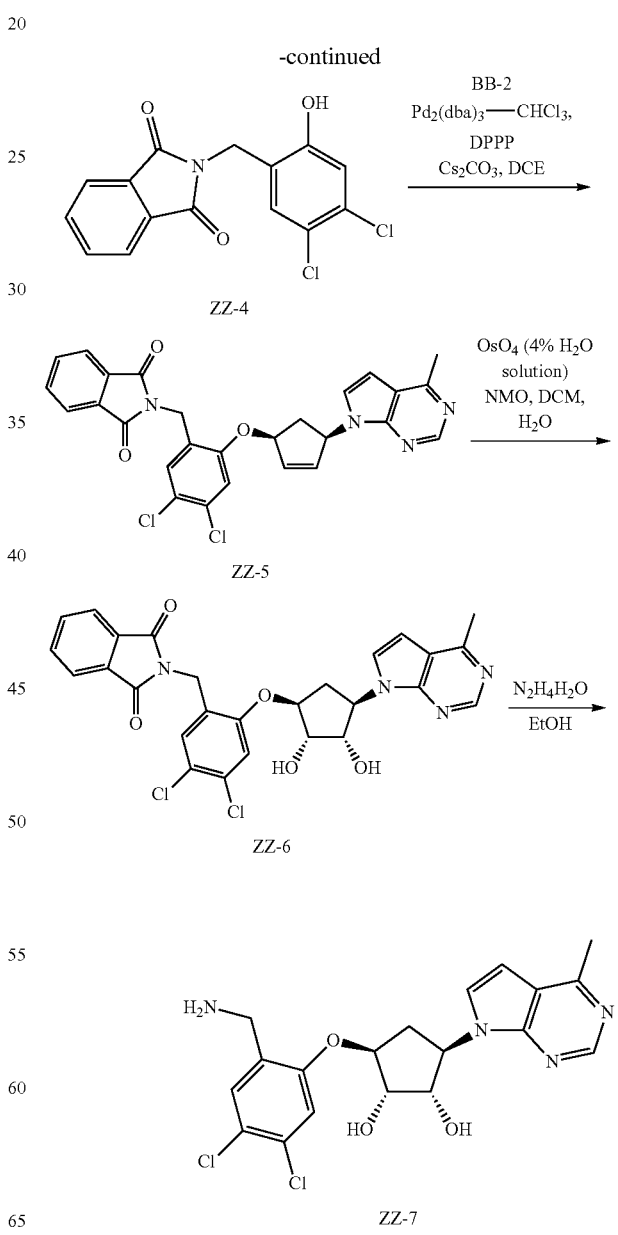

Step 1—Synthesis of (4,5-dichloro-2-methoxyphenyl)methanol (ZZ-2)

To a solution of methoxybenzoic acid (ZZ-1) (500 mg, 2.26 mmol) in anhydrous THF (23 mL) was added $BH_3$.THF (6.79 mL, 6.79 mmol) at 0° C. under $N_2$. After the addition, the reaction mixture was stirred at 30° C. under $N_2$ for 3 hours. The reaction mixture was cooled to −20° C. and quenched with sat. $NH_4Cl$. The reaction mixture was partitioned between EtOAc and $H_2O$. The organic layer was separated and the aqueous layer was extracted with EtOAc. The combined organic layers were washed with brine, dried over $Na_2SO_4$ and concentrated to afford the crude product which was purified via flash column chromatography (EtOAc: Petroleum ether=1%-35%) to afford the ZZ-2 (383 mg, 81.8%) as a white solid. $^1$H NMR (400 MHz, DMSO-$d_6$) δ ppm 7.49 (s, 1H), 7.22 (s, 1H), 5.28 (t, J=5.6 Hz), 4.44 (d, J=6 Hz), 3.31 (s, 3H)

Step 2—Synthesis of 2-(4,5-dichloro-2-methoxybenzyl)isoindoline-1,3-dione (ZZ-3)

To a solution of ZZ-2 (230 mg, 1.11 mmol) and phthalimide (163 mg, 1.11 mmol) in anhydrous THF (12 mL) was added $PPh_3$ (291 mg, 2.30 mmol). The reaction mixture was stirred at −20° C. under $N_2$ for 30 min. To the above solution was added DEAD (193 mg, 1.11 mmol) at −10° C.~−20° C. After the addition, the reaction mixture was became a yellow solution, which was warmed to 25° C. and stirred for 2 hours. The reaction mixture was concentrated and the residue was purified via flash column (12.0 g gel, EtOAc: petroleum Ether=10%-35%) to afford the crude product and further purified via prep-TLC (EtOAc: petroleum=1%-15%) to afford the product ZZ-3 (30 mg, 8%) as a white solid and used as is in the next step.

Step 3—Synthesis of 2-(4,5-dichloro-2-hydroxybenzyl)isoindoline-1,3-dione (ZZ-4)

To a solution of ZZ-3 (50 mg, 0.15 mmol) in DCM (2.00 mL) was added $BBr_3$ (0.20 mL) dropwise at 0° C. After the addition, the reaction was stirred at 0° C. for 2 hours. The reaction mixture was quenched with MeOH carefully. The resulting mixture was partitioned between DCM and sat. $NaHCO_3$. The organic layer was washed with brine, dried over $Na_2SO_4$ and concentrated to afford the crude product which was purified via prep-TLC (EtOAc: petroleum ether=1:1) to afford ZZ-4 (43 mg, 90%) as a white solid. $^1$H NMR (400 MHz, DMSO-$d_6$) δ ppm 10.50 (s, 1H), 7.94-7.76 (m, 4H), 7.32 (s, 1H), 7.00 (s, 1H), 4.68 (s, 2H)

Step 4—Synthesis of 2-(4,5-dichloro-2-(((1S,4R)-4-(4-methyl-7H-pyrrolo[2,3-d]pyrimidin-7-yl)cyclopent-2-en-1-yl)oxy)benzyl)isoindoline-1,3-dione (ZZ-5)

To a stirred solution of ZZ-4 (43 mg, 0.13 mmol) and tert-butyl ((1S,4R)-4-(4-methyl-7H-pyrrolo[2,3-d]pyrimidin-7-yl)cyclopent-2-en-1-yl) carbonate (42 mg, 0.13 mmol) in DCE (1.50 mL) was added $Cs_2CO_3$ (52 mg, 0.16 mmol), $Pd_2(dba)_3$.$CHCl_3$, (3.5 mg, 0.003 mmol) and dppp (3.3 mg, 0.008 mmol). The reaction mixture was degassed and purged with $N_2$ for 3 times. The resulting solution was stirred for 1.5 hrs at 25° C. The reaction mixture was concentrated and purified via prep-TLC (EtOAc: petroleum ether=1:1) to afford the product ZZ-5 (62 mg, 89%) as a yellow gum and used in the next step directly.

Step 5—Synthesis of 2-(4,5-dichloro-2-(((1S,2S,3S,4R)-2,3-dihydroxy-4-(4-methyl-7H-pyrrolo[2,3-d]pyrimidin-7-yl)cyclopentyl)oxy)benzyl)isoindoline-1,3-dione (ZZ-6)

To a solution of ZZ-5 (62 mg, 0.12 mmol) in THF (2.50 mL) and $H_2O$ (0.50 mL) was added NMO (29.4 mg, 0.251 mmol) followed by $OsO_4$ (136 mg, 0.02 mmol, 4% w/w in t-BuOH). After the addition, the reaction mixture was stirred at 28° C. for 4 hours. The reaction mixture was diluted in $H_2O$ and quenched with sat. $NaHSO_3$. The dark solution was extracted with EtOAc, dried over $Na_2SO_4$ and concentrated to afford the crude product which was purified via prep-TLC (MeOH:DCM=1:10, UV) to afford ZZ-6 (30 mg, 45%) as a yellow solid. $^1$H NMR (400 MHz, DMSO-$d_6$) δ ppm 8.61 (s, 1H), 7.95-7.77 (m, 4H), 7.60 (d, J=3.5 Hz, 1H), 7.56 (s, 1H), 7.36 (s, 1H), 6.73 (d, J=3.5 Hz, 1H), 5.43 (d, J=4.0 Hz, 1H), 5.18-5.05 (m, 2H), 4.81 (s, 2H), 4.70-4.61 (m, J=6.0 Hz, 1H), 4.52-4.41 (m, 1H), 3.99-3.94 (m, 1H), 2.91-2.78 (m, 1H), 2.65 (s, 3H), 1.98-1.86 (m, 1H)

Step 6—Synthesis of (1S,2S,3S,5R)-3-(2-(aminoethyl)-4,5-dichlorophenoxy)-5-(4-methyl-7H-pyrrolo[2,3-d]pyrimidin-7-yl)cyclopentane-1,2-diol (ZZ-7)

To a solution of ZZ-6 (30 mg, 0.05 mmol) in THF (2.5 mL) was added $NH_2NH_2$ (31 mg, 0.81 mmol) drop-wise. After the addition, the reaction solution was stirred at 28° C. for 16 hours. The reaction mixture was filtered and the filtrate was concentrated. The residue was purified via prep-HPLC to afford ZZ-7 (11 mg, 46%) as a white solid. LCMS 423 [M+1]; $^1$H NMR (400 MHz, DMSO-$d_6$) δ ppm 8.62 (s, 1H), 7.66 (d, J=3.8 Hz, 1H), 7.60 (s, 1H), 7.31 (s, 1H), 6.72 (d, J=3.3 Hz, 1H), 5.14-5.05 (m, 2H), 4.63 (m, 1H), 4.00 (m, 1H), 3.74 (s, 2H), 2.89-2.81 (m, 1H), 2.64 (s, 3H), 2.02 (m, 1H)

Example 148 (1S,2S,3S,5R)-3-(2-(aminomethyl)-4,5-difluorophenoxy)-5-(4-methyl-7H-pyrrolo[2,3-d]pyrimidin-7-yl)cyclopentane-1,2-diol was Prepared in a Similar Fashion to ZZ-7 Starting with (4,5-difluoro-2-methoxyphenyl)methanol and Following Steps 2 Through 6 in Scheme ZZ

| Example 148 | | 391 [M + 1] | (1S,2S,3S,5R)-3-(2-(aminomethyl)-4,5-difluorophenoxy)-5-(4-methyl-7H-pyrrolo[2,3-d]pyrimidin-7-yl)cyclopentane-1,2-diol <br> $^1$H NMR (400 MHz, DMSO-d$_6$) δ ppm 8.62 (s, 1H), 7.75-7.57 (m, 1H), 7.51-7.32 (m, 1H), 7.25-7.05 (m, 1H), 6.72 (d, J = 3.5 Hz, 1H), 5.39 (d, J = 18.1 Hz, 1H), 5.20-4.98 (m, 2H), 4.57 (d, J = 4.8 Hz, 2H), 4.01 (d, J = 4.3 Hz, 1H), 3.72 (s, 2H), 2.95-2.72 (m, 1H), 2.62 (s, 3H), 2.00 (ddd, J = 4.5, 9.1, 13.7 Hz, 1H) |
|---|---|---|---|
| (4,5-difluoro-2-meethoxyphenyl)methanol 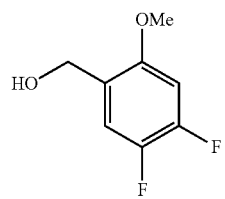 | 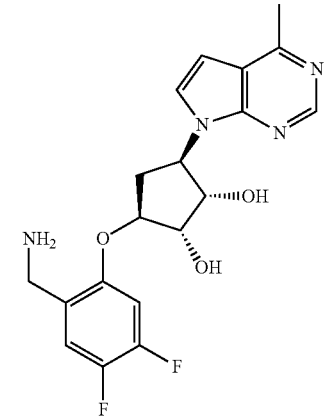 [SMILES: Cc1ncnc2c1ccn2[C@@H]1C[C@H](Oc2cc(F)c(F)cc2CN)[C@@H](O)[C@H]1O] | | |

Example 149 (Scheme AAA)—(1S,2S,3S,5R)-3-(2-(2-amino-1-hydroxyethyl)-4-chlorophenoxy)-5-(4-methyl-7H-pyrrolo[2,3-d]pyrimidin-7-yl)cyclopentane-1,2-diol (AAA-9)

Scheme AAA

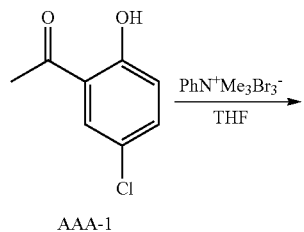

AAA-1

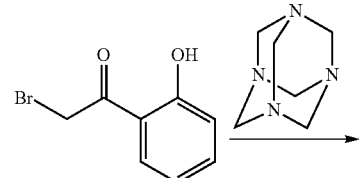

AAA-2

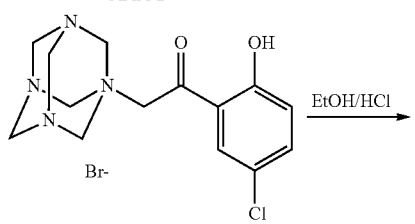

AAA-3

-continued

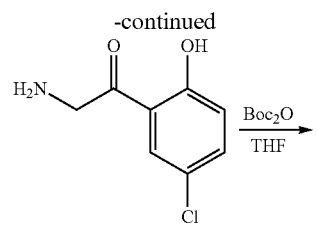

AAA-4

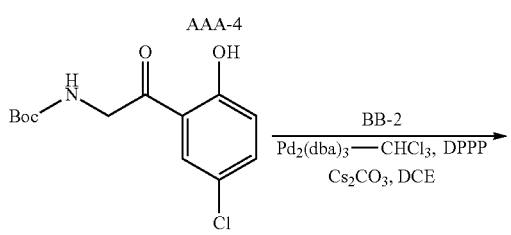

AAA-5

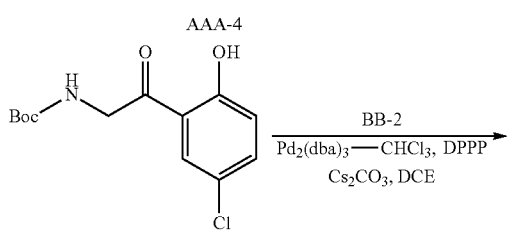

AAA-6

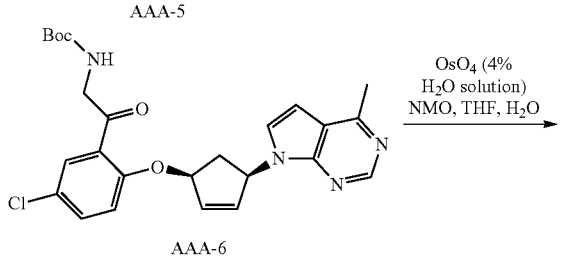

AAA-7

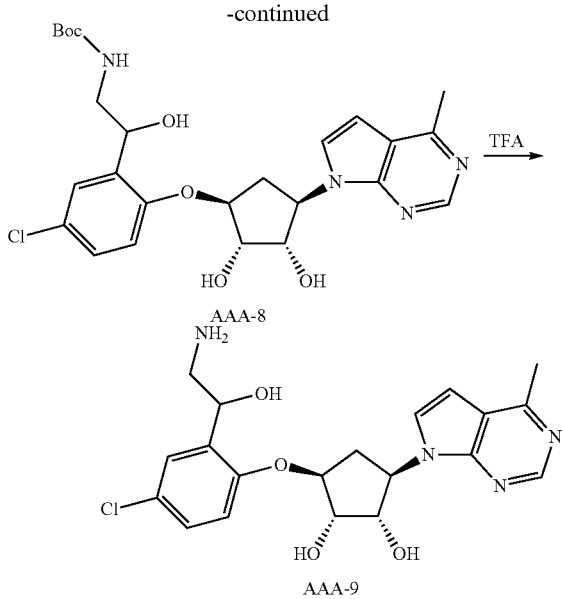

Step 1—Synthesis of 2-bromo-1-(5-chloro-2-hydroxyphenyl)ethan-1-one (AAA-2)

To a yellow solution of 1-(5-chloro-2-hydroxyphenyl)ethan-1-one (AAA-1) (2 g, 11.72 mmol) and in THF (60 mL) was added PhMe₃NBr₃ (4.85 g, 12.9 mmol) at rt (25° C.). The resulting red solution was stirred at rt for 12 hrs in which solid was formed, then the mixture was filtered. The filtrate was concentrated in vacuo and the residue was purified by silica gel chromatography eluted with EtOAc in petroleum ether from 0 to 10% to AAA-2 (2.4 g) as a yellow oil which was used in the next step directly.

Step 2—Synthesis of 2-((3r,5r,7r)-1I4,3,5,7-tetraazaadamantan-1-yl)-1-(5-chloro-2-hydroxyphenyl)ethan-1-one, bromide salt (AAA-3)

To a solution of 1,3,5,7-tetraazaadamantane (4.67 g, 33.3 mmol) in CHCl₃ (40 mL) was added to AAA-2 (2.6 g, 10 mmol) at rt (25° C.). The mixture was stirred at rt for 12 hrs in which solid was formed. The solid was collected by filtration and rinsed with DCM and dried in vacuo to afford crude AAA-3 (3 g, 74%) as a white solid, used in the next step directly.

Step 3—Synthesis of 2-amino-1-(5-chloro-2-hydroxyphenyl)ethan-1-one (AAA-4)

To a suspension of SM1 (3 g, 8 mmol) in EtOH (15 mL) was added conc. HCl (3 mL) at rt (25° C.). The suspension was stirred at rt for 2 hrs. The reaction was evaporated to give AAA-4 (1.5 g, >100%) as yellow oil which was used directly without further purification. LCMS 186 [M+1]

Step 4—Synthesis of tert-butyl(2-(5-chloro-2-hydroxyphenyl)-2-oxoethyl)carbamate (AAA-5)

To a solution of (Boc)₂O (2.29 g, 10.5 mmol) in dioxane (15 mL) was added the solution of AAA-4 (200 mg, solution, neutralized by NaHCO₃ aq.) at 0° C. The reaction solution was stirred at 25° C. The reaction solution was extracted with EtOAc (6 mL×3). The organic layers were separated, dried and evaporated to give the crude product which was purified by flash chromatography with 0-25% EtOAc/petroleum ether, to give AAA-5 (600 mg, 22%) as a white solid and used as is in the next step.

Step 5—Synthesis of tert-butyl(2-(5-chloro-2-(((1S,4R)-4-(4-methyl-7H-pyrrolo[2,3-d]pyrimidin-7-yl)cyclopent-2-en-1-yl)oxy)phenyl)-2-oxoethyl)carbamate (AAA-6)

Using BB-2 and following similar procedures as step 2 in Scheme BB, AAA-6 was obtained (288 mg, 31%) as a yellow gum and used in the next step directly.

Step 6—Synthesis of tert-butyl(2-(5-chloro-2-(((1S,2S,3S,4R)-2,3-dihydroxy-4-(4-methyl-7H-pyrrolo[2,3-d]pyrimidin-7-yl)cyclopentyl)oxy)phenyl)-2-oxoethyl)carbamate (AAA-7)

Starting with AAA-6 and following similar procedures as step 3 in Scheme BB, AAA-7 was obtained (70 mg, 33%) as a white solid. LCMS 517 [M+1]

Step 7—Synthesis of tert-butyl(2-(5-chloro-2-(((1S,2S,3S,4R)-2,3-dihydroxy-4-(4-methyl-7H-pyrrolo[2,3-d]pyrimidin-7-yl)cyclopentyl)oxy)phenyl)-2-hydroxyethyl)carbamate (AAA-8)

To a mixture of AAA-7 (70 mg, 0.14 mmol) in MeOH (1 mL) was added NaBH₄ (15.4 mg, 0.406 mmol). The mixture was stirred at 25° C. for 2 h. The mixture was quenched by 1N HCl aq. (5 mL). The mixture was evaporated to give the crude product AAA-8 (70 mg, >99%) as a white solid.

Step 8—Synthesis of (1S,2S,3S,5R)-3-(2-(2-amino-1-hydroxyethyl)-4-chlorophenoxy)-5-(4-methyl-7H-pyrrolo[2,3-d]pyrimidin-7-yl)cyclopentane-1,2-diol (AAA-9)

Compound AAA-8 (62 mg, 0.12 mmol) was dissolved in DCM (0.6 mL). The mixture was cooled to 0° C. in an ice bath. TFA (0.2 mL) was added to the above mixture dropwise. The reaction mixture was stirred at 25° C. for 2 hours. The reaction solution was neutralized by saturated NaHCO₃ aq. (1 mL), filtered and the filtrate was purified by prep-HPLC directly to give AAA-9 (21 mg, 42%) as a white solid. LCMS 441 [M+23]; $^1$H NMR (400 MHz, MeOD-d₄) δ ppm 8.62 (d, J=2.8 Hz, 1H), 7.58 (dd, J=3.3, 11.3 Hz, 1H), 7.48 (s, 1H), 7.26-7.22 (m, 1H), 7.03 (dd, J=2.1, 8.7 Hz, 1H), 6.75 (t, J=3.8 Hz, 1H), 5.20 (d, J=3.8 Hz, 1H), 5.10 (br. s., 1H), 4.70 (br. s., 2H), 4.22 (d, J=9.5 Hz, 1H), 3.04-2.94 (m, 2H), 2.77 (br. s., 1H), 2.71 (s, 3H), 2.26 (br. s., 1H)

Example 150 (Scheme BBB)—(1S,2S,3S,5R)-3-(2-(aminomethyl)-3,4-dichlorophenoxy)-5-(4-methyl-7H-pyrrolo[2,3-d]pyrimidin-7-yl)cyclopentane-1,2-diol (BBB-8)

Scheme BBB

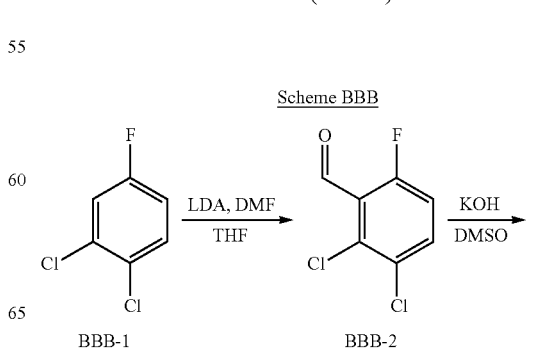

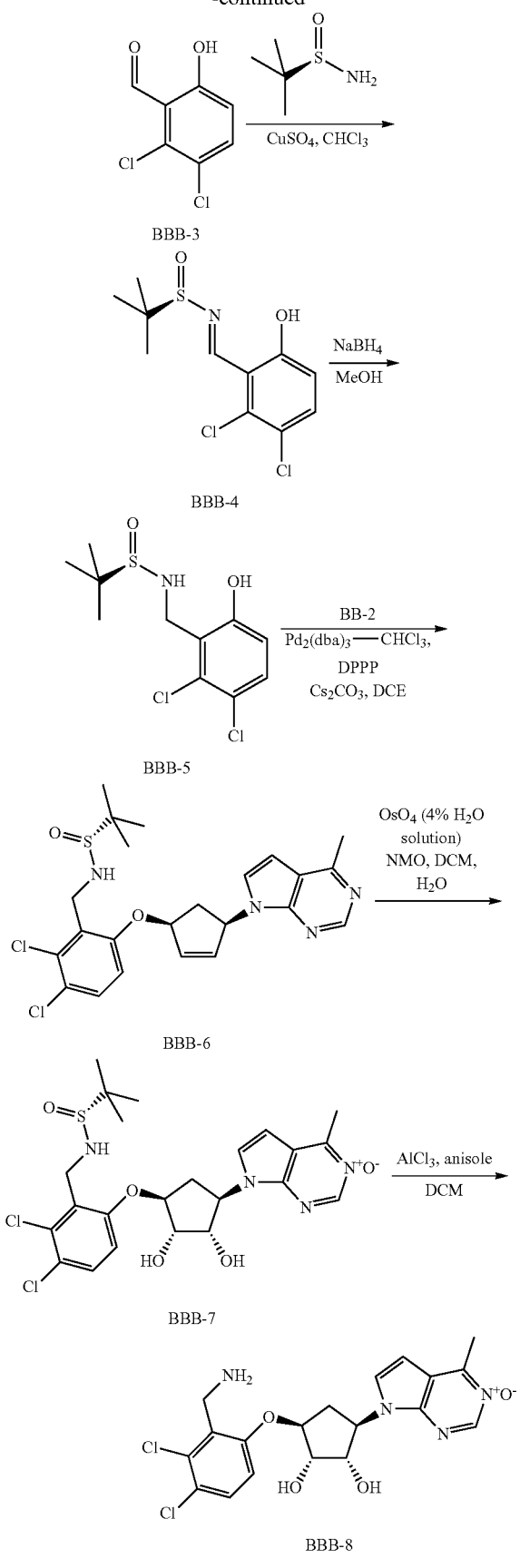

Step 1—Synthesis of 2,3-dichloro-6-fluorobenzaldehyde (BBB-2)

To a solution of 1,2-dichloro-4-fluorobenzene (BBB-1) (2 g, 12.12 mmol) in anhydrous THF (30 mL) was added LDA (6.67 mL, 2M, 13.3 mmol) drop-wise under $N_2$, at −65° C. After the addition, the reaction mixture was stirred at −65° C. for 30 min under $N_2$. To the resulting red solution was added DMF (1.77 g, 24.2 mmol) at −65° C. under $N_2$ and the resulting mixture was stirred at −65° C. for 20 min. The reaction was quenched with water (50 mL) and extracted with EtOAc (30 mL×2). The extract was washed with 1 N HCl (30 mL), brine (30 mL), dried over $Na_2SO_4$ and concentrated to give the crude material which was extracted with petroleum ether (30 mL×3). The extract was concentrated in vacuo to afford BBB-2 (2.2 g, 94%) as a yellow solid. $^1$H NMR (400 MHz, $CDCl_3$) δ ppm 10.44 (s, 1H), 7.66 (dd, J=5.3, 9.0 Hz, 1H), 7.10 (t, J=9.2 Hz, 1H)

Step 2—Synthesis of 2,3-dichloro-6-hydroxybenzaldehyde (BBB-3)

To a yellow solution of crude BBB-2 (2.2 g, 11.4 mmol) in DMSO (10 mL) was added KOH (1280 mg, 22.8 mmol) slowly at 0° C. After addition, the mixture was changed into red mixture and stirred at room temperature (20° C.) for 16 hrs. The mixture was diluted with MTBE (100 mL). The liquid was decanted out and residue was washed with MTBE (100 mL). The residue was then diluted with water (30 mL) and adjusted with 1 N HCl to pH 2 and extracted with EtOAc (20 mL×2). The extract was washed with brine (20 mL), dried over $Na_2SO_4$ and concentrated in vacuo to afford crude BBB-3 (390 mg, 18%) as yellow solid. $^1$H NMR (400 MHz, $CDCl_3$) δ ppm 11.98 (s, 1H), 10.44 (s, 1H), 7.56 (d, J=9.0 Hz, 1H), 6.90 (d, J=9.3 Hz, 1H)

Step 3—Synthesis of (R,E)-N-(2,3-dichloro-6-hydroxybenzylidene)-2-methylpropane-2-sulfinamide (4)

A mixture of crude BBB-3 (150 mg, 0.79 mmol), (R)-2-methylpropane-2-sulfinamide (143 mg, 1.2 mmol) and $CuSO_4$ (376 mg, 2.36 mmol) in $CHCl_3$ (3 mL) was stirred at rt (30° C.) for 5 days. The mixture was filtered and purified by silica gel chromatography eluted with EtOAc in petroleum ether from 0 to 30% to afford BBB-4 (70 mg, 30%) as a light yellow solid. $^1$H NMR (400 MHz, $CDCl_3$) δ ppm 11.98 (s, 1H), 9.28 (s, 1H), 7.49 (d, J=8.8 Hz, 1H), 6.92 (d, J=9.3 Hz, 1H), 1.29 (s, 9H)

Step 4—Synthesis of (R)—N-(2,3-dichloro-6-hydroxybenzyl)-2-methylpropane-2-sulfinamide (BBB-5)

To a solution of BBB-4 (70 mg, 0.238 mmol) in MeOH (3 mL) was added $NaBH_4$ (27 mg, 0.714 mol) at rt (30° C.). The mixture was stirred at rt for 1 h. The mixture was concentrated in vacuo and dissolved in water (5 mL). To the mixture was added $NH_4Cl$ aq (2 mL) in which some solid was formed. The mixture was extracted with EtOAc (5 mL×3). The extract was washed with brine (5 mL), dried over $Na_2SO_4$ and concentrated in vacuo to afford BBB-5 (55 mg, 78%) as a yellow solid. $^1$H NMR (400 MHz, $CDCl_3$) δ ppm 9.31 (br. s., 1H), 7.17 (d, J=8.8 Hz, 1H), 6.69 (d, J=9.0 Hz, 1H), 4.58-4.40 (m, 2H), 4.09-3.97 (m, 1H), 1.27 (s, 9H)

Step 5—Synthesis of (R)—N-(2,3-dichloro-6-(((1S, 4R)-4-(4-methyl-7H-pyrrolo[2,3-d]pyrimidin-7-yl)cyclopent-2-en-1-yl)oxy)benzyl)-2-methylpropane-2-sulfinamide (BBB-6)

Compound BBB-6 (130 mg, 98%, containing 1 eq of DCM) was prepared as a yellow gum from BBB-5 and BB-2 using similar procedures to step 2 of Scheme BB. LCMS 493 [M+1]; $^1$H NMR (400 MHz, CDCl$_3$) δ ppm 8.77 (s, 1H), 7.39-7.31 (m, 2H), 6.84 (d, J=9.0 Hz, 1H), 6.60 (d, J=3.5 Hz, 1H), 6.41 (d, J=5.5 Hz, 1H), 6.22 (d, J=4.8 Hz, 1H), 6.13-6.01 (m, 1H), 5.41-5.35 (m, 1H), 4.63-4.39 (m, 2H), 3.65 (t, J=6.7 Hz, 1H), 3.29-3.09 (m, 1H), 2.73 (s, 3H), 1.98 (td, J=3.8, 14.7 Hz, 1H), 1.18 (s, 9H)

Step 6—Synthesis of N-(2,3-dichloro-6-(((1S,2S,3S,4R)-2,3-dihydroxy-4-(4-methyl-7H-pyrrolo[2,3-d]pyrimidin-7-yl)cyclopentyl)oxy)benzyl)-2-methyl-propane-2-sulfonamide (BBB-7)

Compound BBB-6 was treated in a similar fashion to procedures of step 3 in scheme BB to afford BBB-7 (70 mg, 58%). LCMS 543 [M+16+1]; $^1$H NMR (400 MHz, CDCl$_3$) δ ppm 8.62 (s, 1H), 7.56 (br. s., 1H), 7.19 (d, J=8.8 Hz, 1H), 6.77 (d, J=9.0 Hz, 1H), 6.54 (d, J=3.8 Hz, 1H), 5.64 (t, J=5.5 Hz, 1H), 5.14 (s, 1H), 5.13-5.04 (m, 1H), 4.56-4.50 (m, 1H), 4.47 (dd, J=4.8, 8.5 Hz, 1H), 4.44-4.34 (m, 2H), 4.04 (d, J=4.8 Hz, 1H), 2.83-2.75 (m, 1H), 2.62 (s, 3H), 2.14-2.04 (m, 1H), 1.20 (s, 9H)

Step 7—Synthesis of (1S,2S,3S,5R)-3-(2-(aminoethyl)-3,4-dichlorophenoxy)-5-(4-methyl-7H-pyrrolo[2,3-d]pyrimidin-7-yl)cyclopentane-1,2-diol (BBB-8)

To a solution of BBB-7 (35 mg, 0.064 mmol) in dry DCM (5 mL) was added anisole (170 mg, 1.56 mmol) and AlCl$_3$ (86 mg, 0.64 mmol) at rt (25° C.). The white suspension was stirred at rt for 3 h. The mixture was quenched with NaHCO$_3$ aq (3 mL), followed by potassium sodium tartrate aq (5 mL). The mixture was extracted with EtOAc (5 mL×3). The extract was concentrated in vacuo and purified by TLC (DCM/MeOH=10/1) to afford BBB-8 (8 mg, 29%) as a white solid. LCMS 423 [M+1]; $^1$H NMR (400 MHz, DMSO-d$_6$) δ ppm 8.61 (s, 1H), 7.69 (d, J=3.5 Hz, 1H), 7.49 (d, J=8.8 Hz, 1H), 7.11 (d, J=9.0 Hz, 1H), 6.72 (d, J=3.8 Hz, 1H), 5.44 (br. s., 1H), 5.10 (q, J=9.0 Hz, 2H), 4.64 (d, J=5.3 Hz, 2H), 4.06 (d, J=4.8 Hz, 1H), 3.92 (s, 2H), 2.92-2.81 (m, 1H), 2.64 (s, 3H), 2.05 (ddd, J=4.1, 9.2, 13.8 Hz, 1H)

Example 151 (Scheme CCC)—(1S,2S,3S,5R)-3-(2-(2-aminoethoxy)-4,5-dichlorophenoxy)-5-(4-methyl-7H-pyrrolo[2,3-d]pyrimidin-7-yl)cyclopentane-1,2-diol (CCC-4)

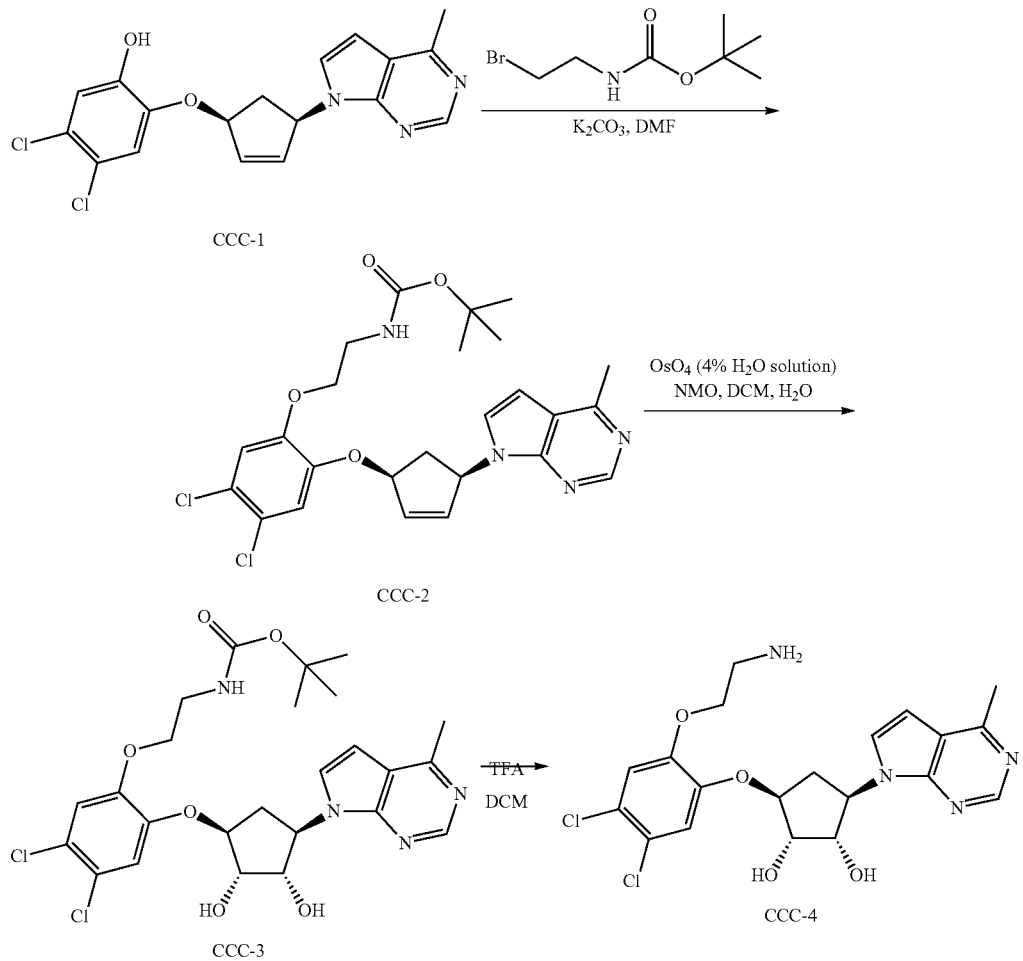

Scheme CCC

Step 1—Synthesis of 4,5-dichloro-2-(((1S,4R)-4-(4-methyl-7H-pyrrolo[2,3-d]pyrimidin-7-yl)cyclopent-2-en-1-yl)oxy)phenol (CCC-1)

Compound CCC-1 was prepared using similar procedures to step 2 in scheme BB with commercially available 4,5-dichlorobenzene-1,2-diol and BB-2.

Step 2—Synthesis of tert-butyl(2-(4,5-dichloro-2-(((1S,4R)-4-(4-methyl-7H-pyrrolo[2,3-d]pyrimidin-7-yl)cyclopent-2-en-1-yl)oxy)phenoxy)ethyl)carbamate (CCC-2)

To a stirred yellow solution of CCC-1 (78 mg, 0.21 mmol) in dry DMF (5 mL) was added K$_2$CO$_3$ (86 mg, 0.62 mmol) and tert-butyl (2-bromoethyl)carbamate (923 mg, 0.42 mmol) at 25° C. and stirred for 20 hours. Water (10 mL) was added to the reaction mixture and extracted with EtOAc (2×20 mL). The combined organic layers were washed with brine (5×20 mL), dried over Na$_2$SO$_4$, filtered and concentrated in vacuum to give the residue which was purified by column chromatography (silica gel, eluted with EtOAc) to give CCC-2 (108 mg, >99%) as a colorless gum. LCMS [M+1] 519; $^1$H NMR (400 MHz, CDCl$_3$) δ ppm 8.77 (s, 1H), 7.42 (d, J=3.5 Hz, 1H), 7.04 (s, 1H), 6.98 (s, 1H), 6.60 (d, J=3.5 Hz, 1H), 6.39 (td, J=1.9, 5.5 Hz, 1H), 6.19 (dd, J=2.3, 5.3 Hz, 1H), 6.06 (dd, J=2.0, 4.8 Hz, 1H), 5.29 (d, J=7.0 Hz, 1H), 5.02 (br. s., 1H), 4.03 (t, J=5.0 Hz, 2H), 3.59-3.47 (m, 2H), 3.10 (td, J=7.7, 15.2 Hz, 1H), 2.73 (s, 3H), 2.07 (t, J=2.9 Hz, 1H), 1.42 (s, 9H)

Step 3—Synthesis of tert-butyl(2-(4,5-dichloro-2-(((1S,2S,3S,4R)-2,3-dihydroxy-4-(4-methyl-7H-pyrrolo[2,3-d]pyrimidin-7-yl)cyclopentyl)oxy)phenoxy)ethyl)carbamate (CCC-3)

Compound CCC-2 was subjected to similar procedures as step 3 in Scheme BB to afford CCC-3 (55 mg, 48%) as brown gum. LCMS [M+23] 575

Step 4—Synthesis of (1S,2S,3S,5R)-3-(2-(2-aminoethoxy)-4,5-dichlorophenoxy)-5-(4-methyl-7H-pyrrolo[2,3-d]pyrimidin-7-yl)cyclopentane-1,2-diol (CCC-4)

Compound CCC-3 was subjected to standard TFA/water deprotection methods similar to step 8 in scheme AAA followed by prep-HPLC to afford CCC-4 (35 mg, 75%). LCMS [M+23] 475; $^1$H NMR (400 MHz, MeOD-d$_4$) δ ppm 8.64 (s, 1H), 7.66 (d, J=3.8 Hz, 1H), 7.37 (s, 1H), 7.29 (s, 1H), 6.79 (d, J=3.5 Hz, 1H), 5.20 (q, J=8.9 Hz, 1H), 4.76-4.68 (m, 1H), 4.66 (dd, J=5.3, 8.0 Hz, 1H), 4.33-4.23 (m, 3H), 3.40-3.36 (m, 2H), 3.01-2.90 (m, 1H), 2.74 (s, 3H), 2.29 (ddd, J=5.0, 8.8, 14.3 Hz, 1H)

Example 152 (1S,2S,3S,5R)-3-(2-(2-aminoethoxy)-4,5-difluorophenoxy)-5-(4-methyl-7H-pyrrolo[2,3-d]pyrimidin-7-yl)cyclopentane-1,2-diol was Prepared in a Similar Fashion to CCC-4 Starting with 4,5-difluorobenzene-1,2-diol and Following Steps 1 Through 4 in Scheme CCC

| Example 152 | | 421 | (1S,2S,3S,5R)-3-(2-(2-aminoethoxy)-4,5-difluorophenoxy)-5-(4-methyl-7H-pyrrolo[2,3-d]pyrimidin-7-yl)cyclopentane-1,2-diol |
|---|---|---|---|
| 4,5-difluorobenzene-1,2-diol 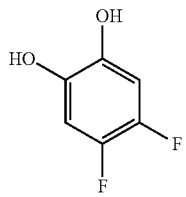 | 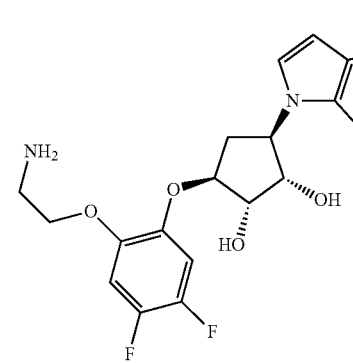 | [M + 1] | $^1$H NMR (400 MHz, MeOD-d$_4$) δ ppm 8.64 (s, 1H), 7.67 (d, J = 3.5 Hz, 1H), 7.26-7.07 (m, 2H), 6.80 (d, J = 4.0 Hz, 1H), 5.19 (q, J = 8.9 Hz, 1H), 4.72-4.64 (m, 2H), 4.33-4.21 (m, 3H), 3.42-3.36 (m, 2H), 2.99-2.87 (m, 1H), 2.75 (s, 3H), 2.33-2.23 (m, 1H) |

Example 153 (Scheme DDD)—(1S,2S,3S,5R)-3-(2-(2-aminoethoxy)-4-chlorophenoxy)-5-(4-methyl-7H-pyrrolo[2,3-d]pyrimidin-7-yl)cyclopentane-1,2-diol (DDD-6)

Scheme DDD

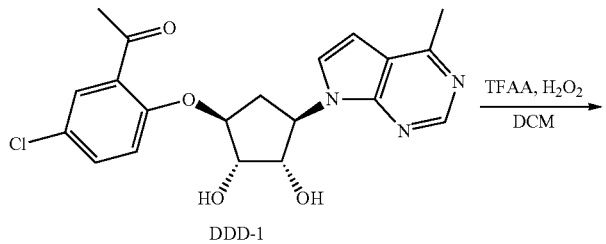

DDD-1

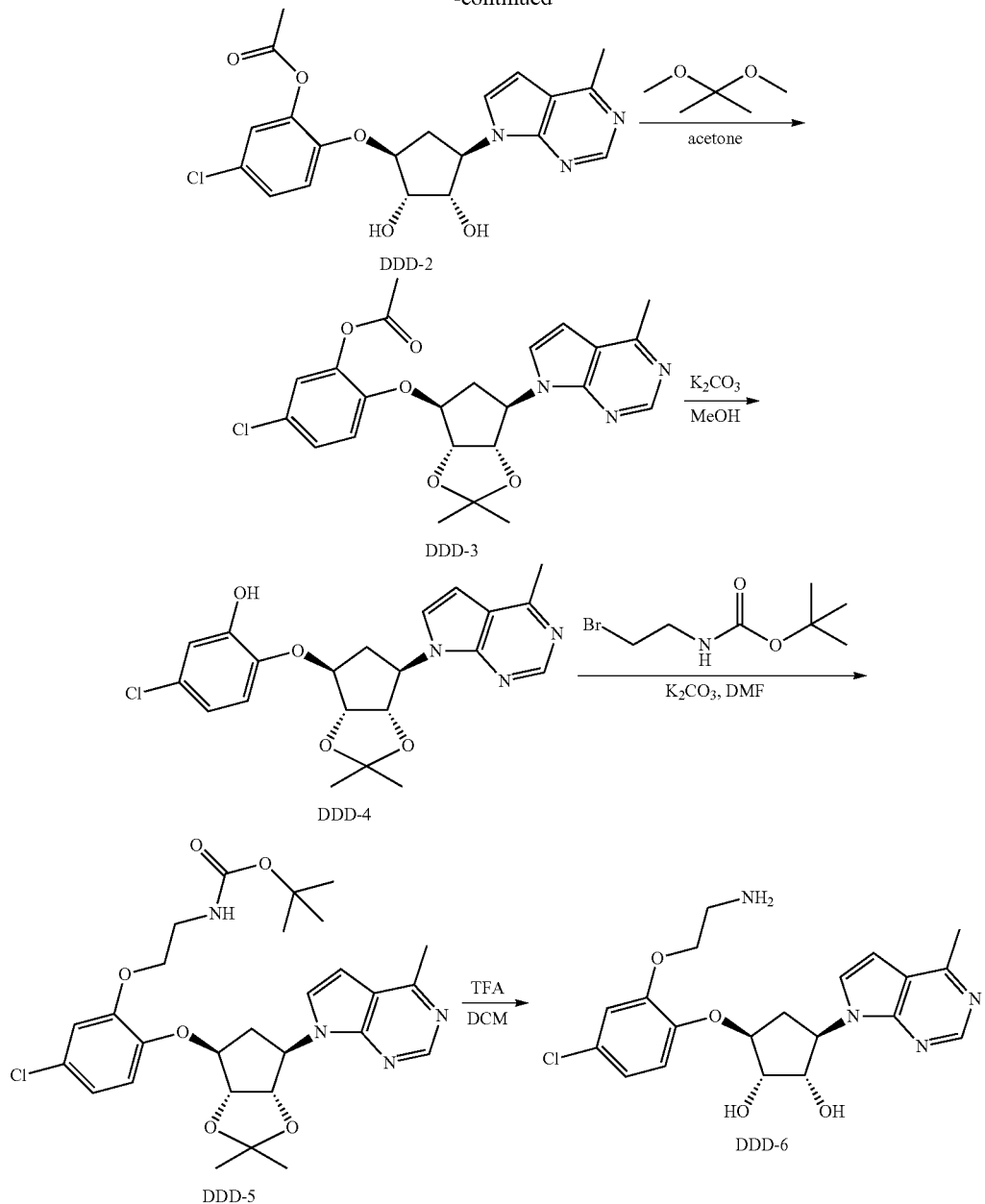

Step 1—Synthesis of 1-(5-chloro-2-(((1S,2S,3S, 4R)-2,3-dihydroxy-4-(4-methyl-7H-pyrrolo[2,3-d] pyrimidin-7-yl)cyclopentyl)oxy)phenyl)ethan-1-one (DDD-1)

Compound DDD-1 was prepared using similar procedures to steps 2 & 3 in scheme BB with commercially available 1-(5-chloro-2-hydroxyphenyl)ethan-1-one and BB-2.

Step 2—Synthesis of 5-chloro-2-(((1S,2S,3S,4R)-2, 3-dihydroxy-4-(4-methyl-7H-pyrrolo[2,3-d]pyrimidin-7-yl)cyclopentyl)oxy)phenyl acetate (DDD-2)

Trifluoroacetic anhydride (1.46 g, 6.95 mmol) cooled to −10° C. was added dropwise and 30% $H_2O_2$ (185 mg, 1.63 mmol) and the solution was stirred for 10 min. To this mixture was added DDD-1 (210 mg, 0.523 mmol) in DCM (3.5 mL) dropwise at 0° C. and stirred at 25° C. for 15 min. Then saturated sodium thiosulfate (2 mL) was added to the reaction solution. The reaction solution was basified by saturated $NaHCO_3$ to pH=7-8, extracted with DCM (30 mL×2). The combined organic layers were washed with brine (40 mL), dried over $Na_2SO_4$, filtered and evaporated to give crude material, which was purified by ISCO (silica gel, 12 g, MeOH/DCM=10%~14%) to give desired product DDD-2 (160 mg, 73%) as a white solid. LCMS [M+1] 418; $^1H$ NMR (400 MHz, $CDCl_3$) δ ppm 8.67 (s, 1H), 7.25 (m, 1H), 7.21 (dd, J=2.5, 8.8 Hz, 1H), 7.12-7.06 (m, 2H), 6.60 (d, J=3.8 Hz, 1H), 4.97 (q, J=8.5 Hz, 1H), 4.78 (t, J=6.0 Hz, 1H), 4.50 (dd, J=5.3, 8.3 Hz, 1H), 4.29 (d, J=5.5 Hz, 1H), 3.12-3.01 (m, 1H), 2.72 (s, 3H), 2.36-2.27 (m, 1H), 2.24 (s, 3H)

Step 2—Synthesis of 5-chloro-2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)phenyl acetate (DDD-3)

To a stirred colorless solution of DDD-2 (160 mg, 0.38 mmol) in acetone (0.64 mL) was added 2,2-dimethoxypropane (6.4 mL) and p-toluenesulfonic acid (73 mg, 0.38 mmol) at 25° C. The reaction was stirred at 25° C. for 1 hour. Then aq.NaHCO3 (3 mL) was added to the reaction mixture until the pH 8.0. Then the mixture was extracted with EtOAc (15 mL×2). The organic layers were separated, washed with brine (20 mL), dried over $Na_2SO_4$ and filtered. The organic layer was evaporated to give the crude product as a colorless gum, which was purified by column chromatography (ether:EtOAc=1:1, Rf~0.55) to give the DDD-3 (126 mg, 72%) as a white solid. LCMS [M+1] 458; $^1$H NMR (400 MHz, $CDCl_3$) δ ppm 8.79 (s, 1H), 7.43 (d, J=3.8 Hz, 1H), 7.25-7.20 (m, 1H), 7.14-7.07 (m, 2H), 6.58 (d, J=3.5 Hz, 1H), 5.46-5.38 (m, 1H), 4.93 (d, J=5.8 Hz, 1H), 4.83-4.74 (m, 2H), 3.06-2.89 (m, 1H), 2.74 (s, 3H), 2.52-2.37 (m, 1H), 2.21 (s, 3H), 1.60 (br. s., 3H), 1.32 (s, 3H)

Step 3—Synthesis of 5-chloro-2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)phenol (DDD-4)

Compound DDD-3 (142 mg, 0.31 mmol) was dissolved in MeOH (3 mL) and $H_2O$ (1 mL). $K_2CO_3$ (85.7 g, 0.62 mmol) was added to the above mixture. The reaction mixture was stirred at 25° C. for 1 hour. The mixture was neutralized with 10% citric acid to pH 6-7. The mixture was diluted with $H_2O$ (10 mL), extracted by EtOAc (10 mL×2). The combined organic layers were washed with brine (10 mL), dried over $Na_2SO_4$, filtered and evaporated to give DDD-4 (140 mg, >99%) as a colorless gum. LCMS [M+1] 416; $^1$H NMR (400 MHz, $CDCl_3$) δ ppm 8.79 (s, 1H), 7.22 (d, J=3.5 Hz, 1H), 6.96-6.90 (m, 2H), 6.87-6.81 (m, 1H), 6.61 (d, J=3.5 Hz, 1H), 5.95-5.74 (m, 1H), 5.27-5.19 (m, 2H), 4.87-4.78 (m, 2H), 2.99-2.87 (m, 1H), 2.74 (s, 3H), 2.61-2.50 (m, 1H), 1.59 (s, 3H), 1.34 (s, 3H)

Step 4—Synthesis of tert-butyl(2-(5-chloro-2-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)phenoxy)ethyl)carbamate (DDD-5)

To a stirred solution of DDD-4 (140 mg, 0.34 mmol) in dry DMF (5 mL) was added $K_2CO_3$ (140 mg, 1.0 mmol) and tert-butyl (2-bromoethyl)carbamate (151 mg, 0.67 mmol) at 25° C. The reaction was stirred at 25° C. for 15 hours. Water (10 mL) was added to the reaction mixture and the mixture was extracted with EtOAc (20 mL×2). The combined organic layers were washed with brine (20 mL×5), dried over $Na_2SO_4$, filtered and concentrated to give crude material which was purified by ISCO (EtOAc/petroleum ether=60%) to give DDD-5 (170 mg, 90%) as a colorless gum. LCMS [M+23] 581; $^1$H NMR (400 MHz, $CDCl_3$) δ ppm 8.80 (s, 1H), 7.77 (d, J=3.8 Hz, 1H), 6.96-6.84 (m, 3H), 6.59 (d, J=3.8 Hz, 1H), 5.50 (d, J=8.0 Hz, 1H), 5.18 (br. s., 1H), 4.92-4.86 (m, 1H), 4.85-4.81 (m, 2H), 4.08-3.98 (m, 2H), 3.65-3.54 (m, 2H), 3.08-2.98 (m, 1H), 2.74 (s, 3H), 2.47 (d, J=14.6 Hz, 1H), 1.59 (s, 3H), 1.42 (s, 9H), 1.31 (s, 3H)

Step 5—Synthesis of (1S,2S,3S,5R)-3-(2-(2-aminoethoxy)-4-chlorophenoxy)-5-(4-methyl-7H-pyrrolo[2,3-d]pyrimidin-7-yl)cyclopentane-1,2-diol (DDD-6)

Compound DDD-5 was subjected to standard TFA/water deprotection methods followed by prep-HPLC to afford DDD-6 (40 mg, 31%). LCMS [M+23] 441; $^1$H NMR (400 MHz, MeOD-$d_4$) δ ppm 8.64 (s, 1H), 7.78 (d, J=3.8 Hz, 1H), 7.14-7.05 (m, 2H), 6.96 (d, J=8.3 Hz, 1H), 6.82 (d, J=3.8 Hz, 1H), 5.41-5.27 (m, 1H), 4.74-4.70 (m, J=5.5 Hz, 1H), 4.67 (dd, J=4.6, 7.9 Hz, 1H), 4.21 (d, J=4.5 Hz, 1H), 4.15-4.07 (m, 2H), 3.18-3.08 (m, 2H), 3.06-2.94 (m, 1H), 2.74 (s, 3H), 2.14 (dd, J=6.8, 14.1 Hz, 1H)

(Scheme EEE)—Synthesis of tert-butyl 5-chloro-8-hydroxy-3,4-dihydroisoquinoline-2(1H)-carboxylate (TP-19)

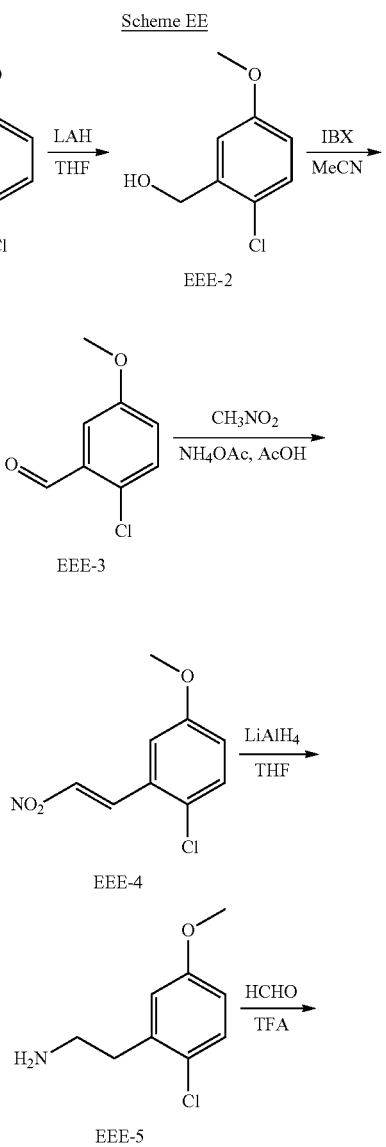

Scheme EE

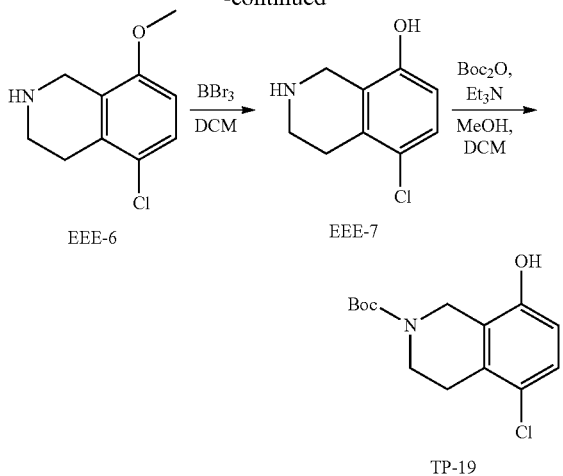

Step 1—Synthesis of (2-chloro-5-methoxyphenyl)methanol (EEE-2)

To a solution of methyl 2-chloro-5-methoxybenzoate EEE-1 (4.55 g, 22.7 mmol) in anhydrous THF (200 mL) was added LiAlH$_4$ (1.72 g, 45.4 mmol) at −10° C.~5° C. portionwise. The temperature was raised to 0° C. After the addition, the reaction was stirred at 0° C. for 2 hours. The reaction mixture was quenched by 5% NaOH. The reaction mixture was filtered through a pad of Celite. To the Celite cake was added THF (100 mL) and EtOAc (100 mL) and stirred sat 25° C. for 0.5 hour. The mixture was filtered and the combined organic layers were dried over Na$_2$SO$_4$ and concentrated to afford the crude EEE-2 (4.5 g) as a colorless oil and used directly in the next step. $^1$H NMR (400 MHz, CDCl$_3$) δ ppm 7.25 (d, J=9.5 Hz, 1H), 7.05 (d, J=2.8 Hz, 1H), 6.78 (dd, J=2.9, 8.7 Hz, 1H), 4.75 (d, J=3.8 Hz, 2H), 3.81 (s, 3H), 2.04-1.94 (m, 1H)

Step 2—Synthesis of 2-chloro-5-methoxybenzaldehyde (EEE-3)

To a solution of EEE-2 (3.63 g, 16.16 mmol) in CH$_3$CN (120 mL) was added IBX (17.7 g, 63.1 mmol) at 25° C. The resulting mixture was heated at 80° C. for 2 hours. The reaction mixture was cooled to 25° C., filtered, and washed with DCM (50 mL). The combined filtrate was concentrated to afford crude material which was purified by ISCO (silica gel, 80 g, EtOAc/petroleum ether=17%) to EEE-3 (1.76 g, 49%) as a white solid. $^1$H NMR (400 MHz, CDCl$_3$) δ ppm 10.45 (s, 1H), 7.42 (d, J=3.0 Hz, 1H), 7.36 (d, J=8.8 Hz, 1H), 7.11 (dd, J=3.3, 8.8 Hz, 1H), 3.86 (s, 3H)

Step 3—Synthesis of (E)-1-chloro-4-methoxy-2-(2-nitrovinyl)benzene (EEE-4)

To a solution of EEE-3 (1.76 g, 10.3 mmol) in AcOH (17.0 mL) was added NH$_4$OAc (0.795 g, 10.3 mmol) followed by MeNO$_2$ (3.15 g, 51.6 mmol). After the addition, the reaction mixture was heated at 85° C. for 10 hours, and then cooled to 28° C. The reaction was diluted in DCM and concentrated to remove AcOH to afford the crude product which was purified via flash column (12 g gel, EtOAc:Petroleum ether=1%~10%) to afford EEE-4 (1.78 g, 81%) as a yellow solid. $^1$H NMR (400 MHz, CDCl$_3$) δ ppm 8.36 (d, J=13.8 Hz, 1H), 7.58 (d, J=13.8 Hz, 1H), 7.39 (d, J=9.0 Hz, 1H), 7.05 (d, J=3.0 Hz, 1H), 6.99 (dd, J=3.0, 9.0 Hz, 1H), 3.85 (s, 3H)

Step 4—Synthesis of 2-(2-chloro-5-methoxyphenyl)ethan-1-amine (EEE-5)

To a solution of EEE-4 (862 mg, 4.04 mmol) in anhydrous THF (40 mL) was added LiAlH$_4$ (613 mg, 16.1 mmol) at −20° C. under N$_2$. After the addition, the reaction mixture was stirred at 25° C. for 1 hour. The reaction mixture was then heated at 50° C. and stirred for 2 hours. The reaction mixture was quenched with drops of water. The reaction mixture was diluted with EtOAx, filtered, and concentrated to afford the crude product which was purified via flash column chromatography (40 g gel, MeOH:DCM=1%~8.0%) to afford EEE-5 (290 mg, 38.7%) as a yellow oil. $^1$H NMR (400 MHz, CDCl$_3$) δ ppm 7.27-7.24 (m, 1H), 6.79 (d, J=2.8 Hz, 1H), 6.72 (dd, J=3.0, 8.8 Hz, 1H), 3.79 (s, 3H), 3.02-2.95 (m, 2H), 2.90-2.80 (m, 2H)

Step 5—Synthesis of 5-chloro-8-methoxy-1,2,3,4-tetrahydroisoquinoline (EEE-6)

To a solution of EEE-5 (195.0 mg, 0.679 mmol) in DCM (7.00 mL) was added TFA (0.70 mL), followed by aqueous HCHO (37%, 110 mg, 1.36 mmol). After the addition, the reaction mixture was stirred at 25° C. for 3 hours. The reaction mixture was diluted in H$_2$O and neutralized by sat. Na$_2$CO$_3$. The mixture was partitioned with EtOAc and H$_2$O. The organic layer was dried over Na$_2$SO$_4$ and concentrated to afford the crude product which was purified by prep-TLC (EtOAc:petroleum ether=1:1) to afford the intermediate (170 mg) which was suspended in aq. HCl (24%, 2 mL) and heated at 110° C. for 3 hours. The reaction mixture was neutralized with sat. Na$_2$CO$_3$ then partitioned between EtOAc and H$_2$O. The organic layer were evaporated to afford the crude product which was purified by prep-TLC thin layer chromatography (EtOAc:petroleum ether=1:0) to afford the product EEE-6 (50.0 mg, 37%) as a yellow gum. $^1$H NMR (400 MHz, DMSO-d$_6$) δ ppm 7.22 (d, J=8.8 Hz, 1H), 6.81 (d, J=8.8 Hz, 1H), 3.76 (s, 3H), 3.70 (s, 2H), 2.91 (t, J=6.0 Hz, 2H), 2.57 (t, J=5.8 Hz, 2H)

Step 6—Synthesis of 5-chloro-1,2,3,4-tetrahydroisoquinolin-8-ol (EEE-7)

To a solution of EEE-6 (50.0 mg, 0.253 mmol) in DCM (4.00 mL) was added BBr$_3$ (0.40 mL, 4.20 mmol) at 0° C. After the addition, the reaction mixture was stirred at 25° C. for 1 hour. The reaction mixture was quenched with MeOH and basified by sat. K$_2$CO$_3$ to pH 11-12. The mixture was extracted with EtOAc. The organic layer was dried over Na$_2$SO$_4$ and concentrated to afford the crude product which was purified by prep-TLC (MeOH:DCM=1:10) to afford EEE-7 (50 mg, >99%) as a yellow gum and used directly in the next step. $^1$H NMR (400 MHz, CDCl$_3$) δ ppm 7.05 (d, J=8.5 Hz, 1H), 6.51 (d, J=9.3 Hz, 1H), 4.00 (s, 2H), 3.16 (t, J=6.0 Hz, 2H), 2.79 (t, J=6.1 Hz, 2H)

Step 7—Synthesis of tert-butyl 5-chloro-8-hydroxy-3,4-dihydroisoquinoline-2(1H)-carboxylate (TP-19)

To a solution of EEE-7 (50 mg, 0.272 mmol) in DCM (5.00 mL) and MeOH (1.00 mL) was added Boc$_2$O (65 mg, 0.300 mmol) followed by Et$_3$N (68.9 mg, 0.681 mmol). After the addition, the reaction mixture was stirred at 25° C. for 2.5 hours. The reaction mixture was neutralized by aq. HCl (0.1 M) to pH 4-5 at 0° C. The resulting mixture was partitioned between DCM and H$_2$O. The organic layer was separated, washed with brine, dried over Na$_2$SO$_4$ and concentrated to afford the crude product which was purified by prep-TLC (MeOH:DCM=1:10) to afford TP-19 (50 mg, 65%) as a white solid.

Examples 154 & 155 were Made in a Similar Fashion to Example 78 in Scheme CC Using the Appropriate NBoc-Protected Tetrahydroisoquinoline in Step 1

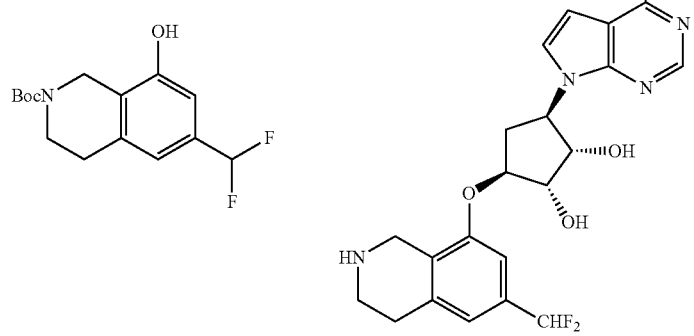

Example 154
TP-14

431 [M + 1]
(1S,2S,3S,5R)-3-((6-(difluoromethyl)-1,2,3,4-tetrahydroisoquinolin-8-yl)oxy)-5-(4-methyl-7H-pyrrolo[2,3-d]pyrimidin-7-yl)cyclopentane-1,2-diol
$^1$H NMR (400MHz, D$_2$O) δ ppm 8.85 (s, 1H), 7.81 (d, J = 3.8 Hz, 1H), 7.14-7.05 (m, 3H), 6.89-6.59 (m, 1H), 5.35 (q, J = 9.0 Hz, 1H), 4.86-4.82 (m, 1H), 4.70-4.67 (m, 1H), 4.37 (s, 2H), 4.32 (d, J = 4.8 Hz, 1H), 3.49 (t, J = 6.1 Hz, 2H), 3.15-3.02 (m, 3H), 2.90 (s, 3H), 2.26-2.15 (m, 1H)

Example 155
TP-8

413 [M + 1]
(1S,2S,3S,5R)-3-((5-fluoro-6-methyl-1,2,3,4-tetrahydroisoquinolin-8-yl)oxy)-5-(4-methyl-7H-pyrrolo[2,3-d]pyrimidin-7-yl)cyclopentane-1,2-diol
$^1$H NMR (400 MHz, MeOD-d$_4$) δ ppm 8.62 (s, 1H), 7.54 (d, J = 3.8 Hz, 1H), 6.86 (d, J = 5.8 Hz, 1H), 6.74 (d, J = 3.8 Hz, 1H), 5.18 (d, J = 8.8 Hz, 1H), 4.73 (dd, J = 5.0, 8.8 Hz, 1H), 4.66 (br s, 1H), 4.24 (s, 2H), 4.17 (d, J = 4.5 Hz, 1H), 3.39 (t, J = 6.3 Hz, 2H), 3.00-2.93 (m, 3H), 2.72 (s, 3H), 2.26 (d, J = 1.8 Hz, 3H), 2.21 (ddd, J = 4.1, 9.3, 13.9 Hz, 1H)

Example 156 (Scheme FFF)—(1S,2S,3R,5S)-3-(4-methyl-7H-pyrrolo[2,3-d]pyrimidin-7-yl)-5-((5,6,7,8-tetrahydropyrido[4,3-d]pyrimidin-4-yl)oxy)cyclopentane-1,2-diol (FFF-4)

Scheme FFF

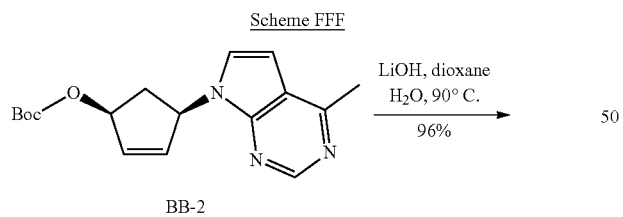

BB-2

LiOH, dioxane
H$_2$O, 90° C.
96%

-continued

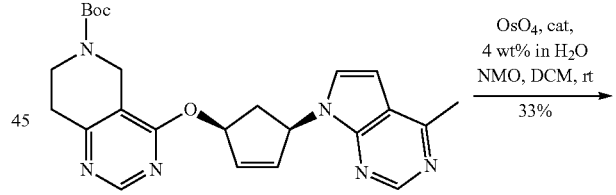

FFF-2

OsO$_4$, cat,
4 wt% in H$_2$O
NMO, DCM, rt
33%

FFF-1

TP-20

NaH, THF
rt, 1h
72%

FFF-3

TFA

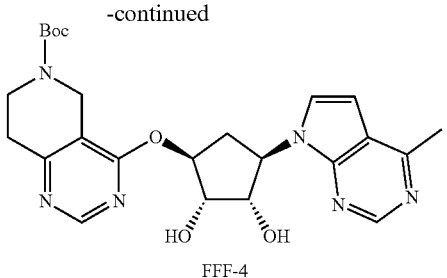

FFF-4

Step 1: Synthesis of (1S,4R)-4-(4-methyl-7H-pyrrolo[2,3-d]pyrimidin-7-yl)cyclopent-2-en-1-ol (FFF-1)

To a solution of BB-2 (650 mg, 2.06 mmol) in dioxane (0.3 mL) and H$_2$O (0.3 mL) was added lithium hydroxide (494 mg, 20.6 mmol). The reaction was heated at 90° C. overnight. The reaction mixture was cooled to r.t., diluted with H$_2$O, extracted with 20% isopropyl alcohol/DCM, the organic layers were combined and purified by ISCO 4 g with 100% EtOAc to 10% MeOH/EtOAc to give 424 mg of FFF-1 (96% yield) as a colorless oil which solidified on standing.

LCMS [M+1] 216.15. $^1$H NMR (400 MHz, CHLOROFORM-d) δ ppm 2.22 (dt, J=15.16, 2.14 Hz, 1H) 2.73 (s, 3H) 3.00 (ddd, J=15.25, 9.20, 7.70 Hz, 1H) 4.89 (br. s., 1H) 5.37 (dq, J=9.23, 2.22 Hz, 1H) 5.58 (br. s., 1H) 5.85 (dd, J=5.50, 2.45 Hz, 1H) 6.25-6.33 (m, 1H) 6.54 (d, J=3.55 Hz, 1H) 7.23 (d, J=3.55 Hz, 1H) 8.69 (s, 1H)

Step 2: Synthesis of tert-butyl 4-(((1S,4R)-4-(4-methyl-7H-pyrrolo[2,3-d]pyrimidin-7-yl)cyclopent-2-en-1-yl)oxy)-7,8-dihydropyrido[4,3-d]pyrimidine-6(5H)-carboxylate (FFF-2)

To a solution of FFF-1 (100 mg, 0.465 mmol) in THF (3 mL, c=0.2 M) was added sodium hydride (27.9 mg, 0.697 mmol) in small batches. After stirring at r.t. for 10 min, tert-butyl 4-chloro-7,8-dihydropyrido[4,3-d]pyrimidine-6(5H)-carboxylate (TP-20) (125 mg, 0.465 mmol) was added. The resulting reaction mixture was stirred at r.t. for 3.5 hrs, and then quenched with H$_2$O, partitioned between EtOAc (20 mL) and H$_2$O (20 mL). The organic phase was separated, washed with brine, dried over Na$_2$SO$_4$, concentrated, purified by column chromatography with 5-10% MeOH/EtOAc to afford 150 mg of FFF-2 (72% yield) as a light yellow foam solid.

LCMS [M+1] 449.15. $^1$H NMR (400 MHz, CHLOROFORM-d) δ ppm 1.44 (s, 9H) 1.87 (d, J=15.04 Hz, 1H) 2.66 (s, 3H) 2.80 (t, J=4.77 Hz, 2H) 3.15 (dt, J=15.31, 7.81 Hz, 1H) 3.57-3.65 (m, 1H) 3.65-3.75 (m, 1H) 4.33 (d, J=17.61 Hz, 1H) 4.44 (d, J=17.12 Hz, 1H) 5.98 (dt, J=4.31, 1.94 Hz, 1H) 6.01-6.07 (m, 1H) 6.07-6.14 (m, 1H) 6.33 (br. s., 1H) 6.52 (d, J=3.18 Hz, 1H) 7.20 (d, J=3.67 Hz, 1H) 8.51 (s, 1H) 8.70 (s, 1H).

Step 3: Synthesis of tert-butyl 4-(((1S,2S,3S,4R)-2,3-dihydroxy-4-(4-methyl-7H-pyrrolo[2,3-d]pyrimidin-7-yl)cyclopentyl)oxy)-7,8-dihydropyrido[4,3-d]pyrimidine-6(5H)-carboxylate (FFF-3)

Compound FFF-2 was treated in similar procedure as step 3 in Scheme BB to give FFF-3 (50 mg, 33%).

LCMS [M+1] 483.20. $^1$H NMR (400 MHz, CHLOROFORM-d) δ ppm 1.49 (s, 9H) 2.36-2.50 (m, 1H) 2.76 (s, 3H) 2.91 (t, J=5.81 Hz, 2H) 3.06-3.22 (m, 1H) 3.62-3.84 (m, 2H) 4.13 (s, 1H) 4.36-4.50 (m, 2H) 4.53 (d, J=6.24 Hz, 1H) 4.93-5.05 (m, 1H) 5.45 (td, J=7.12, 3.12 Hz, 1H) 5.64 (br. s., 1H) 6.61 (d, J=3.67 Hz, 1H) 7.23 (d, J=3.67 Hz, 1H) 8.64 (s, 1H) 8.76 (s, 1H)

Step 4: Synthesis of (1S,2S,3R,5S)-3-(4-methyl-7H-pyrrolo[2,3-d]pyrimidin-7-yl)-5-((5,6,7,8-tetrahydropyrido[4,3-d]pyrimidin-4-yl)oxy)cyclopentane-1,2-diol (FFF-4)

Compound FFF-3 was treated to standard deprotection condition similar to step 3 in Scheme CC to yield FFF-4 (24 mg, 100%).

LCMS [M+1] 383.10. $^1$H NMR (400 MHz, DMSO-d6) δ ppm 2.00-2.11 (m, 1H) 2.92 (s, 3H) 2.94-3.02 (m, 1H) 3.06 (br. s., 2H) 3.48 (br. s., 2H) 4.11 (d, J=3.42 Hz, 1H) 4.25 (br. s., 2H) 4.66 (dd, J=8.86, 4.58 Hz, 1H) 5.22 (q, J=8.93 Hz, 1H) 5.28-5.37 (m, 1H) 7.20 (br. s., 1H) 8.09 (br. s., 1H) 8.69 (s, 1H) 9.18 (br. s., 1H) 9.71 (br. s., 1H) 9.87 (br. s., 1H)

Example 157 (Scheme GGG)—(1S,2S,3R,5S)-3-(4-methyl-7H-pyrrolo[2,3-d]pyrimidin-7-yl)-5-((5,6,7,8-tetrahydro-2,7-naphthyridin-1-yl)oxy)cyclopentane-1,2-diol (GGG-5)

Scheme GGG

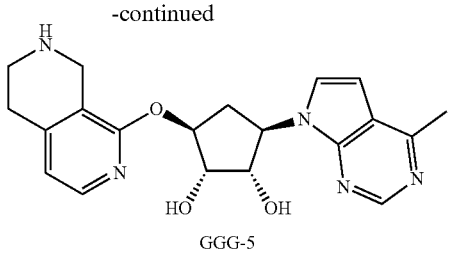

GGG-5

Step 1: Synthesis of tert-butyl 8-chloro-3,4-dihydro-2,7-naphthyridine-2(1H)-carboxylate (GGG-2)

To a solution of tert-butyl 8-hydroxy-3,4-dihydro-2,7-naphthyridine-2(1H)-carboxylate (GGG-1) (250 mg, 0.999 mmol) in CH$_3$CN (2.5 mL) was added POCl$_3$ (2.5 mL) slowly, and heated at 90° C. overnight. The reaction mixture was neutralized by std. NaHCO$_3$, the solvent was removed by rotavapor. The residue was added MeOH 10 mL, the slurry was added (BOC)$_2$ (337 mg, 1.50 mmol, 0.355 mL) and DIPEA (258 mg, 2.00 mmol, 0.331 mL), stirred at r.t. for 30 min. The organic solvent was rotavapored, EtOAc and H$_2$O were added, extracted with EtOAc, the organic layer was concentrated, purified by column chromatography with 30% EtOAc/heptane to give 240 mg of GGG-2 (89% yield) as a colorless oil.

LCMS [M+1] 269.10. $^1$H NMR (400 MHz, CHLOROFORM-d) δ ppm 1.51 (s, 9H) 2.84 (t, J=5.69 Hz, 2H) 3.66 (t, J=5.81 Hz, 2H) 4.56 (s, 2H) 7.03 (d, J=5.01 Hz, 1H) 8.17 (d, J=5.01 Hz, 1H)

Step 2: Synthesis of tert-butyl 8-(((1S,4R)-4-(4-methyl-7H-pyrrolo[2,3-d]pyrimidin-7-yl)cyclopent-2-en-1-yl)oxy)-3,4-dihydro-2,7-naphthyridine-2(1H)-carboxylate (GGG-3)

To a solution of FFF-1 (92 mg, 0.43 mmol) and GGG-2 (115 mg, 0.427 mmol) in DMSO (4.27 mL, c=0.1 M) was treated with potassium butoxide (61.8 mg, 0.534 mmol, 0.534 mL, 1.0 M). The reaction was heated to 120° C. for 15 min. The reaction was cooled to r.t., diluted with H$_2$O and EtOAc (10 mL each). The aqueous phase was extracted with EtOAc (10 mL). The combined organics were washed with H$_2$O (2×15 mL), brine (15 mL), and dried over Na$_2$SO$_4$. The sample was concentrated and purified by preparative HPLC to give 40 mg of GGG-3 as a brown solid (21% yield).

LCMS [M+1] 448.20. $^1$H NMR (400 MHz, CHLOROFORM-d) δ ppm 1.45-1.56 (m, 9H) 1.94 (d, J=14.92 Hz, 1H) 2.63 (s, 3H) 2.68-2.81 (m, 2H) 3.20 (dt, J=15.13, 7.78 Hz, 1H) 3.55-3.69 (m, 2H) 4.33-4.45 (m, 1H) 4.49 (br. s., 1H) 6.06 (br. s., 2H) 6.11 (d, J=4.03 Hz, 1H) 6.45 (br. s., 1H) 6.62 (br. s., 1H) 6.68 (d, J=5.01 Hz, 1H) 7.39 (br. s., 1H) 7.92 (d, J=5.14 Hz, 1H) 8.84 (br. s., 1H)

Step 3: Synthesis of tert-butyl 8-(((1S,2S,3S,4R)-2,3-dihydroxy-4-(4-methyl-7H-pyrrolo[2,3-d]pyrimidin-7-yl)cyclopentyl)oxy)-3,4-dihydro-2,7-naphthyridine-2(1H)-carboxylate (GGG-4)

Compound GGG-3 was treated in similar procedure as step 3 in Scheme BB to give GGG-4 (7.3 mg, 17%).
LCMS [M+1] 481.90. $^1$H NMR (400 MHz, CHLOROFORM-d) δ ppm 1.49 (s, 10H) 2.43-2.54 (m, 1H) 2.75 (s, 3H) 2.81 (t, J=5.75 Hz, 2H) 3.03 (br. s., 1H) 3.63-3.71 (m, 2H) 4.38 (br. s., 1H) 4.47 (br. s., 3H) 4.66 (br. s., 1H) 5.03-5.12 (m, 1H) 5.25-5.32 (m, 1H) 5.48 (s, 1H) 6.60 (d, J=3.55 Hz, 1H) 6.77 (d, J=5.26 Hz, 1H) 7.29 (d, J=3.79 Hz, 1H) 7.93 (d, J=5.14 Hz, 1H) 8.77 (s, 1H)

Step 4: Synthesis of (1S,2S,3R,5S)-3-(4-methyl-7H-pyrrolo[2,3-d]pyrimidin-7-yl)-5-((5,6,7,8-tetrahydro-2,7-naphthyridin-1-yl)oxy)cyclopentane-1,2-diol (GGG-5)

Compound GGG-4 was treated to standard deprotection condition similar to step 3 in Scheme CC to yield GGG-5 (6 mg, 90%).
LCMS [M+1] 382.20 $^1$H NMR (400 MHz, DMSO-d6) δ ppm 1.93-2.02 (m, 1H) 2.86-2.92 (m, 3H) 2.92-2.98 (m, 1H) 3.01 (t, J=5.99 Hz, 2H) 3.57 (s, 2H) 4.08 (d, J=4.03 Hz, 1H) 4.20 (br. s., 2H) 4.66 (dd, J=8.93, 4.52 Hz, 1H) 5.15-5.23 (m, 1H) 5.23-5.29 (m, 1H) 6.91 (d, J=5.26 Hz, 1H) 7.16 (d, J=3.30 Hz, 1H) 7.99-8.06 (m, 2H) 9.13 (s, 1H) 9.52 (br. s., 1H) 9.64 (br. s., 1H)

Example 158 (Scheme HHH)—(1S,2R,3R,5S)-3-((2-methylpyrimidin-4-yl)oxy)-5-((1,2,3,4-tetrahydroisoquinolin-8-yl)oxy)cyclopentane-1,2-diol (HHH-6)

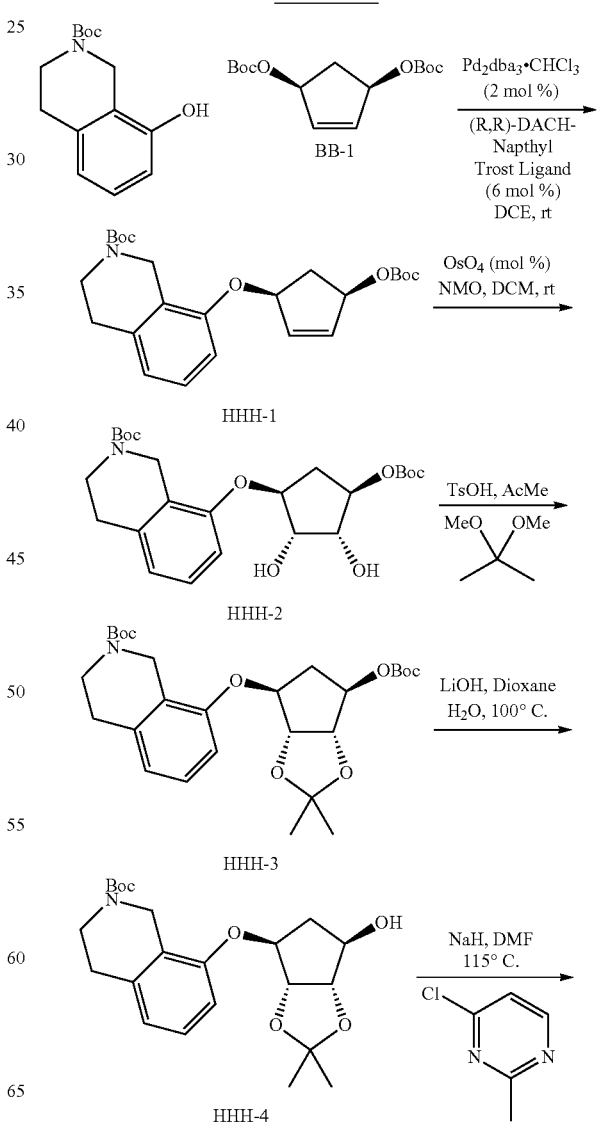

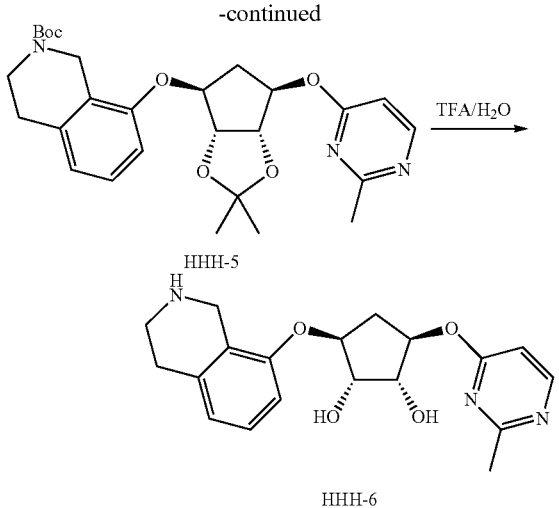

HHH-5

HHH-6

Step 1: Synthesis of tert-butyl 8-(((1S,4R)-4-((tert-butoxycarbonyl)oxy)cyclopent-2-en-1-yl)oxy)-3,4-dihydroisoquinoline-2(1H)-carboxylate (HHH-1)

Vial A: To an oven dried reaction vial, equipped with a magnetic stirbar and cooled under a stream of argon, was added Tris(benzylideneacetone)dipalladium(0)chloroform adduct (44.7 mg, 0.043 mmol) and MFCD02684551 (R,R)-DACH-Naphthyl Trost Ligand (102 mg, 0.129 mmol). The vial was vacuum purged with argon under dynamic vacuum and DCE (3.6 mL), which had been sparged with argon for 30 minutes, was added. The solution was stirred for 30 minutes at rt at which point a bright orange solution of ligated catalyst was obtained. At this stage Vial B was prepared.

Vial B: To an oven dried reaction vial, equipped with a magnetic stirbar and cooled under a stream of argon, was added tert-butyl 8-hydroxy-3,4-dihydroisoquinoline-2(1H)-carboxylate (538 mg, 2.16 mmol), and di-tert-butyl-((1R,3S)-cyclopent-4-ene-1,3-diyl)-bis(carbonate) (BB-1) (prepared as reported in J. Am. Chem. Soc. 2006, 128, 6054-6055) (778 mg, 2.59 mmol). The vial was vacuum purged with argon under dynamic vacuum and DCE (3.6 mL), which had been sparged with argon for 30 minutes, was added followed by the addition of the contents of Vial A via airtight syringe. The reaction was stirred under argon at rt for 14 hours. The reaction was concentrated under vacuum and purified via flash column chromatography (24 g SiO2, Isco, 100% Hept. to 100% EtOAc, 20 mL fractions) to afford HHH-1 (973 mg, >95%) as a yellow foam. LCMS [M+H-Boc-isobutylene]=276 observed; 1H NMR (400 MHz, CHLOROFORM-d) δ ppm 7.12 (t, J=7.9 Hz, 1H), 6.75 (d, J=7.7 Hz, 1H), 6.72 (d, J=8.2 Hz, 1H), 6.22 (td, J=1.4, 5.7 Hz, 1H), 6.18-6.09 (m, 1H), 5.47 (t, J=5.8 Hz, 1H), 5.15 (t, J=5.7 Hz, 1H), 4.59-4.40 (m, J=8.2 Hz, 2H), 3.74-3.54 (m, 2H), 3.05 (td, J=7.4, 14.5 Hz, 1H), 2.81 (t, J=5.7 Hz, 2H), 1.96 (td, J=4.5, 14.5 Hz, 1H), 1.52-1.47 (m, 18H).

Step 2: Synthesis of tert-butyl 8-(((1S,2S,3R,4R)-4-((tert-butoxycarbonyl)oxy)-2,3-dihydroxycyclopentyl)oxy)-3,4-dihydroisoquinoline-2(1H)-carboxylate (HHH-2)

To a scintillation vial, equipped with a magnetic stirbar and containing HHH-1 (225 mg, 0.521 mmol), was added DCM (2.6 mL). To the solution was added 4-Methylmorpholine-N-oxide (NMO) (0.32 mL, 1.50 mmol) as a 50 wt % solution in water followed by the dropwise addition of osmium tetraoxide (130 μL, 0.02 mmol) as a 4 wt % solution in water. The reaction was stirred at rt for 23 hours. The reaction was transferred to a separatory funnel with DCM, diluted with water and further diluted with 1M NaHSO3. The phases were separated and the aqueous phase was extracted with 3 portions of DCM. The combined organic extracts were dried (MgSO4), filtered, and concentrated under vacuum. The crude residue was purified via flash column chromatography (12 g SiO2, Isco, 100% Hept. to 100% EtOAc, 9 mL fractions) to afford HHH-2 (211 mg, 87%) as a white solid. LCMS [M+H-Boc-isobutylene]=310 observed; 1H NMR (400 MHz, CHLOROFORM-d) δ ppm 7.12 (t, J=7.9 Hz, 1H), 6.76 (d, J=7.7 Hz, 1H), 6.71 (d, J=8.2 Hz, 1H), 4.90 (td, J=5.8, 9.0 Hz, 1H), 4.69-4.59 (m, 1H), 4.45 (s, 2H), 4.34 (s, 1H), 4.26 (br. s., 1H), 3.63 (d, J=5.7 Hz, 2H), 2.81 (t, J=5.7 Hz, 3H), 2.03-1.91 (m, J=5.7, 9.3 Hz, 1H), 1.53-1.48 (m, 18H).

Step 3: Synthesis of tert-butyl 8-(((3aR,4S,6R,6aS)-6-((tert-butoxycarbonyl)oxy)-2,2-dimethyltetrahydro-4H-cyclopenta[d][1,3]dioxol-4-yl)oxy)-3,4-dihydroisoquinoline-2(1H)-carboxylate (HHH-3)

To a reaction vial, equipped with a magnetic stirbar and containing HHH-2 (211 mg, 0.453 mmol), was added acetone (0.29 mL), 4-toluenesulfonic acid monohydrate (172 mg, 0.906 mmol) and 2,2-dimethoxypropane (0.56 mL, 4.53 mmol). The reaction was stirred at rt for 1 hour. The reaction was transferred to a separatory funnel with EtOAc and water. The biphasic mixture was diluted with sat. NaHCO3 and the phases were separated. The organic phase was washed with 1 portion half sat. NaHCO3 and the combined aqueous washed were back extracted with 1 portion EtOAc. The combined organic phases were dried (MgSO4), filtered, and concentrated under vacuum. The crude residue was purified via flash column chromatography (12 g SiO2, Isco, 100% Hept to 100% EtOAc, 9 mL fractions) to afford HHH-3 (140.5 mg, 61%) as a white solid. LCMS [M+H-Boc-isobutylene]=350 observed; 1H NMR (400 MHz, CHLOROFORM-d) δ ppm 7.12 (s, 1H), 6.73 (t, J=8.1 Hz, 2H), 4.94 (d, J=4.6 Hz, 1H), 4.80-4.66 (m, 3H), 4.61-4.43 (m, 2H), 3.63 (s, 2H), 2.80 (t, J=5.6 Hz, 2H), 2.47 (td, J=5.4, 15.4 Hz, 1H), 2.25 (td, J=1.5, 15.4 Hz, 1H), 1.49 (s, 12H), 1.45 (s, 9H), 1.31 (s, 3H).

Step 4: Synthesis of tert-butyl 8-(((3aR,4S,6R,6aS)-6-hydroxy-2,2-dimethyltetrahydro-4H-cyclopenta[d][1,3]dioxol-4-yl)oxy)-3,4-dihydroisoquinoline-2(1H)-carboxylate (HHH-4)

To a microwave vial, equipped with a magnetic stirbar and containing HHH-3 (134.5 mg, 0.266 mmol) was added dioxane (1.3 mL) and water (1.3 mL). To the solution was added lithium hydroxide (63.7 mg, 2.66 mmol) and the vial was sealed with a Teflon cap. The vial was placed in a heating block and stirred at 100° C. for 19 hours. The vial was removed from the heating block and allowed to cool to rt. The solution was transferred to a separatory funnel with EtOAc and diluted with water. The phases were separated and the aqueous phase was extracted with 3 portions of EtOAc. The combined organic extracts were dried (MgSO4), filtered, and concentrated under vacuum. The crude residue was purified via flash column chromatography (4 g SiO2, Isco, 100% Hept. to 100% EtOAc, 9 mL fractions) to afford HHH-4 (97.3 mg, 90%) as a white foam. LCMS [M+H-Boc]=306 observed; 1H NMR (400 MHz, CHLOROFORM-d) δ ppm 7.17 (t, J=7.9 Hz, 1H), 6.84 (d, J=8.3 Hz, 1H), 6.81 (d, J=7.7 Hz, 1H), 4.75 (dd, J=5.4, 7.8 Hz, 2H), 4.67 (dd, J=1.3, 5.6 Hz, 1H), 4.55-4.33 (m, 2H), 4.27 (d, J=4.6 Hz, 1H), 3.78-3.49 (m, 2H), 2.82 (t, J=5.7 Hz, 2H), 2.42 (td, J=5.0, 15.0 Hz, 1H), 2.10 (d, J=15.0 Hz, 1H), 1.49 (s, 9H), 1.46 (s, 3H), 1.31 (s, 3H).

Step 5: Synthesis of tert-butyl 8-(((3aR,4S,6R,6aS)-2,2-dimethyl-6-((2-methylpyrimidin-4-yl)oxy)tetrahydro-4H-cyclopenta[d][1,3]dioxol-4-yl)oxy)-3,4-dihydroisoquinoline-2(1H)-carboxylate (HHH-5)

To an oven dried reaction vial, equipped with a magnetic stirbar and containing HHH-4 (43 mg, 0.110 mmol), was added DMF (0.53 mL) and sodium hydride (8.5 mg, 0.210 mmol) as a 60 wt % dispersion in mineral oil. The solution was stirred at rt for 1 hour to produce a dark brown solution of the sodium alkoxide. To the solution was added 4-chloro-2-methylpyrimidine (16.4 mg, 0.127 mmol) and the vial was placed in a heating block and heated at 115° C. for 16 hours. The reaction was quenched carefully by the dropwise addition of water. The solution was further diluted with water and transferred to a separatory funnel with EtOAc. The phases were separated and the aqueous phase was extracted with 4 portions of a 3:1 mixture of DCM/IPA. The combined organic extracts were washed with 1 portion brine, dried (MgSO4), filtered, and concentrated under vacuum. The crude HHH-5 was used in the next step without further purification. LCMS [M+H-Boc]=398 observed Step 6: Synthesis of (1S,2R,3R,5S)-3-((2-methylpyrimidin-4-yl)oxy)-5-((1,2,3,4-tetrahydroisoquinolin-8-yl)oxy)cyclopentane-1,2-diol (HHH-6)

To a round bottom flask, equipped with a magnetic stirbar and containing HHH-5 (53 mg, 0.11 mmol, crude from step 5) was added water (1.0 mL) and TFA (0.5 mL). The solution was stirred at rt for 1 hour. The reaction was transferred to a separatory funnel with DCM and adjusted to basic pH with sat. NaHCO3 aq. The phases were separated and the aqueous phase was extracted with 4 portions of a 3:1 mixture of DCM/IPA. The combined organic extracts were washed with 1 portions sat. NaHCO3 aq., dried (MgSO4), filtered, and concentrated under vacuum. The crude residue was purified by prep-HPLC (Lux Cellulose-1 4.6×100 mm 3μ column, 20% MeOH/DEA @ 120 bar, 4 mL/min) to afford HHH-6 (7.06 mg, 19% over 2 steps) as a white solid. LCMS [M+H]=358 observed; $[\alpha]^{22}D$=+3.7° (c=0.1, MeOH); 1H NMR (400 MHz, METHANOL-d4) δ ppm 8.05 (d, J=6.4 Hz, 1H), 7.15 (t, J=7.9 Hz, 1H), 6.84 (d, J=8.1 Hz, 1H), 6.79 (d, J=7.6 Hz, 1H), 6.67 (d, J=6.5 Hz, 1H), 4.68 (br. s, 2H), 4.61 (td, J=4.2, 8.1 Hz, 1H), 4.26 (t, J=4.3 Hz, 1H), 4.12 (td, J=4.9, 7.4 Hz, 1H), 4.02-3.90 (m, 3H), 2.90 (t, J=5.7 Hz, 2H), 2.74 (td, J=7.7, 15.0 Hz, 1H), 2.47 (s, 3H), 1.62 (td, J=4.7, 14.6 Hz, 1H).

Synthesis of 2-(benzyloxy)-5-fluoro-4-methylbenzoic acid (III-4)

Scheme III

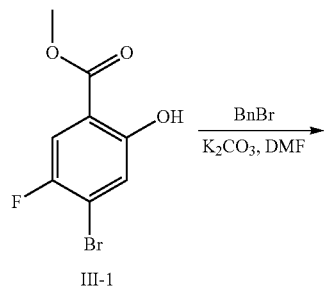

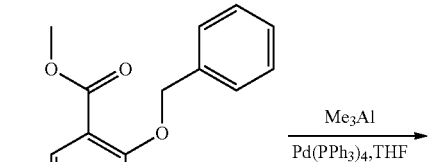

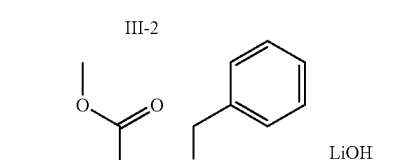

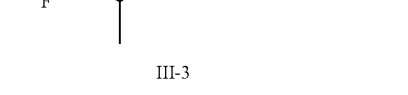

Step 1—Synthesis of methyl 2-(benzyloxy)-4-bromo-5-fluorobenzoate (III-2)

To a solution of methyl 4-bromo-5-fluoro-2-hydroxybenzoate III-1 (1.62 g, 6.505 mmol) in DMF (20 mL) was added K2CO3 (2.7 g, 19.5 mmol) and BnBr (2.23 g, 13 mmol). The mixture was stirred at 16° C. for 3 hrs. The mixture was diluted with water (100 mL). Then the mixture was extracted with EtOAc (50 mL×2). The organic layers were collected, dried and evaporated to give the crude product which was purified by flash chromatography, eluted with petroleum ether/EtOAc from 0-10% to give the III-2 (1.8 g, 82%) as a white solid and used directly in the next step.

Step 2—Synthesis of methyl 2-(benzyloxy)-5-fluoro-4-methylbenzoate (III-3)

A mixture of III-2 (2 g, 5.87 mmol), Pd(Ph3P)4 (339 mg, 0.293 mmol) in THF (2 0 mL) was degassed with N2 four times, then added AlMe3 (7.87 mL, 15.7 mmol, 2M) at 0° then reaction stirred at 80° C. for 24 hours. The reaction was then quenched with aq. potassium sodium tartrate tetrahydrate, extracted with EtOAc three times, the combined organic layers were dried over Na2SO4, removed the solvent in vacuum, the residue was purified by flash biotage (petroleum ether/EtOAc=0-5%) to give III-3 (660 mg, 41%) as a yellow oil. 1H NMR (400 MHz, CDCl3) δ ppm 7.57-7.47 (m, 3H), 7.43-7.37 (m, 2H), 7.36-7.30 (m, 1H), 6.84 (d, J=6.0 Hz, 1H), 5.14 (s, 2H), 3.90 (s, 3H), 2.29 (d, J=2.0 Hz, 3H)

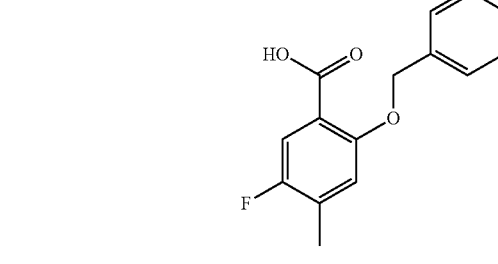

Step 3—Synthesis of 2-(benzyloxy)-5-fluoro-4-methylbenzoic acid (III-4)

To a solution of III-3 (0.71 g, 2.59 mmol) in MeOH (4 mL) was added a solution of LiOH.H₂O (326 gm, 7.77 mmol) in H₂O (4 mL). The reaction mixture was stirred at 20° C. for 2 hours. The reaction solution was evaporated to remove most of the methanol, and then residue was adjusted to pH-2 with 1N HCl. White solids formed and extracted with EtOAc (20 mL×2). The organic layers were dried and evaporated to give III-4 (670 mg, 99.5%) as a white solid. ¹H NMR (400 MHz, CDCl₃) δ ppm 10.76 (br. s., 1H), 7.83 (d, J=9.5 Hz, 1H), 7.52-7.37 (m, 5H), 6.96 (d, J=6.0 Hz, 1H), 5.26 (s, 2H), 2.35 (s, 3H)

Example 159 (Scheme JJJ)—(1S,2S,3S,5R)-3-(2-(aminomethyl)-4-chlorophenoxy)-5-(4-methyl-7H-pyrrolo[2,3-d]pyrimidin-7-yl)cyclopentane-1,2-diol (JJJ-3)

Step 1—Synthesis of 5-chloro-2-(((1S,4R)-4-(4-methyl-7H-pyrrolo[2,3-d]pyrimidin-7-yl)cyclopent-2-en-1-yl)oxy)benzonitrile (JJJ-1)

To a dry microwave vial (purged with N₂) was added BB-2 (100 mg, 0.317 mmol), 5-chloro-2-hydroxybenzonitrile (56 mg, 0.37 mmol), Cs₂CO₃ (114 mg, 0.35 mmol), Pd₂(dba)₃ (8.2 mg, 0.008 mmol) and DPPP (7.85 mg, 0.019 mmol). Then the vial was purged with N₂ three times and DCE (1.5 mL, sparged with N₂ for 30 mins) was added. The black mixture was stirred at 20° C. for 1 hour. Then the reaction mixture was directly purified by prep-TLC (Petroleum ether:EtOAc=1/4) to give JJJ-1 (83 mg, 75%, as a yellow gum. LCMS [M+1] 351; ¹H NMR (400 MHz, CDCl₃) δ ppm 8.77 (s, 1H), 7.56 (d, J=2.8 Hz, 1H), 7.50 (dd, J=2.6, 8.9 Hz, 1H), 7.41 (d, J=3.8 Hz, 1H), 7.00 (d, J=9.0 Hz, 1H), 6.63 (d, J=3.5 Hz, 1H), 6.40 (td, J=1.9, 5.5 Hz, 1H), 6.26 (dd, J=2.4, 5.6 Hz, 1H), 6.14-6.08 (m, 1H), 5.44 (d, J=7.0 Hz, 1H), 3.21-3.11 (m, 1H), 2.73 (s, 3H), 2.04 (td, J=3.2, 14.9 Hz, 1H)

Step 2—Synthesis of 5-chloro-2-(((1S,2S,3S,4R)-2,3-dihydroxy-4-(4-methyl-7H-pyrrolo[2,3-d]pyrimidin-7-yl)cyclopentyl)oxy)benzonitrile (JJJ-2)

To a mixture of JJJ-1 (83 mg, 0.237 mmol) in DCM (6 mL)/H₂O (0.2 mL) was added NMO (96 mg, 0.71 mmol) and OsO₄ (4% in t-BuOH, 80 mg, 0.013 mmol) at 20° C. The brown mixture was stirred at 20° C. for 6 hours. The mixture was diluted with DCM (5 mL) and quenched by sat.Na₂SO₃ (2 mL) and separated. The organic layer was washed with brine (5 mL). The combined aqueous were extracted with DCM (5 mL×2). The combined organic layers were dried over Na₂SO₄, filtered and concentrated to yield crude product (100 mg) as a light yellow solid, which was purified by prep-TLC (EtOAc:MeOH=10:1) to yield JJJ-2 (40 mg, 44%) as a white solid. LCMS [M+1] 385; ¹H NMR (400 MHz, MeOD) δ ppm 8.60 (s, 1H), 7.73 (d, J=2.5 Hz, 1H), 7.66 (d, J=3.5 Hz, 1H), 7.63 (dd, J=2.6, 9.2 Hz, 1H), 7.30 (d, J=9.0 Hz, 1H), 6.76 (d, J=3.5 Hz, 1H), 5.35-5.26 (m, 1H), 4.69 (dd, J=4.9, 8.4 Hz, 1H), 4.21 (d, J=4.5 Hz, 1H), 3.04 (ddd, J=6.8, 9.8, 14.8 Hz, 1H), 2.71 (s, 3H), 2.17 (ddd, J=3.0, 7.7, 14.7 Hz, 1H)

Step 3—Synthesis of (1S,2S,3S,5R)-3-(2-(aminomethyl)-4-chlorophenoxy)-5-(4-methyl-7H-pyrrolo[2,3-d]pyrimidin-7-yl)cyclopentane-1,2-diol (JJJ-3)

A mixture of JJJ-2 (40 mg, 0.104 mmol) and Raney-Ni (8 mg) in EtOH (7 mL)/NH₃.H₂O (0.5 mL) was degassed with H₂ four times. The mixture was stirred at 20° C. under H₂ balloon for 20 hrs. The mixture was filtered and the filtrate was concentrated in vacuo to afford a white solid, which was purified by prep-TLC (DCM:MeOH:NH₃.H₂O=10:1:0.1) to yield product (~20 mg) as yellow gum and lyophilized. The material was purified again by prep-HPLC to give JJJ-3 (9 mg, 22%). LCMS [M+1] 389; ¹H NMR (400 MHz, MeOD) δ ppm 8.60 (s, 1H), 7.56 (d, J=3.8 Hz, 1H), 7.42 (d, J=2.5 Hz, 2H), 7.21 (d, J=8.8 Hz, 1H), 6.74 (d, J=3.5 Hz, 1H), 5.11 (q, J=9.1 Hz, 1H), 4.82-4.76 (m, 2H), 4.29 (dd, J=2.1, 5.1 Hz, 1H), 4.26-4.15 (m, 2H), 3.06-2.92 (m, 1H), 2.72 (s, 3H), 2.37 (ddd, J=5.0, 9.7, 14.4 Hz, 1H)

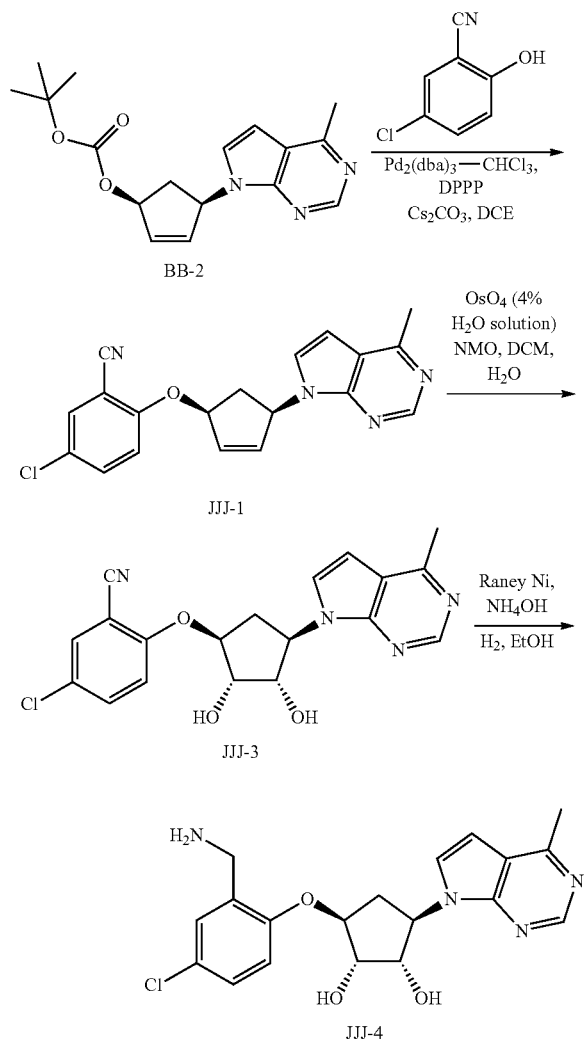

Examples 160 & 161 were Prepared in Using Similar Chemistry in Scheme A Using (4-chloro-3-fluorophenyl)magnesium bromide for Step 8

| Example 160 | 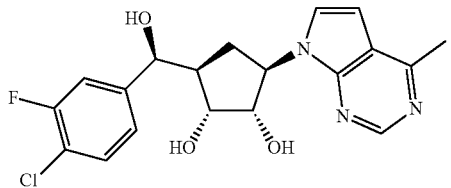 [SMILES: Cc1ncnc2c1ccn2[C@@H]1C[C@H]([C@H](O)c2ccc(Cl)c(F)c2)[C@@H](O)[C@H]1O] | 392 [M + 1] | (1S,2R,3R,5R)-3-((S)-(4-chloro-3-fluorophenyl)(hydroxy)methyl)-5-(4-methyl-7H-pyrrolo[2,3-d]pyrimidin-7-yl)cyclopentane-1,2-diol <br> $^1$H NMR (400 MHz, DMSO-d$_6$) δ ppm 8.59 (s, 1H), 7.65 (d, J = 3.8 Hz, 1H), 7.53 (t, J = 8.0 Hz, 1H), 7.40 (dd, J = 1.8, 10.5 Hz, 1H), 7.27 (dd, J = 1.9, 8.2 Hz, 1H), 6.69 (d, J = 3.5 Hz, 1H), 5.73 (d, J = 4.8 Hz, 1H), 5.02-4.93 (m, 1H), 4.80 (d, J = 7.0 Hz, 1H), 4.64-4.58 (m, 1H), 4.56 (d, J = 3.8 Hz, 1H), 4.28 (td, J = 6.1, 9.9 Hz, 1H), 3.95-3.90 (m, 1H), 2.63 (s, 3H), 2.29-2.21 (m, 1H), 2.02 (td, J = 8.6, 12.9 Hz, 1H), 1.67-1.57 (m, 1H) |
| --- | --- | --- | --- |
| Example 161 | 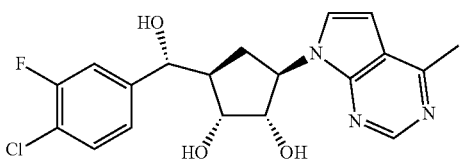 [SMILES: Cc1ncnc2c1ccn2[C@@H]1C[C@H]([C@@H](O)c2ccc(Cl)c(F)c2)[C@@H](O)[C@H]1O] | 392 [M + 1] | (1S,2R,3R,5R)-3-((R)-(4-chloro-3-fluorophenyl)(hydroxy)methyl)-5-(4-methyl-7H-pyrrolo[2,3-d]pyrimidin-7-yl)cyclopentane-1,2-diol <br> $^1$H NMR (400 MHz, DMSO-d6) δ ppm 8.59 (s, 1H), 7.65 (d, J = 3.5 Hz, 1H), 7.51 (t, J = 8.0 Hz, 1H), 7.35 (dd, J = 1.5, 10.5 Hz, 1H), 7.22 (dd, J = 1.9, 8.2 Hz, 1H ), 6.71-6.67 (m, 1H), 5.71 (d, J = 4.8 Hz, 1H), 4.97-4.88 (m, 1H), 4.86 (d, J = 6.5 Hz, 1H), 4.82 (t, J = 4.9 Hz, 1H), 4.67 (d, J = 4.5 Hz, 1H), 4.26-4.18 (m, 1H), 3.90 (q, J = 4.9 Hz, 1H), 2.63 (s, 3H), 2.27-2.18 (m, 1H), 1.89-1.71 (m, 2H) |

Example 162 was Made in a Similar Fashion to Example 99 in Scheme NN Using isoquinolin-8-ol in Step 2

| Example 162 isoquinoluin-8-ol | 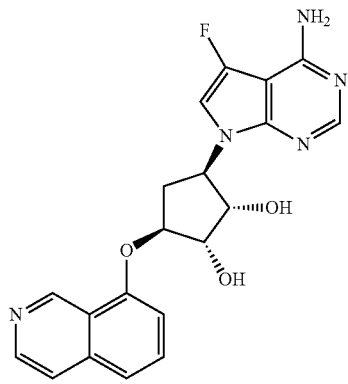 [SMILES: Nc1ncnc2c1c(F)cn2[C@@H]1C[C@H](Oc2cccc3ccncc23)[C@@H](O)[C@H]1O] | 396 LCMS [M + 1] | (1S,2S,3R,5S)-3-(4-amino-5-fluoro-7H-pyrrolo[2,3-d]pyrimidin-7-yl)-5-(isoquinolin-8-yloxy)cyclopentane-1,2-diol <br> $^1$H NMR (400 MHz, MeOD-d$_4$) δ ppm 9.62 (s, 1H), 8.46 (d, J = 5.8 Hz, 1H), 8.04 (s, 1H), 7.79 (d, J = 5.5 Hz, 1H), 7.72 (t, J = 8.0 Hz, 1H), 7.52 (d, J = 8.3 Hz, 1H), 7.21 (d, J = 8.0 Hz, 1H), 7.13 (d, J = 2.0 Hz, 1H), 5.19 (q, J = 9.0 Hz, 1H), 4.68 (br dd, J = 4.9, 8.9 Hz, 2H), 4.33 (br d, J = 4.8 Hz, 1H), 3.12-3.01 (m, 1H), 2.29-2.18(m, 1H) |
| --- | --- | --- | --- |

Synthesis of 6-hydroxy-3,4-dihydrobenzo[f][1,4]oxazepin-5(2H)-one (TP-21) and tert-butyl 6-hydroxy-2,3-dihydrobenzo[f][1,4]oxazepine-4(5H)-carboxylate (TP-22) (Scheme KKK)

Scheme KKK

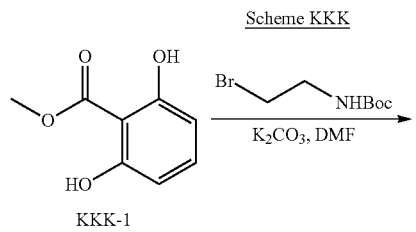

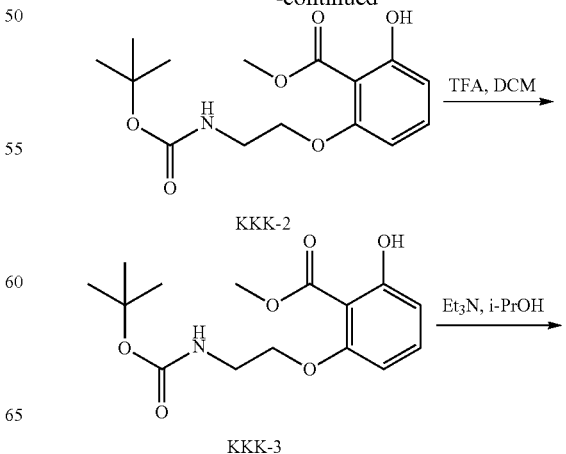

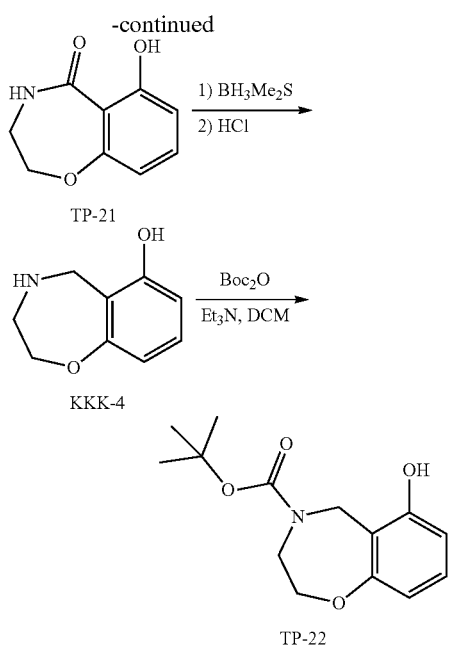

Step 1—Synthesis of methyl 2-(2-((tert-butoxycarbonyl)amino)ethoxy)-6-hydroxybenzoate (KKK-2)

A solution of methyl 2,6-dihydroxybenzoate (1.2 g, 7.14 mmol), tert-butyl (2-bromoethyl)carbamate (2.33 g, 7.14 mmol) and $K_2CO_3$ (2.5 g, 17.8 mmol) in DMF (10 mL) was stirred at 15° C. for 32 h. Water was added to the reaction mixture and extracted with EtOAc three times. The combined organic layers were dried over sodium sulfate, concentrated in vacuo, and the residue was purified by flash chromatography (petroleum ether/EtOAc=10-20%) to give compound KKK-2 (900 mg, 41%) as a white solid and used in the next step directly.

Step 2—Synthesis of methyl 2-(2-((tert-butoxycarbonyl)amino)ethoxy)-6-hydroxybenzoate (KKK-3)

To a solution of compound KKK-2 (900 mg, 2.89 mmol) in DCM (10 ml) was added TFA (2 mL) at 0-5° C., then the reaction mixture was stirred at 15° C. for 2 h. The solvent was removed and the residue (700 mg, >99%) was used to next step directly.

Step 3—Synthesis of 6-hydroxy-3,4-dihydrobenzo[f][1,4]oxazepin-5(2H)-one (TP-21)

To a solution of compound KKK-3 (700 mg, 3.31 mmol) in i-PrOH (6 mL) was added TEA (3.35 g, 33.1 mmol) at 15° C., then the reaction mixture was stirred at 95° C. for 6 h. The solvent was removed, and the residue was purified by flash chromatography (20 g, petroleum ether/EtOAc=10-50%) to give compound TP-21 (480 mg, 81%) as a white solid. $^1$H NMR (400 MHz, CDCl$_3$) δ ppm 12.61 (s, 1H), 7.33-7.29 (m, 1H), 6.70 (d, J=8.3 Hz, 1H), 6.57 (br. s., 1H), 6.53 (d, J=8.0 Hz, 1H), 4.41-4.35 (m, 2H), 3.57 (q, J=4.8 Hz, 2H)

Step 4—Synthesis of 2,3,4,5-tetrahydrobenzo[f][1,4]oxazepin-6-ol (KKK-4)

To a solution of compound TP-21 (100 mg, 0.56 mmol) in anhydrous THF (2 mL) was added BH$_3$-Me$_2$S (127 mg, 1.67 mmol) at 0° C. drop-wise under N$_2$. After the addition, the mixture was heated to 70° C. (reflux) for 3 hours. The reaction mixture was then quenched with 1 mL of MeOH carefully at −10~20° C., then added another 6N HCl 10 mL, then refluxed for 3 h, removed the most solvent under vacuum, then the residue was adjusted pH 8-9 with $K_2CO_3$, extracted with EtOAc three times. The combined organic layers were dried over Na$_2$SO$_4$, filtered and concentrated to give the crude compound KKK-4 (0.5 g, >99%). LCMS [M+1] 166

Step 5—Synthesis of tert-butyl 6-hydroxy-2,3-dihydrobenzo[f][1,4]oxazepine-4(5H)-carboxylate (TP-22)

Crude compound KKK-4 (500 mg, 0.61 mmol) was dissolved in DCM (5 mL) and MeOH (5 mL). (Boc)$_2$O (132 mg, 0.605 mmol) and Et$_3$N (184 mg, 1.82 mmol) were added and the reaction mixture was stirred at 15° C. for 16 hours. DCM (10 mL) was added, then washed with acetic acid (5 mL) and saturated NaCl (5 mL). The organic layer was separated, dried and evaporated to give the residue. Then 10 mL MeOH was added to dissolve the residue, then K$_2$CO$_3$ (200 mg) was added to the mixture. The reaction mixture was stirred at 15° C. for 2 hours. DCM (25 mL×2) was added to the solution, the solution was washed acetic acid (5 mL, pH<7) and saturated NaCl (5 mL). The organic layers were combined, dried and evaporate to give the crude product which was purified by prep-TLC to give compound TP-22 (13 mg, 8%) as a yellow solid. $^1$H NMR (400 MHz, CDCl$_3$) δ ppm 7.62 (br s, 1H), 7.07 (t, J=8.2 Hz, 1H), 6.73 (d, J=7.5 Hz, 1H), 6.64 (d, J=7.8 Hz, 1H), 4.37 (s, 2H), 4.01-3.92 (m, 2H), 3.79-3.70 (m, 2H), 1.40 (s, 9H) LCMS [M-Boc+1] 210.

Synthesis of tert-butyl 6-(1-(tert-butoxycarbonyl)-1H-pyrazol-4-yl)-8-hydroxy-3,4-dihydroisoquinoline-2(1H)-carboxylate (TP-23) (Scheme LLL)

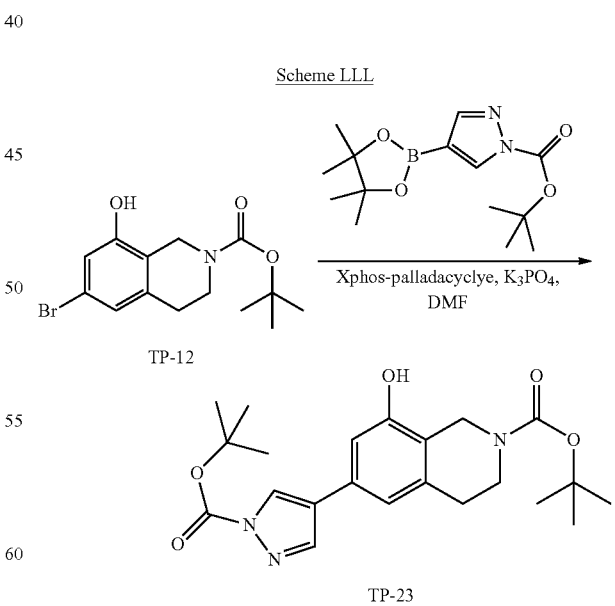

Under an N$_2$ atmosphere, TP-12 (50 mg, 0.15 mmol), tert-butyl 4-(4,4,5,5-tetramethyl-1,3,2-dioxaborolan-2-yl)-1H-pyrazole-1-carboxylate (67 mg, 0.23 mmol), K$_3$PO$_4$ (97 mg, 0.46 mmol) and XPhos-Palladacycle (13 mg, 0.015 mmol) was added to a vial. DMF (1.60 mL) was added and the reaction solution was heated to 50° C. in a microwave for 16 hours. EtOAc and H₂O were added to dilute the reaction solution. The aqueous was extracted with EtOAc (3 mL×2). The organic layers were separated, dried and evaporated to give the crude product, which was purified by prep-TLC (petroleum ether/EtOAc=1/1) to give the desired compound TP-23 (33 mg, 90%) as a colorless oil. LCMS [M-Boc+1] 316.

Synthesis of tert-butyl 6-(1-(tert-butoxycarbonyl)-1H-pyrazol-4-yl)-5-fluoro-8-hydroxy-3,4-dihydroisoquinoline-2(1H)-carboxylate (TP-24) (Scheme MMM)

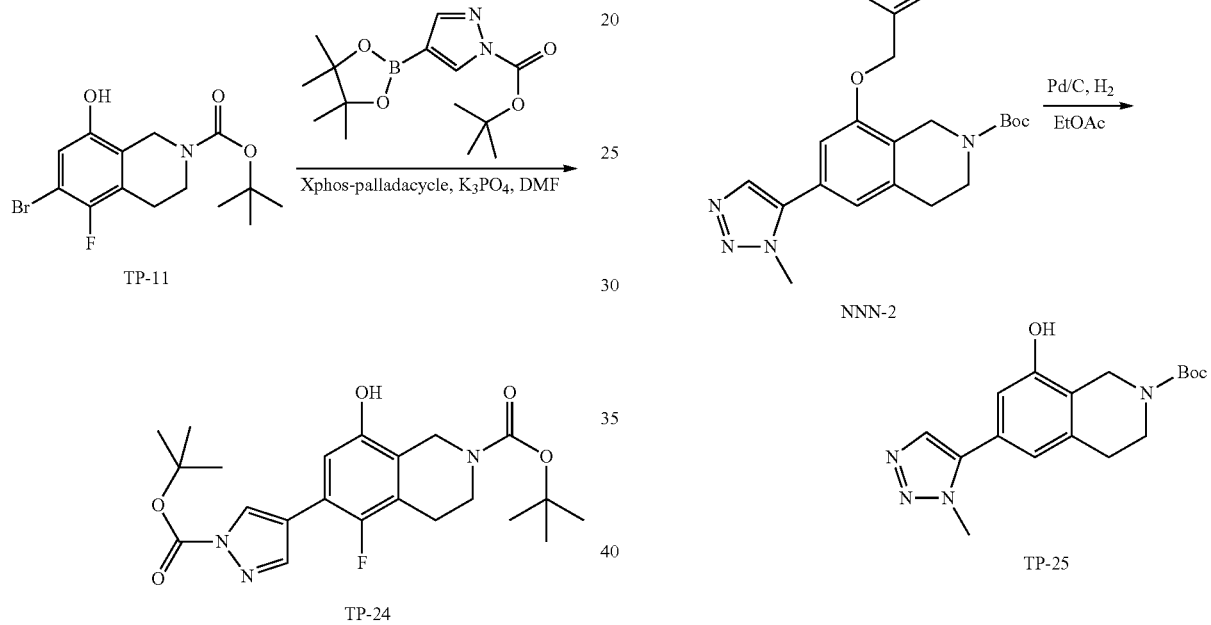

TP-24 was synthesized in a similar fashion to TP-23 (Scheme LLL) starting from TP-11. LCMS [M-Boc+1] 334.

Synthesis of tert-butyl 8-hydroxy-6-(1-methyl-1H-1,2,3-triazol-5-yl)-3,4-dihydroisoquinoline-2(1H)-carboxylate (TP-25) (Scheme NNN)

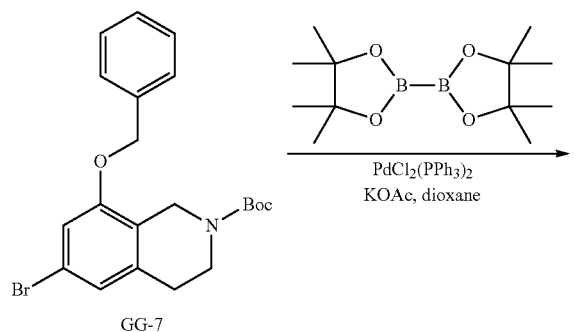

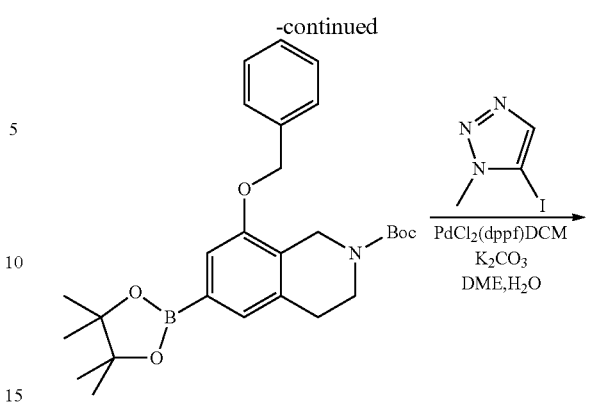

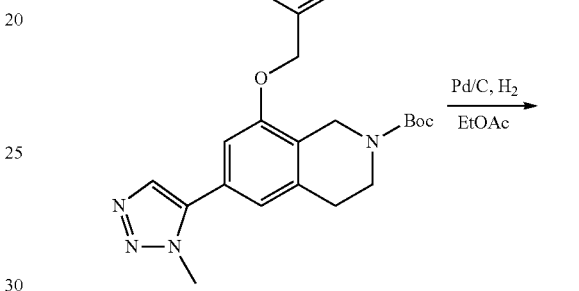

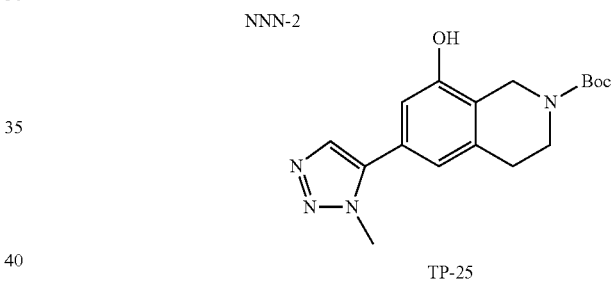

Step 1—Synthesis of tert-butyl 8-(benzyloxy)-6-(4,4,5,5-tetramethyl-1,3,2-dioxaborolan-2-yl)-3,4-dihydroisoquinoline-2(1H)-carboxylate (NNN-1)

A mixture of GG-7 (3.00 g, 7.17 mmol), bis(pinacolato)diboron (2.73 g, 10.8 mmol), KOAc (1.4 g, 14.3 mmol) and PdCl₂(dppf).CH₂Cl₂ (262 mg, 0.36 mmol) in dioxane (30.0 mL) was heated to 80° C. for 16 hours. Water (30 mL) was added to dilute the reaction solution then extracted with EtOAc (30 mL×2). The organic layers were combined, dried and evaporated to give the crude product, which was purified by flash chromatography (120 g silica gel), eluted with petroleum ether/EtOAc 0-20%, to give NNN-1 (3 g, 90%) as a white solid. LCMS [M-Boc+1] 366; ¹H NMR (400 MHz, DMSO-d₆) δ ppm 7.50-7.45 (m, 2H), 7.43-7.39 (m, 2H), 7.37-7.30 (m, 1H), 7.13 (d, J=2.5 Hz, 2H), 5.15 (br. s., 2H), 4.54-4.38 (m, 2H), 3.59-3.50 (m, 2H), 2.77 (t, J=5.5 Hz, 2H), 1.42 (s, 9H), 1.29 (s, 12H)

Step 2—Synthesis of tert-butyl 8-(benzyloxy)-6-(1-methyl-1H-1,2,3-triazol-5-yl)-3,4-dihydroisoquinoline-2(1H)-carboxylate (NNN-2)

A vial under argon containing NNN-1 (800 mg, 1.72 mmol), 5-iodo-1-methyl-1H-1,2,3-triazole (467 mg, 2.23 mmol), PdCl$_2$(dppf)-DCM (126 mg, 0.172 mmol), K$_2$CO$_3$ (475 mg, 3.44 mmol), DME (10.0 mL) and water (1.00 mL) was capped and heated at 80° C. for 16 hours. Water (10.0 mL) was added to the reaction and extracted with EtOAc (10 mL×2). The organic layers were separated, dried and evaporated to give the crude product, which was purified by flash chromatography (80 g), eluted with petroleum ether/EtOAc (1:1) to give NNN-2 (640 mg, 89%) as a colorless oil. LCMS [M+1] 421.

Step 3—Synthesis of tert-butyl 8-hydroxy-6-(1-methyl-1H-1,2,3-triazol-5-yl)-3,4-dihydroisoquinoline-2(1H)-carboxylate (TP-25)

Compound NNN-2 (640 mg, 1.52 mmol) was dissolved in EtOAc (3 mL). Pd/C (162 mg, 1.52 mmol) was added to the above mixture, the reaction mixture was stirred at 25° C. for 48 hours. The solution was diluted with EtOAc (10 mL) and filtered. The filtrate was evaporated to give the crude product, which was purified by flash chromatography, eluted with petroleum ether/EtOAc from 0-30%, to give the desired product TP-25 (320 mg, 64%) as a white solid. LCMS [M+1] 331; $^1$H NMR (400 MHz, DMSO-d$_6$) δ ppm 10.04 (s, 1H), 7.82 (s, 1H), 6.91-6.77 (m, 2H), 4.40 (s, 2H), 4.04 (s, 3H), 3.56 (m, 2H), 2.78 (m, 2H), 1.45 (s, 9H)

Synthesis of tert-butyl 8-hydroxy-6-(thiazol-4-yl)-3,4-dihydroisoquinoline-2(1H)-carboxylate (TP-26) (Scheme OOO)

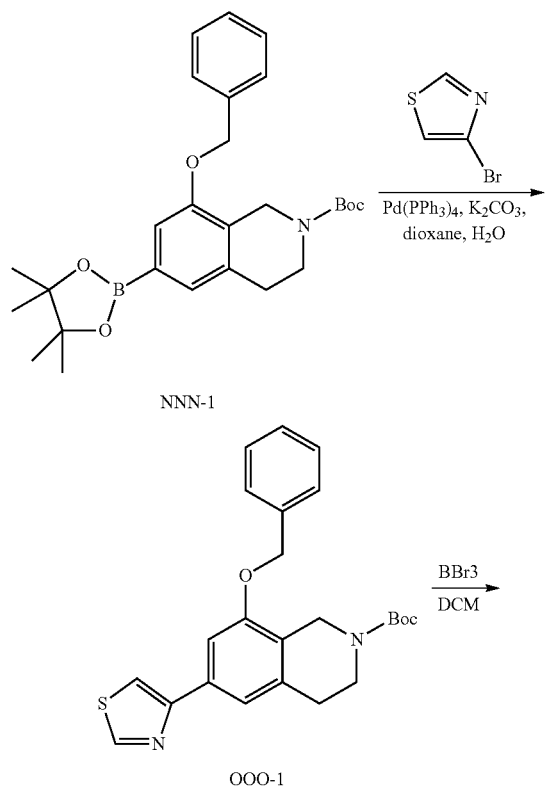

Step 1—Synthesis of tert-butyl 8-(benzyloxy)-6-(thiazol-4-yl)-3,4-dihydroisoquinoline-2(1H)-carboxylate (OOO-1)

A vial under argon containing compound NNN-1 (800 mg, 1.72 mmol), 4-bromothiazole (367 mg, 2.23 mmol), Pd(PPh$_3$)$_4$ (278 mg, 0.241 mmol), K$_2$CO$_3$ (523 mg, 3.78 mmol), dioxane (10 mL) and water (1 mL) was capped and heated at 80° C. for 16 hours. Water (10 mL) was added to the reaction and extracted with EtOAc (10 mL×2). The organic layers were separated, dried and evaporated to give the crude product, which was purified by flash chromatography, eluted with petroleum ether/EtOAc from 0-20%) to give OOO-1 (370 mg, 51%) as a colorless oil. LCMS [M+23] 445

Step 2—Synthesis of 6-(thiazol-4-yl)-1,2,3,4-tetrahydroisoquinolin-8-ol (OOO-2)

Compound OOO-1 (320 mg, 0.76 mmol) was dissolved in DCM (10 mL) and cooled to 0° C. in an ice bath. BBr$_3$ (1.14 g, 4.54 mmol) was added to the reaction solution and stirred at 25° C. for 16 hours. The reaction solution was cooled to 0° C. Methanol (3.00 mL) was added to the reaction solution drop-wise followed by water (20 mL). The reaction solution was washed with DCM (10 mL×2). The aqueous layer was separated. Na$_2$CO$_3$ solid was used to adjust the pH to 9. The final solution of compound OOO-2 was used for the next step directly. LCMS [M+1] 233.

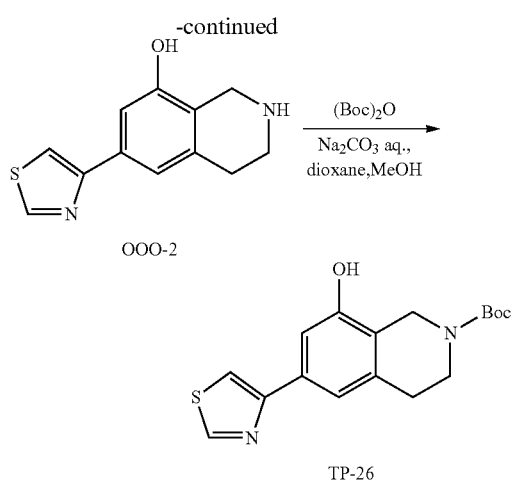

Step 3—Synthesis of tert-butyl 8-hydroxy-6-(thiazol-4-yl)-3,4-dihydroisoquinoline-2(1H)-carboxylate (TP-26)

MeOH (5.00 mL) and dioxane (5.00 mL) were added to the solution of compound OOO-2 (180 mg, reaction solution aqueous, 40.0 mL), then (Boc)$_2$O (335 mg, 1.55 mmol) was added to the reaction and stirred at 25° C. for 16 hours. DCM (20 mL) was added to dilute solution. The pH was adjusted to pH~3 by the addition of 1N HCl aq. The solution was separated and the aqueous layer was extracted with DCM (10 mL). The organic layers were combined and washed with saturated NaCl (20.0 mL). The organic layers were separated, dried and evaporated to give the crude product, which was purified by flash chromatography, eluted with petroleum ether/EtOAc 0-50% to give the TP-26 (180 mg, 70%) as a yellow solid. LCMS [M+1] 333; ¹H NMR (400 MHz, DMSO-d₆) δ ppm 9.78 (s, 1H), 9.16 (d, J=2.0 Hz, 1H), 7.99 (d, J=2.0 Hz, 1H), 7.33 (d, J=1.3 Hz, 1H), 7.24 (s, 1H), 4.38 (s, 2H), 3.56 (m, 2H), 2.77 (m, 2H), 1.44 (s, 9H)

Synthesis of tert-butyl 8-hydroxy-3-methyl-3,4-dihydroisoquinoline-2(1H)-carboxylate (TP-28)
(Scheme PPP)

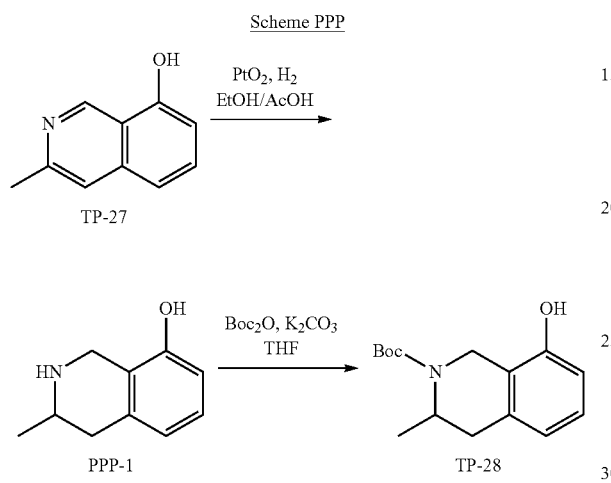

Step 1: Synthesis of 3-methyl-1,2,3,4-tetrahydroisoquinolin-8-ol (PPP-1)

A solution of 3-methylisoquinolin-8-ol (TP-27) [prepared from Tetrahedron Letters 49 (2008) 3725-3728] (100 mg, 0.628 mmol) in EtOH/AcOH (6 mL/0.2 mL) was added PtO₂ (80 mg, 0.35 mmol), hydrogenated under 45 psi H₂ at rt for 16 h. The reaction mixture was filtered and washed with EtOH, the solvent was evaporated to give crude PPP-1 (103 mg, 100%) which was used to the next step without further purification. LCMS [M+1] 163.9.

Step 2: Synthesis of tert-butyl 8-hydroxy-3-methyl-3,4-dihydroisoquinoline-2(1H)-carboxylate (TP-28)

To a solution of PPP-1 (103 mg, 0.628 mmol) in THF (6 mL, 0.1 M) was added Boc₂O (225 mg, 1.03 mmol) and K₂CO₃ (356 mg, 2.57 mmol) at 15° C., stirred at rt for 15 hrs. The solvent was removed, the residue was dissolved in MeOH, added 0.1 g K₂CO₃, stirred for 2 hrs. The solid was filtered and washed with EtOAc, the filtrate was concentrated and purified by preparative TLC to give TP-28 (70 mg, 42%) as yellow solid.

LCMS [M+1-tBu] 207.9. ¹H NMR (400 MHz, CHLOROFORM-d) δ ppm 7.09-7.01 (m, 1H), 6.71 (d, J=7.8 Hz, 1H), 6.63 (d, J=8.0 Hz, 1H), 4.81 (br d, J=17.6 Hz, 1H), 4.63 (br s, 1H), 4.18 (d, J=17.6 Hz, 1H), 3.08 (br dd, J=5.5, 16.1 Hz, 1H), 2.55 (br ddd, J=1.8, 14.6, 16.3 Hz, 1H), 1.54-1.43 (s, 9H), 1.09 (d, J=6.8 Hz, 3H)

Synthesis of tert-butyl 8-hydroxy-6-(oxazol-5-yl)-3,4-dihydroisoquinoline-2(1H)-carboxylate (TP-29)
(Scheme QQQ)

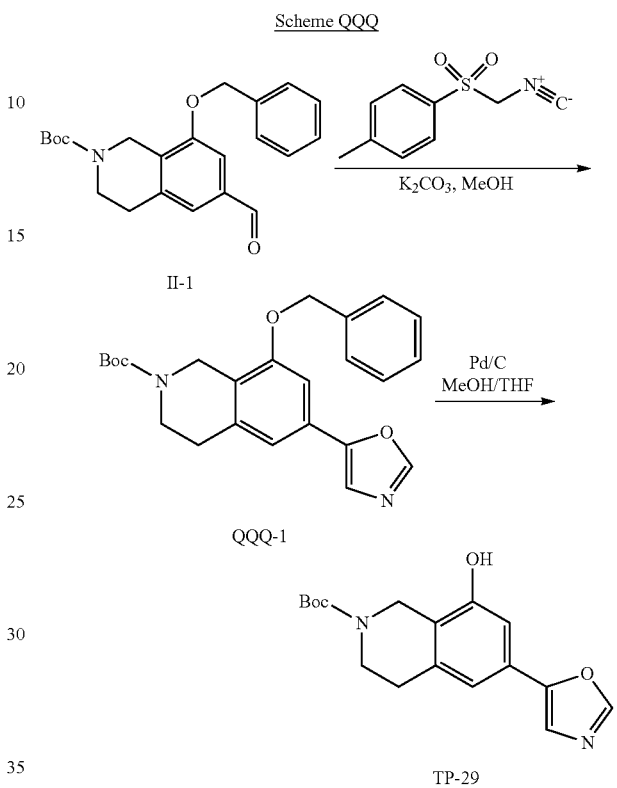

Step 1: Synthesis of tert-butyl 8-(benzyloxy)-6-(oxazol-5-yl)-3,4-dihydroisoquinoline-2(1H)-carboxylate (QQQ-1)

To the solution of II-1 (265 mg, 0.721 mmol) and p-toluenesulfonylmethyl isocyanide (465 mg, 2.38 mmol) in methanol (14.4 mL, c=0.05 M) was added K₂CO₃ (199 mg, 1.44 mmol), the resulting suspension was refluxed overnight. The reaction mixture was concentrated, EtOAc and H₂O were added. The layers were separated; the aqueous was extracted with EtOAc. The organic layers were concentrated, purified by column chromatography with 35% EtOAc/heptane to give QQQ-1 (100 mg, 34%) as colorless oil.

LCMS [M+1-Boc] 307.15. ¹H NMR (400 MHz, CHLOROFORM-d) δ ppm 1.51 (s, 9H) 2.86 (t, J=5.01 Hz, 2H) 3.67 (t, J=5.62 Hz, 2H) 4.62 (s, 2H) 5.16 (br. s., 2H) 7.06 (s, 1H) 7.08 (s, 1H) 7.31 (s, 1H) 7.35 (d, J=7.21 Hz, 1H) 7.41 (t, J=7.34 Hz, 2H) 7.44-7.50 (m, 2H) 7.90 (s, 1H)

Step 2: Synthesis of tert-butyl 8-hydroxy-6-(oxazol-5-yl)-3,4-dihydroisoquinoline-2(1H)-carboxylate (TP-29)

Compound TP-29 was prepared from QQQ-1 in a similar method as step 9 in Scheme GG (79 mg, 100%).

LCMS [M+1-Boc] 217.10. ¹H NMR (400 MHz, CHLOROFORM-d) δ ppm 1.54 (s, 9H) 2.83 (br. s., 2H) 3.67 (t, J=5.69 Hz, 2H) 4.60 (br. s., 2H) 6.95 (br. s., 2H) 7.27 (s, 1H) 7.90 (s, 1H)

Synthesis of tert-butyl 8-hydroxy-6-(1H-pyrazol-3-yl)-3,4-dihydroisoquinoline-2(1H)-carboxylate (TP-30) (Scheme RRR)

Scheme RRR

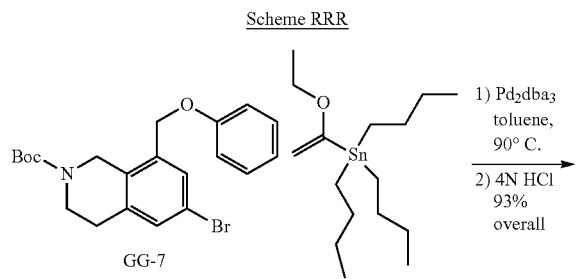

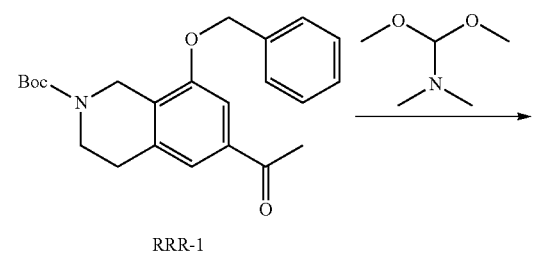

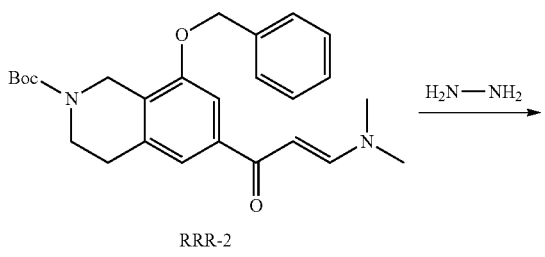

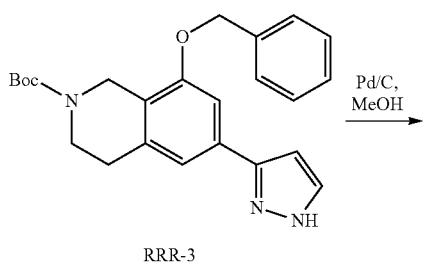

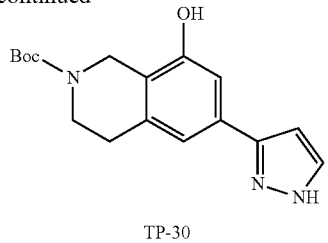

TP-30

Step 1: Synthesis of tert-butyl 6-acetyl-8-(benzyloxy)-3,4-dihydroisoquinoline-2(1H)-carboxylate (RRR-1)

Compound RRR-1 was prepared from GG-7 in a similar method as step 1 in Scheme JJ (360.0 mg, 80.2%).

Step 2: Synthesis of tert-butyl(E)-8-(benzyloxy)-6-(3-(dimethylamino)acryloyl)-3,4-dihydroisoquinoline-2(1H)-carboxylate (RRR-2)

RRR-1 (65 mg, 0.17 mmol) and N,N-dimethylformamide dimethylcetal (0.5 mL) were heated at 100° C. overnight. The rxn mixture was concentrated, purified by column chromatography with 70% EtOAc/heptane to give RRR-2 70 mg (94% yield) as a yellow oil.

LCMS [M+1] 437.20. $^1$H NMR (400 MHz, CHLOROFORM-d) δ ppm 1.50 (s, 9H) 2.77-2.92 (m, 2H) 2.92-3.22 (m, 6H) 3.66 (t, J=5.01 Hz, 2H) 4.62 (s, 2H) 5.17 (br. s., 2H) 5.66 (d, J=12.35 Hz, 1H) 7.28 (br. s., 1H) 7.32 (d, J=7.21 Hz, 1H) 7.38 (t, J=7.27 Hz, 3H) 7.43-7.49 (m, 2H) 7.80 (d, J=12.35 Hz, 1H)

Step 3: Synthesis of tert-butyl 8-(benzyloxy)-6-(1H-pyrazol-3-yl)-3,4-dihydroisoquinoline-2(1H)-carboxylate (RRR-3)

RRR-2 (70 mg, 0.16 mmol) and hydrazine monohydrate (183 mg, 1.28 mmol, 0.178 mL) in 2 mL EtOH was stirred at rt overnight. The reaction mixture was added EtOAc and H$_2$O, the layers were separated, the aqueous was extracted with EtOAc. The organic was combined and washed with brine, dried over Na$_2$SO$_4$, concentrated to give RRR-3 58.8 mg (90% yield) as a solid.

LCMS [M+1-tBu] 350.10. $^1$H NMR (400 MHz, CHLOROFORM-d) δ ppm 1.51 (s, 9H) 2.76-2.93 (m, 2H) 3.67 (t, J=5.50 Hz, 2H) 4.62 (s, 2H) 5.16 (br. s., 2H) 6.59 (d, J=2.32 Hz, 1H) 7.15 (s, 1H) 7.23 (s, 1H) 7.30-7.36 (m, 1H) 7.39 (t, J=7.27 Hz, 2H) 7.44-7.49 (m, 2H) 7.62 (d, J=2.20 Hz, 1H)

Step 4: Synthesis of tert-butyl 8-hydroxy-6-(1H-pyrazol-3-yl)-3,4-dihydroisoquinoline-2(1H)-carboxylate (TP-30)

Compound TP-30 was prepared from RRR-3 in a similar method as step 9 in Scheme GG (32 mg, 70%).

LCMS [M+1-Boc] 216.10. $^1$H NMR (400 MHz, CHLOROFORM-d) δ ppm 1.51 (s, 9H) 2.77 (t, J=5.26 Hz, 2H) 3.62 (t, J=5.50 Hz, 2H) 4.58 (br. s., 2H) 6.46 (br. s., 1H) 6.97 (s, 1H) 7.12 (br. s., 1H) 7.50-7.63 (m, 1H)

Examples 163-171 were Made in a Similar Fashion to Example 78 in Scheme CC Using the Appropriate NBoc-Protected Tetrahydroisoquinoline in Step 1

Example 163
TP-21

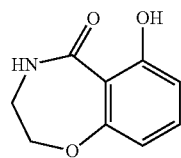 [SMILES: O=C1NCCOc2cccc(O)c21]

Slipped final deprotection step

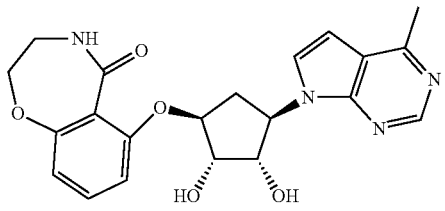 [SMILES: Cc1ncnc2c1ccn2[C@@H]1C[C@H](Oc2cccc3c2C(=O)NCCO3)[C@@H](O)[C@H]1O]

411 LCMS [M + 1]

6-(((1S,2S,3S,4R)-2,3-dihydroxy-4-(4-methyl-7H-pyrrolo[2,3-d]pyrimidin-7-yl)cyclopentyl)oxy)-3,4-dihydrobenzo[f][1,4]oxazepin-5(2H)-one
$^{1}$H NMR (400 MHz, DMSO-$d_6$) δ ppm 8.62 (s, 1H), 8.33 (t, J = 6.1 Hz, 1H), 7.97 (d, J = 3.8 Hz, 1H), 7.38 (t, J = 8.3 Hz, 1H), 6.98 (d, J = 8.3 Hz, 1H), 6.69 (dd, J = 2.0, 5.8 Hz, 2H), 5.35 (d, J = 3.5 Hz, 1H), 5.31-5.23 (m, 1H), 5.08 (d, J = 6.8 Hz, 1H), 4.71 (br d, J = 6.3 Hz, 1H), 4.63-4.56 (m, 1H), 4.11 (br d, J = 4.8 Hz, 2H), 4.00 (br s, 1H), 3.25-3.16 (m, 2H), 2.90-2.80 (m, 1H), 2.64 (s, 3H), 1.72 (m, 1H)

Example 164
TP-22

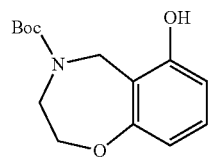

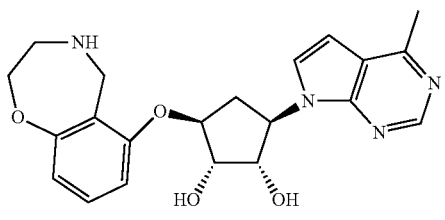 [SMILES: Cc1ncnc2c1ccn2[C@@H]1C[C@H](Oc2cccc3c2CNCCO3)[C@@H](O)[C@H]1O]

397 LCMS [M + 1]

(1S,2S,3R,5S)-3-(4-methyl-7H-pyrrolo[2,3-d]pyrimidin-7-yl)-5-((2,3,4,5-tetrahydrobenzo[f][1,4]oxazepin-6-yl)oxy)cyclopentane-1,2-diol
HCl salt
$^{1}$H NMR (400 MHz, MeOD-$d_4$) δ ppm = 9.12-8.97 (m, 1H), 8.15-7.95 (m, 1H), 7.36-7.26 (m, 1H), 7.25-7.12 (m, 1H), 7.00-6.88 (m, 1H), 6.75 (d, J = 6.5 Hz, 1H), 5.46-5.33 (m, 1H), 4.81-4.73 (m, 2H), 4.68-4.52 (m, 2H), 4.36-4.14 (m, 3H), 3.67-3.56 (m, 2H), 3.12-3.04 (m, 1H), 3.00 (br. s., 3H), 2.40-2.25 (m, 1H)

Example 165
TP-23

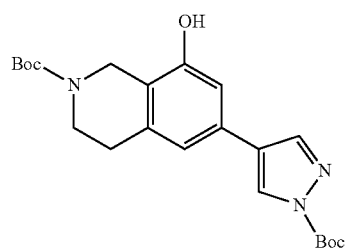 [SMILES: CC(C)(C)OC(=O)N1CCc2cc(-c3cnn(C(=O)OC(C)(C)C)c3)cc(O)c2C1]

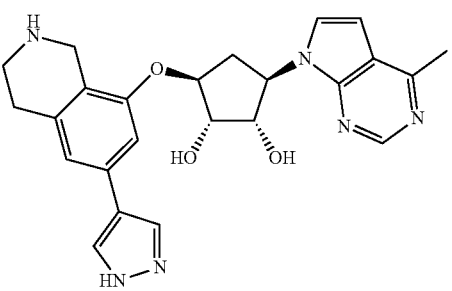 [SMILES: Cc1ncnc2c1ccn2[C@@H]1C[C@H](Oc2cc(-c3cn[nH]c3)cc3c2CNCC3)[C@@H](O)[C@H]1O]

447 LCMS [M + 1]

(1S,2S,3S,5R)-3-((6-(1H-pyrazol-4-yl)-1,2,3,4-tetrahydroisoquinolin-8-yl)oxy)-5-(4-methyl-7H-pyrrolo[2,3-d]pyrimidin-7-yl)cyclopentane-1,2-diol
HCl Salt
$^{1}$H NMR (400 MHz, D$_2$O) δ ppm 8.85-8.80 (m, 1H), 8.00-7.95 (m, 2H), 7.81 (br dd, J = 1.4, 3.9 Hz, 1H), 7.14-7.07 (m, 2H), 7.05 (br d, J = 3.3 Hz, 1H), 5.39-5.27 (m, 2H), 4.92-4.82 (m, 1H), 4.30 (br s, 3H), 3.50-3.39 (m, 2H), 3.11-2.99 (m, 3H), 2.88 (br s, 3H), 2.20 (br s, 1H)

| Example 166 TP-24 | 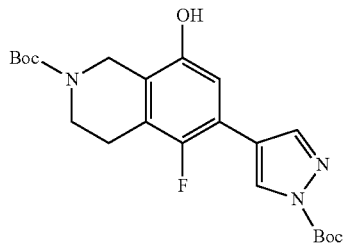 [SMILES: CC(C)(C)OC(=O)N1CCc2c(F)c(-c3cnn(C(=O)OC(C)(C)C)c3)cc(O)c2C1] | 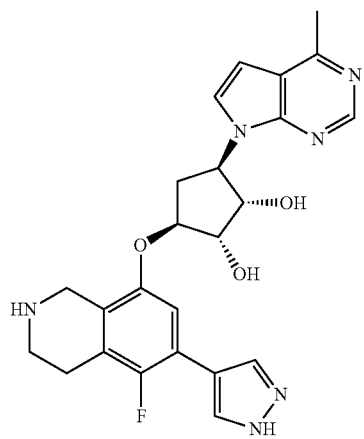 [SMILES: Cc1ncnc2c1ccn2[C@@H]1C[C@H](Oc2cc(-c3cn[nH]c3)c(F)c3c2CNCC3)[C@@H](O)[C@H]1O] | 465 LCMS [M + 1] | (1S,2S,3S,5R)-3-((5-fluoro-6-(1H-pyrazol-4-yl)-1,2,3,4-tetrahydroisoquinolin-8-yl)oxy)-5-(4-methyl-7H-pyrrolo[2,3-d]pyrimidin-7-yl)cyclopentane-1,2-diol HCl salt <br> $^1$H NMR (400 MHz, D$_2$O) δ ppm 8.57 (s, 1H), 8.42 (s, 1H), 8.08 (s, 1H), 7.51 (d, J = 3.8 Hz, 1H), 7.12 (d, J = 5.8 Hz, 1H), 6.80 (s, 1H), 5.22-5.13 (m, J = 8.9, 8.9, 8.9 Hz, 2H), 4.89-4.84 (m, 1H), 4.66-4.61 (m, 1H), 4.39-4.27 (m, 3H), 3.54-3.49 (m, 2H), 3.11-3.04 (m, J = 5.6. 5.6 Hz, 2H), 3.04-2.96 (m, 1H), 2.68 (s, 3H), 2.17-2.07 (m, 1H) |
|---|---|---|---|---|
| Example 167 TP-25 | 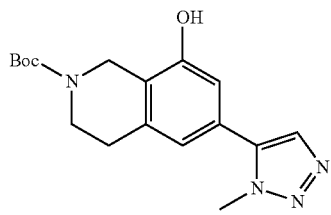 | 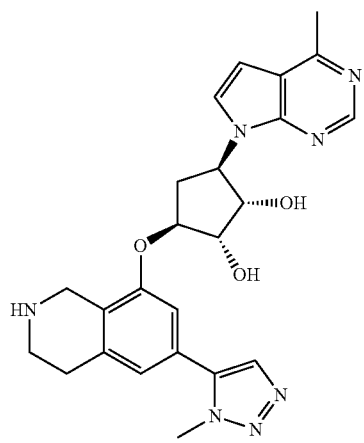 [SMILES: Cc1ncnc2c1ccn2[C@@H]1C[C@H](Oc2cc(-c3cnnn3C)cc3c2CNCC3)[C@@H](O)[C@H]1O] | 462 LCMS [M + 1] | (1S,2S,3S,5R)-3-((6-(1-methyl-1H-1,2,3-triazol-5-yl)-1,2,3,4-tetrahydroisoquinolin-8-yl)oxy)-5-(4-methyl-7H-pyrrolo[2,3-d]pyrimidin-7-yl)cyclopentane-1,2-diol HCl salt <br> $^1$H NMR (400 MHz, D$_2$O) δ ppm 8.93-8.91 (s, 1H), 7.93-7.90 (d, J = 4.0 Hz, 1H), 7.88 (s, 1H), 7.19 (d, J = 4.0 Hz, 1H), 7.14-7.11 (s, 1H), 7.08 (s, 1H), 5.42 (m, 1H), 4.94-4.86 (m, 2H), 4.46 (s, 2H), 4.40 (m, 1H), 4.10 (s, 3H), 3.61-3.54 (m, 2H), 3.24-3.16 (m, 2H), 3.17-3.07 (m, 1H), 2.98 (s, 3H), 2.37-2.26 (m, 1H) |
| Example 168 TP-26 | 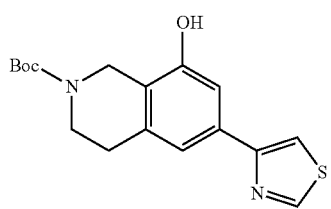 [SMILES: CC(C)(C)OC(=O)N1CCc2cc(-c3cscn3)cc(O)c2C1] | 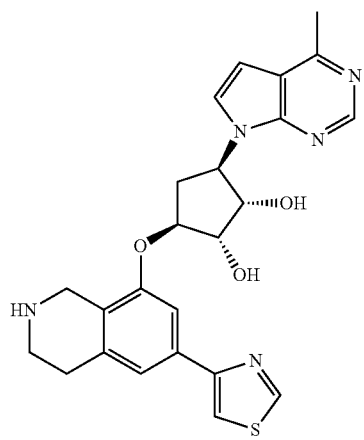 [SMILES: Cc1ncnc2c1ccn2[C@@H]1C[C@H](Oc2cc(-c3cscn3)cc3c2CNCC3)[C@@H](O)[C@H]1O] | 464 LCMS [M + 1] | (1S,2S,3R,5S)-3-(4-methyl-7H-pyrrolo[2,3-d]pyrimidin-7-yl)-5-((6-(thiazol-4-yl)-1,2,3,4-tetrahydroisoquinolin-8-yl)oxy)cyclopentane-1,2-diol HCl Salt <br> $^1$H NMR (400 MHz, D$_2$O) δ ppm 9.09 (d, J = 1.8 Hz, 1H), 8.90 (s, 1H), 7.91 (d, J = 2.0 Hz, 1H), 7.89 (d, J = 4.0 Hz, 1H), 7.45 (s, 1H), 7.44 (s, 1H), 7.17-7.15 (m, 1H), 5.43 (m, 1H), 4.96 (m, 1H), 4.85-4.83 (m, 1H), 4.43 (s, 2H), 4.41 (m, 1H), 3.59-3.54 (m, 2H), 3.23-3.18 (m, 2H), 3.18-3.11 (m, 1H), 2.96 (s, 3H), 2.35-2.26 (m, 1H) |

-continued

| Example 169 TP-27 | 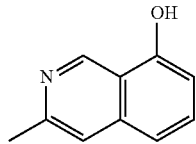 Skipped final deprotection step | 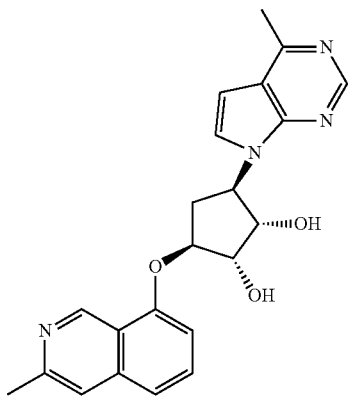 [SMILES: Cc1cc2cccc(O[C@H]3C[C@@H](n4ccc5c(C)ncnc54)[C@H](O)[C@@H]3O)c2cn1] | 391 LCMS [M + 1] | (1S,2S,3R,5S)-3-(4-methyl-7H-pyrrolo[2,3-d]pyrimidin-7-yl)-5-((3-methylisoquinolin-8-yl)oxy)cyclopentane-1,2-diol<br>$^1$H NMR (400MHz, METHANOL-d4) δ ppm 9.56 (s, 1H), 8.57 (s, 1H), 7.71-7.60 (m, 3H), 7.43 (d, J = 8.3 Hz, 1H), 7.13 (d, J = 7.3 Hz, 1H), 6.75 (d, J = 3.8 Hz, 1H), 5.30 (q, J = 8.9 Hz, 1H), 4.98 (m, 1H), 4.91 (m, 1H), 4.38 (d, J = 5.0 Hz, 1H), 3.16-3.08 (m, 1H), 2.72 (s, 3H), 2.70 (s, 3H), 2.45-2.37 (m, 1H) |
| --- | --- | --- | --- | --- |
| Example 170 TP-29 | 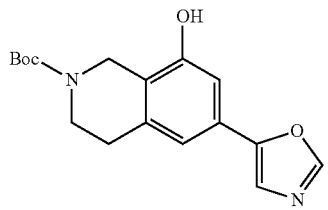 [SMILES: CC(C)(C)OC(=O)N1CCc2cc(-c3cnco3)cc(O)c2C1] | 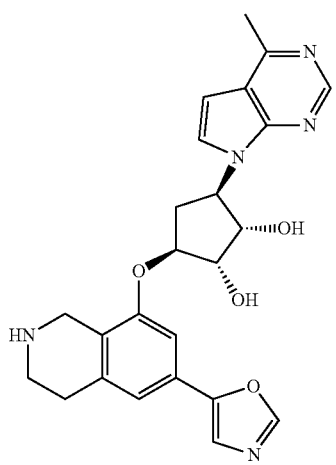 [SMILES: Cc1ncnc2c1ccn2[C@@H]1C[C@H](Oc2cc(-c3cnco3)cc3c2CNCC3)[C@@H](O)[C@H]1O] | 448 LCMS [M + 1] | (1S,2S,3R,5S)-3-(4-methyl-7H-pyrrolo[2,3-d]pyrimidin-7-yl)-5-((6-(oxazol-5-yl)-1,2,3,4-tetrahydroisoquinolin-8-yl)oxy)cyclopentane-1,2-diol<br>$^1$H NMR (400MHz, METHANOL-d4) δ ppm 8.99 (s, 1H), 8.30 (s, 1H), 8.01 (d, J = 3.8 Hz, 1H), 7.63 (s, 1H), 7.35 (d, J = 16.6 Hz, 2H), 7.17 (d, J = 3.8 Hz, 1H), 5.40 (q, J = 9.3 Hz, 1H), 4.79 (dd, J = 5.0, 9.0 Hz, 1H), 4.43 (s, 2H), 4.26 (d, J = 4.5 Hz, 1H), 3.55 (t, J = 6.3 Hz, 2H), 3.23-3.07 (m, 3H), 2.97 (s, 3H), 2.33 (ddd, J = 4.1, 9.6, 13.9 Hz, 1H) |
| Example 171 TP-30 | 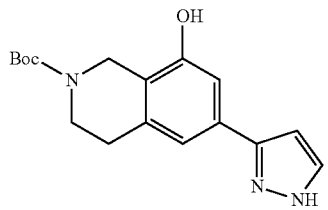 [SMILES: CC(C)(C)OC(=O)N1CCc2cc(-c3cc[nH]n3)cc(O)c2C1] | 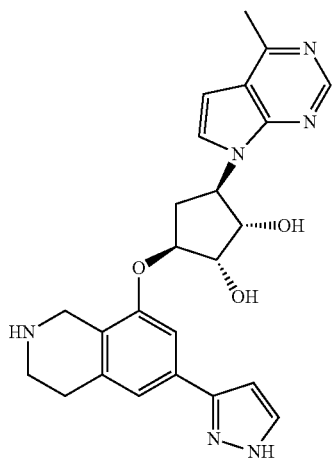 [SMILES: Cc1ncnc2c1ccn2[C@@H]1C[C@H](Oc2cc(-c3cc[nH]n3)cc3c2CNCC3)[C@@H](O)[C@H]1O] | 447 LCMS [M + 1] | (1 =S,2S,3S,5R)-3-((6-(1H-pyrazol-3-yl)-1,2,3,4-tetrahydroisoquinolin-8-yl)oxy)-5-(4-methyl-7H-pyrrolo[2,3-d]pyrimidin-7-yl)cyclopentane-1,2-diol HCl salt<br>$^1$H NMR (400 MHz, D$_2$O) δ ppm = 8.88 (s, 1H), 7.86 (d, J = 3.8 Hz, 1H), 7.79 (d, J = 2.3 Hz, 1H), 7.34 (m, 2H), 7.14 (m, 1H), 6.77 (m, 1H), 5.41 (m, 1H), 4.93 (m, 1H), 4.75-4.70 (m, 1H), 4.44-4.36 (m, 3H), 3.58-3.50 (m, 2H), 3.25-3.07 (m, 3H), 2.93 (s, 3H), 2.31 (m, 1H) |

Example 172 (Scheme SSS)—Synthesis of (1S,2S, 3S,5R)-3-(isoquinolin-8-yloxy)-5-(4-methyl-7H-pyrrolo[2,3-d]pyrimidin-7-yl)cyclopentane-1,2-diol (SSS-6)

Scheme SSS

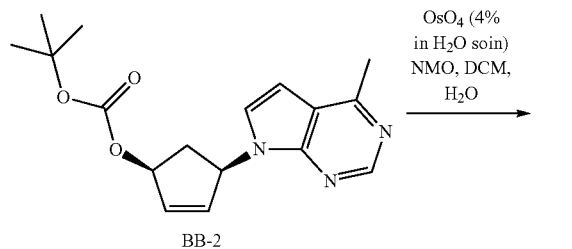

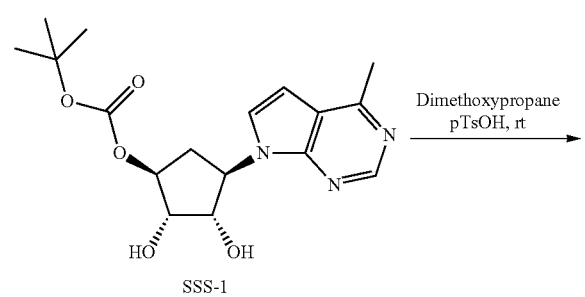

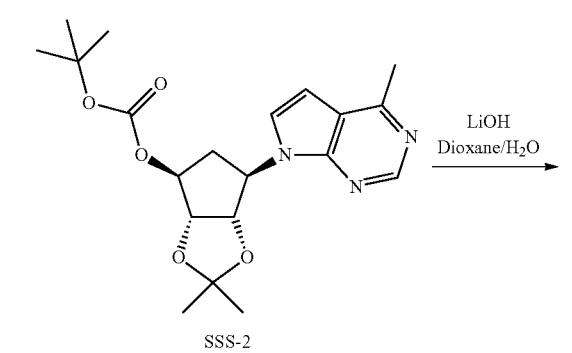

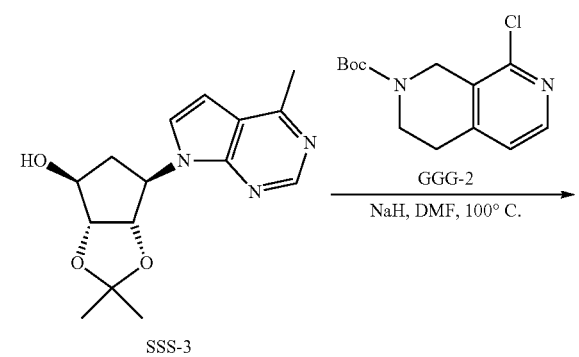

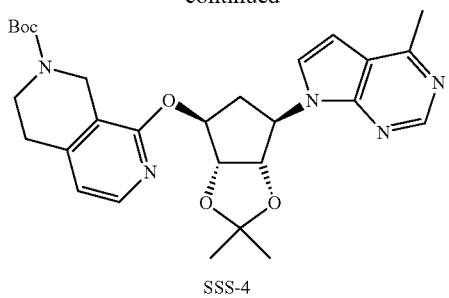

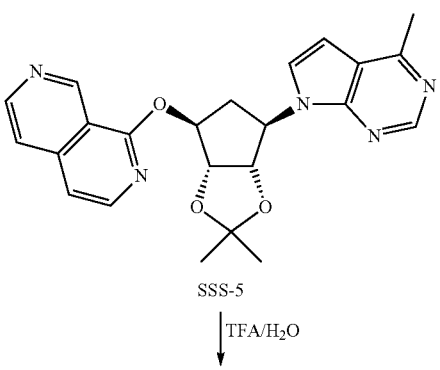

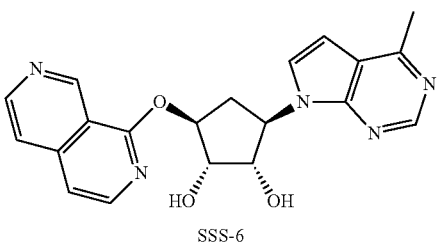

Step 1: Synthesis of tert-butyl((1S,2S,3S,4R)-2,3-dihydroxy-4-(4-methyl-7H-pyrrolo[2,3-d]pyrimidin-7-yl)cyclopentyl) carbonate (SSS-1)

Compound SSS-1 was prepared from BB-2 in a similar method as step 2 in Scheme CC to give 274 mg (82% yield) as a colorless oil.

LCMS [M+1] 350.10. $^1$H NMR (400 MHz, CHLOROFORM-d) δ ppm 1.51 (s, 9H) 2.18 (ddd, J=14.21, 9.14, 5.26 Hz, 1H) 2.71 (s, 3H) 3.02 (dt, J=14.18, 8.07 Hz, 1H) 3.95-4.02 (m, 1H) 4.30 (dd, J=5.38, 2.08 Hz, 1H) 4.51 (dd, J=7.82, 5.50 Hz, 1H) 4.96-5.08 (m, 2H) 6.61 (d, J=3.67 Hz, 1H) 7.29 (d, J=3.67 Hz, 1H) 8.66 (s, 1H)

Step 2: Synthesis of tert-butyl((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl) carbonate (SSS-2)

Compound SSS-2 was prepared from SSS-1 in a similar method as step 3 in Scheme P to give 181 mg (59% yield) as a colorless oil.

LCMS [M+1] 390.15. ¹H NMR (400 MHz, CHLOROFORM-d) δ ppm 1.32 (s, 3H) 1.50 (s, 9H) 1.58 (s, 3H) 2.38-2.48 (m, 1H) 2.73 (s, 3H) 2.84-2.95 (m, 1H) 4.82 (d, J=6.11 Hz, 1H) 4.99 (dd, J=6.54, 3.12 Hz, 1H) 5.06-5.13 (m, 1H) 5.21-5.29 (m, 1H) 6.57 (d, J=3.67 Hz, 1H) 7.31 (d, J=3.67 Hz, 1H) 8.78 (s, 1H)

Step 3: Synthesis of (3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-ol (SSS-3)

Compound SSS-3 was prepared from SSS-2 in a similar method as step 1 in Scheme FFF to give 127 mg (94% yield) as a white solid.

LCMS [M+1] 290.15. ¹H NMR (400 MHz, CHLOROFORM-d) δ ppm 1.33 (s, 3H) 1.55 (s, 3H) 2.20 (dd, J=15.65, 1.34 Hz, 1H) 2.75 (s, 3H) 2.95-3.08 (m, 1H) 4.44-4.50 (m, 1H) 4.80 (d, J=5.38 Hz, 1H) 4.84 (dt, J=10.58, 2.48 Hz, 1H) 4.98 (d, J=5.01 Hz, 1H) 6.15 (d, J=9.41 Hz, 1H) 6.55 (d, J=3.67 Hz, 1H) 8.73 (s, 1H)

Step 4: Synthesis of tert-butyl 8-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-3,4-dihydro-2,7-naphthyridine-2(1H)-carboxylate (SSS-4) and 1-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-2,7-naphthyridine (SSS-5)

To a solution of SSS-3 (80.7 mg, 0.279 mmol) in DMF (5.58 mL, c=0.05 M) was added NaH (16.7 mg, 0.419 mmol, 60%). After stirring for 10 min, GGG-2 (75.0 mg, 0.279 mmol) was added. The resulting reaction mixture was heated at 100° C. for 1.5 h. The reaction was quenched with diluted NaHCO₃, and then partitioned between ethyl acetate (20 mL) and water (20 mL). The organic phase was separated, washed with brine, dried over sodium sulfate, concentrated and purified with column chromatography with 60% EtOAc/heptane to give SSS-4 (15 mg, 10%)

LCMS [M+1] 522.20. ¹H NMR (400 MHz, CHLOROFORM-d) δ ppm 1.34 (s, 3H) 1.50 (s, 9H) 1.60 (s, 3H) 2.45 (d, J=14.18 Hz, 1H) 2.72 (s, 3H) 2.76 (t, J=5.38 Hz, 2H) 3.05 (dt, J=14.61, 7.12 Hz, 1H) 3.60 (br. s., 1H) 3.65 (br. s., 1H) 4.39 (br. s., 2H) 4.94 (d, J=6.24 Hz, 1H) 5.05 (dd, J=6.17, 1.90 Hz, 1H) 5.34 (ddd, J=7.70, 4.95, 2.38 Hz, 1H) 5.60 (br. s., 1H) 6.61 (br. s., 1H) 6.69 (d, J=5.14 Hz, 1H) 7.38 (d, J=3.67 Hz, 1H) 7.95 (d, J=5.14 Hz, 1H) 8.79 (m, 1H) and eluted with 5% MeOH/EtOAc to give SSS-5 (35 mg, 30%)

LCMS [M+1] 418.15. ¹H NMR (400 MHz, CHLOROFORM-d) δ ppm 1.38 (s, 3H) 1.63 (s, 3H) 2.56 (dt, J=14.98, 3.82 Hz, 1H) 2.72 (s, 3H) 3.04-3.19 (m, 1H) 5.11 (d, J=6.11 Hz, 1H) 5.21 (d, J=6.11 Hz, 1H) 5.35-5.46 (m, 1H) 5.83 (dt, J=3.97, 2.05 Hz, 1H) 6.61 (d, J=3.67 Hz, 1H) 7.20 (d, J=5.87 Hz, 1H) 7.39 (d, J=3.67 Hz, 1H) 7.55 (d, J=5.62 Hz, 1H) 8.22 (d, J=5.87 Hz, 1H) 8.70 (br. s., 1H) 8.77 (s, 1H) 9.38 (br. s., 1H)

Step 5: Synthesis of (1S,2S,3S,5R)-3-(isoquinolin-8-yloxy)-5-(4-methyl-7H-pyrrolo[2,3-d]pyrimidin-7-yl)cyclopentane-1,2-diol (SSS-6)

Compound SSS-6 was prepared from SSS-5 in a similar method as step 10 in Scheme A to give 11.6 mg (36% yield) as a white solid.

LCMS [M+1] 378.10. ¹H NMR (700 MHz, DMSO-d6) δ ppm 2.05-2.15 (m, 1H) 2.64-2.72 (m, 3H) 2.98 (ddd, J=14.75, 9.24, 7.48 Hz, 1H) 4.25 (d, J=3.08 Hz, 1H) 4.72 (dd, J=8.69, 4.73 Hz, 1H) 5.21 (q, J=8.88 Hz, 1H) 5.48 (dd, J=5.94, 3.30 Hz, 1H) 6.80 (d, J=3.52 Hz, 1H) 7.43 (d, J=5.94 Hz, 1H) 7.78-7.89 (m, 2H) 8.24 (d, J=5.72 Hz, 1H) 8.64 (s, 1H) 8.80 (br. s., 1H) 9.72 (br. s., 1H)

Example 173 was Made in a Similar Fashion to CC-3 (Example 78) Using the Appropriate Pyrrolopyrimidine in Step 1 of Scheme BB and the Appropriate N-Boc Protected Tetrahydroisoquinoline in Step 1 of Scheme CC

| Example 173 | | | |
|---|---|---|---|
| HG-3 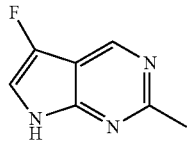 TP-18 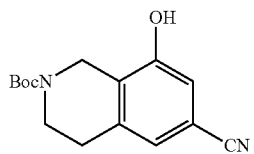 [SMILES: CC(C)(C)OC(=O)N1CCc2cc(C#N)cc(O)c2C1] | 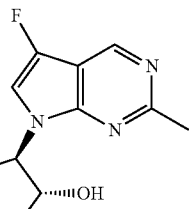 | 424 LCMS [M + 1] | 8-(((1S,2S,3S,4R)-4-(5-fluoro-2-methyl-7H-pyrrolo[2,3-d]pyrimidin-7-yl)-2,3-dihydroxycyclopentyl)oxy)-1,2,3,4-tetrahydroisoquinoline-6-carbonitrile ¹H NMR (400 MHz, MeOD-d4) δ ppm 9.09 (br. s., 1H), 7.66 (d, J = 2.3 Hz, 1H), 7.40 (s, 1H), 7.33 (s, 1H), 5.38 (q, J = 9.1 Hz, 1H), 4.79 (t, J = 5.1 Hz, 1H), 4.60 (dd, J = 5.3, 9.3 Hz, 1H), 4.44 (s, 2H), 4.19 (d, J = 4.8 Hz, 1H), 3.60-3.50 (m, 2H), 3.21-3.13 (m, 2H), 3.02 (td, J = 8.2, 14.5 Hz, 1H), 2.83-2.79 (m, 3H), 2.19 (ddd, J = 4.6, 9.6, 14.1 Hz, 1H) |

Example 174 was Made in a Similar Fashion to NN-5 (Example 99) Using the Appropriate Pyrrolopyrimidine in Step 1 of Scheme BB and the Appropriate N-Boc Protected Tetrahydroisoquinoline in Step 1 of Scheme NN

| Example 174 | | | |
|---|---|---|---|
| 4,5-dichloro-7H-pyrrolo[2,3-d]pyrimidine 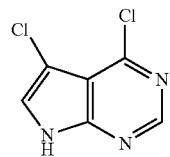 [SMILES: Clc1c[nH]c2ncnc(Cl)c12] TP-18 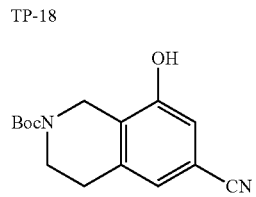 | 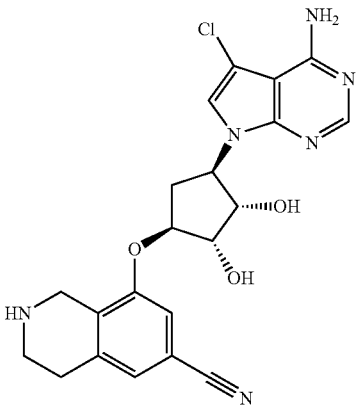 [SMILES: N#Cc1cc2c(c(O[C@H]3C[C@@H](n4cc(Cl)c5c(N)ncnc54)[C@H](O)[C@@H]3O)c1)CNCC2] | 441 LCMS [M + 1] | 8-(((1S,2S,3S,4R)-4-(4-amino-5-chloro-7H-pyrrolo[2,3-d]pyrimidin-7-yl)-2,3-dihydroxycyclopentyl)oxy)-1,2,3,4-tetrahydroisoquinoline-6-carbonitrile HCl salt<br>$^1$H NMR (400 MHz, MeOD-d4) δ ppm 8.30 (s, 1H), 7.68 (s, 1H), 7.46 (s, 1H), 7.30 (s, 1H), 5.29-5.21 (m, 1H), 4.78 (t, J = 5.2 Hz, 1H), 4.62 (dd, J = 5.2, 9.2 Hz, 1H), 4.43 (S, 2H), 4.19 (d, J = 5.1 Hz, 1H), 3.57-3.51 (m, 2H), 3.18 (t, J = 6.1 Hz, 2H), 3.09-2.96 (m, 1H), 2.20 (ddd, J = 4.5, 9.7, 14.0 Hz, 1H) |

Examples 175-179 were Made in a Similar Fashion to SS-5 (Example 121) Using the Appropriate N-Boc Protected Tetrahydroisoquinoline in Step 1 and the Appropriate Pyrrolopyrimidine in Step 2 of Scheme SS. Step 4 in Scheme SS was Not Required for these Examples

| Example 175: HG-3 (step 4 is skipped) | | | |
|---|---|---|---|
| 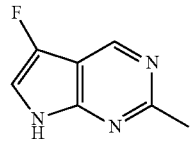 TP-3 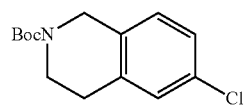 [SMILES: CC(C)(C)OC(=O)N1CCc2cc(Cl)ccc2C1] | 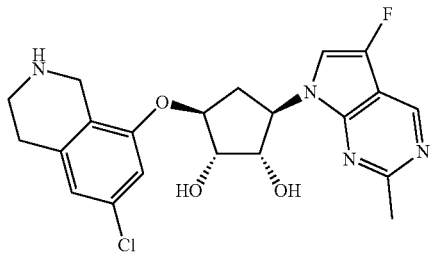 [SMILES: Cc1ncc2c(F)cn([C@@H]3C[C@H](Oc4cc(Cl)cc5c4CNCC5)[C@@H](O)[C@H]3O)c2n1] | 433 LCMS [M + H] | (1S,2S,3S,5R)-3-((6-chloro-1,2,3,4-tetrahydroisoquinolin-8-yl)oxy)-5-(5-fluoro-2-methyl-7H-pyrrolo[2,3-d]pyrimidin-7-yl)cyclopentane-1,2-diol<br>$^1$H NMR (400MHz, DEUTERIUM OXIDE) δ ppm 9.13(s, 1H), 7.61 (d, J = 2.3 Hz, 1H), 6.97(d, J = 4.0 Hz, 2H), 5.40 (br d, J = 8.5 Hz, 1H), 4.72 (br d, J = 2.0 Hz, 1H), 4.58 (dd, J = 4.8, 9.0 Hz, 1H), 4.32-4.27 (m, 3H), 3.46(t, J = 6.1 Hz, 2H), 3.09-3.05 (m, 2H), 3.01 (s, 1H), 2.83 (s, 3H), 2.17-2.07 (m, 1H). |

| Example 176: HG-4 (step 4 is skipped) | | | |
|---|---|---|---|
| 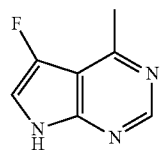 TP-3 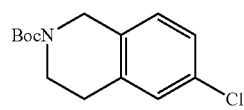 [SMILES: CC(C)(C)OC(=O)N1CCc2cc(Cl)ccc2C1] | 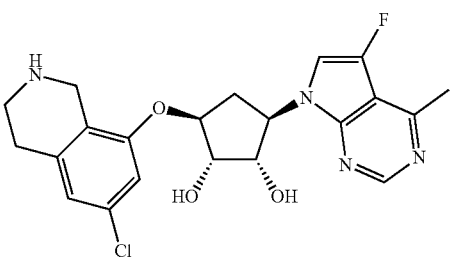 [SMILES: Cc1ncnc2c1c(F)cn2[C@@H]1C[C@H](Oc2cc(Cl)cc3c2CNCC3)[C@@H](O)[C@H]1O] | 433 LCMS [M + H] | (1S,2S,3S,5R)-3-((6-chloro-1,2,3,4-tetrahydroisoquinolin-8-yl)oxy)-5-(5-fluoro-4-methyl-7H-pyrrolo[2,3-d]pyrimidin-7-yl)cyclopentane-1,2-diol<br>$^1$H NMR (400MHz, DEUTERIUM OXIDE) δ ppm 8.88 (s, 1H), 7.69 (d, J = 2.3Hz, 1H), 7.01 (d, J = 4.0Hz, 2H), 5.43 (q, J = 9.0Hz, 1H), 4.89-4.83 (m, 1H), 4.66 (dd, J = 4.8, 8.8 Hz, 1H), 4.41-4.30 (m, 3H), 3.52 (t, J = 6.3 Hz, 2H), 3.17-3.05 (m, 3H), 3.01 (s, 3H), 2.26-2.07 (m, 1H). |

-continued

| Example 177 HG-4 (step 4 is skipped)  TP-6 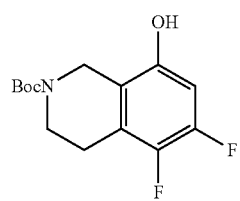 | 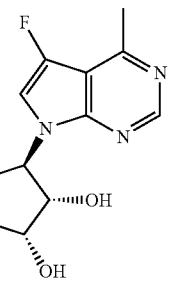 | 435 LCMS [M + 1] | (1S,2S,3S,5R)-3-((5,6-difluoro-1,2,3,4-tetrahydroisoquinolin-8-yl)oxy)-5-(5-fluoro-4-methyl-7H-pyrrolo[2,3-d]pyrimidin-7-yl)cyclopentane-1,2-diol HCl Salt $^1$H NMR (400 MHz, D$_2$O) δ ppm = 8.77 (s, 1H), 7.58 (br s, 1H), 6.92-6.85 (m, 1H), 5.32 (br d, J = 8.3 Hz, 1H), 4.78-4.77 (m, 1H, under D$_2$O), 4.61-4.47 (m, 1H), 4.26 (br s, 3H), 3.46 (br s, 2H), 3.04 (br s, 2H), 2.98 (br d, J = 7.5 Hz, 1H), 2.90 (s, 3H), 2.09 (br s, 1H) |
|---|---|---|---|
| Example 178 HG-4 (step 4 is skipped) 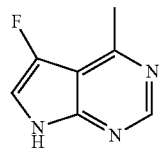 TP-6 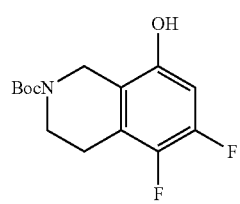 [SMILES: CC(C)(C)OC(=O)N1CCc2c(F)c(F)cc(O)c2C1] |  | 435 LCMS [M + 1] | (1S,2S,3S,5R)-3-((5,6-difluoro-1,2,3,4-tetrahydroisoquinolin-8-yl)oxy)-5-(5-fluoro-2-methyl-7H-pyrrolo[2,3-d]pyrimidin-7-yl)cyclopentane-1,2-diol HCl Salt $^1$H NMR (400MHz, D$_2$O) δ ppm = 9.09 (s, 1H), 7.59 (s, 1H), 6.87 (br dd, J = 6.5, 12.3 Hz, 1H), 5.39-5.30 (m, 1H), 4.58-4.57 (m, 1H), 4.24 (br s, 2H), 3.63 (br d, J = 5.0 Hz, 1H), 3.56 (s, 2H), 3.45 (br t, J = 5.8 Hz, 1H), 3.03 (br s, 2H), 2.99-2.92 (m, 1H), 2.78 (s, 3H), 2.08 (br d, J = 10.5 Hz, 1H) |
| Example 179 HG-6 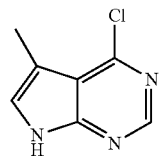 TP-6 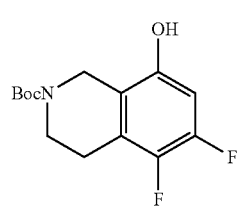 [SMILES: CC(C)(C)OC(=O)N1CCc2c(F)c(F)cc(O)c2C1] | | 432 LCMS [M + 1] | (1S,2S,3R,5S)-3-(4-amino-5-methyl-7H-pyrrolo[2,3-d]pyrimidin-7-yl)-5-((5,6-difluoro-1,2,3,4-tetrahydroisoquinolin-8-yl)oxy)cyclopentane-1,2-diol HCl Salt $^1$H NMR (400 MHz, MeOD-d4) δ ppm = 8.27 (s, 1H), 7.37 (s, 1H), 7.15-7.00 (m, 1H), 5.29-5.11 (m, 1H), 4.73-4.57 (m, 2H), 4.35 (br s, 2H), 4.17 (br d, J = 3.5 Hz, 1H), 3.61-3.49 (m, 2H), 3.13 (br s, 2H), 3.02-2.91 (m, 1H), 2.55-2.44 (m, 3H), 2.23-2.09 (m, 1H) |

Example 180 (Scheme TTT)—(1S,2S,3R,5S)-3-(4-amino-7H-pyrrolo[2,3-d]pyrimidin-7-yl)-5-((5-fluoro-1,2,3,4-tetrahydroisoquinolin-8-yl)oxy)cyclopentane-1,2-diol (TTT-5)

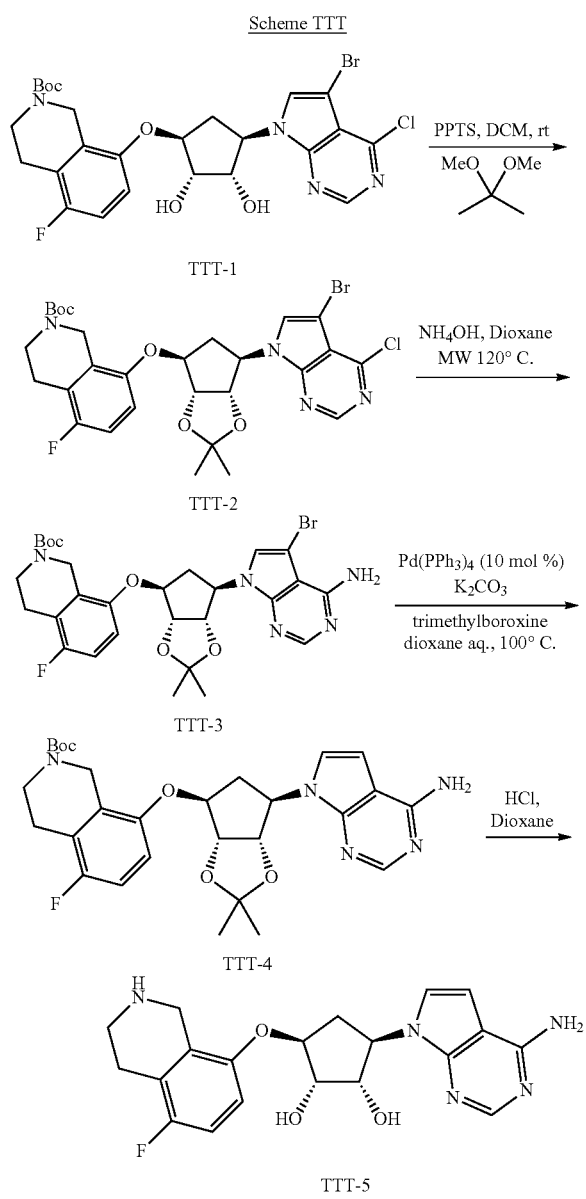

Scheme TTT

Step 1: Synthesis of tert-butyl 8-(((3aR,4S,6R,6aS)-6-(5-bromo-4-chloro-7H-pyrrolo[2,3-d]pyrimidin-7-yl)-2,2-dimethyltetrahydro-4H-cyclopenta[d][1,3]dioxol-4-yl)oxy)-5-fluoro-3,4-dihydroisoquinoline-2(1H)-carboxylate (TTT-2)

Intermediate TTT-1 was prepared by following the general procedures for steps 1-3 in Scheme SS employing TP-2 and 5-bromo-4-chloro-7H-pyrrolo[2,3-d]pyrimidine as the appropriate starting materials.

To a scintillation vial, equipped with a magnetic stirbar and containing intermediate TTT-2 (281 mg, 0.470 mmol), was added DCM (5.0 mL), 2,2-dimethoxypropane (0.58 mL, 4.70 mmol), and PPTS (11.8 mg, 0.047 mmol). The reaction was stirred at rt for 23 hours. The solution was transferred to a separatory funnel with DCM and washed with 2 portions half saturate brine. The organic phase was dried (MgSO$_4$), filtered, and concentrated under vacuum to afford the title compound TTT-2 (266 mg, 89%) as a white solid. LCMS [M+H]=637 observed. $^1$H NMR (400 MHz, CHLOROFORM-d) δ ppm 8.68 (s, 1H), 7.49 (br. s., 1H), 6.97-6.86 (m, 1H), 6.84-6.71 (m, 1H), 5.35 (br. s., 1H), 4.95 (dd, J=2.1, 6.1 Hz, 1H), 4.81 (d, J=6.1 Hz, 2H), 4.48 (br. s., 2H), 3.65 (br. s., 2H), 3.07-2.89 (m, 1H), 2.80 (br. s., 2H), 2.50 (d, J=15.3 Hz, 1H), 1.60 (s, 3H), 1.47 (br. s., 9H), 1.34 (s, 3H).

Step 2: Synthesis of tert-butyl 8-(((3aR,4S,6R,6aS)-6-(4-amino-5-bromo-7H-pyrrolo[2,3-d]pyrimidin-7-yl)-2,2-dimethyltetrahydro-4H-cyclopenta[d][1,3]dioxol-4-yl)oxy)-5-fluoro-3,4-dihydroisoquinoline-2(1H)-carboxylate (TTT-3)

To a microwave vial, equipped with a magnetic stirbar, was added TTT-2 (152 mg, 0.238 mmol) as a solution in dioxane (0.60 mL). To the solution was added ammonium hydroxide (0.6 mL, 5.00 mmol) and the vial was sealed with a Teflon cap. The vial was placed in a microwave reactor and heated to 120 C for 6 hours then allowed to cool to rt overnight. The solution was transferred to a separatory funnel with DCM and diluted with water. The phases were separated and the aqueous phase was extracted with 3 portions of DCM. The combined organic extracts were dried (MgSO$_4$), filtered, and concentrated under vacuum. The crude residue was purified via flash column chromatography (12 g SiO$_2$, Isco, 100% Hept. to 100% EtOAc, 9 mL fractions) to afford the title compound TTT-3 (81 mg, 55%) as a white solid. LCMS [M+H]=618 observed. $^1$H NMR (400 MHz, CHLOROFORM-d) δ ppm 8.31 (s, 1H), 7.16 (s, 1H), 6.98-6.85 (m, 1H), 6.84-6.73 (m, 1H), 5.61 (br. s., 2H), 5.36-5.18 (m, 1H), 4.94 (dd, J=2.5, 6.1 Hz, 1H), 4.82-4.73 (m, 2H), 4.56-4.45 (m, 2H), 3.90-3.42 (m, 2H), 3.02-2.87 (m, 1H), 2.80 (t, J=4.9 Hz, 2H), 2.46 (td, J=4.4, 14.8 Hz, 1H), 1.59 (s, 3H), 1.53-1.42 (m, 9H), 1.33 (s, 3H).

Step 3: Synthesis of tert-butyl 8-(((3aR,4S,6R,6aS)-6-(4-amino-7H-pyrrolo[2,3-d]pyrimidin-7-yl)-2,2-dimethyltetrahydro-4H-cyclopenta[d][1,3]dioxol-4-yl)oxy)-5-fluoro-3,4-dihydroisoquinoline-2(1H)-carboxylate (TTT-4)

To a reaction vial, equipped with a magnetic stirbar, was added TTT-3 (81.0 mg, 0.131 mmol), potassium carbonate (54.3 mg, 0.393 mmol), and Pd(PPh$_3$)$_4$ (15.1 mg, 0.013 mmol). The vial was sealed with a teflon cap and purged with argon under dynamic vacuum. To the vial was added dioxane (0.58 mL) and water (0.07 mL). The vial was transferred to a heating block and heated at 100° C. for 3.5 days. The vial was removed from the heating block and allowed to cool to rt. The reaction was diluted with water and transferred to a separatory funnel with DCM. The phases were separated and the aqueous phase was extracted with 3 portions of DCM. The combined organic extracts were dried (MgSO$_4$), filtered, and concentrated under vacuum. The crude residue was purified via preparative high performance liquid chromatography (Lux 5u Cellulose-2 30×250 mm column, 33% MeOH w/0.05% DEA in CO$_2$, 100 bar, 80 mL/min) to afford the title compound TTT-4 (17.1 mg, 24%) as a white solid. LCMS [M+H]=540 observed. [α]D22=+2.2° (C=0.1, MeOH). $^1$H NMR (400 MHz, CHLOROFORM-d) δ ppm 8.35 (s, 1H), 7.19 (d, J=3.7 Hz, 1H), 6.94-6.85 (m, 1H), 6.84-6.75 (m, 1H), 6.44 (br. s., 1H), 5.34-5.26 (m, 1H), 5.19 (br. s., 2H), 5.01 (dd, J=2.6, 6.2 Hz, 1H), 4.79 (d, J=6.4 Hz, 1H), 4.75 (t, J=5.3 Hz, 1H), 4.44 (br. s., 2H), 3.65 (br. s., 2H), 3.07-2.86 (m, 1H), 2.78 (t, J=5.1 Hz, 2H), 2.59-2.42 (m, 1H), 1.60 (s, 3H), 1.49 (br. s., 9H), 1.33 (s, 3H).

Step 4: Synthesis of (1S,2S,3R,5S)-3-(4-amino-7H-pyrrolo[2,3-d]pyrimidin-7-yl)-5-((5-fluoro-1,2,3,4-tetrahydroisoquinolin-8-yl)oxy)cyclopentane-1,2-diol (TTT-5)

To a scintillation vial, equipped with a magnetic stirbar and containing TTT-4 (17.1 mg, 0.032 mmol), was added water (0.08 mL). To the solution was added hydrochloric acid (0.4 mL, 4.0 M in dioxane, 2 mmol) and the reaction was stirred at rt for 15 hours. The solution was transferred to a separatory funnel with DCM, diluted with water, and neutralized with sat. NaHCO3. The phases were separated and the aqueous phase was extracted with 3 portions of a 3:1 mixture of DCM:IPA. The combined organic extracts were dried (MgSO4), filtered, and concentrated under vacuum. The material thus obtained was freeze-dried to afford the title compound TTT-5 (12.5 mg, >95%) as a white solid. LCMS [M+H]=400 observed. $^1$H NMR (400 MHz, METHANOL-d4) δ ppm 8.08 (s, 1H), 7.22 (d, J=3.7 Hz, 1H), 6.95-6.79 (m, 2H), 6.63 (d, J=3.7 Hz, 1H), 5.12 (q, J=8.6 Hz, 1H), 4.69-4.61 (m, 1H), 4.57 (dd, J=4.8, 8.4 Hz, 1H), 4.16 (d, J=4.3 Hz, 1H), 3.96 (br. s., 2H), 3.08 (t, J=5.1 Hz, 2H), 2.97 (ddd, J=7.3, 9.3, 14.6 Hz, 1H), 2.76 (t, J=5.9 Hz, 2H), 2.04 (ddd, J=3.9, 8.4, 14.1 Hz, 1H).

Example 181 (1S,2S,3S,5R)-3-(3-methyl-5,6,7,8-tetrahydro-2,7-naphthyridin-1-yl)oxy)-5-(4-methyl-7H-pyrrolo[2,3-d]pyrimidin-7-yl)cyclopentane-1,2-diol Scheme UUU

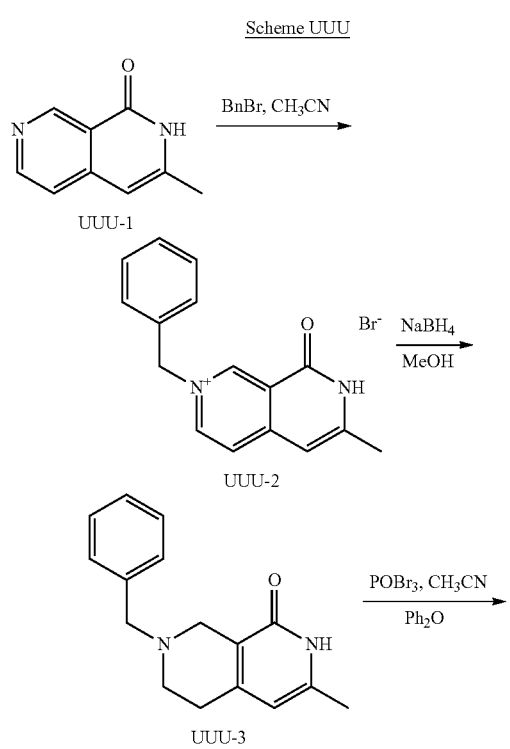

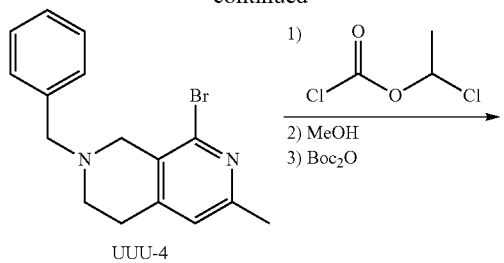

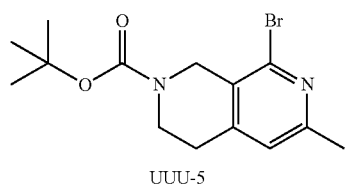

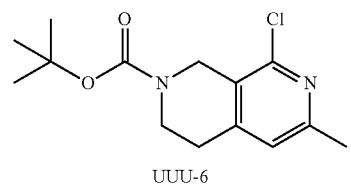

Step 1—Synthesis of 2-benzyl-6-methyl-8-oxo-7,8-dihydro-2,7-naphthyridin-2-ium bromide (UUU-2)

To a mixture of 3-methyl-2,7-naphthyridin-1(2H)-one UUU-1 (prepared in a similar method in patent WO2002068393) (3.9 g, 21.85 mmol) in CH$_3$CN (50 mL) was added BnBr (6.25 g, 36.5 mmol) at rt (25° C.). Then, the mixture was heated at refluxed (85° C.) for 16 hours. The precipitate was collected by filtration, washed with ethanol (30 mL) and dried in vacuo to obtain UUU-2 (4.8 g, 60%) as a yellow solid. LCMS [M-Br] 251; $^1$H NMR (400 MHz, DMSO-d$_6$) δ ppm=12.57 (br s, 1H), 9.77 (s, 1H), 8.88 (d, J=6.8 Hz, 1H), 8.08 (d, J=6.8 Hz, 1H), 7.55 (br d, J=6.8 Hz, 2H), 7.44 (br d, J=7.3 Hz, 3H), 6.70 (s, 1H), 5.86 (s, 2H), 2.40 (s, 3H)

Step 2—Synthesis of 7-benzyl-3-methyl-5,6,7,8-tetrahydro-2,7-naphthyridin-1(2H)-one (UUU-3)

To a solution of compound UUU-2 (4.8 g, 14.49 mmol) in MeOH (50 mL) was added NaBH$_4$ (7.68 g, 203 mmol) in portions for 10 mins at 0° C. then stirred at rt (25° C.) for 4 hours. The mixture was concentrated in vacuo to remove the solvent. DCM (40 mL) was added and filtrated. The filtrate was concentrated in vacuo to get the crude product which was purified by silica gel chromatography (MeOH/DCM=0~10%) to obtain UUU-3 (2.65 g, 72%) as a yellow solid. LCMS [M+1] 255; $^1$H NMR (400 MHz, DMSO-d$_6$) δ ppm=11.33 (br s, 1H), 7.42-7.32 (m, 4H), 7.30-7.24 (m, 1H), 5.78 (s, 1H), 3.63 (s, 2H), 3.11 (s, 2H), 2.59 (br d, J=4.5 Hz, 2H), 2.56 (br d, J=3.5 Hz, 2H), 2.10 (s, 3H)

Step 3-2-benzyl-8-bromo-6-methyl-1,2,3,4-tetrahydro-2,7-naphthyridine (UUU-4)

To a solution of UUU-3 (2.15 g, 8.45 mmol) in CH$_3$CN (20 mL) and Ph$_2$O (40 mL) at rt (25° C.). Then, POBr$_3$ (12.1 g, 42.3 mmol) was added portion-wise and heated at reflux (85° C.) under N$_2$ for 4 hours in which an orange solid began to form after 20 min. The precipitate was collected by filtration, dissolved in water (20 mL), and neutralized with NaHCO$_3$ solution to pH 8. Then, the mixture was extracted with TBME (50 mL×2). The organic layer was washed with brine (25 mL×2), dried over Na$_2$SO$_4$, filtrated and concentrated in vacuo to get crude product which was purified by chromatography (silica gel EtOAc/Petroleum ether=0~40%) to obtain UUU-4 (1.55 g, 58%) as an orange solid. LCMS [M+1] 317; $^1$H NMR (400 MHz, CDCl$_3$) δ ppm=7.40-7.32 (m, 4H), 7.32-7.28 (m, 1H), 6.87 (s, 1H), 3.75 (s, 2H), 3.59 (s, 2H), 2.84-2.78 (m, 2H), 2.69-2.64 (m, 2H), 2.47 (s, 3H)

Step 4—Synthesis of tert-butyl 8-bromo-6-methyl-3,4-dihydro-2,7-naphthyridine-2(1H)-carboxylate (UUU-5) and tert-butyl 8-chloro-6-methyl-3,4-dihydro-2,7-naphthyridine-2(1H)-carboxylate (UUU-6)

To a solution of compound UUU-4 (1.30 g, 4.1 mmol) in DCM (15 mL) was added drop-wise 1-chloroethyl chloroformate (0.62 mL, 5.74 mmol) at rt (0° C.) for 1 min. Then, the mixture was warmed up to rt (20° C.) stirred for 10 mins and heated at refluxed (40° C.) for 2 hours. The mixture was concentrated in vacuo to remove the solvent. Then the solid was dissolved in MeOH (15 mL) and heated at refluxed (63° C.) for 1.5 hours. Then (Boc)$_2$O (1.07 g 4.92 mmol) and Et$_3$N (1.71 mL,12.3 mmol) were added. The mixture was heated at (63° C.) for 16 hours. The mixture was concentrated in vacuo to get crude product which was purified by chromatography (silica gel MeOH/DCM=0~10%) to get product a mixture of compound UUU-5 and UUU-6 in a ~1:1 ratio (872 mg) as a white solid and used directly in the next step. LCMS [M+1] 327 and 283.

Steps 5-7 were Performed in a Similar Manner as Steps 2-4 in Scheme GGG Using FFF-1

Synthesis of tert-butyl-5-fluoro-8-hydroxy-4-methyl-3,4-dihydroisoquinoline-2(1H)-carboxylate (TP-31)

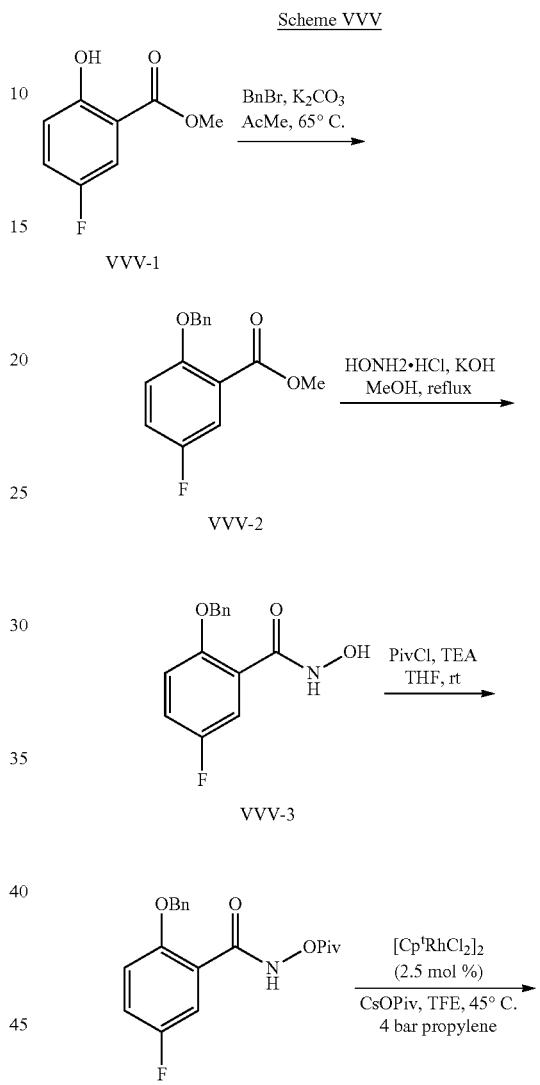

| Example 181 | 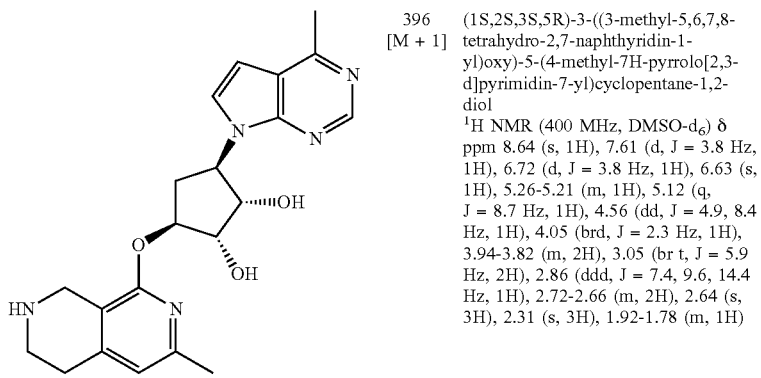 | 396 [M + 1] | (1S,2S,3S,5R)-3-((3-methyl-5,6,7,8-tetrahydro-2,7-naphthyridin-1-yl)oxy)-5-(4-methyl-7H-pyrrolo[2,3-d]pyrimidin-7-yl)cyclopentane-1,2-diol $^1$H NMR (400 MHz, DMSO-d$_6$) δ ppm 8.64 (s, 1H), 7.61 (d, J = 3.8 Hz, 1H), 6.72 (d, J = 3.8 Hz, 1H), 6.63 (s, 1H), 5.26-5.21 (m, 1H), 5.12 (q, J = 8.7 Hz, 1H), 4.56 (dd, J = 4.9, 8.4 Hz, 1H), 4.05 (brd, J = 2.3 Hz, 1H), 3.94-3.82 (m, 2H), 3.05 (br t, J = 5.9 Hz, 2H), 2.86 (ddd, J = 7.4, 9.6, 14.4 Hz, 1H), 2.72-2.66 (m, 2H), 2.64 (s, 3H), 2.31 (s, 3H), 1.92-1.78 (m, 1H) |
|---|---|---|---|

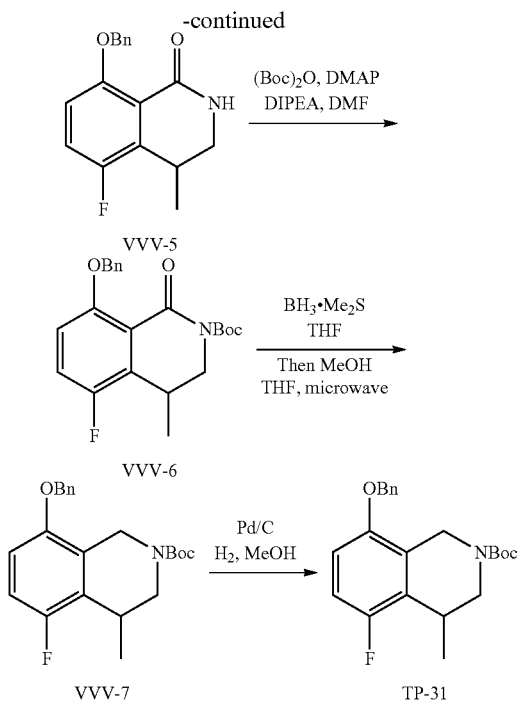

Step 1: Synthesis of methyl 2-(benzyloxy)-5-fluorobenzoate (VVV-2)

To a round bottom flask, equipped with a magnetic stirbar, was added methyl 5-fluoro-2-hydroxybenzoate VVV-1 (3.68 g, 21.6 mmol), potassium carbonate (10.5 g, 75.7 mmol), and acetone (108 mL). To the solution was added benzyl bromide (2.70 mL, 22.7 mmol) and the flask was fitted with a Findenser™. The flask was placed in a heating mantle and heated at 65° C. for 13 hours. The flask was removed from the heating block and allowed to cool to rt. The solids were filtered over a bed of celite and washed with several portions of acetone. The filtrate was concentrated under vacuum and transferred to a separatory funnel with EtOAc (~100 mL). The solution was washed with 2 portions of half sat. brine, dried (MgSO$_4$), filtered, and concentrated under vacuum to afford the title compound VVV-2 (5.64 g, >95% yield) as a white crystalline solid. This material was used in the next step without further purification. $^1$H NMR (400 MHz, CHLOROFORM-d) δ ppm 7.54 (dd, J=3.3, 8.7 Hz, 1H), 7.51-7.45 (m, 2H), 7.44-7.36 (m, 2H), 7.36-7.29 (m, 1H), 7.14 (ddd, J=3.2, 7.5, 9.1 Hz, 1H), 6.97 (dd, J=4.3, 9.0 Hz, 1H), 5.16 (s, 2H), 3.92 (s, 3H). $^{19}$F NMR (376 MHz, CHLOROFORM-d) δ ppm −122.59 (s, 1F).

Step 2: Synthesis of 2-(benzyloxy)-5-fluoro-N-hydroxybenzamide (VVV-3)

To a round bottom flask, equipped with a magnetic stirbar and containing VVV-2 (5.64 g, 21.7 mmol), was added hydroxyl amine hydrochloride (4.52 g, 65.0 mmol), potassium hydroxide (7.29 g, 130 mmol), and methanol (108 mL). The flask was fitted with a Findenser™ and placed in a heating mantle. The reaction was heated at 75° C. for 3.5 hours. The reaction was removed from the heating mantle and allowed to gradually cool to rt. The solution was neutralized with acetic acid and concentrated under vacuum. The residue was transferred to a separatory funnel with EtOAc and diluted with water. The phases were separated and the aqueous phase was extracted with 3 100 mL portions of EtOAc. The organic extracts were dried (MgSO$_4$), filtered, and concentrated under vacuum to afford the title compound VVV-3 (5.62 g, >95% yield) as a white solid. The material was used in the next step without further purification. LCMS [M+H]=262 observed. $^1$H NMR (400 MHz, DMSO-d6) δ ppm 10.71 (s, 1H), 9.18 (d, J=1.5 Hz, 1H), 7.47 (d, J=7.3 Hz, 2H), 7.39 (t, J=7.4 Hz, 2H), 7.35-7.27 (m, 2H), 7.25 (dd, J=3.2, 8.3 Hz, 1H), 7.19-7.13 (m, 1H), 5.20 (s, 2H). $^{19}$F NMR (376 MHz, DMSO-d6) δ ppm −123.18 (s, 1F).

Step 3: Synthesis of 2-(benzyloxy)-5-fluoro-N-(pivaloyloxy)benzamide (VVV-4)

To a round bottom flask, equipped with a magnetic stir bar and containing VVV-3 (3.0 g, 11.5 mmol), was added THF (35 mL) and triethyl amine (1.60 mL, 11.5 mmol) followed by the dropwise addition of pivaloyl chloride (1.55 mL, 12.6 mmol). The reaction was stirred at rt for 30 minutes. The reaction was transferred to a separatory funnel with EtOAc. The solution was washed with 2 portions 1 M HCl aq., 1 portion half saturate NaHCO3, and 2 portions brine. The organic solution was then dried (MgSO$_4$), filtered, and concentrated under vacuum. The crude residue was purified via flash column chromatography (40 g SiO$_2$, Isco, 100% Hept. to 100% EtOAc, 20 mL fractions) to afford the title compound (3.83 g, >95%) as a colorless oil solvated with EtOAc. The oil was taken up in DCM and diluted with Heptane followed by concentration under vacuum. The material obtained was further dried under high vacuum overnight to afford the title compound VVV-4 (3.59 g, 90%) as a white solid. LCMS [M+H]=346 observed. $^1$H NMR (400 MHz, CHLOROFORM-d) δ ppm 10.95 (s, 1H), 7.89 (dd, J=3.2, 9.1 Hz, 1H), 7.53-7.33 (m, 5H), 7.16 (ddd, J=3.3, 7.2, 9.0 Hz, 1H), 7.00 (dd, J=4.1, 9.1 Hz, 1H), 5.27 (s, 2H), 1.35 (s, 9H).

Step 4: Synthesis of 8-(benzyloxy)-5-fluoro-4-methyl-3,4-dihydroisoquinolin-1(2H)-one (VVV-5)

To a scintillation vial, equipped with a magnetic stirbar, was added VVV-4 (500 mg, 1.45 mmol), cesium pivalate (678 mg, 2.90 mmol), and [Cp$^r$RhCl$_2$]$_2$ (25.4 mg, 0.036 mmol). The contents of the vial were transferred to a high pressure reactor and TFE (7.0 mL) was added. The reactor was purged with nitrogen 3 times followed by 3 cycles of purging with propylene gas. The reaction was heated to 45° C. under 4 bar pressure of propylene gas for 20 hours. The solution was transferred to a round bottom flask and concentrated under vacuum. The crude residue was purified via flash column chromatography (24 g SiO$_2$, Isco, 100% Hept. to 100% EtOAc, 9 mL fractions) to afford the title compound VVV-5 (270 mg, 65%, 93:7 r.r.) as a light pink solid. HSCQC and HOESY analyses are consistent with the assigned regioisomer. LCMS [M+H]=286 observed. $^1$H NMR (400 MHz, CHLOROFORM-d) δ ppm 7.55 (d, J=7.5 Hz, 2H), 7.43-7.34 (m, 2H), 7.30 (d, J=7.3 Hz, 1H), 7.10 (t, J=8.8 Hz, 1H), 6.87 (dd, J=4.3, 9.0 Hz, 1H), 5.98 (d, J=3.7 Hz, 1H), 5.29-5.21 (m, 1H), 5.18-5.11 (m, 1H), 3.70 (ddd, J=0.7, 4.0, 12.6 Hz, 1H), 3.38-3.28 (m, 1H), 3.23 (ddd, J=1.5, 6.0, 12.6 Hz, 1H), 1.35 (d, J=7.0 Hz, 3H). $^{19}$F NMR (376 MHz, CHLOROFORM-d) δ ppm −129.24 (s, 1F).

Step 5: Synthesis of tert-butyl-8-(benzyloxy)-5-fluoro-4-methyl-1-oxo-3,4-dihydroisoquinoline-2(1H)-carboxylate (VVV-6)

To a round bottom flask, equipped with a magnetic stirbar, was added VVV-5 (100 mg, 0.350 mmol) as a solution in DMF (4.0 mL). The solution was cooled to 10° C. followed by the addition of (Boc)$_2$O (84.1 mg, 0.386 mmol), DIPEA (92 µL, 0.526 mmol) and DMAP (2.1 mg, 0.017 mmol). The reaction was allowed to stir at rt for 16 hours providing low conversion to desired product. The reaction was then heated at 50° C. for 24 hours and then increased to 75° C. for an additional 24 hours in order to achieve complete consumption of starting material. The reaction was diluted with water and transferred to a separatory funnel with EtOAc. The phases were separated and the organic phase was washed with 1 portion brine, dried (Ns$_2$SO$_4$), filtered, and concentrated under vacuum. The crude residue was purified via flash column chromatography (SiO$_2$, 1% EtOAc/Pet. Ether to 40% EtOAc/Pet. Ether) to afford the title compound VVV-6 (100 mg, 74%) as a colorless gum. LCMS [M+H-Boc]=286 observed.

Step 6: Synthesis of tert-butyl-8-(benzyloxy)-5-fluoro-4-methyl-3,4-dihydroisoquinoline-2(1H)-carboxylate (VVV-7)

To a round bottom flask, equipped with a magnetic stir bar, was added VVV-6 (100 mg, 0.259 mmol) as a solution in THF. The solution was cooled to 0° C. followed by the dropwise addition of BH$_3$.THF. Upon completion of the addition, the reaction was removed from the ice bath and heated to 60° C. under nitrogen for 6 hours. At this stage the reaction was cooled to −10° C. and quenched by the careful dropwise addition of MeOH. The reaction was allowed to stir at −10° C. for 16 hours and then concentrated under vacuum. The crude residue was purified via preparative thin layer chromatography (SiO$_2$, 20% EtOAc/Pet. Ether) to afford the title compound VVV-7 (35.0 mg, 36%) as a colorless gum. LCMS [M+H-lsobutylene]=316 observed.

Step 7: Synthesis of tert-butyl-5-fluoro-8-hydroxy-4-methyl-3,4-dihydroisoquinoline-2(1H)-carboxylate (TP-31)

To a round bottom flask, equipped with a magnetic stirbar, was added VVV-7 (70 mg, 0.190 mmol) as a solution in MeOH (4.5 mL). To the solution was added Pd/C (10.0 mg, 0.094 mmol) and the headspace of the flask was purged with hydrogen 5 times. The reaction was allowed to stir at rt under 1 atm hydrogen gas for 2.5 hours. The reaction was filtered and the solids were washed with DCM. The filtrate was concentrated under vacuum and the crude residue was purified via preparative thin layer chromatography (SiO$_2$, 20% EtOAc/Pet. Ether) to afford the title compound TP-31 (45 mg, 85%) as a colorless gum. LCMS [M+H-lsobutylene]=226 observed. $^1$H NMR (400 MHz, CHLOROFORM-d) δ ppm 6.76 (br t, J=8.8 Hz, 1H), 6.55 (dd, J=4.4, 8.7 Hz, 1H), 5.14-4.78 (m, 2H), 4.22-3.95 (m, 2H), 3.23-2.94 (m, 2H), 1.54-1.46 (s, 9H), 1.23 (d, J=7.3 Hz, 3H).

Synthesis of tert-butyl(8-hydroxy-1,2,3,4-tetrahydronaphthalen-1-yl)carbamate (TP-32)

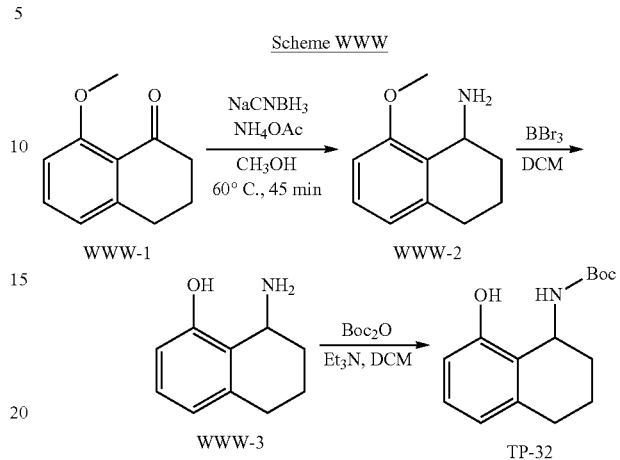

Scheme WWW

Step 1—Synthesis of 8-methoxy-1,2,3,4-tetrahydronaphthalen-1-amine (WWW-2)

To a stirred yellow suspension of 8-methoxy-3,4-dihydronaphthalen-1(2H)-one WWW-1 (600 mg, 3.4 mmol) in MeOH (30 mL) was added CH$_3$COONH$_4$ (5.25 g, 68 mmol) at 15° C. The mixture was stirred at 15° C. for 15 min and then, NaBH$_3$CN (1.5 g, 24 mmol) was added at 15° C. The mixture was irradiated in a microwave reactor at 60° C. for 45 min. The mixture was quenched by sat.NaHCO$_3$ (15 mL) and H$_2$O (15 mL) and stirred at 15° C. for 5 min. The mixture was concentrated to remove MeOH. The residue was extracted with DCM (20 mL×2). The combined organic layers were washed with brine (10 mL), dried over Na$_2$SO$_4$, filtered and concentrated to give crude WWW-2 (580 mg, 96%) as a slight pink gum and used as is in the next step.

Step 2—Synthesis of 8-amino-5,6,7,8-tetrahydronaphthalen-1-ol (WWW-3)

Compound WWW-2 (550 mg, 3.10 mmol) was dissolved in HCl/dioxane (5.00 mL), the solution was stirred at 15° C. for 10 min. Then the solution was evaporated to give a residue. The residue was dissolved in DCM and cooled to 0° C. on an ice bath. Then BBr$_3$ (7.77 mg, 31.0 mmol) was added to the reaction solution dropwise. The reaction solution was stirred at 20° C. for 5 hrs. The reaction solution was quenched with MeOH (8.00 mL), then the pH of the solution was adjusted to pH=7 by the addition of saturated aq NaHCO$_3$. The final solution of WWW-3 was used for the next step directly (100 mL).

Step 3—Synthesis of tert-butyl(8-hydroxy-1,2,3,4-tetrahydronaphthalen-1-yl)carbamate (TP-32)

To a solution of (Boc)$_2$O (730 mg, 3.34 mmol) in dioxane (5.00 mL) was added the solution of compound WWW-3 (solution in aq. sat. NaHCO$_3$, 15 mL~3.3 mmol) at 0° C. in one portion. The reaction solution was stirred at 20° C. for 50 hours. The reaction was extracted with DCM (2×) and the organics combined and washed with sat. citric acid (2×15 mL), aq sat. Na$_2$CO$_3$ (2×15 mL), and brine (2×15 mL). The organics were dried and evaporated to give a residue which was purified by prep-TLC (Petroleum Ether/EtOAc=4/1) to give TP-32 (410 mg, 50%) as a white solid. LCMS [M-tBu+1] 207; ¹H NMR (400 MHz, DMSO-d₆) δ ppm 9.20 (s, 1H), 6.96 (t, J=7.8 Hz, 1H), 6.78 (br d, J=7.5 Hz, 1H), 6.57 (d, J=7.7 Hz, 1H), 6.51 (d, J=7.4 Hz, 1H), 4.80-4.71 (m, 1H), 2.72-2.63 (m, 1H), 2.61-2.53 (m, 1H), 1.89-1.74 (m, 2H), 1.67-1.46 (m, 2H), 1.39 (s, 9H)

Synthesis of tert-butyl(5-hydroxychroman-3-yl)carbamate (TP-33)

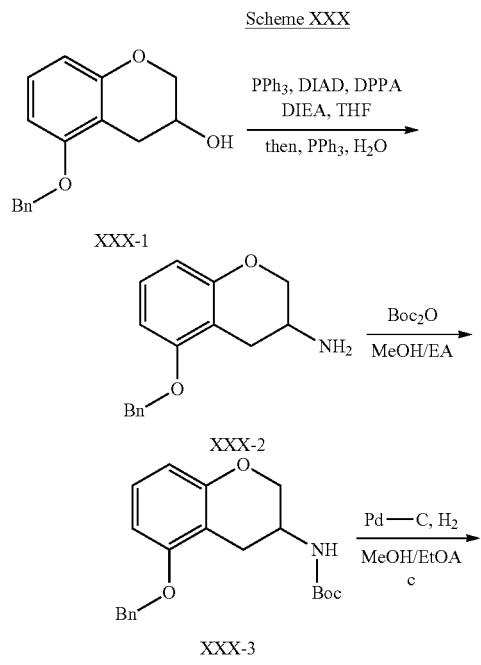

Step 1—Synthesis of 5-(benzyloxy)chroman-3-amine (XXX-2)

Compound XXX-1 (700 mg, 2.73 mmol, prepared using exact procedures in literature *J. Org. Chem,* 2013, 78, 7859-7884) was introduced to similar Mitsunobu and Staudinger procedures in the same reference to give the product XXX-2 (520 mg, 75%) as a colorless gum, used in the next step directly. LCMS [M+1] 266; ¹H NMR (400 MHz, CDCl₃) δ ppm 7.48-7.36 (m, 4H), 7.36-7.30 (m, 1H), 7.07 (t, J=8.3 Hz, 1H), 6.52 (dd, J=2.5, 8.3 Hz, 2H), 5.07 (s, 2H), 4.18-4.07 (m, 1H), 3.80 (ddd, J=1.0, 7.3, 10.5 Hz, 1H), 3.43-3.29 (m, 1H), 3.07 (dd, J=5.0, 16.6 Hz, 1H), 2.50 (dd, J=7.3, 16.8 Hz, 1H)

Step 2—Synthesis of tert-butyl(5-(benzyloxy)chroman-3-yl)carbamate (XXX-3)

To a solution of XXX-2 (520 mg, 2.04 mmol) in dry MeOH (20 mL) was added Boc₂O (889 mg, 4.07 mmol) at rt and stirred for 30 min (20 mL of EtOAc added for solubility). The mixture was concentrated in vacuo to afford crude material which was purified by silica gel chromatography eluted with EtOAc in petroleum ether from 0 to 50% then EtOAc in DCM from 0 to 50% to afford XXX-3 (620 mg, 76%) as white solid. LCMS [M-tBu+1] 300; ¹H NMR (400 MHz, CDCl₃) δ ppm 7.45-7.36 (m, 4H), 7.34 (br d, J=6.8 Hz, 1H), 7.12-7.05 (m, 1H), 6.53 (d, J=8.3 Hz, 2H), 5.06 (s, 2H), 4.91-4.79 (m, 1H), 4.26-4.15 (m, 1H), 4.08 (br s, 2H), 3.01-2.92 (m, 1H), 2.81-2.69 (m, 1H), 1.44 (s, 9H)

Step 3—Synthesis of tert-butyl(5-hydroxychroman-3-yl)carbamate (TP-33)

A mixture of XXX-3 (620 mg, 2.43 mmol) and Pd/C (300 mg) in MeOH/EtOAc (10 mL/10 mL) was degassed with H₂ four times. The mixture was stirred at rt under an H₂ balloon for 16 hrs. The mixture was filtered and concentrated. (Excess Boc₂O from the previous step also Boc-protected the phenol, therefore MeOH (20 mL) and K₂CO₃ (2 g) were added and stirred for 2 h, then filtered). The mixture was filtered and concentrated. The crude material was diluted with EtOAc and was washed with brine (15 mL), dried over Na₂SO₄ and concentrated in vacuo then lyophilized to afford TP-33 (420 mg, 91%) as a white solid. LCMS [M-tBu+1] 210; ¹H NMR (400 MHz, CDCl₃) δ ppm 6.99 (t, J=8.2 Hz, 1H), 6.48 (d, J=8.3 Hz, 1H), 6.40 (d, J=8.0 Hz, 1H), 5.19 (br s, 1H), 4.96-4.89 (m, 1H), 4.22 (br s, 1H), 4.15-4.03 (m, 2H), 2.91 (dd, J=5.5, 16.8 Hz, 1H), 2.71 (br d, J=17.3 Hz, 1H), 1.45 (s, 9H)

Example 182 and Example 183

(Scheme YYY)—(1S,2S,3S,5R)-3-((-5-fluoro-4-methyl-1,2,3,4-tetrahydroisoquinolin-8-yl)oxy)-5-(4-methyl-7H-pyrrolo[2,3-d]pyrimidin-7-yl)cyclopentane-1,2-diol hydrochloride (YYY-3-isomer 1 and YYY-3-isomer 2)

Scheme YYY

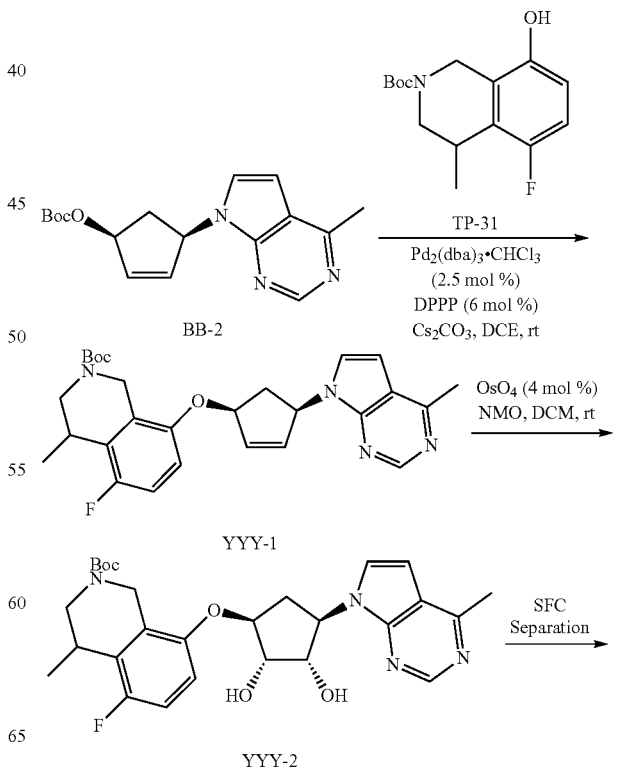

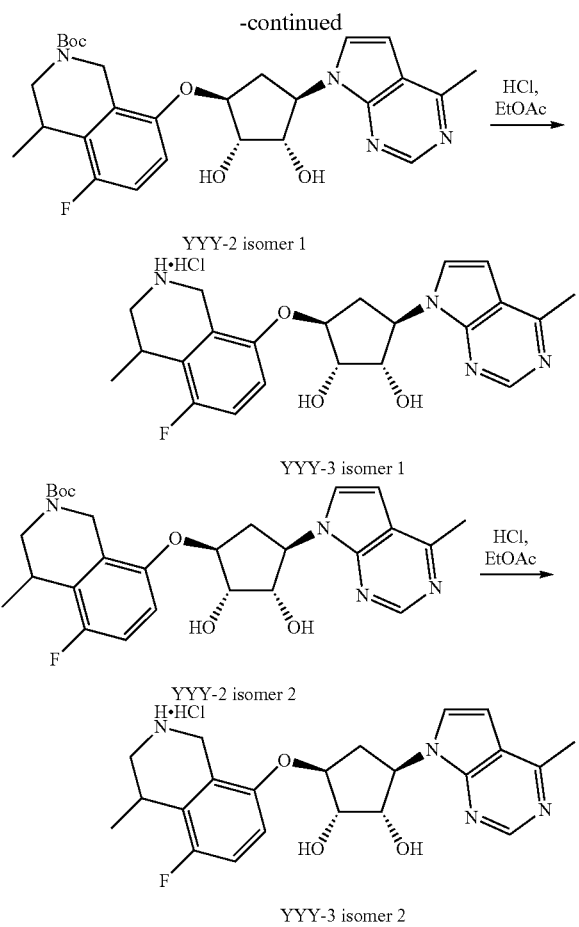

YYY-2 isomer 1

YYY-3 isomer 1

YYY-2 isomer 2

YYY-3 isomer 2

Step 1: Synthesis of tert-butyl-5-fluoro-4-methyl-8-(((1S,4R)-4-(4-methyl-7H-pyrrolo[2,3-d]pyrimidin-7-yl)cyclopent-2-en-1-yl)oxy)-3,4-dihydroisoquinoline-2(1H)-carboxylate (YYY-1)

To a microwave vial, equipped with a magnetic stirbar, was added TP-31 (45 mg, 0.160 mmol), BB-2 (50.4 mg, 0.160 mmol), Pd$_2$(dba)$_3$·CHCl$_3$ (4.14 mg, 0.004 mmol), DPPP (3.96 mg, 0.010 mmol), and cesium carbonate (57.3 mg, 0.176 mmol). The vial was purged with nitrogen under dynamic vacuum and freshly degassed DCE (1.0 mL) was added. The solution was stirred at rt under nitrogen for 1 hour. The solution was concentrated under vacuum and the crude residue was purified via preparative thin layer chromatography (SiO$_2$, 33% EtOAc/Pet. Ether) to afford the title compound YYY-1 (60 mg, 86%) as a gum. LCMS [M+H]=579 observed. 1H NMR (400 MHz, CHLOROFORM-d) δ ppm 8.76 (s, 1H), 7.35-7.28 (m, 1H), 6.84 (br t, J=8.7 Hz, 1H), 6.73-6.51 (m, 2H), 6.37 (br s, 1H), 6.19-5.99 (m, 2H), 5.28 (br s, 1H), 4.24-3.95 (m, 2H), 3.22-3.05 (m, 3H), 2.73 (d, J=2.5 Hz, 3H), 1.96 (br d, J=14.6 Hz, 1H), 1.69-1.63 (m, 1H), 1.50 (s, 9H), 1.23 (t, J=7.0 Hz, 3H)

Step 2: Synthesis of tert-butyl-8-(((1S,2S,3S,4R)-2,3-dihydroxy-4-(4-methyl-7H-pyrrolo[2,3-d]pyrimidin-7-yl)cyclopentyl)oxy)-5-fluoro-4-methyl-3,4-dihydroisoquinoline-2(1H)-carboxylate (YYY-2)

To a reaction vial, equipped with a magnetic stirbar, was added YYY-1 (60.0 mg, 0.130 mmol) as a solution in DCM (6.0 mL). To the solution was added water (0.2 mL), NMO (44.1 mg, 0.376 mmol) and OsO$_4$ (112 mg, 0.0176 mmol). The reaction was allowed to stir at rt for 5 hours. The reaction was quenched with sat. Na$_2$SO$_3$ (5 mL) and transferred to a separatory funnel with DCM. The phases were separated and the aqueous phase was extracted with 1 portion DCM. The combined organic extracts were dried (Na$_2$SO$_4$), filtered, and concentrated under vacuum. The crude residue was purified via preparative thin layer chromatography to afford the title compound YYY-2 (35 mg, 54%) as a colorless gum. LCMS [M+H]=513 observed.

Step 3: Synthesis of tert-butyl-8-(((1S,2S,3S,4R)-2,3-dihydroxy-4-(4-methyl-7H-pyrrolo[2,3-d]pyrimidin-7-yl)cyclopentyl)oxy)-5-fluoro-4-methyl-3,4-dihydroisoquinoline-2(1H)-carboxylate (YYY-2-isomer 1 & YYY-2-isomer 2)

YYY-2 (30 mg, 0.058 mmol) was further purified via preparative super-critical fluid chromatography (OD 250 mm×30 mm×5 µm, 0.1% NH$_4$OH/IPA to 30% NH$_4$OH/IPA, 60 mL/min) to afford the separated diastereomers YYY-2-isomer 1 (15 mg, 50%) and YYY-2-isomer 2 (15 mg, 50%) as white solids. LCMS [M+H]=513 observed.

Step 4 employing YYY-2-isomer 1: Synthesis of (1S,2S,3S,5R)-3-((-5-fluoro-4-methyl-1,2,3,4-tetrahydroisoquinolin-8-yl)oxy)-5-(4-methyl-7H-pyrrolo[2,3-d]pyrimidin-7-yl)cyclopentane-1,2-diol hydrochloride (YYY-3-isomer 1)

To a reaction vial, equipped with a magnetic stirbar, was added YYY-2-isomer 1 (15 mg, 0.029 mmol) as a solution in EtOAc (1.0 mL). The solution was cooled to 0° C. followed by the addition of HCl (4M EtOAc, 59 µL). The reaction was removed from the ice bath and stirred at rt for 16 hours. The solution was concentrated under vacuum followed by free-drying to afford the title compound YYY-3-isomer 1 (8.26 mg, 63%) as a white solid. LCMS [M+H]=413 observed. $^1$H NMR (400 MHz, METHANOL-d4) δ ppm 9.05 (d, J=3.3 Hz, 1H), 8.08 (d, J=2.4 Hz, 1H), 7.24 (d, J=3.7 Hz, 1H), 7.15-6.99 (m, 2H), 5.41 (q, J=9.3 Hz, 1H), 4.76 (br d, J=4.8 Hz, 2H), 4.52-4.41 (m, 1H), 4.36-4.27 (m, 1H), 4.23 (d, J=4.8 Hz, 1H), 3.57-3.40 (m, 3H), 3.12-2.99 (m, 4H), 2.27 (dt, J=5.1, 9.5 Hz, 1H), 1.47 (d, J=6.7 Hz, 3H).

Step 4 employing YYY-2-isomer 2: Synthesis of (1S,2S,3S,5R)-3-((-5-fluoro-4-methyl-1,2,3,4-tetrahydroisoquinolin-8-yl)oxy)-5-(4-methyl-7H-pyrrolo[2,3-d]pyrimidin-7-yl)cyclopentane-1,2-diol hydrochloride (YYY-3-isomer 2))

To a reaction vial, equipped with a magnetic stirbar, was added YYY-2-isomer 2 (15 mg, 0.029 mmol) as a solution in EtOAc (1.0 mL). The solution was cooled to 0° C. followed by the addition of HCl (4M EtOAc, 59 µL). The reaction was removed from the ice bath and stirred at rt for 16 hours. The solution was concentrated under vacuum followed by free-drying to afford the title compound YYY-2-isomer 2 (8.48 mg, 70%) as a white solid. LCMS [M+H]=413 observed. $^1$H NMR (400 MHz, METHANOL-d4) δ ppm 9.04 (d, J=3.0 Hz, 1H), 8.06 (d, J=3.2 Hz, 1H), 7.24 (d, J=3.7 Hz, 1H), 7.16-7.01 (m, 2H), 5.42 (q, J=9.4 Hz, 1H), 4.77-4.70 (m, 2H), 4.48-4.39 (m, 1H), 4.36-4.27 (m, 1H), 4.21 (d, J=4.7 Hz, 1H), 3.55-3.40 (m, 3H), 3.17-2.96 (m, 4H), 2.33-2.18 (m, 1H), 1.46 (d, J=6.7 Hz, 3H).

Examples 184-189 were Made in a Similar Fashion as Examples 182 & 183 (Scheme YYY) Starting with the Appropriate Racemic Tetrahydroisoquinoline in Step 1 and Separating the Diastereomers Prior to the Final Deprotection

| Examples 184 & 185 TP-28 | | | |
|---|---|---|---|
| 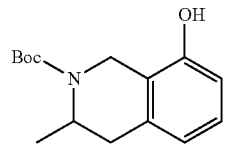 | 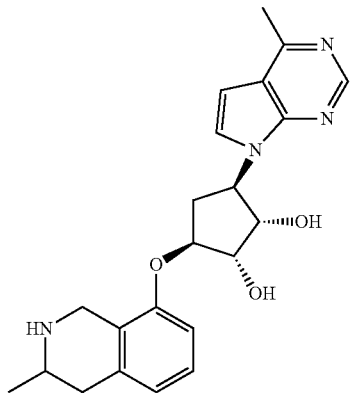 [SMILES: Cc1ncnc2c1ccn2[C@@H]1C[C@H](Oc2cccc3c2CNC(C)C3)[C@@H](O)[C@H]1O] | 395 LCMS [M + 1] | (1S,2S,3S,5R)-3-((3-methyl-1,2,3,4-tetrahydroisoquinolin-8-yl)oxy)-5-(4-methyl-7H-pyrrolo[2,3-d]pyrimidin-7-yl)cyclopentane-1,2-diol Example 184 (Isomer 1) - $^1$H NMR (400MHz, METHANOL-d4) δ ppm 9.07 (s, 1H), 8.08 (d, J = 3.8 Hz, 1H), 7.31 (t, J = 8.0 Hz, 1H), 7.25 (d, J = 3.8 Hz, 1H), 7.01 (d, J = 8.3 Hz, 1H), 6.90 (d, J = 7.8 Hz, 1H), 5.42 (q, J = 9.2 Hz, 1H), 4.83-4.73 (m, 2H), 4.54 (d, J = 16.3 Hz, 1H), 4.34 (d, J = 16.6 Hz, 1H), 4.24 (d, J = 4.5 Hz, 1H), 3.73-3.62 (m, 1H), 3.23-3.04 (m, 2H), 3.03-2.91 (m, 4H), 2.32-2.23 (m, 1H), 1.54 (d, J = 6.5 Hz, 3H). Example 185 (Isomer 2) - $^1$H NMR (400MHz, METHANOL-d4) 9.08 (s, 1H), 8.06 (d, J = 3.8 Hz, 1H), 7.31 (t, J = 8.0 Hz, 1H), 7.24 (d, J = 3.8 Hz, 1H), 7.01 (d, J = 8.3 Hz, 1H), 6.90 (d, J = 7.5 Hz, 1H), 5.41 (q, J = 9.2 Hz, 1H), 4.84-4.73 (m, 2H), 4.59-4.50 (m, 1H), 4.34 (d, J = 16.8 Hz, 1H), 4.22 (d, J = 5.0 Hz, 1H), 3.70-3.60 (m, 1H), 3.21-3.05 (m, 2H), 3.04-2.92 (m, 4H), 2.34-2.25 (m, 1H), 1.55 (d, J = 6.3Hz, 3H) |
| Examples 186 & 187 TP-32 | | | |
| 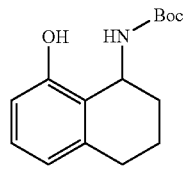 | 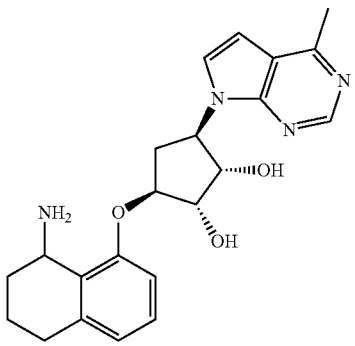 | 378 LCMS [M − 16 + 1] | (1S,2S,3S,5R)-3-((8-amino-5,6,7 8-tetrahydronaphthalen-1-yl)oxy)-5-(4-methyl-7H-pyrrolo[2,3-d]pyrimidin-7-yl)cyclopentane-1,2-diol Example 186 (Isomer 1) - $^1$H NMR (400 MHz, MeOD-d$_4$) δ ppm 8.71 (s, 1H), 7.74 (d, J = 3.8 Hz, 1H), 7.34 (t, J = 8.0 Hz, 1H), 7.05 (d, J = 8.3 Hz, 1H), 6.89 (d, J = 7.8 Hz, 1H), 6.86 (d, J = 3.5 Hz, 1H), 5.18 (q, J = 9.4 Hz, 1H), 4.84-4.79 (m, 3H), 4.22 (d, J = 5.3 Hz, 1H), 3.06 (td, J = 8.4, 14.3 Hz, 1H), 2.98-2.88 (m, 1H), 2.88-2.81 (m, 1H), 2.80 (s, 3H), 2.50 (ddd, J = 4.3, 10.0, 14.1 Hz, 1H), 2.25-2.10 (m, 2H), 1.98-1.89 (m, 2H) Example 187 (Isomer 2) - $^1$H NMR (400 MHz, MeOD-d$_4$) δ ppm 8.63 (s, 1H), 7.53 (d, J = 3.5 Hz, 1H), 7.15 (t, J = 8.0 Hz, 1H), 6.89 (d, J = 8.3 Hz, 1H), 6.78-6.72 (m, 2H), 5.18 (q, J = 9.1 Hz, 1H), 4.82 (dd, J = 5.0, 8.5 Hz, 1H), 4.78-4.72 (m, 1H), 4.40-4.29 (m, 2H), 3.04-2.93 (m, 1H), 2.89-2.74 (m, 2H), 2.73 (s, 3H), 2.36-2.23 (m, 1H), 2.02-1.86 (m, 3H), 1.80 (d, J = 4.5 Hz, 1H) |
| Example 188 & 189 TP-33 | | | |
| 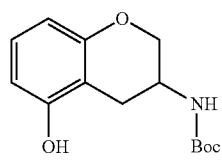 [SMILES: CC(C)(C)OC(=O)NC1COc2cccc(O)c2C1] | 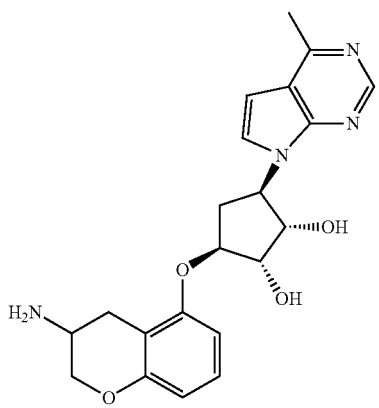 [SMILES: Cc1ncnc2c1ccn2[C@@H]1C[C@H](Oc2cccc3c2CC(N)CO3)[C@@H](O)[C@H]1O] | 397 LCMS [M + 1] | (1S,2S,3S,5R)-3-((3-aminochroman-5-yl)oxy)-5-(4-methyl-7H-pyrrolo[2,3-d]pyrimidin-7-yl)cyclopentane-1,2-diol Example 188 (Isomer 1) - $^1$H NMR (400 MHz, D$_2$O) δ ppm 8.82 (s, 1H), 7.81 (d, J = 3.8 Hz, 1H), 7.15 (t, J = 8.3 Hz, 1H), 7.08 (d, J = 4.0 Hz, 1H), 6.65 (d, J = 7.8 Hz, 1H), 6.56 (d, J = 8.3 Hz, 1H), 5.33 (q, J = 9.1 Hz, 1H), 4.77-4.73 (m, 1H), 4.62 (dd, J = 5.1, 8.7 Hz, 1H), 4.32-4.22 (m, 2H), 4.14 (d, J = 11.3 Hz, 1H), 3.97 (br d, J = 1.8 Hz, 1H), 3.13 (dd, J = 6.3, 18.1 Hz, 1H), 3.02 (ddd, J = 7.0, 9.8, 15.1 Hz, 1H), 2.87 (m, 4H), 2.21-2.12 (m, 1H) Example 189 (Isomer 2) - $^1$H NMR (400 MHz, D$_2$O) δ ppm 8.84 (s, 1H), 7.80 (d, J = 4.0 Hz, 1H), 7.17 (t, J = 8.3 Hz, 1H), 7.10 (d, J = 3.8 Hz, 1H), 6.66 (d, J = 8.0 Hz, 1H), 6.58 (d, J = 8.5 Hz, 1H), 5.41-5.31 (m, 1H), 4.77 (br s, 2H), 4.36-4.28 (m, 2H), 4.17 (br d, J = 12.0 Hz, 1H), 4.01 (br d, J = 1.5 Hz, 1H), 3.20-3.10 (m, 1H), 3.09-2.99 (m, 1H), 2.94 (brs, 1H), 2.90 (s, 3H), 2.23-2.12 (m, 1H) |

Example 190 (Scheme ZZZ)—(1S,2S,3S,5R)-3-(6-(difluoromethyl)-5-fluoro-1,2,3,4-tetrahydroisoquinolin-8-yl)oxy)-5-(4-methyl-7H-pyrrolo[2,3-d]pyrimidin-7-yl)cyclopentane-1,2-diol (ZZZ-16)
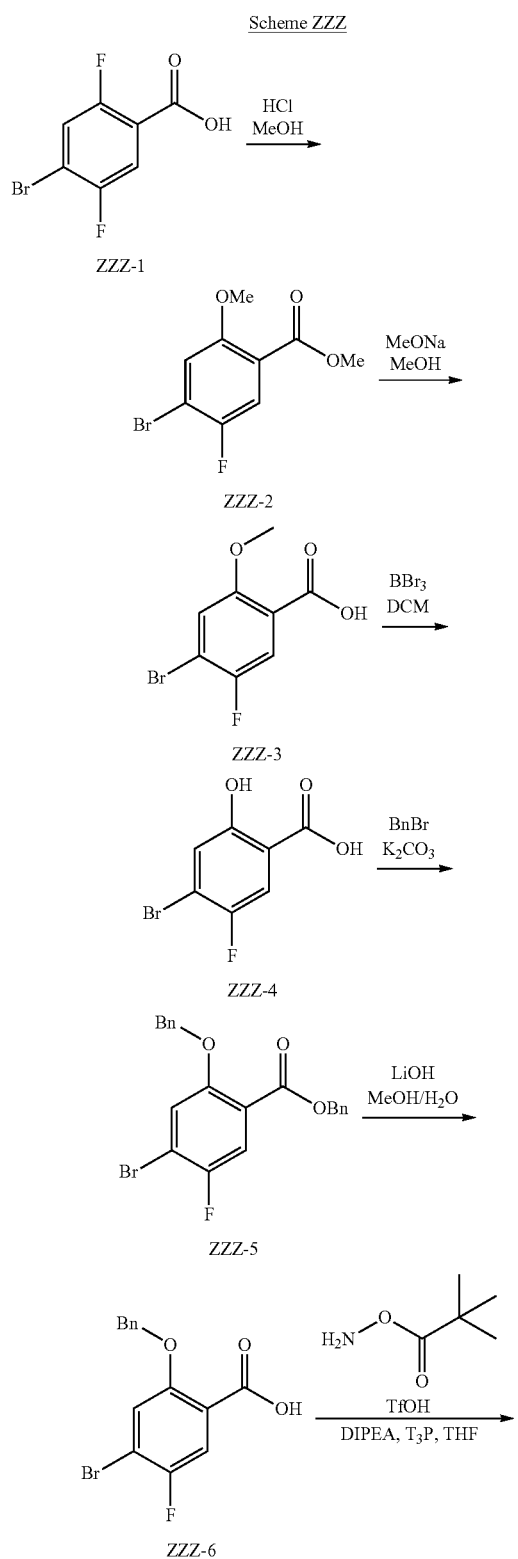
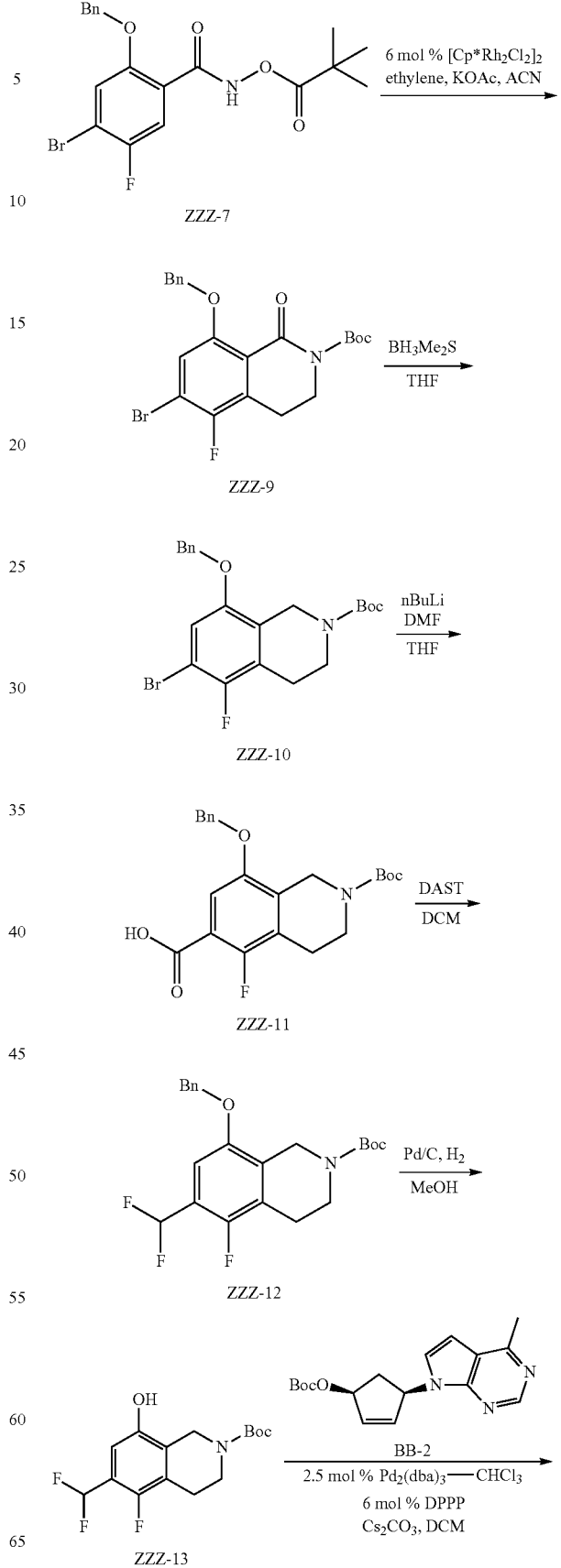

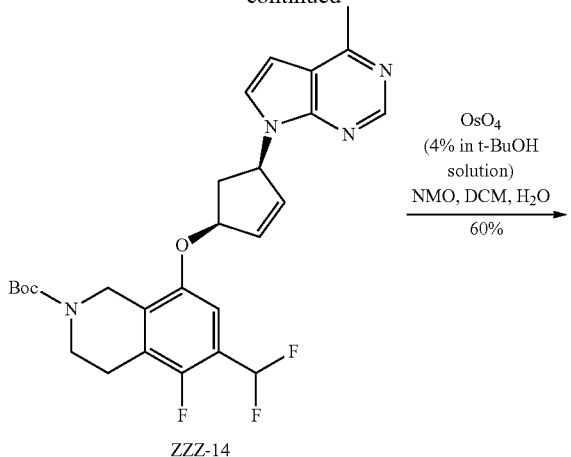

ZZZ-14

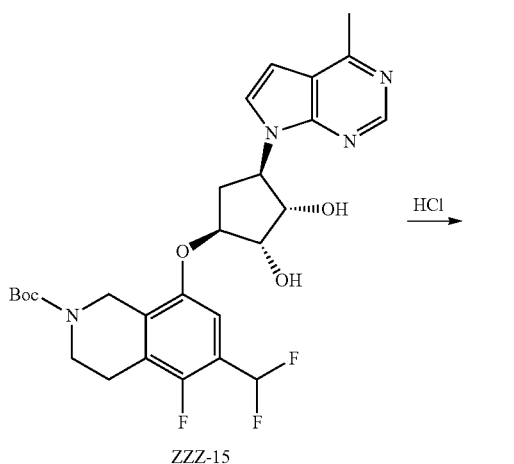

ZZZ-15

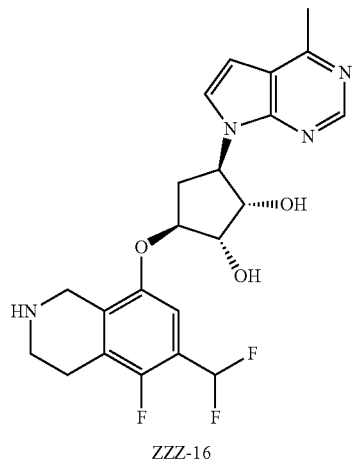

ZZZ-16

Step 1—Synthesis of methyl 4-bromo-5-fluoro-2-methoxybenzoate (ZZZ-2)

A solution of 4-bromo-2,5-difluorobenzoic acid ZZZ-1 (95 g, 400.85 mmol) in 4M HCl/MeOH (1500 mL) was heated at 65° C. for 3 hours. The mixture was concentrated in vacuum to get ZZZ-2 (100 g, >99%) as a light yellow solid. $^1$H NMR (400 MHz, DMSO-d$_6$) δ ppm 7.93 (dd, J=5.5, 9.8 Hz, 1H), 7.81 (dd, J=6.0, 8.5 Hz, 1H), 3.92-3.85 (m, 3H)

Step 2—Synthesis of 4-bromo-5-fluoro-2-methoxybenzoic acid (ZZZ-3)

To a solution of ZZZ-2 (80 g, 7.97 mmol) in dry DMF (1200 mL) was added a solution MeONa (~17.2 g, 319 mmol, 8 g Na dissolved in 80 mL MeOH obtained) at 0° C. The mixture was stirred at 0° C. for 10 mins, then warmed up to rt (25° C.) and stirred for 1 h. To the mixture was added TBME (1 L) then, poured into ice water (800 mL). The mixture was extracted with TBME (500 mL×4). The organic layer was washed with brine (300 mL×2) dried over Na$_2$SO$_4$, filtered and concentrated to get product the methyl ether, methyl ester (12.1 g) as light yellow gum. The aqueous layer contained the carboxylic acid and was neutralized with HCl (1M) to pH=5 then, extracted with EtOAc (800 mL×3). The organic layer was washed with brine (400 mL×2), dried over Na$_2$SO$_4$, filtered and concentrated to obtain ZZZ-3 (100 g, >99% crude) as a yellow oil and used directly in the next step. NMR contained DMF. $^1$H NMR (400 MHz, DMSO-d$_6$) δ ppm 7.59 (d, J=8.8 Hz, 1H), 7.46 (d, J=5.8 Hz, 1H), 3.83 (s, 3H)

Step 3—Synthesis of 4-bromo-5-fluoro-2-hydroxybenzoic acid (ZZZ-4)

To a solution of ZZZ-3 (~60 g crude, 240.93 mmol) in dry DCM (600 mL) was added BBr$_3$ (68.3 mL dissolved in DCM 600 mL, 723 mmol) at rt (20° C.). The mixture was stirred at rt (20° C.) for 2 h. The mixture was poured water (500 mL) and extracted with DCM (800 mL×3). The organic layer was washed with brine (300 mL×2) dried over Na$_2$SO$_4$ filtered and concentrated to obtain ZZZ-4 (35 g, 62%) as a yellow gum. $^1$H NMR (400 MHz, DMSO-d$_6$) δ ppm 7.62 (d, J=9.0 Hz, 1H), 7.33 (d, J=5.8 Hz, 1H)

Step 4—Synthesis of benzyl 2-(benzyloxy)-4-bromo-5-fluorobenzoate (ZZZ-5)

To a solution of ZZZ-4 (35 g, 148.93 mmol) in dry DMF (300 mL) was added K$_2$CO$_3$ (41.2 g, 298 mmol) and BnBr (38.2 g, 223 mmol). The mixture was stirred at 25° C. for 16 hrs. The mixture was diluted with water (200 mL) and extracted with EtOAc (300 mL×3). The organic layers were collected, dried and concentrated to give a crude light yellow oil which was purified by combi-flash (silica gel EtOAc/Petroleum ether=0-8%) to obtain ZZZ-5 (22 g, 36%) as a light yellow solid. $^1$H NMR (400 MHz, CDCl$_3$) δ ppm 7.67 (d, J=8.6 Hz, 1H), 7.48-7.32 (m, 10H), 7.25 (d, J=5.5 Hz, 1H), 5.36 (s, 2H), 5.14 (s, 2H)

Step 5—Synthesis of 2-(benzyloxy)-4-bromo-5-fluorobenzoic acid (ZZZ-6)

To a solution of ZZZ-5 (22 g, 52.98 mmol) in MeOH (200 mL) was added a solution of LiOH.H$_2$O (6.67 g, 159 mmol) in H$_2$O (200 mL). The reaction mixture was stirred at 20° C. for 4 hours. The reaction mixture was extracted with EtOAc (150 mL×2). The water layer was neutralized with 1 M aq. HCl at 0° C. to pH 4-5, then extracted with EtOAc (200 mL×2). The organic layer was washed with brine (50 mL×2) dried over Na$_2$SO$_4$, filtered and concentrated to obtain ZZZ-6 (12.5 g, 73%) as a white solid. LCMS [M+1] 324.96; $^1$H NMR (400 MHz, DMSO-d$_6$) δ ppm 13.16 (br s, 1H), 7.66-7.56 (m, 2H), 7.53-7.46 (m, 2H), 7.45-7.37 (m, 1H), 7.45-7.37 (m, 1H), 7.37-7.30 (m, 1H), 5.22 (s, 2H)

Step 6—Synthesis of 2-(benzyloxy)-4-bromo-5-fluoro-N-(pivaloyloxy)benzamide (ZZZ-7)

To a solution of ZZZ-6 (23 g, 70.74 mmol) in THF (300 mL) was added O-pivaloylhydroxylamine (35.4 g, 141 mmol), DIPEA (54.9 g, 424 mmol) at rt (25° C.). Then T3P (113 g, 177 mmol) was added at 0° C. After addition the mixture was stirred 0° C. for 10 mins then, warmed up to rt (20° C.) and stirred for 16 hours. The mixture was concentrated to remove most of the solvent. The remaining mixture was diluted with EtOAc (80 mL), washed with sat. aq NaHCO$_3$ (50 mL) and extracted with EtOAc (100 mL×2). The organic layer was washed with brine (50 mL×2) dried over Na$_2$SO$_4$, filtered and concentrated to give the crude product (42 g) as a yellow gum which was purified by chromatography (silica gel, EtOAc/Petroleum ether=0-25%) to afford ZZZ-7 (26 g, 87%) as a light yellow solid. LCMS [M+1] 424; $^1$H NMR (400 MHz, CDCl$_3$) δ ppm 10.80 (br s, 1H), 7.93 (d, J=8.8 Hz, 1H), 7.51-7.34 (m, 5H), 7.27-7.23 (m, 1H), 5.24 (s, 2H), 1.33 (s, 9H)

Step 7—Synthesis of 8-(benzyloxy)-6-bromo-5-fluoro-3,4-dihydroisoquinolin-1(2H)-one (ZZZ-8)

To a suspension of ZZZ-7 (26 g, 64 mmol) in MeCN (600 mL) was added KOAc (6.91 g, 70.4 mmol) and [Cp*Rh$_2$Cl$_2$]$_2$ (2.37 g, 3.84 mmol) in vessel was cooled to 0° C. in which ethylene was purged into the vessel for 30 mins and sealed. The reaction was stirred at rt (20° C.) for 16 hours. The mixture was concentrated to give crude product (26 g) as a yellow solid which was purified by chromatography (silica gel petroleum ether:EtOAc=0-100%) to obtain ZZZ-8 (12 g, 59%) as a yellow solid. LCMS [M+1] 351; $^1$H NMR (400 MHz, DMSO-d$_6$) δ ppm 7.92 (br s, 1H), 7.56 (d, J=7.0 Hz, 2H), 7.44-7.35 (m, 3H), 7.34-7.28 (m, 1H), 5.19 (s, 2H), 3.30 (dt, J=3.6, 6.2 Hz, 2H), 2.86 (t, J=6.1 Hz, 2H)

Step 8—Synthesis of tert-butyl 8-(benzyloxy)-6-bromo-5-fluoro-1-oxo-3,4-dihydroisoquinoline-2(1H)-carboxylate (ZZZ-9)

To a solution of ZZZ-8 (11 g, 33.113 mmol) in THF (40 mL) and DCM (120 mL) was added Boc$_2$O (11.6 g, 53 mmol), DIPEA (15 g, 116 mmol) and DMAP (607 mg, 4.97 mmol). After the addition, the mixture was stirred at rt (22° C.) for 16 hours. The reaction was concentrated to get the crude material (17.2 g) as a yellow gum which was then purified by combi-flash (EtOAc/petroleum ether=0-20%) to obtain ZZZ-9 (14.52 g, 97%) as a light yellow solid. LCMS [M+23] 472; $^1$H NMR (400 MHz, DMSO-d$_6$) δ ppm 7.63-7.22 (m, 6H), 5.32-5.14 (m, 2H), 3.86 (t, J=6.0 Hz, 2H), 2.97 (t, J=5.9 Hz, 2H), 1.50 (s, 9H)

Step 9—Synthesis of tert-butyl 8-(benzyloxy)-6-bromo-5-fluoro-3,4-dihydroisoquinoline-2(1H)-carboxylate (ZZZ-10)

To a solution of ZZZ-9 (14.81 g, 32.9 mmol) in THF (150 mL) was added BH$_3$Me$_2$S (19.7 mL, 197 mmol) at rt (25° C.). The mixture was heated at 70° C. for 1 hour. The reaction was quenched with MeOH (40 mL) slowly. The mixture was refluxed (65° C.) for 16 hr. The mixture was concentrated to give the crude product (26 g) as a yellow gum in which water (60 mL) was added the product extracted with EtOAc (100 mL×2). The organic layer was washed with brine (50 mL×2) dried over Na$_2$SO$_4$ filtrated and concentrated to get crude material (17 g) which was purified by chromatography (silica gel, EtOAc/petroleum ether=0-25%) to afford ZZZ-10 (13.2 g) as a light yellow gum which was lyophilized to get ZZZ-10 (13.06 g, 91%) was obtained as a white solid. LCMS [M-Boc+1] 337; $^1$H NMR (400 MHz, CDCl$_3$) δ ppm 7.44-7.31 (m, 5H), 6.92 (d, J=5.5 Hz, 1H), 5.04 (br s, 2H), 4.51 (s, 2H), 3.63 (br t, J=5.8 Hz, 2H), 2.88-2.72 (m, 2H), 1.50 (s, 9H)

Step 10—Synthesis of tert-butyl 8-(benzyloxy)-5-fluoro-6-formyl-3,4-dihydroisoquinoline-2(1H)-carboxylate (ZZZ-11)

In an oven dried round bottom flask was added ZZZ-10 (285 mg, 0.653 mmol) and dry THF (4.35 mL, 0.15 M). A solution of DMF (0.98 mL, 0.98 mmol, 1M in THF) was added to and the mixture was cooled to −78° C. with dry ice/acetone. nBuLi (0.92 mL, 1.47 mmol, 1.6M in hexanes) was added drop-wise and stirred at −78° C. for 30 min in which the reaction turned from clear to yellow. LCMS still showed ~50% of ZZZ-10 and therefore another 0.5 eq of DMF (0.49 mL, 0.49 mmol, 1M in THF) and nBuLi (0.46 mL, 0.735 mmol, 1M in hexanes) were added and stirred for 25 min. The reaction was quenched with water and extracted with EtOAc. The aqueous layer was extracted with EtOAc 3×. The combined organics were washed with water and dried over Na$_2$SO$_4$, filtered and concentrated to a crude yellow oil (404 mg) which was purified by ISCO 25 g 0-20% EtOAc/Heptanes to afford ZZZ-11 as a clear oil (215 mg, 60%). LCMS [M+1] 286; $^1$H NMR (400 MHz, CDCl$_3$) δ ppm 10.35 (s, 1H), 7.49-7.32 (m, 5H), 7.23 (d, J=5.3 Hz, 1H), 5.13 (br. s., 2H), 4.64 (s, 2H), 3.69 (t, J=5.7 Hz, 2H), 2.86 (t, J=5.1 Hz, 2H), 1.52 (s, 9H)

Step 11—Synthesis of tert-butyl 8-(benzyloxy)-6-(difluoromethyl)-5-fluoro-3,4-dihydroisoquinoline-2(1H)-carboxylate (ZZZ-12)

To a solution of ZZZ-11 (418 mg, 1.08 mmol) was added DCM (10.8 mL, 0.1M). The solution was cooled to 0° C. then DAST (0.36 mL, 2.71 mmol) was added drop-wise and stirred for 4 h at r.t. LCMS shows ~25% of product. The reaction was cooled down to 0° C. and DAST was re-added drop-wise (0.36 mL, 2.71 mmol) and stirred at r.t. for 2 hours. The reaction was not complete and an additional 2 eq was added and stirred for 2 h. The reaction was then neutralized with sat. aq. NaHCO$_3$. The layers were separated and the aqueous layer was extracted with DCM 2×, dried over Na$_2$SO$_4$, filtered and concentrated then purified by ISCO 12 g 0-15% EtOAc/Heptanes to afford ZZZ-12 as a white solid (322 mg, 73%). LCMS [M-Boc+1] 308; $^1$H NMR (400 MHz, CDCl$_3$) δ ppm 7.47-7.32 (m, 5H), 7.03-6.75 (m, 2H), 5.10 (br. s., 2H), 4.59 (br. s., 2H), 3.66 (t, J=5.6 Hz, 2H), 2.84-2.75 (m, 2H), 1.50 (s, 9H)

Step 12—Synthesis of tert-butyl 6-(difluoromethyl)-5-fluoro-8-hydroxy-3,4-dihydroisoquinoline-2(1H)-carboxylate (ZZZ-13)

In round bottom flask was added ZZZ-12 (322 mg, 0.79 mmol) and MeOH (15.8 mL, 0.05 M). 10% Pd/C (30 mg) was added and a hydrogen balloon was added. The reaction was stirred at r.t. overnight. The reaction was filtered with a syringe and filter tip. The crude white material (252 mg) was dissolved in DCM:MeOH (~2:1) for complete solubility to added into an ISCO 12 g and purified with 0-25% EtOAc/heptanes to give ZZZ-13 as a white solid (239 mg, 95%). LCMS [M-Boc+1] 218; $^1$H NMR (400 MHz, CDCl$_3$) δ ppm 6.99-6.62 (m, 2H), 4.55 (br. s., 2H), 3.66 (t, J=5.9 Hz, 2H), 2.79 (br. s., 2H), 1.52 (s, 9H)

Step 13—Synthesis of tert-butyl 6-(difluoromethyl)-5-fluoro-8-(((1S,4R)-4-(4-methyl-7H-pyrrolo[2,3-d]pyrimidin-7-yl)cyclopent-2-en-1-yl)oxy)-3,4-dihydroisoquinoline-2(1H)-carboxylate (ZZZ-14)

To a microwave vial (which was dried with heat gun, then cooled under a stream of N₂) was added compound BB-2 (238 mg, 0.753 mmol), ZZZ-13 (239 mg, 0.753 mmol), Cs₂CO₃ (270 mg, 0.829 mmol), DPPP (18.7 mg, 0.0452 mmol) and Pd₂(dba)₃-CHCl₃ (19.5 mg, 0.02 mmol), the vial was purged with N₂ for five and DCE (3 mL, sparged with N₂ for 30 mins) was added. The vial was purged with N₂ three more times. The solution was stirred at 18° C. under N₂ for 55 min. The reaction mixture was purified by prep-TLC (EtOAc/petroleum ether=1.5:1) to give product ZZZ-14 (330 mg, 85%) as a colorless gum. LCMS [M+1] 515; ¹H NMR (400 MHz, CDCl₃) δ ppm 8.78 (s, 1H), 7.29 (br d, J=3.4 Hz, 1H), 7.04-6.72 (m, 2H), 6.59 (br d, J=3.0 Hz, 1H), 6.39 (br d, J=5.3 Hz, 1H), 6.19 (br d, J=4.6 Hz, 1H), 6.08 (br dd, J=2.2, 4.3 Hz, 1H), 5.40-5.32 (m, 1H), 4.50 (br s, 2H), 3.73-3.57 (m, 2H), 3.26-3.16 (m, 1H), 2.80 (br t, J=5.4 Hz, 2H), 2.74 (s, 3H), 1.52 (s, 9H)

Step 14—Synthesis of tert-butyl 6-(difluoromethyl)-8-(((1S,2S,3S,4R)-2,3-dihydroxy-4-(4-methyl-7H-pyrrolo[2,3-d]pyrimidin-7-yl)cyclopentyl)oxy)-5-fluoro-3,4-dihydroisoquinoline-2(1H)-carboxylate (ZZZ-15)

To a mixture of ZZZ-14 (330 mg, 0.641 mmol) in DCM (10 mL)/H₂O (0.4 mL) was added NMO (225 mg, 1.92 mmol) and OsO₄ (4% in t-BuOH, 285 mg, 0.045 mmol) at 15° C. The black solution was stirred at 18° C. for 3 hours. The mixture was quenched with sat. aq. Na₂SO₃ (5 mL) and diluted with DCM (10 mL) and separated. The aqueous layer was extracted with DCM (5 mL). The combined organic layers were washed with brine (10 mL), dried over Na₂SO₄, filtered and concentrated to yield crude product (450 mg) as a brown solid, which was purified by prep-TLC (first, EtOAc/MeOH=20:1, second, EtOAc) to afford ZZZ-15 (210 mg, 60%) as a light yellow solid. LCMS [M+1] 549; ¹H NMR (400 MHz, CDCl₃) δ ppm 8.69 (s, 1H), 7.22 (d, J=3.8 Hz, 1H), 7.10 (br d, J=5.3 Hz, 1H), 7.04-6.73 (m, 1H), 6.61 (d, J=3.8 Hz, 1H), 5.03-4.88 (m, 1H), 4.80 (br s, 1H), 4.60-4.39 (m, 3H), 4.36-4.24 (m, 1H), 3.65 (br d, J=5.8 Hz, 2H), 3.46-3.29 (m, 1H), 3.20-3.02 (m, 1H), 2.80 (br t, J=5.4 Hz, 2H), 2.74 (s, 3H), 2.62 (s, 1H), 2.39 (s, 1H), 1.56-1.34 (m, 9H)

Step 15—Synthesis of (1S,2S,3S,5R)-3-(6-(difluoromethyl)-5-fluoro-1,2,3,4-tetrahydroisoquinolin-8-yl)oxy)-5-(4-methyl-7H-pyrrolo[2,3-d]pyrimidin-7-yl)cyclopentane-1,2-diol (ZZZ-16)

To a solution of ZZZ-15 (210 mg, 0.383 mmol) in DCM (2 mL) was added HCl (g)/dioxane (4 N, 0.766 mL, 3.06 mmol) at 0° C. The mixture was stirred at 23° C. for 2 hours. Solid was precipitated. The solvent was decanted and the solid dried and lyophilized lyophilized to give ZZZ-16 as 2HCl salt+2H₂O (165 mg, 83%) as a light yellow solid. LCMS [M+1] 449; ¹H NMR (400 MHz, D₂O) δ ppm 8.93 (s, 1H), 7.91 (d, J=3.8 Hz, 1H), 7.24-6.88 (m, 3H), 5.41 (q, J=9.0 Hz, 1H), 4.87 (br dd, J=2.4, 4.4 Hz, 1H), 4.75 (dd, J=5.0, 8.8 Hz, 1H), 4.45 (s, 2H), 4.39 (br d, J=5.0 Hz, 1H), 3.58 (t, J=6.3 Hz, 2H), 3.19-3.07 (m, 3H), 2.99 (s, 3H), 2.35-2.24 (m, 1H).

Example 191 (Scheme AAAA)—Synthesis of (1S,2S,3S,5R)-3-((4-fluoro-3-methoxy-5,6,7,8-tetrahydro-2,7-naphthyridin-1-yl)oxy)-5-(4-methyl-7H-pyrrolo[2,3-d]pyrimidin-7-yl)cyclopentane-1,2-diol (AAAA-6)

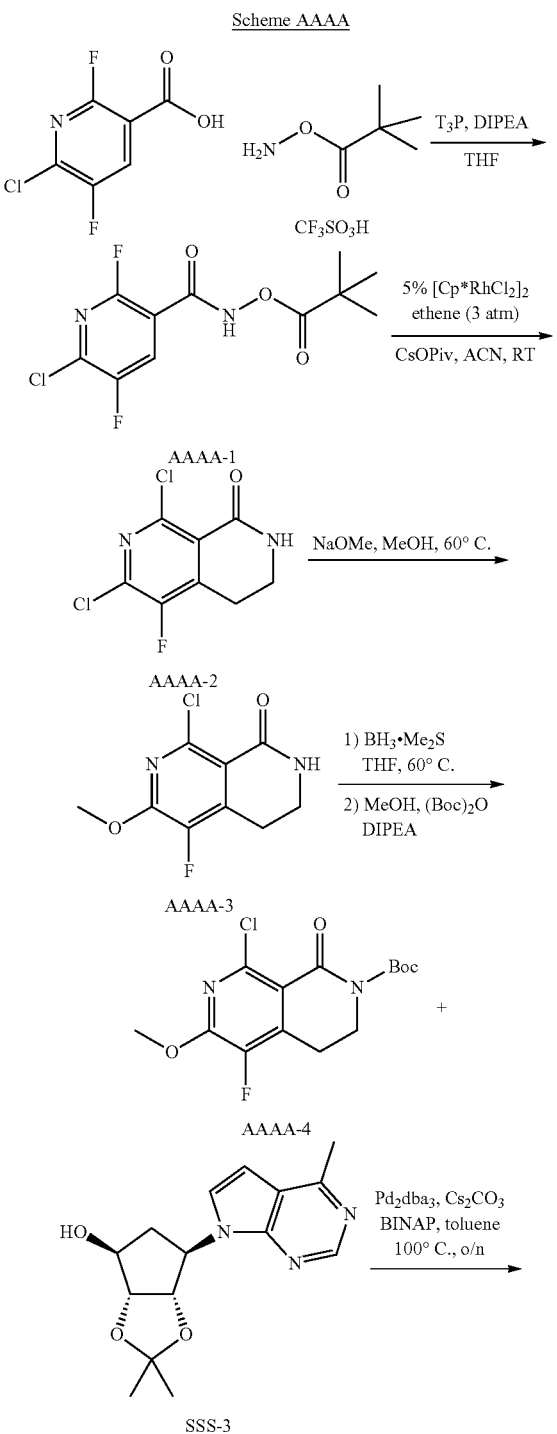

Scheme AAAA

-continued

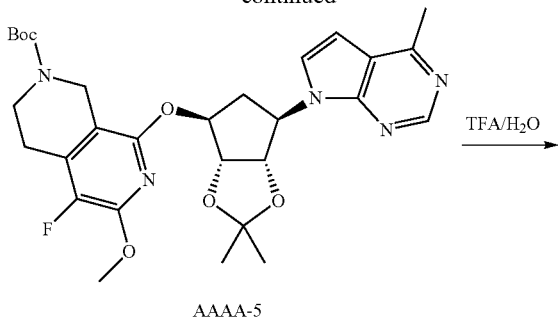

AAAA-5

TFA/H₂O →

AAAA-6

Step 1: Synthesis of 2,6-dichloro-5-fluoro-N-(pivaloyloxy)nicotinamide (AAAA-1)

Compound AAAA-1 was prepared in a similar method as step 4 in Scheme FF using 2,6-dichloro-5-fluoronicotinic acid to give 5.85 g (80% yield) as a white solid. ¹H NMR (400 MHz, CHLOROFORM-d) ä ppm 9.91 (br. s., 1H) 8.02 (d, J=5.14 Hz, 1H) 1.37 (s, 9H)

Step 2: Synthesis of 6,8-dichloro-5-fluoro-3,4-dihydro-2,7-naphthyridin-1(2H)-one (AAAA-2)

Compound AAAA-2 was prepared from AAAA-1 in a similar method as step 4 in Scheme GG using cesium pivalate to give 1.47 g (33% yield) as a yellow solid. LCMS [M+1-2Cl] 167.0. ¹H NMR (400 MHz, CHLOROFORM-d) ä ppm 6.13 (br. s., 1H) 3.59 (td, J=6.45, 3.48 Hz, 2H) 3.09 (t, J=6.42 Hz, 2H)

Step 3: Synthesis of 8-chloro-5-fluoro-6-methoxy-3,4-dihydro-2,7-naphthyridin-1(2H)-one (AAAA-3)

To a solution of AAAA-2 (200 mg, 0.85 mmol) in 20 mL MeOH was added sodium methoxide (161 mg, 2.98 mmol, 5.96 mL, 0.5 M), the solution was heated at 60 C for 1 hr. The reaction was concentrated, redissolved in DCM, washed with H₂O twice, DCM was rotavapored, the crude was purified by column chromatography with 100% EtOAc to give 100 mg of AAAA-3 (51% yield) as an off white solid. LCMS [M+1] 231.0. ¹H NMR (400 MHz, CHLOROFORM-d) ppm 5.96 (br. s., 1H) 4.09 (s, 3H) 3.52 (td, J=6.39, 3.48 Hz, 2H) 3.03 (t, J=6.24 Hz, 2H)

Step 4: Synthesis of tert-butyl 8-chloro-5-fluoro-6-methoxy-3,4-dihydro-2,7-naphthyridine-2(1H)-carboxylate (AAAA-4)

Compound AAAA-4 was prepared from AAAA-3 in a similar method as step 5 in Scheme GG to give 105 mg (76% yield) as a colorless oil. LCMS [M+1-Boc] 217.0. ¹H NMR (400 MHz, CHLOROFORM-d) ä ppm 4.48 (s, 2H) 4.00 (s, 3H) 3.63 (t, J=5.93 Hz, 2H) 2.82 (t, J=5.69 Hz, 2H) 1.50 (s, 9H)

Step 5: Synthesis of tert-butyl 8-(((3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-yl)oxy)-5-fluoro-6-methoxy-3,4-dihydro-2,7-naphthyridine-2(1H)-carboxylate (AAAA-5)

The mixture of (3aR,4S,6R,6aS)-2,2-dimethyl-6-(4-methyl-7H-pyrrolo[2,3-d]pyrimidin-7-yl)tetrahydro-4H-cyclopenta[d][1,3]dioxol-4-ol (SSS-3) (98.0 mg, 0.34 mmol), AAAA-4 (107 mg, 0.339 mmol), cesium carbonate (221 mg, 0.677 mmol), tris(dibenzylideneacetone)dipalladium (31.0 mg, 0.0339 mmol) and BINAP (42.2 mg, 0.0677 mmol) in toluene (6.77 mL, c=0.05 M) was degassed and purged with N₂ three times. The reaction mixture was heated at 100° C. overnight, LCMS indicated the reaction didn't complete. Cesium carbonate (221 mg, 0.677 mmol), tris(dibenzylideneacetone)dipalladium (31.0 mg, 0.0339 mmol) and BINAP (42.2 mg, 0.0677 mmol) were added, degassed and continued to heat at 100° C. for 2 days. The reaction mixture was cooled to rt, H₂O was added, extracted with EtOAc, the crude was concentrated and purified by column chromatography with 85% EtOAc/heptane to give 60 mg (31% yield) yellow oil. LCMS [M+1] 570.1. ¹H NMR (400 MHz, CHLOROFORM-d) ä ppm 8.79 (s, 1H) 7.37 (d, J=3.67 Hz, 1H) 6.61 (br. s., 1H) 5.47 (br. s., 1H) 5.35 (ddd, J=7.95, 5.26, 2.69 Hz, 1H) 4.98-5.05 (m, 1H) 4.89 (d, J=6.24 Hz, 1H) 4.36 (br. s., 2H) 3.99 (s, 3H) 3.56-3.64 (m, 2H) 3.01 (dt, J=14.55, 7.27 Hz, 1H) 2.78 (t, J=5.26 Hz, 2H) 2.73 (s, 3H) 2.41-2.52 (m, 1H) 1.60 (s, 3H) 1.50 (s, 9H) 1.33 (s, 3H)

Step 6: Synthesis of (1S,2S,3S,5R)-3-((4-fluoro-3-methoxy-5,6,7,8-tetrahydro-2,7-naphthyridin-1-yl)oxy)-5-(4-methyl-7H-pyrrolo[2,3-d]pyrimidin-7-yl)cyclopentane-1,2-diol (AAAA-6)

Compound AAAA-6 was prepared from AAAA-5 in a similar method as step 10 in Scheme A to give 19.7 mg (33% yield). LCMS [M+1] 430.0. ¹H NMR (400 MHz, DMSO-d6) ä ppm 9.68 (br. s., 1H) 9.56 (br. s., 1H) 9.07 (s, 1H) 7.99 (br. s., 1H) 7.10 (br. s., 1H) 5.11-5.26 (m, 2H) 4.64 (dd, J=9.05, 4.65 Hz, 1H) 4.15 (br. s., 2H) 4.10 (d, J=4.03 Hz, 1H) 3.94 (s, 3H) 3.38 (br. s., 2H) 2.91-3.03 (m, 3H) 2.87 (s, 3H) 1.95-2.05 (m, 1H)

Examples 192 & 193 were Prepared in a Similar Fashion to Example 191 Except that Sodium Ethoxide in Ethanol was Used in Step 3 of Scheme AAAA for Example 192 and Sodium Isopropoxide in Isopropanol was Used in Step 3 of Scheme AAAA for Example 193

| Example 192 | 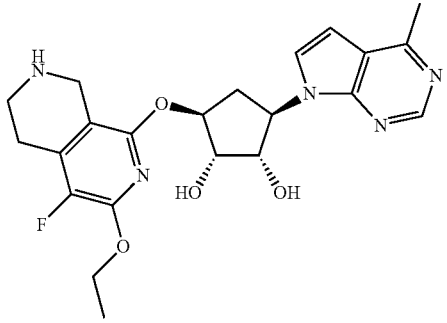 [SMILES: CCOc1nc(O[C@H]2C[C@@H](n3ccc4c(C)ncnc43)[C@H](O)[C@@H]2O)c2c(c1F)CCNC2] | 444.05 [M + 1] | (1S,2S,3S,5R)-3-((3-ethoxy-4-fluoro-5,6,7,8-tetrahydro-2,7-naphthyridin-1-yl)oxy)-5-(4-methyl-7H-pyrrolo[2,3-d]pyrimidin-7-yl)cyclopentane-1,2-diol<br>$^1$H NMR (400 MHz, DMSO-d6) ä ppm 9.50 (br. s., 1H) 9.40 (br. s., 1H) 8.99 (br. s., 1H) 7.93 (br. s., 1H) 7.04 (br. s., 1H) 5.19 (q, J = 9.17 Hz, 1H) 5.07-5.13 (m, 1H) 4.63 (dd, J = 9.05, 4.52 Hz, 1H) 4.34-4.51 (m, 2H) 4.15 (br. s., 2H) 4.09 (d, J = 4.16 Hz, 1H) 3.39 (br. s., 2H) 2.88-3.03 (m, 3H) 2.83 (s, 3H) 1.93-2.03 (m, 1H) 1.33 (t, J = 6.97 Hz, 3H) |
| --- | --- | --- | --- |
| Example 193 | 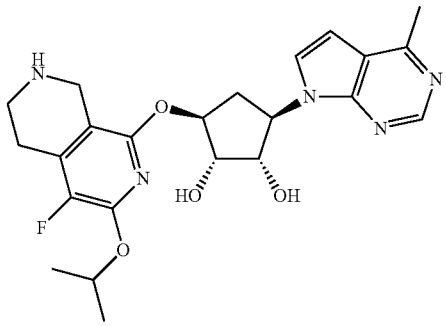 [SMILES: Cc1ncnc2c1ccn2[C@@H]1C[C@H](Oc2nc(OC(C)C)c(F)c3c2CNCC3)[C@@H](O)[C@H]1O] | 458.00 [M + 1] | (1S,2S,3S,5R)-3-((4-fluoro-3-isopropoxy-5,6,7,8-tetrahydro-2,7-naphthyridin-1-yl)oxy)-5-(4-methyl-7H-pyrrolo[2,3-d]pyrimidin-7-yl)cyclopentane-1,2-diol<br>$^1$H NMR (400 MHz, DMSO-d6) ä ppm 9.98 (br. s., 1H) 9.82 (br. s., 1H) 9.21 (s, 1H) 8.10 (d, J = 3.67 Hz, 1H) 7.22 (d, J = 3.67 Hz, 1H) 5.18-5.30 (m, 2H) 5.10 (d, J = 5.14 Hz, 1H) 4.67 (dd, J = 9.11, 4.46 Hz, 1H) 4.13 (d, J = 4.52 Hz, 2H) 4.09 (d, J = 4.03 Hz, 1H) 3.36 (br. s., 2H) 2.96-3.03 (m, 2H) 2.94 (m, 4H) 1.96-2.08 (m, 1H) 1.35 (d, J = 6.1 Hz, 3H) 1.29 (d, J = 6.1 Hz, 3H) |

Scheme BBBB—Synthesis of 2-chloro-6-(difluoromethyl)nicotinic acid (BBBB-4)

Scheme BBBB

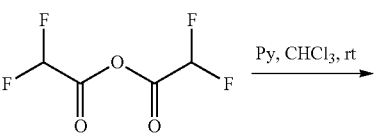

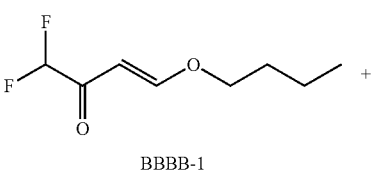

BBBB-1

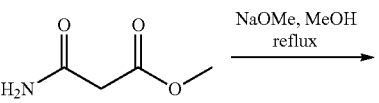

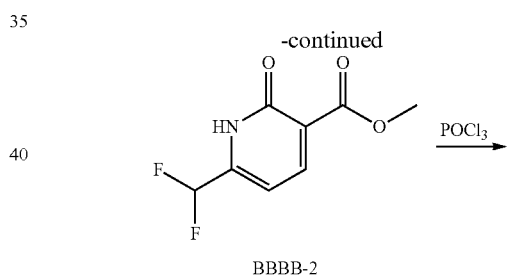

BBBB-2

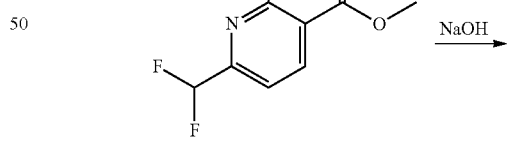

BBBB-3

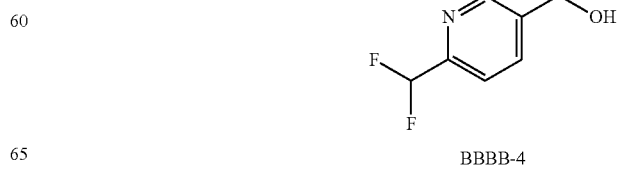

BBBB-4

Step 1: Synthesis of (E)-4-butoxy-1,1-difluorobut-3-en-2-one (BBBB-1)

Compound BBBB-1 was prepared according to WO20080269059. $^1$H NMR (400 MHz, CHLOROFORM-d) ä ppm 7.86 (d, J=12.47 Hz, 1H) 5.90 (d, 1H) 5.77 (t, J=56 Hz, 1H) 4.01 (t, J=6.48 Hz, 2H) 1.68-1.80 (m, 2H) 1.41-1.48 (m, 2H) 0.97 (t, J=7.40 Hz, 3H)

Step 2: Synthesis of methyl 6-(difluoromethyl)-2-oxo-1,2-dihydropyridine-3-carboxylate (BBBB-2)

Compound BBBB-2 was prepared according to WO20080269059. $^1$H NMR (400 MHz, DMSO-d6) ä ppm 12.18 (br. s., 1H) 8.20 (d, J=5.87 Hz, 1H) 7.05 (br. s., 1H) 6.86 (t, J=52 Hz, 1H) 3.81 (s, 3H)

Step 3: Synthesis of methyl 2-chloro-6-(difluoromethyl)nicotinate (BBBB-3)

A mixture of BBBB-2 (3340 mg, 16.44 mmol) and phosphors oxychloride (10 mL) was heated at 110° C. for 24 hrs, cooled to rt, ice water was added, neutralized by solid KOH. The reaction mixture was extracted with EtOAc three times, the organic layers were combined and concentrated, purified by column chromatography with 18% EtOAc/heptane to give 3.27 g (90% yield) of BBBB-3 as a white solid. $^1$H NMR (400 MHz, CHLOROFORM-d) ä ppm 8.31 (d, J=7.83 Hz, 1H) 7.67 (d, J=7.83 Hz, 1H) 6.61 (t, J=56 Hz, 1H) 4.00 (s, 3H); 19F NMR (376 MHz, CHLOROFORM-d) ä ppm −116.82 (s, 1F)

Step 4: Synthesis of 2-chloro-6-(difluoromethyl)nicotinic acid (BBBB-4)

To a solution of BBBB-3 (1160 mg, 5.235 mmol) in 20 mL MeOH was added sodium hydroxide (1050 mg, 26.2 mmol, 5.23 mL, 5 M), heated at 65° C. for 4 hrs. The reaction mixture was neutralized by 1 N HCl to pH 4, the solvent was removed, the solid was dried over vacuo and used for next step.

Example 194 was Made in a Similar Fashion to Example 191 (Scheme AAAA) Except that Step 3 is Omitted

| Example 194 | | | |
|---|---|---|---|
| 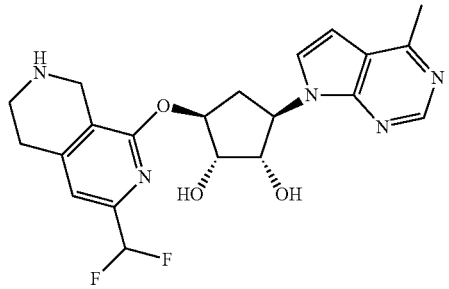 [SMILES: Cc1ncnc2c1ccn2[C@@H]1C[C@H](Oc2nc(C(F)F)cc3c2CNCC3)[C@@H](O)[C@H]1O] | 432.05 [M + 1] | (1S,2S,3S,5R)-3-((3-(difluoromethyl)-5,6,7,8-tetrahydro-2,7-naphthyridin-1-yl)oxy)-5-(4-methyl-7H-pyrrolo[2,3-d]pyrimidin-7-yl)cyclopentane-1,2-diol 1H NMR (400 MHz, DMSO-d6) ä ppm 10.27 (br. s., 1H) 10.13 (br. s., 1H) 9.22 (s, 1H) 8.12 (d, J = 3.67 Hz, 1H) 7.15-7.28 (m, 2H) 6.84 (t, J = 56 Hz, 1H) 5.12-5.30 (m, 2H) 4.69 (dd, J = 8.93, 4.65 Hz, 1H) 4.08-4.27 (m, 3H) 3.38 (d, J = 9.66 Hz, 2H) 3.10 (br. s., 2H) 2.86-3.00 (m, 4H) 1.92-2.10 (m, 1H) | |

Examples 195 & 196 were Made in a Similar Fashion to Example 99 in Scheme NN Using the Appropriate NBoc-Protected Tetrahydroisoquinoline in Step 2

| Example 195 TP-14 | 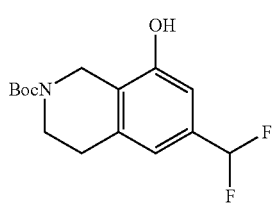 | 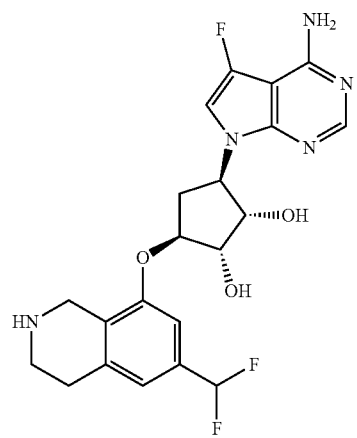 [SMILES: Nc1ncnc2c1c(F)cn2[C@@H]1C[C@H](Oc2cc(C(F)F)cc3c2CNCC3)[C@@H](O)[C@H]1O] | 450.2 [M + 1] | (1S,2S,3R,5S)-3-(4-amino-5-fluoro-7H-pyrrolo[2,3-d]pyrimidin-7-yl)-5-((6-(difluoromethyl)-1,2,3,4-tetrahydroisoquinolin-8-yl)oxy)cyclopentane-1,2-diol $^1$H NMR (400 MHz, D$_2$O, HCl salt) δ ppm 8.20 (s, 1H), 7.25 (d, J = 2.0 Hz, 1H), 7.12 (s, 1H), 7.09 (s, 1H), 6.77 (t, J = 56.0 Hz, 1H), 5.29-5.17 (m, 1H), 4.84-4.81 (m, 1H), 4.56 (dd, J = 5.0, 8.8 Hz, 1H), 4.37 (s, 2H), 4.29 (d, J = 4.3 Hz, 1H), 3.50 (t, J = 6.3 Hz, 2H), 3.13 (t, J = 6.3 Hz, 2H), 3.03 (ddd, J = 7.2, 9.3, 14.9 Hz, 1H), 2.15-2.01 (m, 1H) |
|---|---|---|---|---|

| Example 196 ZZZ-13 | 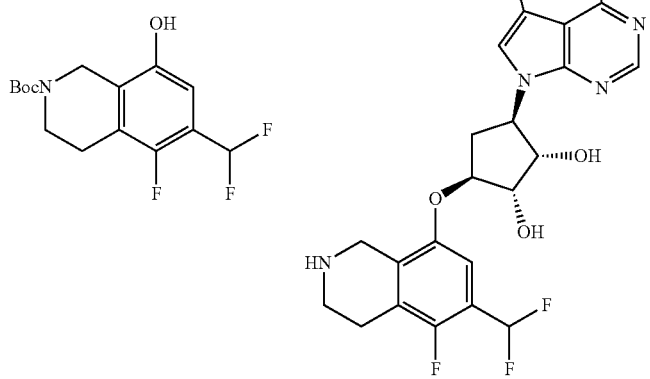 | 468.1 [M + 1] | (1S,2S,3R,5S)-3-(4-amino-5-fluoro-7H-pyrrolo[2,3-d]pyrimidin-7-yl)-5-((6-(difluoromethyl)-5-fluoro-1,2,3,4-tetrahydroisoquinolin-8-yl)oxy)cyclopentane-1,2-diol<br>¹H NMR (400 MHz, DMSO-d6, HCl salt) δ ppm 9.84 (br s, 2H), 8.76 (br s, 1H), 8.43 (s, 1H), 7.70 (d, J = 1.8 Hz, 1H), 7.38-7.02 (m, 2H), 5.07 (q, J = 9.1 Hz, 1H), 4.71-4.56 (m, 1H), 4.47 (dd, J = 4.9, 9.4 Hz, 1H), 4.23 (br s, 2H), 3.99 (br d, J = 5.0 Hz, 1H), 3.37 (br s, 2H), 3.03-2.95 (m, 2H), 2.93-2.80 (m, 1H), 1.96-1.81 (m, 1H) |

Scheme CCCC—Synthesis of tert-butyl 8-hydroxy-6-(isoxazol-4-yl)-3,4-dihydroisoquinoline-2(1H)-carboxylate (TP-34)

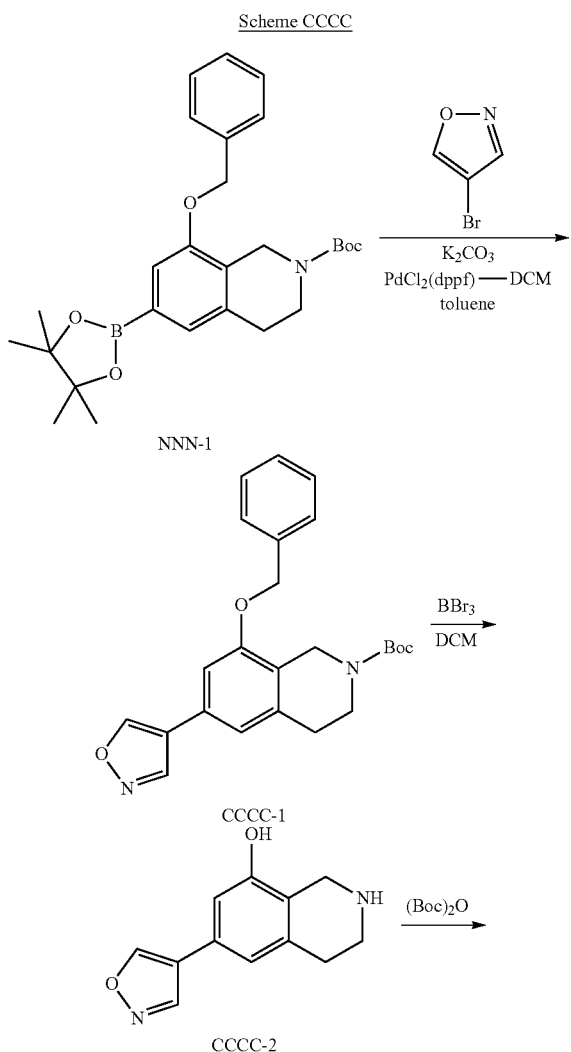

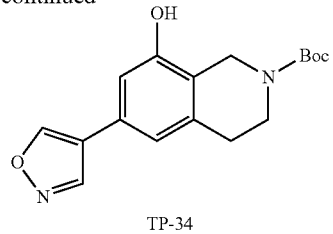

TP-34

Step 1—Synthesis of tert-butyl 8-(benzyloxy)-6-(isoxazol-4-yl)-3,4-dihydroisoquinoline-2(1H)-carboxylate (CCCC-1)

A solution of NNN-1 (600 mg, 1.29 mmol), 4-bromoisoxazole (286 mg, 1.93 mmol), K₂CO₃ (535 mg, 3.87 mmol) and PdCl₂(dppf)-DCM (94 mg, 0.129 mmol) in toluene (2.5 mL) and water (1.5 mL) was stirred under N₂ atmosphere at 75° C. for 16 h. The reaction mixture was then cooled to r.t. Water was added and the mixture was extracted with EtOAc (3×5 mL). The combined organic layers were washed with brine (5 mL), dried over Na₂SO₄, filtered and concentrated. The crude product was purified by column chromatography with EtOAc/petroleum ether from 15-85% to give a colorless oil CCCC-1 (160 mg, 31%). LCMS [M-tBu+1] 350.9

Step 2—Synthesis of 6-(isoxazol-4-yl)-1,2,3,4-tetrahydroisoquinolin-8-ol (CCCC-2)

Compound CCCC-1 (140 mg, 0.344 mmol) was dissolved in DCM (10 mL). The reaction solution was cooled to 0° C. in an ice bath. BBr₃ (518 mg, 2.07 mol) was added. The reaction became from a suspension to a clear yellow solution. The reaction mixture was stirred at 25° C. for 16 hours. The reaction was cooled to 0° C. and MeOH (2 mL) was added to the reaction drop-wise followed by water (20 mL). The reaction solution was washed with DCM (10 mL×2). The aqueous layer was separated and pH which was adjusted to pH 9, using NaHCO₃ solid. The final solution of CCCC-2 was used for the next step directly without further purification (23 mL, aq soln crude, >99%).

Synthesis of tert-butyl 8-hydroxy-6-(isoxazol-4-yl)-3,4-dihydroisoquinoline-2(1H)-carboxylate (TP-34)

MeOH (5 mL) and dioxane (5 mL) were added to the solution of CCCC-2 (23 mL aq), then Boc₂O (83 mg, 0.38 mmol) was added to the reaction solution, the solution was stirred at 25° C. for 16 hours. The pH of the reaction solution was adjusted to pH~3 by the addition of 1N HCl aq. The solution was separated, then aqueous layer was extracted with DCM (10 mL). The organic layers were combined and washed with saturated NaCl (20.0 mL). The organic layer was separated, dried and evaporated to give the crude product, which was purified by flash chromatography, eluted with petroleum ether/EtOAc from 0-50%, to give the desired product as white solid of TP-34 (84 mg, 77% yield over 2 steps). MS [M-Boc+1] 217.1; $^1$H NMR (400 MHz, DMSO-d6) δ ppm 9.83 (s, 1H), 9.32 (s, 1H), 9.02 (s, 1H), 6.97 (s, 1H), 6.89 (s, 1H), 4.36 (s, 2H), 3.55 (m, 2H), 2.75 (m, 2H), 1.44 (s, 9H)

Example 197 was Prepared Using the Chemistry Depicted in Scheme CC and Employing Compound TP-34

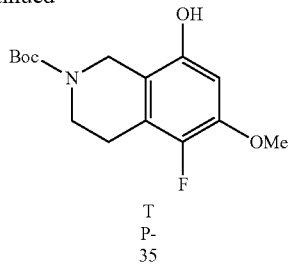

Step 1—Synthesis of tert-butyl 8-(benzyloxy)-5-fluoro-6-methoxy-3,4-dihydroisoquinoline-2(1H)-carboxylate (DDDD-1)

Vial A was charged with t-BuBrettPhos (49 mg, 0.10 mmol), NaOtBu (67.8 mg, 0.706 mmol) and ZZZ-10 (220

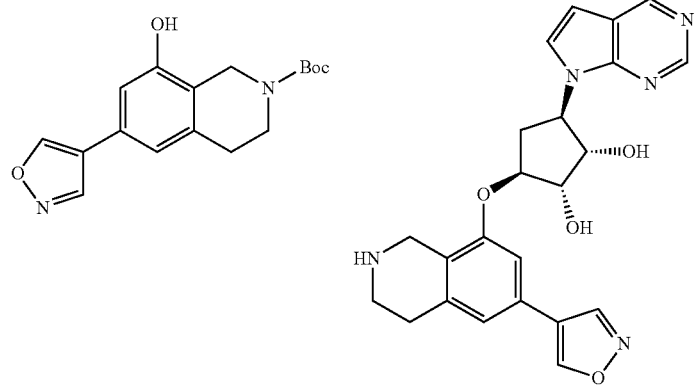

| Example 197 TP-34 | | 448.1 [M + 1] | (1S,2S,3S,5R)-3-((6-(isoxazol-4-yl)-1,2,3,4-tetrahydroisoquinolin-8-yl)oxy)-5-(4-methyl-7H-pyrrolo[2,3-d]pyrimidin-7-yl)cyclopentane-1,2-diol $^1$H NMR (400 MHz, D$_2$O) δ ppm 8.98 (s, 1H), 8.83 (s, 1H), 8.80 (s, 1H), 7.80 (d, J = 3.8 Hz, 1H), 7.15 (s, 1H), 7.12-7.07 (m, 2H), 5.35 (q, J = 9.0 Hz, 1H), 4.90-4.86 (m, 1H), 4.69-4.65 (m, 1H), 4.39-4.31 (m, 3H), 3.50 (t, J = 6.3 Hz, 2H), 3.17-3.01 (m, 3H), 2.89 (s, 3H), 2.28-2.16 (m, 1H) |

Scheme DDDD—Synthesis of tert-butyl 5-fluoro-8-hydroxy-6-methoxy-3,4-dihydroisoquinoline-2(1H)-carboxylate (TP-35)

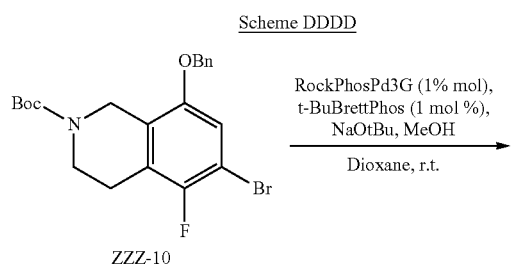

mg, 0.504 mmol) in dioxane (3 mL). The vial was degassed with N$_2$ three times. Then MeOH (81 mg, 2.52 mmol) was added to the vial A. Vial B was charged with RockPhosPd3G (85 mg, 0.10 mmol) and degassed with N$_2$ three times followed by addition of dioxane (2 mL) and stirred for 1 min. The precatalyst from vial B was transferred into vial A and the reaction solution was stirred at 25° C. for 16 hours. EtOAc (10 mL) was added to dilute the solution and washed with water (5 mL×2). The organic layers were separated, dried and evaporated to give the crude product, which was purified by flash chromatography, eluted with EtOAc/petroleum ether from 0-15% to give the desired product as colorless oil DDDD-1 (110 mg, 56%). LCMS [M-Boc+1] 287.9; $^1$H NMR (400 MHz, DMSO-d$_6$) δ ppm 7.54-7.27 (m, 5H), 6.83 (d, J=7.5 Hz, 1H), 5.15 (s, 2H), 4.43-4.26 (m, 2H), 3.82 (s, 3H), 3.53 (t, J=5.8 Hz, 2H), 2.71-2.66 (m, 2H), 1.42 (s, 9H)

Step 2—Synthesis of tert-butyl 5-fluoro-8-hydroxy-6-methoxy-3,4-dihydroisoquinoline-2(1H)-carboxylate (TP-35)

Compound DDDD-1 (110 mg, 0.28 mmol) was dissolved in MeOH (3 mL) and EtOAc (1 mL) followed by addition of Pd/C (15 mg, 0.142 mmol). The solution was degassed with H$_2$ four times and stirred at 25° C. for 16 hours under an H$_2$ balloon. The reaction was diluted with DCM (5 mL), filtered, and concentrated to give TP-35 as a white solid (70 mg, 83%). LCMS [M-tBu+1] 242.1; $^1$H NMR (400 MHz, DMSO-d$_6$) δ ppm 9.58 (s, 1H), 6.46 (d, J=7.3 Hz, 1H), 4.28 (s, 2H), 3.74 (s, 3H), 3.55-3.50 (m, 2H), 2.65 (m, 2H), 1.43 (s, 9H)

Compound TP-36 was prepared using similar chemistry as Scheme DDDD using EtOH in Step 1

| TP-36 | 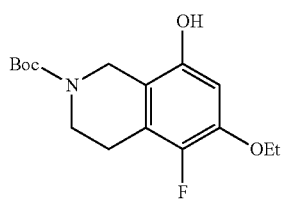 | 256 [M − tBu + 1] | tert-butyl 6-ethoxy-5-fluoro-8-hydroxy-3,4-dihydroisoquinoline-2(1H)-carboxylate<br>$^1$H NMR (400 MHz, DMSO-d6) δ ppm 9.52 (s, 1H), 6.44 (d, J = 7.0 Hz, 1H), 4.28 (s, 2H), 3.99 (q, J = 6.9 Hz, 2H), 3.55-3.49 (m, 2H), 2.64 (br t, J = 6.0 Hz, 2H), 1.43 (s, 9H), 1.32 (t, J = 6.9 Hz, 3H) |

Examples 198 & 199 were Prepared Using Similar Chemistry Depicted in Scheme CC and Employing Compounds TP-35 & TP-36 Respectively

| Example 198 TP-35 | 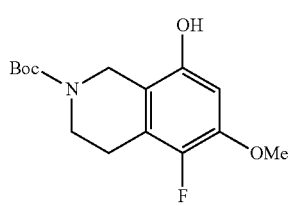 | 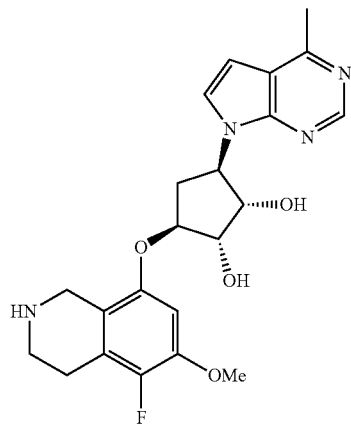 [SMILES: COc1cc(O[C@H]2C[C@@H](n3ccc4c(C)ncnc43)[C@H](O)[C@@H]2O)c2c(c1F)CCNC2] | 428.9 [M + 1] | (1S,2S,3S,5R)-3-((5-fluoro-6-methoxy-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, MeOD, HCl salt) δ ppm 9.05 (s, 1H), 8.09 (d, J = 3.7 Hz, 1H), 7.25 (d, J = 3.7 Hz, 1H), 6.93-6.85 (m, 1H), 5.40 (q, J = 9.3 Hz, 1H), 4.94-4.90 (m, 1H), 4.81-4.66 (m, 1H), 4.33 (s, 2H), 4.21 (d, J = 5.0 Hz, 1H), 3.93 (s, 3H), 3.57-3.47 (m, 2H), 3.14-3.05 (m, 3H), 3.02 (s, 3H), 2.37-2.24 (m, 1H) |
| Example 199 TP-36 | 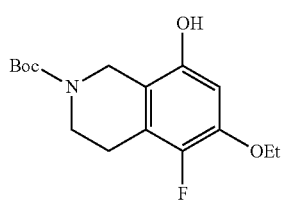 | 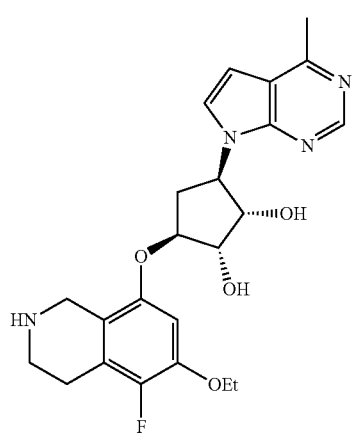 [SMILES: CCOc1cc(O[C@H]2C[C@@H](n3ccc4c(C)ncnc43)[C@H](O)[C@@H]2O)c2c(c1F)CCNC2] | 443.1 [M + 1] | (1S,2S,3S,5R)-3-((6-ethoxy-5-fluoro-1,2,3,4-tetrahydroisoquinolin-8-yl)oxy)-5-(4-methyl-7H-pyrrolo[2,3-d]pyrimidin-7-yl)cyclopentane-1,2-diol<br>$^1$H NMR (400 MHz, D$_2$O, HCl salt) δ ppm 8.82 (s, 1H), 7.84-7.74 (m, 1H), 7.08 (d, J = 3.8 Hz, 1H), 6.70 (d, J = 7.2 Hz, 1H), 5.28 (q, J = 9.1 Hz, 1H), 4.76-4.73 (m, 1H), 4.66-4.58 (m, 1H), 4.36-4.20 (m, 3H), 4.18-4.05 (m, 2H), 3.45 (t, J = 6.4 Hz, 2H), 3.08-2.93 (m, 3H), 2.87 (s, 3H), 2.23-2.09 (m, 1H), 1.31 (t, J = 7.0 Hz, 3H) |

Scheme EEEE—Synthesis of tert-butyl 6-(difluoromethoxy)-5-fluoro-8-hydroxy-3,4-dihydroisoquinoline-2(1H)-carboxylate (TP-37)

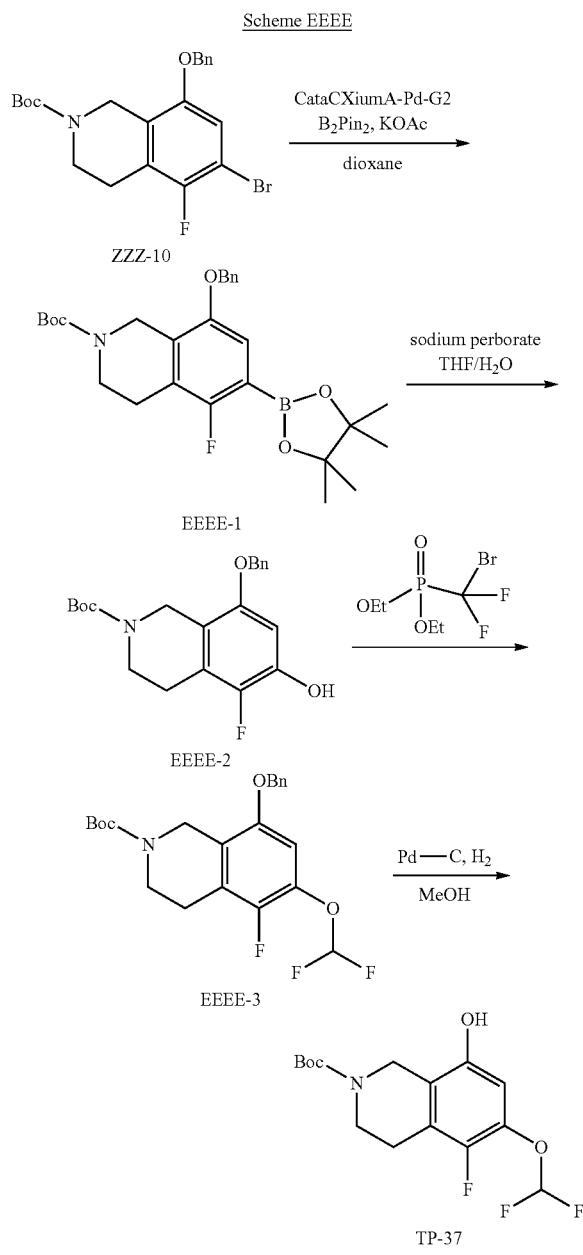

Step 1—Synthesis of tert-butyl 8-(benzyloxy)-5-fluoro-6-(4,4,5,5-tetramethyl-1,3,2-dioxaborolan-2-yl)-3,4-dihydroisoquinoline-2(1H)-carboxylate (EEEE-1)

To a solution of ZZZ-10 (500 mg, 1.15 mmol) in dioxane (29 mL) was added bis(pinacolato)diboron (1.46 g, 5.73 mmol). The solution was degassed with $N_2$ for 10 min and cataCXium® A-Pd-G2 (76.6 mg, 0.12 mmol) and KOAc (337 mg, 1.79 mmol) were added to the reaction solution under $N_2$ atmosphere. The reaction was heated at 80° C. for 16 hours. Water (10 mL) was added and the reaction was extracted with EtOAc (10 mL×2). The organic layers were separated, dried and evaporated to give the crude product, which was purified by flash chromatography, eluted with petroleum ether/EtOAc 0-20% to give EEEE-1 (78%, 443 mg) as a gray solid. LCMS [M-Boc+1] 384.0; $^1$H NMR (400 MHz, DMSO-$d_6$) δ ppm 7.52-7.32 (m, 5H), 7.05 (d, J=4.3 Hz, 1H), 5.13 (s, 2H), 4.47 (br s, 2H), 3.57 (br t, J=5.8 Hz, 2H), 2.72-2.66 (m, 2H), 1.43 (s, 9H), 1.30 (s, 12H)

Step 2—Synthesis of tert-butyl 8-(benzyloxy)-5-fluoro-6-hydroxy-3,4-dihydroisoquinoline-2(1H)-carboxylate (EEEE-2)

To a solution of EEEE-1 (430 mg, 0.89 mmol) in THF (4 mL) and water (4 mL) was added sodium perborate (306 mg, 3.74 mmol) in one portion at RT under $N_2$. The reaction solution was stirred at room temperature for 8 hours. The mixture was diluted with EtOAc (10 mL) and water (5 mL). The organic layer was separated, dried and evaporated to give the crude product, which was purified by flash chromatography, eluted with petroleum ether/EtOAc 0-20% to give EEEE-2 (150 mg, 45%) as a white solid. LCMS [M+Na] 396.

Step 3—Synthesis of tert-butyl 8-(benzyloxy)-6-(difluoromethoxy)-5-fluoro-3,4-dihydroisoquinoline-2(1H)-carboxylate (EEEE-3)

KOH (165 mg, 2.95 mol) was suspended in a mixture of acetonitrile (1 mL) and water (1 mL) and cooled to −20° C. Compound EEEE-2 (110 mg, 0.295 mmol) was added portion-wise, followed by diethyl (bromo-difluoromethyl) phosphonate (157 mg, 0.59 mmol) over 15 min. The mixture was warmed to 25° C. for 2 days. Water was added to the reaction solution and extracted with EtOAc (10 mL×3). The organic layers were separated, dried and concentrated to give the crude product, which was purified by flash chromatography, eluted with petroleum ether/EtOAc 0-10%, to give EEEE-3 (100 mg, 80%) as a white solid. LCMS [M-Boc+1] 324.

Step 4—Synthesis of tert-butyl 6-(difluoromethoxy)-5-fluoro-8-hydroxy-3,4-dihydroisoquinoline-2(1H)-carboxylate (TP-37)

To a solution of EEEE-3 (100 mg, 0.23 mmol) in MeOH (5 mL) was added Pd/C (25 mg, 0.024 mmol). The mixture was degassed and purged with $H_2$ three times. The resulting mixture was stirred at r.t. (28° C.) for 16 hours. The reaction was diluted with DCM (20 mL) and filtered and concentrated to give TP-37 as a white solid (75 mg, 95%). LCMS [M-tBu+1] 278.0; $^1$H NMR (400 MHz, DMSO-$d_6$) δ ppm 9.99 (bs, 1H), 7.31 (t, J=74 Hz, 1H), 6.62 (d, J=8 Hz, 1H), 4.33 (s, 2H), 3.55 (t, J=8 Hz, 2H), 2.69 (t, J=8 Hz, 2H), 1.43 (s, 9H)

Example 200 was Prepared Using Similar Chemistry Depicted in Scheme CC and Employing Compound TP-37

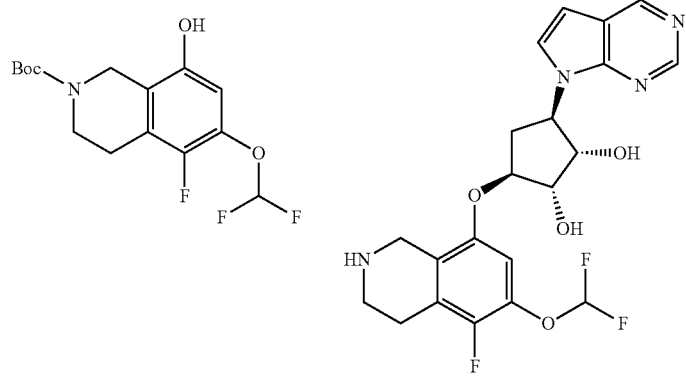

| Example 200 TP-37 | 465.1 [M + 1] | (1S,2S,3S,5R)-3-((6-(difluoromethoxy)-5-fluoro-1,2,3,4-tetrahydroisoquinolin-8-yl)oxy)-5-(4-methyl-7H-pyrrolo[2,3-d]pyrimidin-7-yl)cyclopentane-1,2-diol $^1$H NMR (400 MHz, D$_2$O, HCl salt) δ ppm 8.85 (s, 1H), 7.82 (d, J = 3.8 Hz, 1H), 7.11 (d, J = 3.8 Hz, 1H), 6.98-6.58 (m, 2H), 5.32 (q, J = 9.0 Hz, 1H), 4.76-4.73 (m, 1H), 4.67-4.62 (m, 1H), 4.35-4.25 (m, 3H), 3.49 (t, J = 6.3 Hz, 2H), 3.10-2.96 (m, 3H), 2.90 (s, 3H), 2.24-2.12 (m, 1H) |
|---|---|---|

Scheme FFFF—Synthesis of tert-butyl 5-fluoro-8-hydroxy-6-isopropoxy-3,4-dihydroisoquinoline-2(1H)-carboxylate (TP-38)

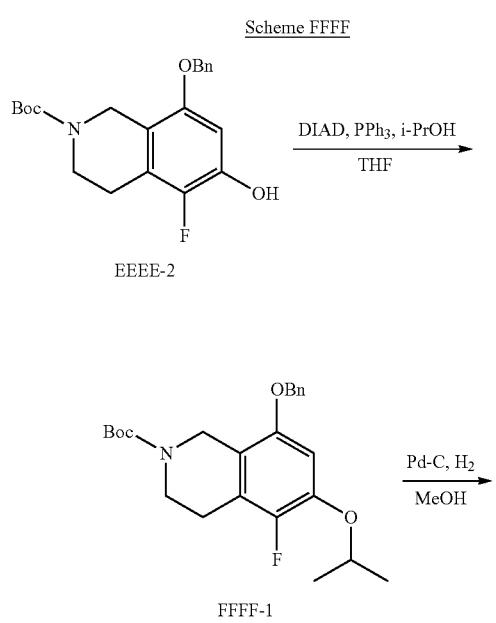

Step 1—Synthesis of tert-butyl 8-(benzyloxy)-5-fluoro-6-isopropoxy-3,4-dihydroisoquinoline-2(1H)-carboxylate (FFFF-1)

To a solution of EEEE-2 (170 mg, 0.455 mmol) in THF (3 mL) was cooled with an ice bath and PPh$_3$ (478 mg, 1.82 mmol) was added under N$_2$. DIAD (368 mg, 1.82 mmol) was added dropwise and the reaction was stirred at 25° C. for 30 min which became a white suspension. Then iPrOH (82.1 mg, 1.37 mmol) was added to the reaction solution in one portion and stirred at 15° C. for 16 hours. The mixture was diluted with EtOAc (50 mL) and H$_2$O (100 mL). The mixture was separated and the aqueous layer was extracted with EtOAc (50 mL). The combined organic layers were washed with brine (50 mL), dried over Na$_2$SO$_4$, filtered and concentrated.

The crude product was purified by flash chromatography, eluted with petroleum ether/EtOAc 0-20% to give FFFF-1 (160 mg, 85%) as a colorless oil. LCMS [M-tBu+1] 270.1; $^1$H NMR (400 MHz, DMSO-d$_6$) δ ppm 7.50-7.29 (m, 5H), 6.78 (d, J=7.0 Hz, 1H), 5.15 (s, 2H), 4.65-4.53 (m, 1H), 4.38 (br d, J=2.8 Hz, 2H), 3.54 (t, J=5.9 Hz, 2H), 2.74-2.62 (m, 2H), 1.43 (s, 9H), 1.23 (d, J=6.0 Hz, 6H)

Step 2—Synthesis of tert-butyl 5-fluoro-8-hydroxy-6-isopropoxy-3,4-dihydroisoquinoline-2(1H)-carboxylate (TP-38)

To a solution of FFFF-1 (160 mg, 0.385 mmol) in MeOH (5 mL) was added Pd/C (41 mg, 0.039 mmol). The mixture was degassed and purged with H$_2$ three times using a H$_2$ balloon then stirred at room temperature (28° C.) for 16 hours under a H$_2$ balloon. The reaction was diluted with DCM (20.0 mL) filtered and concentrated to give TP-38 as a yellow solid (118 mg, 94%). $^1$H NMR (400 MHz, DMSO-d$_6$) δ ppm 9.50 (br d, J=2.5 Hz, 1H), 6.45 (d, J=7.3 Hz, 1H), 4.41 (td, J=6.0, 12.0 Hz, 1H), 4.28 (s, 2H), 3.52 (t, J=5.6 Hz, 2H), 2.64 (br t, J=5.8 Hz, 2H), 1.42 (s, 9H), 1.26 (d, J=6.0 Hz, 6H)

Example 201 was Prepared Using Similar Chemistry Depicted in Scheme CC and Employing Compound TP-38

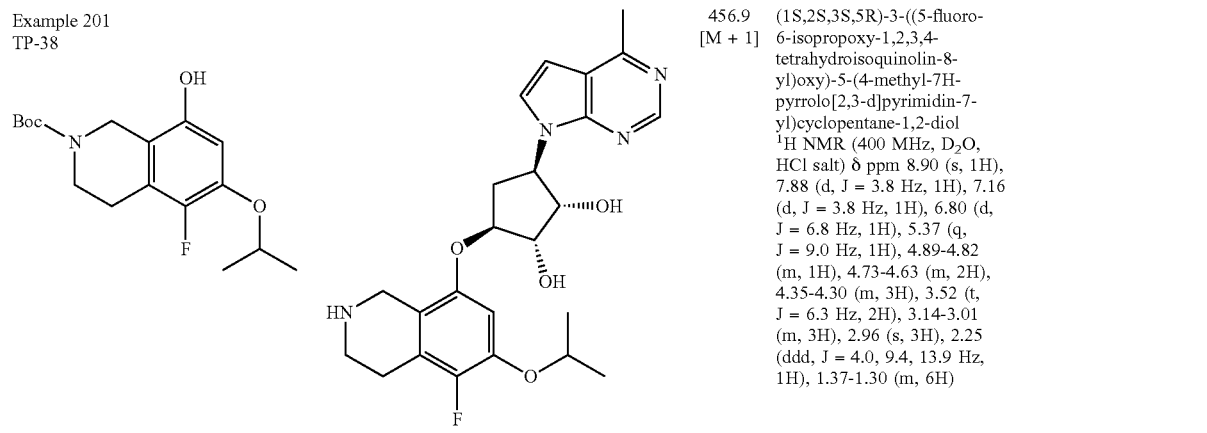

Example 201
TP-38

456.9 [M + 1]

(1S,2S,3S,5R)-3-((5-fluoro-6-isopropoxy-1,2,3,4-tetrahydroisoquinolin-8-yl)oxy)-5-(4-methyl-7H-pyrrolo[2,3-d]pyrimidin-7-yl)cyclopentane-1,2-diol
$^1$H NMR (400 MHz, D$_2$O, HCl salt) δ ppm 8.90 (s, 1H), 7.88 (d, J = 3.8 Hz, 1H), 7.16 (d, J = 3.8 Hz, 1H), 6.80 (d, J = 6.8 Hz, 1H), 5.37 (q, J = 9.0 Hz, 1H), 4.89-4.82 (m, 1H), 4.73-4.63 (m, 2H), 4.35-4.30 (m, 3H), 3.52 (t, J = 6.3 Hz, 2H), 3.14-3.01 (m, 3H), 2.96 (s, 3H), 2.25 (ddd, J = 4.0, 9.4, 13.9 Hz, 1H), 1.37-1.30 (m, 6H)

Scheme GGGG—Synthesis of tert-butyl 8-cyano-6-hydroxy-2,3-dihydrobenzo[f][1,4]oxazepine-4(5H)-carboxylate (TP-39)

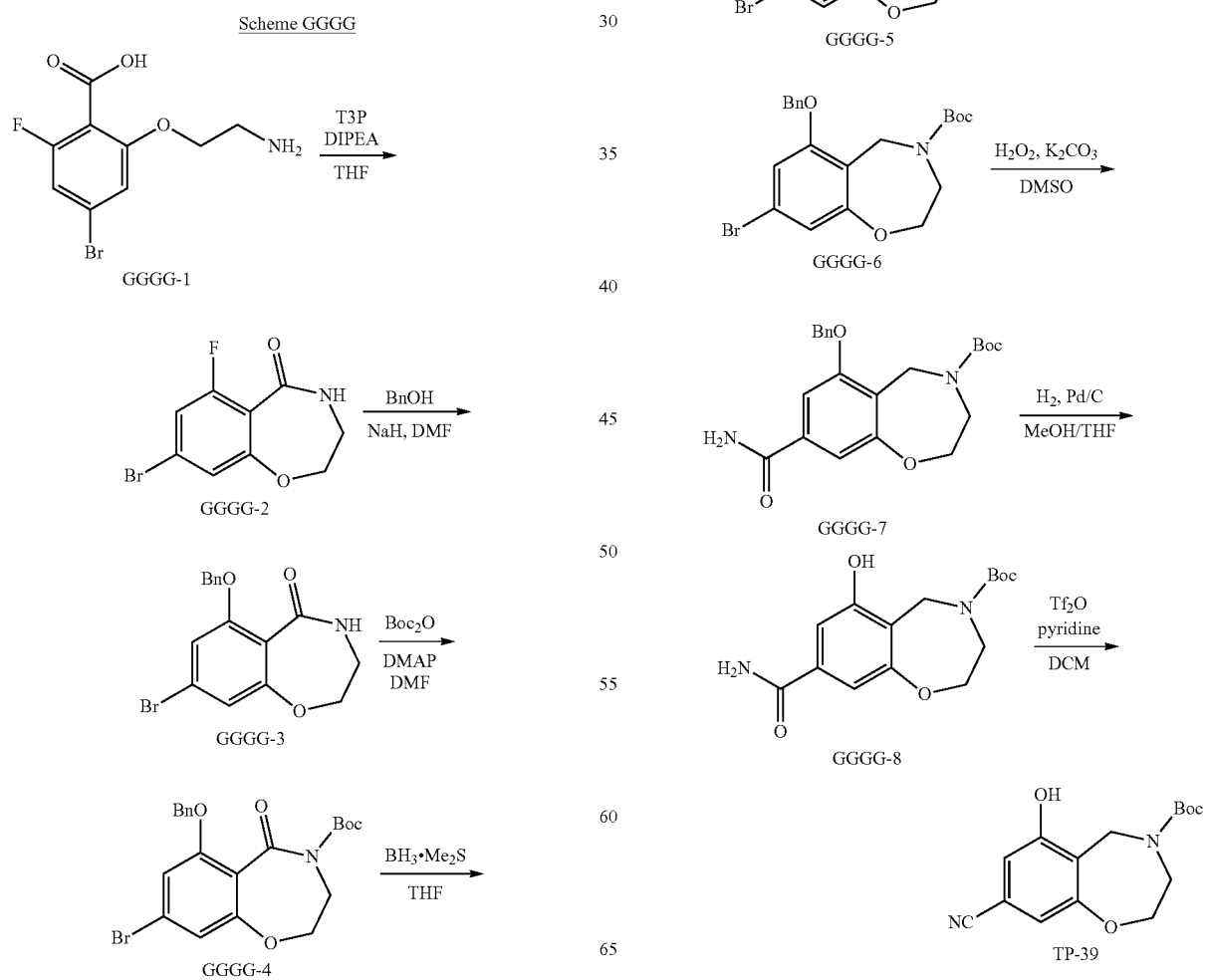

Step 1—Synthesis of 8-bromo-6-fluoro-3,4-dihydrobenzo[f][1,4]oxazepin-5(2H)-one (GGGG-2)

To a suspension of GGGG-1 (13.8 g, 43.87 mmol, prepared using reference patent US2015/64196) in dry THF (400 mL) was added DIPEA (28.3 g, 219 mmol) and T3P (50% in EtOAc, 41.9 g, 65.8 mmol) at 0° C. The mixture was stirred at 0° C. for 10 h then at rt 25° C. for 6 h. The mixture was poured into water (400 mL) and extracted with EtOAc (400 mL×2). The extract was washed with brine (300 mL), dried over $Na_2SO_4$ and concentrated to give GGGG-2 (9500 mg, 83%) as a light yellow solid. LCMS [M+1] 261.6; $^1$H NMR (400 MHz, DMSO-$d_6$) δ ppm 8.57 (br s, 1H), 7.44 (dd, J=1.8, 9.5 Hz, 1H), 7.22 (s, 1H), 4.22 (t, J=5.5 Hz, 2H), 3.27 (q, J=5.6 Hz, 2H)

Step 2—Synthesis of 6-(benzyloxy)-8-bromo-3,4-dihydrobenzo[f][1,4]oxazepin-5(2H)-one (GGGG-3)

To a suspension 60% NaH (6 g, 150 mmol) in dry DMF (140 mL) was added a solution of GGGG-2 (6.5 g, 25 mmol) and BnOH (5.41 g, 50 mmol) in dry DMF (70 mL) at rt 25° C. under $N_2$, then was stirred at rt 25° C. under $N_2$ for 16 h. The mixture was poured into ice water (400 mL) in which solid was formed. The mixture was filtered. The solid was washed with water and dried in vacuo to afford GGGG-3 (9500 mg, >99%) as a white solid. LCMS [M+1] 347.7; $^1$H NMR (400 MHz, DMSO-$d_6$) δ ppm 8.27 (br t, J=5.7 Hz, 1H), 7.47 (d, J=6.6 Hz, 2H), 7.42-7.36 (m, 2H), 7.35-7.29 (m, 1H), 7.26-7.15 (m, 1H), 6.93 (d, J=1.4 Hz, 1H), 5.19 (s, 2H), 4.12 (t, J=5.5 Hz, 2H), 3.18 (q, J=5.6 Hz, 2H).

Step 3—Synthesis of tert-butyl 6-(benzyloxy)-8-bromo-5-oxo-2,3-dihydrobenzo[f][1,4]oxazepine-4 (5H)-carboxylate (GGGG-4)

To a solution of GGGG-3 (7.3 g, 21 mmol) in DMF (150 mL) was added $Boc_2O$ (6.86 g, 31.43 mmol), DIPEA (8.13 g, 62.9 mmol) and DMAP (256 mg, 2.1 mmol) at rt 25° C. for 2 h. The mixture was poured into water. The solid was collected by filtration and washed with water. The solid was dissolved in EtOAc/THF (50 mL/50 mL) and dried over $Na_2SO_4$ and concentrated in vacuo to afford crude GGGG-4 (10 g, >99%) as a yellow gum and used directly in the next step without further purification.

Step 4—Synthesis of tert-butyl 6-(benzyloxy)-8-bromo-2,3-dihydrobenzo[f][1,4]oxazepine-4(5H)-carboxylate (GGGG-5)

To a solution of GGGG-4 (10 g, 21 mmol) in THF (150 mL) was added $BH_3.Me_2S$ (8.39 mL, 83.9 mmol) at rt 25° C. The mixture was stirred at 60° C. under $N_2$ for 16 h then stand at rt for 2 days. The reaction was quenched with MeOH (70 mL) slowly. Then the mixture was refluxed for 16 h and concentrated. The crude product was purified by column chromatography (120 g silica column, EtOAc in petroleum ether from 0% to 50%) to afford GGGG-5 (3130 mg, 34%) as a white solid. LCMS [M+23] 456; $^1$H NMR (400 MHz, $CDCl_3$) δ ppm 7.52-7.31 (m, 5H), 6.84 (bs, 1H), 6.82 (bs, 1H), 5.06 (br s, 2H), 4.64 (br s, 2H), 4.15-4.10 (m, 2H), 3.80 (br s, 2H), 1.29 (br s, 9H)

Step 5—Synthesis of tert-butyl 6-(benzyloxy)-8-cyano-2,3-dihydrobenzo[f][1,4]oxazepine-4(5H)-carboxylate (GGGG-6)

Compound GGGG-5 (680 mg, 1.57 mmol), $Zn(CN)_2$ (368 mg, 3.13 mmol) and $Pd(PPh_3)_4$ (181 mg, 0.157 mmol) in DMF (10 ml) was sparged with $N_2$ for 10 min. The mixture was stirred at 120° C. for 3 h. The mixture was cooled, filtered, and concentrated. The residue was purified by silica gel chromatography eluted with EtOAc in petroleum ether from 0 to 50% to afford GGGG-6 (520 mg, 87%) as a white solid. LCMS [M-Boc+1] 280.9.

Step 6—Synthesis of tert-butyl 6-(benzyloxy)-8-carbamoyl-2,3-dihydrobenzo[f][1,4]oxazepine-4 (5H)-carboxylate (GGGG-7)

To a solution of GGGG-6 (520 mg, 1.37 mmol) and $K_2CO_3$ (189 mg, 1.37 mmol) in DMSO (5 mL) was added 30% $H_2O_2$ (465 mg, 4.1 mmol) at rt 25° C. slowly. Note: gas evolved and exothermic. The mixture was stirred at rt 25° C. for 1 h. The mixture was poured into water (10 mL) and filtered. The solid was washed with water. The solid was suspended in MeOH (30 mL) and concentrated in vacuo to afford GGGG-7 (520 mg, 96%) as a white solid. LCMS [M+Na] 421.

Step 7—Synthesis of tert-butyl 8-carbamoyl-6-hydroxy-2,3-dihydrobenzo[f][1,4]oxazepine-4(5H)-carboxylate (GGGG-8)

A mixture of GGGG-7 (520 mg, 1.31 mmol) and Pd/C (125 mg) in MeOH/THF (15 mL/15 mL) was degassed with $H_2$ four times. The mixture was stirred at 25° C. under a $H_2$ balloon for 16 h. The mixture was filtered and concentrated in vacuo to afford GGGG-8 (400 mg, 99%) as a white solid. $^1$H NMR (400 MHz, DMSO-$d_6$, rotamers) δ ppm 9.85 (br s, 1H), 7.80 (br s, 1H), 7.22 (br s, 1H), 7.11-6.97 (m, 1H), 6.92 (br s, 1H), 4.57 (br s, 2H), 4.20-4.03 (m, 2H), 3.68 (br s, 2H), 1.42-1.13 (m, 9H)

Step 8—Synthesis of tert-butyl 8-cyano-6-hydroxy-2,3-dihydrobenzo[f][1,4]oxazepine-4(5H)-carboxylate (TP-39)

To a suspension of GGGG-8 (100 mg, 0.324 mol) and pyridine (128 mg, 1.62 mol) in anhydrous DCM (2 mL) was added $Tf_2O$ (275 mg, 0.973 mol) at 0° C. and stirred for 0.5 h. The reaction mixture was warmed to 25° C. and stirred for 16 h. The mixture was concentrated in vacuo to dryness. The residue was dissolved in MeOH (3 mL), followed by $K_2CO_3$ (300 mg). The mixture was stirred at rt 25° C. for 16 h. The reaction was filtered and purified by prep-TLC (petroleum ether/EtOAc 1:1) to afford TP-39 (55 mg, 58%) as a white solid. LCMS [M-Boc+1] 190.8; $^1$H NMR (400 MHz, DMSO-$d_6$, rotamers) δ ppm 10.47 (br s, 1H), 6.83 (br s, 2H), 4.70-4.51 (m, 2H), 4.22-4.18 (m, 2H), 3.69 (br s, 2H), 1.46-1.21 (m, 9H)

Scheme HHHH—Synthesis of tert-butyl 8-fluoro-6-hydroxy-2,3-dihydrobenzo[f][1,4]oxazepine-4(5H)-carboxylate (TP-40)

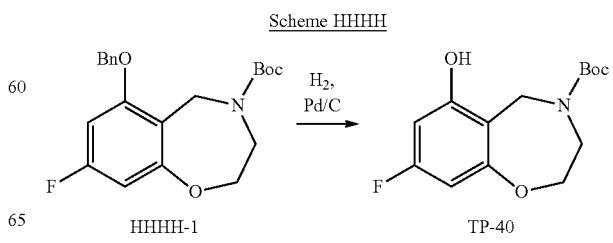

Scheme HHHH

To a solution of HHHH-1 (prepared using similar method as steps 1-4 in Scheme GGGG using 2-(2-aminoethoxy)-4,6-difluorobenzoic acid, 1980 mg, 5.302 mmol) in MeOH (74 mL) was added 10% wet Pd/C (590 mg) at 25° C. The mixture was stirred at 25° C. under a H$_2$ balloon for 1.2 hours. The reaction was filtered and concentrated to yield TP-40 (1420 mg, 95%) as a white solid. LCMS [M-Boc+1] 184.8 $^1$H NMR (400 MHz, DMSO-d$_6$, rotamers) δ ppm 10.60-9.69 (bs, 1H), 6.34-6.30 (m, 1H), 6.26-6.12 (m, 1H), 4.63-4.39 (m, 2H), 4.23-4.01 (m, 2H), 3.75-3.58 (m, 2H), 1.46-1.20 (m, 9H); $^1$H NMR (400 MHz, DMSO-d$_6$, Variable temp 80° C.) δ ppm 6.33 (br d, J=10.3 Hz, 1H), 6.19 (dd, J=2.3, 10.3 Hz, 1H), 4.53 (s, 2H), 4.19-4.06 (m, 2H), 3.69 (br t, J=4.4 Hz, 2H), 1.36 (s, 9H)

Scheme IIII—Synthesis of tert-butyl 8-chloro-6-hydroxy-2,3-dihydrobenzo[f][1,4]oxazepine-4(5H)-carboxylate (TP-41)

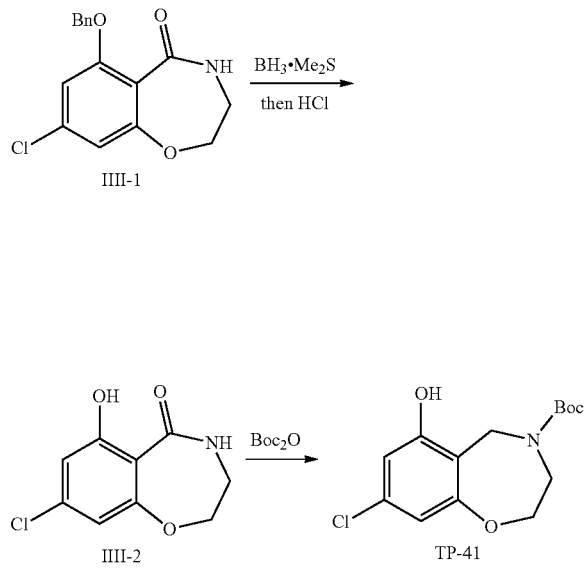

Step 1—Synthesis of 8-chloro-2,3,4,5-tetrahydrobenzo[f][1,4]oxazepin-6-ol (IIII-2)

To a solution of IIII-1 (prepared using similar method as steps 1-3 in Scheme GGGG using 2-(2-aminoethoxy)-4-chloro-6-fluorobenzoic acid, 1000 mg, 3.292 mmol) in dry THF (11 mL) was added BH$_3$·Me$_2$S (2.63 mL, 26.3 mmol) at rt 25° C. under N$_2$. After addition, the mixture was heated at 70° C. for 16 hours. The mixture was cooled to rt (25° C.) and quenched with MeOH (3 mL). The mixture was concentrated as a white solid. The crude product was dissolved in conc HCl (13.7 mL) and heated at 110° C. for 16 hours. The mixture was concentrated to obtain IIII-2 (860 mg, >99%) as a light yellow solid which was used in next step directly. LCMS [M+1] 199.7

Step 2—Synthesis of tert-butyl 8-chloro-6-hydroxy-2,3-dihydrobenzo[f][1,4]oxazepine-4(5H)-carboxylate (TP-41)

To a solution of IIII-2 (1171 mg, 3.3 mmol) in MeOH (21 mL) was added TEA (3.58 mL, 25.6 mmol) and Boc$_2$O (1.32 g, 6.02 mmol) then stirred at r.t. for 2 hours. The mixture was concentrated in vacuum to get crude product (1032 mg) as white solid. The crude product purified by combi-flash (EtOAc/Petroleum ether=0~50%) to afford TP-41 (520 mg, 30%) as a white solid. LCMS [M-tBu+1] 243.6; $^1$H NMR (400 MHz, DMSO-d$_6$, rotamers) δ ppm 10.13 (s, 1H), 6.61-6.57 (m, 1H), 6.45 (bs, 1H), 4.61-4.46 (m, 2H), 4.25-4.05 (m, 2H), 3.66 (br s, 2H), 1.42-1.27 (m, 9H)

Examples 202-204 were Prepared Using Similar Chemistry Depicted in Scheme CC and Employing Compounds TP-39, TP-40 & TP-41 Respectively

| Example 202 TP-39 | | |
|---|---|---|
| 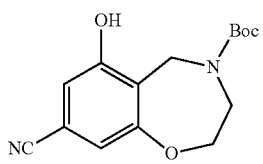 | 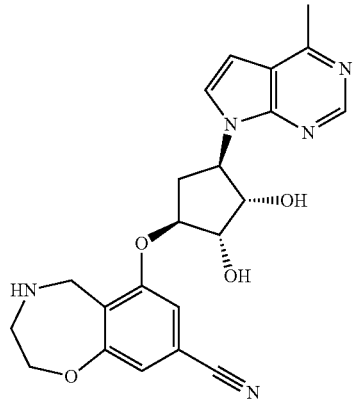 [SMILES: Cc1ncnc2c1ccn2[C@@H]1C[C@H](Oc2cc(C#N)cc3c2CNCCO3)[C@@H](O)[C@H]1O] | 422.2 [M + 1] 6-(((1S,2S,3S,4R)-2,3-dihydroxy-4-(4-methyl-7H-pyrrolo[2,3-d]pyrimidin-7-yl)cyclopentyl)oxy)-2,3,4,5-tetrahydrobenzo[f][1,4]oxazepine-8-carbonitrile $^1$H NMR (400 MHz, D$_2$O, HCl salt) δ ppm 8.86 (s, 1H), 7.85 (d, J = 3.8 Hz, 1H), 7.25 (d, J = 1.0 Hz, 1H), 7.20 (d, J = 1.3 Hz, 1H), 7.11 (d, J = 3.8 Hz, 1H), 5.35 (q, J = 9.2 Hz, 1H), 4.86-4.80 (m, 2H), 4.60 (q, J = 14.8 Hz, 2H), 4.43-4.26 (m, 3H), 3.66 (t, J = 4.9 Hz, 2H), 3.15-3.04 (m, 1H), 2.91 (s, 3H), 2.28-2.18 (m, 1H) |

-continued

| Example 203 TP-40 | 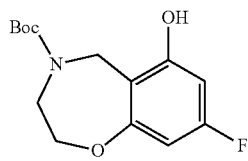 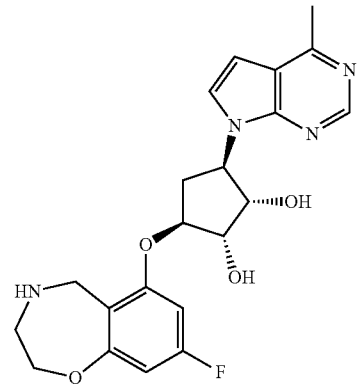 [SMILES: Cc1ncnc2c1ccn2[C@@H]1C[C@H](Oc2cc(F)cc3c2CNCCO3)[C@@H](O)[C@H]1O] | 414.9 [M + 1] | (1S,2S,3S,5R)-3-((8-fluoro-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol <br> ¹H NMR (400 MHz, MeOD, HCl salt) δ ppm = 9.07 (s, 1H), 8.12 (d, J = 4.0 Hz, 1H), 7.25 (d, J = 3.8 Hz, 1H), 6.86 (dd, J = 2.5, 10.8 Hz, 1H), 6.59 (dd, J = 2.4, 9.4 Hz, 1H), 5.40 (q, J = 9.3 Hz, 1H), 4.77 (dd, J = 5.0, 9.3 Hz, 2H), 4.62-4.50 (m, 2H), 4.34 (tdt, J = 4.5, 9.3, 13.6 Hz, 2H), 4.25 (d, J = 5.0 Hz, 1H), 3.65 (t, J = 4.6 Hz, 2H), 3.13-3.04 (m, 1H), 3.02 (s, 3H), 2.36 (ddd, J = 4.4, 9.7, 14.3 Hz, 1H) |
| --- | --- | --- | --- |
| Example 204 TP-41 | 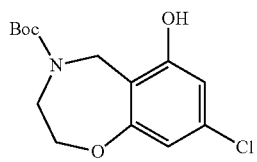 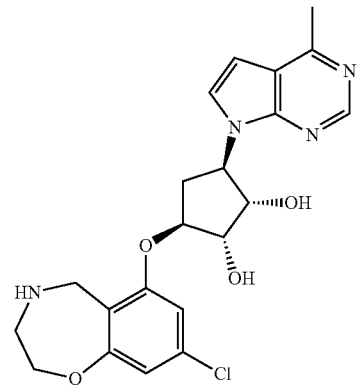 [SMILES: Cc1ncnc2c1ccn2[C@@H]1C[C@H](Oc2cc(Cl)cc3c2CNCCO3)[C@@H](O)[C@H]1O] | 431.1 [M + 1] | (1S,2S,3S,5R)-3-((8-chloro-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol <br> ¹H NMR (400 MHz, MeOD) δ ppm 8.65 (s, 1H), 7.59 (d, J = 3.7 Hz, 1H), 6.90 (d, J = 1.9 Hz, 1H), 6.78 (d, J = 3.6 Hz, 1H), 6.71 (d, J = 1.9 Hz, 1H), 5.24 (q, J = 9.0 Hz, 1H), 4.73-4.66 (m, 2H), 4.21 (d, J = 5.1 Hz, 1H), 4.16-4.04 (m, 4H), 3.22-3.17 (m, 2H), 3.00 (ddd, J = 7.5, 9.2, 14.4 Hz, 1H), 2.74 (s, 3H), 2.29-2.15 (m, 1H) |

Scheme JJJJ—Synthesis of tert-butyl 8-(difluoromethyl)-6-hydroxy-2,3-dihydrobenzo[f][1,4]oxazepine-4(5H)-carboxylate (TP-42)

Scheme JJJJ

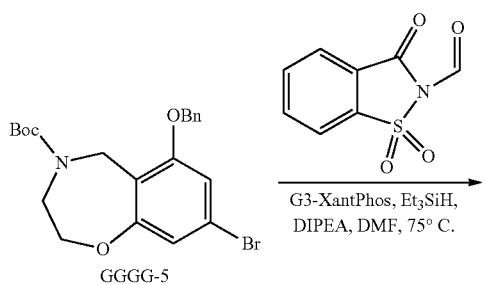

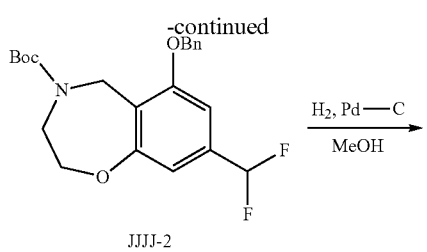

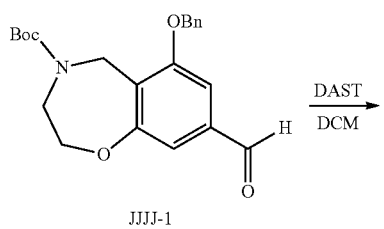

Step 1—Synthesis of tert-butyl 6-(benzyloxy)-8-formyl-2,3-dihydrobenzo[f][1,4]oxazepine-4(5H)-carboxylate (JJJJ-1)

Ref. Manabe, K. et al. *Org. Lett.*, 2013, 5370-5373. A reaction vial was added a solution of GGGG-5 (1.64 g, 3.62 mmol) in anhydrous DMF (18 mL) and N-formylsaccharin (1200 mg, 5.66 mmol), G3 Xantphos (107 mg, 0.113 mmol) and DIPEA (634 mg, 4.91 mmol). The mixture was sparged with N₂ for 4 min. To the above solution was added Et₃SiH (571 mg, 4.91 mmol) at 0° C. After the addition, the resulting mixture was sparged with N₂ for 5 min and then heated at 75° C. for 16 hours. The reaction mixture was partitioned between EtOAc and water. The organic layer was separated and the aqueous layer was extracted with EtOAc (30 mL×3). The combined organic layers were washed with brine, dried over Na$_2$SO$_4$ and concentrated to afford the crude product which was purified via flash column (20 g, gel, EtOAc: petroleum ether 1%-14%) to afford JJJJ-1 (730 mg, 53%) as a white solid. $^1$H NMR (400 MHz, CDCl$_3$, rotamers) δ ppm 9.87 (br s, 1H), 7.59-7.30 (m, 5H), 7.21 (bs, 1H), 7.14 (bs, 1H), 5.16 (br s, 2H), 4.75 (br s, 2H), 4.24-4.17, (m, 2H), 3.85 (br s, 2H), 1.54-1.13 (m, 9H)

Step 2—Synthesis of tert-butyl 6-(benzyloxy)-8-(difluoromethyl)-2,3-dihydrobenzo[f][1,4]oxazepine-4(5H)-carboxylate (JJJJ-2)

To a solution of JJJJ-1 (930 mg, 2.43 mmol) in anhydrous DCM (49 mL) was added DAST (3.91 g, 24.3 mmol) at 0° C. under N$_2$. After the addition, the reaction mixture was warmed to room temperature (32° C.) and stirred at this temperature for 16 hours. The reaction solution was diluted in DCM (50 mL) and sat. aq NaHCO$_3$ and stirred until CO$_2$ evolution ceased. The reaction mixture was partitioned between DCM and H$_2$O. The organic layer was separated, washed with brine, dried over Na$_2$SO$_4$ and concentrated to afford the crude product which was purified via flash column (EtOAc: petroleum ether 1%-15%) to afford JJJJ-2 (530 mg, 54%) as a white solid. $^1$H NMR (400 MHz, CDCl$_3$, rotamers) δ ppm 7.58-7.29 (m, 5H), 6.82 (bs, 1H), 6.79 (bs, 1H), 6.54 (t, J=54 Hz, 1H), 5.12 (br s, 2H), 4.72 (br s, 2H), 4.21-4.07 (m, 2H), 3.83 (br s, 2H), 1.54-1.13 (m, 9H)

Step 3—Synthesis of tert-butyl 8-(difluoromethyl)-6-hydroxy-2,3-dihydrobenzo[f][1,4]oxazepine-4(5H)-carboxylate (TP-42)

To a solution of JJJJ-2 (530 mg, 1.31 mmol) in MeOH (13 mL) was added Pd/C (139 mg, 0.0163 mmol). The mixture was degassed and purged with H$_2$ three times, then stirred at rt (35° C.) for 16 hours. The reaction was filtered through celite and concentrated. The residue was lyophilized to remove the residual solvent to give TP-42 (360 mg, 87%) as a white solid. LCMS [M-tBu+1] 259.7; $^1$H NMR (400 MHz, DMSO-d$_6$, rotamers) δ ppm 10.21-9.89 (m, 1H), 7.02-6.47 (m, 3H), 4.65-4.49 (m, 2H), 4.22-4.04 (m, 2H), 3.74-3.62 (m, 2H), 1.46-1.11 (m, 9H)

Example 205 was Prepared Using Similar Chemistry Depicted in Scheme CC and Employing Compound TP-42

Scheme KKKK—Synthesis of tert-butyl 6-hydroxy-8-methyl-2,3-dihydrobenzo[f][1,4]oxazepine-4(5H)-carboxylate (TP-43)

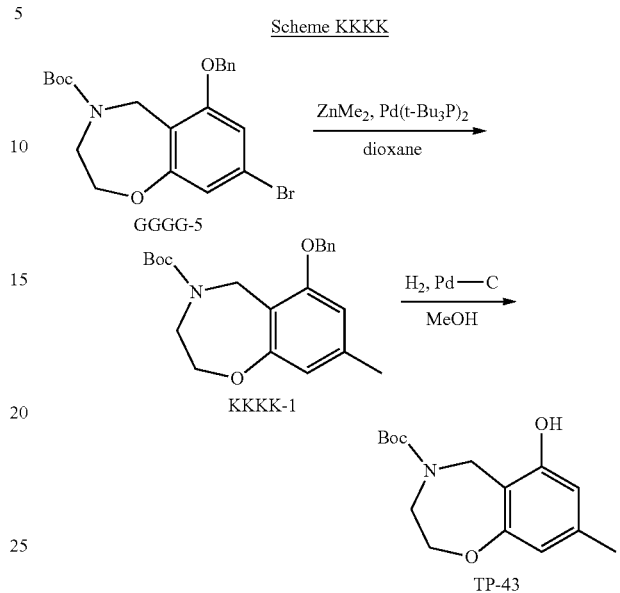

Step 1 Synthesis of tert-butyl 6-(benzyloxy)-8-methyl-2,3-dihydrobenzo[f][1,4]oxazepine-4(5H)-carboxylate (KKKK-1)

A solution of GGGG-5 (200 mg, 0.46 mmol) in dioxane (9.21 mL) was degassed with N$_2$ for 5 min. Then bis(tri-tert-butylphosphine)Pd(0) (23.5 mg, 0.05 mmol) and (Me)$_2$Zn (0.921 mL, 0.92 mmol) was then added to the reaction solution and heated at 90° C. for 16 hours. The reaction solution was poured into EtOAc and 1N HCl (20 mL:20 mL). The mixture was separated and the water layer was washed with EtOAc (20 mL×2). The organic layers were separated, dried and evaporated to give the crude product, which was purified by flash chromatography, eluted with petroleum ether/EtOAc from 0-25%, to afford KKKK-1 (160 mg, 94%) as a yellow solid. LCMS [M+Na]

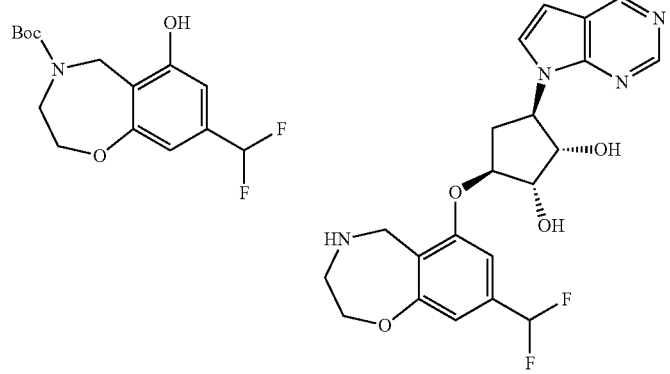

Example 205
TP-42

447.1 [M + 1]  (1S,2S,3S,5R)-3-((8-(difluoromethyl)-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol
$^1$H NMR (400 MHz, D$_2$O, HCl salt) δ ppm 8.90 (s, 1H), 7.89 (d, J = 3.9 Hz, 1H), 7.15 (d, J = 3.7 Hz, 1H), 7.08 (s, 1H), 7.02 (s, 1H), 6.77 (t, J = 55.8 Hz, 1H), 5.37 (q, J = 9.0 Hz, 1H), 4.91-4.84 (m, 1H), 4.73-4.68 (m, 1H), 4.60 (dd, J = 13.4, 30.7 Hz, 2H), 4.45-4.24 (m, 3H), 3.67 (t, J = 4.8 Hz, 2H), 3.15-3.04 (m, 1H), 2.90 (s, 3H), 2.33-2.20 (m, 1H)

392.1; $^1$H NMR (400 MHz, DMSO-d$_6$, rotamers) δ ppm 7.57-7.30 (m, 5H), 6.62 (bs, 1H), 6.39 (s, 1H), 5.09 (bs, 2H), 4.65-4.60 (m, 2H), 4.17-4.04 (m, 2H), 3.68 (br s, 2H), 2.22 (s, 3H), 1.42-1.15 (m, 9H)

Step 2—Synthesis of tert-butyl 6-hydroxy-8-methyl-2,3-dihydrobenzo[f][1,4]oxazepine-4(5H)-carboxylate (TP-43)

Compound KKKK-1 (160 mg, 0.433 mmol) was dissolved in MeOH (8.00 mL). Then Pd/C was added to the reaction solution, then was degassed with H$_2$ four times and stirred at 30° C. under H$_2$ (balloon) for 16 hours. DCM (20 mL) was added to dilute the reaction solution, then filtered and concentrated to give the crude product, which was purified by flash chromatography, eluted with petroleum ether/EtOAc from 0-25%, to give TP-43 (100 mg, 83%) as a white solid. LCMS [M-Boc+1] 179.9; $^1$H NMR (400 MHz, DMSO-d$_6$, rotamers) δ ppm 9.41 (s, 1H), 6.37-6.35 (m, 1H), 6.22-6.20 (m, 1H), 4.58-4.42 (m, 2H), 4.13-3.95 (m, 2H), 3.70-3.59 (m, 2H), 2.13 (s, 3H), 1.41-1.27 (m, 9H)

Example 206 was Prepared Using Similar Chemistry Depicted in Scheme CC and Employing Compound TP-43

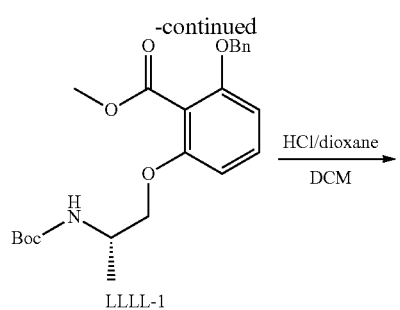

LLLL-1

HCl/dioxane
DCM

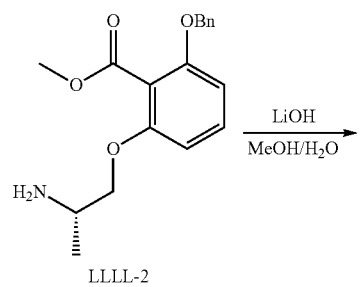

LLLL-2

LiOH
MeOH/H$_2$O

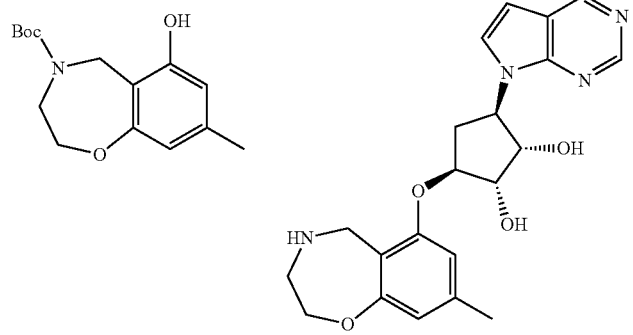

| Example 206 TP-43 | | 411.1 [M + 1] | (1S,2S,3S,5R)-3-((8-methyl-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol<br>$^1$H NMR (400 MHz, D$_2$O, HCl salt) δ ppm 8.89 (s, 1H), 7.87 (d, J = 3.8 Hz, 1H), 7.14 (d, J = 3.8 Hz, 1H), 6.78 (s, 1H), 6.71 (s, 1H), 5.38 (q, J = 9.0 Hz, 1H), 4.77-4.70 (m, 2H), 4.62-4.47 (m, 2H), 4.40-4.22 (m, 3H), 3.63 (t, J = 4.8 Hz, 2H), 3.09 (ddd, J = 7.3, 9.3, 14.7 Hz, 1H), 2.95 (s, 3H), 2.32 (s, 3H), 2.28-2.16 (m, 1H) |

Scheme LLLL—Synthesis of tert-butyl(S)-6-hydroxy-3-methyl-2,3-dihydrobenzo[f][1,4]oxazepine-4(5H)-carboxylate (TP-44)

Scheme LLLL

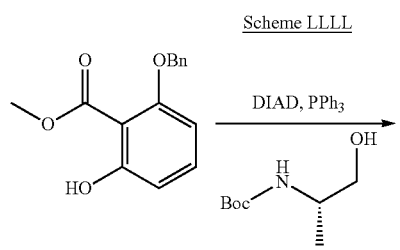

DIAD, PPh$_3$

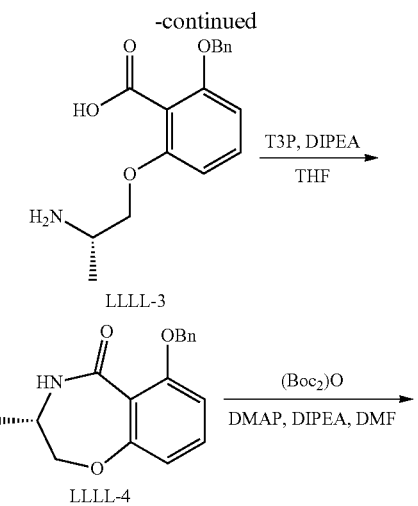

LLLL-3

T3P, DIPEA
THF

LLLL-4

(Boc)$_2$O
DMAP, DIPEA, DMF

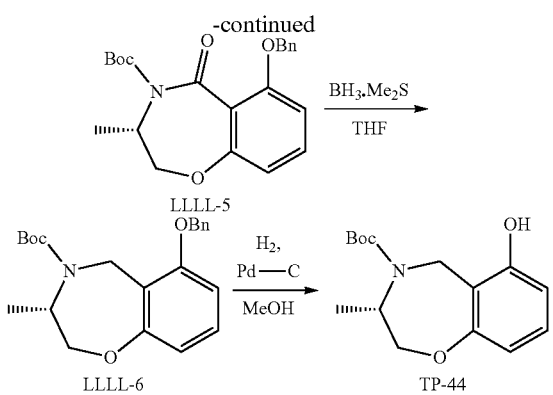

Step 1 Synthesis of methyl(S)-2-(benzyloxy)-6-(2-((tert-butoxycarbonyl)amino)propoxy)benzoate (LLLL-1)

To a solution of methyl 2-(benzyloxy)-6-hydroxybenzoate (2.80 mg, 10.8 mmol) in THF (40.0 mL) were added PPh$_3$ (7.11 g, 27.1 mmol) in an ice bath under N$_2$. DIAD (5.48 g, 27.1 mmol) was added to the above mixture drop-wise then stirred at 25° C. for 40 min. Then tert-butyl (S)-(1-hydroxypropan-2-yl)carbamate (5.70 g, 32.5 mmol) in dry THF (20.0 mL) was added and the reaction stirred at 28° C. for 16 hours. The mixture was diluted with EtOAc (50 mL) and H$_2$O (100 mL). The mixture was separated and the aqueous layer was extracted with EtOAc (50 mL). The combined organic layers were washed with brine (50 mL), dried over Na$_2$SO$_4$, filtered and concentrated to yield crude product which was purified by ISCO (120 g silica gel, petroleum ether:EtOAc=4:1) to yield LLLL-1 (3.50 g, 78%) as a colorless gum. $^1$H NMR (400 MHz, DMSO-d$_6$) δ ppm 7.42-7.35 (m, 4H), 7.34-7.29 (m, 2H), 6.83-6.75 (m, 2H), 6.71 (d, J=8.5 Hz, 1H), 5.16 (s, 2H), 3.95-3.92 (m, 1H), 3.80-3.70 (m, 5H), 1.43-1.34 (m, 9H), 1.08 (d, J=6.5 Hz, 3H)

Step 2—Synthesis of methyl(S)-2-(2-aminopropoxy)-6-(benzyloxy)benzoate (LLLL-2)

To a solution of LLLL-1 (4.30 g, 10.3 mmol) in DCM (10 mL) was added HCl(g)/dioxane (~4N, 20 mL) at 0° C. The mixture was stirred 25° C. for 2 hours. The mixture was concentrated to yield LLLL-2 as the HCl salt (4.00 g, >99%) as a yellow solid, which was used in next step directly.

Step 3—Synthesis of (S)-2-(2-aminopropoxy)-6-(benzyloxy)benzoic acid (LLLL-3)

To a suspension of LLLL-2 (4.0 g, 3.17 mmol) in MeOH (60 mL) and water (12 mL) was added LiOH.H$_2$O (3.46 g, 82.4 mmol) at 25° C. The mixture was stirred 75° C. for 15 hours. The pH of the solution was adjusted to pH-3 with 1N. The solution was evaporated to give the crude product LLLL-3 (3.10 g, >99%) as a white solid which was used for the next step directly without further purification.

Step 4—Synthesis of (S)-6-(benzyloxy)-3-methyl-3,4-dihydrobenzo[f][1,4]oxazepin-5(2H)-one (LLLL-4)

To a suspension of LLLL-3 (4.00 g, 5.77 mmol) in dry THF (60 mL) was added DIPEA (3.73 g, 28.9 mmol) and T3P (50% in EtOAc, 7.35 g, 11.5 mmol) at 0° C. The mixture was stirred 25° C. for 15 hours. The reaction was not complete and DIPEA (3.73 g, 28.9 mmol) and T3P (50% in EtOAc, 7.35 g, 11.5 mmol) was and stirred for another 16 hours. EtOAc (40.0 mL) was added to dilute the solution. The solution was washed with 1N HCl (30 mL), saturated aq NaHCO$_3$ (30 mL) and brine (30 mL). The organic layers were separated, dried and evaporated to give the crude product which was purified by flash chromatography, eluted with petroleum ether/EtOAc from 0-50% to give the desired product LLLL-4 (900 mg, 55%) as a white solid. LCMS [M+1] 283.9; $^1$H NMR (400 MHz, DMSO-d$_6$) δ ppm 8.09 (d, J=6.3 Hz, 1H), 7.51-7.44 (m, 2H), 7.41-7.25 (m, 4H), 6.99-6.91 (m, 1H), 6.68 (dd, J=0.9, 8.2 Hz, 1H), 5.15 (s, 2H), 3.97 (dd, J=4.3, 10.3 Hz, 1H), 3.86-3.77 (m, 1H), 3.46-3.44 (m, 1H), 1.05 (d, J=6.5 Hz, 3H)

Step 5—Synthesis of tert-butyl(S)-6-(benzyloxy)-3-methyl-5-oxo-2,3-dihydrobenzo[f][1,4]oxazepine-4(5H)-carboxylate (LLLL-5)

To a solution of LLLL-4 (900 mg, 3.18 mmol) in DMF (20.0 mL) were added DIPEA (1.23 g, 9.53 mmol) and DMAP (38.8 mg, 0.318 mmol) at 25° C. Boc$_2$O (1.04 mg, 4.76 mmol) and the reaction mixture was stirred at 25° C. for 16 hours. The mixture was diluted with ice-water (20 mL) and extracted with EtOAc (20 mL×2). The combined organic layers were washed with brine (30 mL×5), dried over Na$_2$SO$_4$ and filtered, concentrated in vacuo to afford crude which was purified by ISCO (4 g silica gel, EtOAc: petroleum ether=18%-20%) to yield LLLL-5 (720 mg, 59%) as a white solid and used directly in the next step. LCMS [M-Boc+1] 238.9

Step 6—Synthesis of tert-butyl(S)-6-(benzyloxy)-3-methyl-2,3-dihydrobenzo[f][1,4]oxazepine-4(5H)-carboxylate (LLLL-6)

To a solution of LLLL-5 (720 mg, 1.88 mmol) in THF (20 mL) was added BH$_3$.Me$_2$S (10 M, 0.751 mL, 7.51 mmol) at 0° C. The mixture was stirred at 74° C. under N$_2$ for 2 hours. The reaction was quenched with MeOH (5 mL) slowly and heated at reflux for 16 hours. The mixture was concentrated to give the crude product which was purified by combi flash (40 g silica column, EtOAc in petroleum ether from 9-10% to afford LLLL-6 (530 mg, 76.4%) as a colorless gum. LCMS [M-Boc+1] 270.0; $^1$H NMR (400 MHz, DMSO-d$_6$, rotamers) δ ppm 7.54-7.32 (m, 5H), 7.06 (t, J=8.2 Hz, 1H), 6.70 (d, J=8.3 Hz, 1H), 6.46 (dd, J=0.8, 8.3 Hz, 1H), 5.35-4.97 (m, 3H), 4.54-4.30 (m, 1H), 4.24-4.02 (m, 3H), 1.39-1.22 (m, 9H), 1.06 (m, 3H)

Step 7—Synthesis of tert-butyl(S)-6-hydroxy-3-methyl-2,3-dihydrobenzo[f][1,4]oxazepine-4(5H)-carboxylate (TP-44)

To a solution of LLLL-6 (530 mg, 1.43 mmol) in MeOH (10.0 mL) was added wet 10% Pd/C (100 mg). The reaction solution was stirred at 30° C. under a H$_2$ balloon for 16 h. Then the mixture was filtered through celite, washed with MeOH, and concentrated to give TP-44 (360 mg, 90%) as a white solid. $^1$H NMR (400 MHz, DMSO-d$_6$, rotamers) δ ppm 9.61-9.49 (m, 1H), 6.87 (t, J=8.2 Hz, 1H), 6.44 (d, J=7.8 Hz, 1H), 6.26 (dd, J=1.0, 8.0 Hz, 1H), 5.23-4.94 (m, 1H), 4.54-4.28 (m, 1H), 4.15-4.00 (m, 3H), 1.39-1.25 (m, 9H), 1.06 (d, J=6.8 Hz, 3H)

Compound TP-45 was Prepared Using Similar Conditions as Scheme LLLL Using tert-butyl(R)-(1-hydroxypropan-2-yl)carbamate in Step 1

| TP-45 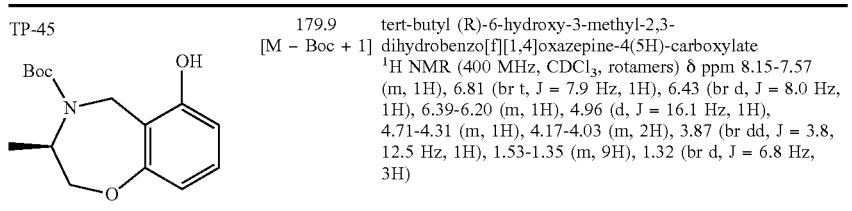 | 179.9 [M − Boc + 1] | tert-butyl (R)-6-hydroxy-3-methyl-2,3-dihydrobenzo[f][1,4]oxazepine-4(5H)-carboxylate <br> $^1$H NMR (400 MHz, CDCl$_3$, rotamers) δ ppm 8.15-7.57 (m, 1H), 6.81 (br t, J = 7.9 Hz, 1H), 6.43 (br d, J = 8.0 Hz, 1H), 6.39-6.20 (m, 1H), 4.96 (d, J = 16.1 Hz, 1H), 4.71-4.31 (m, 1H), 4.17-4.03 (m, 2H), 3.87 (br dd, J = 3.8, 12.5 Hz, 1H), 1.53-1.35 (m, 9H), 1.32 (br d, J = 6.8 Hz, 3H) |

Examples 207 & 208 were Prepared Using Similar Chemistry Depicted in Scheme CC and Employing Compounds TP-44 & TP-45, Respectively

| Example 207 TP-44 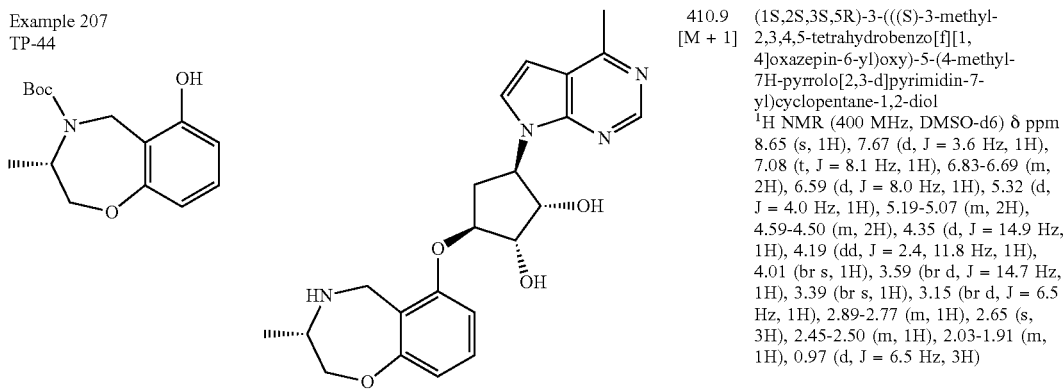 | 410.9 [M + 1] | (1S,2S,3S,5R)-3-(((S)-3-methyl-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol <br> $^1$H NMR (400 MHz, DMSO-d6) δ ppm 8.65 (s, 1H), 7.67 (d, J = 3.6 Hz, 1H), 7.08 (t, J = 8.1 Hz, 1H), 6.83-6.69 (m, 2H), 6.59 (d, J = 8.0 Hz, 1H), 5.32 (d, J = 4.0 Hz, 1H), 5.19-5.07 (m, 2H), 4.59-4.50 (m, 2H), 4.35 (d, J = 14.9 Hz, 1H), 4.19 (dd, J = 2.4, 11.8 Hz, 1H), 4.01 (br s, 1H), 3.59 (br d, J = 14.7 Hz, 1H), 3.39 (br s, 1H), 3.15 (br d, J = 6.5 Hz, 1H), 2.89-2.77 (m, 1H), 2.65 (s, 3H), 2.45-2.50 (m, 1H), 2.03-1.91 (m, 1H), 0.97 (d, J = 6.5 Hz, 3H) |
| Example 208 TP-45 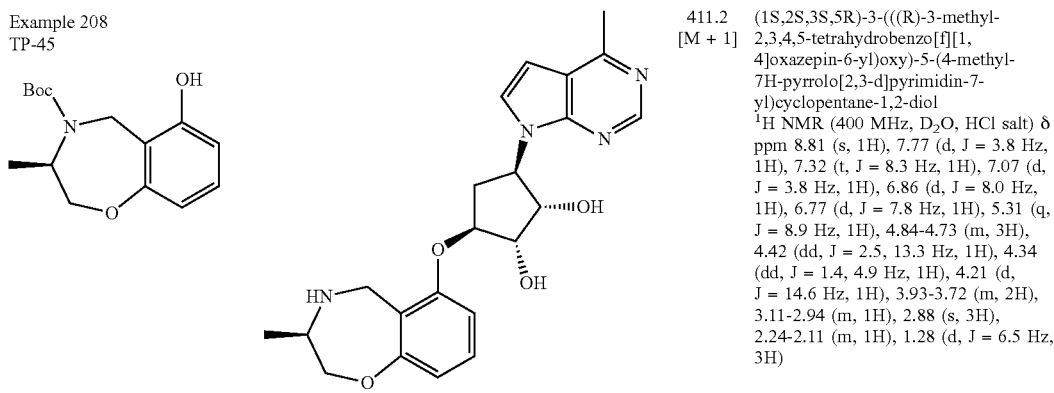 | 411.2 [M + 1] | (1S,2S,3S,5R)-3-(((R)-3-methyl-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol <br> $^1$H NMR (400 MHz, D$_2$O, HCl salt) δ ppm 8.81 (s, 1H), 7.77 (d, J = 3.8 Hz, 1H), 7.32 (t, J = 8.3 Hz, 1H), 7.07 (d, J = 3.8 Hz, 1H), 6.86 (d, J = 8.0 Hz, 1H), 6.77 (d, J = 7.8 Hz, 1H), 5.31 (q, J = 8.9 Hz, 1H), 4.84-4.73 (m, 3H), 4.42 (dd, J = 2.5, 13.3 Hz, 1H), 4.34 (dd, J = 1.4, 4.9 Hz, 1H), 4.21 (d, J = 14.6 Hz, 1H), 3.93-3.72 (m, 2H), 3.11-2.94 (m, 1H), 2.88 (s, 3H), 2.24-2.11 (m, 1H), 1.28 (d, J = 6.5 Hz, 3H) |

Scheme MMMM—Synthesis of tert-butyl(R)-6-hydroxy-2-methyl-2,3-dihydrobenzo[f][1,4]oxazepine-4(5H)-carboxylate (TP-46)

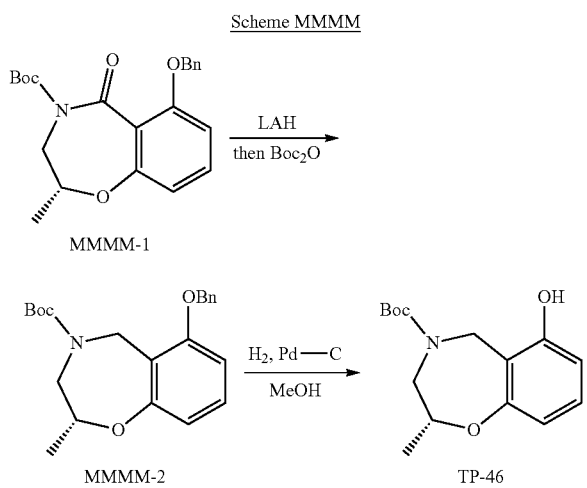

Step 1—Synthesis of tert-butyl(R)-6-(benzyloxy)-2-methyl-2,3-dihydrobenzo[f][1,4]oxazepine-4(5H)-carboxylate (MMMM-1)

To a compound MMMM-1 (prepared in a similar method as steps 1-5 in Scheme LLLL using tert-butyl (R)-(2-hydroxypropyl)carbamate), 500 mg, (1.5 mmol) in dry THF (10.0 mL) was added LAH (233 mg, 6.14 mmol) at 25° C. The mixture was stirred at 75° C. for 2 h. The reaction was cooled to r.t., in which water (2.0 mL) was added to the reaction followed by Boc$_2$O (670 mg, 3.07 mmol). The mixture was stirred for 2.5 h at r.t., then water was added and the reaction extracted with EtOAc (10 mL×3), dried with Na$_2$SO$_4$, concentrated to give the crude product which was purified by ISCO (20 g, silica gel, EtOAc/petroleum ether=15%) to yield MMMM-2 (520 mg, 92%) as a colorless gum. LCMS [M-Boc+1] 269.9

Step 2—Synthesis of tert-butyl(R)-6-hydroxy-2-methyl-2,3-dihydrobenzo[f][1,4]oxazepine-4(5H)-carboxylate (TP-46)

Compound MMMM-2 (520 mg, 1.3 mmol) dissolved in MeOH (10 mL) was added Pd/C (100 mg, 0.940 mmol). The reaction solution was stirred at 25° C. under H$_2$ for 2 h. Then the mixture was filtered through celite, washed with MeOH, and concentrated. The residue was purified by ISCO (20 g, silica gel, EtOAc/petroleum ether=25%) to afford TP-46 (234 mg, 67%) as a white solid. LCMS [M-Boc+1] 179.7; $^1$H NMR (400 MHz, CDCl$_3$) δ ppm 7.55 (s, 1H), 7.06 (t, J=8.1 Hz, 1H), 6.73 (d, J=8.1 Hz, 1H), 6.67-6.55 (m, 1H), 4.64 (d, J=14.7 Hz, 1H), 4.15-4.07 (m, 1H), 3.90 (br d, J=14.4 Hz, 1H), 3.84-3.76 (m, 1H), 3.29 (dd, J=8.9, 14.5 Hz, 1H), 1.41 (s, 9H), 1.29 (d, J=6.5 Hz, 3H)

Compound TP-47 was Prepared in a Similar Method as Scheme MMMM Using tert-butyl(S)-(2-hydroxypropyl)carbamate

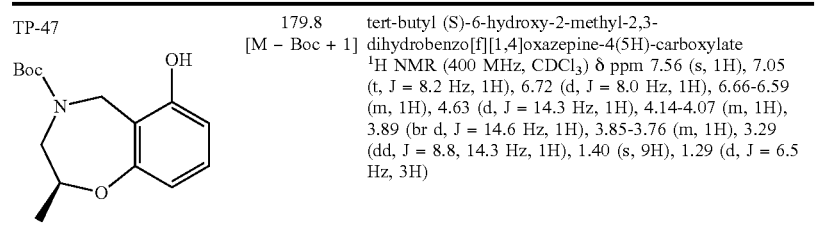

| | | |
|---|---|---|
| TP-47 | 179.8 [M − Boc + 1] | tert-butyl (S)-6-hydroxy-2-methyl-2,3-dihydrobenzo[f][1,4]oxazepine-4(5H)-carboxylate $^1$H NMR (400 MHz, CDCl$_3$) δ ppm 7.56 (s, 1H), 7.05 (t, J = 8.2 Hz, 1H), 6.72 (d, J = 8.0 Hz, 1H), 6.66-6.59 (m, 1H), 4.63 (d, J = 14.3 Hz, 1H), 4.14-4.07 (m, 1H), 3.89 (br d, J = 14.6 Hz, 1H), 3.85-3.76 (m, 1H), 3.29 (dd, J = 8.8, 14.3 Hz, 1H), 1.40 (s, 9H), 1.29 (d, J = 6.5 Hz, 3H) |

Examples 209 & 210 were Prepared Using Similar Chemistry Depicted in Scheme CC and Employing Compounds TP-46 & TP-47, Respectively

| | | |
|---|---|---|
| Example 209 TP-46 | 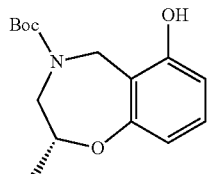 | 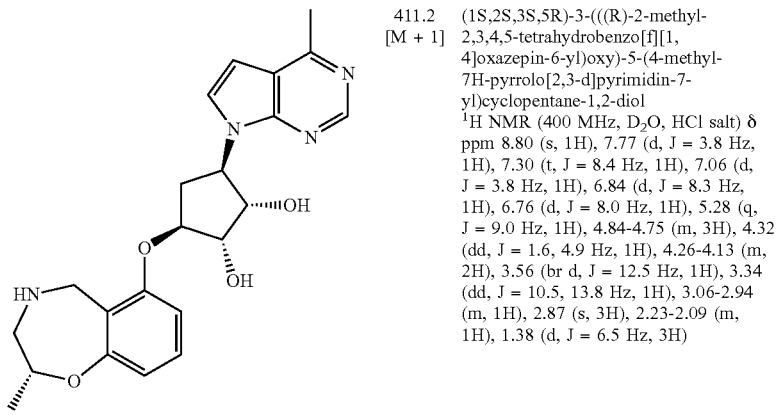 411.2 [M + 1] (1S,2S,3S,5R)-3-(((R)-2-methyl-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol $^1$H NMR (400 MHz, D$_2$O, HCl salt) δ ppm 8.80 (s, 1H), 7.77 (d, J = 3.8 Hz, 1H), 7.30 (t, J = 8.4 Hz, 1H), 7.06 (d, J = 3.8 Hz, 1H), 6.84 (d, J = 8.3 Hz, 1H), 6.76 (d, J = 8.0 Hz, 1H), 5.28 (q, J = 9.0 Hz, 1H), 4.84-4.75 (m, 3H), 4.32 (dd, J = 1.6, 4.9 Hz, 1H), 4.26-4.13 (m, 2H), 3.56 (br d, J = 12.5 Hz, 1H), 3.34 (dd, J = 10.5, 13.8 Hz, 1H), 3.06-2.94 (m, 1H), 2.87 (s, 3H), 2.23-2.09 (m, 1H), 1.38 (d, J = 6.5 Hz, 3H) |

-continued

| Example 210 TP-47 | 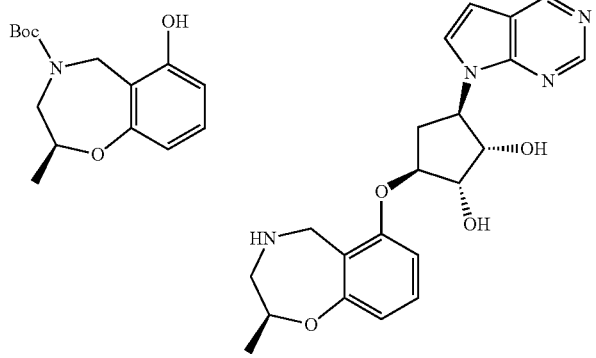 | 410.9 [M + 1] | (1S,2S,3S,5R)-3-(((S)-2-methyl-2,3,4,5-tetrahydrobenzo[f][1,4]oxazepin-6-yl)oxy)-5-(4-methyl-7H-pyrrolo[2,3-d]pyrimidin-7-yl)cyclopentane-1,2-diol <br> ¹H NMR (400 MHz, MeOD, HCl salt) δ ppm 9.04 (s, 1H), 8.09 (d, J = 3.8 Hz, 1H), 7.36 (t, J = 8.2 Hz, 1H), 7.22 (d, J = 3.8 Hz, 1H), 6.98 (d, J = 8.3 Hz, 1H), 6.80 (d, J = 8.3 Hz, 1H), 5.42 (q, J = 9.2 Hz, 1H), 4.81-4.72 (m, 3H), 4.33 (d, J = 16 Hz, 1H), 4.29-4.22 (m, 2H), 3.63-3.60 (m, 1H), 3.42-3.39 (m, H), 3.14-3.05 (m, 1H), 3.01 (s, 3H), 2.33 (ddd, J = 4.4, 9.8, 14.2 Hz, 1H), 1.48 (d, J = 6.5 Hz, 3H) |

Scheme NNNN—Synthesis of tert-butyl-6-(difluoromethyl)-5-fluoro-8-hydroxy-4-methyl-3,4-dihydroisoquinoline-2(1H)-carboxylate (TP-48)

Scheme NNNN

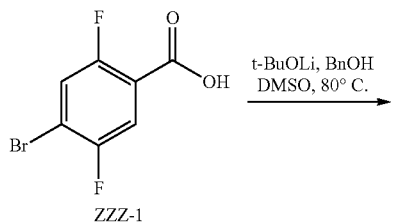
ZZZ-1 t-BuOLi, BnOH
DMSO, 80° C.

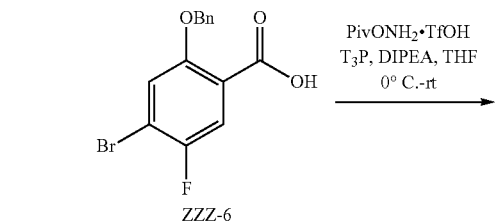
ZZZ-6

PivONH₂·TfOH
T₃P, DIPEA, THF
0° C.-rt

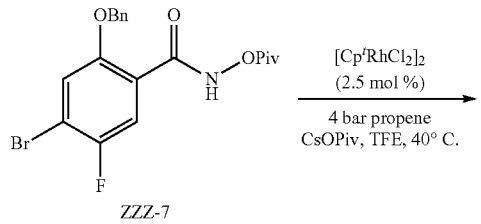
ZZZ-7

[Cp*RhCl₂]₂
(2.5 mol %)
4 bar propene
CsOPiv, TFE, 40° C.

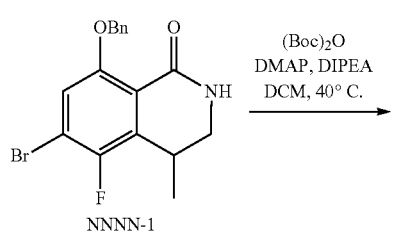
NNNN-1

(Boc)₂O
DMAP, DIPEA
DCM, 40° C.

-continued

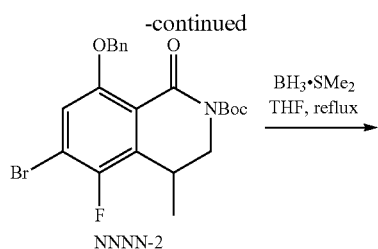
NNNN-2

BH₃·SMe₂
THF, reflux

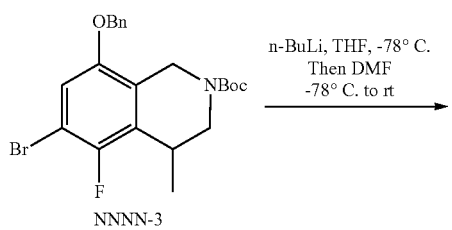
NNNN-3 n-BuLi, THF, -78° C.
Then DMF
-78° C. to rt

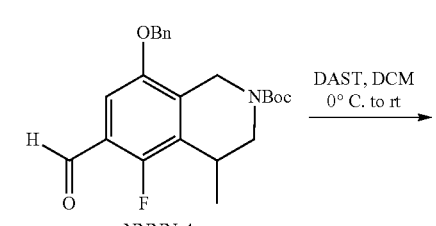
NNNN-4

DAST, DCM
0° C. to rt

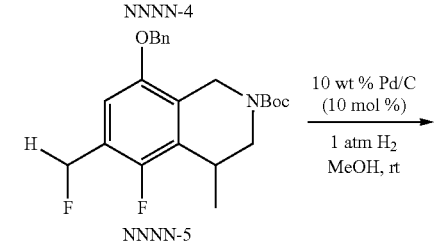
NNNN-5

10 wt % Pd/C
(10 mol %)
1 atm H₂
MeOH, rt

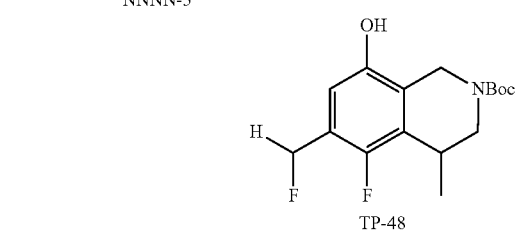
TP-48

Step 1: Synthesis of 2-(benzyloxy)-4-bromo-5-fluorobenzoic acid (ZZZ-6)

To a round bottom flask, equipped with a magnetic stirbar, was added lithium tert-butoxide (3.81 g, 47.6 mmol) and DMSO (119 mL, 0.2M). The flask was fitted with a fendenser and benzyl alcohol (4.95 mL, 47.6 mmol) was added. The flask was placed in a heating mantle and heated to 80° C. for 5 minutes. The flask was removed and ZZZ-1 (5.64 g, 23.8 mmol) was added. The flask was returned to the heating mantle adn heated at 80° C. for 17 hours. The reaction was removed from the heating mantle and allowed to cool to rt. The solution was poured into 1.2 L of water and acidified with 48 mL of 1M HCl aq. resulting in a tan precipitate. The solids were filtered and washed with water. The solids were collected and dried in a vacuum oven for 3.5 hours at 80° C. to afford the title compound ZZZ-6 (7.21 g, 93%) as a light tan solid. $^1$H NMR (400 MHz, DMSO-d6) δ ppm 13.10 (br. s., 1H), 7.61 (d, J=8.8 Hz, 1H), 7.57 (d, J=5.6 Hz, 1H), 7.48 (d, J=7.1 Hz, 2H), 7.44-7.36 (m, 2H), 7.35-7.28 (m, 1H), 5.22 (s, 2H).

Step 2: Synthesis of 2-(benzyloxy)-4-bromo-5-fluoro-N-(pivaloyloxy)benzamide (ZZZ-7)

To a round bottom flask, equipped with a magnetic stirbar, was added ZZZ-6 (5.73 g, 17.6 mmol) and THF (176 mL, 0.1M). The solution was cooled to 0° C. and T3P (24.7 g, 38.8 mmol) was added as a 50% wt. solution in EtOAc. After the addition, the reaction mixture was stirred for 30 min at 25° C. To the above solution was added DIPEA (18.4 mL, 106 mmol) followed by FF-3 (5.18 g, 19.4 mmol). After the addition, the reaction mixture was stirred at 25° C. for 1 hour. The reaction was quenched with water, diluted with EtOAc, and transferred to a separatory funnel. The phases were separated and the organic phase was washed with 1 portion 10% citric acid, 1 portion sat. NaHCO$_3$, and 1 portion brine. The organic extract was then dried (MgSO$_4$), filtered, and concentrated under vacuum. The crude residue was purified via flash column chromatography (12 g SiO$_2$, Isco, 100% Hept. to 100% EtOAc, 9 mL fractions) to afford the title compound ZZZ-7 (6.24 g, 83%) as a white solid. $^1$H NMR (400 MHz, CHLOROFORM-d) δ ppm 10.79 (s, 1H), 7.94 (d, J=8.9 Hz, 1H), 7.52-7.35 (m, 5H), 7.27-7.23 (m, 1H), 5.26 (s, 2H), 1.34 (s, 9H).

Step 3: Synthesis of 8-(benzyloxy)-6-bromo-5-fluoro-4-methyl-3,4-dihydroisoquinolin-1(2H)-one (NNNN-1)

To a 80 mL steel reactor was added ZZZ-7 (4.00 g, 9.43 mmol), Cesium pivalate (4.41 g, 18.9 mmol), [Cp$^r$RhCl$_2$]$_2$ (166 mg, 0.236 mmol) and trifluoroethanol (47 mL, 0.2M). The reactor was purged with nitrogen 3 times followed by 3 cycles of purging with propylene gas. The reaction was heated to 40° C. under 4 bar of propylene gas for 3 days. The solution was quenched with NaHCO$_3$ aq. and transferred to a separatory funnel with DCM. The phases were separated and the aqueous phase was extracted with 2 portions DCM. The combined organic extracts were dried (MgSO$_4$), filtered, and concentrated under vacuum. The crude residue was purified via flash column chromatography (40 g SiO$_2$, Isco, 100% Hept. to 10% MeOH/EtOAc, 25 mL fractions) to afford the title compound NNNN-1 (2.27 g, 66%, 9:1 r.r.) as a brown solid. LCMS [M+H]=364 observed. $^1$H NMR (400 MHz, CHLOROFORM-d) δ ppm 7.55 (d, J=7.5 Hz, 2H), 7.47-7.36 (m, 2H), 7.35-7.28 (m, 1H), 7.13 (d, J=5.5 Hz, 1H), 5.92 (d, J=3.8 Hz, 1H), 5.27-5.19 (m, 1H), 5.16-5.10 (m, 1H), 3.69 (dd, J=4.0, 12.7 Hz, 1H), 3.40-3.30 (m, 1H), 3.23 (ddd, J=1.3, 6.0, 12.6 Hz, 1H), 1.36 (d, J=7.1 Hz, 3H).

Step 4: Synthesis of tert-butyl-8-(benzyloxy)-6-bromo-5-fluoro-4-methyl-1-oxo-3,4-dihydroisoquinoline-2(1H)-carboxylate (NNNN-2)

To a round bottom flask, equipped with a magnetic stirbar and containing NNNN-1 (1.20 g, 3.29 mmol) was added DCM (11.0 mL, 0.3M), DIPEA (0.86 mL, 4.94 mmol), (Boc)$_2$O (1.08 g, 4.94 mmol), and DMAP (60.4 mg, 0.494 mmol). The flask was fitted with a findenser and placed in a heating block. The reaction was heated at 40° C. for 16 hours. The flask was removed from the heating block and allowed to cool to rt. The reaction was quenched with water and transferred to a separatory funnel with DCM. The phases were separated and the aqueous phase was extracted with 2 portions DCM. The combined organic extracts were dried (MgSO$_4$), filtered, and concentrated under vacuum. The crude residue was purified via flash column chromatography (40 g SiO$_2$, Isco, 100% Hept to 100% EtOAc, 9 mL fractions) to afford the title compound NNNN-2 (1.41 g, 92%) as a white foam. LCMS [M+H-Boc]=364 observed. $^1$H NMR (400 MHz, CHLOROFORM-d) δ ppm 7.55 (d, J=7.5 Hz, 2H), 7.44-7.35 (m, 2H), 7.32 (d, J=7.3 Hz, 1H), 7.11 (d, J=5.6 Hz, 1H), 5.28-5.20 (m, 1H), 5.18-5.09 (m, 1H), 4.21 (dd, J=2.2, 13.2 Hz, 1H), 3.61 (dd, J=3.2, 13.1 Hz, 1H), 3.39-3.27 (m, 1H), 1.59 (s, 9H), 1.33 (d, J=7.1 Hz, 3H).

Step 5: Synthesis of tert-butyl-8-(benzyloxy)-6-bromo-5-fluoro-4-methyl-3,4-dihydroisoquinoline-2(1H)-carboxylate (NNNN-3)

To a round bottom flask, equipped with a magnetic stirbar and containing NNNN-2 (1.41 g, 3.04 mmol), was added THF (15 mL, 0.2M) and borane dimethylsulfide complex (1.44 mL, 15.2 mmol). The flask was fitted with a findenser and transferred to a heating block. The reaction was heated at 70° C. for 30 minutes. The flask was removed from the heating block and allowed to cool gradually to rt. The reaction was quenched by dropwise addition of methanol until the evolution of gas was complete, followed by dilution with heptane. The solution was concentrated under vacuum. The crude residue was purified via flash column chromatography (40 g SiO$_2$, Isco, 100% Hept to 10% EtOAc/Hept. to 100% EtOAc, 9 mL fractions) to afford the title compound NNNN-3 (1.13 g, 82%) as a white foam. LCMS [M+H-Boc]=350 observed. $^1$H NMR (400 MHz, CHLOROFORM-d) δ ppm 7.47-7.30 (m, 5H), 6.93 (d, J=5.5 Hz, 1H), 5.18-4.79 (m, 3H), 4.26-3.96 (m, 2H), 3.28-2.95 (m, 2H), 1.51 (s, 9H), 1.25 (d, J=6.8 Hz, 3H).

Step 6: Synthesis of tert-butyl-8-(benzyloxy)-5-fluoro-6-formyl-4-methyl-3,4-dihydroisoquinoline-2(1H)-carboxylate (NNNN-4)

Note: nBuLi was titrated, THF was dried over activated 4A molecular sieves, and syringe needles were oven dried @ 85 C under vacuum prior to use.

A round bottom flask containing NNNN-3 (1.00 g, 2.22 mmol) was dried under high vacuum overnight, equipped with a magnetic stirbar, and purged with argon under dynamic vacuum. To the flask was added THF (11.0 mL, 0.2M) and the solution was cooled to −78° C. with a AcMe/dry ice bath. To the cooled solution was added n-butyl lithium (1.7 mL, 2.30 mmol) dropwise to induce metal-halogen exchange. The reaction was stirred at −78° C. under argon for 30 minutes.

Note: The reaction turns bright orange upon dropwise addition of nBuLi.

To the solution was added DMF (0.26 mL, 3.4 mmol) dropwise at −78° C. At this stage, the ice bath was removed and the reaction was allowed to warm gradually to room temperature.

Note: The reaction turns pale yellow upon warming to room temperature.

The reaction was reverse quenched by addition of the reaction solution to sat. NH$_4$Cl aq. (10 mL). The aqueous phase was extracted with 4 portions DCM. The combined organic extracts were dried (MgSO$_4$), filtered, and concentrated under vacuum. The crude residue was purified via flash column chromatography (24 g SiO$_2$, Isco, 100% Hept. to 100% EtOAc, 20 mL fractions) to afford the title compound NNNN-4 (885 mg, >95%) as a white waxy solid. LCMS [M+H-Boc]=300 observed. $^1$H NMR (400 MHz, CHLOROFORM-d) δ ppm 10.34 (s, 1H), 7.48-7.31 (m, 5H), 7.21 (d, J=5.3 Hz, 1H), 5.29-4.87 (m, 3H), 4.32-4.03 (m, 2H), 3.35-3.18 (m, 1H), 3.17-3.00 (m, 1H), 1.52 (s, 9H), 1.29 (d, J=6.8 Hz, 3H).

Step 7: Synthesis of tert-butyl-8-(benzyloxy)-6-(difluoromethyl)-5-fluoro-4-methyl-3,4-dihydroisoquinoline-2(1H)-carboxylate (NNNN-5)

A scintillation vial, equipped with a magnetic stirbar and containing NNNN-4 (1.77 g, 4.43 mmol), was purged with argon under dynamic vacuum. The vial was charged with DCM (44 mL, 0.1M) and the solution was cooled to 0° C. followed by the dropwise addition of DAST (1.46 mL, 11.1 mmol). The ice bath was removed and the solution was allowed to gradually warm to rt. The reaction was stirred under argon for 24 hours. During the course of the reaction, 2 additional aliquots of DAST (1.46 mL, 11.1 mmol) were added at 12 and 17 hours respectively to drive conversion (7.5 equivalents of DAST total). The reaction was quenched via the dropwise addition of sat. NaHCO$_3$ aq. CAUTION: Rapid evolution of CO$_2$ gas occurs during quench. The contents of the vial were transferred to a separatory funnel with DCM and diluted with water. The phases were separated and the aqueous phase was extracted with 3 portions DCM. The combined organic extracts were dried (MgSO$_4$), filtered, and concentrated under vacuum. The crude residue was purified via flash column chromatography (40 g SiO$_2$, Isco, 100% Hept. to 100% EtOAc, 20 mL fractions) to afford the title compound NNNN-5 (1.59 g, 85%) as a pale yellow gum. LCMS [M+H-Boc]=322 observed. $^1$H NMR (400 MHz, CHLOROFORM-d) δ ppm 7.49-7.29 (m, 5H), 6.95 (d, J=5.3 Hz, 1H), 6.89 (t, J=55.1 Hz, 1H), 5.22-4.90 (m, 3H), 4.27-4.02 (m, 2H), 3.28-2.96 (m, 2H), 1.51 (s, 9H), 1.26 (d, J=7.0 Hz, 3H).

Step 8: Synthesis of tert-butyl-6-(difluoromethyl)-5-fluoro-8-hydroxy-4-methyl-3,4-dihydroisoquinoline-2(1H)-carboxylate (TP-48)

To a 500 mL round bottom flask, equipped with a magnetic stirbar and containing NNNN-5 (1.65 g, 3.91 mmol), was added methanol (78 mL, 0.05M). To the solution was added Pd/C 10 wt % (417 mg, 0.391 mmol) and the solution was purged with hydrogen gas under dynamic vacuum. The reaction was stirred vigorously under 1 atm of hydrogen for 1.5 hours. The reaction was filtered over celite, the solids washed with DCM, and the filtrate concentrated under vacuum. The crude residue was purified via flash column chromatography (24 g SiO$_2$, Isco, 100% Hept. to 100% EtOAc, 20 mL fractions) to afford the title compound TP-48 (1.15 g, 88%) as a white foam. LCMS [M+H-Boc]=232 observed. $^1$H NMR (400 MHz, CHLOROFORM-d) δ ppm 7.00-6.65 (m, 2H), 5.22-4.79 (m, 1H), 4.29-3.94 (m, 2H), 3.28-2.95 (m, 2H), 1.58-1.51 (m, 9H), 1.23 (d, J=7.0 Hz, 3H).

Scheme OOOO—Synthesis of tert-butyl-5-fluoro-8-hydroxy-1-methyl-3,4-dihydroisoquinoline-2(1H)-carboxylate (TP-49)

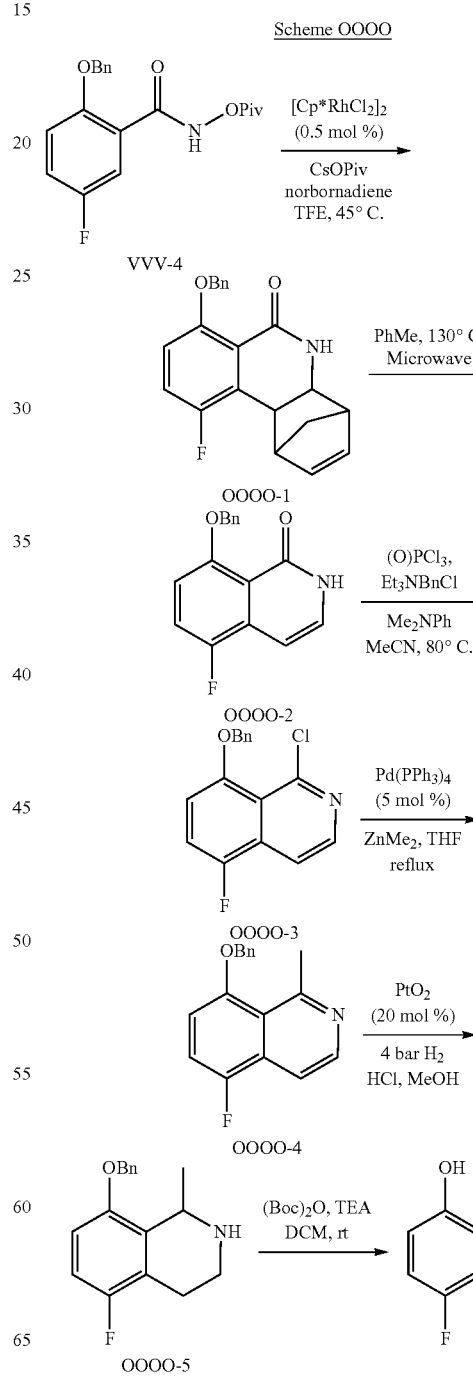

Step 1: Synthesis of 7-(benzyloxy)-10-fluoro-1,4a, 5,10b-tetrahydro-1,4-methanophenanthridin-6(4H)-one (OOOO-1)

To a round bottom flask, equipped with a magnetic stirbar, was added VVV-4 (2.29 g, 6.63 mmol), cesium pivalate (3.10 g, 13.3 mmol), [Cp*RhCl$_2$]$_2$ (20.5 mg, 0.0332 mmol), and trifluoroethanol (33 mL, 0.2M). The flask was capped with a rubber septum and norbornadiene (0.74 mL, 7.29 mmol) was added. The flask was placed in a heating mantle and the reaction was heated to 45° C. for 40 minutes. The flask was removed from the heating block and allowed to cool to rt. The solution was diluted with water followed by DCM and the phases were separated. The organic phase was washed with 1 portion water, dried (MgSO$_4$), filtered, and concentrated under vacuum. The crude residue was further dried under high vacuum to afford the title compound OOOO-1 as an orange solid which was used in the next step without further purification. LCMS [M+H]=336 observed.

Step 2: Synthesis of 8-(benzyloxy)-5-fluoroisoquinolin-1(2H)-one (OOOO-2)

To a microwave vial, equipped with a magnetic stirbar, was added OOOO-1 (~6.63 mmol) as a solution in toluene (15 mL, 0.44M). The vial was sealed with a teflon cap and placed in the microwave reactor. The reaction was heated to 130° C. for 1 hour. The solution was transferred to a round bottom flask with DCM and concentrated under vacuum. The crude residue was further dried under high vacuum to afford the title compound OOOO-2 (1.79 g, >95%) as a brown solid which was used in the next step without further purification. LCMS [M+H]=270 observed. $^1$H NMR (400 MHz, DMSO-d6) δ ppm 11.07 (br. s., 1H), 7.62 (d, J=7.2 Hz, 2H), 7.46 (t, J=9.3 Hz, 1H), 7.39 (t, J=7.5 Hz, 2H), 7.33-7.27 (m, 1H), 7.24-7.19 (m, 1H), 7.00 (dd, J=4.2, 9.0 Hz, 1H), 6.45 (d, J=7.1 Hz, 1H), 5.20 (s, 2H).

Step 3: Synthesis of 8-(benzyloxy)-1-chloro-5-fluoroisoquinoline (OOOO-3)

To a reaction vial, equipped with a magnetic stirbar, was added benzyltriethylammonium chloride (846 mg, 3.71 mmol) and OOOO-2 (500 mg, 1.86 mmol) as a solution in acetonitrile (19 mL, 0.1M). The vial was sealed with a teflon cap and dimethylaniline (0.35 mL, 2.79 mmol) was added followed by the dropwise addition of phosphorous oxychloride (1.04 mL, 11.1 mmol). The vial was placed in a heating block and heated at 80° C. for 10 minutes. The solution was concentrated and the crude residue was transferred to a separatory funnel with DCM and diluted with water. The phases were separated and the aqueous phase was extracted with 2 portions DCM. The combined organic extracts were dried (MgSO$_4$), filtered, and concentrated under vacuum. The crude residue was purified via flash column chromatography (24 g SiO$_2$, Isco, 100% Hept. to 100% EtOAc, 9 mL fractions) to afford the title compound OOOO-3 (465 mg, 87%) as a light orange solid. LCMS [M+H]=288 observed. $^1$H NMR (400 MHz, CHLOROFORM-d) δ ppm 8.32 (d, J=5.6 Hz, 1H), 7.78 (d, J=5.6 Hz, 1H), 7.56 (d, J=7.2 Hz, 2H), 7.48-7.28 (m, 4H), 6.97 (dd, J=4.3, 8.7 Hz, 1H), 5.27 (s, 2H).

Step 4: Synthesis of 8-(benzyloxy)-5-fluoro-1-methylisoquinoline (OOOO-4)

To an oven dried reaction vial, equipped with a magnetic stirbar and cooled under a stream of argon, was added OOOO-3 (422 mg, 1.47 mmol) and Pd(PPh$_3$)$_4$ (84.7 mg, 0.0733 mmol). The vial was capped with a rubber septum and purged with argon under dynamic vacuum. To the vial was added THF (7.33 mL, 0.2M) followed by the dropwise addition of dimethyl zinc (2.20 mL, 4.40 mmol). The vial was sealed with a teflon cap and placed in a heating block. The reaction was refluxed at 75° C. for 1 hour. The vial was removed from the heating block and allowed to cool to rt. The reaction was carefully quenched by the dropwise addition of sat. NH$_4$Cl aq. The solution was transferred to a separatory funnel with DCM. The phases were separated and the aqueous phase was extracted with 3 portions DCM. The combined organic extracts were washed with 1 portion brine, dried (MgSO$_4$), filtered, and concentrated under vacuum. The crude residue was purified via flash column chromatography (12 g SiO$_2$, Isco, 100% Hept. to 100% EtOAc, 9 mL fractions) to afford (356 mg) of a light orange solid. The isolated material was re-subjected to flash column chromatography (12 g SiO$_2$, Isco, 100% Hept. to 10% MeOH/EtOAc, 9 mL fractions) to afford the title compound OOOO-4 (310 mg, 79%) as a white solid. The isolated solid was used in the next step with ~80% purity based on $^1$H NMR analysis. LCMS [M+H]=268 observed. $^1$H NMR (400 MHz, CHLOROFORM-d) d=8.43 (d, J=5.7 Hz, 1H), 7.68 (d, J=5.9 Hz, 1H), 7.50 (d, J=7.1 Hz, 2H), 7.47-7.39 (m, 3H), 7.22 (t, J=8.9 Hz, 1H), 6.86 (dd, J=4.3, 8.6 Hz, 1H), 5.22 (s, 2H), 3.10 (s, 3H).

Step 5: Synthesis of 5-fluoro-1-methyl-1,2,3,4-tetrahydroisoquinolin-8-ol (OOOO-5)

To a steel reactor was added OOOO-4 (250 mg, 0.935 mmol), PtO$_2$ (42.5 mg, 0.187 mmol), ethanol (15 mL) and acetic acid (0.5 mL). The solution was hydrogenated under 45 psi of hydrogen gas at rt for 20 hours. The solution was filtered through celite and the solids washed with ethanol. The filtrate was concentrated under vacuum to give the title compound OOOO-5 (178 mg, >95%) as slight yellow solid which was used in the next step without further purification. $^1$H NMR (400 MHz, METHANOL-d4) δ ppm 6.92-6.85 (m, 1H), 6.71-6.65 (m, 1H), 4.69 (q, J=6.7 Hz, 1H), 3.51-3.37 (m, 2H), 3.06-2.84 (m, 2H), 1.62 (d, J=6.8 Hz, 3H)

Step 6: Synthesis of tert-butyl 5-fluoro-8-hydroxy-1-methyl-3,4-dihydroisoquinoline-2(1H)-carboxylate (TP-49)

To a round bottom flask, equipped with a magnetic stirbar and containing OOOO-5 (130 mg, 0.717 mmol), was added methanol (10 mL, 0.07M), (Boc)$_2$O (157 mg, 0.717 mmol), and trimethylamine (145 mg, 1.43 mmol). The reaction was stirred at 25° C. for 2.5 hours. The solution was concentrated under vacuum. The crude residue was purified via flash column chromatography (20 g SiO$_2$, Isco, 25% EtOAc/pet ether) to afford the title compound TP-49 (158 mg, 78%) as a white solid. $^1$H NMR (400 MHz, CHLOROFORM-d) δ ppm 6.81-6.69 (m, 1H), 6.55 (dd, J=4.4, 8.7 Hz, 1H), 5.54-5.20 (m, 1H), 4.32-4.03 (m, 1H), 3.36-3.07 (m, 1H), 2.86-2.66 (m, 2H), 1.51 (s, 9H), 1.43 (d, J=6.6 Hz, 3H).

Examples 211-214 were Made in a Similar Fashion as Examples 182 & 183 (Scheme YYY) Starting with the Appropriate Racemic Tetrahydroisoquinoline in Step 1 and Separating the Diastereomers Prior to the Final Deprotection

| Examples 211 & 212: TP-48 | | 463 observed [M + H] | (1S,2S,3S,5R)-3-((6-(difluoromethyl)-5-fluoro-4-methyl-1,2,3,4-tetrahydroisoquinolin-8-yl)oxy)-5-(4-methyl-7H-pyrrolo[2,3-d]pyrimidin-7-yl)cyclopentane-1,2-diol<br>Example 211 (Isomer 1) - $^1$H NMR (400 MHz, DEUTERIUM OXIDE) δ ppm 8.83 (s, 1H), 7.80 (br s, 1H), 7.14-6.80 (m, 3H), 5.32 (q, J = 9.0 Hz, 1H), 4.78 (br s, 2H), 4.48-4.37 (m, 1H), 4.32-4.18 (m, 2H), 3.50-3.32 (m, 3H), 3.10-2.98 (m, 1H), 2.89 (s, 3H), 2.24-2.13 (m, 1H), 1.33 (d, J = 6.8 Hz, 3H).<br>Example 212 (Isomer 2) - $^1$H NMR (400 MHz, DEUTERIUM OXIDE) δ ppm 8.83 (s, 1H), 7.80 (d, J = 3.7 Hz, 1H), 7.14-6.77 (m, 3H), 5.32 (q, J = 9.1 Hz, 1H), 4.80-4.78 (m, 1H), 4.64 (br dd, J = 5.0, 8.9 Hz, 1H), 4.47-4.35 (m, 1H), 4.30-4.20 (m, 2H), 3.51-3.30 (m, 3H), 3.09-2.95 (m, 1H), 2.88 (s, 3H), 2.26-2.10 (m, 1H), 1.32 (d, J = 6.8 Hz, 3H). |
|---|---|---|---|
| 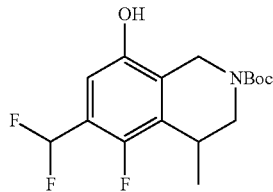 | 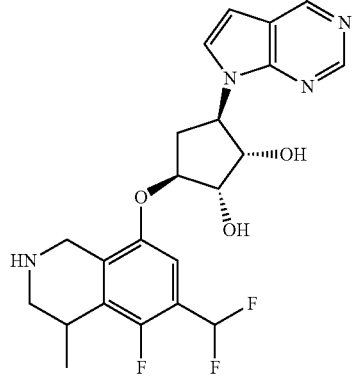 | | |
| Examples 213 & 214: TP-49 | | 413 observed [M + H] | (1S,2S,3S,5R)-3-((5-fluoro-1-methyl-1,2,3,4-tetrahydroisoquinolin-8-yl)oxy)-5-(4-methyl-7H-pyrrolo[2,3-d]pyrimidin-7-yl)cyclopentane-1,2-diol<br>Example 213 (Isomer 1) - $^1$H NMR (400 MHz, METHANOL-d4) δ ppm 9.04 (s, 1H), 8.03 (d, J = 3.3 Hz, 1H), 7.23 (d, J = 3.4 Hz, 1H), 7.14-6.96 (m, 2H), 5.39 (q, J = 9.1 Hz, 1H), 4.79 (br dd, J = 4.9, 9.3 Hz, 3H), 4.27 (br d, J = 4.2 Hz, 1H), 3.67-3.48 (m, 2H), 3.19-2.95 (m, 6H), 2.29 (br t, J = 10.1 Hz, 1H), 1.75 (d, J = 6.5 Hz, 3H).<br>Example 214 (Isomer 2) - $^1$H NMR (400 MHz, METHANOL-d4) ? = 9.03 (s, 1H), 8.08 (d, J = 3.4 Hz, 1H), 7.25 (d, J = 3.4 Hz, 1H), 7.14-7.01 (m, 2H), 5.37 (q, J = 9.2 Hz, 1H), 4.82-4.73 (m, 3H), 4.22 (br d, J = 4.5 Hz, 1H), 3.63-3.54 (m, 2H), 3.20-2.99 (m, 6H), 2.38 (ddd, J = 3.9, 9.7, 13.8 Hz, 1H), 1.75 (d, J = 6.6 Hz, 3H) |
| 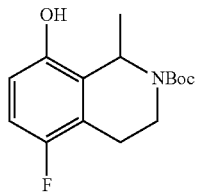 | 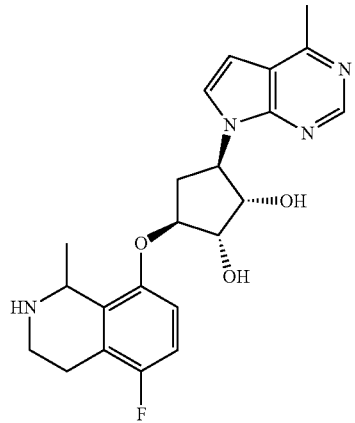 [SMILES: Cc1ncnc2c1ccn2[C@@H]1C[C@H](Oc2ccc(F)c3c2C(C)NCC3)[C@@H](O)[C@H]1O] | | |

Examples 215 & 216 were Made in a Similar Fashion as Examples 182 & 183 (Scheme YYY) Starting with the Appropriate Racemic Tetrahydroisoquinoline in Step 1, Performing Aminolysis in a Similar Fashion to Step 4 (Scheme NN), and Separating the Diastereomers Prior to the Final Deprotection

| Examples 215 & 216: TP-48 | | | |
|---|---|---|---|
| 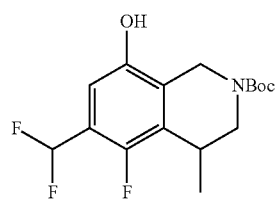 | 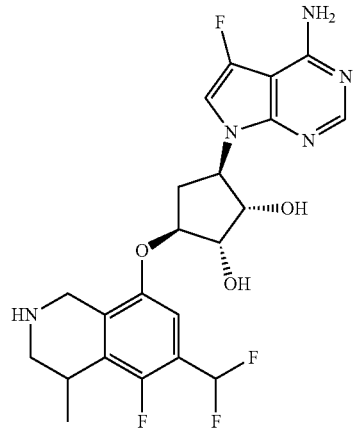 [SMILES: CC1CNCc2c(O[C@H]3C[C@@H](n4cc(F)c5c(N)ncnc54)[C@H](O)[C@@H]3O)cc(C(F)F)c(F)c21] | 482 observed [M + H] | (1S,2S,3R, 5S)-3-(4-amino-5-fluoro-7H-pyrrolo[2,3-d]pyrimidin-7-yl)-5-((6-(difluoromethyl)-5-fluoro-4-methyl-1,2,3,4-tetrahydroisoquinolin-8-yl)oxy)cyclopentane-1,2-diol<br>Example 215 (Isomer 1) - $^1$H NMR (400 MHz, DEUTERIUM OXIDE) δ ppm 8.24 (s, 1H), 7.30 (s, 1H), 7.21-6.88 (m, 2H), 5.36-5.21 (m, 1H), 4.87 (br d, J = 1.8 Hz, 1H), 4.57 (br dd, J = 5.1, 8.7 Hz, 1H), 4.51-4.42 (m, 1H), 4.36-4.23 (m, 2H), 3.58-3.43 (m, 3H), 3.14-2.99 (m, 1H), 2.17-2.06 (m, 1H), 1.41 (d, J = 6.5 Hz, 3H).<br>Example 216 (Isomer 2) - $^1$H NMR (400 MHz, DEUTERIUM OXIDE) δ ppm 8.22 (s, 1H), 7.28 (d, J = 2.0 Hz, 1H), 7.21-6.85 (m, 2H), 5.30-5.16 (m, 1H), 4.86 (br d, J = 1.5 Hz, 1H), 4.56 (dd, J = 5.0, 9.0 Hz, 1H), 4.46 (br d, J = 16.8 Hz, 1H), 4.37-4.20 (m, 2H), 3.61-3.41 (m, 3H), 3.02 (ddd, J = 7.5, 9.2, 14.9 Hz, 1H), 2.18-2.02 (m, 1H), 1.53-1.34 (m, 3H). |

Biological Examples

Biochemical Assay Methods

Compounds were solubilized in DMSO and serially diluted, using 3-fold dilutions, into 100% DMSO at a concentration 50-fold greater than the desired assay concentration. Following dilution, 1 ul was added to an empty 96-well microtiter plate. PRMT5/MEP50 protein complex was combined with H4(1-21) peptide (SGRGKGGKGLG-KGGAKRHRKV) in PRMT5 assay buffer (50 mM Tris pH 8.5, 50 mM NaCl, 5 mM MgCl$_2$, 1 mM EDTA, 1 mM TCEP) and 44 ul was added to the microtiter plate containing compound. S-Adenosyl-L-methionine (SAM) was prepared by combining $^3$H labelled SAM with unlabelled SAM in PRMT5 assay buffer such that the final SAM concentration was 10 uM and the specific activity was 0.2 uCi/ul. The reaction was initiated by adding 5 ul of SAM stock to the microtiter plate. The final reaction conditions were 10 nM PRMT5/MEP50 complex, 200 nM peptide and 1 uM SAM. Following a 25 minute incubation at room temperature, the reaction was stopped with the addition of 100 uL of 20% TCA. The 3H-peptide product was captured using a 96-well filter plate (MSIPN4B, Millipore) and washed 5 times with PBS buffer. Scintillation fluid (100 ul) was added to the dried filter plate and counted in a liquid scintillation counter. IC$_{50}$ values were determined by fitting the data to the standard 4-paramater dose response equation using Pfizer proprietary software.

Results for the biochemical assay of examples are summarized in Table 1, shown as IC$_{50}$ values in μM.

TABLE 1

| PRMT5 Enzyme Inhibition | |
|---|---|
| Example | PRMT5 IC50 (uM) |
| 1 | 0.510 |
| 2 | 8.382 |
| 3 | 0.032 |
| 4 | 0.681 |
| 5 | 0.025 |
| 6 | 0.423 |
| 7 | 0.120 |
| 8 | 3.389 |
| 9 | 0.060 |
| 10 | 0.941 |
| 11 | 0.020 |
| 12 | 0.478 |
| 13 | 0.016 |
| 14 | 0.719 |
| 15 | >200 |
| 16 | >200 |
| 17 | 2.767 |
| 18 | 3.701 |
| 19 | 0.064 |
| 20 | 17.09 |
| 21 | 0.217 |
| 22 | 0.003 |
| 23 | 0.572 |
| 24 | 0.071 |
| 25 | 0.056 |
| 26 | 0.704 |
| 27 | 0.449 |
| 28 | 5.769 |
| 29 | >200 |
| 30 | >200 |
| 31 | 0.466 |
| 32 | 15.69 |
| 33 | 3.580 |
| 34 | 59.47 |
| 35 | 0.150 |
| 36 | 2.697 |
| 37 | 0.266 |
| 38 | 15.71 |
| 39 | 0.114 |
| 40 | 2.045 |
| 41 | 0.046 |
| 42 | 1.387 |
| 43 | 0.879 |

TABLE 1-continued

PRMT5 Enzyme Inhibition

| Example | PRMT5 IC50 (uM) |
|---|---|
| 44 | 16.97 |
| 45 | |
| 46 | 0.297 |
| 47 | 29.47 |
| 48 | 0.005 |
| 49 | 0.105 |
| 50 | 18.89 |
| 51 | 0.676 |
| 52 | 0.906 |
| 53 | 0.006 |
| 54 | 0.126 |
| 55 | 0.002 |
| 56 | 0.002 |
| 57 | 0.048 |
| 58 | 0.289 |
| 59 | 5.743 |
| 60 | >200 |
| 61 | 2.124 |
| 62 | 0.025 |
| 63 | 1.057 |
| 64 | >200 |
| 65 | >200 |
| 66 | 0.004 |
| 67 | >200 |
| 68 | >200 |
| 69 | >200 |
| 70 | 13.56 |
| 71 | 0.069 |
| 72 | 0.022 |
| 73 | 6.885 |
| 74 | 63.29 |
| 75 | 37.85 |
| 76 | 143.59 |
| 77 | 0.065 |
| 78 | 0.001 |
| 79 | 0.083 |
| 80 | 0.130 |
| 81 | 1.666 |
| 82 | 0.991 |
| 83 | 0.020 |
| 84 | 0.002 |
| 85 | 0.002 |
| 86 | 0.004 |
| 87 | 0.002 |
| 88 | 0.001 |
| 89 | 0.001 |
| 90 | 0.002 |
| 91 | 0.001 |
| 92 | 0.001 |
| 93 | 0.001 |
| 94 | 0.001 |
| 95 | 0.006 |
| 96 | 0.019 |
| 97 | 0.065 |
| 98 | 0.011 |
| 99 | 0.002 |
| 100 | 0.001 |
| 101 | 0.001 |
| 102 | 0.001 |
| 103 | 0.001 |
| 104 | 0.001 |
| 105 | 0.001 |
| 106 | 0.002 |
| 107 | 0.001 |
| 108 | 0.001 |
| 109 | 0.001 |
| 110 | 0.008 |
| 111 | 0.028 |
| 112 | 0.004 |
| 113 | 0.001 |
| 114 | 0.004 |
| 115 | 0.147 |
| 116 | 0.257 |
| 117 | 0.005 |
| 118 | 0.002 |
| 119 | 0.001 |
| 120 | 0.001 |
| 121 | 0.001 |
| 122 | 0.003 |
| 123 | 0.002 |
| 124 | 0.002 |
| 125 | 0.001 |
| 126 | 0.001 |
| 127 | 0.009 |
| 128 | 0.001 |
| 129 | 0.001 |
| 130 | 0.001 |
| 131 | 0.001 |
| 132 | 0.002 |
| 133 | 0.001 |
| 134 | 0.001 |
| 135 | 10.22 |
| 136 | 11.11 |
| 137 | 0.123 |
| 138 | 0.002 |
| 139 | 0.001 |
| 140 | 0.017 |
| 141 | 3.931 |
| 142 | 0.011 |
| 143 | 0.006 |
| 144 | 0.077 |
| 145 | 0.011 |
| 146 | 0.027 |
| 147 | 0.024 |
| 148 | 0.002 |
| 149 | 0.069 |
| 150 | 0.071 |
| 151 | 0.078 |
| 152 | 0.008 |
| 153 | 0.005 |
| 154 | 0.001 |
| 155 | 0.002 |
| 156 | 0.107 |
| 157 | 0.004 |
| 158 | >200 |
| 159 | 0.005 |
| 160 | 0.009 |
| 161 | 0.201 |
| 162 | 0.042 |
| 163 | >200 |
| 164 | 0.004 |
| 165 | 0.002 |
| 166 | 0.003 |
| 167 | |
| 168 | |
| 169 | 0.037 |
| 170 | 0.001 |
| 171 | 0.014 |
| 172 | 1.285 |
| 173 | 0.003 |
| 174 | |
| 175 | 0.005 |
| 176 | 0.002 |
| 177 | 0.004 |
| 178 | 0.002 |
| 179 | 0.001 |
| 180 | 0.003 |
| 181 | 0.001 |
| 182 | 0.002 |
| 183 | 0.001 |
| 184 | 0.001 |
| 185 | 0.006 |
| 186 | 0.012 |
| 187 | 0.971 |
| 188 | 0.004 |
| 189 | 0.604 |
| 190 | 0.001 |
| 191 | 0.001 |
| 192 | 0.055 |
| 193 | 0.180 |

TABLE 1-continued

PRMT5 Enzyme Inhibition

| Example | PRMT5 IC50 (uM) |
|---|---|
| 194 | 0.001 |
| 195 | 0.001 |
| 196 | 0.001 |
| 197 | 0.001 |
| 198 | 0.001 |
| 199 | 0.091 |
| 200 | 0.001 |
| 201 | 0.310 |
| 202 | 0.001 |
| 203 | 0.001 |
| 204 | 0.002 |
| 205 | 0.001 |
| 206 | 0.002 |
| 207 | 0.024 |
| 208 | 0.008 |
| 209 | 0.005 |
| 210 | 0.001 |
| 211 | 0.001 |
| 212 | 0.001 |
| 213 | 0.001 |
| 214 | 0.008 |
| 215 | 0.001 |
| 216 | 0.001 |

A549 Proliferation Assay

A549 lung adenocarcinoma cells (American Type Culture Collection) were maintained in DMEM growth media (Life Technologies) supplemented with 10% v/v heat inactivated fetal bovine serum (Sigma) and cultured at 37° C., 5% $CO_2$. Exponentially growing A549 cells were plated in 96-well black tissue culture treated plates (Corning) at a density of 2500 cells/ml in a volume of 100 µl culture media and allowed to adhere overnight at 37° C., 5% $CO_2$. The following day, compound plates were prepared by making nine-point 3.3-fold dilutions in DMSO with a top concentration of 10 mM. Compounds were further diluted in culture media and 11 µl was added to the cells (final top assay concentration was 10 µM and DMSO was 0.2%). Cells were incubated with compound at 37° C., 5% $CO_2$ for 7 days with media and compound replacement on day 4. Cell viability was assayed on Day 7 by adding 100 µl Cell Titer Glo (Promega) reagent to the plate to measure the amount of ATP present in the cells. Luminescence was read using the Envision 2104 Multilabel Reader (Perkin Elmer). The 50% inhibitory concentration ($IC_{50}$) was determined using a 4-parameter fit model normalized to the DMSO control in dose response.

Results for the A549 proliferation assay of examples are summarized in Table 2, shown as IC50 values in µM.

TABLE 2

A549 Cell Proliferation IC50

| Example | A549 Cell IC50 (uM) |
|---|---|
| 3 | 1.098 |
| 5 | 0.932 |
| 11 | 1.394 |
| 13 | 0.971 |
| 19 | 1.072 |
| 22 | 0.135 |
| 25 | 1.673 |
| 48 | 0.192 |
| 53 | 0.227 |
| 55 | 3.168 |
| 56 | 0.378 |
| 66 | 6.813 |
| 77 | 1.123 |
| 78 | 1.615 |
| 84 | 0.500 |
| 85 | 0.920 |
| 86 | 1.840 |
| 87 | 0.296 |
| 88 | 0.545 |
| 89 | 0.195 |
| 90 | 0.948 |
| 91 | 0.119 |
| 92 | 0.312 |
| 93 | 0.140 |
| 94 | 0.115 |
| 95 | 8.130 |
| 98 | 1.494 |
| 99 | 0.728 |
| 100 | 0.185 |
| 101 | 0.112 |
| 102 | 0.192 |
| 103 | 0.201 |
| 104 | 0.460 |
| 105 | 0.383 |
| 106 | 3.847 |
| 107 | 0.991 |
| 108 | 0.163 |
| 109 | 0.067 |
| 114 | 3.940 |
| 117 | 7.141 |
| 118 | 4.840 |
| 119 | 0.556 |
| 120 | 0.442 |
| 121 | 0.938 |
| 122 | 4.478 |
| 123 | 0.452 |
| 124 | 3.828 |
| 125 | 0.637 |
| 126 | 0.498 |
| 128 | 0.597 |
| 129 | 1.045 |
| 130 | 0.983 |
| 131 | 0.482 |
| 132 | 2.751 |
| 133 | 0.443 |
| 134 | 0.640 |
| 138 | 1.477 |
| 139 | 0.637 |
| 140 | 2.380 |
| 143 | 1.402 |
| 146 | 7.069 |
| 148 | 4.883 |
| 154 | 0.002 |
| 159 | 5.199 |
| 160 | 0.405 |
| 164 | 3.859 |
| 165 | 0.766 |
| 166 | 0.039 |
| 169 | 0.743 |
| 173 | 3.572 |
| 175 | 3.229 |
| 176 | 1.563 |
| 177 | 2.374 |
| 178 | 4.057 |
| 180 | 0.159 |
| 181 | 1.140 |
| 182 | 2.180 |
| 183 | 0.136 |
| 184 | 1.398 |
| 186 | 9.533 |
| 188 | 6.473 |
| 190 | 0.007 |
| 191 | 7.017 |
| 194 | 0.111 |
| 195 | 0.022 |

TABLE 2-continued

A549 Cell Proliferation IC50

| Example | A549 Cell IC50 (uM) |
|---|---|
| 196 | 0.003 |
| 197 | 3.461 |
| 198 | 3.822 |
| 200 | 0.140 |
| 202 | 1.765 |
| 203 | 0.677 |
| 204 | 0.720 |
| 205 | 0.248 |
| 206 | 6.548 |
| 207 | 1.479 |
| 210 | 1.546 |
| 211 | 0.014 |
| 212 | 0.002 |
| 213 | 1.198 |
| 214 | 1.081 |
| 215 | 0.001 |
| 216 | 0.006 |

Molecular Biology

Gene encoding full length PRMT5 open reading frame (ORF) was fused directly at Ala2 to MDYKDDDDKGRAT sequence encoding Flag tag (SEQ ID: 1) and full length untagged MEP50 (SEQ ID: 2) were codon optimized for mammalian expression and synthetized by GenScript, Piscataway, N.J. Synthetized genes were cloned into insect cell expression vector pFASTBac Dual (Life Technologies) using standard restriction enzyme based cloning procedures. In the final construct PRMT5 ORF was under control of polyhedrin promoter (polH) while MEP50 ORF was under control of p10 promoter. Additionally, MEP50 (SEQ ID: 2) was subcloned into pFASTBac1 vector using standard restriction enzyme based cloning procedures.

Protein Expression

Viruses were generated using standard Bac-to-Bac viral generation protocols (Life Technologies) and amplified to high-titer passage two (P2) stocks. Protein over expression was conducted in exponentially growing Sf21 cells infected at 2×106 with P2 viral stock at MOI=1 of PRMT5-Mep50 dual construct virus and Mep50 construct virus at 1:1 ratio. The co-expression protocol was used to supplement additional Mep50 for FlagPRMT5-Mep50 heterodimer formation. Cells were harvested at 72 h post infection by centrifugation and frozen pellet was stored at −80° C.

Protein Purification

FlagPRMT5-Mep50 complex was purified from cell lysate using Flag affinity chromatography. Cell were lyzed in 50 mM Tris 7.5, 200 mM NaCl, 10% glycerol, 0.25 mM TCEP supplemented with EDTA-free protease inhibitor cocktail (Roche). 1.5 ml of lysis buffer was added per 1 g of frozen pellet. The clarified lysate was obtained by centrifugation of cell lysate at 10,000 g for 1 h at 4 C. 5 ml of Anti-FLAG M2 Agarose (Sigma) for 3 h to isolate was added to the clarified lysate to isolate FlagPRMT5-Mep50. Following batch binding for 3 h at 4 C, Flag resin bound to FlagPRMT5-Mep50 washed with 20 column volumes (CV) of 50 mM Tris 7.5, 200 mM NaCl, 10% glycerol, 0.25 mM TCEP followed by elution of FlagPRMT5-Mep50 complex using 3 CV of 50 mM Tris 7.5, 200 mM NaCl, 10% glycerol, 0.25 mM TCEP supplemented with 200 ug/ml of FLAG Peptide (DYKDDDDK). FlagPRMT5-Mep50 was further purified using S300 26/600 column (GE Healthcare) pre-equilibrated with 2 CV of 25 mM Tris pH7.5, 150 mM NaCl, 5% glycerol, 0.5 mM TCEP buffer. Peak fractions containing FlagPRMT5-Mep50 complex were concentrated to 1.6 mg/ml, flash frozen in small aliquots using liquid nitrogen and stored at −80° C.

Sequences

```
                                              SEQ ID: 1
MDYKDDDDKGRATAAMAVGGAGGSRVSSGRDLNCVPEIADTLGAVAKQGF

DFLCMPVFHPRFKREFIQEPAKNRPGPQTRSDLLLSGRDWNTLIVGKLSP

WIRPDSKVEKIRRNSEAAMLQELNFGAYLGLPAFLLPLNQEDNTNLARVL

TNHIHTGHHSSMFWMRVPLVAPEDLRDDIIENAPTTHTEEYSGEEKTWMW

WHNFRTLCDYSKRIAVALEIGADLPSNHVIDRWLGEPIKAAILPTSIFLT

NKKGFPVLSKMHQRLIFRLLKLEVQFIITGTNHHSEKEFCSYLQYLEYLS

QNRPPPNAYELFAKGYEDYLQSPLQPLMDNLESQTYEVFEKDPIKYSQYQ

QAIYKCLLDRVPEEEKDTNVQVLMVLGAGRGPLVNASLRAAKQADRRIKL

YAVEKNPNAVVTLENWQFEEWGSQVTVVSSDMREWVAPEKADIIVSELLG

SFADNELSPECLDGAQHFLKDDGVSIPGEYTSFLAPISSSKLYNEVRACR

EKDRDPEAQFEMPYVVRLHNFHQLSAPQPCFTFSHPNRDPMIDNNRYCTL

EFPVEVNTVLHGFAGYFETVLYQDITLSIRPETHSPGMFSWFPILFPIKQ

PITVREGQTICVRFWRCSNSKKVWYEWAVTAPVCSAIHNPTGRSYTIGL*

SEQ ID: 2
MRKETPPPLVPPAAREWNLPPNAPACMERQLEAARYRSDGALLLGASSLS

GRCWAGSLWLFKDPCAAPNEGFCSAGVQTEAGVADLTWVGERGILVASDS

GAVELWELDENETLIVSKFCKYEHDDIVSTVSVLSSGTQAVSGSKDICIK

VWDLAQQVVLSSYRAHAAQVTCVAASPHKDSVFLSCSEDNRILLWDTRCP

KPASQIGCSAPGYLPTSLAWHPQQSEVFVFGDENGTVSLVDTKSTSCVLS

SAVHSQCVTGLVFSPHSVPFLASLSEDCSLAVLDSSLSELFRSQAHRDFV

RDATWSPLNHSLLTTVGWDHQVVHHVVPTEPLPAPGPASVTE*
```

We claim:

1. A compound of formula (I):

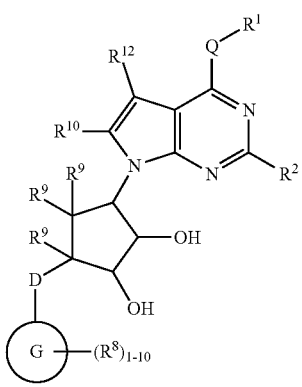

(I)

or a pharmaceutically acceptable salt thereof, wherein:

$R^1$ is selected from the group consisting of $(C_1\text{-}C_8)$alkyl, $(C_1\text{-}C_8)$haloalkyl, hydroxy, $(C_1\text{-}C_8)$alkoxy, $(C_5\text{-}C_{12})$aryl, 5-12 membered heteroaryl, $(C_3\text{-}C_{10})$cycloalkyl, 3-12 membered heterocyclyl, $OR^4$, $SR^4$ and $N(R^4)_2$;

$R^2$ is hydrogen, halogen, $(C_1\text{-}C_8)$alkyl, hydroxy, $(C_1\text{-}C_8)$alkoxy or $N(R^5)_2$, where each $R^5$ is independently hydrogen or $(C_1\text{-}C_8)$alkyl, or two $R^5$ join to form a 4-6 membered heterocyclic ring containing 1-3 heteroatoms selected from N, O and S;

each $R^3$ is independently selected from hydrogen, hydroxy, $NH_2$; $(C_1\text{-}C_8)$alkyl or heteroalkyl having 1-8 atoms, or when D is $C(R^3)_2$, $R^3$ is additionally selected from fluorine, $(C_1\text{-}C_8)$alkylene or heteroalkylene bound to an atom on G to form a ring fused to G, where $R^3$ is optionally substituted with 1-6 $R^8$;

each $R^9$ is independently hydrogen or fluorine;

D is $C(R^3)_2$, $NR^3$, O, S or $S(O)_{1-2}$;

G is a $(C_5\text{-}C_{12})$aryl ring system or a 5-12 membered heteroaryl ring system, wherein said $(C_5\text{-}C_{12})$aryl ring system or a 5-12 membered heteroaryl ring system is fused to $(C_3\text{-}C_{10})$cycloalkyl or heterocyclyl ring system;

each $R^8$ is absent or is independently selected from the group consisting of $(C_1\text{-}C_8)$alkyl, $(C_1\text{-}C_8)$haloalkyl, hydroxy, $(C_1\text{-}C_8)$alkoxy, $(C_5\text{-}C_{12})$aryl, 5-12 membered heteroaryl, $(C_3\text{-}C_{10})$cycloalkyl, 3-12 membered heterocyclyl, $OR^4$, $SR^4$, $N(R^4)_2$, CN, halogen and $CON(R^4)_2$, where two $R^8$ optionally join to form a 4-6 membered spiro-cycloalkyl ring, a cycloalkyl fused ring, or an alkylene bridge spanning G, and where two $R^8$ optionally join to form carbonyl;

each $R^4$ is independently $A\text{-}R^{14}$, where A is absent, $(C_1\text{-}C_3)$alkyl, $-C(O)-$ or $-SO_2-$, and $R^{14}$ is hydrogen, $(C_1\text{-}C_8)$alkyl, $(C_5\text{-}C_{12})$aryl, 5-12 membered heteroaryl, $(C_3\text{-}C_{10})$cycloalkyl or 3-12 membered heterocyclyl, or two $R^4$ join to form a 4-6 membered heterocyclic ring containing 1-3 heteroatoms selected from N, O and S;

Q is absent or is a divalent moiety selected from O, S, NH and $(C_1\text{-}C_8)$alkylene;

$R^{10}$ is independently selected from hydrogen, $(C_1\text{-}C_8)$alkyl, hydroxy, $(C_1\text{-}C_8)$alkoxy, halogen, SH, $S-(C_1\text{-}C_8)$alkyl and $N(R^{11})_2$ where each $R^{11}$ is independently hydrogen, $(C_1\text{-}C_8)$alkyl, $(C_5\text{-}C_{12})$aryl or 5-12 membered heteroaryl; and $R^{12}$ is independently selected from hydrogen, $(C_1-C_8)$ alkyl, hydroxy, $(C_1-C_8)$alkoxy, fluoro, chloro, bromo, iodo, SH, S—$(C_1-C_8)$alkyl and $N(R^{13})_2$ where each $R^{13}$ is independently hydrogen, $(C_1-C_8)$alkyl, $(C_5-C_{12})$aryl or 5-12 membered heteroaryl.

2. A compound of formula (II):

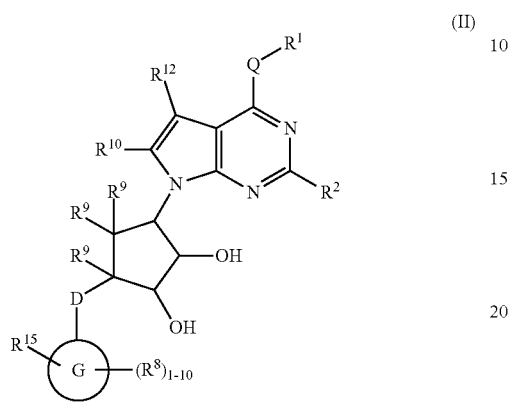

(II)

or a pharmaceutically acceptable salt thereof, wherein:
$R^1$ is selected from the group consisting of $(C_1-C_8)$alkyl, $(C_1-C_8)$haloalkyl, hydroxy, $(C_1-C_8)$alkoxy, $(C_5-C_{12})$ aryl, 5-12 membered heteroaryl, $(C_3-C_{10})$cycloalkyl, 3-12 membered heterocyclyl, $OR^4$, $SR^4$ and $N(R^4)_2$;

$R^2$ is hydrogen, halogen, $(C_1-C_8)$alkyl, hydroxy, $(C_1-C_8)$ alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

each $R^3$ is independently selected from hydrogen, hydroxy, $NH_2$; $(C_1-C_8)$alkyl or heteroalkyl having 1-8 atoms, or when D is $C(R^3)_2$, $R^3$ is additionally selected from fluorine, $(C_1-C_8)$alkylene or heteroalkylene bound to an atom on G to form a ring fused to G, where $R^3$ is optionally substituted with 1-6 $R^8$;

each $R^9$ is independently hydrogen or fluorine;
D is $C(R^3)_2$, O, or $S(O)_{1-2}$;
G is a $(C_5-C_{12})$aryl, or a 5-12 membered heteroaryl, ring system;

$R^{15}$ is heteroalkyl having 1-8 atoms bound to an atom on G and optionally substituted with 1-6 $R^8$, or $R^{15}$ is heteroalkylene bound to an atom on G, optionally substituted with 1-6 $R^8$, and bound to an adjacent atom on G;

each $R^8$ is absent or is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$, $N(R^4)_2$, CN, halogen and $CON(R^4)^2$, where two $R^8$ optionally join to form a 4-6 membered spiro-cycloalkyl ring, a cycloalkyl fused ring, or an alkylene bridge spanning G, and where two $R^8$ optionally join to form carbonyl;

each $R^4$ is independently $A-R^{14}$, where A is absent, $(C_1-C_3)$alkyl, —C(O)— or —$SO_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

Q is absent or is a divalent moiety selected from O, S, NH and $(C_1-C_8)$alkylene;

$R^{10}$ is independently selected from hydrogen, $(C_1-C_8)$ alkyl, hydroxy, $(C_1-C_8)$alkoxy, halogen, SH, S—$(C_1-C_8)$alkyl and $N(R^{11})_2$ where each $R^{11}$ is independently hydrogen, $(C_1-C_8)$alkyl, $(C_5-C_{12})$aryl or 5-12 membered heteroaryl; and $R^{12}$ is independently selected from hydrogen, $(C_1-C_8)$ alkyl, hydroxy, $(C_1-C_8)$alkoxy, fluoro, chloro, bromo, iodo, SH, S—$(C_1-C_8)$alkyl and $N(R^{13})_2$ where each $R^{13}$ is independently hydrogen, $(C_1-C_8)$alkyl, $(C_5-C_{12})$aryl or 5-12 membered heteroaryl;

provided that D is $S(O)_{1-2}$ when G is $C_{10}$aryl or a 10-membered heteroaryl.

3. A compound of formula (III):

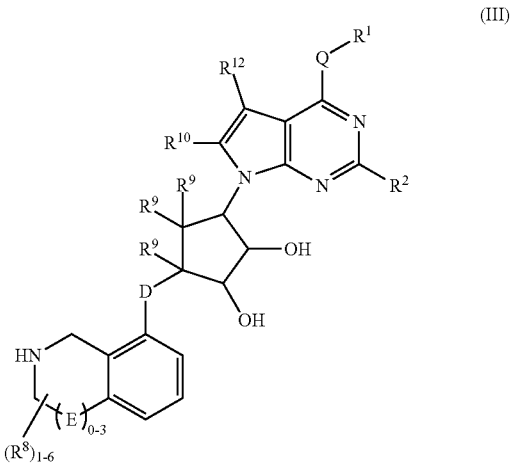

(III)

or a pharmaceutically acceptable salt thereof, wherein:
$R^1$ is independently selected from the group consisting of $(C_1-C_8)$alkyl, $(C_1-C_8)$haloalkyl, hydroxy, $(C_1-C_8)$ alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$;

$R^2$ is hydrogen, halogen, $(C_1-C_8)$alkyl, hydroxy, $(C_1-C_8)$ alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

each $R^3$ is independently hydrogen, hydroxy or $NH_2$; or when D is $C(R^3)_2$, $R^3$ is additionally selected from fluorine;

each $R^9$ is independently hydrogen or fluorine;
D is $C(R^3)_2$, O, or $S(O)_{1-2}$;
E is $NR^1$, $CH_2$, $C(R^1)_2$, O or —$S(O)_2$;

each $R^8$ is absent or is independently selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$, $N(R^4)_2$, CN, halogen and $CON(R^4)^2$, where two $R^8$ optionally join to form a 4-6 membered spiro-cycloalkyl ring, or a cycloalkyl fused ring, and where two $R^8$ optionally join to form carbonyl;

each $R^4$ is independently $A-R^{14}$, where A is absent, $(C_1-C_3)$alkyl, —C(O)— or —$SO_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two R⁴ join to form a 4-6 membered heterocyclic ring containing 1-3 heteroatoms selected from N, O and S; and Q is absent or is a divalent moiety selected from O, S, NH and (C₁-C₈)alkylene;

$R^{10}$ is independently selected from hydrogen, (C₁-C₈)alkyl, hydroxy, (C₁-C₈)alkoxy, halogen, SH, 5-(C₁-C₈)alkyl and N(R¹¹)₂ where each $R^{11}$ is independently hydrogen, (C₁-C₈)alkyl, (C₅-C₁₂)aryl or 5-12 membered heteroaryl; and $R^{12}$ is independently selected from hydrogen, (C₁-C₈)alkyl, hydroxy, (C₁-C₈)alkoxy, fluoro, chloro, bromo, SH, S—(C₁-C₈)alkyl and N(R¹³)₂ where each $R^{13}$ is independently hydrogen, (C₁-C₈)alkyl, (C₅-C₁₂)aryl or 5-12 membered heteroaryl.

4. A compound of formula (IV):

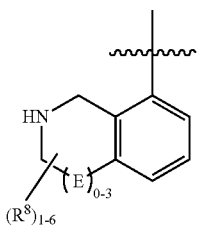

(IV)

or a pharmaceutically acceptable salt thereof, wherein:

each $R^1$ is independently selected from the group consisting of (C₁-C₈)alkyl, (C₁-C₈)haloalkyl, hydroxy, (C₁-C₈)alkoxy, (C₅-C₁₂)aryl, 5-12 membered heteroaryl, (C₃-C₁₀)cycloalkyl, 3-12 membered heterocyclyl, OR⁴, SR⁴ and N(R⁴)₂;

$R^2$ is hydrogen, halogen, (C₁-C₈)alkyl, hydroxy, (C₁-C₈)alkoxy or N(R⁵)₂, where each $R^5$ is independently hydrogen or (C₁-C₈)alkyl, or two R⁵ join to form a 4-6 membered heterocyclic ring containing 1-3 heteroatoms selected from N, O and S;

each $R^3$ is independently hydrogen, hydroxy or NH₂; or when D is C(R³)₂, R³ is additionally selected from fluorine;

each $R^9$ is independently hydrogen or fluorine;

B is N or C;

E is NR¹, CH₂, C(R¹)₂, O or —S(O)₂;

each $R^8$ is absent or is independently selected from the group consisting of (C₁-C₈)alkyl, (C₁-C₈)haloalkyl, hydroxy, (C₁-C₈)alkoxy, (C₅-C₁₂)aryl, 5-12 membered heteroaryl, (C₃-C₁₀)cycloalkyl, 3-12 membered heterocyclyl, OR⁴, SR⁴, N(R⁴)₂, CN, halogen and CON(R⁴)², where two R⁸ optionally join to form a 4-6 membered spiro-cycloalkyl ring, or a cycloalkyl fused ring, and where two R⁸ optionally join to form carbonyl;

each $R^4$ is independently A-R¹⁴, where A is absent, (C₁-C₃)alkyl, —C(O)— or —SO₂—, and R¹⁴ is hydrogen, (C₁-C₈)alkyl, (C₅-C₁₂)aryl, 5-12 membered heteroaryl, (C₃-C₁₀)cycloalkyl or 3-12 membered heterocyclyl, or two R⁴ join to form a 4-6 membered heterocyclic ring containing 1-3 heteroatoms selected from N, O and S;

Q is absent or is a divalent moiety selected from O, S, NH and (C₁-C₈)alkylene $R^{10}$ is independently selected from hydrogen, (C₁-C₈)alkyl, hydroxy, (C₁-C₈)alkoxy, halogen, SH, (C₁-C₈)alkyl and N(R¹¹)₂ where each $R^{11}$ is independently hydrogen, (C₁-C₈)alkyl, (C₅-C₁₂)aryl or 5-12 membered heteroaryl; and $R^{12}$ is independently selected from hydrogen, (C₁-C₈)alkyl, hydroxy, (C₁-C₈)alkoxy, fluoro, chloro, bromo, SH, S—(C₁-C₈)alkyl and N(R¹³)₂ where each $R^{13}$ is independently hydrogen, (C₁-C₈)alkyl, (C₅-C₁₂)aryl or 5-12 membered heteroaryl.

5. The compound or pharmaceutically acceptable salt of claim 3, wherein:

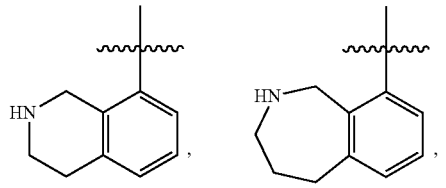

is selected from:

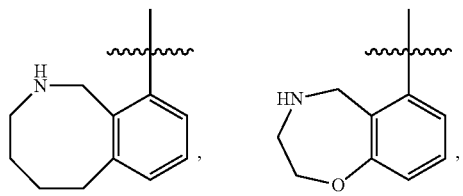

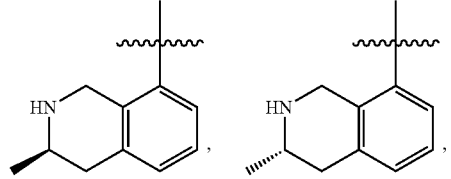

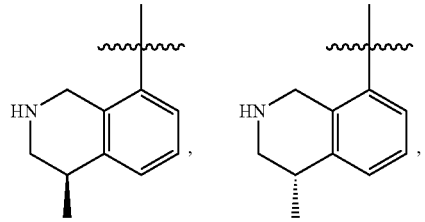

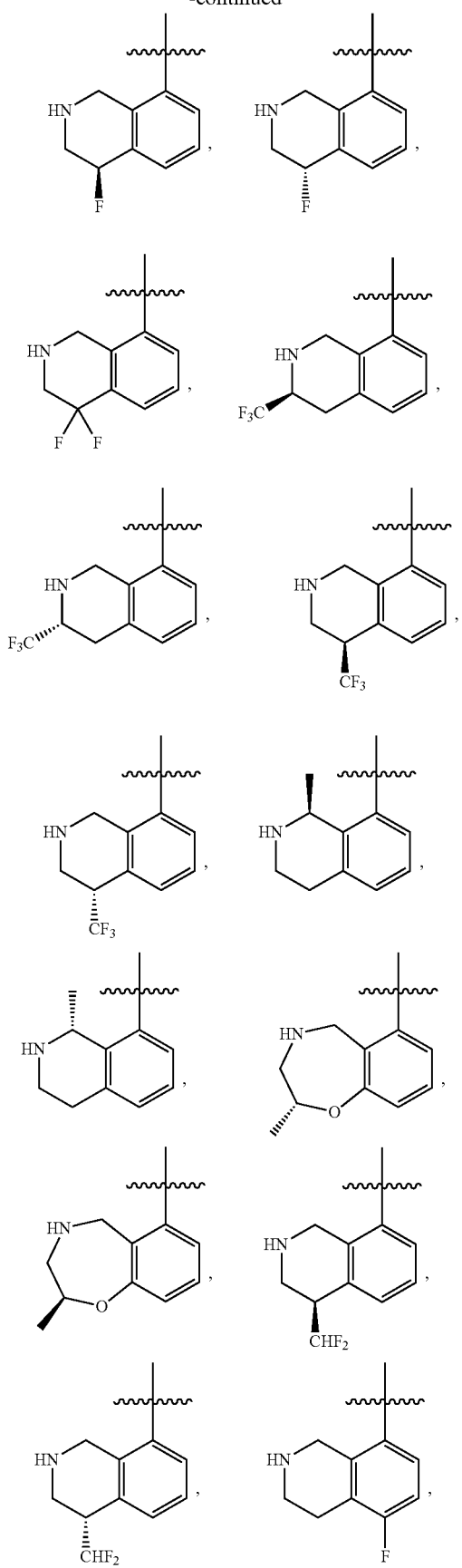
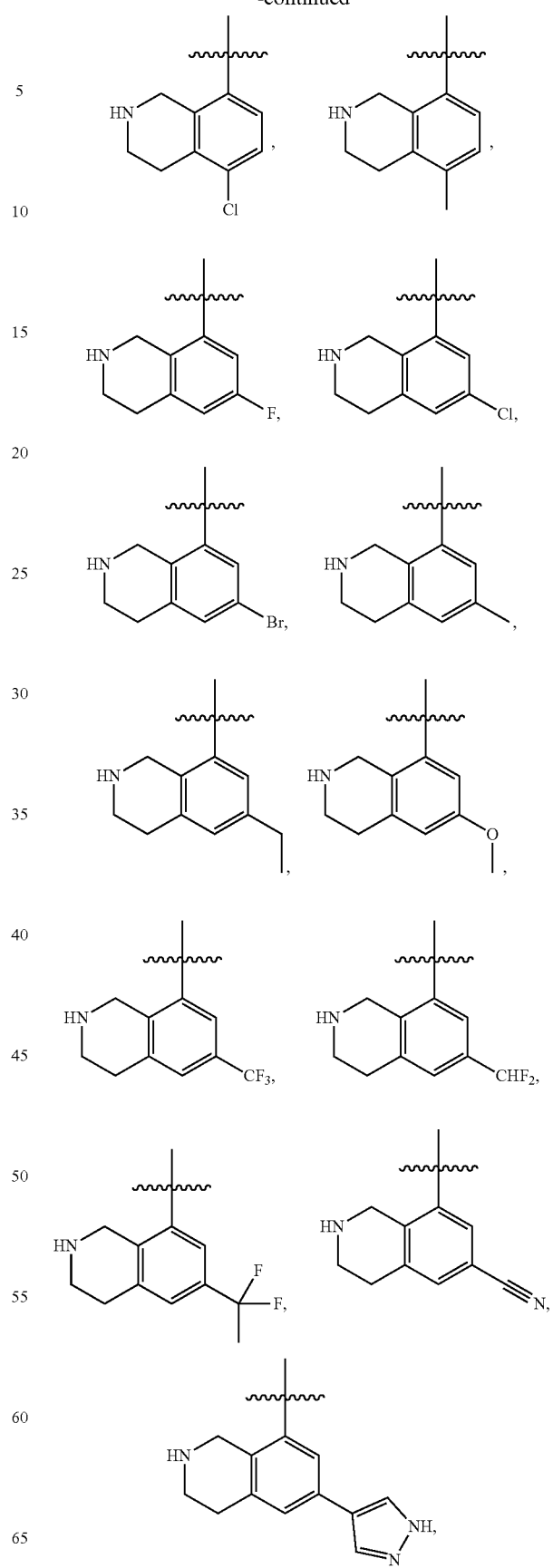

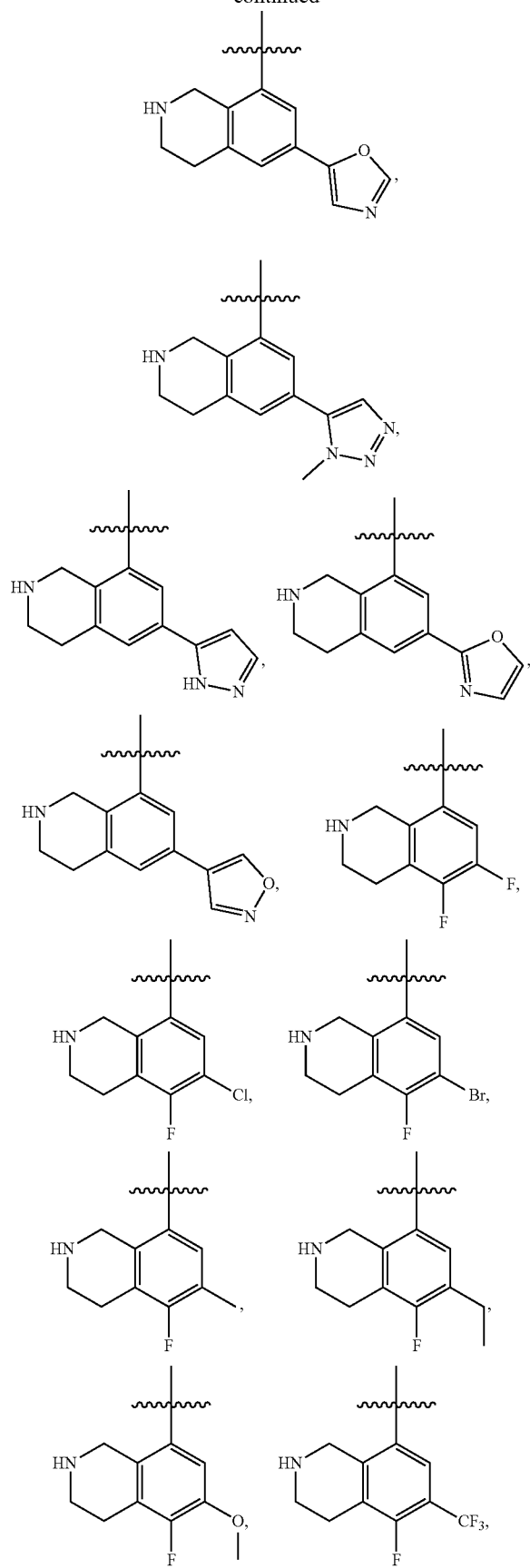
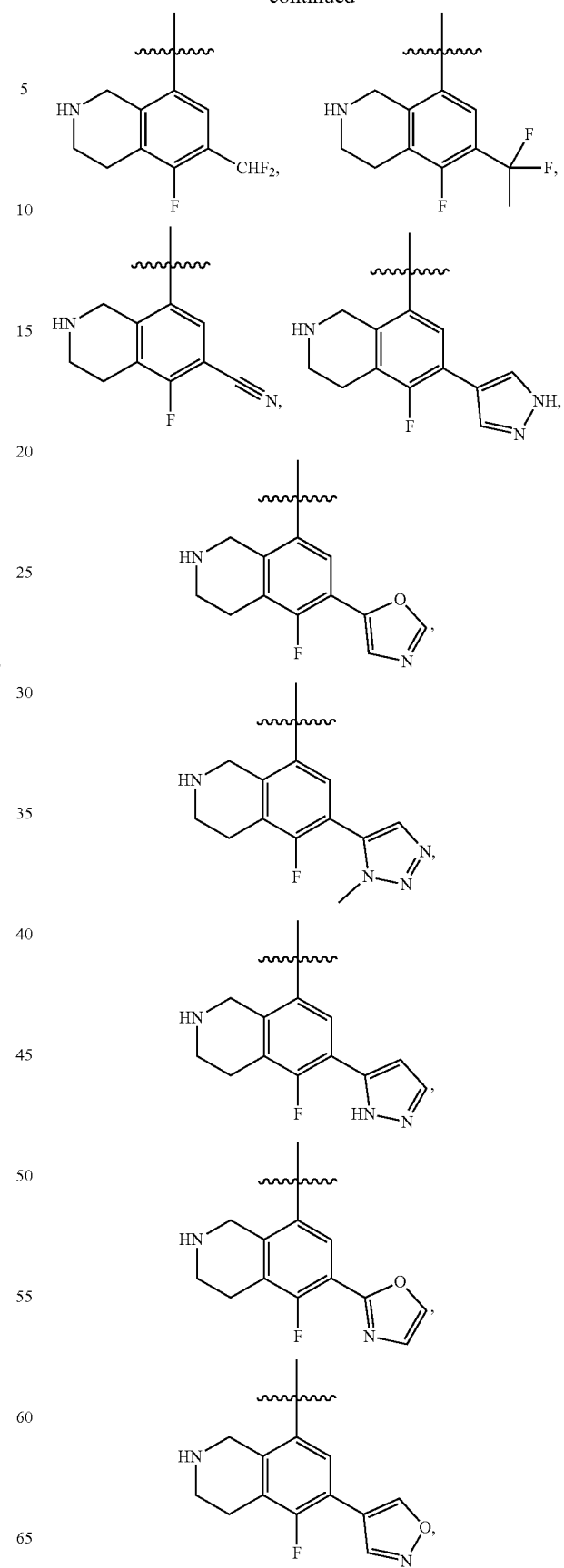

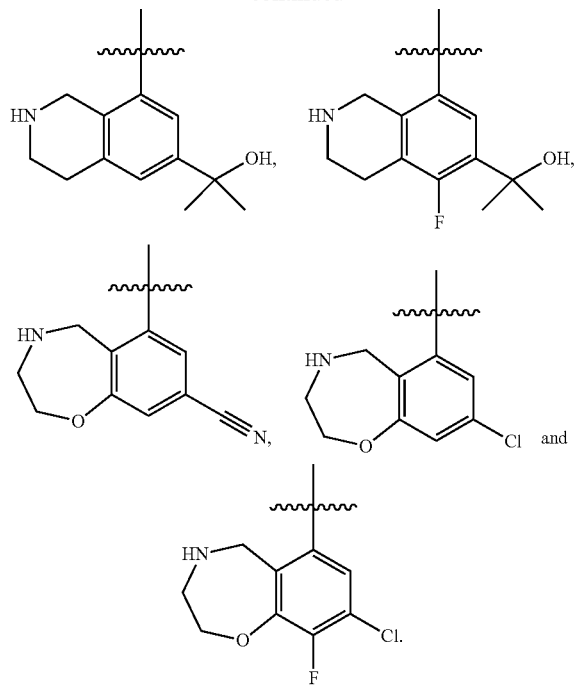
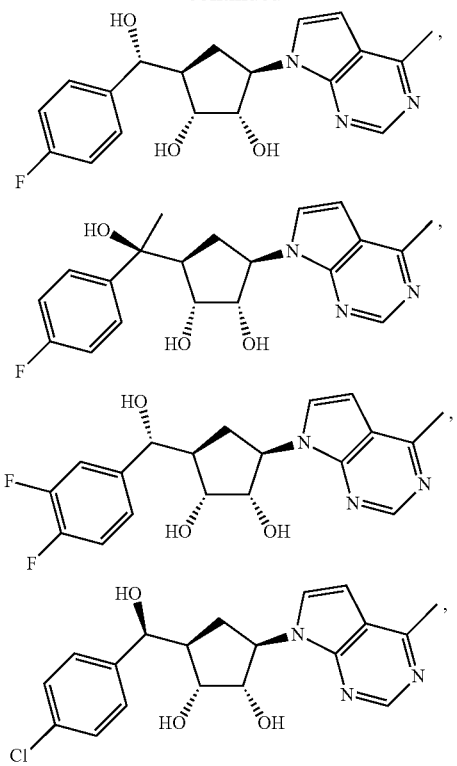
6. The compound or pharmaceutically acceptable salt of claim 5, wherein:
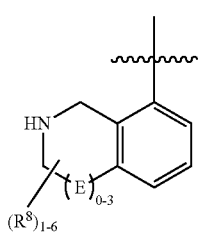
is:
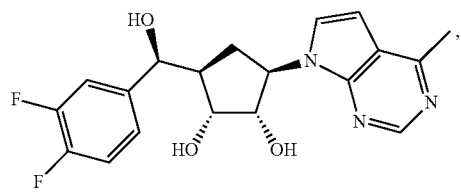
7. A compound selected from:
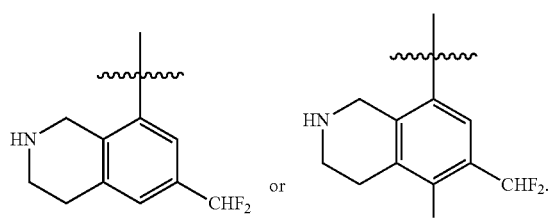
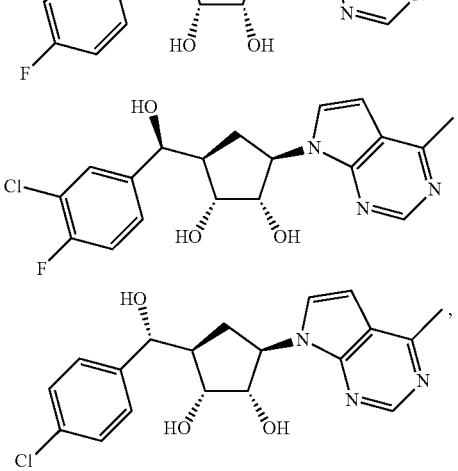
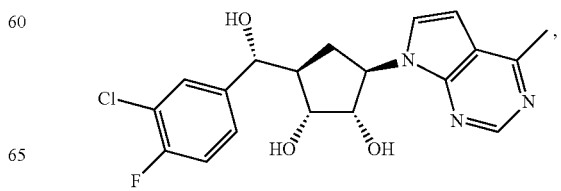

435
-continued
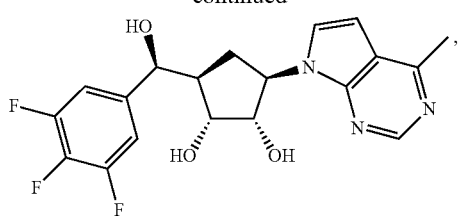
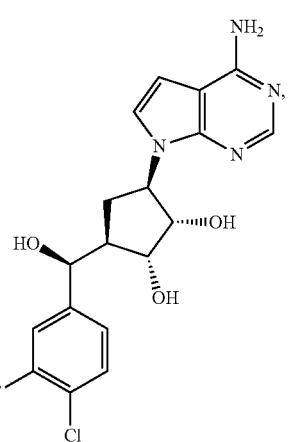
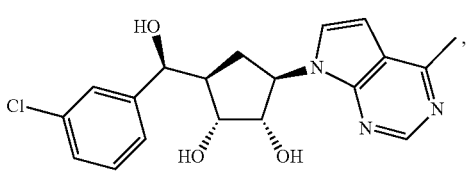
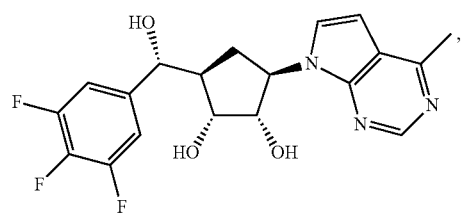
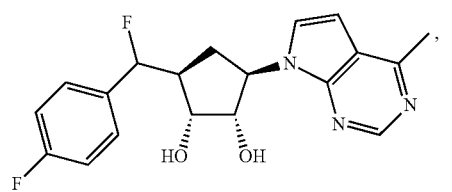
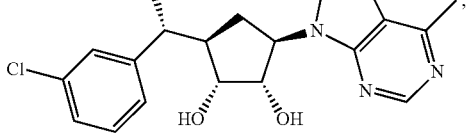
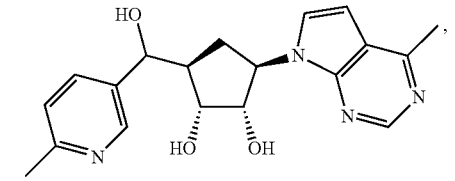
436
-continued
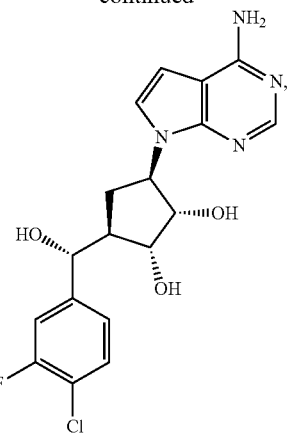
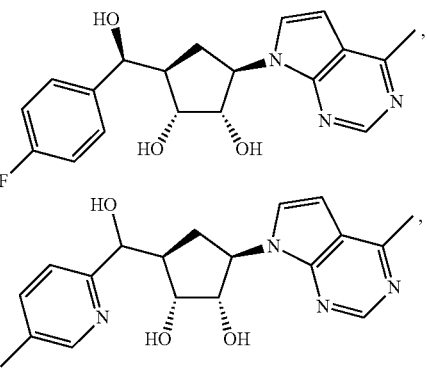
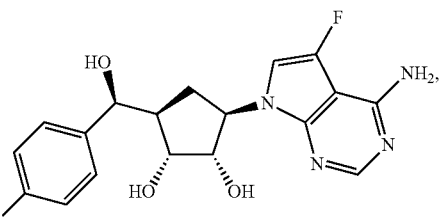
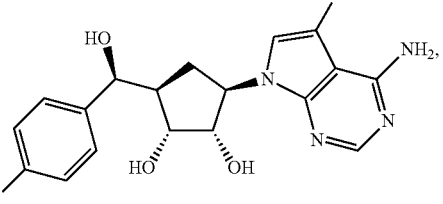
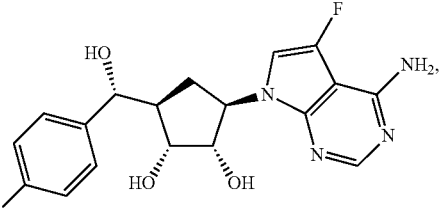
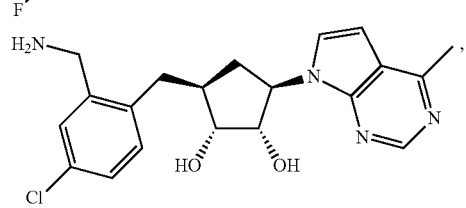
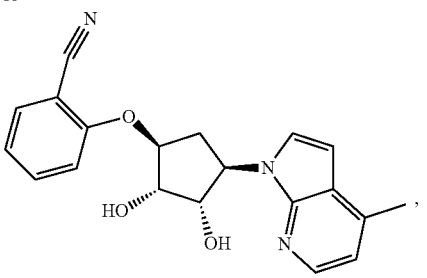

437
-continued
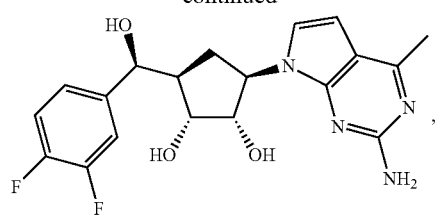
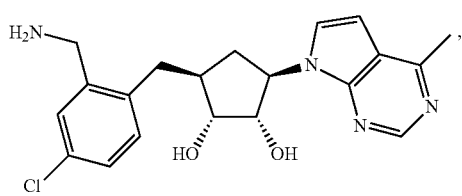
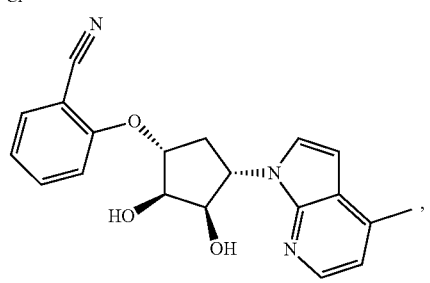
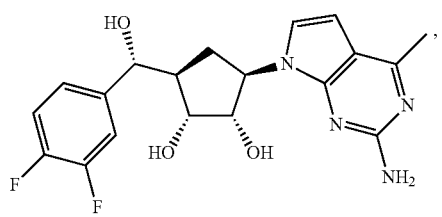
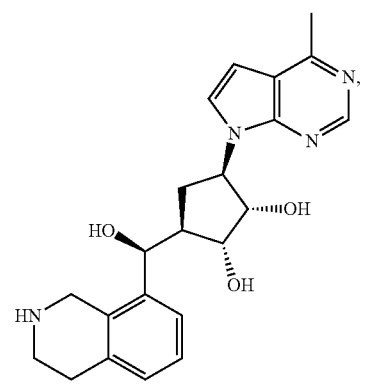
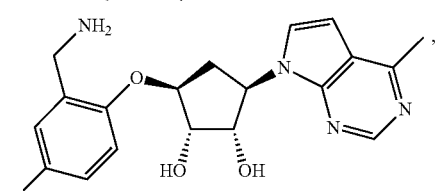
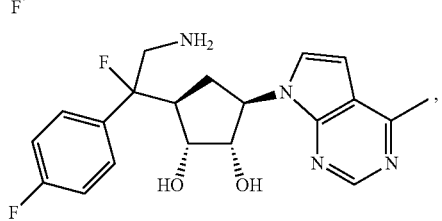
438
-continued
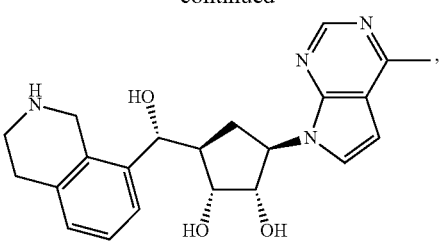
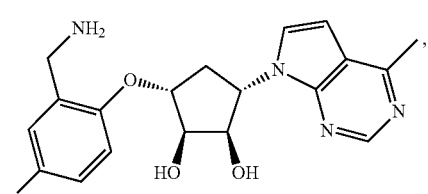
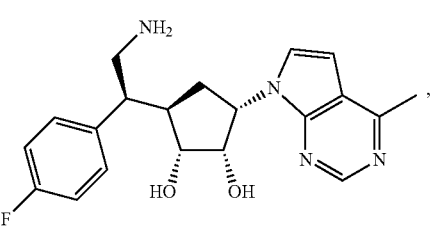
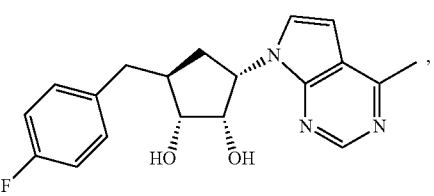
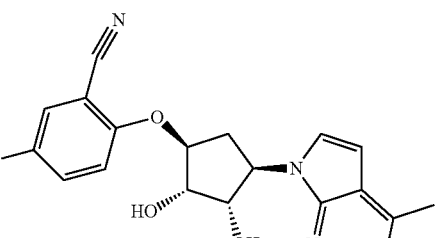
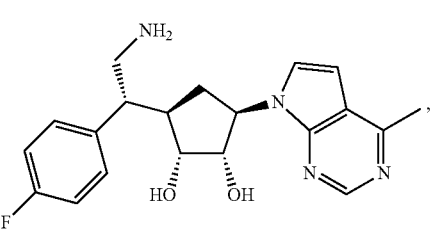
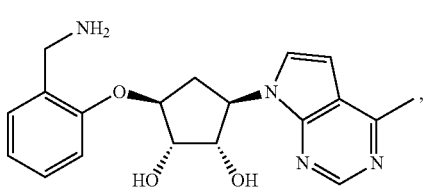

439
-continued
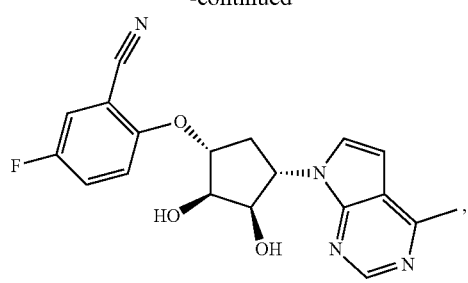
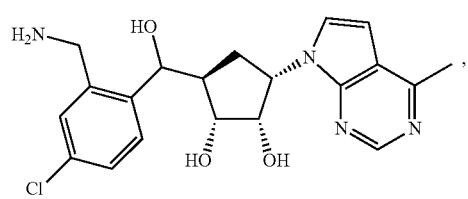
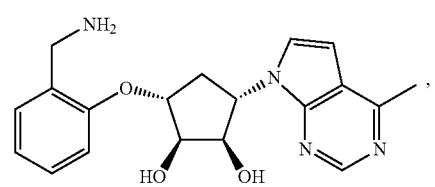
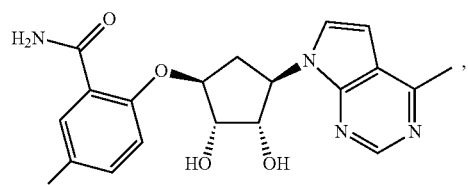
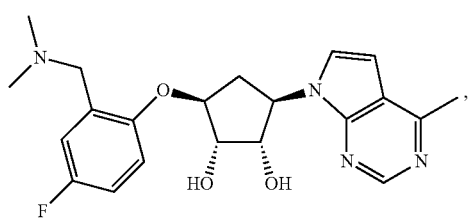
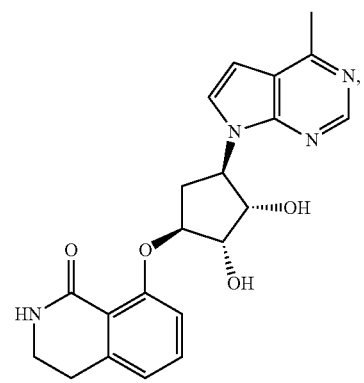
440
-continued
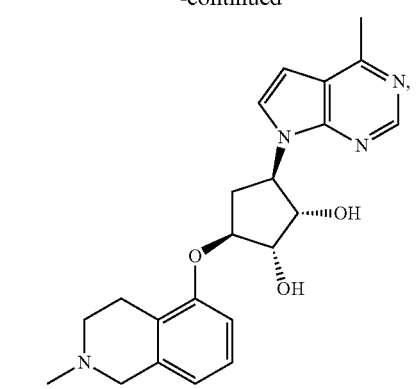
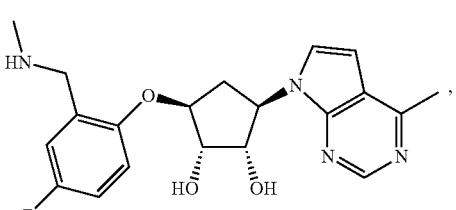
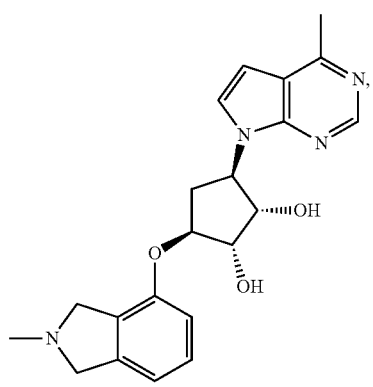
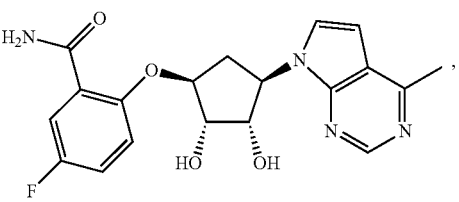
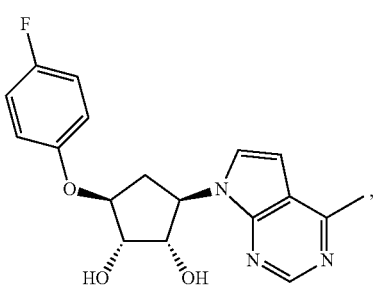

441
-continued
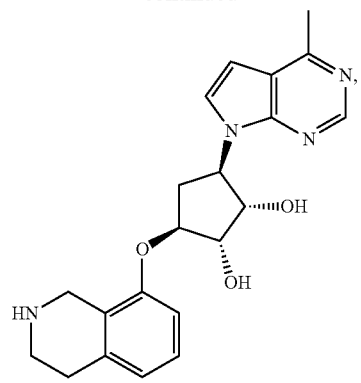
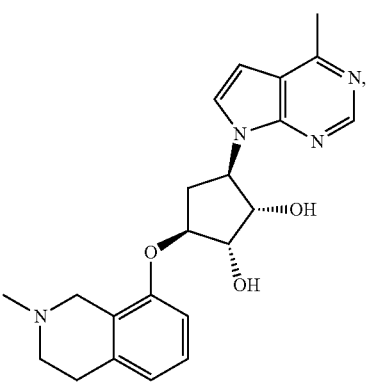
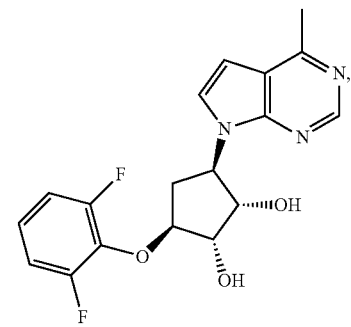
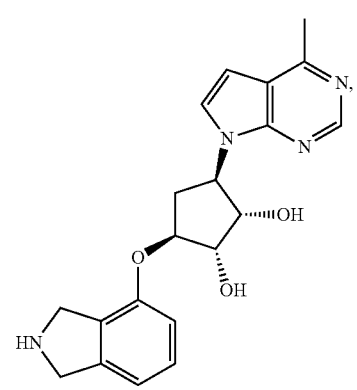
442
-continued
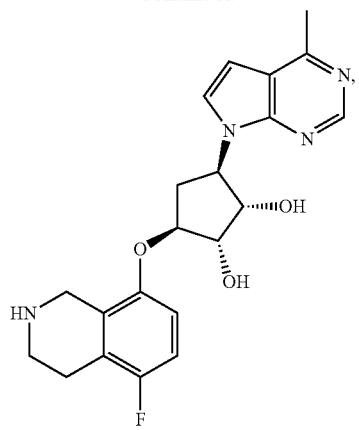
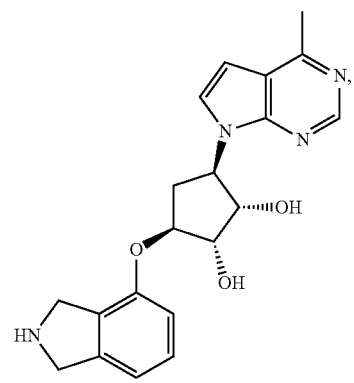
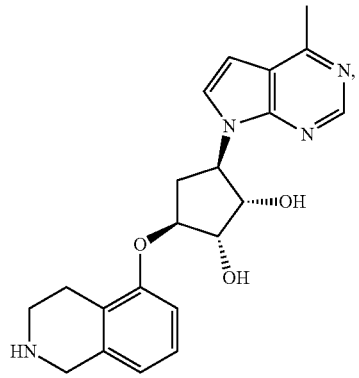
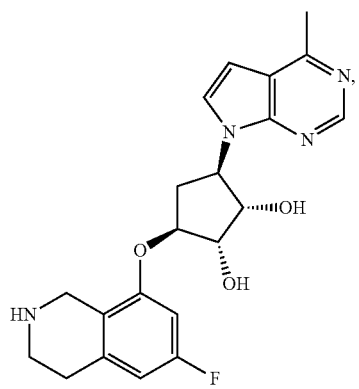

443
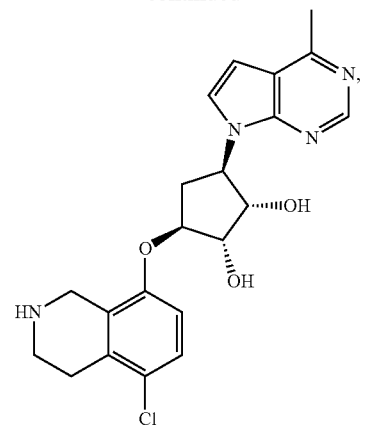
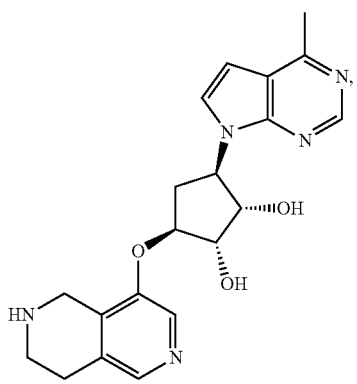
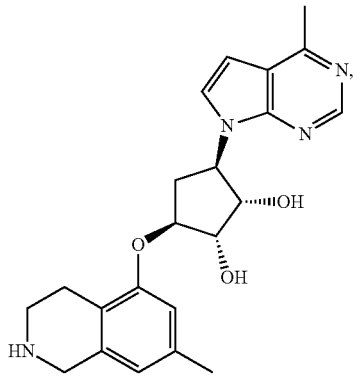
444
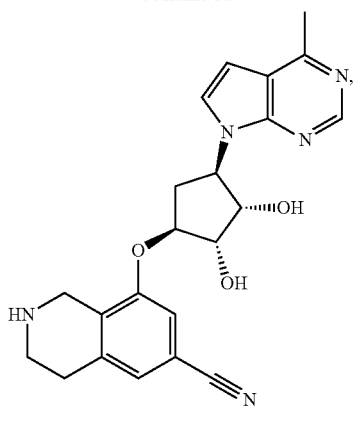
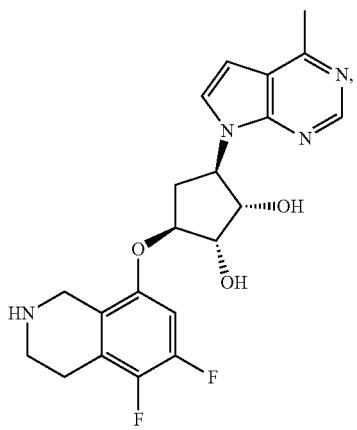

445
-continued
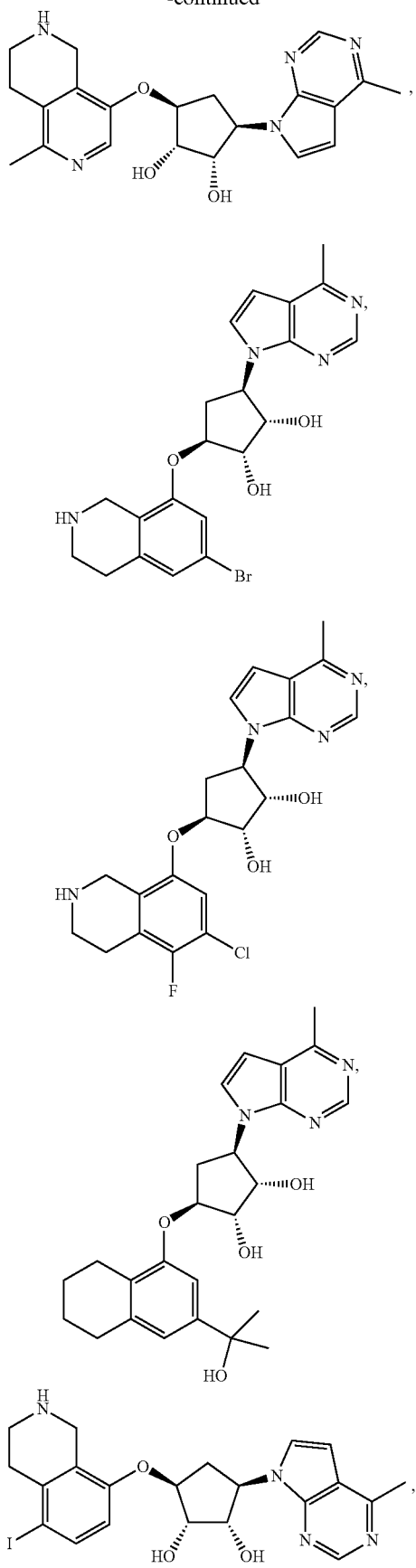
446
-continued
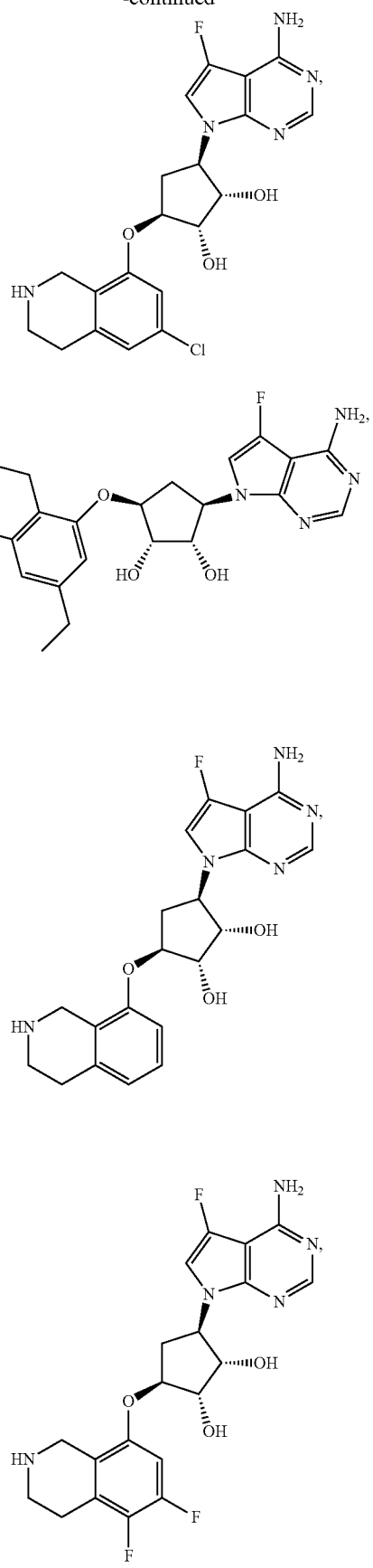

447
-continued
448
-continued
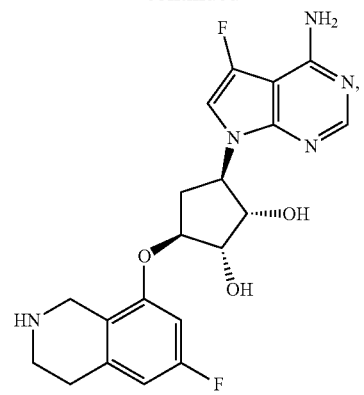
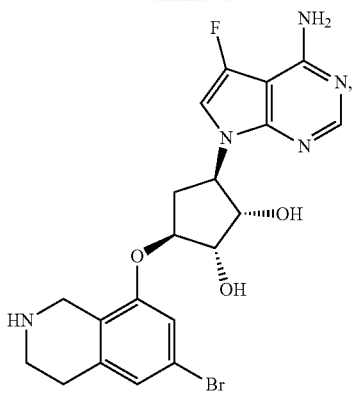

449
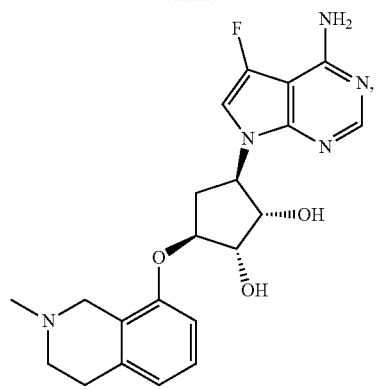
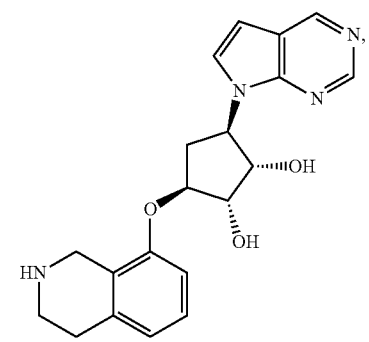
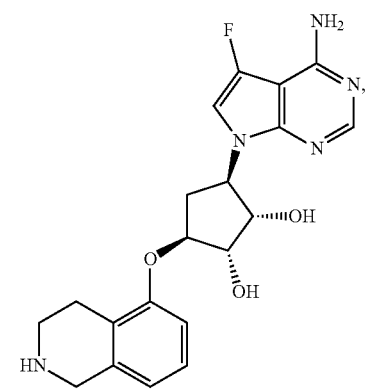
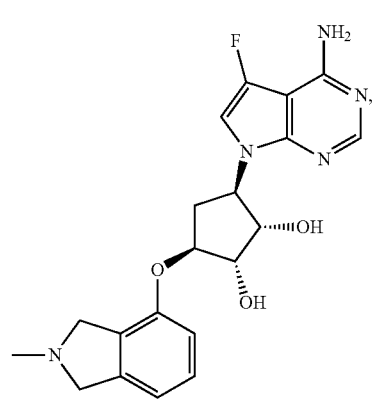
450
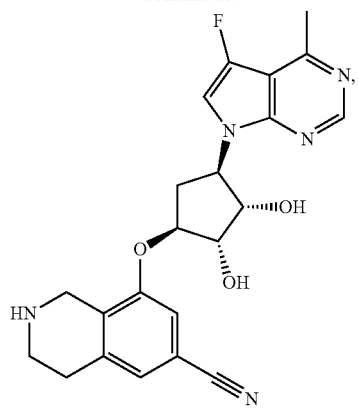
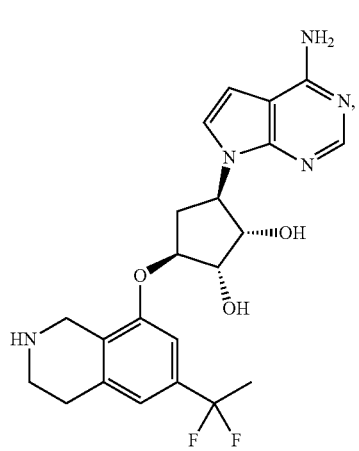
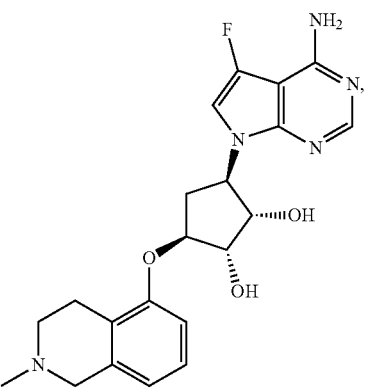
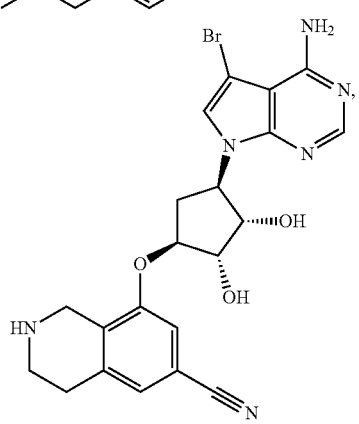

-continued
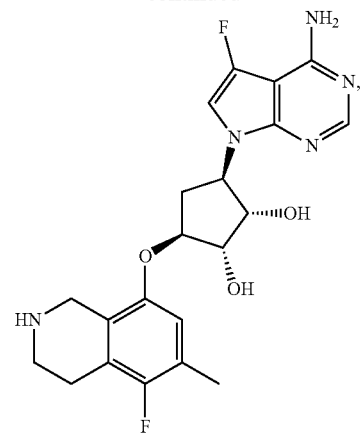
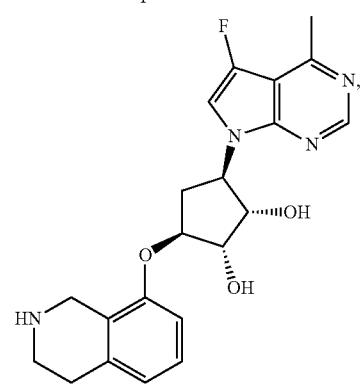
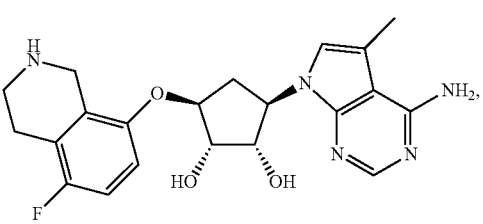
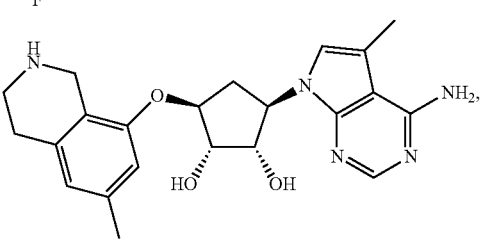
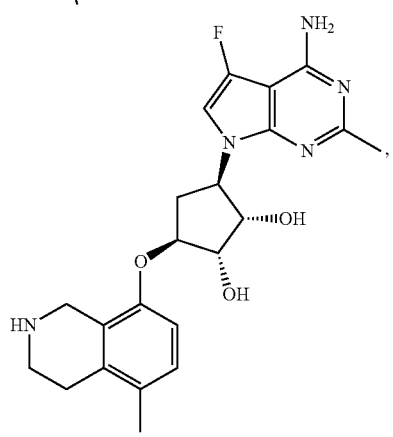
-continued
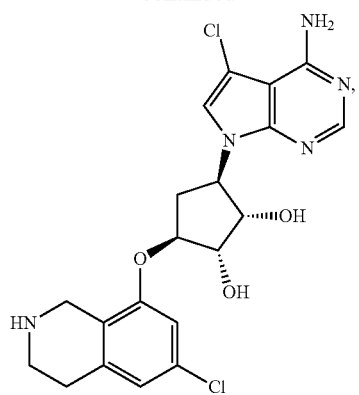
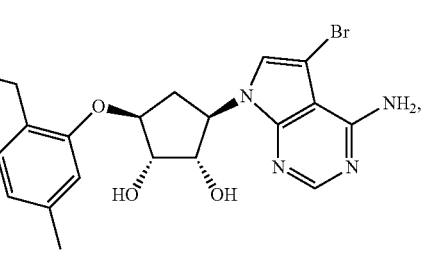
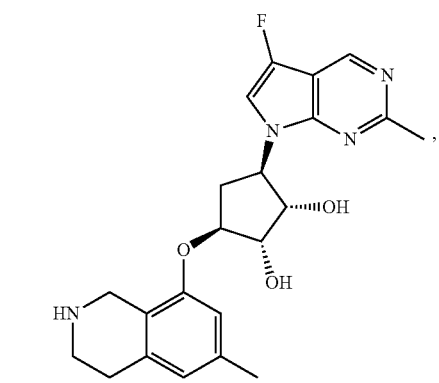
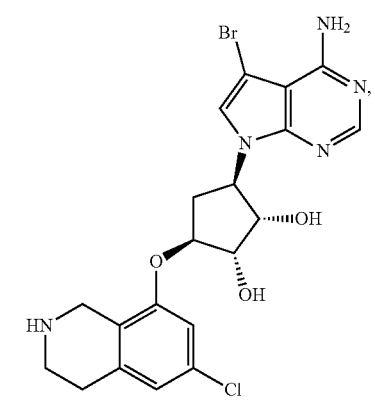

453
-continued
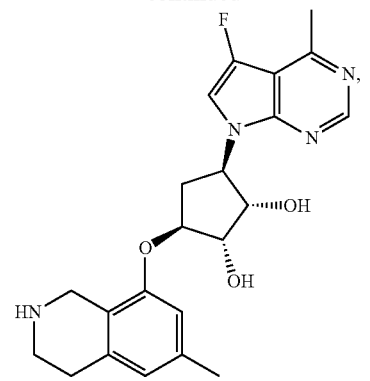
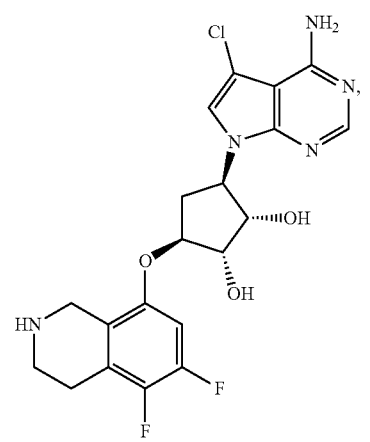
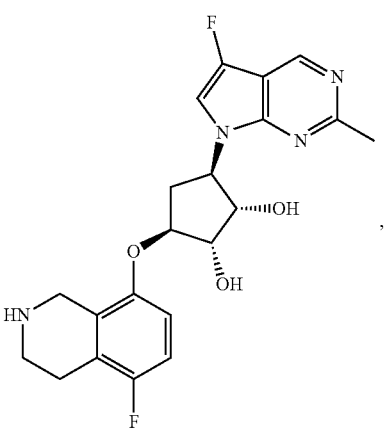
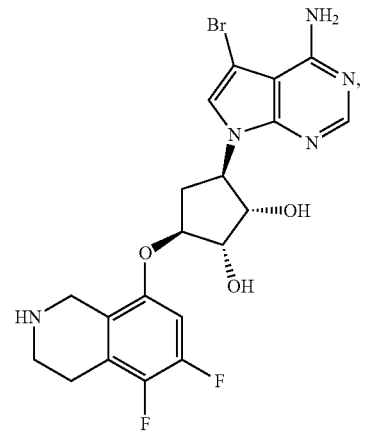
454
-continued
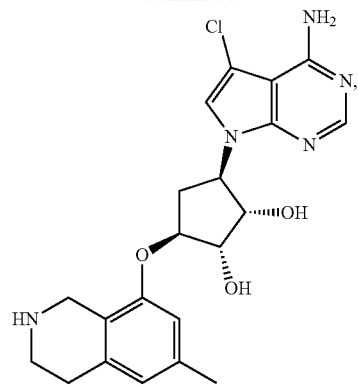
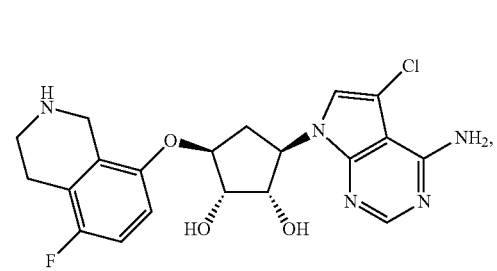
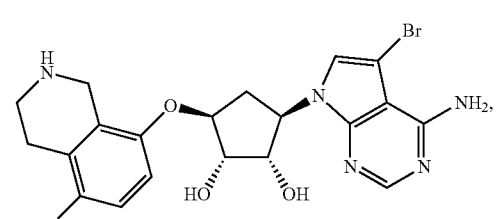
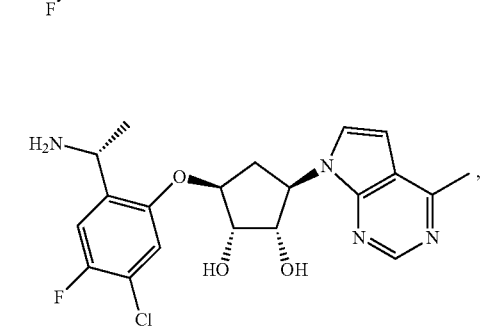
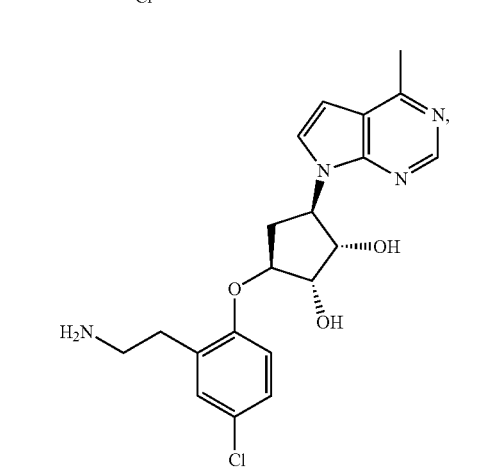

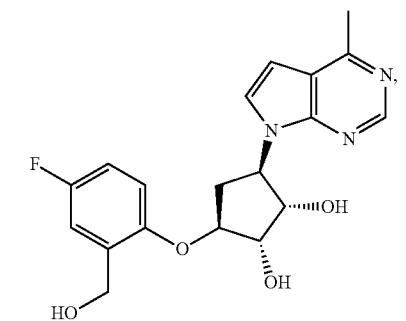
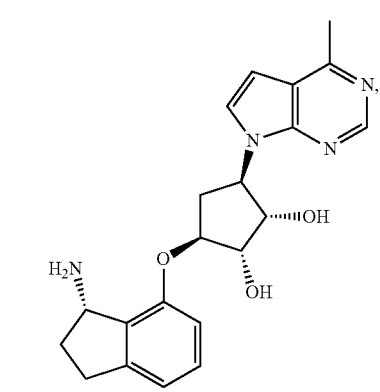
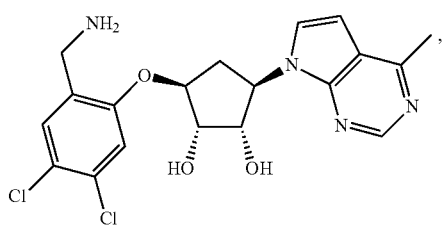
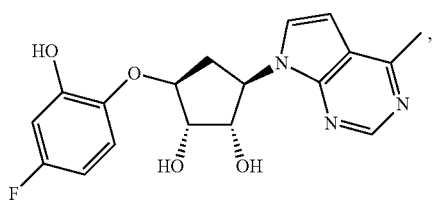
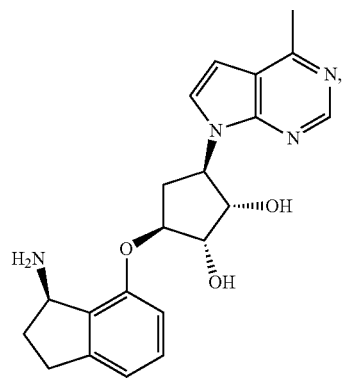
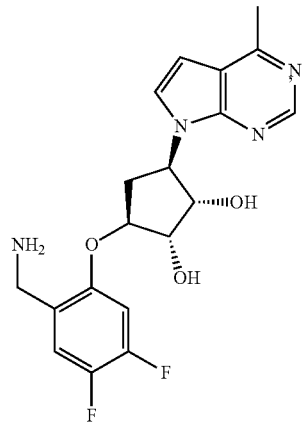
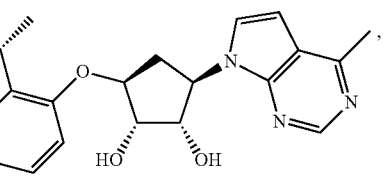
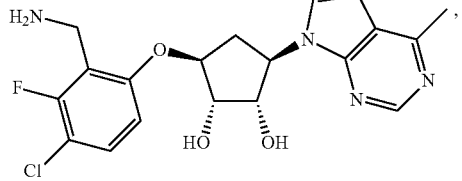
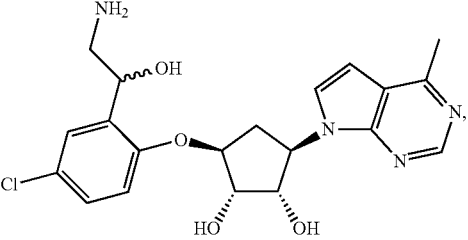
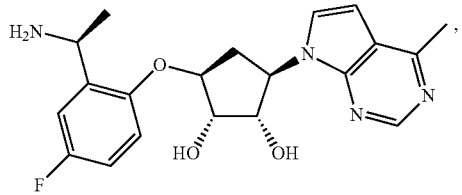
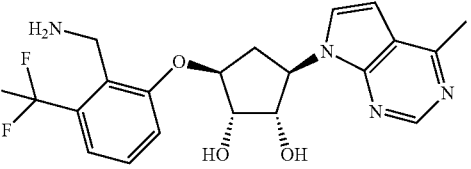
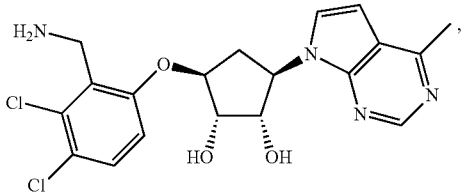

| 457 | 458 |
|---|---|
| -continued | -continued |
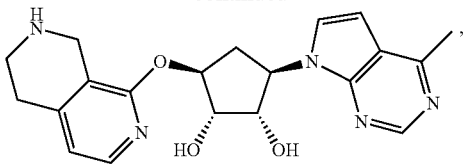
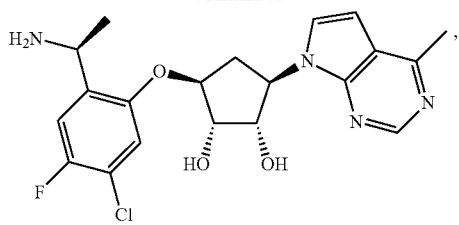
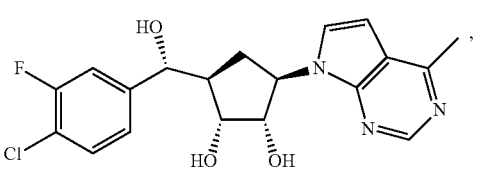
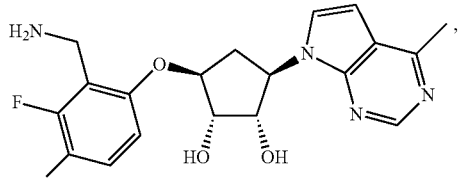
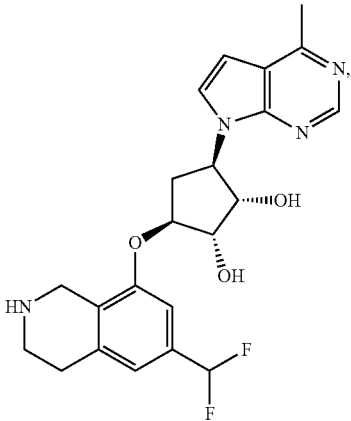
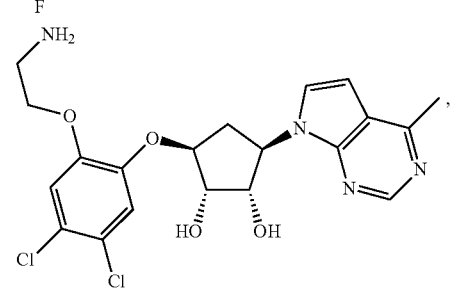
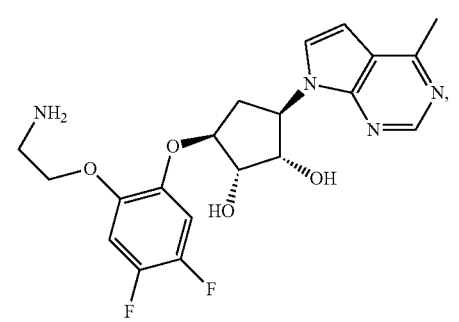
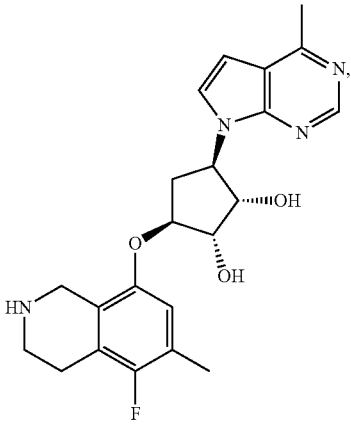
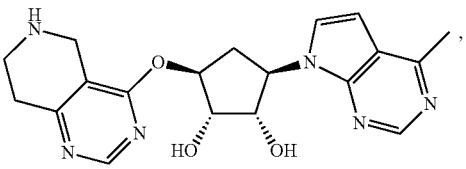
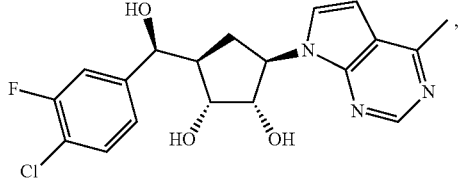
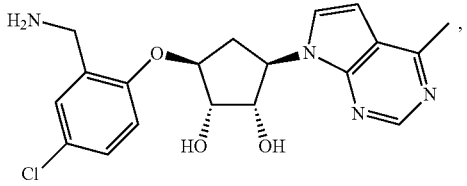
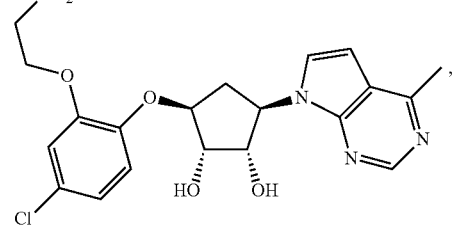

459
-continued
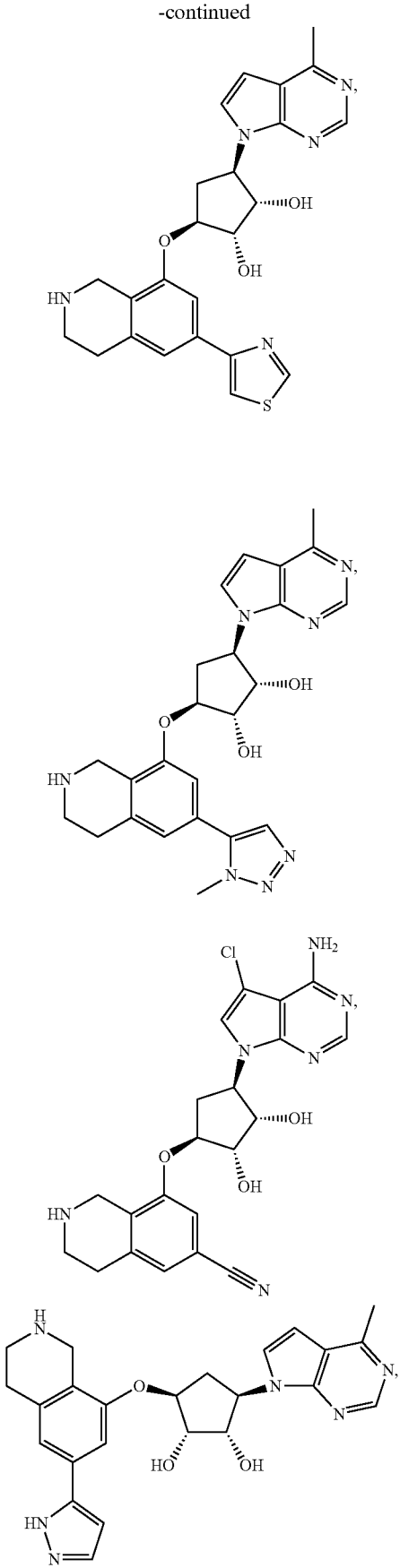
460
-continued
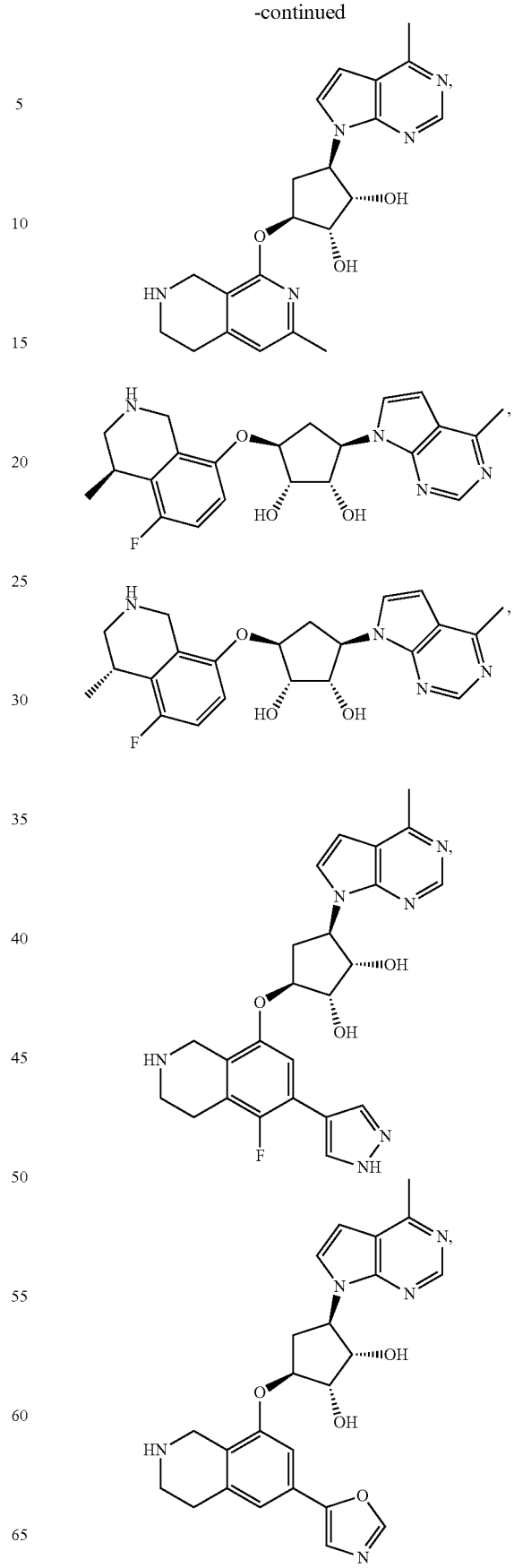

461
-continued
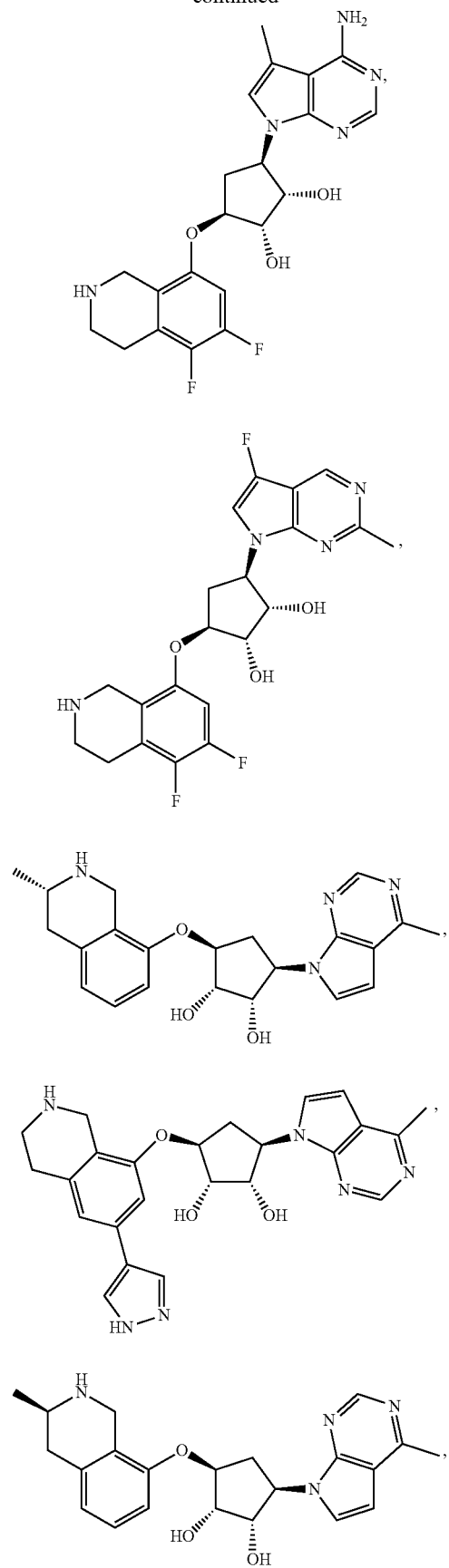
462
-continued
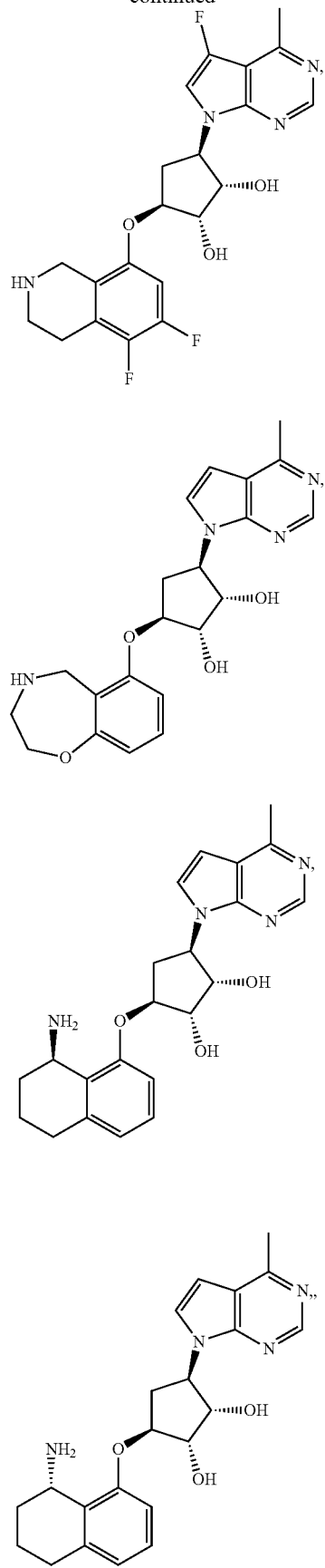

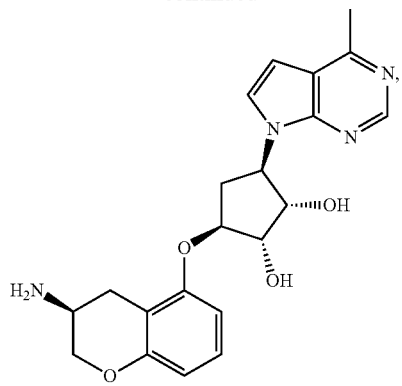
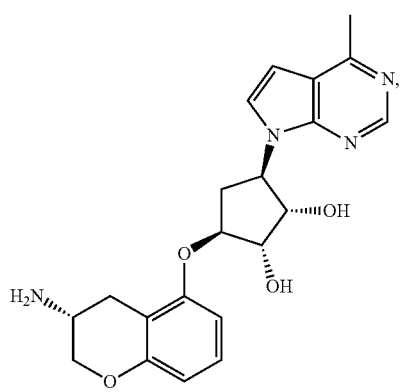
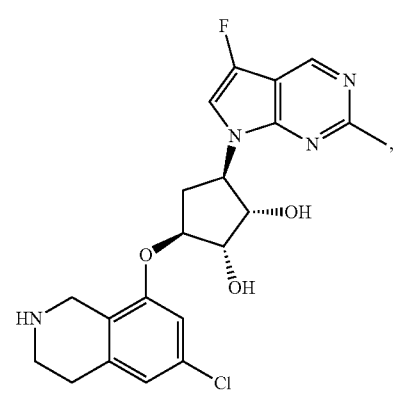
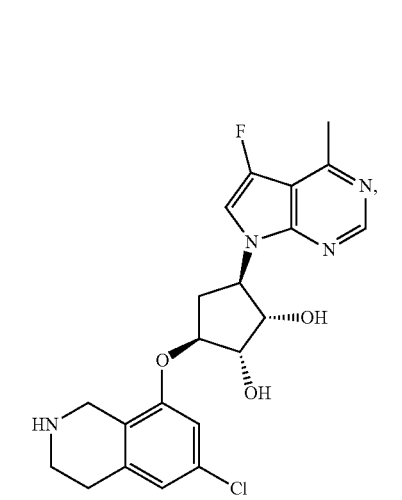
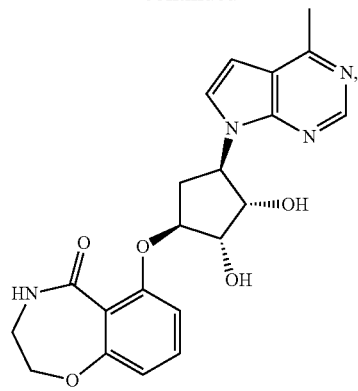
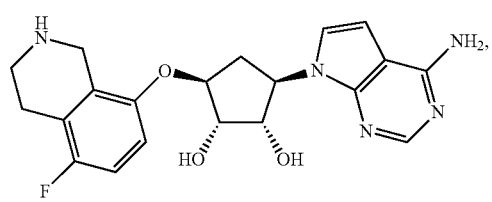
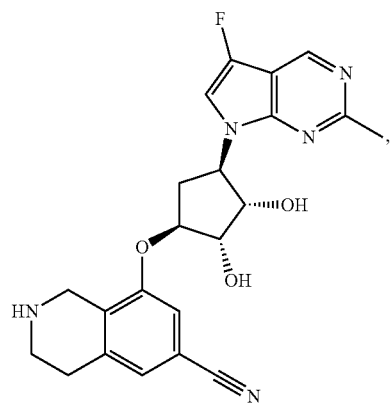
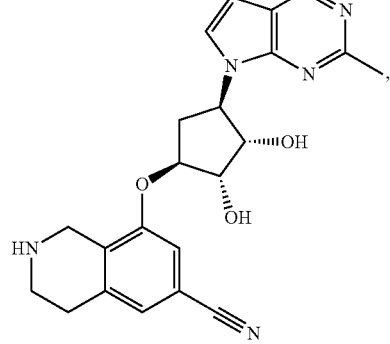

465
-continued
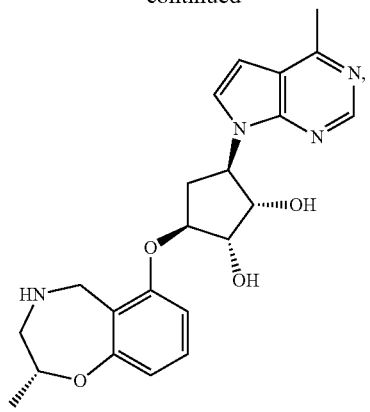
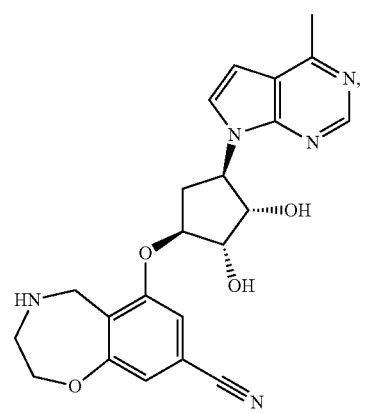
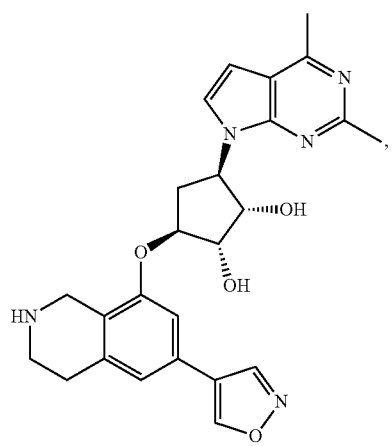
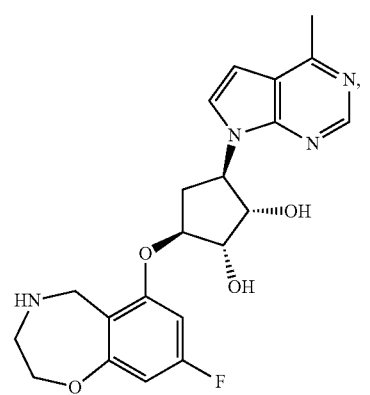
466
-continued
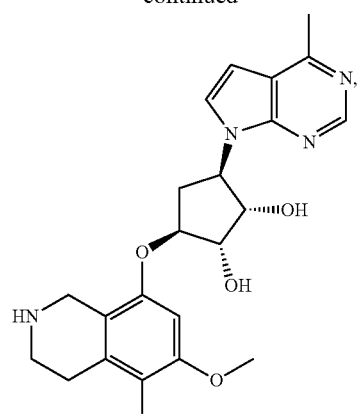
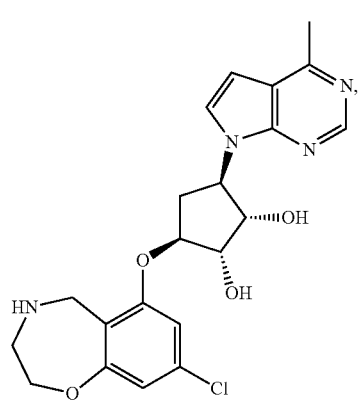
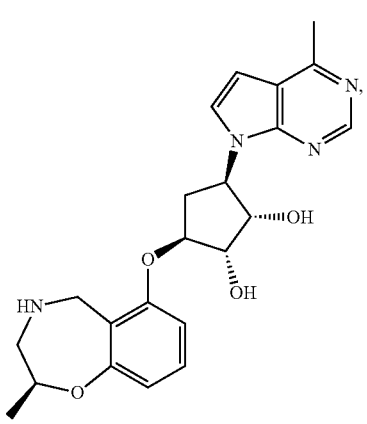
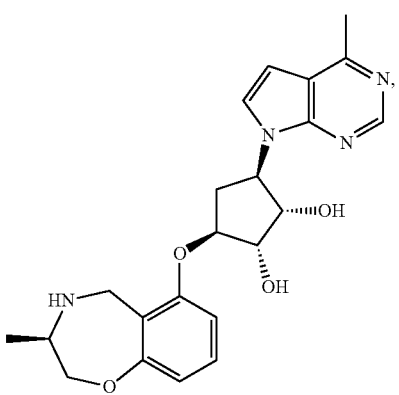

467
-continued
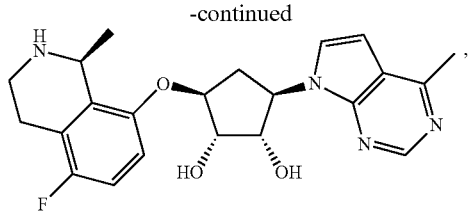
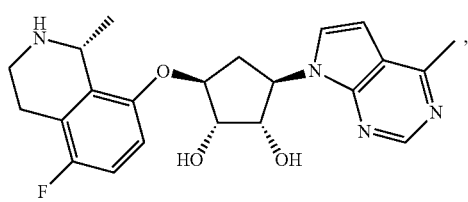
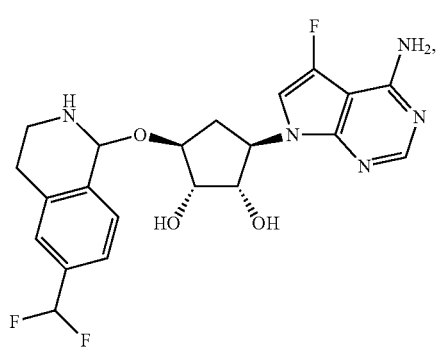
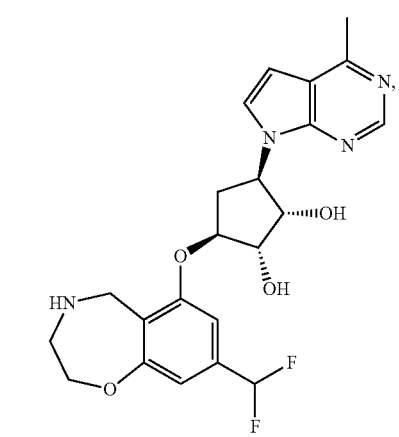
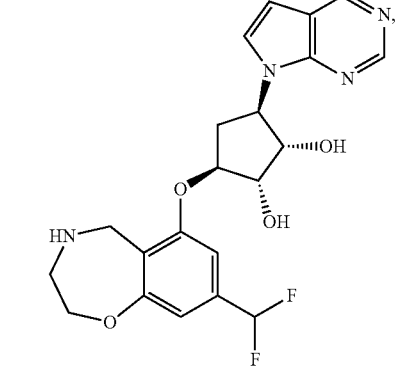
468
-continued
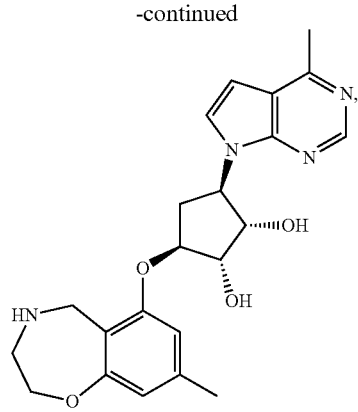
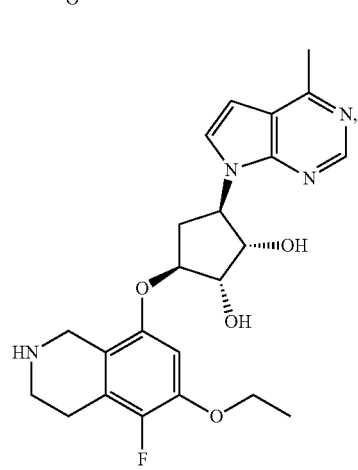
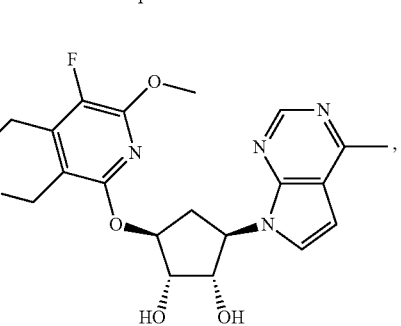
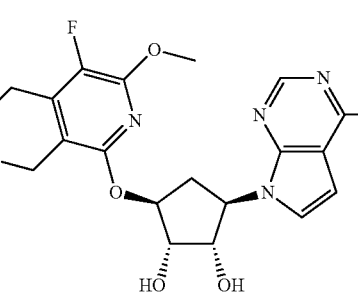

469
-continued
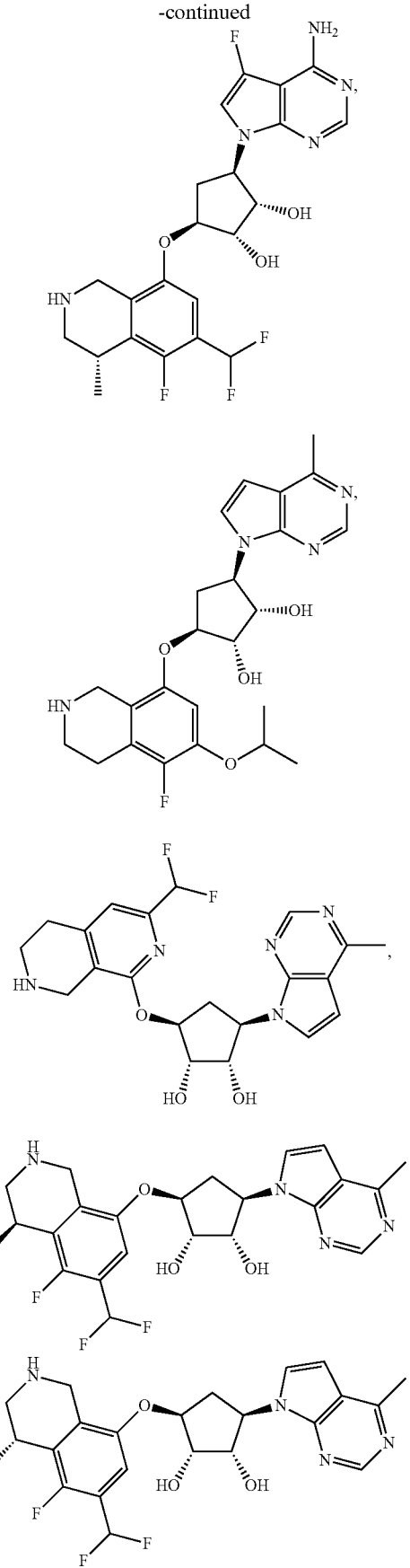
470
-continued
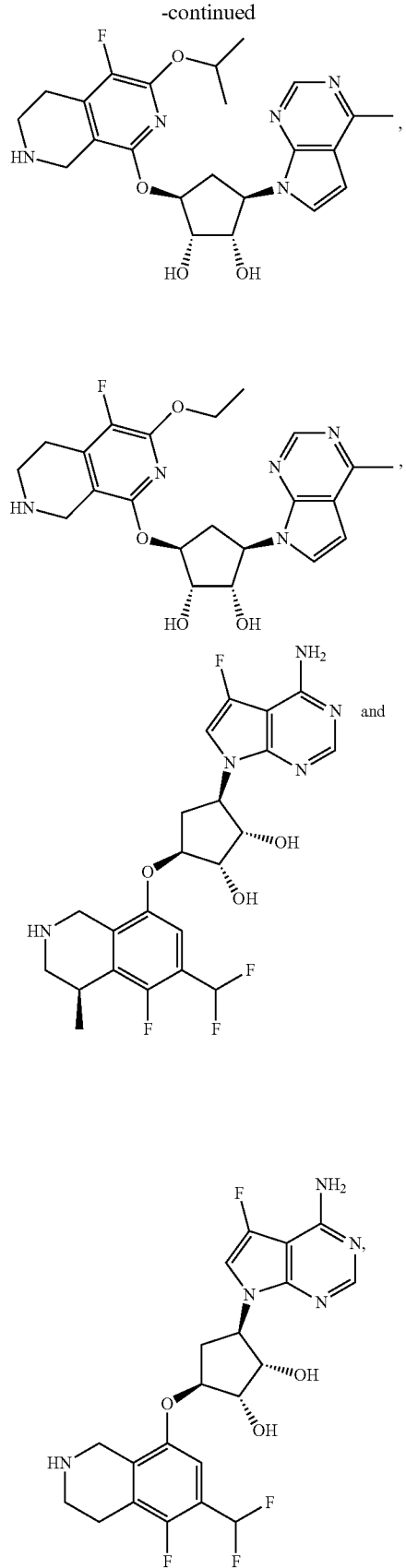
or a pharmaceutically acceptable salt thereof.

8. A compound selected from:
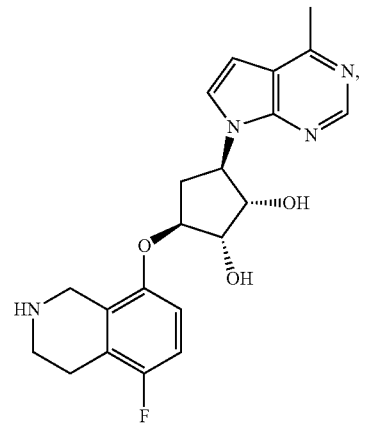
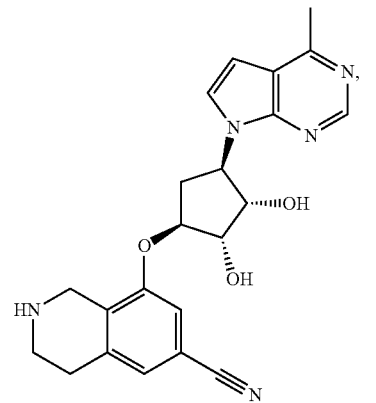
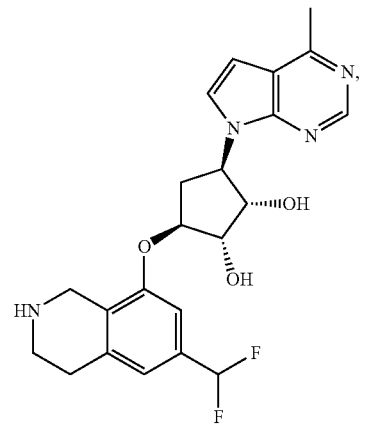
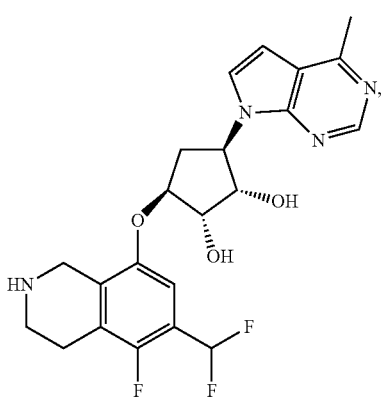
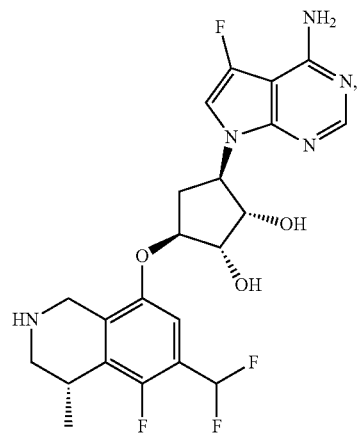
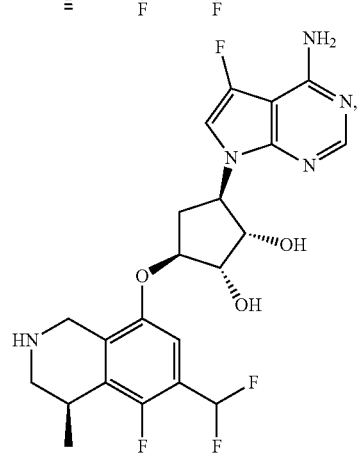
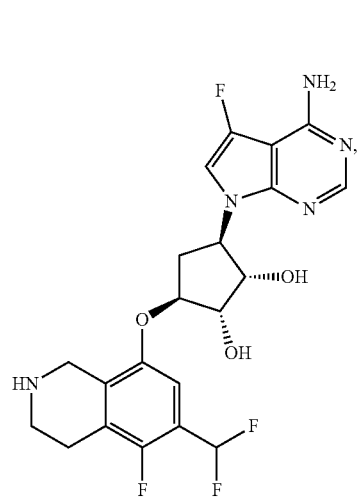
or a pharmaceutically acceptable salt thereof.
9. A compound selected from:
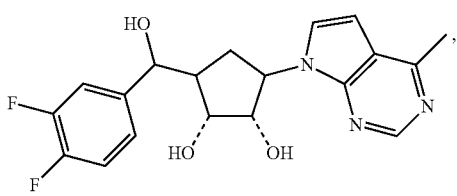

473
-continued
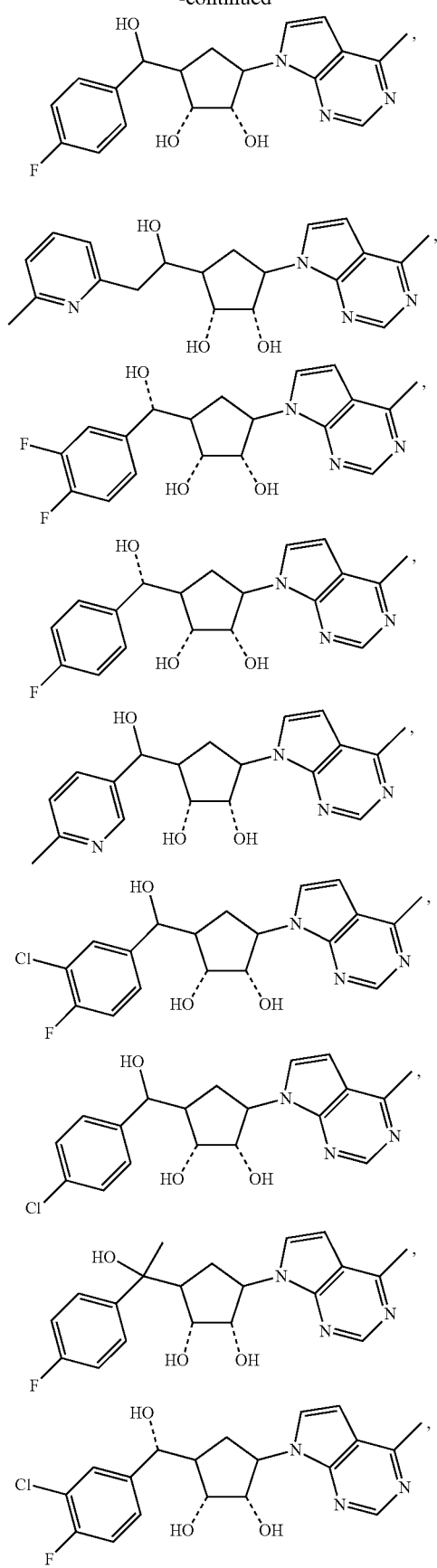
474
-continued
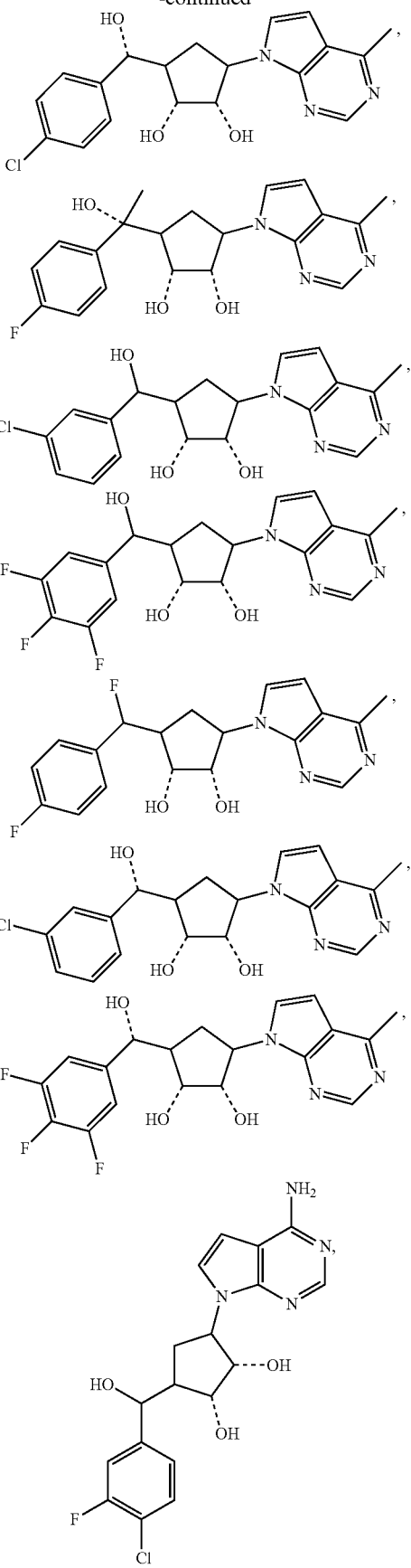

-continued
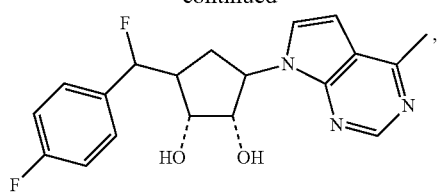
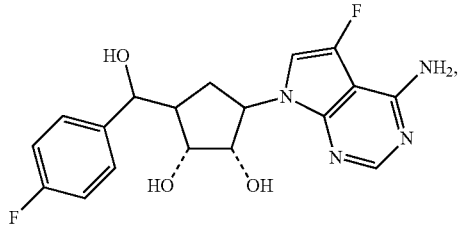
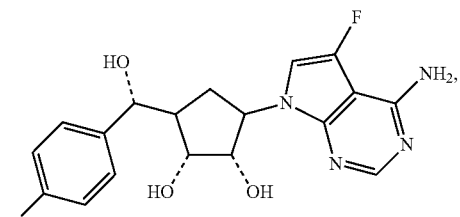
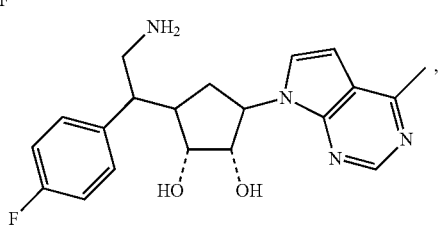
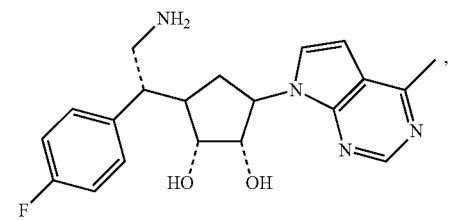
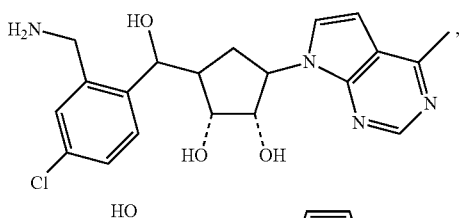
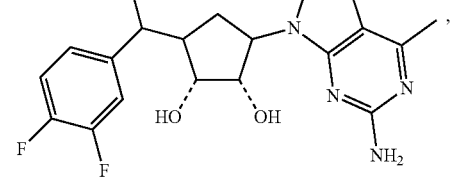
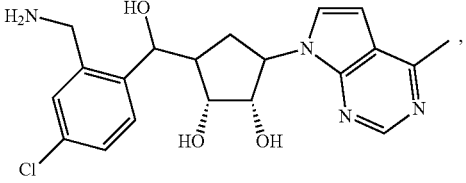
-continued
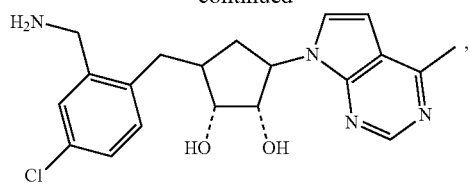
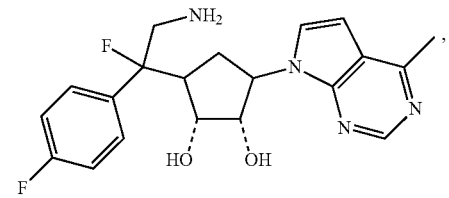
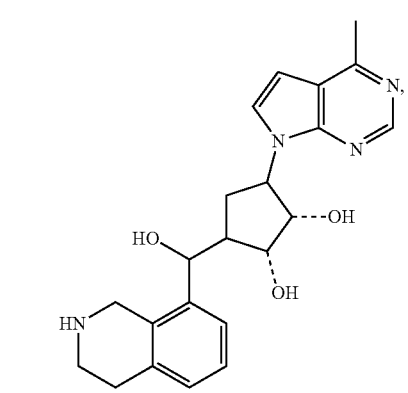
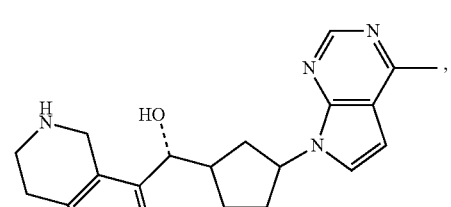
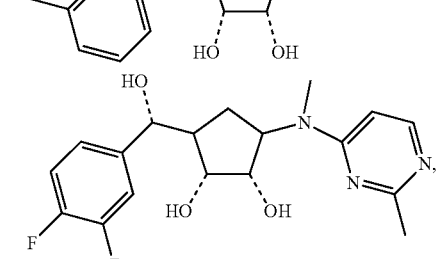
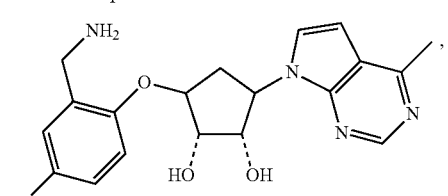
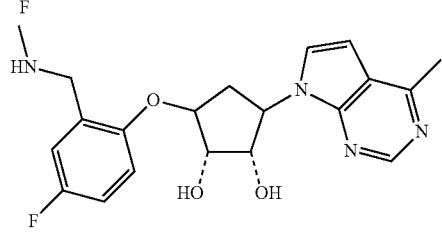

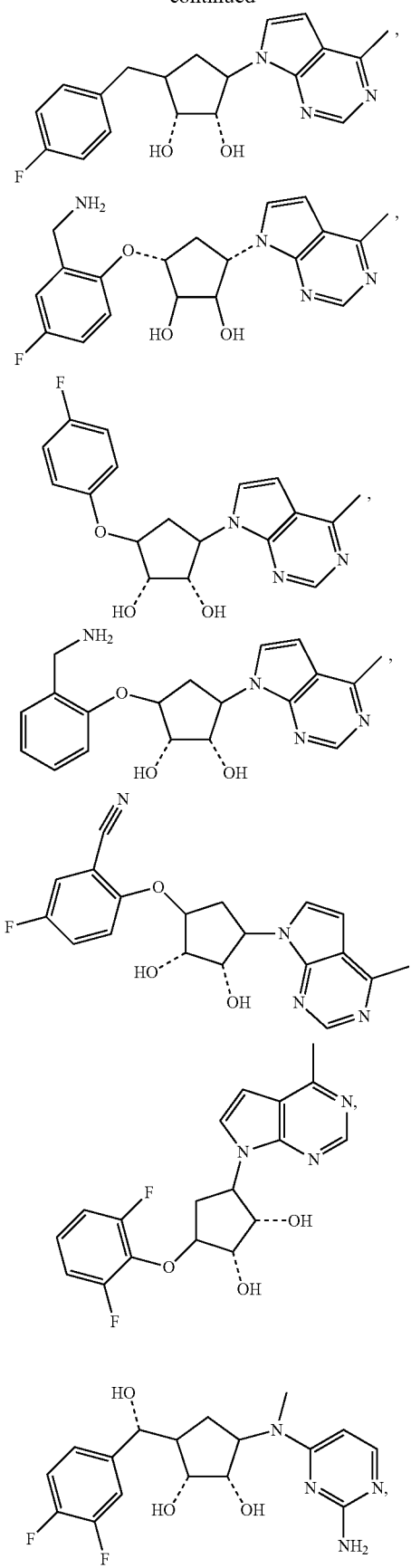
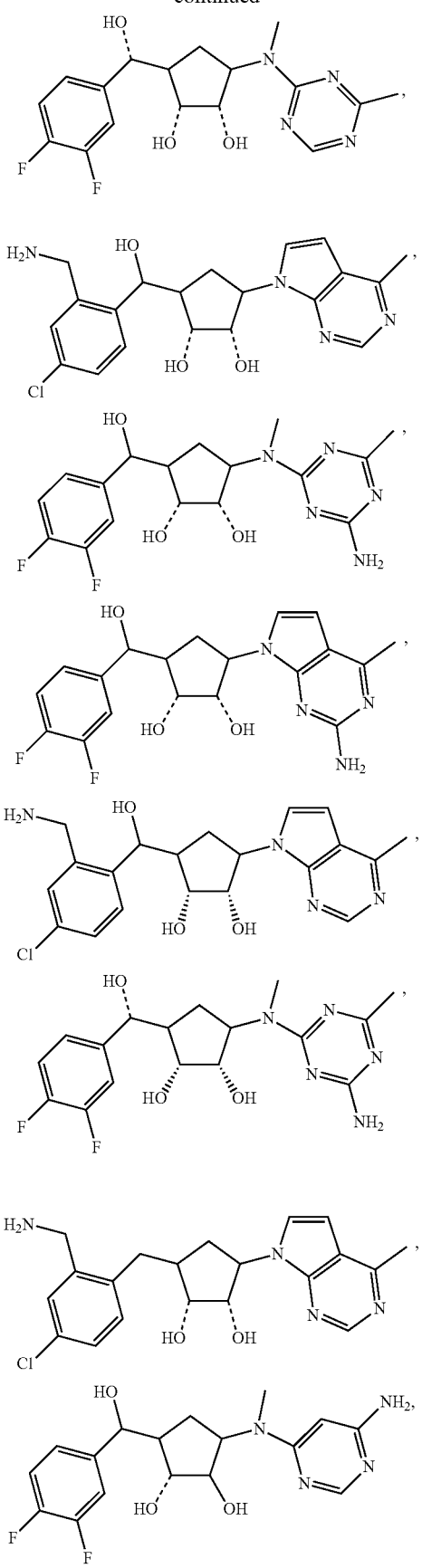

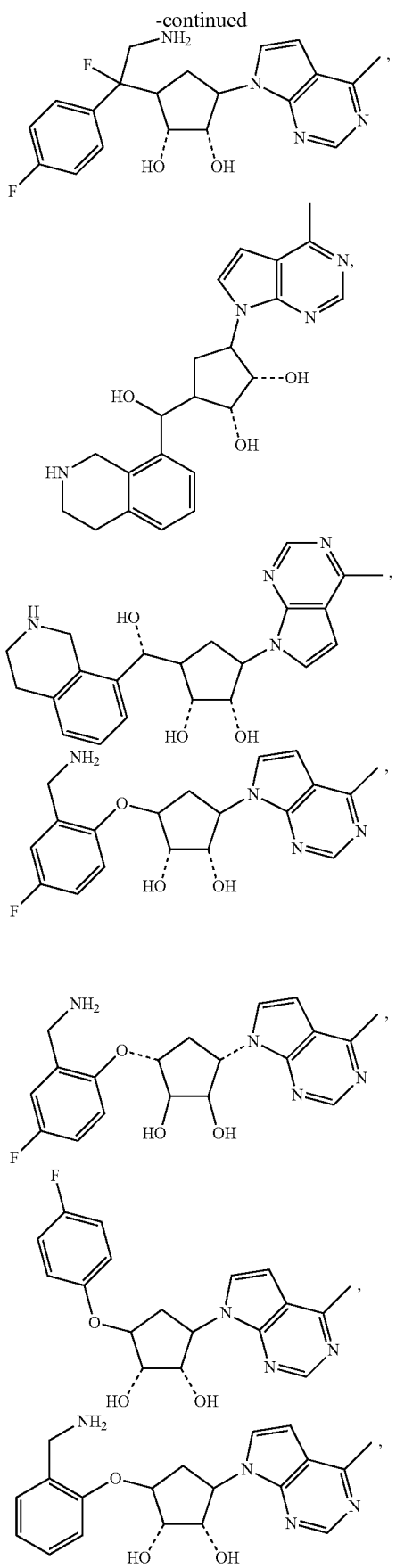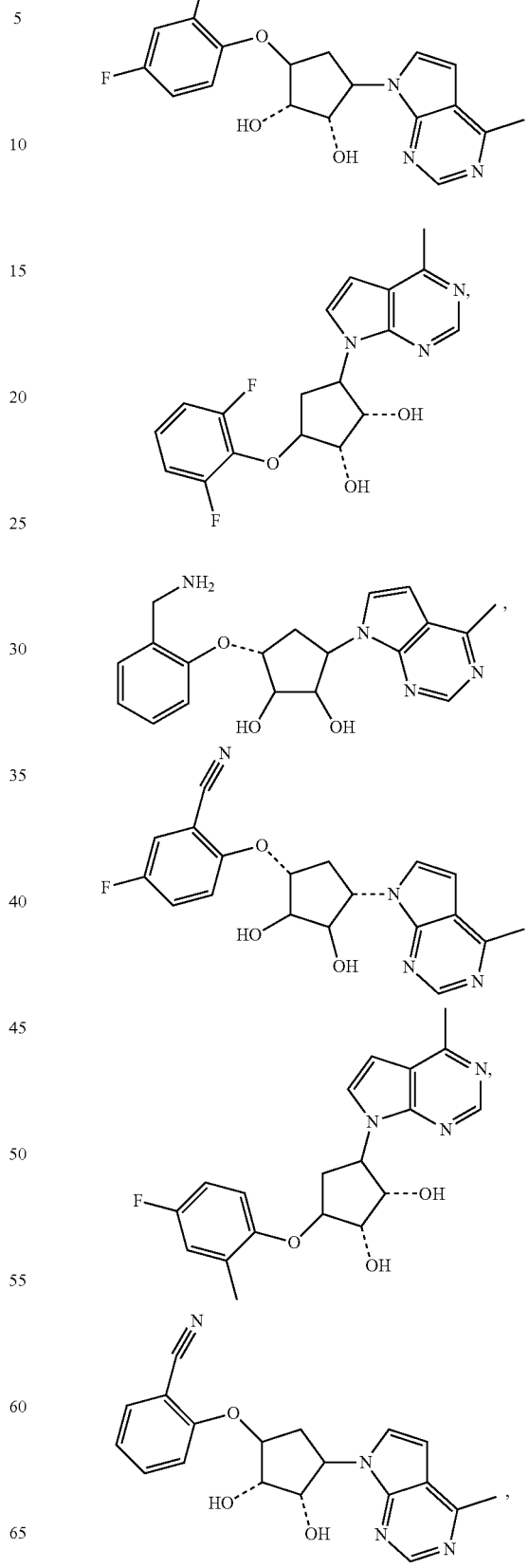

481
-continued
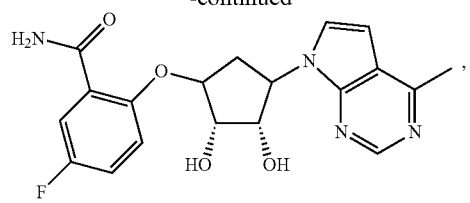
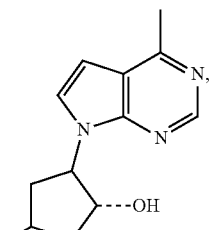
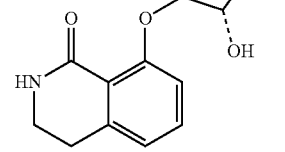
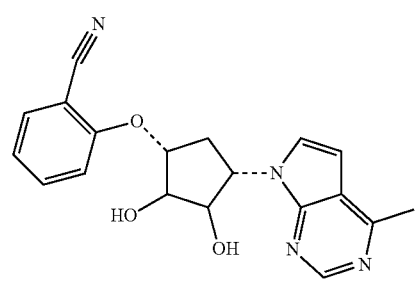
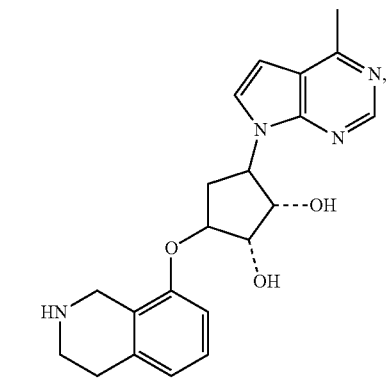
482
-continued
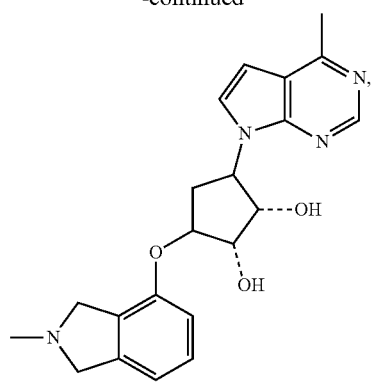
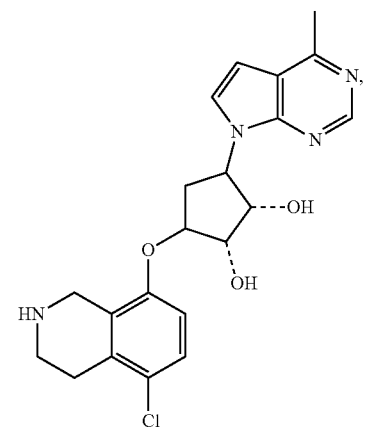
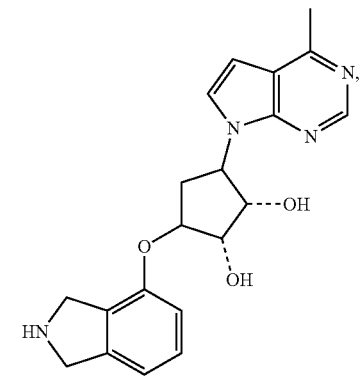
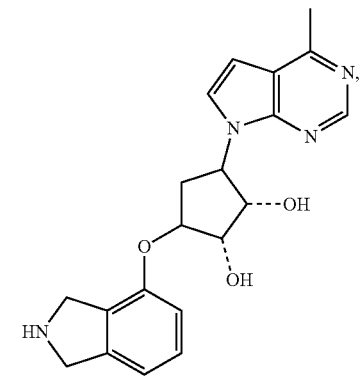

483
-continued
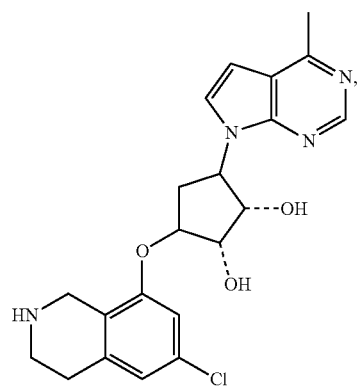
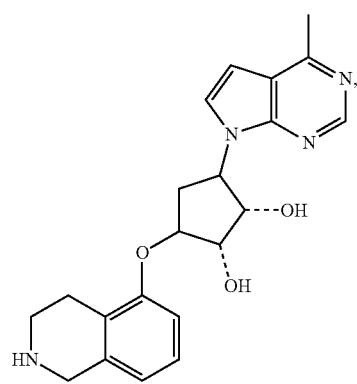
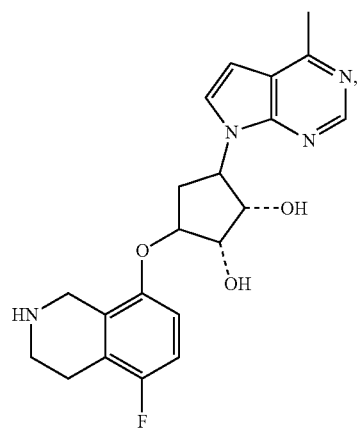
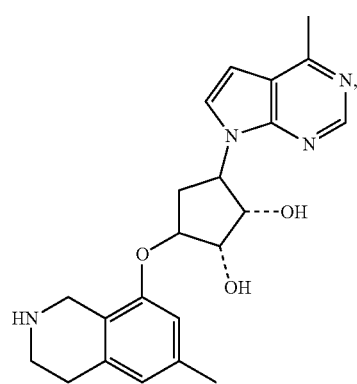
484
-continued
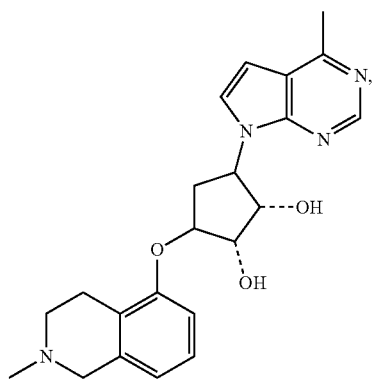
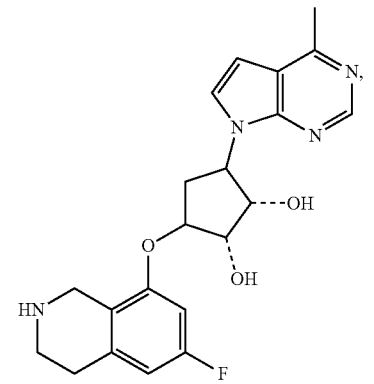
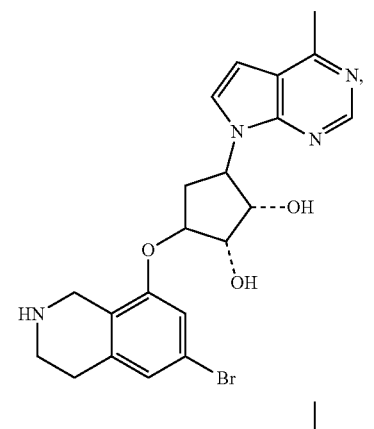
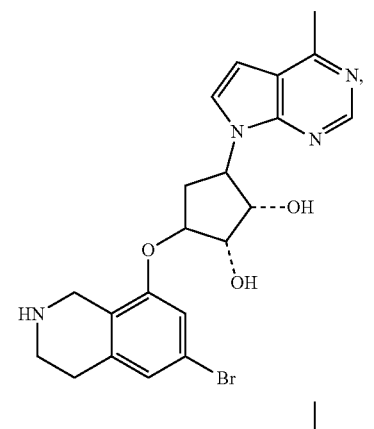

485
-continued
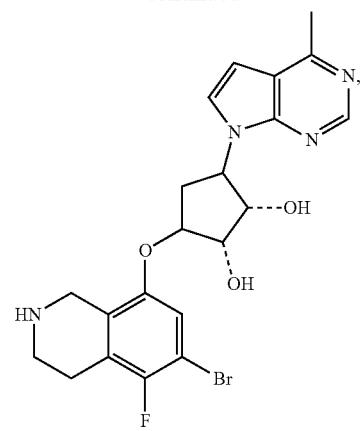
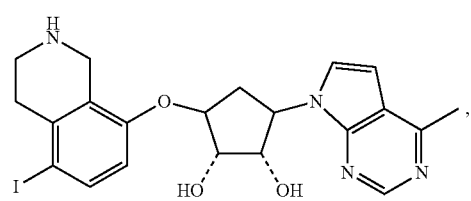
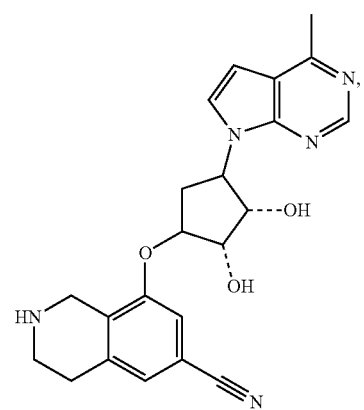
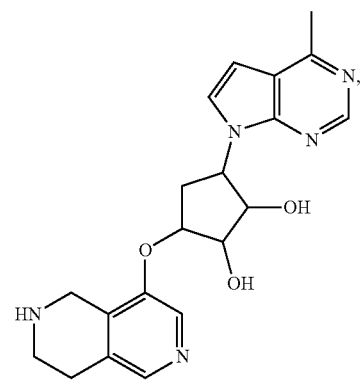
486
-continued
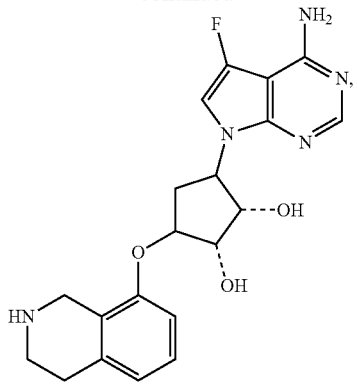
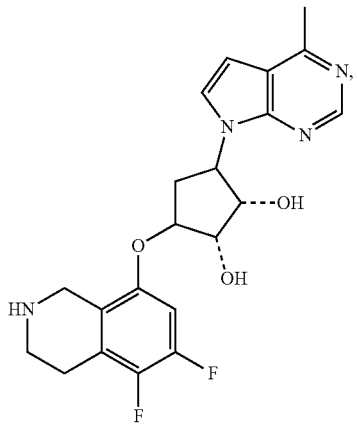
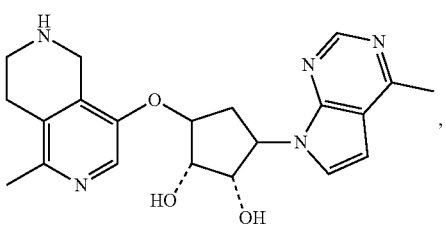
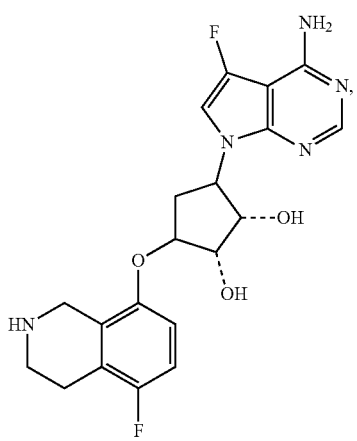

487
-continued
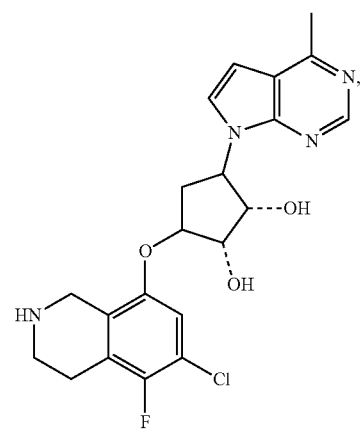
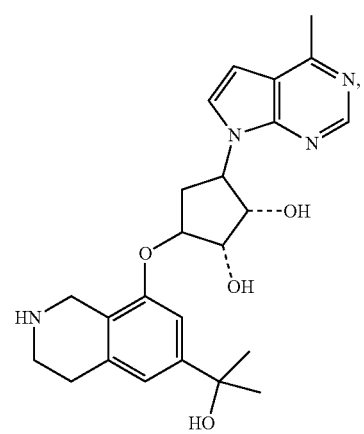
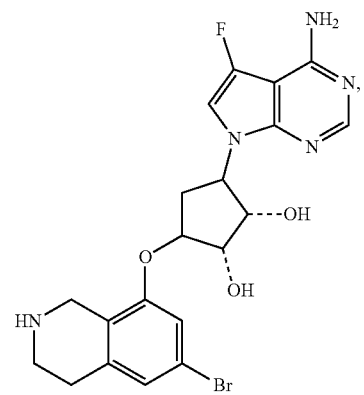
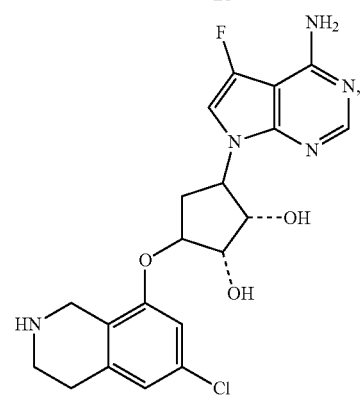
488
-continued
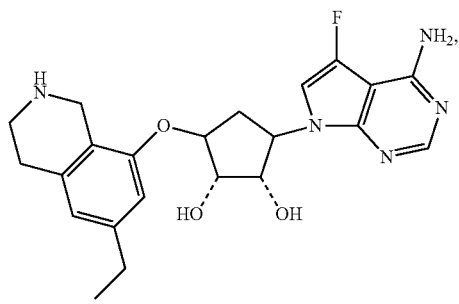
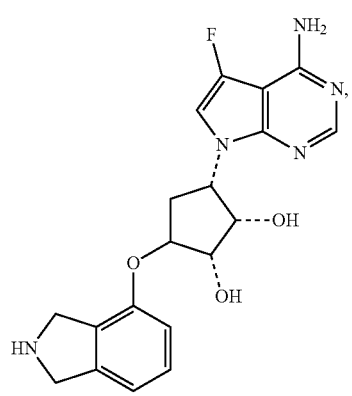
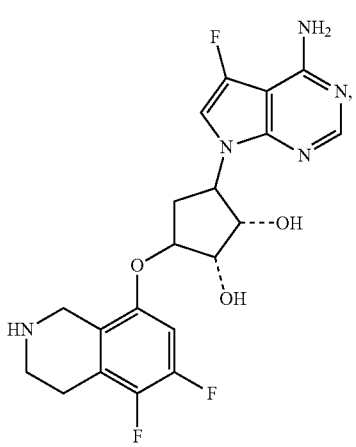
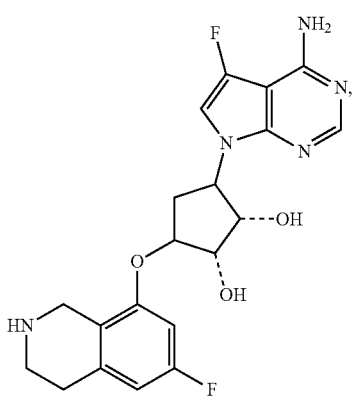

489
-continued
490
-continued
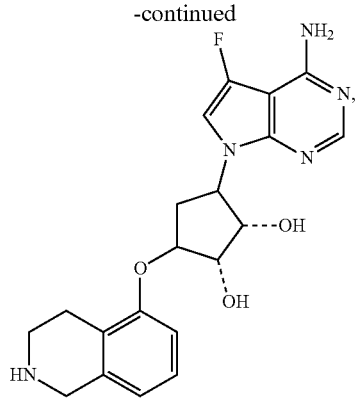
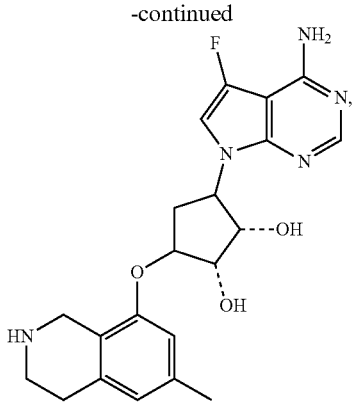
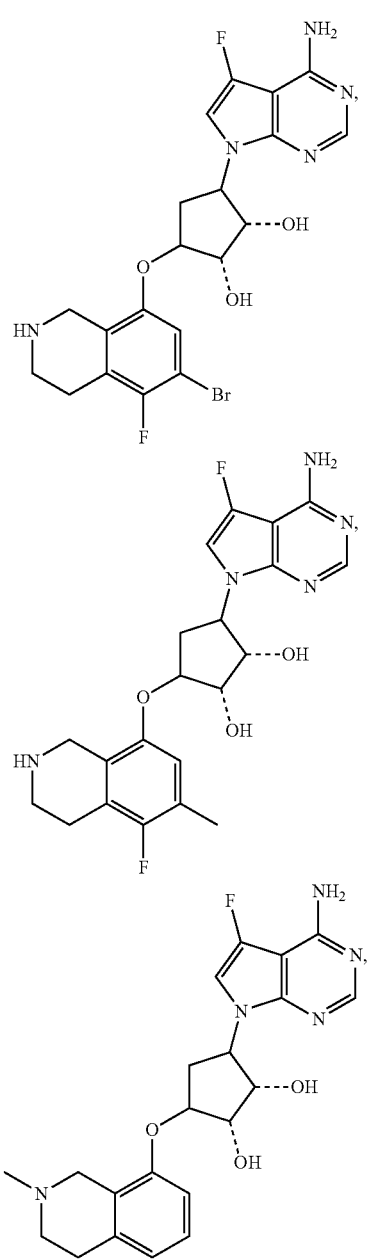

491
-continued
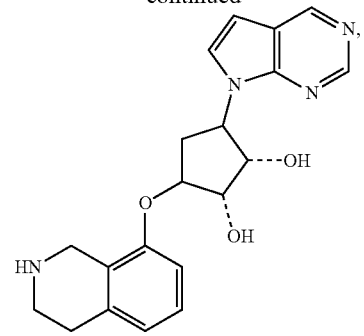
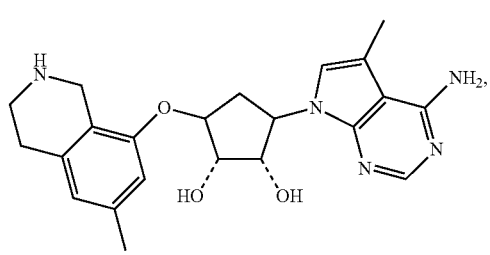
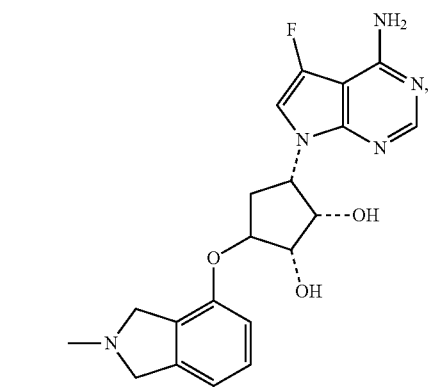 [SMILES: CN1Cc2cccc(OC3C[C@H](n4cc(F)c5c(N)ncnc54)[C@H](O)[C@@H]3O)c2C1]
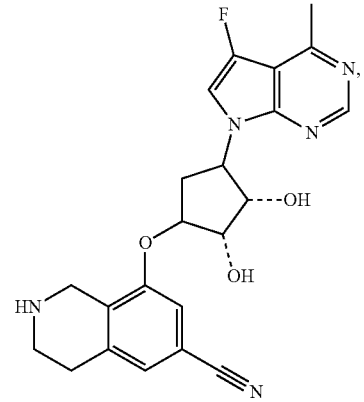
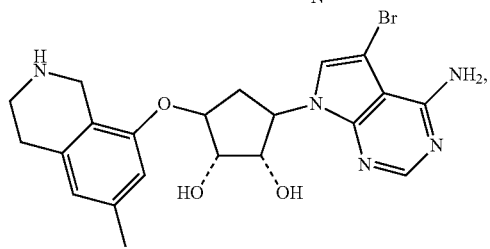
492
-continued
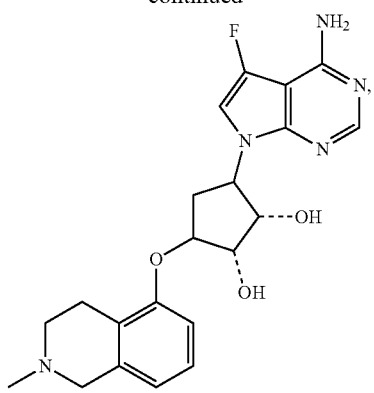
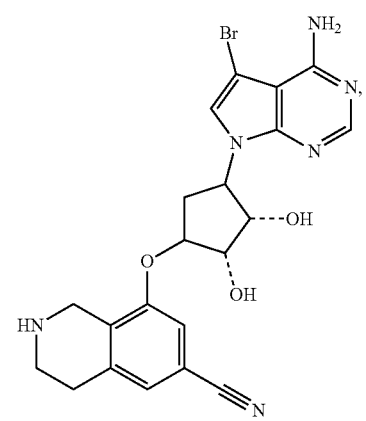
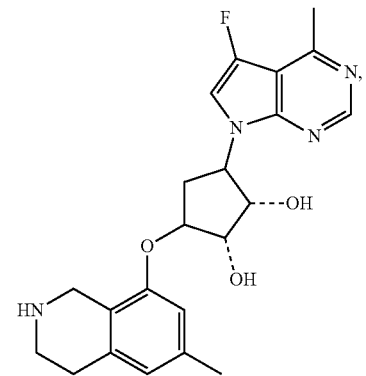
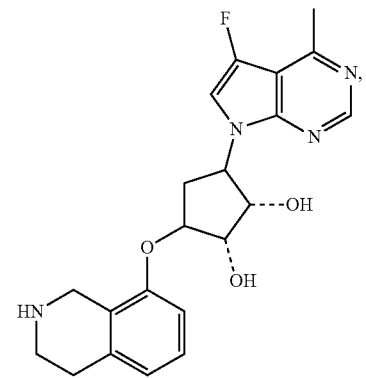

493
-continued
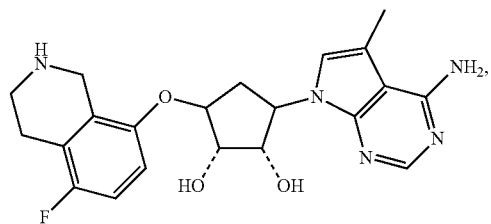
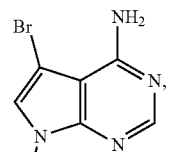
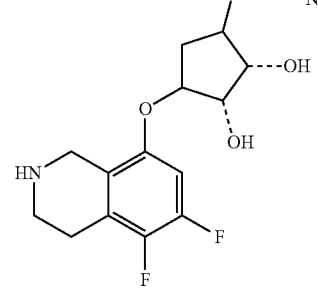
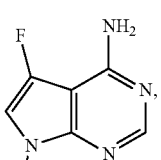
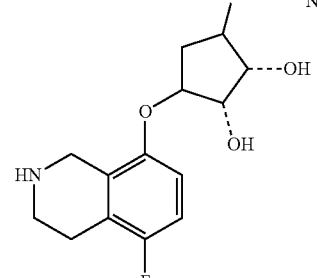
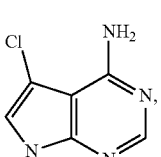
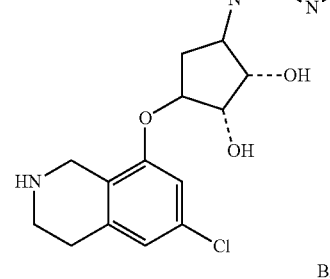
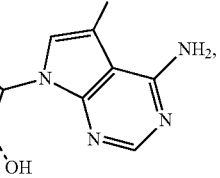
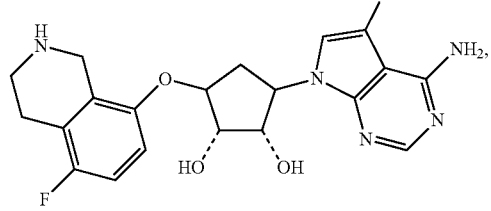
494
-continued
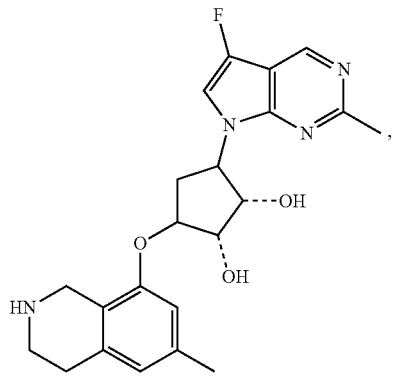
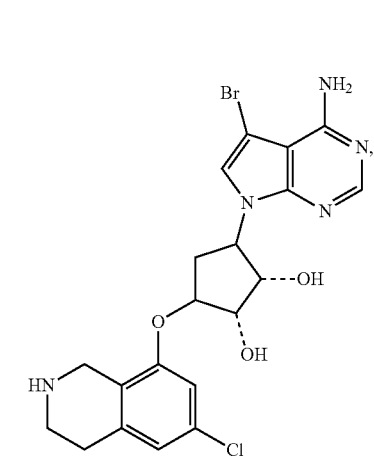
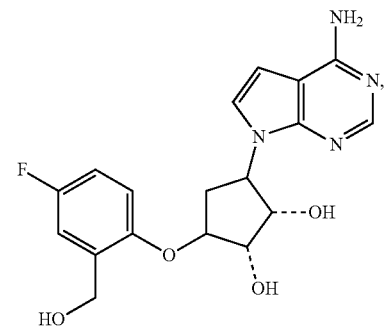
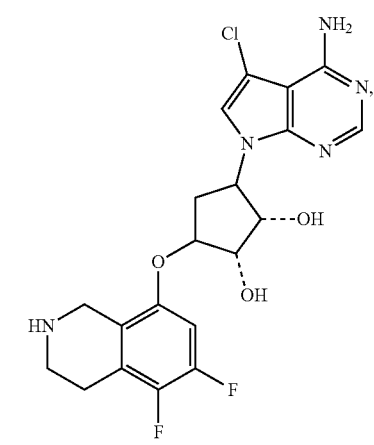

495
-continued
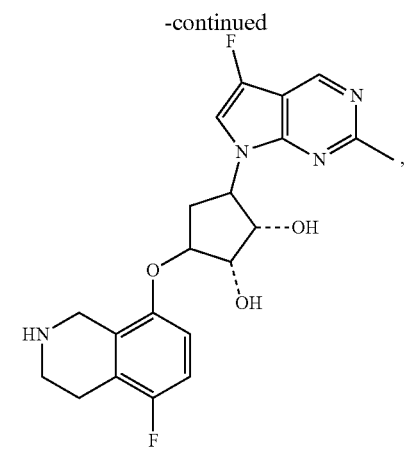
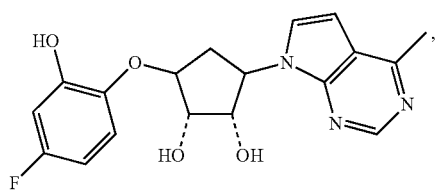
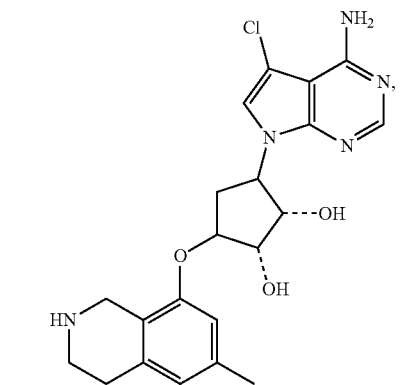
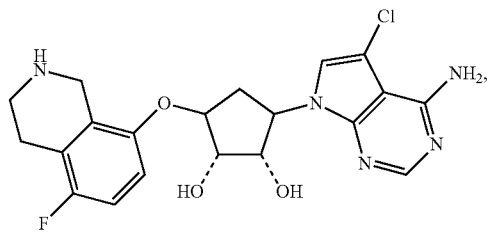
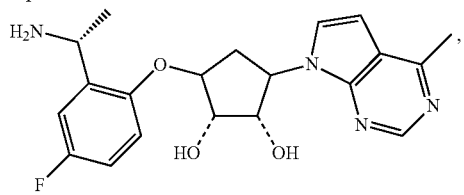
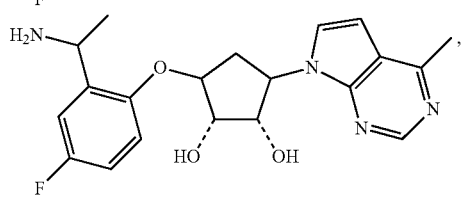
496
-continued
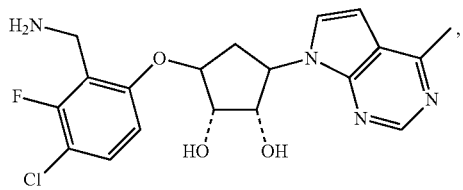
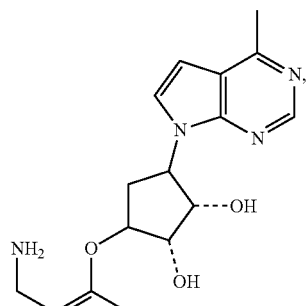
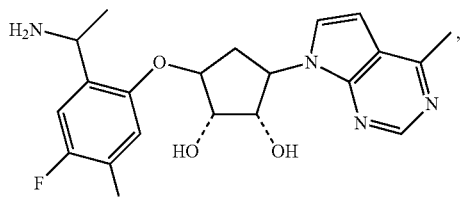
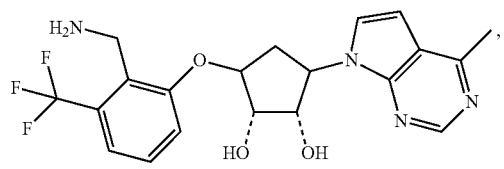
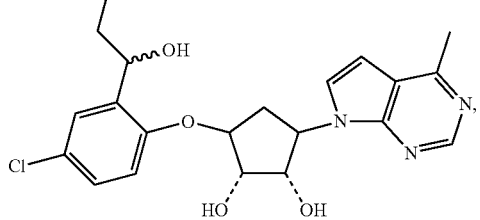
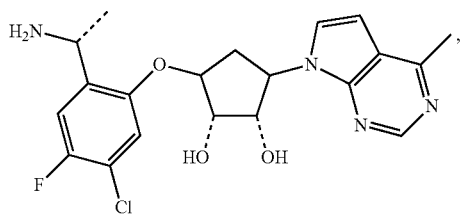
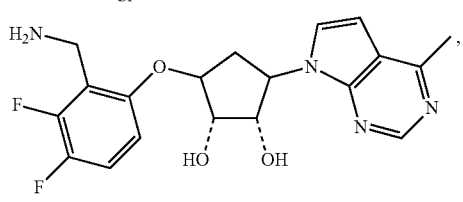

497
-continued
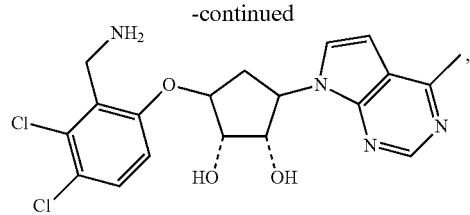
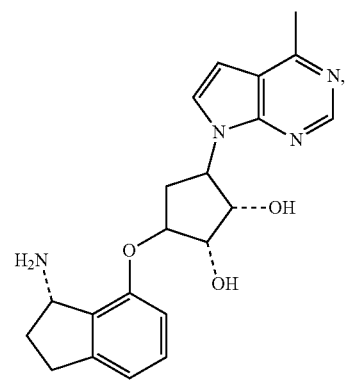
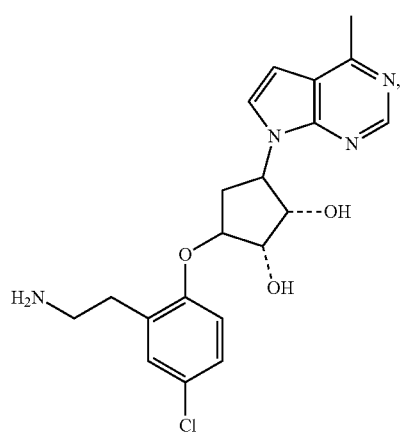
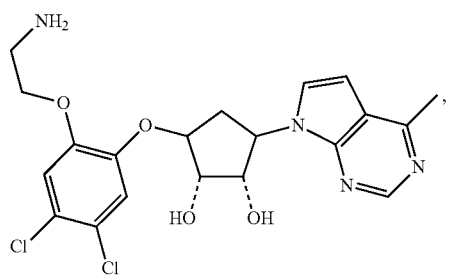
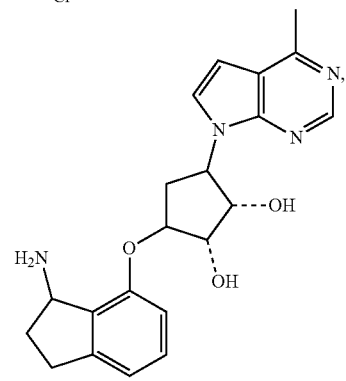
498
-continued
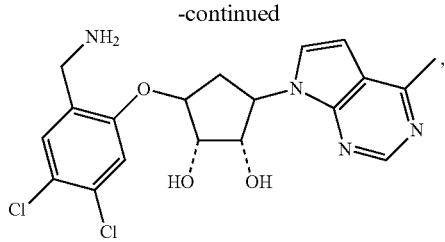
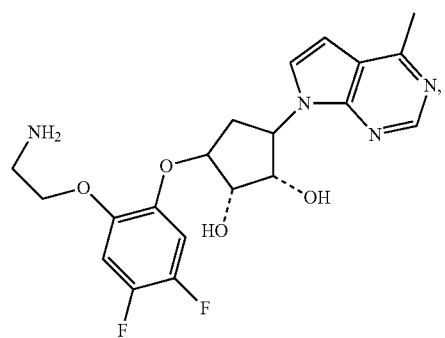
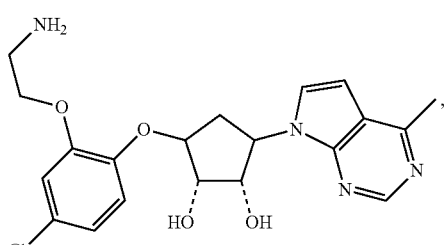
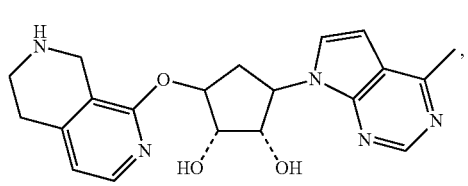
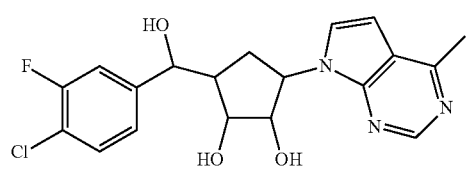
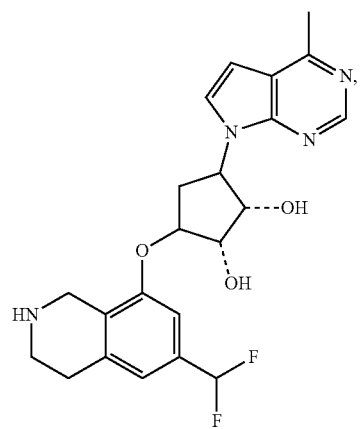

499
-continued
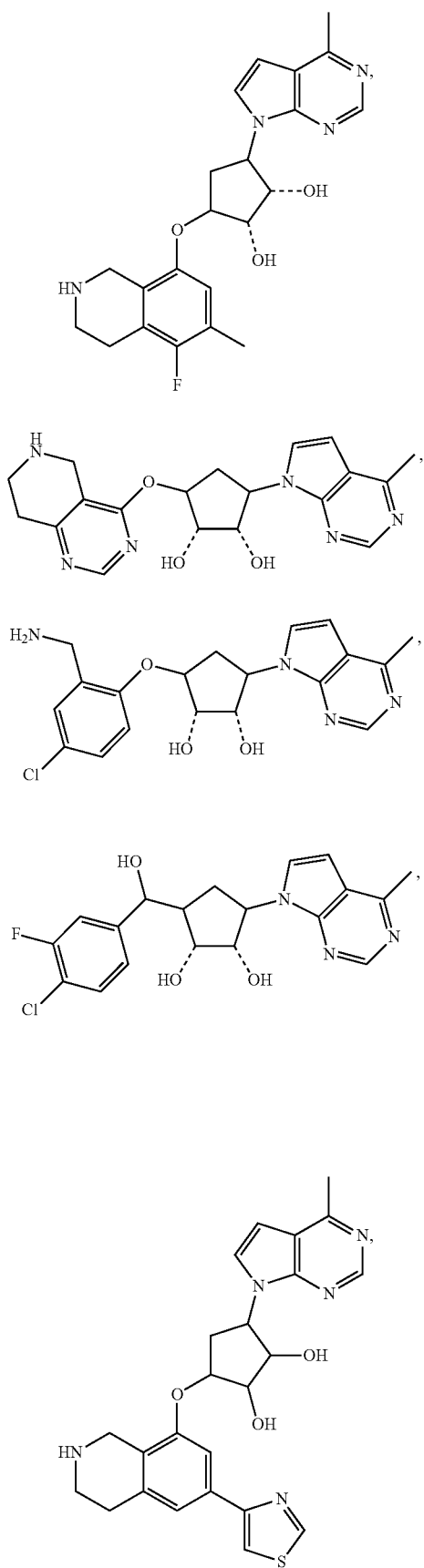
500
-continued
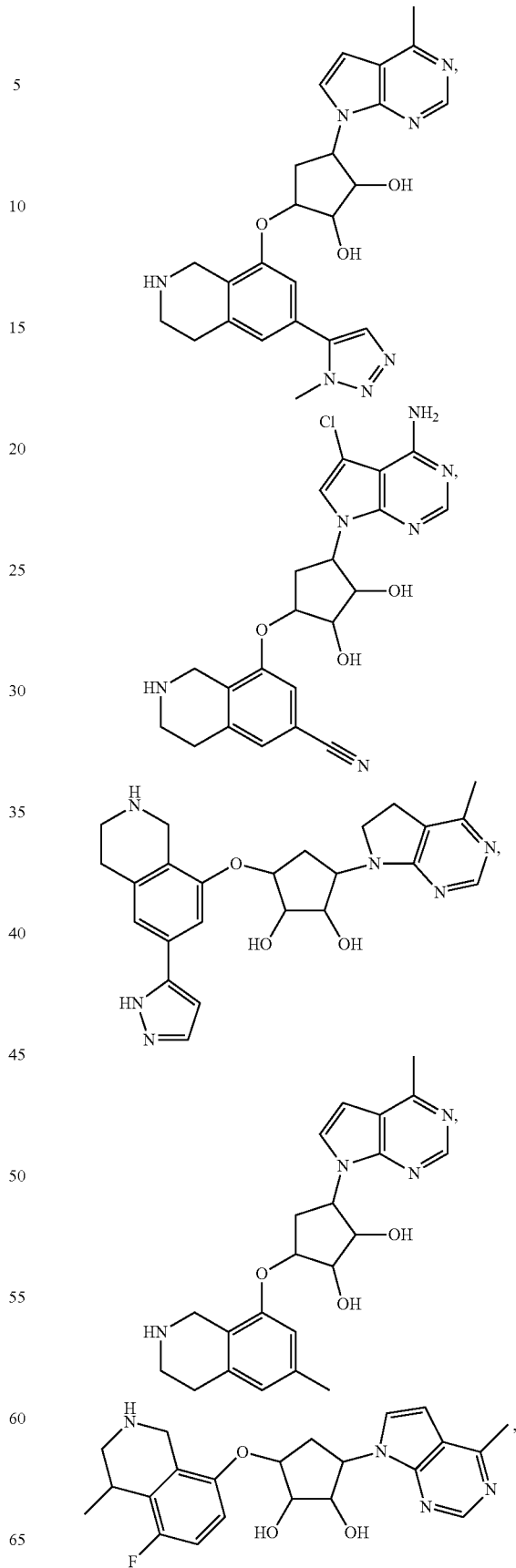

501
-continued
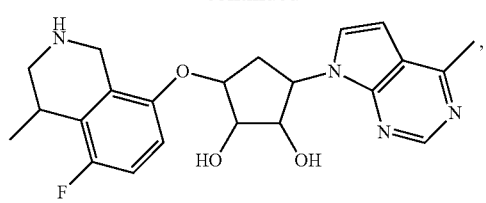
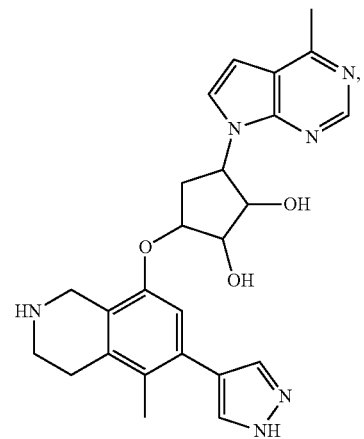
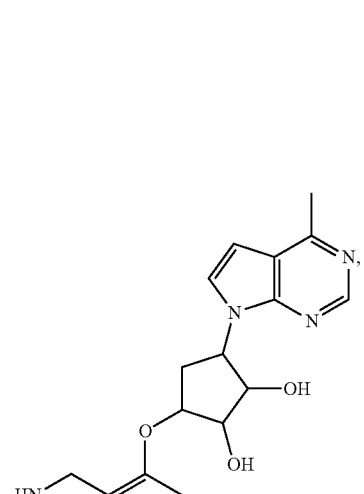
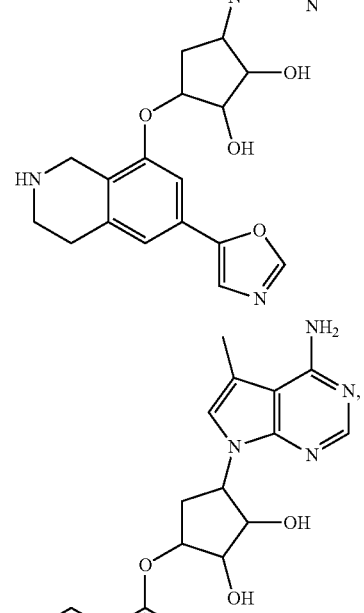
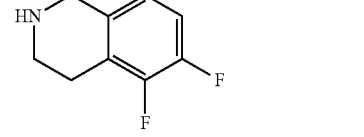
502
-continued
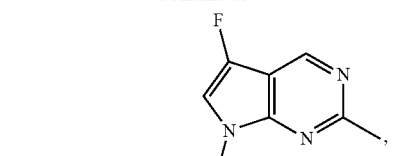
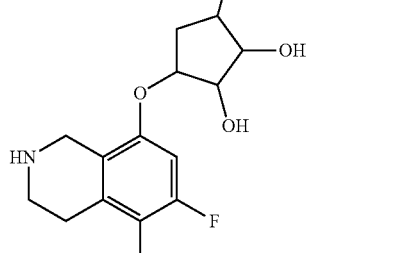
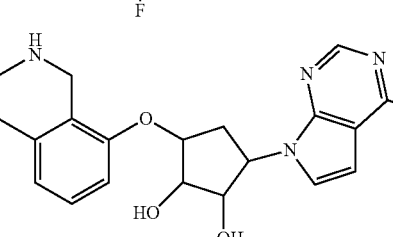
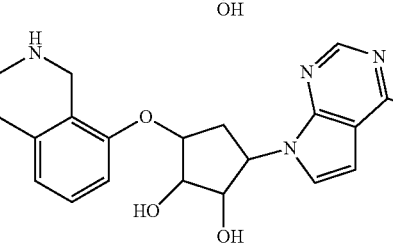
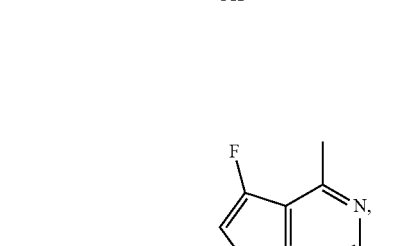
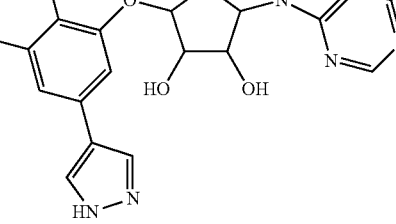

-continued
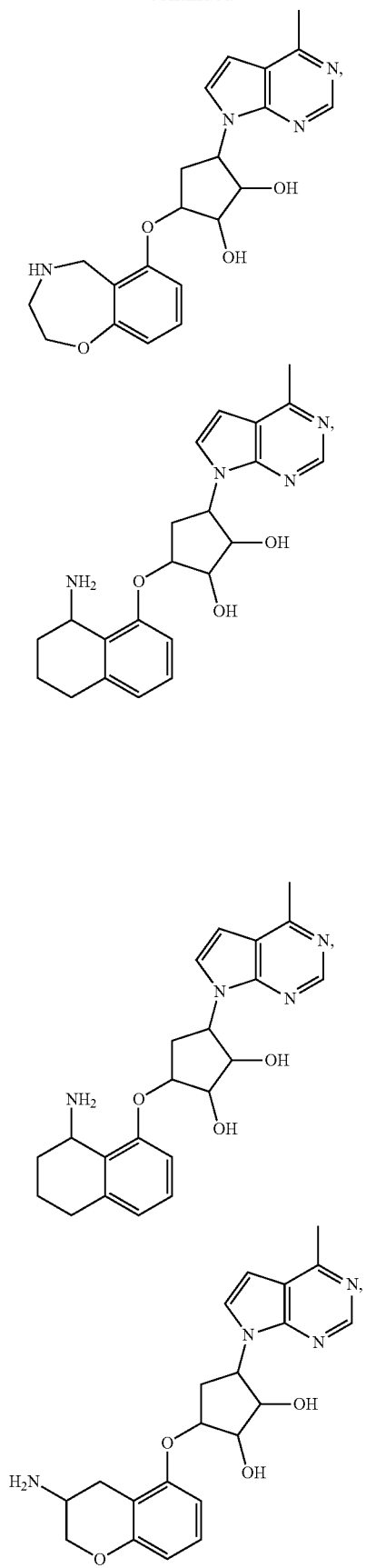
-continued
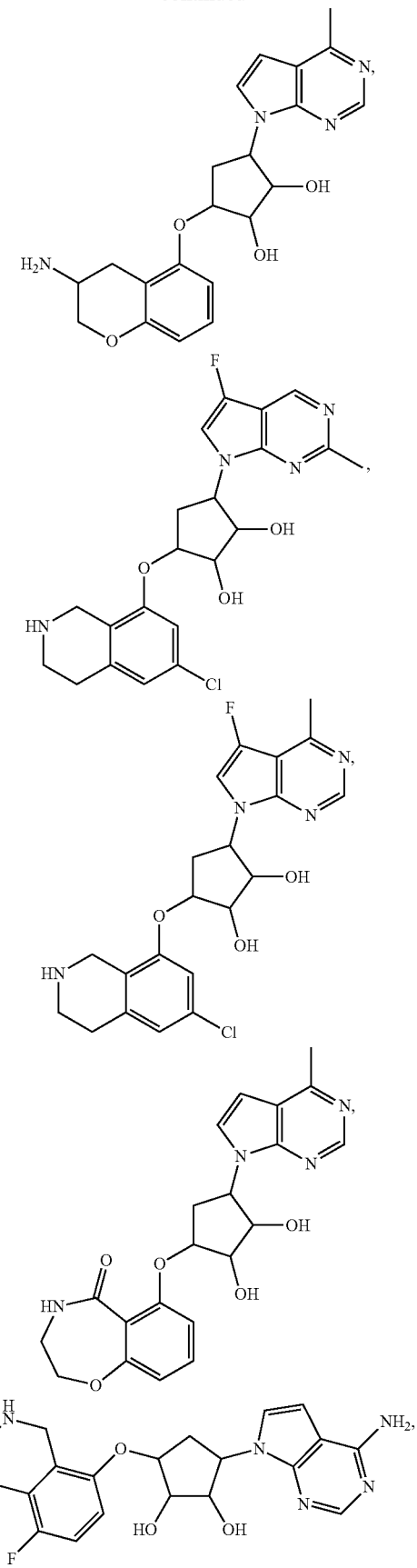

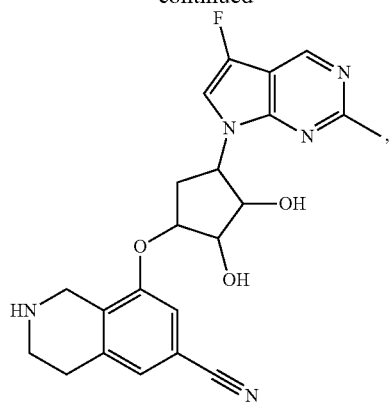
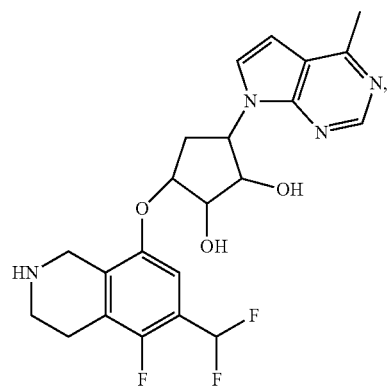
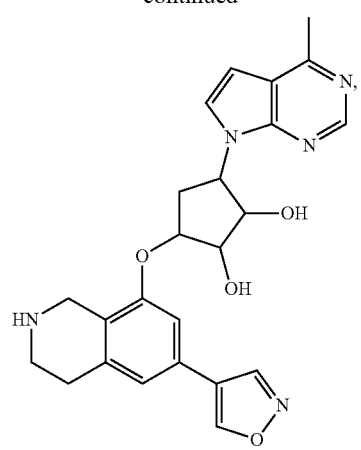
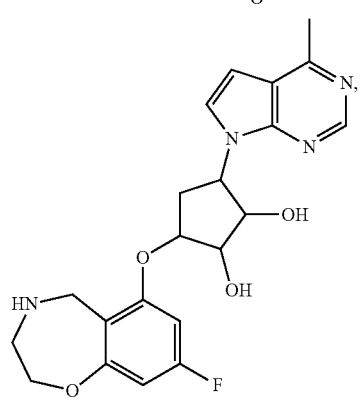

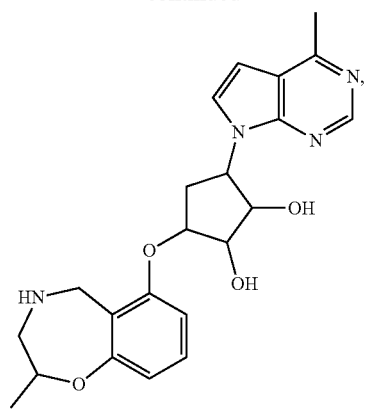
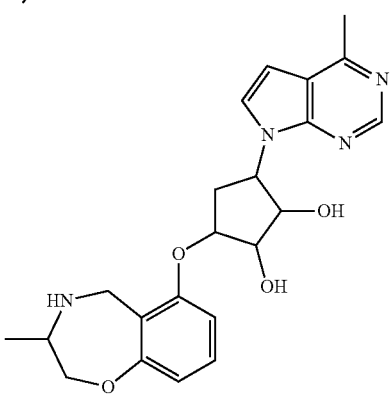
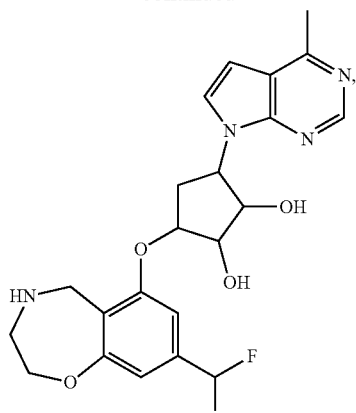

509
-continued
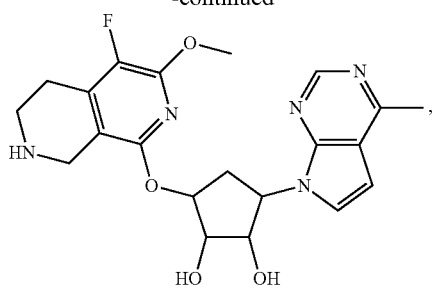
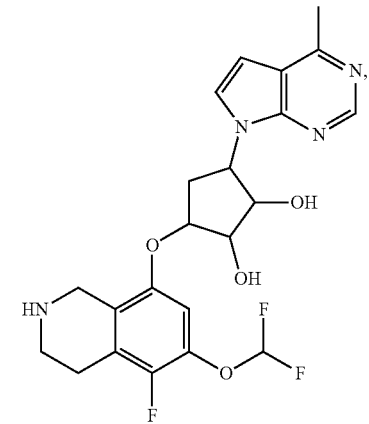
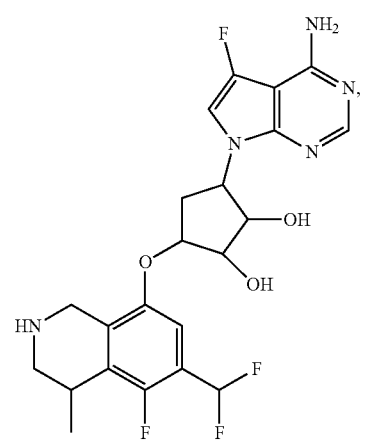
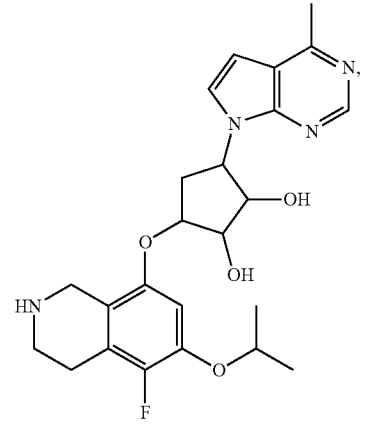
510
-continued
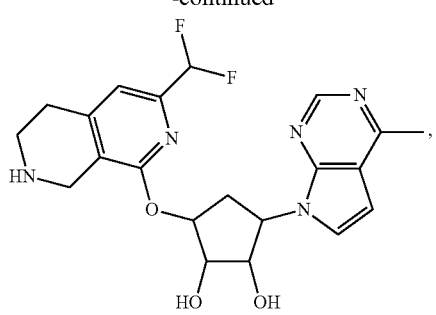
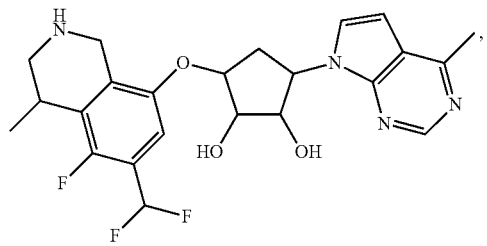
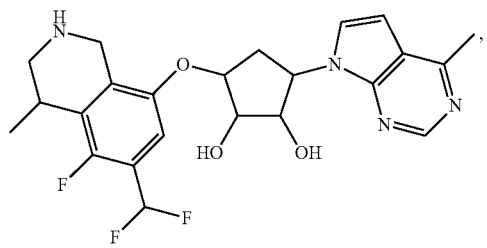
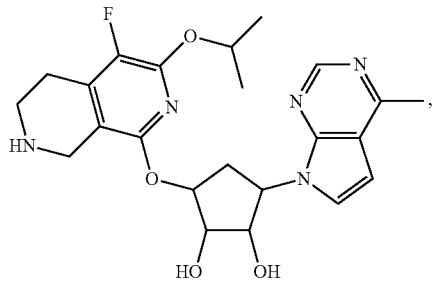
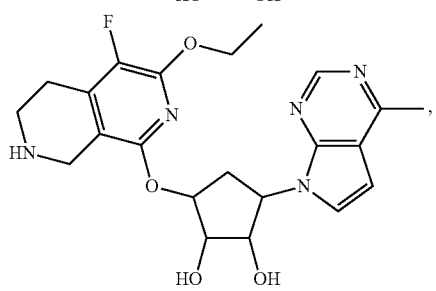

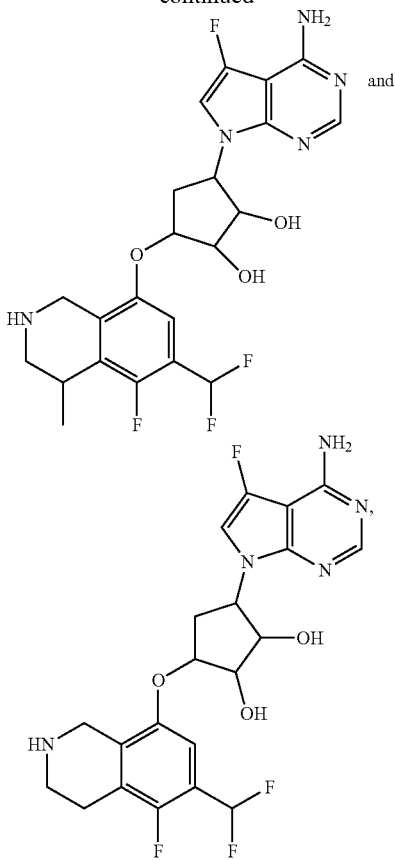

or a pharmaceutically acceptable salt thereof.

10. A compound of any of claims 1-4 and 7-9, wherein said salt is selected from acetate, aspartate, benzoate, besylate, bicarbonate, carbonate, bisulphate, sulfate, borate, camsylate, citrate, edisylate, esylate, formate, fumarate, gluceptate, gluconate, glucuronate, hexafluorophosphate, hibenzate, hydrochloride, chloride, hydrobromide, bromide, hydroiodide, iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine and zinc salts.

11. A compound of any of claims 1-4 and 7-9, wherein said salt is selected from hydrochloride, tosylate and mesylate salts.

12. A pharmaceutical composition comprising a compound according to any one of claims 1-4 and 7-9 or a pharmaceutically acceptable salt thereof, and a pharmaceutically acceptable carrier.

13. The compound: (1S,2S,3S,5R)-3-((6-(difluoromethyl)-5-fluoro-1,2,3,4-tetrahydroisoquinolin-8-yl)oxy)-5-(4-methyl-7H-pyrrolo[2,3-d]pyrimidin-7-yl)cyclopentane-1,2-diol, having the structure:

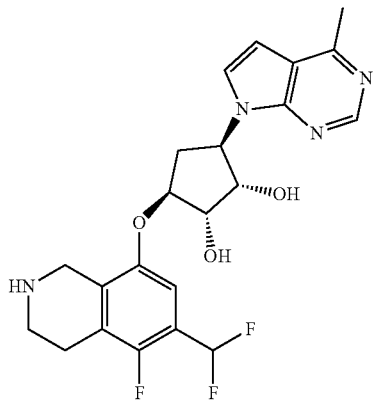 [SMILES: Cc1ncnc2c1ccn2[C@@H]1C[C@H](Oc2cc(C(F)F)c(F)c3c2CNCC3)[C@@H](O)[C@H]1O]

or a pharmaceutically acceptable salt thereof.

14. The compound of claim 13, wherein said salt is selected from acetate, aspartate, benzoate, besylate, bicarbonate, carbonate, bisulphate, sulfate, borate, camsylate, citrate, edisylate, esylate, formate, fumarate, gluceptate, gluconate, glucuronate, hexafluorophosphate, hibenzate, hydrochloride, chloride, hydrobromide, bromide, hydroiodide, iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine and zinc salts.

15. A pharmaceutical composition comprising the compound: (1S,2S,3S,5R)-3-((6-(difluoromethyl)-5-fluoro-1,2,3,4-tetrahydroisoquinolin-8-yl)oxy)-5-(4-methyl-7H-pyrrolo[2,3-d]pyrimidin-7-yl)cyclopentane-1,2-diol, having the structure:

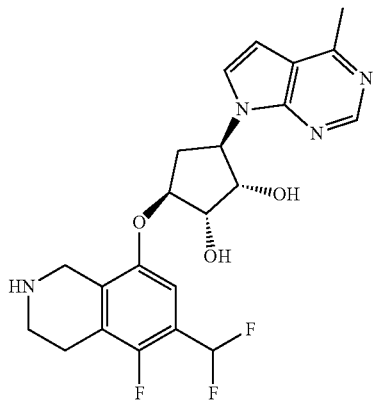 [SMILES: Cc1ncnc2c1ccn2[C@@H]1C[C@H](Oc2cc(C(F)F)c(F)c3c2CNCC3)[C@@H](O)[C@H]1O]

or a pharmaceutically acceptable salt thereof, and a pharmaceutically acceptable carrier.

16. A compound of any of claims 1-4 and 7-9, wherein said salt is selected from phosphate, hydrogen phosphate and dihydrogen phosphate.

17. A compound of any of claims 13-14, wherein said salt is selected from phosphate, hydrogen phosphate and dihydrogen phosphate.

* * * * *

SEQUENCE LISTING

```
<160> NUMBER OF SEQ ID NOS: 2

<210> SEQ ID NO 1
<211> LENGTH: 649
<212> TYPE: PRT
<213> ORGANISM: Homo sapiens

<400> SEQUENCE: 1

Met Asp Tyr Lys Asp Asp Asp Asp Lys Gly Arg Ala Thr Ala Ala Met
1               5                   10                  15
```

Ala Val Gly Gly Ala Gly Ser Arg Val Ser Ser Gly Arg Asp Leu
            20                  25                  30

Asn Cys Val Pro Glu Ile Ala Asp Thr Leu Gly Ala Val Ala Lys Gln
            35                  40                  45

Gly Phe Asp Phe Leu Cys Met Pro Val Phe His Pro Arg Phe Lys Arg
50                      55                  60

Glu Phe Ile Gln Glu Pro Ala Lys Asn Arg Pro Gly Pro Gln Thr Arg
65                      70                  75                  80

Ser Asp Leu Leu Leu Ser Gly Arg Asp Trp Asn Thr Leu Ile Val Gly
                    85                  90                  95

Lys Leu Ser Pro Trp Ile Arg Pro Asp Ser Lys Val Glu Lys Ile Arg
                100                 105                 110

Arg Asn Ser Glu Ala Ala Met Leu Gln Glu Leu Asn Phe Gly Ala Tyr
            115                 120                 125

Leu Gly Leu Pro Ala Phe Leu Leu Pro Leu Asn Gln Glu Asp Asn Thr
130                     135                 140

Asn Leu Ala Arg Val Leu Thr Asn His Ile His Thr Gly His His Ser
145                     150                 155                 160

Ser Met Phe Trp Met Arg Val Pro Leu Val Ala Pro Glu Asp Leu Arg
                165                 170                 175

Asp Asp Ile Ile Glu Asn Ala Pro Thr Thr His Thr Gly Glu Tyr Ser
                180                 185                 190

Gly Glu Glu Lys Thr Trp Met Trp Trp His Asn Phe Arg Thr Leu Cys
                195                 200                 205

Asp Tyr Ser Lys Arg Ile Ala Val Ala Leu Glu Ile Gly Ala Asp Leu
210                     215                 220

Pro Ser Asn His Val Ile Asp Arg Trp Leu Gly Glu Pro Ile Lys Ala
225                     230                 235                 240

Ala Ile Leu Pro Thr Ser Ile Phe Leu Thr Asn Lys Lys Gly Phe Pro
                245                 250                 255

Val Leu Ser Lys Met His Gln Arg Leu Ile Phe Arg Leu Leu Lys Leu
                260                 265                 270

Glu Val Gln Phe Ile Ile Thr Gly Thr Asn His His Ser Glu Lys Glu
                275                 280                 285

Phe Cys Ser Tyr Leu Gln Tyr Leu Glu Tyr Leu Ser Gln Asn Arg Pro
            290                 295                 300

Pro Pro Asn Ala Tyr Glu Leu Phe Ala Lys Gly Tyr Glu Asp Tyr Leu
305                     310                 315                 320

Gln Ser Pro Leu Gln Pro Leu Met Asp Asn Leu Glu Ser Gln Thr Tyr
                    325                 330                 335

Glu Val Phe Glu Lys Asp Pro Ile Lys Tyr Ser Gln Tyr Gln Gln Ala
                340                 345                 350

Ile Tyr Lys Cys Leu Leu Asp Arg Val Pro Glu Glu Lys Asp Thr
            355                 360                 365

Asn Val Gln Val Leu Met Val Leu Gly Ala Gly Arg Gly Pro Leu Val
            370                 375                 380

Asn Ala Ser Leu Arg Ala Ala Lys Gln Ala Asp Arg Arg Ile Lys Leu
385                     390                 395                 400

Tyr Ala Val Glu Lys Asn Pro Asn Ala Val Val Thr Leu Glu Asn Trp
                405                 410                 415

Gln Phe Glu Glu Trp Gly Ser Gln Val Thr Val Val Ser Ser Asp Met
                420                 425                 430

```
Arg Glu Trp Val Ala Pro Glu Lys Ala Asp Ile Ile Val Ser Glu Leu
            435                 440                 445

Leu Gly Ser Phe Ala Asp Asn Glu Leu Ser Pro Glu Cys Leu Asp Gly
    450                 455                 460

Ala Gln His Phe Leu Lys Asp Asp Gly Val Ser Ile Pro Gly Glu Tyr
465                 470                 475                 480

Thr Ser Phe Leu Ala Pro Ile Ser Ser Ser Lys Leu Tyr Asn Glu Val
                485                 490                 495

Arg Ala Cys Arg Glu Lys Asp Arg Asp Pro Glu Ala Gln Phe Glu Met
            500                 505                 510

Pro Tyr Val Val Arg Leu His Asn Phe His Gln Leu Ser Ala Pro Gln
        515                 520                 525

Pro Cys Phe Thr Phe Ser His Pro Asn Arg Asp Pro Met Ile Asp Asn
    530                 535                 540

Asn Arg Tyr Cys Thr Leu Glu Phe Pro Val Glu Val Asn Thr Val Leu
545                 550                 555                 560

His Gly Phe Ala Gly Tyr Phe Glu Thr Val Leu Tyr Gln Asp Ile Thr
                565                 570                 575

Leu Ser Ile Arg Pro Glu Thr His Ser Pro Gly Met Phe Ser Trp Phe
            580                 585                 590

Pro Ile Leu Phe Pro Ile Lys Gln Pro Ile Thr Val Arg Glu Gly Gln
        595                 600                 605

Thr Ile Cys Val Arg Phe Trp Arg Cys Ser Asn Ser Lys Lys Val Trp
    610                 615                 620

Tyr Glu Trp Ala Val Thr Ala Pro Val Cys Ser Ala Ile His Asn Pro
625                 630                 635                 640

Thr Gly Arg Ser Tyr Thr Ile Gly Leu
                645

<210> SEQ ID NO 2
<211> LENGTH: 342
<212> TYPE: PRT
<213> ORGANISM: Homo sapiens

<400> SEQUENCE: 2

Met Arg Lys Glu Thr Pro Pro Pro Leu Val Pro Pro Ala Ala Arg Glu
1               5                   10                  15

Trp Asn Leu Pro Pro Asn Ala Pro Ala Cys Met Glu Arg Gln Leu Glu
                20                  25                  30

Ala Ala Arg Tyr Arg Ser Asp Gly Ala Leu Leu Leu Gly Ala Ser Ser
            35                  40                  45

Leu Ser Gly Arg Cys Trp Ala Gly Ser Leu Trp Leu Phe Lys Asp Pro
    50                  55                  60

Cys Ala Ala Pro Asn Glu Gly Phe Cys Ser Ala Gly Val Gln Thr Glu
65                  70                  75                  80

Ala Gly Val Ala Asp Leu Thr Trp Val Gly Glu Arg Gly Ile Leu Val
                85                  90                  95

Ala Ser Asp Ser Gly Ala Val Glu Leu Trp Glu Leu Asp Glu Asn Glu
            100                 105                 110

Thr Leu Ile Val Ser Lys Phe Cys Lys Tyr Glu His Asp Asp Ile Val
    115                 120                 125

Ser Thr Val Ser Val Leu Ser Ser Gly Thr Gln Ala Val Ser Gly Ser
130                 135                 140

Lys Asp Ile Cys Ile Lys Val Trp Asp Leu Ala Gln Gln Val Val Leu
145                 150                 155                 160
```

-continued

```
Ser Ser Tyr Arg Ala His Ala Ala Gln Val Thr Cys Val Ala Ala Ser
            165                 170                 175
Pro His Lys Asp Ser Val Phe Leu Ser Cys Ser Glu Asp Asn Arg Ile
            180                 185                 190
Leu Leu Trp Asp Thr Arg Cys Pro Lys Pro Ala Ser Gln Ile Gly Cys
        195                 200                 205
Ser Ala Pro Gly Tyr Leu Pro Thr Ser Leu Ala Trp His Pro Gln Gln
        210                 215                 220
Ser Glu Val Phe Val Phe Gly Asp Glu Asn Gly Thr Val Ser Leu Val
225                 230                 235                 240
Asp Thr Lys Ser Thr Ser Cys Val Leu Ser Ser Ala Val His Ser Gln
            245                 250                 255
Cys Val Thr Gly Leu Val Phe Ser Pro His Ser Val Pro Phe Leu Ala
            260                 265                 270
Ser Leu Ser Glu Asp Cys Ser Leu Ala Val Leu Asp Ser Ser Leu Ser
        275                 280                 285
Glu Leu Phe Arg Ser Gln Ala His Arg Asp Phe Val Arg Asp Ala Thr
        290                 295                 300
Trp Ser Pro Leu Asn His Ser Leu Leu Thr Thr Val Gly Trp Asp His
305                 310                 315                 320
Gln Val Val His His Val Val Pro Thr Glu Pro Leu Pro Ala Pro Gly
            325                 330                 335
Pro Ala Ser Val Thr Glu
            340
```